(12) United States Patent
Alliel et al.

(10) Patent No.: US 7,534,439 B2
(45) Date of Patent: May 19, 2009

(54) NUCLEIC SEQUENCE AND DEDUCED PROTEIN SEQUENCE FAMILY WITH HUMAN ENDOGENOUS RETROVIRAL MOTIFS, AND THEIR USES

(75) Inventors: Patrick M. Alliel, Clamart (FR); Jean-Pierre Perin, Le Plessis-Robinson (FR); Francois Rieger, Boulogne (FR)

(73) Assignee: Institut National de la Sante Et de la Recherche Medical-INSERM, Paris (FR)

( * ) Notice: Subject to any disclaimer, the term of this patent is extended or adjusted under 35 U.S.C. 154(b) by 235 days.

(21) Appl. No.: 11/028,539

(22) Filed: Jan. 5, 2005

(65) Prior Publication Data

US 2005/0118573 A1 Jun. 2, 2005

Related U.S. Application Data

(62) Division of application No. 09/719,554, filed as application No. PCT/FR99/01513 on Jun. 23, 1999, now Pat. No. 6,919,438.

(30) Foreign Application Priority Data

Jun. 23, 1998 (FR) .................................. 98 07920

(51) Int. Cl.
*A61K 39/12* (2006.01)
(52) U.S. Cl. ................. 424/187.1; 424/204.1
(58) Field of Classification Search ...................... None
See application file for complete search history.

(56) References Cited

U.S. PATENT DOCUMENTS 6,184,025 B1 2/2001 Perron et al.

FOREIGN PATENT DOCUMENTS

WO WO 99/02696 * 1/1999

OTHER PUBLICATIONS

Mi, S., et al., "Syncytin is a captive retroviral envelope protein involved in human placental morphogenesis," Nature, vol. 403, Feb. 17, 2000, pp. 785-789.

Knerr, I., et al., "Transcriptional effects of hypoxia on fusiogenic syncytin and its receptor ASCT2 in human cytotrophoblast BeWo cells and in ex vivo perfused placental cotyledons," Am J Obstet Gynecol, vol. 189, No. 2, Aug. 2003, pp. 583-588.

Knerr, I., et al., "Syncytin, a novel human endogenous retroviral gene in human placenta: Evidence for its dysregulation in preeclampsia and HELLP sydrome," Am J Obstet Gynecol, vol. 186, No. 2, Feb. 2002, pp. 210-213.

Antony, J. M., et al., "Human endogenous retrovirus glycoprotein-mediated induction of redox reactants causes oligodendrocyte death and demyelination," Nature Neuroscience, vol. 7, No. 10, Oct. 2004, pp. 1088-1095.

Jolivet-Reynaud, C., et al., "Specificities of Multiple Sclerosis Cerebrospinal Fluid and Serum Antibodies against Mimotopes," Clinical Immunology, vol. 93, No. 3, Dec. 1999, pp. 283-293.

Fujinami, R. S., et al., "Endogenous Retroviruses: Are They the Cause of Multiple Sclerosis?," Trends in Microbiology, vol. 7, No. 7, Jul. 1999, pp. 263-264.

Steiner, I., et al., "Infection and the Etiology and Pathogenesis of Multiple Sclerosis," Current Neurology and Neuroscience Reports, vol. 1, No. 3., May 2001, pp. 271-276.

* cited by examiner

*Primary Examiner*—Stacy B Chen
(74) *Attorney, Agent, or Firm*—Oblon, Spivak, McClelland, Maier & Neustadt, P.C.

(57) ABSTRACT

The invention concerns a novel nucleic sequence and deduced protein sequence family with whole or partial human endogenous retroviral motifs. The invention also concerns the detection and/or the use of said nucleic sequences and said corresponding protein sequences or fragments of said sequences, for diagnostic, prophylactic and therapeutic uses, in particular for neuropathological conditions with autoimmune constituent such as multiple sclerosis. Said purified nucleic acid sequences comprise all or part of a sequence coding for a human endogenous retroviral sequence having at least eny-type retroviral motifs, corresponding to the sequence SEQ ID NO: 1 or to a sequence having a homology level with said sequence SEQ ID NO: 1 not less than 80% of more than 190 nucleotides or not less than 70% on more than 600 nucleotides for env-type domains. The invention further concerns the use of the flanking or adjacent sequence of said sequences and controlled by the latter, as diagnostic reagents.

3 Claims, 64 Drawing Sheets

| Sequence | Position | Annotation |
|---|---|---|
| CCCTGGGGCGGGCTTCCTTTCTGGGATGAGGGCAAAACGCCTGGAGATACAGCAATTATCTTGCAACTGAG | 71 | |
| AGACAGGACTAGCTGGATTTCCTAGGCCGACTAAGAATCCCTAAGCCTAGCTGGGAAGGTGACCACGTCCAC | 143 | |
| CTTTAAACACGGGGCTTGCAACTTAGCTCACACCTGACCAATCAGAGAGCTCACTAAAATGCTAATTAGGCA | 215 | |
| AAGACAGGAGGTAAAGAAAATAGCCAATCATCTATTGCCTGAGAGCACAGCAGGAGGGACAACAATCGGGATA | 287 | Repeated |
| TAAACCCAGGCATTCGAGCTGGCAACAGCAGCCCCCCTTTGGGTCCCTTCCCTTTGTATGGGAGCTGTTTTC | 359 | region |
| ATGCTATTTCACTCTATTAAATCTTGCAACTGCACTCTTCTGGTCCATGTTTCTTACGGCTCGAGCTGAGCT | 431 | R1 |
| TTTGCTCACCGTCCACCACTGCTGTTTGCCACCACCGCAGACCTGCCGCTGACTCCCATCCCTCTGGATCCT | 503 | |
| GCAGGGTGTCCGCTGTGCTCCTGATCCAGCGAGGCGCCCATTGCCGCTCCCAATTGGGCTAAAGGCTTGCCA | 575 | |
| TTGTTCCTGCACGGCTAAGTGCCTGGGTTTGTTCTAATTGAGCTGAACACTAGTCACTGGGTTCCATGGTTC | 647 | |
| TCTTCTGTGACCCACGGCTTCTAATAGAACTATAACACTTACCACATGGCCCAAGATTCCATTCCTTGGAAT | 719 | |
| CCGTGAGGCCAAGAACTCCAGGTCAGAGAATACGAGGCTTGCCACCATCTTGGAAGCGGCCTGCTACCATCT | 791 | |
| TGGAAGTGGTTCACCACCATCTTGGGAGCTCTGTGAGCAAGGACCCCCCGGTAACATTTTGGCAACCACGAA | 863 | |
| CGGACATCCAAAGTGGTGAGTAATATTGGACCACTTTCACTTGCTATTCTGTCCTATCCTTCCTTAGAATTG | 935 | |
| GAGGAAAATACCGGGCACTTGTCGGCCAGTTAAAAACGATTAGTGTGGCCACCGGACTTAAGACTCAGGTGT | 1007 | |
| GAGGCTATCTGGGGAAGGGCTTTCTAACAACCCCCAACCCTTCTGGGTTGGGGACTTGGTTTGCCTCAAGCC | 1079 | |
| AGCTTCCACTTTCAGTTTTCTTGGGGAAGCCGAGGGCCGACTAGAGGCAGAAAGCTGTCGTCCTGAACTCCC | 1151 | |
| GGCAGTAGCCGGTTGAGATCATGGTGTAGCCAGAAGTCTCAACAGTCGCCCATGCATGCACCCCTATCTTTC | 1223 | |
| CTTCTGACCCATACCTCCTGGGTCCCAACCACAACTTTCTTCAAAGTGTAGCCCCAAAATTCTCCTTACCTC | 1295 | |
| TGAATATACTTCCTCTGATCCCTGCCTCCTAGGTACTATTGGTTCAGACTTCCATTTCCTCTAGCAAGTTGT | 1367 | |
| ATCTCCAAAGGGATCTAAGGAAGCTCTGCGCTGCCTCCTTAGGCACCTAGGCTATAACCCAGGGAGTCTTAT | 1439 | |
| CCCTGGTGTCCCTCCCAATTTAGGCATACAGCTCTTGACATGGGCAGTTATGTAGGACCCACTCCCCACCAC | 1511 | |
| CCTTGCCAGGGCCCCAAGTTTGTAAATGGCTGAGGGAAAAGAGAGACAGAGGAGAGAGAGAAATGGAGGA | 1583 | |
| GAAAGAGAGAGAGACAGAGAGGAGAGAGAGACAGTGAGAGAGACAGAAGAGAGAGAGAGACAAAGAGGAGAG | 1655 | |
| AGAGAGAGTCAAAGAGAAAGAAAGAGAAAGAAATAGTAAAAAACAGTGTGCCCTATTCCTTTAAAAGCCA | 1727 | |
| GGGTAAATTTAAAACCTGTACTTGATAATTGAAGGTCTTCTCTGTGACCCTATAGCACTCCAATCCACTTTG | 1799 | |
| TGGTCAGTGTAAATAAGAGCATAGGCCGAAAGCACTGAGGCCATTGACAACCCGTAGCTTCCCTATCAAAAA | 1871 | |
| TCCTTAACCCAGTAACCCGCAGATGGACCAAATGCATTCAGTCGGTAGCGCAACTGCTTTGCTAAAAGTAGA | 1943 | |
| AAAGTAACTTTTAGAGGAAACCTCATTGTGAGCACACCTCACCTGTTCAGAATTATTCTAATAAAAAAAGCA | 2015 | |
| AAAAGGTAGCTTACTAACTCAAAAATCTTAAAGTATGGGGCTATTCTGTTAGAAAAAGGTAATGTAACTCCA | 2087 | |
| ACCACTGATAATTCCCTTAACCCAGCAGATTTCCTAACGGGATTTAAATCTTAATTACCATACAAAGGTCCG | 2159 | |
| ACCAGACCTAGGCGGAACTCCCCTTCAGGACAGGACGATAGATGGTTCCTCCCAGGTGATTGAGGAAAAAAC | 2231 | |
| CACAATGGGTATTCAGTAATTGATACGGGGACTCTTGTGGAAGCAGAGTTAGAAAAATTGCCTAATAACTGG | 2303 | |
| TCTCCTCAAACGTGTGAGCTGTTTGCACTCAGCCAAGCCTTAAAGTACTTACAGAATCAAAAGACTATCTCA | 2375 | |
| ATCCTGATTCAAAAGGTTAGCTACACCCCTCTCTGTAATGCATTTGCATAAGAACTTGTTTATGGGAATGCAT | 2447 | |
| CTTGATGGGGCAGCTGGGTTGTTATAAAATAGGAACCCAGCCCAGCTCTAGGACTCACCCCTGAGCGCAAAG | 2519 | Repeated |
| GCAATGTTGGGCATGCTGGTAAAGGACCACTAGAATCCAGCAGCCCAGACCCCTTTCTTTGTGGTCAAGAAA | 2591 | region |
| GGCGGGAAAAGGGGTGCAGGACTGCTACATCGGTAAGCATAACTAATCCGATAAACAGAGGTCCATGGGTGG | 2663 | In tandem |
| TTACGCACCCTGGAAAGGAACTCACCCCTGAGCACAAAGGCAATGTTGGGCACGCTGGTAAAGGACCACTAG | 2735 | R2 |
| AATCCAGCAGCCTGGACCCCTTTCTTTGTGGTCAAGAGAGGCAGGAAACAGGTGCAGGACTGCAACATCAG | 2807 | |
| TGAGCATAACTAATTCGATAAGCAGAGGTCCATGGGTGGTGATGCACCCTGGAAAGAATAAGCATTAGGACC | 2879 | |
| ATAGAGGACACTCCAGGACTAAAGCTCATCGGAAAATGACTAGGGTTGCTGGCATCCCTATGTTCTTTTTTC | 2951 | |
| AGATGGGAAACGTTCCCCGCAAGACAAAAACGCCCCTAAGACGTATTCTGGAGAATTGGGACCAATTTGACC | 3023 | |
| CTCAGACACTAAGAAAGAAACGACTTATATTCTTCTGCAGTGCCGCCTGGCACTCCTGAGGGAAGTATAAAT | 3095 | |
| TATAACACCATCTTACAGCTAGACCTCTTTTGTAGAAAAGGCAAATGGAGTGAAGTGCCATAAGTACAAACT | 3167 | |
| TTCTTTTCATTAAGAGACAACTCACAATTATGTAAAAAGTGTGATTTATGCCCTACAGGAAGCCTTCAGAGT | 3239 | |
| CTACCTCCCTATCCCAGCATCCCCGACTCCTTCCCAACTAATAAGGACCCCCCTTCAACCCAAATGGTCCA | 3311 | |
| AAAGGAGATAGACAAAAGGGTAAACAGTGAACCAAAGAGTGCCAATATTCCCCAATTATGACCCCTCCAAGC | 3383 | |
| AGTGGGAGGAAGAGAATTCGGCCCAGCCAGATGCATGTGCCTTTTTCTCTCCCAGACTTAAAGCAAATAAA | 3455 | |
| AACAGACTTAGGTAAATTCTCAGATAACCCTGATGGCTATATTGATGTTTTACAAGGGTTAGGACAATTCTT | 3527 | |
| TGATCTGACATGGAGAGATATAATGTCACTGCTAAATCAGACACTAACCCCAAATGAGAGAAGTGCCACCAT | 3599 | |
| AACTGCAGCCTGAGAGTTTGGCGATCTCTGGTATCTCAGTCAGGTCAATGATAGGATGACAACAGAGGAAAG | 3671 | Gag |
| AGAATGATTCCCCACAGGGCCAGCAGGCAGTTCCCAGTCTAGACCCTCATTGGGACACAGAATCAGAACATGG | 3743 | domain |
| AGATTGGTGCTGCAGACATTTGCTAACTTGTGTGCTAGAAGGACTAAGAAAACTAGGAAGAAGTCTATGAA | 3815 | |
| TTACTCAATGATGTCCACCATAACACAGGGAAGGGAAGAAAATTCTACTGCCTTTCTGGAGAGACTAAGGGA | 3887 | |
| GGCATTGAGGAAGCGTGCCTCTCTGTCACCTGACTCTTCTGAAGGCCAACTAATCTTAAAGCGTAAGTTTAT | 3959 | |
| CACTCAGTCAGCTGCAGACATTAGAAAAAAACTTCAAAAGTCTGCCGTAGGCCCGGAGCAAAACTTAGAAAC | 4031 | |
| CCTATTGAACTTGGCAACCTCGGTTTTTTATAATAGAGATCAGGAGGAGCAGGCGGAACAGGACAAACGGGA | 4103 | |
| TTAAAAAAAAAGGCCACCGCTTTAGTCATGACCCTCAGGCAAGGTGGACTTTGGAGGCTCTGGAAAAGGGAAAA | 4175 | |
| GCTGGGCAAATTGAATGCCTAATAGGGCTTGCTTCCAGTGCGGCTACAAGGACACTTTAAAAAAGATTGTC | 4247 | |
| CAAGTAGAAGTAAGCCGCCCCCTCGTCCATGCCCCTTATTTCAAGGGAATCACTGGAAGGCCCACTGCCCCA | 4319 | |
| GGGGACAAAGGTCCTCTGAGTCAGAAGCCACTAACCAGATGATCCAGCAGCAGGACTGAGGGTGCCTGGGGC | 4391 | |
| AAGCGCCATCCCATGCCATCACCCTCACAGAGCCCTGGGTATGCTTGACCATTGAGGGCCAGGAGGTTGTCT | 4463 | |
| CCTGGACACTGGTGCGGTCTTCTTAGTCTTACTCTTCTGTCGGACAACTGTCCTCCAGATCTGTCACTAT | 4535 | |
| CTGAGGGGGTCCTAAGACGGGCAGTCACTAGATACTTCTCCCAGCCACTAAGTTATGACTGGGGAGCTTTAT | 4607 | |
| TCTTTTCACATGCTTTTCTAATTATGCTTGAAAGCCCCACTACCTTGTTAGGGAGAGACATTCTAGCAAAAG | 4679 | |
| CAGGGGCCATTATACACCTGAACATAGGAGAAGGAACACCCGTTTGTTGTCCCCTGCTTGAGGAAGGAATTA | 4751 | |
| ATCCTGAAGTCTGGGCAACAGAAGGACAATATGGACGAGCAAAGAATGCCCGTCCTGTTCAAGTTAAACTAA | 4823 | |
| AGGATTCCACCTCCTTTCCCTACCAAAGGCAGTACCCCCTCAGACCCCAACAAGGCCCAACAAGGACTCCAAAAGA | 4895 | |
| TTGTTAAGGACCTAAAAGCCCAAGGCCTAGTAAAAACATGCAGTAACCCCTGCAGTACTCCAATTTTAGGAG | 4967 | |
| TACAGAAACCCAACAGACAGTGGAGGTTAGTGCAAGATCTCAGGATTATCAATGAGGCTGTTGTTCCTCTAT | 5039 | Pol |
| AGCCAGCTGTACCTAGCCCTTATACTCTGCTTTCCCAAATACCAGAGGAAGCAGAGTGGTTTACAGTCCTGG | 5111 | domain |
| ACCTTCAGGATGCCTTCTTCTGCATCCCTGTACATCCTGACTCTCAATTCTTGTTTGCCTTTGAAGATACTT | 5183 | |

*FIG. 1A*

```
CAAACCCAACATCTCAACTCACCTGGACTATTTTACCCCAAGGGTTCAGGGATAGTCCCCATCTATTTGGCC   5255
AGGCATTAGCCCAAGACTTGAGCCAATCCTCATACCTGGACACTTGTCCTTCGGTAGGTGGATGATTTACTT   5327
TTGGCCGCCCATTCAGAAACCTTGTGCCATCAAGCCACCCAAGCGCTCTTCAATTTCCTCGCTACCTGTGGC   5399
TACATGGTTTCCAAACCAAAGGCTCAACTCTGCTCACAGCAGGTTACTTAGGGCTAAAATTATCCAAAGGCA   5471
CCAGGGCCCTCAGTGAGGAACACATCCAGCCTATACTGGCTTATCCTCATCCCAAAACCCTAAAGCAACTAA   5543
GGGGATTCCTTGGCGTAATAGGTTTCTGCCGAAAATGGATTCCCAGGTATGGCGAAATAGCCAGGTCATTAA   5615
ATACACTAATTAAGGAAACTCAGAAAGCCAATACCCATTTAGTAAGATGGACAACTGAAGTAGAAGTGGCTT   5687
TCCAGGCCCTAACCCAAGCCCCAGTGTTAAGTTTGCCAACAGGGCAAGACTTTTCTTCATATGTCACAGAAA   5759
AAACAGGAATAGCTCTAGGAGTCCTTACACAGATCCGAGGGATGAGCTTGCAACCTGTGGCATACCTGACTA   5831
AGGAAATTGATGTAGTGGCAAAGGGTTGACCTCATTGTTTACGGGTAGTGGTGGCAGTAGCAGTCTTAGTAT   5903
CTGAAGCAGTTAAAATAATACAGGGAAGAGATCTTACTGTGTGGACATCTCATGATGTGAATGGCATACTCA   5975
CTGCTAAAGGAGACTTGTGGCTGTCAGACAACTGTTTACTTAAATGTCAGGCCTCTATTACTTGAAGGGCCAG   6047
TGCTGCGACTGTGCACTTGTGCAACTCTTAACCCAGCCACATTTCTTCCAGACAATGAAGAAAAGATAAAAC   6119
ATAACTGTCAACAAGTAATTTCTCAAACCTATGCCACTCGAGGGGACCTTTTAGAGGTTCCTTTGACTGATC   6191
CCGACCTCAACTTGTATACTGATGGAAGTTCCTTTGTAGAAAAAGGACTTCGAAAAGTGGGGTATGCAGTGG   6263
TCAGTGATAATGGAATACTTGAAAGTAATCCCCTCACTCCAGACAACTAGTGCTCAGCTAGCAGAACTAATAG   6335
CCCTCACTTGGGCACTAGAATTAGGAGAAGAAAAAAGGGCAAATATATATACAGACTCTAAATATGCTTACC   6407
TAGTCCTCCATGCCCATGCAGCAATATGGAAAGAAAGGGAATTCCTAACTTCTGAGAGAACACCTATCAAAC   6479
ATCAGGAAGCCATTAGGAAATTATTATTGGCTGTACAGAAACCTAAAGAGGTGGCAGTCTTACACTGCCGGG   6551
GTCATCAGAAAGGAAAGGAAAGGGAAATAGAAGAGAACTGCCAAGCAGATATTGAAGCCAAAAGAGCTGCAA   6623
GGCAGGACCCTCCATTAGAAATGCTTATAAAACAACCCCTAGTATAGGGTAATCCCCTCCGGGAAACCAAGC   6695
CCCAGTACTCAGCAGGAGAAACAGAATGGGGAACCTCACGAGGACAGTTTTCTCCCCTCGGGACGGCTAGCC   6767
ACTGAAGAAGGGAAAATACTTTTGCCTGCAACTATCCAATGGAAATTACTTAAAACCCTTCATCAAACCTTT   6839
CACTTAGGCATCGATAGCACCCATCAGATGGCCAAATCATTATTTACTGGACCAGGCCTTTTCAAAACTATC   6911
AAGCAGATAGTCAGGGCCTGTGAAGTGTGCCAGAGAAATAATCCCCTGCCTTATCGCCAAGCTCCTTCAGGA   6983
GAACAAAGAACAGGCCATTACCCTGGAGAAGACTGGCAACTGATTTTACCCACAAGCCCAAACCTCAGGGAT   7055
TTCAGTATCTACTAGTCTGGGTAGATACTTTCACGGGTTGGGCAGAGGCCTTCCCCTGTAGGACAGAAAAGG   7127
CCCAAGAGGTAATAAAGGCACTAGTTCATGAAATAATTCCCAGATTCGGACTTCCCCGAGGCTTACAGAGTG   7199
ACAATAGCCCTGCTTTCCAGGCCACAGTAACCCAGGGAGTATCCCAGGCGTTAGGTATACGATATCACTTAC   7271
ACTGCGCCTGAAAGGCCACAGTCCTCAGGGAAGGTCAGAAAAATGAATGAAACACTCAAAGGACATCTAAAAA   7343
AGCAAACCCAGGAAACCCACCTCACATGGCCTGCTCTGTTGCCTATAGCCTTAAAAAGAATCTGCAACTTTC   7415
CCCAAAAAGCAGGACTTAGCCCATACGAAATGCTGTATGGAAGGCCCTTCATAACCAATGACCTTGTGCTTG   7487
ACCCAAGACAGCCAACTTAGTTGCAGACATCACCTCCTTAGCCAAATATCAACAAGTTCTTAAAACATTACA   7559
AGGAACCTATCCCTGAGAAGAGGGAAAAGAACTATTCCACCCTTGTGACATGGTATTAGTCAAGTCCCTTCC   7631
CTCTAATTCCCCATCCCTAGATACATCCTGGGAAGGACCCTACCCAGTCATTTTATCTACCCCAACTGCGGT   7703
TAAAGTGGCCTGGAGTGGAGTCTTGGATACATCACACTTGAGTCAAATCCTGGATACTGCCAAAGGAACCTGA   7775
AAATCCAGGAGACAACGCTAGCTATTCCTGTGAACCTCTAGAGGATTTGCGCCTGCTCTTCAAACAACAACC   7847
AGGAGGAAAGTAACTAAAATCATAAATCCCCATGGCCCTCCCTTATCATATTTTTCTCTTTACTGTTCTTTT   7919
ACCCTCTTTCACTCTCACTGCACCCCCTCCATGCCGCTGTGATGACCAGTAGCTCCCCTTACCAAGAGTTTCT   7991
ATGGAGAATGCAGCGTCCCGGAAATATTGATGCCCATCGTATAGGAGTCTTTCTAAGGGAACCCCCACCTT   8063
CACTGCCCACACCCTATATGCCCCGCAACTGCTATCACTCTGCCACTCTTTGCATGCATGCAAATACTCATTA   8135
TTGGACAGGAAAAATGATTAATCCTAGTTGTCCTGGAGGACTTGGAGTCACTGTCTGTTGGACTTACTTCAC   8207
CCAAACTGGTATGTCTGATGGGGGTGGAGTTCAAGATCAGGCAAGAGAAAAACATGTAAAAGAAGTAATCTC   8279
CCAACTCACCCGGGTACATGGCACCTCTAGCCCCCTACAAAGGACTAGATCTCTCAAAACTACATGAAACCCT   8351
CCGTACCCATACTCGCCTGGTAAGCCTATTTAATACCACCCTCACTGGGCTCCATGAGGTCTCGGCCCAAAA   8423
CCCTACTAACTGTTGGATATGCCTCCCCCTGAACTTCAGGCCATATGTTTCAATCCCTGTACCTGAACAATG   8495
GAACAACTTCAGCACAGAAATAAACACCACTTCCGTTTTAGTAGGACCTCTTGTTTCCAATCTGGAAATAAC   8567
CCATACCTCAAACCTCACCTGTGTAAAATTTAGCAATACTACATACAACCAACTCCCAATGCATCAGGTG   8639
GGTAACTCCTCCCACACAAATAGTCTGCCTACCCTCAGGAATATTTTTGTCTGTGGTACCTCAGCCTATCG   8711
TTGTTTGAATGGCTCTTCAGAATCTATGTGCTTCCTCTCATTCTTAGTGCCCCTATGACCATCTACACTGA   8783
ACAAGATTTATACAGTTATGTCATATCTAACCCCGCAACAAAAGAGTACCCATTCTTCCTTTTGTTATAGG   8855
AGCAGGAGTGCTAGGTGCACTAGGTACTGGCATTGGCGGTATCACAACCTCTACTCAGTTCTACTACAAACT   8927
ATCTCAAGAACTAAATGGGGACATGGAACGGGTCGCCGACTCCCTGGTCACCTTGCAAGATCAACTTAACTC   8999
CCTAGCAGCAGTAGTCCTTCAAAATCGAAGAGCTTTAGACTTGCTAACCGCTGAAAGAGGGGGAACCTGTTT   9071
ATTTTTAGGGGAAGAATGCTGTTATTATGTTAATCAATCCGGAATCGTCACTGAGAAAGTTAAAGAAATTCG   9143
AGATCGAATACAACGTAGAGCAGAGGAGCTTCGAAACACTGGACCCTGGGGCCTCCTCAGCCAATGGATGCC   9215
CTGGATTCTCCCCTTCTTAGGACCTCTAGCAGCTATAATATTGCTACTCCTCTTTGGACCCTGTATCTTTAA   9287
CCTCCTTGTTAACTTTGTCTTCCAGAATGGAAGCTGTAAAACTCAAAATGGAGCCCAAGATGCAGTCCAA   9359
GACTAAGATCTACCGCAGACCCCTGGACCGGCCTGCTAGCCCACGATCTGATGTTAATGACATCAAAGGCAC   9431
CCCTCCTGAGGAAATCTCAGCTGCACAACCTCTACTACGCCCCAATTCAGCAGGAAGCAGTTAGAGCGGTC   9503
TCGGCCAACCTCCCCAACAGCACTTAGGTTTTCCTGTTGAGATGGGGGACTGAGAGACAGGACTAGCTGGAT   9575
TTCCTAGGCTGACTAAGAATCCCTAAGCCTAGCTGGGAAGGTGACCACATCCACCTTTAAACACGGGGCTTG   9647
CAACTTAGCTCACACCTGACCAATCAGAGAGCTCACTAAAATGCTAATTAGGCAAGACAGGAGGTAAAGAA   9719
ATAGCCAATCATCTATTGCCTGAGAGCACAGCAGGAGGACAATGATCGGGATATAAACCCAAGTCTTCGAG   9791
CCGGCAACGGCAACCCCCTTTGGGTCCCCTCCCTTTGTATGGGAGCTCTGTTTTCATGCTATTTCACTCTAT   9863
TAAATCTTGCAACTGCACTCTTCTGGTCCATGTTTCTTACGGCTTGAGCTGAGCTTTCGCTCGCCATCCACC   9935
ACTGCTGTTTGCCGCCACCGCAGACCCGCCGCTGACTCCCATCCCTCTGGATCATGCAGGGTGTCCGCTGTG   10007
CTCCTGATCCAGCGAGGCACCCATTGCCGCTCCCAATCGGGCTGAAGGCTCCATTGTTCCTGCATGGCTA   10079
AGTGCCTGGGTTCATCCTAATTGAGCTGAACACTAGTCACTGGGTTCCATGGTTCTCTTCTGTGACCCACAG   10151
CTTCTAATAGAGCTATAACACTCACCGCATGGCCCAAGGTTCCATTCCTTGAATCCATAAGGCCAAGAACCC   10223
CAGGTCAGAGAACACGAGGCTTGCCACCATCTTGGGAGCTCTGTGAGCAAGGACCCCCAAGTAACACAACCA   10295
TGAGGGTGCAAATGCATGGGCCACTAATGGTAGAGCAAGAAAACAGAAGGGCCCTGGTTCCTCGAAGGCATC   10367
AGTGAGCTGAAATGCCTGCCCTGGATGTCCTATTCCTAGGTGTTTTTCTGCCTGAAGCAGATTAAACCCTTT   10439
GTTCACTTCTCCAAGTAGGGCTTCTATTACAGCCCAAATCAATCCCCACCCCAGATGACAT              10500
```

Env domain

Repeated region R1

*FIG. 1B*

```
ACTGAGAGACAGGACTAGCTGGATTTCCTAGGCCGACTAAGAATCCCTAAGCCTAGCTGGGAAGGTGACC
::::::::::::::::::::::::::::::::::::::  ::::::::::::::::::::::::::::::
ACTGAGAGACAGGACTAGCTGGATTTCCTAGGCTGACTAAGAATCCCTAAGCCTAGCTGGGAAGGTGACC
ACGTCCACCTTTAAACACGGGGCTTGCAACTTAGCTCACACCTGACCAATCAGAGAGCTCACTAAAATGC
::  ::::::::::::::::::::::::::::::::::::::::::::::::::::::::::::::::::
ACATCCACCTTTAAACACGGGGCTTGCAACTTAGCTCACACCTGACCAATCAGAGAGCTCACTAAAATGC
TAATTAGGCAAAGACAGGAGGTAAAGAAATAGCCAATCATCTATTGCCTGAGAGCACAGCAGGAGGGACA
::::::::::::::::::::::::::::::::::::::::::::::::::::::::::::::::::::::
TAATTAGGCAAAGACAGGAGGTAAAGAAATAGCCAATCATCTATTGCCTGAGAGCACAGCAGGAGGGACA
ACAATCGGGATATAAACCCAGGCATTCGAGCTGGCAACAGCAGCCCCCCTTTGGGTCCCTTCCCTTTGTA
:  ::::::::::::::::  :  :::::::  ::::::  :::  :::::  :::::::::: ::::::::::
ATGATCGGGATATAAACCCAAGTCTTCGAGCCGGCAACGGCAACCCCC-TTTGGGTCCCCTCCCTTTGTA
TGGGAGCT--GTTTTCATGCTATTTCACTCTATTAAATCTTGCAACTGCACTCTTCTGGTCCATGTTTCT
:::::::::  ::::::::::::::::::::::::::::::::::::::::::::::::::::::::::::
TGGGAGCTCTGTTTTCATGCTATTTCACTCTATTAAATCTTGCAACTGCACTCTTCTGGTCCATGTTTCT
TACGGCTCGAGCTGAGCTTTTGCTCACCGTCCACCACTGCTGTTTGCCACCACCGCAGACCTGCCGCTGA
::::::  ::::::::::::::  ::::  ::::::::::::::::::::::  :::::::::  ::::::
TACGGCTTGAGCTGAGCTTTCGCTCGCCATCCACCACTGCTGTTTGCCGCCACCGCAGACCCGCCGCTGA
CTCCCATCCCTCTGGATCCTGCAGGGTGTCCGCTGTGCTCCTGATCCAGCGAGGCGCCCATTGCCGCTCC
::::::::::::::::::  ::::::::::::::::::::::::::::::::::::  ::::::::::::
CTCCCATCCCTCTGGATCATGCAGGGTGTCCGCTGTGCTCCTGATCCAGCGAGGCACCCATTGCCGCTCC
CAATTGGGCTAAAGGCTTGCCATTGTTCCTGCACGGCTAAGTGCCTGGGTTTGTTCTAATTGAGCTGAAC
::::  ::::::::::::::::::::::::::::  ::::::::::::::::  :  ::::::::::::::
CAATCGGGCTAAAGGCTTGCCATTGTTCCTGCATGGCTAAGTGCCTGGGTTCATCCTAATTGAGCTGAAC
ACTAGTCACTGGGTTCCATGGTTCTCTTCTGTGACCCACGGCTTCTAATAGAACTATAACACTTACCACA
::::::::::::::::::::::::::::::::::::::::  :::::::::::  ::::::::::  :::
ACTAGTCACTGGGTTCCATGGTTCTCTTCTGTGACCCACAGCTTCTAATAGAGCTATAACACTCACCGCA
TGGCCCAAGATTCCATTCCTTGGAATCCGTGAGGCCAAGAACTCCAGGTCAGAGAATACGAGGCTTGCCA
::::::::  ::::::::::::  ::::  :  :::::::::  ::::::::::::::::  ::::::::::
TGGCCCAAGGTTCCATTCCTTG-AATCCATAAGGCCAAGAACCCCAGGTCAGAGAACACGAGGCTTGCCA
CCATCTTGGAAGC
:::::::::  :::
CCATCTTGGGAGC
```

*FIG. 3*

IPMALPYHIFLFTVLLPSFTLTAPPPCRCMTSSSPYQEFLWRMQRPGNIDAPSYRSLSKG
TPTFTAHTHMPRNCYHSATLCMHANTHYWTGKMINPSCPGGLGVTVCWTYFTQTGMSDGG
GVQDQAREKHVKEVISQLTRVHGTSSPYKGLDLSKLHETLRTHTRLVSLFNTTLTGLHEV
SAQNPTNCWICLPLNFRPYVSIPVPEQWNNFSTEINTTSVLVGPLVSNLEITHTSNLTCV
KFSNTTYTTNSQCIRWVTFPTQIVCLPSGIFFVCGTSAYRCLNGSSESMCFLS<u>FLVPPMT
IYTEQDLYSYVISKPRNKRVPILPFVIGAGVLGALGTGIGGITTSTQFYYKLSQELNGDM
ERVADSLVTLQDQLNSLAAVVLQNRRALDLLTAERGGTCLFLGEECCYYVNQSGIVTEKVKE</u>IRDRIQRRAEELR
NTGPWGLLSQWMPWILPFLGPLAAIILLLLFGPCIFNLLVNFVSSRIEAVKLQMEPKMQSKTKIYRRPLDRPASP
<u>RSDV</u>NDIKGTPPEEISAAQPLLRPNSAGSS

FIG. 4

1) NSLAAVVLQNRRALDLLTAESGGTFLFLEEKC
2) NSLAAVVLQNRRALDLLTAERGGTCLFLGEEC
3) DSLAAVTLQNHQGLDLLTAEKGGLCYFLGEDC
4) DSLAAVTLQNHQGLDLLIAEKGGLCTFLGEEC
5) DSLAAVTLQNCRGLDLLTAEKGGHYTFLGEEC
6)           <u>LQNRRGLDLLFLKEGGLC</u>
7) DSLAKVVLQNRRGLDLLTAEQGGICLALQEKC

FIG. 5

TSFVEKANGVKCHKYKLSFHXETTHNYVKSVIYALQEAFRVYLPILPASPTPSPTNKDPPSTQMVQKEIDKRVNSEPKS
ANIPQLXPLQAVGGREFGPARVHVPFSLPDLKQIKTDLGKFSDNPDGYIDVLQGLGQFFDLTWRDIMSLLNQTLTPNER
SATITAAXEFGDLWYLSQVNDRMTTEEREXFPTGQQAVPSLDPHWDTESEHGDWCCRHLLTCVLEGLRKTRKKSMNYSM
MSTITQGREENPTAFLERLREALRKRASLSPDSSEGQLILKRKFITQSAADIRKKLQKSAVGPEQNLETLLNLATSVFY
NRDQEEQAEQDKRDXKKGHRFSHDPQASGLWRLWKREKLGKLNAXXGLLPVRSTRTLXKRLSKXKXAAPSSMPLISRES
LEGPLPQGTKVLXVRSHXPD/<u>SSSRT</u>

FIG. 6

```
CCTGGCACTCCTGAGGGAAGTATAAATTATAACACCATCTTACAGCTAGACCTCTTTTGTAGAAAAGGCA
::::::  ::::::::::::::::::::::::::::::::::::::::::::::::::::::::: ::::
CCTGGC-CTCCTGAGGGAAGTATAAATTATAACACCATCTTACAGCTAGACCTCTTTTGTAGAAAAGAAG
-CAAATGGAGTGAAGTGCCATAAGTACAAACTTTCTTTTCATTAAGAGACAACTCACAATTATGTAAAAA
 ::::::::::::::::::: :::::::::::::::::::::::::::: ::::: ::::::::::::::
GCAAATGGAGTGAAGTGCCATATGTACAAACTTTCTTTTCATTAAGAGATAACTCCCAATTATGTAAAAA
GTGTGATTTATGCCCTACAGGAAGCCTTCAGAGTCTACCTCCCTATCCCAGCAT--CCCCGACTCCTTCC
:::::::::::::::::::::::::::: :::::::::::::::::: :::::::   :::::::::::
GTGTGATTTATGCCCTACAGGAAGCCCTCAGAGTCTACCTCCCGACCCCAGCAAGACCCCAACTCCTTCT
CCAACTAATAAGGACCCCCCTTCAACCCAAATGGTCCAAAAGGAGATAGACAAAAGGGTAAACAGTGAAC
::::::::::::::::::::::::::::::::::::::::::::::::::::::::::::::::  ::::
CCAACTAATAAGGACCCCCCTTCAACCCAAATGGTCCAAAAGGAGATAGACAAAGGGGTAAACAATGAAC
CAAAGAGTGCCAATATTCCCCAATTATGACCC-CTCCAAGCAGTGGGAGGAAGAGAATTCGGCCCAGCCA
:::::::::::::::: : : ::::::  ::  : ::::::::::::::::::: :: ::::  ::::::
CAAAGAGTGCCAATATTACACGATTAT-ACTCGCTCCAAGCAGTGGGAGGA-GA-ATTT-GGCCCAGCCA
GAGTGCATGTGCCTTTTTCTCTCCCAGACTTAAAGCAAATAAAAACAGACTTAGGTAAATTCTCAGATAA
 : ::::::::  :::::::::::: ::::: :::: :::: ::: ::::::::::::::::::::::::
GCGTGCATGTACCTTTTTCTCTCTCAGATTTAAAGCAAATTAAAATAGACCTAGGTAAATTCTCAGATAA
CCCTGATGGCTATATTGATGTTTTACAAGGGTTAGGACAATTCTTTGATCTGACATGGAGAGATATAATG
::::::::::::::::::::::::::::::::::::::::: :::::::::::::::::::::::::::
CCCTGATGGCTATATTGATGTTTTACAAGGGTTAGGACAATCCTTTGATCTGACATGGAGAGATATAATG
TCACTGCTAAATCAGACACTAACCCCAAATGAGAGAAGTGCCACCATAACTGCAGCCTGAGAGTTTGGCG
: :::::::::::::::::::::::::::  :::::: ::::::: :::::::::::::::::::::::
TTACTGCTAAATCAGACACTAACCCCAAATGAAAAAAGTGCTGCCATAACAGCAGCCTGAGAGTTTGGCG
ATCTCTGGTATCTCAGTCAGGTCAATGATAGGATGACAACAGAGGAAAGAGAATGATTCCCCACAGGCCA
 : ::::::::::::::::::::::::::::::::::::::::::: ::::::::::::::::::::::
AACTCTGGTATCTCAGTCAGGTCAATGATAGGATGACAACAGATGAAAGAGAATGATTCCCCACAGGCCA
GCAGGCAGTTCCCAGTCTAGACCCTCATTGGGACACAGAATCAGAACATGGAGATTGGTGCTGCAGACAT
:::::::::::::::: ::::::::::::: ::::::::::::::: ::::::::::: ::::::::::
GCAGGCAGTTCCCAGTGTAGACCCTCATTAGGACACAGAATCAGAACTTGGAGATTGGTGCCACAGACAT
TTGCTAACTTGTGTGCTAGAAGGACTAAGGAAAACTAGGAAGAAGTCTATGAATTACTCAATGATGTCCA
:::::::::: :::::::::::::::::::::::::::::::::::   : :::::::::::::::::
TTGCTAACTTGCGTGCTAGAAGGACTAAGGAAAACTAGGAAGAAGCCCATGAATTATTCAATGATGTCCC
CCATAACACAGGGAAGGGAAGAAAATCCTACTGCCTTTCTGGAGAGACTAAGGGAGGCATTGAGGAAGCG
: :::::::::::::  :::::::::::::::::::::::::::::::::::::::  ::::::::::
CTATAACACAGGGAAAGGAAGAAAATCCTACTGCCTTTCTGGAGAGACTAAGGGAAGGATTGAGGAAGCA
TGCCTCTCTGTCACCTGACTCTTCTGAAGGCCAACTAATCTTAAAGCGTAAGTTTATCACTCAGTCAGCT
: :::: :::::::::::::: :::::: ::::::::::::::: ::::::::::::::::::::::::
TACCTCCCTGTCACCTGACTCTATTAAAGGCCAACTAATCTTAAAGGATAAGTTTATCACTCAGTCAGCT
GCAGACATTAGAAAAAAACTTCAAAAGTCTGCCGTAGGCCCGGAGCAAAACTTAGAAACCCTATTGAACT
:::::  ::::: ::::::::::::::: :: :::::::::::::::::::::::::::::::: :::::
GCAGAGATTAAGAAAAAACTTCAAAAGTATGCCTTAGGCCCAGAGCAAAACTTAGAAACCCTACTGAACT
TGGCAACCTCGGTTTTTTATAATAGAGATCAGGAGGAGCAGGCGGAACAGGACAAACGGGATTAAAAAAA
::::::::::  :::::::::::::::::::::::  ::::: :::::::  ::::::::: ::::::::
TGGCAACCTCAGTTTTTTATAATAGAGATCAGGAAGAGCAGG-GGAATGGGACAAATGGGATAAAAAAAA
A-------GGCCACCGCTTTAGTCATGACCCTCAGGCAAGTGGACTTTGGAGGCTCTGGAAAAGGGAAAA
         ::   ::   :::::::::: :: :::::::::::::: :::::::::::::::::::::
AAAAAAAAGGTGACTGCTTTAGTCGTGGCCCTCAGGCAAATGGACTTTGGAGGCTCCAGAAAAGGGAAAA
GCTGGGCAAATTGAATGCCTAATAGGGCTTGCTTCCAGTGCGGTCTACAAGGACACTTTAAAAAAGATTG
 ::::  :::::::::::::::  ::::::::: :::::: :::::::::::::::::::::::::::::
GCTGAGCAAATTGAATGCCTAACAGGGCTTGCTTCTAGTGTGGTCTACAAGGACACTTTAAAAAAGATTG
TCCAAGTAGAAGTAAGCCGGCCCCCTCGTCCATGCCCCTTATTTCAAGGGAATCACTGGAAGGCCCACTGC
:::::::::  : :::::::::::::::::::::::::::  :::::::::::::::::::::::::::
TCCAAGTAGAAACAAGCTGCCCCCCTTGTCCATGCCCCTTATGTCAAGGGAATCACTGGAAGGCCCACTGC
CCCAGGGGACAAAGGTCCTCTGAGTCAGAAGCCACTAACCAGATGATCCAGCAGCAGGACTGAGGGTGCC
::::::  ::   ::::::::::::::::::::::::::: :::: :::::::::::::::::: ::::
CCCAGGAGATGAAGGTCCTCTGAGTCAGAAGCCACTAACCAGATAATCCAGCAGCAGGACTGAGGATGCC
TGGGGCAAGCGCCATCCCATGCCATCACCCTCACAGAGCCCTGGGTATGCTTGACCATTGAGGGCCAGGA
 :::::::::::: ::::::::::::::::::::::::::: ::::::::::::::::::::::::::::
CAGGGCAAGCGCCAGCCCATGCCATCACCCTCACAGAGCCTTGGGTATGCTTGACCATTGAGGGCCAGGA
GGTT----GTCCTGGACACTGGTGCGGTCTTCTTAGTCTTACTCTTCTGTCCCGGACAACTGTCCTCC
::::    ::::: ::::: :::::: :::::: ::  :::::: :::::: :::::::::::::::
GGTTCACTGTCTCTTGGACACTGGTATGGCCTTCTCAGTCTTACTCTCCTGTCCTGGACAACTGTCCTTC
```

*FIG.7*

```
01/                         TAAATCCCCATGGCCCTCCCTTATCATATTTTCT
02/                         TAAATCCCC-TGGCCCTCCCTTATCATATTTTCT
03/                         TAAATCCCCATGGCCCTCCCTTATCATATTTTCT
04/                         TAGATCCTCATGGCCCTCC-TTGTCATATTTTTT

01/CTTTACTGTTCTTTTA-CCCTCTTTCACTCTCACTGCACCCCCTCCATGCCGCTGTATGACC
02/CTTTACTGTTCTCTTACCCCCCTTTCACTCTCACTGCACCCCGTCCATGCCACTGCACCCCC
03/CTTTACTGTTCTCTTA-CCCCCTTTCTCTCTCACTGCACCCCCTCCATGCTGCTGTACAACC
04/CTTTACTGTTCTCTTA-CCCCCTTTCACTCTCACTGAACCCCCTCCATGCCACTGTACTACC

01/AGT------------------AGCTCCCCTTACCAAGAGTTTCTATGGAGAATGCAGCGT
02/GTCCATGCCCGTCTCATGCCAGTAGCTCCCCTTAGCAAGAGTTTCTATGGAGAATGCAGCGT
03/AGC------------------AGCTCCCCTTACCAAGAGTTTCTATGAAGAATGCGGCTT
04/AGT------------------AGCTCCCATTACCAAGAGCTTCTATGGACAATGCGGCTT

01/CCCGGAAATATTGATGCCCCATCGTATAGGAGTCTTTCTAAGGGAACCCCCACCTTCACTGC
02/CCCGGAAATATTGATGCCCCATTGTATAGGAGTTTATCTAAGGGAACCCCCACCTTCACTGC
03/CCCAGAAATATTGATGCCCCATCAAATAGGAGTTTACCTAAAGGAAACTCCACCTTCACTGC
04/CCTGGAAATATTGATGACCCATCGTATAGGAGTTTTTCTAAAGGAAACCCCATTTTCACCAC

01/CCACACCCATATGCCCCGCAACTGCTATCACTCTGCCACTCTTTGCATGCATGCAAATACTC
02/CCACACCCATATGCCCCACAACTGCTATAACTCTGCCACTCTTTGCATGCATGCAAATACTC
03/CCACACCCATATGCCCCACAACTGCTATAACTCTGCCACTCTTTGCATGCATGCAAATACTC
04/CCACACCTATATGACCC-------------------------------------------

01/ATTATTGGACAGGAAAATGATTAATCCTAGTTGTCCTGGAGGACTTGGAGTCACTGTCTGT
02/ATTATTGGACAGGAAAAACGATTAATCCCAGTTGTCCTGGAGGACTTGGAG-----------
03/ATTATTGGACAGGGAAAATGATTAATCCTAGTTGTCCTGGAAGACTTGGAGCCACTGTCTGT
04/-------------------------------------------------------------

01/TGGACTTACTTCACCCAAACTGGTATGTCTGATGGGGGTGGAGTTCAAGATCAGGCAAGAGA
02/--GACTCACTTCACTCATACCAGTATGTCTGATGGGGGTGGAGTTCAAGATCAGGCAACAGA
03/CGGACTTACTTCACCCATACTGGTATGTCTGAGGGGGGTGGAGTTCAAGATCAGGCAAGAGA
04/-------------------------------------------------------------

01/AAAACATGTAAAGAAGTAATCTCCCAACTCACCCGGGTACATGGCACCTCTAGCCCCTACA
02/AAAACACATAAAGGAAGTAATCTCCCAACTGACCTGGGTACATAGCACCCCTGGCCCCTACA
03/AAAACATGTAAAGGAAGTAACCTCCCAACTGACCCGGGTACATAGCACCCCTAGCCCCTACA
04/-------------------------------------------------------------

01/AAGGACTAGATCTCTCAAAACTACATGAAACCCTCCGTACCCATACTCGCCTGGTAAGCCTA
02/AAGGACTAGATCTCTCAAAACTACATGAAACCCTCCATACCCATACTGGCCTGGTAAGCCTA
03/AAGGACTAGATCTCTTAAAACTACATGAAACCCTCCATACCCATACTTGCCTGGTAAGCCTA
04/-------------------------------------------------------------

01/TTTAATACCACCCTCACTGGGCTCCATGAGGTCTCGGCCCAAAACCCTACTAACTGTTGGAT
02/TTTAATACCACCCTGACTGGGCTCCATGAGGTCTCGGCCCAAAACCCTACTAACTGTTGGAT
03/TTTAATACCACCCTCACTGGGCTCCATGAGGTCTCGGTCCAAAACCCTACTAACTGTTGGTT
04/-------------------------------------------------------------

01/ATGCCTCCCCCTGAACTTCAGGCCATATGTTTCAATCCCTGTACCTGAACAATGGAACAACT
02/GTGCCTCCCCCTGCACTTTAGGCCATACATTTCAATCCCTATACCTGAACAATGGAACAACT
03/GTGCCTCCCCCTGTATTTCAGGCCATGCATTTCAATCCCTGTACCTGAACAATGGAACAACT
04/----------TGCACTTCAGGCCATACATTTCAATCCCTGTA-------------------
```

FIG. 8A

```
01/TCAGCACAGAAATAAACACCACTTCCGTTTTAGTAGGACCTCTTGTTTCCAATCTGGAAATA
02/TCAGCACAGAAATAAACACCACTTCTGTTTTAGTAGGTCCTC---TTTCCAATCTGGAAATA
03/ACAGCACAGAAATAAACACCACTTCCGTTTTAGTAGGACCTCTTGTTTCCAATCTGGAAATA
------------------------------------------------------------

01/ACCCATACCTCAAACCTCACCTGTGTAAAATTTAGCAATACTACATACACAACCAACTCCCA
02/ACCCATACCTCAAACCTCACCTGTGTAAAATTTAGCAATACTATAGACACAGCCAACTCCCA
03/ACCCATACCTCAAACCTCACCTGTGTAAAATTTAGCAATACTGTAGACACAACCAACTCCCA
04/------------------------------------------------------------

01/ATGCATCAGGTGGGTAACTCCTCCCACACAAATAGTCTGCCTACCCTCAGGAATATTTTTTG
02/ATGCATCAGGTGGGTAACTCCTCCCACACGAATAGTCTGCCTACCCTCAGGAATATTTTTTG
03/ATGCATCAGGTGGGTAACTCCTCCCACACGAATAGTCTGCCTACCCTCAGGAATATTTTTTG
04/------------------------------------------------------------

01/TCTGTGGTACCTCAGCCTATCGTTGTTTGAATGGCTCTTCAGAATCTATGTGCTTCCTCTCA
02/TCTGTGGTACCTCAGCCTATCATTGTTTGAATGGCTCTTCAGAATCTGTGTGCTTCCTCTCA
03/TCTGTGGTACCTTAGCCTATCGTTGTTTGAATGGCTCTTCAGAATCTATGTGCTTCCTCTCA
04/------------------------------------------------------------

01/TTCTTAGTGCCCCCTATGACCATCTACACTGAACAAGATTTATACAGTTATGTCATATCTAA
02/TTCTTAGTGGCCCCTATGCCCATCTACACTGAACAAGATTTATACAATCATGTCATACCTAA
03/TTCTTAGTGCCCCC-ATGACCATTTACACTGAACAAGATTTATACAATTATGTTGTACCTAA
04/------------------------------------------------------------

01/GCCCCGCAACAAAAGAGTACCCATTCTTCCTTTTGTTATAGGAGCAGGAGTGCTAGGTGCAC
02/GCCCCGCAACAAAAGAGTACCCATTCTTCCTTTTGTTATTGGAGCAGGAGTGCTAGGCGGAG
03/GCCCCACAACAAAAGAGTACTCATTCTTCCTTTTGTTATCGGAGCAGGAGTGCTAGGTGGAC
04/------------------------------------------------------------

01/TAGGTACTGGCATTGGCGGTATCACAACCTCTACTCAGTTCTACTACAAACTATCTCAAGAA
02/TAGCTACTGGCATTGGCGGTATCACAACCTCTACTCAGTTCTACTACAAACTGTCTCAAGAA
03/TAGGTTCTGGCATTGGCGGTACCACAACCTCTACTCAGTTCTACTACAAACTATCTCAAGAA
04/------------------------------------------------------------

01/CTAAATGGGACATGGAACGGGTCGCCGACTCCCTGGTCACCTTGCAAGATCAACTTAACTC
02/CTTAAAGGTGACATGGAATGGGTCGCTGATACCCTGGTCACCTTGCAAGATCAACTTAACTC
03/CTCAATGGTGACATGGAATGGGTTGCCGACTCCCTGGTCACCTTGCAAGATCAACTTAACTT
04/------------------------------------------------------------

01/CCTAGCAGCAGTAGTCCTTCAAAATCGAAGAGCTTTAGACTTGCTAACCGCTGAAAGAGGGG
02/CCTAGCAGCAGTAGTCCTTCAAAATCGAAGAGCTTTAGACTTGCTAACCGCGGAAAGCGGGG
03/CCTAGCATCAGTAGTCCTTCAAAATTGAAGAGCTTTAGACTTGCTAACCTCTGAAAGAGGGG
04/------------------------------------------------------------

01/GAACCTGTTTATTTTTAGGGGAAGAATGCTGTTATTATGTT-------------------
02/GAACCTTTTTATTTTTAGAGGAAAAATGCTGTTGTTATGTT-------------------
03/GAAGCTGTTTATTTTTAGGGGAAGAATGTTGTTATTATGTTATTTTAGCGGAAGAATGTTGT
04/------------------------------------------------------------

01/---------AATCAATCCGGAATCGTCACTGAGAAAGTTAAAGAAATTCGAGATCGAATACA
02/---------AATCAATCCGGAATCATCACCGAGAAAGTTAAAGAAATTCAAGGTCGAATATA
03/TATTATGTTAATCAATCCTGAATTGTCACAGAGAAAGTTGAAGAAATTCGAGATTGAATACA
04/------------------------------------------------------------

01/ACGTAGAGCAGAGGAGCTTCGAAA-CACTGGACCCTGGGGCCTCCTCAGCCAATGGATGCCCT
02/ACGTAGAGCAAAGGAGCTGCAAAA-CACTGGACCCTGGGGCCTCCTCAGCCAATGGATGCCCT
03/ACGTAGAACAGAGGAGCTTCAAAAACACCAGACCCTGGGGCCTCCTCAGCCAATGGATGCCCT
04/------------------------------------------------------------
```

*FIG. 8B*

```
01/GGATTCTCCCCTTCTTAGGACCTCTAGCAGCTATAATATTGCTACTCCTCTTTGGACCCTGTA
02/GGATTCTCCCCTTCTTAGGACCTCTAGCAGCTATAATATTGTTACTCCTCTTTGGACCCTGTA
03/GGATTCTCCCCTTCTTAGGATCTCTAGCAGCTCTAATATTGATACTCCTCTTTGGACCCTGTA
04/----------------------------------------------------------------

01/TCTTTAACCTCCTTGTTAACTTTGTCTCTTCCAGAATCGAAGCTGTAAAACTA----------
02/TCTTTAACCTCCTTGTTAAGTTTGTCTTTTCCAGAATCGAAGCAGTAAAACTACAAATCGTTC
03/TCTTTAACCTCCTTGTTAAGTTTGTCTCTTCCAGAATCAAAGTTGTAAAGCTACAAATCGTTC
04/TCTTTAACCTCCTTGTTAAGCTTGTCTCTTGCAGAATCGAAGCTGTAAAACTACAAATGCTTG

01/--CAAATGGAGCCCAAGATGCAGTCCAAGACTAAGATCTACCGCAGACCCCTGGACCGGCCTG
02/TTCAAATGGAGCCCCAGATGCAGTCCATGAGTAAAATCTACCACGGACCCCTGGACCGGCCTG
03/TTCAAATGGAACCCCAGATGAAGTCCATGACTAAGATCTACCGTGGACCCCTGGACCGGCCTA
04/TTAAAATAGAGCCCCAGATGCAGTCCATGGCTAAGATCTACCACGGACCCCTGGACCGGCCTG

01/CTAGCCCACGATCTGATGTTAATGACATCAAAGGCACCCCTCCTGAGGAAATCTCAGCTGCAC
02/CTAGCCCATGCTCTGATGTTAATGACATCAAAGGCACCCCTCCCGAGGAAATCTCAACTGCAC
03/CTAGCCCATGCTCCAATTGTAATGATATCGAACGCACCCCTCCCGAGGAAATCTCAACTGCAC
04/CTAGCCCATGCTCTGATGTTGATGACATTGAAGGCACGGCTTCCGAGGAAATCTCAACTGCAC

01/AACCTCTACTACGCCCCAATTCAGCAGGAAGCAGTTAGAGCGGTCGTCGGCCAACCTCCCC
02/AACCTCTACTACGCCCCAATTCAGCAGGAAGCAGTTAGAGTGGTTGTTGGCCAACCTCCCC
03/AACCCCTACTATGCCCCAATTCCGCAGGAAGCAGTTAGACTGGTCGTCAGCCAACCTCCCC

04/GACCCCTACTACACCCCAATTTAGCGGGAAGCAATTAGAGCAGCCTATGGCCACCTCCCC
```

FIG. 8C

```
CTTCCCCAACTAATAAGGACCCCCCTTTCAACCCAAACAGTCCAAAAGGACATAGACAAGGA      3
CTTCCCCAACTAATAAGGACCCCCCTTTCAACCCAAACAGTCCAAAAGGACATAGACAAAGGA     4
CTTCCCCAACTAATAAGGACCCCCC-TTCAACCCAAATGGTCCAAAAGGAGATAGACAAAGG      5
CTTCTCCAACTAATAAGGACCCCCC-TTCAACCCAAATGGTCCAAAAGGAGATAGACAAAGGG    6
CTTCCCCAAATAATAAGAACCCCCC-TTCAACCCAAACGGTCCAAAGGAGATAGACAAAGGG     7

GTAAACAATGAACCAAAGAGTGCCAATATTCCCTGGTTATGCACCCTCCAAGCGGTGGGAG--    3
GTAAACAATGAACCAAAGAGTGCCAATATTCCCTGGTTATGCACCCTCCAAGCGGTGGGAG--    4
GTAAACAGTGAACCAAAGAGTGCCAATATTCCCCAATTATGACCCCTCCAAGCAGTGGGAGGA    5
GTAAACAATGAACCAAAGAGTGCCAATATTACACGATTATACTCGCTCCAAGCAGTGGGAG--    6
GTAAACAACTAACCAAAGAATGCCAATATTCCCCGATTATGCCCCCTCCAAGCGGTGGGAG--    7

A-AGAATTCGGCCCAGCCAGAGTGCATGTACCTTTTCTCTCTCAC-ACTTGAAGCAAATTAAA    3
A-AGAATTCGGCCCAGCCAGAGTGCATGTACCTTTTCTCTCTCAC-ACTTGAAGCAAATTAAA    4
AGAGAATTCGGCCCAGCCAGAGTGCATGTGCCTTTTCTCTCCCAG-ACTTAAAGCAAATAAAA    5
-GAGAATTTGGCCCAGCCAGCGTGCATGTACCTTTTCTCTCTCAG-ATTTAAAGCAAATTAAA    6
-GAGAATTCGGCCCAGCCAGAGTGCACGTACCTTTTCTCTCTAGACTTTAAA----TTAAA     7

ATAGACNTAGGTNAATTNTCAGATAGCCCTGATGGYTATATTGATGTTTTACAAGGATTAGGA   3
ATAGACXTAGGTXAATTXTCAGATAGCCCTGATGGXTATATTGATGTTTTACAAGGATTAGGA   4
ACAGACTTAGGTAAATTCTCAGATAACCCTGATGGCTATATTGATGTTTTACAAGGGTTAGGA   5
ATAGACCTAGGTAAATTCTCAGATAACCCTGATGGCTATATTGATGTTTTACAAGGGTTAGGA   6
ATAGACCTAGGTAAATTCTCAGATAACCCTAATGGCTATATTGATGTTTTACAAGGTTTAGGA   7

TTCCTGAGTTCTTGCACTAACCTCAAAT               1
CAATCCTTTGATCTGACATGGAGAGATATAATATTACTGCTAAATCAGACGCTAACCTCAAAT   3
CAATCCTTTGATCTGACATGGAGAGATATAATATTACTGCTAAATCAGACGCTAACCTCAAAT   4
CAATTCTTTGATCTGACATGGAGAGATATAATGTCACTGCTAAATCAGACACTAACCCCAAAT   5
CAATCCTTTGATCTGACATGGAGAGATATAATGTTACTGCTAAATCAGACACTAACCCCAAAT   6
CAATCCTTTGATCTGATATGGAGAGATATAATGTTACTGCTAAATCAGACACTAACCCCAAAT   7

GAGAGAAGTGCCGCCATAACTGCAACCCAAGAGTTTGGCGATCCCTGGTATCTCAGTCAGGTC   1
GAGAGAAGTGCTGCCATAACTGGAGCCCGAGAGTTTGGCAATCTCTGGTATCTCAGTCAGGTC   3
GAGAGAAGTGCTGCCATAACTGGAGCCCGAGAGTTTGGCAATCTCTGGTATCTCAGTCAGGTC   4
GAGAGAAGTGCCACCATAACTGCAGCCTGAGAGTTTGGCGATCTCTGGTATCTCAGTCAGGTC   5
GAAAAAGTGCTGCCATAACAGCAGCCTGAGAGTTTGGCGAACTCTGGTATCTCAGTCAGGTC    6
GACAGAAGTGTCGCCGTAACTGGAGCCCGAGAGTTTGGCAATCTCTGGTATCTCAGTCAGGTC   7

AATGACAGGATGACAACAGAGGAAAGATAATGATTCCCCACAGGCCAGCAGGCAGTTCCCAGT   1
AATGATAGGATGACAACGGAGGAAAGAGAACGATTCCCCACAGGGCAGCAGGCAGTTCCCAGT   3
AATGATAGGATGACAACGGAGGAAAGAGAACGATTCCCCACAGGGCAGCAGGCAGTTCCCAGT   4
AATGATAGGATGACAACAGAGGAAAGAGAATGATTCCCCACAGGCCAGCAGGCAGTTCCCAGT   5
AATGATAGGATGACAACAGATGAAAGAGAATGATTCCCCACAGGCCAGCAGGCAGTTCCCAGT   6
AATGATAGGATGACAACAGAGGAAAGAGAACGATTCCCCACAGGCCAGCAGGCAGTTCCCAGT   7

GTAGACCCTCATTAGGACACAGAATCAGAACATGGAGATTGGTGCCGCAGACATTTGCTAACT   1
                                                          AACT   2
GTAGCTCCTCATTGGGACACAGAATCAGAACATGGAGATTGGTGCCGCAGACATTTACTAACT   3
GTAGCTCCTCATTGGGACACAGAATCAGAACATGGAGATTGGTGCCGCAGACATTT          4
CTAGACCCTCATTGGGACACAGAATCAGAACATGGAGATTGGTGCTGCAGACATTTGCTAACT   5
GTAGACCCTCATTAGGACACAGAATCAGAACTTGGAGATTGGTGCCACAGACATTTGCTAACT   6
GTAGACCCTCACTGGGACACAGAATCAGAACATGGAGATTGGTGCCGCAGACATTTGCTAACT   7
```

*FIG. 9A*

```
TGCGTGCTAGAAGGACTAAGGAAAACTAGGAAGA----TATGAATTATTCAATGATGTCCACT    1
TGCGTGCTAGAAGGACTAAGGAAAACTAGGAAGA---CTATGAATTATTCAATGATGTCCACT    2
TGCGTGCTAGAAGGACTAAGGAAAACTAGGAAGA---CTATGAATTATTCAATGATGTCCACT    3
TGTGTGCTAGAAGGACTAAGGAAAACTAGGAAGAAGTCTATGAATTACTCAATGATGTCCACA    5
TGCGTGCTAGAAGGACTAAGGAAAACTAGGAAGAAGCCCATGAATTATTCAATGATGTCCCCT    6
TGCGTGCTAGAAGGACTAAGGAAAACTAGAAAGAAGCCTGTGAGTTATTCAATGATGTCCACT    7

ATAACACAGGGGAAAGGAAGAAAATCCTACTGCCTTTCTGGAGAGACTAAGGGAGGCATTGAG    1
ATAACACAGGGGAAAGGAAGAAAATCCTACTGCCTTTCTGGAGAGACTAAGGGAGGCATTGAG    2
ATAACACAGGGGAAAGGAAGAAAATCCTACTGCCTTTCTGGAGAGACTAAGGGAGGCATTGAG    3
ATAACACAGGG-AAGGGAAGAAAATCCTACTGCCTTTCTGGAGAGACTAAGGGAGGCATTGAG    5
ATAACACAGGG-AAAGGAAGAAAATCCTACTGCCTTTCTGGAGAGACTAAGGGAAGGATTGAG    6
ATAACACAGGG-AAAGGAAGAAAATCCTACCGCCTTTCTGGAGTGACTAACGGAGGCATTGAG    7

GAAGCATACC---AGGCAAGTGGACATTGGAGGCTCTGGAAAAGGGAAAAGTTGGGAAAAGTA    1
GAAGCATACC---AGGCAAGTGGACATTGGAGGCTCTGGAAAAGGGAAAAGTTGGGCAAATTG    2
GAAGCATACC---AGGCAAGTGGACATTGGAGGCTCTGGAAAAGGGAAAAGTTGGGCAAATTG    3
GAAGCGTGCC232AGGCAAGTGGACTTTGGAGGCTCTGGAAAAGGGAAAAGCTGGGCAAATTG    5
GAAGCATACC238AGGCAAATGGACTTTGGAGGCTCCAGAAAAGGGAAAAGCTGAGCAAATTG    6
GAAGCATACC233AGGCAAGCGGACTTTGGAGGCACTGGAAAAGGGAAAAGCTAGGCAAATCA    7

TATGTCTAATAGGGCTTGCTTCCAGTGTGGTCTACAAGGACACTTTAAAAAAGATTGTCC-AA    1
AATGCCTAATAGGGCTTGCTTCCAGTGCAGTCTACAAGGACGCTTTAGAAAAGATTGTCC-AA    2
AATGCCTAA                                                         3
AATGCCTAATAGGGCTTGCTTCCAGTGCGGTCTACAAGGACACTTTAAAAAAGATTGTCC-AA    5
AATGCCTAACAGGGCTTGCTTCTAGTGTGGTCTACAAGGACACTTTAAAAAAGATTGTCC-AA    6
AATGCCTAATAGGGTTTGCTTCCAGTGCGGTCTACAAGGACACTTTAAAAAAGATTGTCCAAA    7

-TAGAAATAAGCCACCACCTCGTCCATGCCCCTTATGTCAAGGGAATCACTGGAAGGCCCACT    1
GTAGAAATAAGCCGCCCC-TCGTCCATGCCCCTTATGTCAAGGGAATCACTGGAAGGCCTACT    2
GTAGAAGTAAGCCGCCCCCTCGTCCATGCCCCTTATTTCAAGGGAATCACTGGAAGGCCCACT    5
GTAGAAACAAGCTGCCCCCTTGTCCATGCCCCTTATGTCAAGGGAATCACTGGAAGGCCCACT    6
-TAGAAATAAGCCGCCCCCTCGTCCATGCACCTCGTGTCAAGGGAATCACTGTAAGGCCCACT    7

GCCCCAGGGGATGAAGGTCCTCTGAGTCAGAAGCCACTAACCAGATGA    1
GCCCCAGGGGACGAAGGTCCTCTGAGTCAGAAGCCACTAACCTGATGA    2
GCCCCAGGGGACAAAGGTCCTCTGAGTCAGAAGCCACTAACCAGATGA    5
GCCCCAGGAGATGAAGGTCCTCTGAGTCAGAAGCCACTAACCAGATAA    6
GCCCCAGGGGACGTAGGTCCTCTGAGTCAGAAGCCACTAACCAGATGA    7
```

*FIG. 9B*

```
RTPLSTQTVQKDIDKGVNNEPKSANIPWLCTLQAVGEEFGPARVHVPFSLSHLKQIKIDG    SDSPTS
 - =  === ===-=== == ======== =  ===== =============  ===== = =  == ===
KDPPSTQMVQKEIDKRVNSEPKSANIPQLPLQAVGGREFGPARVHVPFSLPDLKQIKTDLGKFSDNPDS

YIDVLQGLGQSFDLTWRDIILLLNQTLTSNERSAAITGAREFGNLWYLSQVNDRMTTEERERFPTGQS
========== ========- ====== ======-==-= ===-================ ======
YIDVLQGLGQFFDLTWRDIMSLLNQTLTPNERSATITAAXEFGDLWYLSQVNDRMTTEEREXFPTGQS

AVPSVAPHWDTESEHGDWCRRHLLTCVLEGLRKTRK TMNYSMMSTITQGK
====- ============= ==================--============-
AVPSLDPHWDTESEHGDWCCRHLLTCVLEGLRKTRKKSMNYSMMSTITQGR
```

FIG. 10

```
GTCTACCTAGCCA-AGGCATATTCTTCTTATGTGGAACATCAACCTATATCTGCCTCCCCACTAACTGGA
:::: :::: :: ::: ::::: :: : ::::: :: ::: ::::: :: : :: ::
GTCTGCCTACCCTCAGGAATATTTTTTGTCTGTGGTACCTCAGCCTATCGTTGTTTGA--A-TGGCTCTT
CAGGCACC-TGAACCTTAGTCT--TTCTAAGTCCCAAC-ATTAACATTGCCCCAGGAAATCAGACCC-TA
::: : :: :: ::: :::: ::: :: : :: :::: : : : : : ::: ::
CAGAATCTATGTGC-TTCCTCTCATTCTTAGTGCCCCTATGACCATCTACACTGAACA--AGATTTATA
TTGGTACCTGTCAAAGCTAAAGTCCCGTCAGTGCAGAGCCATACAACTAATATCCCTAT-TTATAGGGTT
: :: ::::: : :::: : ::::: : :::: : :: : : ::: : : :::::::
CAGTTA--TGTCATATCTAA-GCCCCGCAACAAAAGAGT-ACCCAT-TC-T-TCCTTTTGTTATAGGAGC
AGGAATGGCTAC-TGCTAC-AGGAACTGGAATAGCCGGTTTATCTACTTC-ATT-A-TCCTACTACCATA
:::: :: ::: ::: :: ::: ::::: :: : :::: : :: :: : :: ::::::: : :
AGGAGTG-CTAGGTGC-ACTAGGTACTGGCATTGGCGGTATCACAACCTCTACTCAGTTCTACTACAA-A
CACTCTCAAAGAATTTCTCAGACAGTTTGCAAGAAATAATGAAATCTATTCTTACTTTACAATCCCAA-T
: :::::: ::: : : :::::: :: :: :::: ::: ::: :
CTATCTCAA-GAACTAAATGGGGACATGGAACGGGTCGCCGAC-TCCCTGGTCACCTTGCAAGATCAACT
TAGACTCTTTGGCAGCAAT-GACTCTCCAAAACCGCCGAGGCCCACACCTCCTCACTGCTGAGAAAGGAG
:: :::: : :::::: : : : :: :::: :: :: :: :: :::: :: ::: :
TA-ACTCCCTAGCAGCAGTAGTC-CTTCAAAATCGAAGAGCTTTAGACTTGCTAACCGCTGAAAGAGGGG
GACTCTGCACCTTCTTAGGGGAAGAGTGTTGTTTTACACTAACCAGTCAGGGATAGT-AC-GAGAT-GC
:: ::: :: :::::::::: :: :::: ::: ::: :: :: :: :: :: :::: :
GAACCTGTTTATTTTTAGGGGAAGAATGCTGTTATTATGTTAATCAATCCGGAATCGTCACTGAGAAAGT
CACCTGGCATTT-ACAGGAAAGGGCTTCTGATATCAGACAATGCCTTTCAAACTCTTATACCAA---CCT
: : ::: :: : :: : : : : :::: : :: :: :::: :: :: :::
TAAA-GAAATTCGAGATCGAATA-CAACGTAGAGCAGAGGA-GC-TTCGAAACACTGGACCCTGGGGCCT
CTGGAGT---TGGGCAACATGGCTTCTTCCATTTCTAGGTCCCATGGCAGCCATCTTGCTGTTACTCACC
: :: ::: : ::: :::: :: :: :::: :: :: :: : :: :::: :
CCTCAGCCAATGGATGCCCTGGATTCTCCCCTTCTTAGGACCTCTAGCAGCTATAATATTGCTACTCCTC
TTTGGGCCCTGTATTTTTAAGCTTCTTGTCAAATTTGTTTCCTCTAGGATCGAAGCCATCAAGCTACAGA
::::: :::::::: ::::: ::: :: ::::: :: :: :: :::: : : :: :
TTTGGACCCTGTATCTTTAACCTCCTTGTTAACTTTGTCTCTTCCAGAATCGAAGC--T---G-TAAA-A
TGGTCTTACAAATGGAACCCCAAATG-AGTTCAACTAACAACTTCTACCAAGGACCCCTGGAACGATCCA
:: :::::::::: ::: ::: ::: ::: :: :::::::::: :: :: :
----CT-ACAAATGGAGCCCAAGATGCAGTCCAAG-ACTAAGATCTACCGCAGACCCCTGGACCGGCCTG
CTGGC--ACT-TCC-AC-T-A--GCC-T-AGAGATTCCCCTCTGGAAGACA-CTACAACTGCAGGGCCCC
:: :: :: :: : : :: : : :::::: :: :: : :: :: ::::: :: :
CTAGCCCACGATCTGATGTTAATGACATCAAAGGCACCCCTCCTGAGGAAATCT-CAGCTGCACAACCTC
TTCTTTGCCCCTATCCAGCAGGAAGTAGCTAGAGCGGTCATCGGCCAAATTCCC-AACAGCAGTTGGGGT
: :: :::::: :: :::::::::: :: :::::::::: :::::::: :::: ::::::: :: :: :
TACTACGCCCCAATTCAGCAGGAAGCAGTTAGAGCGGTCGTCGGCCAACCTCCCCAACAGCACTTAGGTT
GTCCTGTTTAGAGGGGGG
::::::: ::: :::::
TTCCTGTTGAGATGGGGG
```

*FIG. 11*

```
ACCTTGCAAGATCAACTTA-ACTCCCTAGCAGCAGT-AGTCCTTCAAAATCGAAGAGCTTTAGACTTGCT
:: :: :::    :::  : : ::::   :  :::::::: : :: : ::::: ::   :::   ::::  : ::
ACTTTACAATCCCAAATAAGACTCTTTGGCAGCAGTGACTC-TCCAAAACCGCTGAGGCCTAGATCTCCT

AACCGCTGAAAGAGGGGGAACCTGTTTATTTTTAGGGGAAGAATGCTGTTATTATGTTAATCAATCCGGA
 ::  :::::::: :::  :::    :::     :: :::::::::::: :: :::: :::   ::: :: :: ::
CACTGCTGAAAAAGGAGGACTCTGCACCTTCTTAGGGGAAGAGTGTTGTTTTTACACTAACCAGTCAGGG

ATCGTCACTGAGAAAGTTAAAGAAATTCGAGATCGAATA--CAACGTAGAGCAGAGGAGCTTCGAAACAC
:: : :: :::::   :     :    :   :  : ::  ::: :  :  : : :::: :   ::: :::   :
ATAG-CA-TGAGAT-GCCACCCAGCGTTTACAG-GAAAAGGCTTCTGAAATCAGACGCCTTTC-AAATTC

TGGACCCTGGGGCCTCCTCAGCCAATGGATGCCCTGGATTCTCCCCTTCTTAGGACCTCTAGCAGCTATA
:    ::     :::: ::    :::   : :::  :::::::::: :::: ::  : :::::  ::
TTATACCAA---CCTCTGGAGT---TGGGCAACATGGCTTCTCCCCTTTCTAGGTCCCGTGGCAGCCATC

ATATTGCTACTCCTCTTTGGACCCTGTATCTTTAACCTCCTTGTTAACTTTGTCTCTTCCAGAATCGAAG
  :: :::::  :::::: :::::: ::: ::::  :::::::::: :::::  :: ::::::::::: :
TTGCTGTTACTCGCCTTTGGGCCCCGTATTTTTAACCTTCTTGTCAAATTTGTTTGGTCTAGAATCGAGG

C--T---G-TAAA-A----CT-ACAAATGGAGCCCAAGATGCAGTCCAAG-ACTAAGATCTACCGCAGAC
:  :   : :: :  :        :: :::::: :: ::: ::: ::: :::  : ::   :::::::    :::
CCATCAAGCTACAGATGGTCTTACAAATCGAACCCCAAATG-AGTTCAACTAACAACTTCTACCGAGGAC

CCCTGGACCGGCCTGCTAGCCCACGATCTGATGTTAATGACATCAAAG-GCACCCCTCCTGA-GGAAATC
::::::::: : :: ::: ::  ::  ::  ::      : : : :  ::::::  ::::::   ::: :
CCCTGGACTGACCAGCTGGC--ACT-TCCCCTG-----GCC-T-AGAGAGTTCCCCTC-TGAAGGACA-C

T-CAGCTGCACAACCTCTACTACGCCCCAATTCAGCAGGAAGCAGTTAGAGCGGTCGTCGGCCAACCTCC
: :: :::::  ::  :: ::  :::::::  ::::::::: :: :: :::::::   ::: ::::   :::
TACAACTGCAAAGCCCCTTCTTCGCCCCTATCCAGCAGGAAGTAGCTAGAGCAGTCATCGGCCAAATTCC

CCAACAGCACTTAGGTTTTCCTGTTGAGATGGGGG
:   :::::::: :: ::  : ::::::::::  :: :::
C-AACAGCAGTTGGGGTGTCCTGTTGAT-TGAGGG
```

FIG. 12

```
agttgcaattccttgcctcaactctgagagaaacccagccacatctccagcaaacaaga
|||||||||||||||||||| ||| ||||| ||||||||| |||||||||||||| ||||||
agttgcaattccttgcctccactgtgagacaaacccagacacatctccagcacacaaga 2299 acttcaaaacacctgaactgcagcagccaggcgttcctccaggaccacctcccaggat
||||| ||| ||| ||| ||| |||||| |||||||||| ||| ||||||||||
acttcgaaatgcctcaacctcaggtgccaggggttcctccagaaccttctccccaggag 2359 cttgcttcaagtgccggaaatctgaccattgggccaaggaatgcctgcagccaggattc
|||||| |||||||| |||||||| ||| |||||||||||||||| ||| ||||||||
cttgctacaagtgccagaaatctggccactgggccaaggaatgcccacagaccaggattc 2419 ctcctaagccacgtcccatttgtgcaggacccactggaaatcggactgtccaactcacc
|||||||||  ||||||  | ||  |||||||| ||||| |||||| ||||||||||
ctcctaagctgtatccatctctgtgggacccactaaaaatcagactgttcaactcacc 2479 cggcagccaatcccagagcccctggaactctggcccaaggctctctgactgactccttc
||||||||  |  |||||||||||||||||||||   ||||||||||||||||||| |||||
tggcagccacttccagagcccctggaactctagcccaaggctctctgactgacccctct 2539 cagatcttctcggcttagcagctgaagactgacactgcccgatcacttcagaagtcccct
|||||||| ||||||||||||||||||||||||||||||||| |||| | || |||| | |
gagatcttcttggcttagcagctgaagactgacactgccagatcgcctcggaagcctaca 2599 ggaccatcacggatactgagcttcaggtaactctcacagtggaggctaagtccatcccct
|||||||||| |||    ||| |||||||||||||||| |||| |||||| |||||
ggaccatcacagat-----gctccaggtaactctcacagtagagggtaagtctgtccct 2654 gtttaatcgatacaggggctacccactccacatcaccttcttttcaagggcctgtttccc
|||||| |||  | ||||||||||||| |||||| ||||||||||||||||||||||||||
tcttaatcaatatggaggctacccactgcacattaccttcttttcaagggcctgtttcct 2714 tttccccataactgttgtgggtattgacggccaagcttcaaaacccctaaaactcccc
|| || |||||||||||||||||||||||||||| ||||| ||||| |||||||||||
ttgcctccataactgttgtgggtattgacggccaggcttctaaacctcttaaaactcccc 2774 cactctggtgccaacttggacaacattctttatgcactcttttcagttatcctcacct
||||| ||  ||||||||||| | ||||||| |||||| ||||  ||||||| ||| |
aactctagtaccaacttagacaatactcttttaagcactcctttttagttatccccactt 2834 gcccagttcccttattaggccgagacattttaaccaaattatctgcttccccgactattc
|||||||||||||| ||||||||||||| || ||| ||||||||||||||| ||||||||
gcccagttcccttatgaggccgagacacttcaactaaattatctgcttccctgactattc 2894 ctgggctacagccacatctccttgccgcccttcttcccaacccaaagcctccttcatatc
|||| |||||||  |||||  ||  |||||||||||||||  |||||||||||||    |||
ctggactacagctacatctcattgctgcccttcttcccaatccaaagcctcctttgcatc 2954 ttcctctcatatcccccaccttaacccacaagtatgggacacctctactccctccctgg
||| | | |||||||| |||||||||||||||||| || |||||||| |||||| |||
ttcttgt---atccccaaccttaacccacaagtataagatacctctattccctccttgg 3011
```

*FIG. 13A*

```
caaccgatcacacgcccattactatcccatzaaaacctaatcacccttaccctgctcaat
||| ||||  | ||| |||| |||  |||||||||||||||||  |||||||  ||||||
tgaccaatcatgcacccctzaccatctcatzaaaacctaatcactcttaccccggctcaat 3071 gccagtatcccataccacaacaggctttaaagggattgaagcctgttatcacttgcctgc
||||   ||||||||| ||  |||||||||  |||||  ||||||||||||||| ||||||
gccaagatcccatcccacagcatgctttaaaaggattaaaacctgttatcactcgcctgc 3131 tacagcacgggcttctaaaacctataaactctccatacaattcccccattttacctgtct
|| |||| || |||  ||||  ||||||||||||||  ||||||||||||||||||||||
tagagcatggccttttaaagcctataaactctccttacaattcccccattttacctgtcc 3191 aaaaaccagataagtcttacaggttagttcagaatctgcaccttatcaaccaaattgttt
| |||||||  |||  ||||||||||    |||  |||||   ||||||||  ||||||||
tagaaccagacaagccttacaggtt----caggatctgtgtcttatcaatgaaattgttt 3247 tgcctatccaccctgtagcacccaactcgtacactcttttgtcctcaatgccttccccca
|  |||||||||||||| | |   |||  || |||||| | |||||||| ||| ||  | |
tccctatccaccctgtggtgctgaacccatatactctcctatcctcaataccttcctcta 3307 caactcactattccgttcttgatcttaaagatgctttttcactattccctgcacccct
|||| || ||||| ||||| |||  |||||||| |||||||  |||| ||||||||  |
caacccattattctgttctagatctcaaacatgctttctttactatcctttacaccctt 3367 catcccagcctctctttgctttacctggactgaccctgacacccatcagtcccagcagc
|| |||||||||||||  | |||||||||||||||||||||||||||||||||||||||
caacccagcctctcttcgttttcacctggactgaccctgacacccatcagtcccagcagc 3427 ttacctgggctgtactgccgcaaggcttcagggacagcccttattacttcagccaagctc
||||||||||||| || ||||| |||||||||| ||||||||| |  ||||||||||||
ttacctgggctgtaatgctgcaaggtttcaggggcagcccttattatttcagccaagctc 3487 tttctcatgattactttctttccacctctctgcttctcaccttattcaatatattgatg
|||||||||||||||||||||||||||  || ||||||||||||||||||||||||| ||
tttctcatgattactttctttccaccctctcacttctcaccttattcaatatattggtg 3547 accttctactttgtagccctcctttaaatcttctcaacaagacaccctcctgctccttc
|   ||||  |||||||||||||||   |||||||||||||||||||  | |||||||||
atgttcttctttgtagccctcctttgaatcttctcaacaagacacacttctgctccttc 3607 aacatttgttctccaaaggatatcgggtatcccccctccaaagctcaaatttcttctccat
| ||||| ||||||||||||||||        |||||||||||||||||  ||||||||||
agcatttattctccaaaggatatc-------cccctccaaagctcaaatgtcttctccat 3660 ctgttacatacctcggcataattcttcatgaaaacacatgtgctctccctgccaattgcg
|  ||||  |||| |||||||||||||||||   |||||  |||||||| |  | | |
ccgttacctaccttggcataattcttcataaaaacacacgtgccctccctgctgatagtg 3720 tctccaactgatctctcaaatcccaacctcttctacaaaacaacaactcctttccctcct
|||   ||||||||||||| |||||||| ||||||||||||||||||||| |||| ||||
tctg--actgatctctcaaacccaacccctcctacaaaacaacaactcttttccatcct 3778 aggcatggttggatactttgcctttggatacctggttttgccatcctaacaaaatcatt
|||||||||||||||||||| |  ||||||||||||||||||||||||||||||| ||||
aggcatggttggatactttcgtgttaggatacctggttttgccatcctaacaaaaccatt 3838
```

```
ataaaactcacaaaagcaaacctagctgacccatagattctaaatcctttcccactc
||||||||||||||||||||||||||| |||||||||||| |||||| ||||||||||
ataaaactcacaaaaggaaacctagttgacccatagatcctaaatcgtttcccactc 3898 ctctttccattccttgaagacagctttagagactgctcccacactagctctcctgtctc
|||||||||||||||||||||||||||||||||||||  ||||  |||||||||||| |||
ctctttccattccttgaagacagctttagagactgtctccactctagctctccctgactc 3958 atcccaacccttttcattacacacagcccgaagtgcagggctgtgcagtcggaattcttac
|||||||  |||||||||||||||||||| |||||||||||||||||||||||| |||||||
atcccaacacttttcattacacacagctgaagtgcagggctgtgcagtcagaattcttac 4018 acaaggaccgggaccatgccctgtagccttttgtccaaacaacttgaccttactgtttt
||||||||||||| |   ||||||||||||||||||||||||||||||||||||||||
acaaggaccgggatcgcatcctgtagccttttgtccaaacaacttgaccttactgtttt 4078 aggctcgccatcatgtctccatgcggtagcttccgctgccctaatactttagaggccct
|||||  |||||||||||||||||  ||  |  ||  ||||  |||||||||||||||||
aggctggccatcatgtctccatgcagcgtctgctgccaccctaatactttagaggccct 4138 caaaatcacaaactatgctcaactcactctctacagctctcacaacttccaaaatctatt
||||||||||||||||||||||||||| |||||||||||||| || |||||||||||||
caaaatcacaaactatgctcaactcattctctacagctctcataatttccaaaatctatt 4198 ttctttctcacacctgacgcatatactttctgctccccggctccttcagctgtattcact
||||| ||||||||||| ||||||||||||||||||||||||||| | || |||||
ttcttcctcacacctgacacatatactttctgctccccggctccttcagatatactcact 4258 ctttgttgagtctcccacaattaccattcttcctggcccagacttcaatctggcctccca
|  || | |||||||||||||  |||||||| ||||||||| |||||||| |||||||||
c--cattattctcccacaattaccattattcctggcctggacttcaatccggcctccca 4316 cattattctggataccacacctgaccctgatgattgtatgtctctgatctacctgacatt
||||||||||||||||| ||||||||||| |||| || ||  ||||||||| |||||| ||
cattattctggataccatacctgaccctcatgactgcatctctctgatccacctgacgtt 4376 cacccatttccccatatttccttctttctgttcctcatgttgatcacatttggtttac
|||||||||||||| ||||||||||   | ||||||| ||||||||| ||||||||
cacccatttccccacatttccttctgccctgtttctcaccctgatcacacttggtttat 4436 tgacggcagttccaccaggcctgatcgccactcaccagcaaaggcaggctatgctat
|||  |||||||||||||||||  ||||||||||||||||||||||||| ||||||||
tgatggcagttccaccaggcctaatcgccactcaccagcaaaggcaggatatgctat 4493 gaactgattgccttaactcgggccttcactcttgcaaagggactacacgtcaatatttat
|||||  |||||||| ||  || ||||||||||||||||  |||||||| ||||| |||
gaactagttgccttaattcaagccctcactcttgcaaaaggactacgtgtcaatatctat 4553 actgactctaaatatgccttccatatcttgcaccaccatgctgttatatgggctgaaaga
|||||  |||||||||||| |||||| |||||||||||||  |||||||||||||||||
actgattctaaatatgcctttcatattctgcaccaccatgcggtcatatgggctgaaaga 4613 ggtttcctcactacgcaagggtcctccatcattaatgcctctttaataaaaactcttctc
||||||||||||||  |||| |||||||||||||||||||||||  ||||| ||| |||
ggtttcctcactacacaagtgtcctccatcattaatgcctctttaagaaaa-ctctgctc 4672
```

*FIG. 13C*

```
aaggctgctttacttccaaaggaagctggagtcacacactgcaaggccaccaaaagccg
||||||||||||||||||||||||||||| ||||  ||||||||||| ||  |||||| |
aaggctgctttacttccaaaggaagctggggtcattcactgcaagcggcatcaaaagact   4732 tcagatcccattactctaggaaatgcttatgctgataaggtagctaaagaagcacctagc
||||||||||||  ||||||| ||||||||||||||||||||||| ||||| | ||||| |||||
tcagatcccattgctctaggcaatgcttatgctgataaggtggctagacaagcagctagc   4792 gttcaacttctgtccctcatggccagttttctccttcccatcagtcattcccacctac
||||||||| |||||||||||||||||||||||||||| |||| |||| |||||||||
tctccaactttttgtccctcatggccagttttctccttcacatccgtcactcccacctac   4852 tcccccattgaaacttccgcctatcaatctcttctcacacaaggcaaatggttcttagac
||| |     ||||||||||| |||||||  ||||| | | |||||  |||||||||||||||
tccacagctgaaacttccacctatcaagctcttccccgcaaggtaaatggttcttagac   4912 caaggaaaatatctccttccagcctcacaggcccattctattctgtcatcatttcataac
|||||||||||||||||||||||||||||||||||||||||||||||| |||||||||||
caaggaaaatatctccttccagcctcacaggcccattctattctgtcgtcatttcataac   4972 ctcttccatgtaggttacaagccactagtccacctcttagaacctctcattccctt-cca
|| ||||||||||||||||||||||||| |    |||||||  ||||||||||||||| |||
cttttccatgtaggttacaagccactagcctgtctcttaggacctctcattccctttcca   5032 tcgtggaaacatatcctcaaggaaatcacttctcagtgttccatctgctattctactacc
|| ||||||  |||||||||||| |||||||||||||||||||||||||||| |||||
tcatggaaatctatcctcaaggagatcacttctcagtgttccatctgctattctgctacc   5092 cctcaggattgttcaggccccctcccctccctacacatcaagctcggggatttgcccct
||||||||||||||||||| ||||||  |||||||||  ||||||||||||||||||||||
cctcaggattgttcaggcctcctcccctttcctacacataaagctcggggatttgcccct   5152 gcccaggactggcaaattgactttactcacatgccctgagtcaggaaactaaaatacctc
||||||||||||||||||||||||||||||||||||    ||||||  ||||||||||| |||
gcccaggactggcaaattgactttactcacatgcctcgggtcagaaaactaaaatatctc   5212 ttggtctgggtagacactgtcactggatgggtagaggcctttcccacagggtctgagaag
|| |||||||||||||||| ||||||||  |||||||||||||||| ||| |||||||||
ttagtctgggtagacactttcactgggtgggtagaggcctttcccatagagtctgagaag   5272 gccactgcagtcatttcttcccttctgtcagacataattccttgggttggccttcccacc
|||||  || |||||||||||||||||||||||||||||||||||| |||||||||||| |
gccaccgcggtcatttcttcccttctgtcagacataattccttggtttggccttcccttc   5332 tctatacagtccaataacggagcagcctttattagtcaaatcacctgagcagttttcag
||||||||||  ||||||||  |||||||||||||||  ||||||||  ||||||||  ||||
tctatacagtctgataacggaccagcctttactagttaaatcacccaagcagtttctcag   5392 gctcttggtattcagtggaaccttcgtacccttactgtcctcaatcttcaggaaaggta
|||||||||||||||||||||||||| || ||||||        ||||||||||||||||
gctcttggtattcagtggaaccttcatatcccttaacatcctcaatcttcaggaaaggta   5452 gaatggactaatggtctttttaaaaacacaccccaccaaactcagcctccaacttaaaaag
|| |||||||||||||||||||| |||||||||| |||||||||||||||||||||||||
aaaccgactaatggtctttttaaagacacacctcaccaagctcagcctccaacttaaaaag   5512
```

*FIG. 13D*

```
TGCCTTTATTTCCGTAGGCTGGTCATATGGCGCTAGCACTCACATAAAGCTACCGAGGAG
AGCGAATGAAACCAAAATCACTTTACCTTCACAGCACGAGGCCGTCGTCCCTCTCGATAT
TTGGCCCGTGTGTCGCATACCGCCCTCTGGACGTGGTGATCAAATAAACTCCCTAGCTCC
CCGCCGCTCGACGCCATCTTGCCTACTTTGATCCTCGCAGGGAGGACAACATCCGCCCTA
CTGAGCTCCCTTTTATCCAATAAGAGAGCGGGATGAGTTAAGGAGTGCCAGGATTGGCTG
GAGAATCGACAGCGTCGGCCATCGTTTCCTGCGTGCGAAGATTTGATGAACGAGGTGCCG
CCCCCGAGCGGCTCGGCGGAGAGGCGCGGTGGGTGACAGAAGCTTTCTTGTCCCACCCAC
TACAGGCTTACGGCAGGATGCGCAGCGGGGAGAGGGGCGGGGCCGCAGGGGCGGGGCC
GATCGATCTCCTCCGGCTCCGACGTCCTCGGCCTGCCGGGTCCCGGGTCCTTTGCGGCGC
TAGGGTGGGCGAACCCAGAGCGACGCTCCGGGACGATGTGGGGCAGCGATCGCCTGGCGG
GTGCTGGGGGAGGCGGGGCGGCAGTGACTGTGGCCTTCACCAACGCTCGCGACTGCTTCC
TCCACCTGCCGCGGCGTCTCGTGGCCCAGCTGCATCTGCTGCAGGTAACCTGCCGGCCCC
GAGCCACCTGATCTTCAGCCTGGGGTCGGACGAGGCCGAAGCCTCTCAGGGACGCGGCGG
GACACCGGCTGCCACCCGGGCGCCGCCGAAGCGCGCAGAGATCAGGGTCCCTCGACGGCA
GGGCCCTTCTGGGTAGTCTCTGGATCCCACAAGTCCAGTGCAGCCCTGGGCTCGTCTTAT
CCCAGGTCTTTTCACTTGGTGAAACTGAACCTAGAAACGTCCTAATATTCTACCACTGTT
TTTATAAATATTCCTTATTCCAGGCTGGAAAAGCTCCTGAGAAGTGGTTTGTTTTTATTA
TTTTAAAAGGTGTTTTCCTTGCCAGCCATTTCCAGTTAACCTGCGCTGCTGCCGTCCGGG
CCGCGAGAGCGGGACGCAGAGTTGTTGGCGGAGCCCCTGTCGGTTCCCGGGGACTAAGCA
CCGCGTCCCATGAGCGGGAAAGGTTAATACAATGATGGTTCTGCCCTGCGTCGCTGACGC
GGAACACAGCTGTAGTGTGTTAGGAACACATAACGTAGTTAAGATCACTTGAAGCTCTGC
GATCAGTCGCCCTTCTGGACGTTGTGGTTAGGATGTTTCACAGTTCTAACCACTGGTGGA
GATACAGCGTCCATATTTTCATAATTAAAAATAGAGGCACATGGTCTCACGAGTTTGAGT
GTACTTATGGGGCAAAAGGACGGCGTATTTGAAATCCTCATAAATCCTGGATGCATGGT
ACCCACCAGTGGCTAATCTATGCAATGAATAGAGTTTGCAATAATTTCAAGCATCCCTTC
TTTCCACTTGAGTTACTTCCCCATACCTAGGGGAAGATATTTTTGGTCCACTGAAAACAT
GAGTTCAGCAGAATCCTCCTATCATCGTCGTTATTATTTTTACCACTAAGTAGACAATC
TTTTGGTTTTTGATGGGCTTTATGGCTAGAGACAAATCAGTCACTGTCACCAAGTTCCAG
GTAGAAGTTGGTTCAGTGCTCTGTCAGCTTCGATGGGATTTTTCAACATGTTTTCAAATC
TGCACTTAATAGTAGGAATGCTTTCTTACAGTAACTCTAATTTGATCCTAAGATGTAGTT
GTTACCTTACATTCATCACTGTTTAAGAATTTAGTGGTCTTGATCTTTGTTTAAATTTT
GAGCCTTCGGGAAGTACTTATAAGAATTAATTCATGCATATCTTTTTGAAATGTAAATGT
CTTTAGCCCTGGAACAAATTGCTGTTTCTGTTCAGCCCATATTAGCAGAATAGGTCAACT
TTACTTTCTAATTATCAATGTAATAAGTTTATTACTTTATAGATTCCATAAATCTATACA
TTTATTCCTCGATGAATTATATAAATTTATAGAATTTATGTTTTATAGAAAATTTGGAAA
GCATGGAAAATTATTAACAAGAAAATAAGTTACCCATAATCCCAGAACTTAGAGGTGACT
AATGTTGACAGTTTGGATCAAATCTTCCAGTTTTGTTTCTAATCTTTATTTTAACATAA
ATGAGGTCCTGTATACACACGTACAGTTTTGTGTCCTGGTGTTTTTATTTAATGTTATTA
TGAGTGTTTTATTTTGTTAAAAGGTCATCATTTTAAGTTGTTAATTAGTATTCTAGCACA
AATTTGCCATAATTTATTTAATTGTTTACTATGATTGACCATTTAGATTGTACTTAATTT
TTAGGCATTAGAAGTGATAAACTATATTTTAATCAGACGTTGAAAATAACACATCTTTGT
TTAGAAAACATCATTTTATTTCTGGTTGTCTAGGATAGATTCCCAGAATTCTTGGGTTAG
AGGCCATAGATAATTATGAAAGCAGAAGATTCACAAGTGGGAGTTAATACTTGAATTA
CTTTATTTGGGGTGAAGCATTGAGTGCATAATACAGATCATGCAGTAATGGGAAGAAGGG
TTGGAACAATGGTTTTCTGGCCTATGTCAGACTTACCTTGAAGCTTTTAAGAATACAGAT
GTTCTGATCAACCCTCAGACCTATTAAATCAGACCTAAAATCTTAGGGAATAGGCTTTAG
GCATCTCTAATTTTAAAAAATTTATTCAGGCTACTTGGATGCACAAAAGAGTTGAGACCT
ACTGTCCTAGAATCATAGAATTTTAATGACGATAGAGACCTTAAGCATCTAGGTCGTTTC
TGTACTTTTACATGTAAGGAAACTGGCATTCCTAGGCCAGTACCATTGCCATGCAGCTAA
TTTGCCCTCTTGTCTATAGCTCACTCTGCATCACCCAACCTACCGTTCTCACTGTTTCTT
CTATAACCAATCTCCTTCCCACTTCTGTTCTCTTACTCATGCCATTCTTCCCTCAGTCAT
TTTTCTTCCTTCCATACAAATTCCATGTCTTTAAAAAGGAATAATCCTACCTCCTCCACA
```

*FIG. 14A*

```
TAGCTTTCCAATTCTCTGTTGCCCACATTTGTCTCCCTTTCAATACTTCTCTGTTGTGTT
ATGTGACACATCACATTTGATATACTCTGTACTGTGTTTCAAGTATTGTATTCTCTTGTT
TACTCAAGTCATTATTTCAGGACTGACTACCCAGTAGATGCTTTAAGTCAGGATTTCTCA
ACCTTGGCACTGTTGACATTTTGAGCTGGATAATTTTTTGTTTTGGGGGCTCTCCTGTAC
ATTTTAAGATGTTTAACAGCACCCTTGGCCTCTATCCAGTAGACGCCTGTACTGCCTCCC
CCTATCTGTGACAACCAAAAAGGTCTTCAGACATTGTCAGATGTCTACTGAAGGACAAAA
TCACCTCTGGTTGAGAACCACCGCTTCAACTAAGTTATCTTCTCTGTACTCAGAACTTGA
TGTGATTGCAGCAGGGGAGAGGATTCATATACACAGTGAATGCAAACGAACCTAAATCA
CCATTCGGATATGGCCACACAATTTTCATTTCCCTTGTGTTAGCAAGAGATACCCTAGGC
TTTGGACCTGATTATTCCTAAGGCATTCTGATGTATGGTTTTACCTGCAGATTTCCTGGT
AATACTGATACCTCAGTTTGGGTCAAAGAAGGTCAATTAATTGATTGATTTGATTTGACT
CCTGGAAAAGACGCTCCTTTCTAGCTGTCTCTTTCTTCTCTTTACCTGAATAGCCAGGGC
TCTGTGGTTCAAGTGAAGTATTTTGACATAAAAATTAACTTAGAACATTGGTCTGCAGAG
TTTGCTCAATATAACTGAGCACATATTGTGGCTTTATGGAGCTGGTTACTACTTTTTGAC
CAAATAAATAATTAGAAGTATTTTTCCTCCTCAATAAGGTTCATTTTTCCTTTTTTCAGT
GAGCTGGTAGAGTTTCCTTTTTTGATATTTCAGGGCATCTTTCATATTTCCATCTCTTAA
GTTTCTTCATATGAAGTAGAATTTATCTGGATTATGTATTGCTGACTCTGATGAAAACCC
ATAGAAAGCATCTGGGGCTTGATCACCTTCATTCTTGTAATAGCTCACACGGTTACAGCT
GATATGGTAACTTAAGACTTTTGATTCCAAATCTAGGCAAAATACACTCAGTTGAAAGAA
TTTGTCAGCCAGAACAGTTGGACTGTTCTGTGAAAATTGTGAGAAAAATTACACAACTAA
GTGATACATGATGATGGCTTTCTTAAATATAAAATTGTAATAACATGGTTAATTTCCAGT
ACGTTATATTGTCCCAGAAGTGGCTCCAACATTGTTTGAAATTTGTCTCATTTAAAGAAA
CATAAGCTGGCTATGGTGGCTCACGCCTGTAATCCCAGCACTTTGGGAGGCTGAGGCAGG
CAGATCACCTGAGGTCAGGAGTTCGAGACCAGCCTGGCCAACATGGTAAAACCCCATCTC
TACTAAAAATACAAAAATTAGCCGGGCATTTGGTGGGGCCTGTAATCCCAGCTACTTGG
GAGGCTGAGGCAGGAGAATTGCTTGAATCTGGGAGGTGGAGGTTGCAGTGAGCCGAGATT
GTGCCACTGCCCTCCAGCCTGGGTGACAGAGTGAGTCTCCGTCTCAAGAAAAAAAAAAAA
AAAAGCAAGAAACATAAAGACTGGGCATGTTGGCTCATGCCTGTAATCCCAGCACTTTGA
GAGACTGAGGTGGGAAGATCACTTGAGCCCAGGAGGTTAAGGCTGCAGTGAGCCGTGATT
TTGCCACTGTACTCGAGCCTGGGCAACACAGTGAGATCCTGTCTCAGGAAAAAAAAAATT
GCATGTAAATGAATGAATTTGATATTTAATATTTTAAATTATGAAAACTGTTCTGTAGAG
ATGTAGATCTTGCCATGTTGCCCAGGCTGGCTTTGAACTTCTGGGCTCAAACAATCCTCC
TGTCTCAGTCTCCCAAAGTATAAAGATTACACATGTGAGCCACTGCACCTGGCCTAATAT
TTTTAACTTAATGAATTTATTTTGATATAAATAAATTAATAACACTGAAGCTTCCTGATA
TAATAAGTCTTTTTGTGTGTGACGGGTTCTCACTCTGTTGCCCAGACTGGAGTGTAAT
GGCACTATCATGGCTCACTGTAGCCTCAACCTCCCTGACTCAAGTGATCCTCCCACCTCG
GCTTCCTGAGTAGATGGGACCACAGGCGTATGCCACCACACCTGGCTGATTTTTAAAATT
TATTATTGATACATATTAATAAAATTATTTTTATTTTAAAAATGATATATGTGGCTGGGC
ATGGTGGCTCATGCCTGTAATCCCGACAGTTTGGGAGGCCGAGGTGGGAGGATCACTTGA
GACCAGGAGCTTAAGACCAGCCTAAGCAACATAGTGAGATCCCATCTCTATAGAAAAAAA
AAATGGCTAGGTGTGGTGGTGTATGCCTATATTCCCAGCTACTCAGGAGACTGAGGTGAG
AGGATTGCTAGAGCCCAGGAGTTTCAAGTTACAGTGACCTATGATTGTGCCAGTGCACTC
CAGCCTGGGCAACAGAGCAAAATCCTGTCTCAAAAAAAAAAAAAGTTCGAAAATGCTTAT
GATGCAATATAAGTAGTGGAAAAGGATATTAAATTGTGCCTATATGAACACAACTATATG
AAAAACTTGCACATAGAGAAAAGGATTAACAAGAAATAGACCAAATTGTTCACATGGTTG
TCTTGTTTGTGGAGAGAATATCAGTAGTTCATTGTTTCCTTCCAAGTTTATATGTTTTC
CGAGGTCTCTATAATGAGTTTGTAATTGTTAATCATAGAAACCCTTTTTTGGTCCTTG
GCCACAAACTTACATGTTTTAATGTAATTGCTTTTTTAATGAGAATAAATGTTATATTTT
GCTTTTTTAAAACCTATATTCCCATAGTTATATGAGCCCTTACAATTATTAAGAGGCTGC
ATAATATAACGTTTCTGGAAGGGTACAGAAGAAACAGCAGTAATTACCTCTGAGAACAGA
GACATGGCTTCACATTTTACCCTTTTGTACGTTTTGTGCTTTTGCCACATGCATTTATTA
TTCTTCCAATAAATAAGTAAATAAATATGGATTGTATACTCCATCTGGTTGGTGTTTCAT
AATTCTAAAATTATATTGCTACATTTTAAAGATGATATGTGTTTCTACTTATTAACGTA
```

*FIG. 14B*

```
TATGTTAAATAGTAAATTTATATCTTATTTAATAATTTCCCTATTGATAGACATTTAAG
ACAGTCTCAAGTGTTCACTATCATAGAAAATACTGCACAGATAGCTTTTGCTATAGTTTC
TTTTTTCTTTGAATCGTTAATTGGGAATAAATGCTCAAATAGTTATATGTGGCTCAACTG
CTATTTAAGTTTATTGACTGACTGCTGCCATTTTGAATTCTGAAGGGGTTGATTAAATTT
ATAATGCTGCCATAAGAATATAAGGGTATTGGCTTCATTAGCATCCACCAGCATTGGGTG
TTGGAAATGATTATAGATTTTTAAATGCTACAACAAATGTAGATAACAGAGAACTATCTA
TAGAACTCTTTTTGGACATGTGAATTGTAATAATAGTTTATTTTCATGTGAATCCAGAAA
AATGTATACGAAAACCTTTTTTCCTCTCATTTCTTATATGAATAGAATCAAGCTATAGAA
GTGGTCTGGAGTCACCAGCCTGCATTCTTGAGCTGGGTGGAAGGCAGGCATTTTAGTGAT
GGGGGACAGGTAAGCACATGTGATGGCAATAACTTTCTTCTAATATCACATAATATAGCA
ATAGAAATAAAATTAAAAGTTTAGATTTTTTGTTAAAGGAGGTGAGATGTCACCTAATTT
GTATGCTATTATGTAACTAGTCTAGGATATTGAAGCTGACTATACTCTGTTTTAGGTCA
TTATCTTGTAGTTTACCATACTCCCTACTTGCTTCTTATTCTACTATTTAACTCATTTTC
CACATCCCCTAATTTTGGTTTCATGAAATTATTTTTCCTTCTGAATTACTAGGTTCTACT
TACTATTATTAAACTTTATTTCTGACATATTTTATAACCTTCCATGGTCTCACTTGATTA
AAAATAAAAAATTCAGCTGGGTGCGGTGGCTCACACCTATAATCCCAGCACTTTGGGAGG
CCAAGGTGGGCGGATAATTTGAGGTCAGGAGTTGGAGACCAGCCTGCCCAACGTGGTGAA
ACCCCCCCTCTCTACTAAAAATTCAAAAATTAGCTGGGCATGGTGGCAGGTGCCTGTAAT
CCCAGCTACTCAGGAGGCTGAGGCAGGAGAATTGCTTGAACCTGGGAGGTGGAGGTTGCA
GTGAGCTGAGATTGCACTGCTGCACTTCAGCTGGGTGACAAGAGCGAAACAATGTCTTGA
AAAAAAATAAAAATAAAAAATTCTACAACACAGGGTTATTATTTTTCCATTTTTGTTTT
CCCTTATGAGTTTAATATGTTTAGATTATAAACCTGAAAGCTTGAATACCTATGTCTATC
TTTTGTTTCTTATGTTTATCAAGTTATTCCTTTAAACATTTTCTAAACTGTAAGAATAA
TGTGAGGCTGGGCTCAATGGCTTATGCCTGTAATCCCAGTGCTTTGGGAGGCCAAGGTGG
GAGGACCACTTGAGGCCACGAGTTCAAGATTAGCCTGGCTAGGCAACATAGCAAGACCCT
ATCTCTATAAAAAATTAAAAAAATTAGCTGGGCATGGTAGCAAATGCTTGTAGTCCCAG
CTACTCAGCAGACTGAGGTAGGAGGAATGCTTGAGACCAGGAATTTGAGTGACCTATGAT
TATGCACTCCAGCCCGGGCAATAGCAAGACCCTATCTCTTAAAAGAAGAAGATGTAGTAA
TAATACATATTCATTATAACTATTTTACCATTGAAAGTAAAAAATGAGTTTTTACCTTTT
CCCAGTCCCATCCTCAGAATGGGGATCTCAGTAGACCTTTAGGATTGGAAGAATGAGATC
ATTCATATTTCTGCAATTATTACCCCACAAAATATTTCAGATACCTTTCCATGTATTAC
AAACAATGTGCATTTAACATGTCTCTCTCTTTCTCTCTCTCTGTGTGCGTCTTCATGA
TCCTCTGTTGCAGCCCTGCCAGTAAGACACTATCTCCTGAAGAATCACTGATAGGAACAG
AAAGTGGACTGGCTAGGCCAGGAGTCCTTAGCTTCTTAGGGGGCAGGAGCTGCTTTGTGC
TTTCTCAGAATCAGATATATATGTGGACTGAAACATTTAAAAACAGAATAGCCAAGGGTG
CTATACGTTTAAAACTTATATAGATGGGGCTACATTGCTCTCTATTACTAATTTCCCATG
ACAATACACGAGAGTGCCATGTCTTTTTAACTTGTTTTGAGCACAGACTAATCTTGTTTA
TGCATGTTTTTTGATGAGAATAGGCTACTCATGAGAAATCTGTAAACCTAACACTAGTCC
CTTGCATACTCTAAATTGTTGCTAGAATCTTAAAATTTTAGCACCAGACGGACCTTAGAA
ATCATTAACTTTGGTGCTTTGTTCTACAATACAAGGAGATGGAATATTTTACCCAGGATT
GCTTAGCAGGTTACAGTTCTGCCCTCTGAGTACCCAGCACTTCCCTGTGGGCAACATCAA
CTTCCTGATTTTCAAGTCTTAATTAGTACTCTGAAGAATCCTACTTGTTTTAACTCCCA
TTTGCTTTGAAGTGACTTTACCTGATTTTTTAGATCCCTTATTGCAGCAATGCCACTAA
GAAACTGAGTCTCTAGCTTCTTGGTGGGCAGGAGCTGCTTTGTGCTTGCTCAGAATCATC
CTTTTCAGTAAGGGAGATATTGAAGAGAAATCTACTGAGGAGTCTGGGGGTGAGGCACTC
AGGGAAATCCTGCTCCAGTCCACAAAAGCAGAGAGGAAGGGTTGGTTACCTAGAGTATTT
AACATGCAGAGGCTTTGGATTTTACTCCTTTAATCCTTGGAAATGCCTATGGAAGGGGAA
AGGAAGTAAGATGGTGACTCCAGCTTATAGACATACTAGTGTTACATATATTTAAACTAT
AATAGGAGGGTATTATTAGTTTTACTTAACTTTCAACTGTGAAGGATTATACTTCTCAAT
ATTTGTCTCCAGTGTCTATTTCAGTGTATTTTCACTTTTCTTGAAGCAGCATGTCTGTT
GCAAAACTTCTAGAAATAATGAGAATATTTATATATTAGATCAAGCCATAACTTGATGAT
ATAGTCATTTCTTCTTATATTTTTTACTTACATTTTTACATTTTAATGATTACTTTCATT
TTTGAAAAACATGTCATGCTGAGATGTATTTTTCTTCATTCTGTAATTAGTTATGAAACA
```

*FIG. 14C*

```
GTTTTTCCTAAAATGCTGAGTATATCAAGTCTTGGCTAAGAATAAGTAATAAATATTTGC
CACATGAAAGACTACACATATAGCCAGGTGCAGTGGCTTGCACCTGTTTTCCCAGCTACC
CAGGAGGCTGAGGCAGGAGGATTGCTTGAGCCCAGGGTTTCCAGGCTGCAGTGAACTATG
ATTGTACCACTCTACTCCAGAATGGGTGACAGAGCCAGGCCCCATCTCTCAAAACAGAAA
AGAAAGATTACATAGACTACATATACACCCCATCCAAAACATACACACATCTACTTA
ACCTAAAATGGTAAGAAGATAACTTCTTATTTTCTAATATATGACACAGAAAGTTTTTT
TAAAGTAGTTTTAAATTTTTAATTTTTTCTAGGTATTTCTCAAGCCATGTTCCCATGTGG
TATCTTGTCAACAAGTTGAGGTGGAACCCCTCTCAGCAGATGATTGGGAGATACTGGTAA
AGAAAACCAAATAAGAACTATCTCATTTAAGGTTAAATTACTTCACAATATCAATGTCTT
TAGCTTTCTCTAAGCTTTATTATATATTCTGAGTTGGTTTTGAATTATAAGAATGAATTG
GGGCCAGGCACAGTAGCTCATGCCTATAGTCCCAGCACTTTGGGAGGCCAAGGCAGGTGG
ATTGCTTGAGTCCAGGAGTTCAAGACCAGGCTGGGCAACATGGTGAAACCCCGTATCTAC
TAAAAATACAAAAATTAGCCAGGCATGGTAGTGCATGCCATTAGTCCCAGTCACTTGGGA
GGCTGAGGCAGGAGAATCGCTTGAGCCCGTAAAGTCAAGGCTGCAGTGAGTCAGGATCTT
GCCATTGTACTCCAGTCTGGAAAACAGAGTGAGACCTTGTCTCAAATAAAAAAGAATGA
ATTGATAGAGATCTAATGTACAACCTGACAACTATAGGTAATAAAATTGTATTGGGGATT
CATGTTAAATGAGTAGATTTTAACTACTCTTACCACAAAAACACAAAAGTGGGTAACTGT
GAGATGATGTATATGTTAATTTACTTCACTATAGTAACCATTATACTATCTATATGTAGC
TCATAACACCATGTCGTGTATATTAAATATGCACATTAAAATTTGTTTTTTAAAAAAAGA
ATTGAGATTTTTTTTAACTAGATATGGAGTGGACAAATGTAAAGTGAATTGATCTTTTC
GTCTGTTGGTTCTAGGAGCTGCATGCTGTTTCCCTTGAACAACATCTTCTAGATCAAATT
CGAATAGTTTTTCCAAAAGCCATTTTTCCTGTTTGGGTTGATCAACAAACGTACATATTT
ATCCAAATTGGTAGGTGCTATTGTAATATTTGCTGTCATATTCTACACTATAGCATTGAG
TCCAAAGTAGAAATGAATGTGCACTAATGAGCTTTATTTTCTACACAGTTGCACTAATAC
CAGCTGCCTCTTATGGAAGGCTGGAAACTGACACCAAACTCCTTATTCAGCCAAAGACAC
GCCGAGCCAAAGAGAATACATTTTCAAAAGCTGATGCTGAATATAAAAAACTTCATAGTT
ATGGAAGAGACCAGAAAGGAATGATGAAAGAACTTCAAACCAAGCAACTTCAGTCAAATA
CTGTGGGAATCACTGAATCTAATGAAAACGAGTCAGAGATTCCAGTTGACTCATCATCAG
TAGCAAGTTTATGGACTATGATAGGAAGCATTTTTCCTTTCAATCTGAGAAGAAACAAG
AGACATCTTGGGGTTTAACTGAAATCAATGCATTCAAAAATATGCAGTCAAAGGTTGTTC
CTCTAGACAATATTTTCAGAGTATGCAAATCTCAACCTCCTAGTATATATAACGCGTCAG
CAACCTCTGTTTTTCATAAACACTGTGCCATTCATGTATTTCCATGGGACCAGGAATATT
TTGATGTAGAGCCCAGCTTTACTGTGACATATGGAAAGCTAGTTAAGCTACTTTCTCCAA
AGCAACAGCAAAGTAAAACAAAACAAATGTGTTATCACCTGAAAAGAGAAGCAGATGT
CAGAGCCACTAGATCAAAAAAAATTAGGTCAGATCATAATGAAGAAGATGAGAAGGCCT
GTGTGCTACAAGTAGTCTGGAATGGACTTGAAGAATTGAACAATGCCATCAAATATACCA
AAAATGTAGAAGTTCTCCATCTTGGGAAAGTCTGGGTTAGTATAAATTTTATAACTTGGG
AGAAATTTTATGTGGCTTAAACATCCCCAAATTATGAATTAGAATAGTATTTCATATATA
AATTGAAAATCAATTAAAAAGAAACACAGTGCCTAAAGGCACTTGGGGGACACATTTACG
CTTTGCAGTAAAGTCCTTGTTTGGATAAAGATTGTATGTTTTCTGGCCAAGTAAGCTTGA
ATAGGTACAAGCTTAGATAGGTTCAGGCCAGAGAGGTCAAAATTACTTGCCTGAGATTGC
ATAGCTAGTGTTACAACTAGGATTCAAACCCAGGCAGATTGACTTGGGGGTTCATCAGGA
TGGAGTGCCCTACAAAGCCTCCCATCTTTAATGCTTGCAGATTTGTTCCCCAGTTACCGA
AAGCAACTTGTTAATATTAGGGAAAAGGGCCAGTGTAGGGAGAGATCCATGGCATGAGGT
AACCTTCCTGCTGCATGTGGTGGCACCTGGATTGGAATGCATCCAGGAGCTGCTTACCCT
GCCGGTGTCTGCTCTTTAATTTGTGTATAACGGAGAGGAAGTAGACAGGGCAACTAGTGC
TCCAGCCCCTCATCCTGGCCACAAATATTAATGCTACCTTTATATGACATAAGTCACTAG
TCCATTTATTGGAACCTAAATTTGAACCACTGTAAAGTAAGACTTCATAGTGATAAAGAG
AGGAACTTGTTAGGAAAGAGAATAAAATAGAAAGAGAAGGTTGTCTCCTTTTGTAGATTT
TTTTTTTTCTCCAACAGTTTTACCTGTGACCTTTATACAAATAACTGACAAAGCATTAA
TCTCTTTGGCCTACATCATTTTCTTTTCTATTTTTTTTTCCACAAGATGGAGTTTCACT
CTTCTTGCCCAAGCTGGAGTGCAGTGGCATGATCTGGCTCACTGCAACCTCCGCCTCCCA
```

FIG. 14D

```
CGTTCAAGTGGTTCTCCTGCCTCAGCCTCCTGAGTAGCTGGGACTACAGGCATGCACCAC
CACGCCTGGCTAATTTTTGTATTTTTAGTAGAAACTGGGTTTCACCATGTTAGCCAGCC
TGGTCTGGAACTCCTGACCTCAGGTGATCTGCCTGCCTCGGCCTCCCAAAGTGCTGGGAT
TACAGGCATGAGCCACTGCTCCTGGCCGGCCTACATCATTTTCTAAAGCTCCAGACCATT
CTTTTCTTTTCTTTTCTTTTCTTTTCTTTTCTTTTCTTTTCTTTTCTTTTCTTTTTTCTC
TTCTCTTCTCTTCTCTTCTCTTCTCTTCTCTTCTCTTCTTTTCTTTTCTTTTTTGAG
TTAGAAGCTTGCTTGTTGCCCAGGCTGGAGTGCAGTGGCACCACCTCCACTCACTACAA
CCTCCACCTCCCAGGTTCAAATGATTCTCCTGCCTCAGCCTTCAGAGTAGCTGGGACTAC
AAGTGTGCGCCACCACTCCTGGCTAATTTTTGTATTTTTAGTAGGGACGAGGTTTCACCA
TGTTGGCCAGGCTAGTCTTGAACTCCTGGTCTCAAGTGATCCGCCTGCCTCAGTCTCCCA
AGGTGCTGGGATTACAGGCGTGAGCCACTGTGCCTGGCCTCAGATCATTATTTTCTGTTA
GCTTTAAACTGTCCGTTCAGGAGATCCCACTGCATCCTCAAATTCAAAATATCTAACACT
GAGCTTATGATTTAGCTGGTTCTGTCATTAGATGGGAATATCCTTTTATTTCCTTGAAAT
TATATGGTGAGAACAGGGAGAAGTGCTGATGGTAAAGTCCTGTGATTAAGATAGCAATAA
GGACTCCGCCCTTCCCACTCCACTGAAGGTTGAAGAGCCATGGACAATGAGAAGTCACAG
TAGGTGAAATCAGGTACTAAAATGGACTTGGCTTGAGAGATCAAAATTGATCACTTGGTG
ATACAACTAACAAATTCATGTTAACTTGAACCTTTATTACCCTGTGAAGCATGGTGATTA
AAAAAAAACAACAAACAAACAGGAAACTTGATTGTTAAATTCTCTTTAAGTCAGAATATG
TACCTTAGAGTTTTTATTTATGCTTTTGTCTACCATTAATATGTCTGCACCTGCTCTTTA
GAAGTTAATAGAGAGTAAAGTCGTCTTTATGTCTTTCAGTGCTTACTTATATTTGGGAAG
TTGAGAAAAATTTTTAACATCATTATTGATATATATATATATATATATATATATATATAT
ATATATATATATATATATAGATAATTTTTTTTTTTCTTGAGACGGAGTCTCACT
CTGTCGCCCAGGCCGGAGTGTGGTGGCGATCTCCACTCAATGCAAGCTCTGCCTCCCAGG
TTCAAGCGATTCTCTTGCCTCAGCCTCCCGAGTAGCTAGGATACAGGCTCCCACCACCAC
GCCTGGCTAATTTTGTAGTTTTAGTAGAGACGAGGTTTCACCATATTGGCCACGCTGGT
CTCAAACTCCTGACCTTGTGATCCGCCCACCTCGGCCTCCCAAAGTGCTGGGATTACAGG
CGTGAGCCACTGCGCCCGGCTGAGGTAAAATTTAAAGTGTACAATTCAGTCATTTTTAGT
ATATTTATACTAGTTGTACAGCCATCACCACAATCTAAGTTTAGAACATTTTCATTAGGG
GGTGGGAGAAATTTTACTCTGCTTTTTAGATTAAGTTTCTGTCTGGATCTAATCATTTAA
TCAGACAATCAGGCAGATTGTCTGTGATTAGTTTTGGCCATTCCAGCTTCTTCATTGGTT
GTTAACTTTCACAAATAAAGGCTGCTCAAAGATTAGAAATAACATTTAATTTGAATGTAA
ATGTGCCATAGTTTAAAAGATGGGTTTGGTGAATACAGTCAAATACATACATTTAAAGCT
CTAATTCTGAAGATTATGTAAAGAAAAGGAAAGAAATGTAGGGAGAGGATTGAAATGTTC
ATGGTATAACAATATCTGAACATCCATCTGGTCACACCGTTGGTATTTGAATGTTTTGTC
CTCCTCAAATTCATATGTCGAAATCCCAACTCCCAAGGTGATCGTATTAGGAGGTGTGGT
CTTTGGGAAGTGATTAGGTCATGAAGGTGAAGCCTTCATGAATGGGATTCGTGCTCTTAT
AAAAGAGAACTGTGAGAAATAAGTTTCTGTCGTTTGTTAGCCACCCAGTTTAGGATATTT
TGATATAGCAGCCTGCATGGACTGAGACAACTATGAGTTATTATGATAGCTTCTGTTATT
TCACCTAAATTCATAGAAGCTAATATATCAATATTTATGCTATGAAATATTTCTTAACCA
AGCTTTGAATATATTTATATTTTTGTTTATTTTAAATTTCAGATTCCAGATGACCTGAG
GAAGAGACTAAATATAGAAATGCATGCCGTAGTCAGGATAACTCCAGTGGAAGTTACCCC
TAAAATTCCAAGATCTCTAAAGTTACAACCTAGAGAGAATTTAGTGAGTTCAAATATATA
TGTTACATCAAAATTCTTTTACACGTTTTGTAAGATTTCTAGTTGCTTTAGCTAAGTAAT
AAGAATGTTGTATTCCTTTTTGATACAAATCTTTTTTTATTGTGTTAAACTATATATAAC
ATAAAATATGCCATGTTCGCCATTTTTAAGTGTATAATTCAAAGGCATTAATTACATTCA
TAATATTGTACAACCATCACCACTATCTATATCCAGAACTTTTCCATCACCCCAAAGAGA
AACTTGGTACCCATTAAACAATAATTCCCCGTCCACTCCTTTCCCCAGTCCCTGGTAATC
TCTAATGTATATTGTGTCTCTATGAATTTACTTATTCTAGATATTTCATATATAAGTAGA
AGTATGCATTTGTCTTATGTATCTGACTTATTTCATTTAACATAATGTTTTCAAGGCTCA
TCTGTGTTGTATGTATCAGAATGTTATTCCTTTTCATGGCTGAATACTATTCCATTGACT
GCATATACCACATTTGTTTATCCATTCATCTGTTGATGGACACTTGGGTTGTTTCCACAT
```

*FIG. 14E*

```
TTTTGGCTGCTGTGAATAATGCTACAGTGAACATTGGTGTACAAGTATCTGTTTGAGTTC
CTCTTTTCAGCTCCTTTGGGATATACCTAGGAATTATGTTTAACTTTTTGAGAAGCTGAG
AAATCTTTAATAAATGATAACACAAATACTTATATTTGCCAATGCAAATATGAATATTTT
TGGCTTTTAAGAGATTGATCATTTTGCCACGTGGTTGTAATTAAAAAAAATTGTCCCATG
TTGTTTCAGTATTAATATTGTAGCCTAAAAGAGTGCTAGACTGTTTTACTTTTTACTCAG
TTAATTCTTTGGATACTGGTAGAGTCAGGAAATGAGATATTGAACTTAAAGATCTTTGCA
GGTGGGGTCCAGTGGCTCACACCTGTAATCCTAGCACTTTGGGAAGCTGAGGTGGGAGGA
TTGCTTGAGGCCAAGAGTTTGAGAATAGCCTGGGCAACATAGCAAGACCCCATCTCTACA
AAAAAATTAAAAAAAAAATTAAGCCAGGCGTGGTAGCTCACGCCTGTATCCCAACACTT
CGGGAGGCTGAGATGGGTGGATCACTTGAGGTCAGGAGTTGGAGACCAGCCTGGCCAACA
TGGTGAAACCCCATCTCTACTAAAAATACCAAAATTATCGGGGCGTGGTGCTAATCCTGT
AATCTCAGCTACTCAGGAGGCTGAGGCAGGAGAACCACTTGAACTGAGGAGGTGGAAGTT
GCAGTGAGCCTAGATCTCACCACTGCACTCCAGCCTGGGTAACAGAGCGAGACTCTATTT
CAAAAAAAGTAAAAATAAAAATTAGACACATGTGGTGGCACATGCCTGTAGTCCTAGCTA
CTCAGGAGGCTGACTGAAGTGGGAGGATCTCTTGAGCCCAGGAGTTCCACACTGCAGTGA
GCTATGATTGTGCCACTGCACTCCAGCCTAGGCAATATCTCAAAAAAAATTTTTTTAAAT
AGATTATTAGGCCAGACGTGGTGGCTCATGCCAGTAATCCCAGCACTTTGGAAGGCCAAG
GCAGGCGGATCACCTGAGGCCAGGAGTTTGAGACCAGCCTGGCCAACATGGTGAAACCCC
ATGTCTACCAAAAATACAAAAATTAGCTGCAATGTCTATAATCCCAGCTACTTGGGAGCC
TGAGGCAAGCGAATCGCTTGAACCCGGGAGGCAGAGGTTGCAGTGAGTGGAGACTGCGCC
ACTGCACTCCAGCCTGGGCGATACAGCGAGATTCTGTCTCAAAGAAAAGGAATTTGTTT
TCCTGTCTTTATCGTAGAGGGAGGAAAGGGAGAATGGGGTTGGAATGGTTATTGAGTGAG
CCACATTATGGTAGATGTATCACTGGGCATAGAGAAAAGGAGCATTTAAAACTTTTCCGC
CTAACAGATGTTTCTTCAGGCTACACTGCACTCATTGTGCTAACTGTAATGTCAAATCCC
AGACCTGTGCCTATAGAACATGAACATCCTTCATTGGATTTGTTTGGTCAGGCTTACACT
TTATTAGGAAGATCAGATGTTAAAATAAGGGTGTTAAAGTTAAGTTCAGATATGAGGATA
ATTCATTACTATTCCTTTTTCTGGCAGCCTAAAGACATAAGTGAAGAAGACATAAAAACT
GTATTTTATTCATGGCTACAGCAGTCTACTACCACCATGCTTCCTTTGGTAATATCAGAG
GAAGAATTTATTAAGCTGGAAACTAAAGATGGTGAGTACATTTGTTATTTTGACTTTTTT
TTCTATTTAAATAGTTGTACATTTTTAATTGTTCTTGCAACCTGTCATACCTGTGAACAG
TATGTGAATAGTGAAATATAATTATGATAATTAAACAGTAGTTTTTATGTATTGAAAAAT
ATCTTTGGCCGGGTGCAGTGGCTCATGCCTGTAATCCCAGCACTTTGGGAGGCCGAGGCA
GGCGGATCACTTGAGGCCAGGAGTTCGAGAGCAGCCTGCCAACATGGCGCAACCCTATCT
ATACAAAAAAATACAAAAATTAGCCTGACATAGTGGTGTATGCCTGTAGTCCCAGCTACT
TGGGAGGCTGAGGCAGAAGGATCACTTGAGCCCAGGAGGTCTGTGTTCCTGCCACTGCAC
TCCAGCCTGGGCAGCAGAGTGAGACCCTGTTGGGGGGAAAAAAAAAAAAGTCTTTAACTT
AAATAAATTTGACATTTAAAATCTTAAATTATTTCATCTCTGTTTCAGTACTAACTCTGC
ATTTATTACTTTCTTTTTAATAGGACTGAAGGAATTTTCTCTGAGTATAGTTCATTCTTG
GGAAAAAGAAAAAGATAAAAATATTTTTCTGTTGAGTCCCAATTTGCTGCAGAAGACTAC
AATACAAGTAATAGCATGTTATTGAATATTTAATAAAATACTATTTGTTACATATGATTG
ATAATAAAGTATGAAGTTCCTTGTAACACCTTGCATTGTGAAGTGTATTAAAAACCTGCT
AAGAGTAAGGAATAACTTGATTTAAAATATTTTATTCTGTAATCTCTTTAAATTATCTGT
ACAAATTATTGACTTAACCTAAATTTAAAAATGAATGCCTTAGCACAATTAAGTTCCAAG
AATAGAGTTGATCATGTTAACTGGTAAATGGATCATGATTTAAAATTCTTCTAGGATTGA
AACAAATGAAAACGTAGTTTTAAGGGTTTGATTTTTAAATTCCTATTTTTACATGCAAT
TTTACTGCACAACCCATCTTATTTTGACAGTTCTTAAATTCGCAACTCTTCAGAAATATT
ATCAGATCACTTTTCTTTGCTTCCATAAGTTTTTTATTATTATATTATTATTTTTTTTT
TTTAAAAGACGGTGTCTCACTTTGTCGCCCAGGCTGGAGTGCAGTGGCATGATCATGGCT
CACTGCAGCCTCGACCTCCCAGGCTCAGGTGATTCTCCCACCTCAGCCTCCCAAGTAGCT
GGGACCACAGGCGAATGCCATGATGCCTGGCTAATTTTGTATGTTTGTAGAGATAGGG
TTTCACCATGTTGCCCAGAATTGTCTTGAACTCCTGGGTTCAAGCAGTTGTTCTGCCTTG
CCCACCCAAAGTTGTGGGATTACAAGTGTGAGCCACTGCGCCCAGCTATTCTAGAAGTAT
```

*FIG. 14F*

```
TTTAAGAGTCATCTTTTTTTTTTTTGAGATGGAGTCTCACTCTGTCACCCAGGCTGGA
GTGCAGTGGCACACTCTCGGCTCACTGCAACCTCCACCTCCTGGGTTCAAGTGATTCTCC
TGCCTCAGCTTCCCTAGTAGCTAGGATTACAGGCGCATGCCACCATGCCCTGCTATTTT
TGTAGTTTTAGTAGAGACGAGATTTCACCATGTTGGCCAGGCTGCTCTTGAACTCCTGAC
CTCAAGTGATCTGCCCTCCTCAGCCTCCCAAAGTGCTGGGATTCTAAGTGTAAACCACCA
CACCCAGCCAAGAGTGGTCTTTTTACAATATTATTTTTGATTAGGACATTCATTCTTGT
CATAAAATTGAAGATACTCTAGTCATTTAGAATTTCATTGTTTTGGAACTAGACATTGTT
TCTTTATTTTTGAAATGTTATTGAAGGAATACCATTTGGAGAAGATACAAATGTAAGAAT
TGTGAAAAGGATAATTGTGACACAAATCAAAATTATAGATAAAAATATACCTGTAAAATG
TATTAAGGCAATAACATTCTTTCTGCTTGTTGACCATAAATATTTATATTCCCTGGATGG
GTACATTGTTATTGTCAAGGGTGTTTAAATAATGATCTTGCATGCATAATTTATTCTCTC
TGGTATAACAGAATCAGCAATTTAGTTTTCTGGGACCCGAGAAAAACATGCAAAAGACAT
ACTTTGAAATGTAAAACTGATTTTTCCTTGCAACTGTAGGTCCTTCTAGATCCTATGGTA
AAAGAAGAAAACAGTGAGGAAATTGACTTTATTCTTCCTTTTTTAAAGCTGAGCTCTTTG
GGGTAAGAAGTTATGGCCAAACTAGCATGTTAGACATGTTTTTAACACTATATCTGGCAG
AGTTTTCAATGTAAATATTAAAGTAGATGTTAATGTCAATAAGTGATCTTAATAATGCAT
CAGTAGATATTTTTTCAAGGATTGTCTCTATCTTCACGCCTAGCTTATAATTTGCCTTGT
CGTCTTTTTTTTTTCTCTTTATTTTTATGTTTTTATCCATCCCTGGTGGTAGGGGATAA
CCTTGTCTTCTTCGATAACAAGAAGTCTGAAGCTTATTAGAAATTTTACTTTGAGAATTG
ATCGATGAGAAGAAAGCAACTAGATATCACGTGGATCATATATGCTTGAATAAAACAATA
ATTCTTAGAACAAATAAATACATTTAAAAGTTAAAGCCAAAAACATTAGTTGAATGTTT
AAAAATATTTCAAATTAAGTTATTCCTTCACTGTCTTGTATTACTGTAATAATTTGGATT
ATTTGTGTTTTTCTCAACTTTTAAAACAAATATTTAAAAAATTCCTCTTTTGATTAAGTA
GGGCTAGATAAAATATAAAAAATATTTTTAAACTCCTCTTAATTTCCATATTTCTTATA
TAATATGAGAATCTCTTATAAACACTACCTCTTAGAAGTCTCCACAGAAGCTTTGGTAGA
TGTAGTAGTAGGGATTTGATTTCTTAGAATGGTATAATCTGTAAATGTTTAGTAAAAGG
ATTAAACGATAAAGTCAAAATGTTTATAGCACAGTGTTATTAATATAAAATAAAATCTC
TTTTTTTTTTTTGAGATGGACTCTCACTTTGTCACTCAGGCTGGAGTGCAGTGTTGCAA
TCTCAGCTCATTGCAACCTCCGCCTCCTGGGTTCAAGCAATCCTTCCGCATCAGCCTCCT
AAGTAGCTGGGATTACAAGCATGCACCACCACACCTGCCTAATTTTTGTATTTTAGTA
GAGATGGGGTTTCACCATGTTGGCCAGGCTGGTCTCAAGTGATCCGCCTGCCTCAGCCTC
CCAAAGTGCTGGGATTACAGGCGTGAACCACTGTGCCCAGCATAAAGTAAAATCTCTTCA
GACTCTCATGTGATCATGTAAAGTGGCAGGCAGTCACAGTCAAGAAGTAGTTTAAAGTTC
ATGTTTGTAAAATATAATCTACAGATTGATACTGGATTTCATAGGTAATGTTTAAGAGAA
AATAAGTTTTTAGTTATCCTCAGTACTTCAAAAGCACCCATTTATGATTATGTTGATTAC
TAAACTAAATCATTTGGGGGCTAGAGGTGTTTTTTTATGTGTTAAGATTCCTTAAGGAGT
TCTATTAGGGCAAAACTTTTAGTAACTGCATATTTAAAAGTAATAAAACTAATTTTAAA
AGCTTGGAGGCTGGGCGCGGTGGCTCACACCTGTAATTCCAGCACTTTGGGAGGCCAAGG
CGGGTGGATCACTTGAGGTCAGGAGTTTGAGACGAGCCTGAGCAACATGGTGAAACCTTG
TCTCTACTAAAAATACAGAAATTAGCCAGGTGTGGTGGTGGGCACCTGTAATCCCAGCTA
CTCGGGAGGCTAAGGCAGGAGAATTGCTCGAACTTGGGAGGCAGAGGTTGCAGTGAGCCG
AGATCATGCCACTGCACTCCAGCCTGGGTGACAGAGCAAGACTCCGTCTCAAAAAAAAAA
AAAAAAAAAGCTTGAAGTCAGATTCGACATTAATCAGTATACTTTCTCTCAAGTAGGGG
ACAATTTCTAAGATTTTAGTCTTTTAAAATTTATTAACTAGTCTGAGCATGGTGGCTTGT
GTCTATAATCCCAGCACTTTGTGGGCCGAGGCAGATGGATCACTTGAGCCCAGGAGTTG
GAGACTAGCCTGGGCAACATGGCAAAACCCCGTCTCTACAACAAATGCACACACAAAAA
CCCAATCAGCTGGGTGTGGTGTTACACTCCTGAAGTCCCAGCTACTCGGGAGGCTGAGGC
AGGAGGATCACCTTTGCCAGGGCGTTTGAGGCTGCAGGGAGCTGGGTTCACACCACTGCG
CTCCAGCCTGGATGACACAGCAAGCCCCTTTCTCAAAAAAAAAAAGATAAAAAATTAAAT
TAAATTAATTAACTACACTGGGAAGGCAAAATTCAGCATTTTTTATAGCTAAATTTTAT
CCTGCTTCAGTCTTTTATCATGTAACTATGTATATTTTTTACAGAGGAGTGAATTCCTTA
GGCGTATCCTCCTTGGAGCACATCACTCACAGCCTCCTGGGACGCCCTTTGTCTCGGCAG
```

FIG. 14G

```
CTGATGTCTCTTGTTGCAGGACTTAGGAATGGAGCTCTTTTACTCACAGGAGGAAAGGTA
AGTGGTTAAGGTGTGTTCATTTTTCTGTAACATTTAATAACTTTTCATTTATCTTTCTTT
GGGTTTTGACCATCTATTATATAGGGTGGGTTTTGACCATCTATTATATAGGGTTTATAC
GACATATGGAAAGCATTCATTTATTCACTAATATTTCTGTGTGTCTGCTTTTAGGTGTTG
GGGGAGTGATGACGAATAAGACTGATGTTCTCCATGCCCTTTTTCTGTGTCAGTTGATAC
AATTATATGGTTTTTCTTTTTAGGCTATTAGGTGTTGATAGGGTTGAGTAACTTACAAA
TGTTGAACCAGCCTTGCATACCTGTGATAAATACCACGTAGTTGTGGTGTATCATTCTTT
CTACATTGCTGAGTTTTATCTGCTAATGTTCTGTTGAGCTTTTGTCCATTTAAGTTTGAA
AGTGATTAGTTTGCAGTTTTCTGTTTTTGTGTTGTCTTTGTCTGGTTTTGCTATCCGTGT
AAATCTGGCCTCATAAAATGAGATGGGAAGTATTCTCTCCTCTTCTTTTGTTTTTTGGA
AGAGGTTGTATAAAATTGAGGCTGAATCTTGGTGGTTGCCACAATGACAGGAACTATTTC
TGTGACTGAATATATTGGGAATTCCTATAAAGCAATTATTTTCTAGGGAAGTGGAAAATC
AACTTTAGCCAAAGCAATCTGTAAAGAAGCATTTGACAAACTGGATGCCCATGTGGAGAG
AGTTGACTGTAAAGCTTTACGAGGTATGAGTATGGTAACACTCTATATAAATCCCTTTTT
CATTAGAAAGACAGGAATGTTATACATAATGCTGTCAATCTAATAAATACACATATCATC
TAGTCTTTAACTTTTCTGTTTATCATTTAGTCATTAAAATTTCTTTGGCTTTCTAATGTT
TTTGATAAAATTTCTAAAACTCTCCATATTTAATGGAGGCCTATTTTTTTTCTAGCCAG
AACTTTTTGTAGACTACATTTCTGGAAGTGCTCACTGACACCACTCTGAAAAATTAGTAC
TTAGAATATACTCTAATTGGTATAAATGATCTCTGAATTGCTATGGAAAACTGGGAGAAT
GGTTGCTTCAGGGGAGAGAAAGTAGGAGGCTGTGGACAGCAATGAGGAGAATTACAGTTC
ACCATATAACACTTTTGTACTTTTAAAGTCCTTAACATTTACATTATTATCTATTCAATT
AAAAAATATTGGGAAGATTTTACTTTGAACAGTTAATTTTTCCCCATGGGTACCGCTGT
CATATAGTTCCAACTAATCATGAACTTGTGTATTTCCTGTTCTTTGTAAATTTAAACTTT
GTAACTCACCAGGAAGTTTGAAGCCAAATTTGTGTTTCAAATATAGCAACTCCAGGATCT
CTAGGCAGATGCATTTGCATTTGATTTTAAATGAATCTTGATCCCTTACTCTCACTTATG
TTTTCCCACATCCTACTTTTTTATTTTGTTGTAAGCCATCTAAAATTCTCAATGGGATG
AAACTGGGTATAAATGAATACATGCATACAGGAATTATAGTAGCATATTCCTTTTCTTTT
TTCTTTTTTTTTTTTTTGAGACAGAGTCTTGCTCTGTAGCCCAGGCTGGAGTGCAGTGG
TGCGATCTCGGCTCACTATAGCCTCCACCTCCCAGGTTCAAGCAATTCTCGTGCCTCAAC
CTCCCGAGTAATTGGGACTACAGGTGCATGCCACCACACCTGGCTAATTTTGTATTTTT
TAGTAGAGATGGGGTTTCACCATGTTGGCCAGGCTGATCTCAAACTCCTGACCTCAAAGT
GATCTGCCTGCCTTGGTTTCCCAAAGTGCTGGGATTACTAGCATAAGCCACTGCACCTGG
CCTCCTTTTCTGAGTTTTATAAAATTTGATACTTTACTGCACGCTTTGAGACTGTATTAA
TTGAACCATGTTGATGAACAAGTTTTTGTGATGGGTATATTAATAAAATATAGATCAAAT
TTTTATAGTTAAATCAATATCGAGCTTTTCTAGTGCTTTCAAAAGGACAACCTGAATTTT
CCCAGCACTGAAATGATACTGAAACCATTTCATATCTTCTGTATTAAGGAAAAAGGCTTG
AAAACATACAAAAAACCCTAGAGGTGGCTTTCTCAGAGGCAGTGTGGATGCAGCCATCTG
TTGTCCTGCTGGATGACCTTGACCTCATTGCTGGACTGCCTGCTGTCCCGGAACATGAGC
ACAGTCCTGATGCGGTGCAGAGCCAGCGGCTTGCTCATGGTAAATGCATCCACCACTGGC
TTAAGGTCTTGTTCTTTTGTCAGTCAGCATTTTAGTCTTAACAATAAATCTACTCTCTT
CAGAGAATAATATATGTGTTATGTTAAGTGTTGTGTTTGAGGCCCCTGATGGCATTCTAC
AGTTGTCCTATAGACTGTAATAGCAAAATTGGTAGAGTAAAAACAGTGTGAAAATTCTGC
AACTTCATGGTTAGTCCTTTAGGGTTTTTCATTCTCCCTTACTTATTGTTTAATTTACAG
ATTTACTCTTTTGTTCATTTGACAAATATTTGTCAAATGCTTGTGCACAGTCTGTATTCT
CAAATTCTAGGAGAAAAAGAAGGGTGAACAGTATTAGCGCAGAACGATACTAATAATGAT
GGCTACTGTGTATGAGTAGCCAGCCCTTTCTTGGCTTTCTTGGATTGCTTTGTATTCTAC
ATGAAGATATTCCCTGGGCTTTACAGGTCAATAAATGGAAATTCAGAGAGATTAATTTGA
CCAGGGTGACCAACAAGGAGATGACAGCATACACTATGCGAGAAGTATACACAGAGTAGT
GTAGGAGCATATAACCTAAACTGGGGGTGAGGTGGGATAAGGAGTTATCAGGGAAGGCTT
TTTGGAGGAGTTGACAACTGAGCCGAGTTTTGATGGAAGAGTAGAAATTAGCATGAACCA
ATTTCATGCTAATAAAGAAGCAAAGGAAGCGTGGTCTACAGGCAAAAGCACAGAGGTACA
GGAAGTAATGATATGTTGGGGAATACCCTGTTGACTGGAGCTTAGAGTGCAAGGAGAGGA
```

*FIG. 14H*

```
GTGCTAGGGAGGTGAGGTTGGAGGGTTTGGCAGCATTGACTTGCTTCAAGGTTCTTAAGA
GCTGAAATAGATATAAAATGCAACTAAGAGTGGCTTGGATTATTATTACCTAGTGTGTTA
ATCTCAAATTTTGAAATCTATAGCATCTATAGGACTGGTGTTACTAATCTTACACTCGAT
CTGTTACTGTTCTTATACTAGATCTATTAGTCCAGTGTTTAAGGGAGTGGTGCAGATTTC
TAGGTCAGGACAGGACTCAGATGTACATTATTAATGCCTATTTCAGTTCTGACCTTCTCA
TATGAAACCTTATAAGACCTGGGGTAGGAAGAGATTGTTCTGGAAGTCATAGGAATATGA
ACTGTATTTTGTTTAACAAACAATACAGTATGGAAATTTATCACCCTTCCAGAATATTTA
TTTCAGAGACAAATTTTTATCATTCGTTCATTTATTTCATAAGATCCACGAGTAGGGAAC
CTCACTAGACATTGCTCTGAGTATATGGTCTGAGTTTGCAGTACCTCTTGTGTCTCCATT
AGATTTATTAGGTCCTCAATAGATAAATCAGGGAATAACTAGATGGATTCATTTTTTAAA
GACATGAAAGAGCGATACCATACATACTGCACCTTAAAGGTCAACCTTAGAGTATCATTA
TTTTTAATGAATGTATAATTTTTAAATTTCATGTTTACTTTTCCTAAGCTTTTGCACTAT
ATTGCTTAATTCCAGCTTTGAATGATATGATAAAGAGTTTATCTCCATGGGAAGTTTGG
TTGCACTGATTGCCACAAGTCAGTCTCAGCAATCTCTACATCCTTTACTTGTTTCTGCTC
AAGGAGTTCACATATTTCAGTGCGTCCAACACATTCAGCCTCCTAATCAGGTAATACACT
ACTTGTAAGGATTATTGAATTATGTCCCTTTTATAGAAATTATTTTTCAATTTTATTAGT
AATTCGTGGCTTTAAATTTATGCTTCTCTTAATGATTTTAAGGATATGTAAGTCAACATT
TGGTGCATATTGTGCTAGAGGCATAAATTATAATTTATAGCCACCTGAAATGTTAGTATG
CGCTTTCCAAGAAAATGACTTTTTGAAAATGGTATTTCTTTGAATGAGAAAGAACAGAG
AGAAATAGATAGATGGCTTTTAAACACTTCATTAATTAAACTTTTTTTTTCCACCATCAC
ATAATGGCACTTAGTCCCCTTTGGGAACTCATGAGGGTTTTAGTGGTAGTGAGCTGAAAG
AAATATGTTCCAGGACTGGCAAACATATTCTAAATTCTTTAAAATTTTCACCTAGCATCT
ACCCTAAATATTCAGACCCTGTGCTAGTTAACTGCTATTGAAGAACAAAGGTATTATATC
TATTATTAAGGATAATAGAATGGTATTTGAGATATTGGTCATTGAATATGAATATGTTTT
GAGAAATAAGTTTTATAGGAACCAAAAAAAAATTCTTAAAGGAACCATATATTACTAAAA
ATGCTTCTTATTGGAGAAAGAAATGACAATCATTTATTAATGTGATTTTTTCACAACTTT
ATTAAGATATAATTTAAGTACAACAAACTCACATAAAGTGTACAATTTGATCAGTTTTAA
CATATGTAGATGCCATGAAACCATCACCACAATTAAGGAAACAAACATTTTCATCACTCC
AGAAGTCTCCTAGCCCTTTTACTACCCATTCCTCCCCTGCTCCATCCCCAGACAACTACC
AATTTGCTTTCTGTCACTATAGATTTGTCAACCTGATTTTCTCCAAATATACATTCAAAA
ATATACAGTTGAATACAATTGGAAATTCGAATTTTGTGTTTTTTCTTTAGGAACAAAGA
TGTGAAATTCTGTGTAATGTAATAAAAAATAAATTGGACTGTGATATAAACAAGTTCACC
GATCTTGACCTGCAGCATGTAGCTAAAGAAACTGGCGGGTTTGTGGCTAGAGATTTTACA
GTACTTGTGGATCGAGCCATACATTCTCGACTCTCTCGTCAGAGTATATCCACCAGAGAA
AGTATGTTTTACTATTAAAACCTGAACTTGGAATCTTCTTTCTATTGTGGAGAAATGTAA
TTGTAGTAAGACAAGAATTAAATATATTCCATTGTAGTATTTGAATAAGCAGTTATTTGA
GTAGAAAATTAGTGTTTCCAGCTAAGATGATGGCATATTTTGAAAATTCATATAGTGAAT
ATAACTAGTAAAAGAAGTTTTGTTTATTTTAAACAGAATTAGTTTTAACAACATTGGAC
TTCCAAAAGGCTCTCCGCGGATTTCTTCCTGCGTCTTTGCGAAGTGTCAACCTGCATAAA
CCTAGAGACCTGGGTTGGGACAAGATTGGTGGGTTACATGAAGTTAGGCAGATACTCATG
GATACTATCCAGTTACCTGCCAAGGTATGTTTAAAAAAAGAAAAAGTGAATACTTACTCC
CAGAAGAACCACTGTATTATTGGCTTTGGCTTTATGTGTCAGCTTGCCCAATCTCCGTGT
GAGTCAACAAGTGTTTACTGAGTTACCAAATAAATGTCTTAACACTATTTTAGGTACTTT
AACAAATTTTAATTTTATTAATTAATTTTTTATTAGAATTGAGACCTCACTCTGTCATCT
AGGCTGGAGTACACTCACAGCTCACTGCAACCTCAAACTCCTGGGCTCAAGCAATCCTCC
TGCCTCAGCCTCCCCAGTAGCTAGAACTACAGGCATGAACCACCATGCCCGGCCAACTCT
TTAATTTTCTTAGAGACGGAGTCTTGCTATGTTGCCCAGGCAGACAGATTTTAATGTGTA
TGATGCAGTCTTTGATGATAAGAAACTTATAATGGAAAGCTGAGGTGATAGTTACAGTAA
ATACATTTTGATGTATAATTCTGTTTGCTTTAATCATTCAAATTGTAGTAAAGCAAGATG
AACTGTCTGCTGGGATTTGAGCAGAAATGGATAGGAATAAACTAGGAGGTAGAAGAGTTA
TCAAGGTTCACAGGACTGATGGGTGAAGCTAGATTTCCAGACCCGGGATGTCAGTCCTTG
AAAAGCAGACTTGGCAGGCATAGACGAGGCAGATAGCAGGATAAAGGAGACAAATGTAGA
```

*FIG. 14I*

```
GGCTCTACTTTGGAAGCTCTTATGAATCAGAACTTGGAAATGGAACCTCTTCTGATTTGG
TATCTTGTGCAGTCATCATTATACAGTTCTGAAATATAAAGCTATATGTTGGTGTAAAGT
TGCAGTGATTTCTCTCCTAACCAGCCCCACATATTCTTCCTGGTTGGTTGGTTCTTCAGT
AAAATAGTCTTGTTTCTTGCTTACACTAATTGGTAATTTGCATTCCTTGTTAAGATTTTC
AAGACAGGGCTGGGAGCAAGGAACCAAAGTAGCGCGTGGTTGTGATTACCTTTGGTTTCT
TTGAGGTTTCTCTTACCTAGTGGCTTTAAAACATCTTTAGGAGCAGTTCCATTTTATAGT
AAACTTAAATTCTGTTATCATGAACAGTTGAGGATAATGAATAATTTGATACAATAATGT
AAGAAATTCCTGAAAACAAAGTGTTATCTGTGATACTTTTGCTGCATAGTAAGCACAATG
AAGTGTACTGATAATGTTTCAACAGGAAAGTGTTTTGATTAAATGTGGGCAGTATCACTG
TTCTACTAGCATTCAACATCTCTTCTAAAAATTAATAGTGGTTCACTGTAATTTTATTGG
TACATGTAACATCTGTACATGTGTTTGGTTATCTATATGTTTCCTGGTTTTTTGTACATT
TGCTTTATTAATTTAGGCTTTTTTTTTTTTTTTTTGAGACAGTCTCACTCTATCATC
CAGACTAGAGTGCAGTGGCACAATTATGGCTCACTGCAGCCTTGACCTCCTGGGCTTAGG
TGATTCTTCCACCTCAGCCTCCTGAGTAGCTGGGACTACAGGCACATGCCACCATGCCCA
GCTAATTTTTGTATGTTTTGTAGAGACGAGGTTTCACCATATTGCCCAGGCTGGTCTCAA
ACTCCTGGGCTCAAGCTATCTGCGTGCCTTGACCTCCCAAAGTGCTAGGATTACAGGTGT
GAGCCACTATGCCTAGCCTAACTCAGACTTTAAAAATATAAAAGCAATTCATTTTATTC
CCAAGAACAGTAAGGTGGTGGTTTAATTTTAGTCTTTAATTCTGTTTTTAATTTATTCTA
TTTAGAAATGTCCCAGAAACTTAGTATAACTTTACTTTCTGAAAATGAAGAAACCTGTCC
TTGGGCATTAGTGTGTTGGATTTAAGCAACAAAGTTAAAAAAACCTACCCTGTGTTATGG
CAATTTTCACTTGATGGTGGTTCTATAACACAGGTATCAGTGAACCTTTATAAAAGATGA
ACAACTTTTCAGCTTGCTTAATTTCAGTTAATTAACATGTATACTTATCTATGTTAATGT
TTTATTGCTTAAAATGTTTAATTTTTATATTTGGTAAACAGATAGTTTTTCTCTCCCCC
TCTTCCTTCCATCTTTCATTACTACAATTTACCATGCAGAGCTCACAATGTCTCTCTGCA
CCAAGCTCCATGACTCAGGATTTGCCTGGAGTTCCTGGGAAAGACCAGTTGTTTTCACAG
CCTCCAGTGTTAAGGACAGCTTCACAAGAGGGTTGCCAAGAACTTACACAAGAACAAAGA
GATCAACTGAGGGCAGATATCAGTATTATCAAAGGCAGATACCGGAGCCAAAGTGGAGTA
TGGCTTTTTCCCCCTCATTATAATTGTTAAAACTTCTTAAAAATTGTTTCACCCTTTTGA
TATATATTTCTTTGACTTATAAACGAGCTATATTTATAAACAAGGGACCAGAACACATTA
ACTCAGTCATGGTTATGTGCTTCCTTGCTTTCAATGTTTCATTATCTTATAAGGAAGAGA
ACGTATGGTCTCTTGAAAAAACTGACAATAAGAAGTAACAACTGGACTACCACATTTTTT
TTTACATCCTTAATTTAACTCTTCGTCAATTTCTTTTTTTACTTAAGGAGGACGAATCCA
TGAACCAACCAGGACCAATCAAAACCAGACTGGCTATTAGTCAGTCACATTTAATGACTG
CACTTGGTCACACAAGACCATCCATTAGTGAAGATGACTGGAAGAATTTTGCTGAGCTGT
AAGTAACAGATTCTGTTTTGGAAGTACAGCTACTATTACAAGTGACATAGTATTACACTT
AAACCTTTAAAGTTCGTGTTTAAAATAAAAATATTTTGAATATTTAAAAGCTAATTCAAA
AAATATGTGTCGTAGCTATGCATTAAAAAACCCCAAAATGTCAGAAGTACAGAAGTCAAA
ATTGAGTTTTCATTAACCAGTTCATTTGATTATATTTGAATTATTCATAATGGACTCATT
TAATTTTAGTAACTTTGGGCTGGGTGCTGTGGCTCATGCCTGTAATCCCAGCTCTTTGGG
AGGCCAAGGCAGGTGGATCACCTGAGGTCAGGAGTTCGAGGCAAGCCTAACCAACACGGG
GAAACCCCATCTCTACTAAAAATACAAAAATTAGCCAGGTGTGGTGGCATGTGCCTGTAG
TCCCAGCTACTTGGGAGGCTGAGACAGGAGAATTGCTTGAACCCAGGAGGTGGAGGTTGC
AGTGAGCCGAGATTGCACCACTGCACTCCATCCAGCCTGGGCACAGAGCGAGACTGTGT
CTCAAAAAAAAAAAAAAAAAAATTTAGTAACTTCGAAGAAATAAGAAGGAAAATTAAAAGT
TGAAAGTGATTCTAATGTATAGTTTATAAAATTTTGTTATAAAAATACCTGTTTTGCCTT
CAAAATAATTTATATTAATATTTTATTGACCTCAAGAACATTTAAATACATTCAGATTTA
TTCATTTGTGGACCACATTTGTTATACATTGGATTTAAAGGATCCTTGCAATTGAGTTTA
TGGCCACCTATGCATCTGAGACCCATGGACTGGGAACCATTCTAGGTCAATGATTCAGTG
TGATTCAATTTAAGAGATGTTTATTCCTGGTCTTTAGAAGCTGCTACCTTTGTTATCTA
ATTTTGCAGTACTTTGAAGTATGTATGTATGTGTACATACGTTAGTGCTATGTATTTATT
AAAGAAGAATCAGAAAACAGAGGTAAGGAAAAATAAGGAAACAAATTTCTGTTAAGCCCA
CCACCTCCCAAAGCATATTTGTTTATATGCTTATATATGTTTCCTATTATGGTAAGAAC
AGTCTGTACATATTGCTATATAGCAGTCCCCCTTTATCCACATACATCCTGAAAATTGTT
TTACATTTTAAATGTTAACTACTTTATTGTTTTTAAATGTCATTTTATAGTGTAGCTATG
```

*FIG. 14J*

```
GTGGTTGAATATTAGAAATTCCTTATTTTGGTCACATATCCTGATCAGTAGTTGGTCTTC
TGGAGATAGTGATTTTTCACTAGAGATGACTTTAGGACCTATTCAGGTTTTTTTTAAGAT
CCCAATTTAAGGAAAGACTATTCTCATTATTGATTTGCTATATGCAGGGAAATTTATTT
CGAAAGGTTTTTCAGTTGGCTTTTAGGGAAGATTATATATTCTCTTTTTTTTTTTTGGC
CTTTTCCCACATGTTCTAAAAATGATATATTCTTTAACTCCTATGAAAATACATTGTTTC
AGTAATTGAAGATGCTGATTAAAGTCATATCTCTACACATTTTTTAAAATTTGAGATAGA
TGGGACTTTGTCCCTTCTTACACCATTCACTTATTCACTTGGAAAAACTATTATCCAATA
CTTATGTGGCAGACACTGTTTCTGGCACAAGGGATTCAGCAGTGAACAAAACTGCCTTTT
TGGAGTTTACATTCTACTAGTGGAAAGCGACAACAAGCAGATAGACACATTCAGTATATA
ATTCACTGTCAGATGGTGGTGGTAAGTCCTATGTAGGAAGAAAAGCAGGGTAAGGAGGCT
TGGAGTAACTGGAGTGAGTCATAGATGGACTTGTCAGGAAAGGGTTTCTGAAGAGGTGGT
ATTTGGGCAGAGATCTAAATAAAATGAAGCAACAAGCCATGAGAATATCCGGGGAAAAT
GTTCTGGGCAGAAGCATCAAGCATAGAACTTGTGGTATGATATTTATTCTAGCACACATT
AATTTTAAAAATGTATAAAAGACATCCATTTAATCATATTAAAGATTTCCATGATTCATT
TAGACTTAGTCAGAAACCAAATTTATATTTTCTTTTTAAATAATTTTATCTCAACTCTTA
TTTTACCCAATAGGGGCCAGAGTTACTCAGCAAATACATTGGAGCAAGTGAACAAGCTGT
TCGGGATATTTTTATTAGGTTGGTAGCCTATGAATGTTTTTAAAGTAACTGACTCTGTTA
TTATTTATCAATCAGTGCTTTTTTTGGTCTTGTTTTTTGAAGAACTGATATTTGAAACCT
GTGGTTTATGTGAATTATTAATAAGCTAGAGGACGTGGATTCTCTATTTCATCAAATAAT
ACAAAACATTTTAGATATTAAATTTTGGAAATTATTTGGTTTTGTTTTACAATAGAAATA
CTCCTCAAAGTGGAATCGAAGTGGTTATTCAAAGAAATCTCAGAGTAGATTCTTATATGA
AGCAAATAATTGCCCCTAATTTATCTCTAAATTTTGTAAGTTCTAAATTCTTTTTTCCCC
CAGTTTCTAATTTATCTCTTATAAGTCAAGAGTCCATCTGGCCAATTTAATTTCAGTGAG
TGTAACTATTTTGCATATATTAAAAACTGTATATGAATACAGAAGATGGTATTTAAGGA
TGAAAATAATTATTCAAATGTGATAGCATTATGGGGAGTTTTAAAATAAAAGTTACTGTT
TTATTCTTCCAAAAATTTTATTATAAAGTATACAGTTAAGAGAATATACATAAAATACAT
ATGCAGCTTAAGGAAGAATAATAAAATGAATACTTCATGTATTCACCACCGAGTTTACCA
GGAAAAAGCATAAACAAAATAAACCTCTTCCACGTAATTCCTGGGTTAAAGAGAAGTTAT
AGTGGAAAATATTTGGGAGCAAACGATAATGAAAATACTATCCATTAAAATTGTTAGATG
TTGCAAAACTGATTTCAAGGAAAATTTATAGTGTTAAATGTTTAGAAAAGAAAAAAGGTT
AGAAGTTAACCACTTATGTATCTATCTCATGAAATTAGGAAAATTATAGATATAAACTAA
AAAATATGTTAAAAGGGAAATAATAAAGATAAGAATGAAGTTTAATGAAACACAAAACAG
AGAAGCTCACAAAGCCAAGATTTATTTTTGAACACCGAGTACAATTGACAAATCTCTAA
CAAGTTTGATTAAGAAAAAGAAAGCATGAATAAACAATTTTAGGGATAAAAAGGGAAAC
ATCGCTAAAGATATCCCAGAAATGTAAAAGATAATAAGGGAATATTATGAAAATATTCAT
GCCAATACATTTGAAAACTTAGGTGACATAGACAAAACAAAATTGACCAAAATTGAGCA
AAAAAGAAACAAAATCTGAGTAGTCCTGTAACTTAGTAAAAATTGAGTTAGAAAAGTTAA
AGAAGTCTTTACACAAATCAAACATCAGACTCAGTTTTCTAGGAGAGTTTTGCCAAACAT
TCAAGTAGCAGATAATTCTGGTCTATTTTGGCCCCAGAAGATATATTTTACTTGCCATG
CATTTAATGAGATAGCTGTTGATTTTTTTCAATCACCGTGACAGGTGTTTTATATTAGGT
GTTATTCGCCAGACATCTAGTCCACCTGTTGCCAGATATGGAATTAATATTCACTTATTT
TGAATTAAAATTTGTTAATAAATTAATAAAACAAAGTCAAAGTTCAAATTATTAAAAAAG
TAAAAGAAATAAAATATATTTATAGAGAGCCCTTACAAAACAGTACCAACATAATGAGC
TTTCCAAATTTTGAATGGGCAAAATAAATGAATAGGCATTTCACAAAAGAAGGAAGGGTG
GCCAATAAGTATATATTAATATAAAAATGGTTACTTGTAATAGGAATCAAAAGTGTTTGA
CTTATTGACTAAGAGTCAGTTTTTGTTTTGATCCCTGTTAGTCTATCCAGAAGGCATGGG
TCTTAATAAACACCTTGACCTCAACAGTTTACTGAATACAAGGGTAATTTCATATGCCTT
GCCTTCTTTAAGGGTTTGTTGTAAAGATTAAAATAAATACATAAATATATATAAATACAT
TTATATGTATTTATATGTAATTACATACAACTTGCCTTCTTTAAGGGTTTGTTGTAAAAA
TTAAAAGAAGTATATAAATATATATAAATACATAAAATAAATACATTCATATATGTATAT
GAAATCACTTTGCCAACTATGAAGCCTGATTCAAATATGAAATGTTGTTTGTTTTTCCCA
GAGCACAGGCTGCAAAGCCCTGCATTCTTTTCTTTGATGAATTTGAATCCATTGCTCCTC
```

FIG. 14K

```
GGCGGGGTCATGATAATACAGGAGTTACAGACCGAGTAGTTAACCAGTTGCTGACTCAGT
TGGATGGAGTAGAAGGCTTACAGGGTAATAATTATAAATACAGAAATAGAATGTTATAAC
AAAATGTCATCATGTCATCAGATTTTGGTAAAAAAATGTTCTTTTTTCCTCTAGGTGTTT
ATGTATTGGCTGCTACTAGTCGCCCTGACTTGATTGACCCTGCCCTGCTTAGGCCTGGTC
GACTAGATAAATGTGTATACTGTCCTCCTCCTGATCAGGTGACAATTTCATATTTAGAGT
CCAAAACCCAACAAATGCTACACTCTTTCCTTGTGAGCTTTACTTCTGCCAGGTAATGGC
AATTGTCCTTAGAAGACCAGCTTTCTTAGGGAAAAGCTTTAGCCACTGTTTGCTCAAAGC
ATAAAAGATTCTGAATTAGATGCAAAGCCTTTTTTTGGCCCAGTGCAAGTCTGAAAACT
TTGTAATCCTTCTGTGTTGGCTGATTGGGGAAAAAAAATGCAAGAAACCTAATGTATTA
TATTTTCACATTATCTTCTGTTCAAAGATTACATACTTCCATTATCCTGTCAAAAAAAA
ACTCTGATACAGAATCAAGCATGTGAATCGTAAGCATGTAAGCAGGTTTCATAGAGATAA
TTTTTCAACTCTTCCTTGTCCTGTGTTGTTCCAACTCTTATTCTCCAATTTAGAAGCAAA
CAAATAAATGAATGAAAGAACAGATAGACAAATGAATAGTCAAAGGTATAAAGTATCTGT
ATATATGTTACATGTAGCTATTATTTAAATTATTTAGATTTTCCTTTTGAAATACCTTCT
TGGCACACTTGCCTAAATCTAGAAAATAAGCACTGTGTGAATAAGAAATTATTTACACTG
AATATTTTGTAGGTTTTTGGGTTTTTGTTTTTCAGACAAGGTCTCACTTTGTCACCCAGG
CTGGAGTACACTGGTACGATCACAACTCACTGCAGCCTCTATGGCCCAGGCTCAAGCAAT
CTCCCCACCTCAGCCTCCCGAGTAGCTGGGACCACAGGCACACGCTACCATGCCCAGATA
ATTTTATTATTAATTTTTGTATAGAGATGGGGTCTCCCTGTGTTGCCCAGGCTTTCTTGA
ACTCCAGGGCTCAAGTGATCCTCCCACCTCAACCTCCCAAAGTGTTGGGATTACAGGCGT
GAGCCACCATGCCCAGCCTTAAGAGTGTTTGATTTTCATTCATTTTCCTATATATATTAT
TTCTGTTGGGGAAAAAATTCCAAGGAAGATAAATAGTAGGCTGTTGGTACATTTCTCAAC
TTACTTATAAAGCTTTTTAGATATATAAGGTTAATTTATGAAGAAAATCATAAGATACAC
AATTTAAGATAATATTTTTAATTTTATTTTTTATTTGTTAAATAAATTTTTCTCCTTTCA
GGTGTCACGTCTTGAAATTTTAAATGTCCTCAGTGACTCTCTACCTCTGGCAGATGATGT
TGACCTTCAGCATGTAGCATCAGTAACTGACTCCTTTACTGGAGCTGATCTGAAAGCTTT
ACTTTACAATGCCCAATTGGAGGCCTTACATGGAATGCTGCTCTCGAGTGGACTCCAGGC
AAGTTATATGAGGAAGTTGTTATGACATTTTATGAGTGATAAAAGAAGTACAATGTCAAA
ATTTCCACCTTAAAAAATGCTATTTTTAAACAACTTTGGTAAAACTGTATAGAAACATA
AATTTACCTTTAGTTGAATGTTCCATAGTTGGAATATGGGTTTTGCAGAGAATTTATAAT
TATGAAGTTTGATGTCTGTTTCTTTAACATTACCTTAATATTGGCAAAACATGTTGGTG
TTTGCAAGGATATTATTTAAATTGGGATACCATGAATTAAATACTACAAACAAAAATAAT
TAGAGTTTTTTGTTTGTTTGTACTTTAACTTTTAAAAAATAATCAGTTAAAGTTGTTGTT
TTGAAGCTCACATTGTTCCAATCTGGCCAATAGGAGCCCCTTTTGTATGGCTCCTGTATC
TTTATGACATGTCCTCATCATTCTTGAATCACTTCCTCACTTCCAGATACAGTAAGTTAT
TCTTGGCCAGGTGCAGTGGTTCACGCCTGTAATCCCAGCACTTTGGCAGGCCAAGGCAGG
AGGATCATTTGGGCCTAGTTTGAGACCAAATCATGGTTGCACAAACTGTACCCACTATGG
ACAACAGAGTGGGATCTTGTCTCTGTGAAAAATTTAAAAATTAGCTGGGCATGGTGGCAC
ATACCTGTAGTCCTAGCTTCTTGGGAGAGGCTGTGGCAGGAGGATCGCTTGAGTAAATCC
AGGATGCAGTGAGCCATGCTTGTGCCACTGCACTCCAGCATGGATGACAGAATGAGACCC
TGCCCCCAAAAAGAAAAATATTCTTGGTTTATCTTGTACTTTCTGTATCCCAGCCCTAG
CATCAGCCTTTTCTCTAAAGACAGTATTATGATTTTAATATTTACAGTAGATATTTGAAC
TGTTACATTATAGACTTTACCATATATTTTCTAGGAAGGATTATTCTATTACTCTTCTTT
ACCACATTTGTTTGGAATGTCTACAGAACCTACAGTTTCTAAATCAGAAACTCCCTAGGT
TTTTGCTATTTTGGCAAGCCATTGAAGTTCTTCCCTCTCCCTTTACTACCAGAAAGGTGT
GTATTTGTAGAGCTCTCTATAATGAGAAAGCACTCTATAACATGGTTGATTCATCATTTT
GGAGTAGAAAAGTATGAATGGAAAGTCAGAGACATAAAAATAAAGCCCAGAGGTCTGAGT
CTTAGCTTCATTACAGACTTTCTTGGGGGATGGTTGGTAAATTATCTACACATTCTATCT
TGTCTTTATAATTTTAATAGTTAAATTTTTACCATGTGCCTCAAAACCGTTAGAGAATTA
ATGAGCTCTTTGAAAAATGCTTCTAAGTTTCTTGTATTGCTCTAATAGAATGCTATCTAT
GTTATTATTTATTTCTGAGACTAAAATTGTTTACATCTTTAAACTGGTTGTCCTTTTGTG
TATTTTAGGATGGAAGTTCCAGCTCTGATAGTGACCTAAGTCTGTCTTCAATGGTCTTTC
TTAACCATAGCAGTGGCTCTGACGATTCAGCTGGAGATGGAGAATGTGGCTTAGATCAGT
CCCTTGTTTCTTTAGAGATGTCCGAGATCCTTCCAGATGAATCAAAATTCAATATGTACC
```

*FIG. 14L*

```
TTGTTCTTCAGAAGATCAGATGGTAGAGTCTAGGAGGTAGTGTGTTTTAATCAGAGATCT
GAGAGGCAAAGATCATTGCATGAGATCAGGGACCCATGCAAAGGAGTGAGAAAAAAAACT
GGGTTAAGGAGCCTGCTGCATGGCAACTCCTGGGAACAGTGGCCACTGGGGCCTGGGACA
TGTTGATTGCAGCCCAGGACTGTTAAAACCAGTGTGAGAGAACATGGGTATGGAAGTACT
AGCTAGCAGGATCATGACCCCGATGCTGGGATGGGGCATCAAGCATTAGTACATGGAGAT
TCAGTACATCCAGATGCAGTACATGGAGACTATATGCGTAACTGCTGACTTTGGGCTTCT
TTCAGATTGGAGCAGAGGTAGAGGTGAGTGGGAATATTCTCAATAGAGGGAACTAAATAG
GCATACCTAATAAAGGAGACCAGGATATTGCAGACAGTAGCCTCATGTTTGGCTCACCTG
TTCAAAAAGTTCTCTTGTTCTTGAGCAGTGGTGCCTTAAAAGGTAACTTGAGAAGCAGTC
GATTATTTGTTCAGCCTGGAGACTCTTGGGATATTTTACTATCTTTGATTGAATAGATTT
AAATGTACACAGCTCTCATAACTTGCCCCATGAAGCATATCCATGAAAGGCACTATACTT
GTTAAAAGATTGGTTTGTACTTTTTAAATGTAGTACTTTTAATAAAACAGGAAAAATAGA
AGTTCTGATGCAGTTATATGCATTTTATATAGAATGTGTTCTTAATTGGAAAAAATTTGT
CGTAGTTCCTTTGAGTTCATTTACAGTTTTTAGTAGGAATTGTATTTTCTACTGTTGTAC
TTGCTGTTACTAAAGAAAGATGGTCGTGATTACCATCTGAATTTTTTTTCTATACATTGA
TCTTTAGCTGCTACTTAGTCATTTCTGTTTAGACTTGAGCTCTTTTTCATATTTTTTTTT
TTTGTTTCTCAGTATCCAGAATTATTTGCAAACTTGCCCATACGACAAAGAACAGGAATA
CTGTTGTATGGTCCGCCTGGAACAGGAAAAACCTTACTAGCTGGGGTAATTGCACGAGAG
AGTAGAATGAATTTTATAAGTGTCAAGGTATGTTGTCTACTTATCTTCTTTTTTTATTTA
GGTAAAATTAACATAAATGCAGTTAGCCATTTCAAAGTGTAAATTCACTGGCATTTAGTG
CATTCACAATGCTATGCAACCACCACCTCTCTCTAATTTCAAAACTTTTTCATTCCACTC
CTCCTCTTGCTTATCCCCTGGCAACCATTCATCTGCTTTTTGTCTCTATGGATTTGCCTT
TTCTGTATATTTCATATAAAACAAATCATGCAATATGTGACCTTTTTGTCTGGCTTCTT
TCACTTATGTAATGTTTTCATGGTTCATCCAGGTAGTAGCATGTATCAGTACTTCATTCC
TTTGCATGACTGAATAATGTTACCATACTTTGTTTATCCACTTATCAGTGGTGAACATTT
GAATTGTTTCTACCTTTTGACTATTATGAATAATGTTGCTGTAAATATTCATGCACAAAT
TTCTCCACGGATATGTTTTCATTTCTCTTGGGTATAAACTGAGGAGTAGAATTCTTGGGT
CTTAGGGTAATTCTCTAACTTTTCAAAGAACCACCAAACTGTCTTTCACACCAACTGCAC
CATTCCCACTAGCAGTGTGGGGGGTTCCTGATTCTCCACATCTTTACCAACACCATTATG
TTTCTCAATTGTGGGCTAGTCTCACATTTGGAAAGCTAGTGGGAGCAGCGATCCATCTAT
TAAAAGTTGTATGAAATTGAGTAATGAGCCACCTCTCTCTTGTAGGGCTTATTATGTTCT
TGCTTAAGGCAATCTTCATGCATTGTGAACAGAATTATACATAAATGCTCAGATAAAAGG
GCAAACCATTCTTAAAGGGAGTAGACAACTAGAGGCAGGAGACCATACTGAGGCAGGAAG
CTGGGGTTTTTATGGTTCTGTTACTTTTGACTATATCTCACCATTGCTTTTGTCAAAGTG
AGACTAGGTCTAAGTTTTTTTCAGGTATAAGGTGAGTGTGGTAATTAAGGGGCATGCTAG
CAGATCATTTTGGGTAATGCTTCACAGTCCACCACTGGTGTGTCATTGTGGTCGCAGATC
CAGTATCTTAGCTGTGTAATTTCAGACATCAGCAATATTAGTTTAACAAAGGGCAATTAG
ATTCCAAGACAAAGGAATCGTGTATTATTCTAGCCTTATTCAAACTTGATTTATAAATCA
GTTTAGTAATTTATTTATTTGTTTCTGTATTTATTTTATTTCTTTGAGATGGAGTCTCA
CTCTATTGGCCAGGCTGGAGTGTAGTGATGCAATCTTGGCTTACTGCAACCTCTGCCTCC
TGGGTTCAAGCTATTCTCCTGCCTCAGCCTCCCGAGTAGCTGGGATTACAGGCTAATTTT
TGTATTTTAGTAGAGATGGGGTTTCACCATGTTGGCCAGGCTGGTCTTGAACTCCTGAC
CTCGAGTGATCTGCCCGCCTTGGCCTCCCAAAGTTCTGGGATTACAGACGTGAGCTACCG
TGCCCAGCTCAGTTTAGTAATGTATAACTGGGTTTTACCCAGTTGTAAATTACTCTTTTG
TCGTGTTTTTTTGAGAACTGGCAATGACGGAGAAACTAAAAGTGCCAGGCTGTTGCCTTG
TTCCTGTTATTTTGCCTTAGTTTTTTTTTTTTTTTTTTTCTCTGAGACTGAGTCTTG
TTGTGTTACCAGGCTAGAGTGGAGTGGCATGATCTCGGCTCACTGCAACCTCTGCCTCCT
GGGTTCAAGTGATTCCTGCCTCAGCCTCCCGAGTAGCTGGGATTACAGGCGCCTGCCACC
GCACCCGGTGAATTTTGTATTTTTAGTAGAGACGGGATTTTACCATGTTGGCCAGGCTG
GCCTCGACCTCCTGACCTCATGATCCACCAGCTTCGGCCTCCCAAAGTGCTGGGATTACA
GGCGAGAACCACCGTGCCCGGTCTTGCCTTAGTTATTTCTTGTTCCCTCCTCTAGTCCTA
TAGTTCTCTGACTGTATTGAGGAAATGTAATTAAATATTATTATGTTAATAGATATTTAT
```

*FIG. 14M*

```
CCACAATATCCAATTTTTAGACATTTAAATTGCTCCCAGGCAATGTGGTAATGAACATTC
TTGCAGCTGAATATATGCACATATCTAATTGTTTCACTAGGATAGAGGTGGAATTGTATA
ACAGGGAGCTCACATTTTTAAGGCTTTTGAAATGTATTGCCAAATTGCCTGCCAGATAT
ACTGCACCATCACTAACATTGTGTGTTGCAGTATTTTCTAAACTTGGCCCTTTTGATTT
TAGAAAAATGATATCAATAATTTACATTTCTTTGATTAAAGTGTAGAAGTTATAATTTTT
CATATTATTCATTGTCATTTGTATTTTATCTTTTCTAACTTGTCTCTTCATCCCCTTTGC
TCCGTTTTCTATTGGAGTGCAACTTTATTTGTAAGAATTCTTTTTAATTTCTGTGACTGG
AATTTTTTTTCTAGTTTGTTATTTCCCGTTCATTTCTTAAAATATAATTGTGTTTGCCA
ACAATCCATTATCTTTTGTTTTGTAATGGTAGTATTTATACATATTAAATTATCTCTTTC
TTTTTTCAGATATGAAAGCTTTCAAAATCCAAAGAGGAGAAAAAATCAAGTGGAACAAT
GTTTCGACCTGGACAGAAAGTAACTTTAGCATAAAATATACTTCTTTTTGATTTGGTTCT
GTTAAGTTTTTTGATGGCTTTTCCATATGTTGTAACAGGAAAAAATGGTGTCTATGAAT
TTCTTCTTAATTTAACAAATTTGGTTAATTTATAAAATCACAGATTGGTAAATGCTATAA
TTATGTAATGATCAGGATTGAGATTAATACTGTAGTATAAATTGGGACATTATAACAGAT
TCCATATTTTATTTCCTAAAATCTAAATTCAGTCTTTAATGAAATAATATTAGCCAAATG
GTGGAACTAATTTATTTCTTTTGAGGAAAAGATAATAAAGAATGTAATTAAATTTAAATT
TCTTGGAATTCCCAGTTGTATATTCATCACCTTTGTAGCATTTGACAAATTTTATGCTTA
GCAGCTTCTTCACTGTTTTGAAATAAAATATCCTATTACCTACTGATACAATTATCTGTT
CTTTGTATATCAAAAAATGTGAAATTTACACATAATTCAAATACATTTAATTATCCGCTC
AACCAGAAATGAAATCACATCCCTCTACTATACTACATCCAGCTCCAAGCCCAAGATATT
TAAATGACATCCATTCCTCTCCTAGTTCCAGTTATGATTTTATCTTGATATTCTCTCATA
TATGAACTAAATTATAAAGTTAGCCACCATCAATACAATCTGCGTATCTAATATCTTAAC
TATATAGTAATGGGGTAAGGGAACAGCAAAAGGAGAACATTAATTAAAATATACAAGTA
AGCCTGGGCAACATAGTGAGACCCCATCTCTTAAAAAAAAATTAGCCATGCATGATGGT
ATGCCTCTAGTCCCAGCTACTTGGGAGGCTGAGGTAGGAGGATCACTTGCTCCCAGGAGG
TTCAAGGTTCTAAACCAGCAAAGCTCAGAATCCCAGGGGATAGAAACAAAGACTTAGTGG
ATCACTAGTATTAAACTGAGACACGTCACCCTGCATTGCACTTTGTTTCTCAGTTCTTTG
ATGAAATCACTGAGCTGACATACCTGCCCTCTTTTCACCATAAAGTGAGTTTCATGATCA
GAAGCAATGTCTATGGATAGCCTAACAAACAATGTAAAAACCATTTAGTAAGTTCATGA
AGGGTGGTGGTGGTAAAAATTTGGAGAACATACAAAACAAATACAATTCCAAGGTGTGTC
CCCTCCAGGAAGGACAAATTGCTGCCTGCTCTGTGATAGAAGAGGATCAGATGTAATCAA
CCTGCCGTCAGACTTGGGCTGTTCTCTCCTGGGTGTGGACTTGCCTGGTTGGTCACTGCT
GCTGACAAGTAGGCTGTCAATATAGCTGGGTTGTCATGTCAGCTGTGGTGAGGGGGAAGT
CCACATTGTGGAGGCCACATCCCTGCACTCTTGGCCAATTTGACCATGAATCTTAAGCAC
TGGGGTGGCTGGAAAAGACAGCCGATTGACATCCATACAGAGGTCATCTTGACCACTTGA
TTAGTATAAGCACTGAAGGCTTTTAACTGAGCATTCACATAGGACACAAATATTCTGATT
CTTTGGGCCCATTCCAAGAACTCTGGGCATACTTTTCCTCCAGACCTCATACCCAGTTGT
GTTCTTTCCAAATTTCTGGTCATCTGGTTATGTTATTAGCCACTATCTGTGAATCAGCAT
AGATTTTTATATCAGACATCTCTACCTCCTGACAGAATGGAGGAGATATGTTACTTAACA
ATTCTGTTCCCTTGGAAGATTTCCTGTCTCCACTGTTTGTAAGGGCTACTCCCTCAATGT
AGCAGTAATGCTTTCACTCTGATGGGAAGTCACAGTGGAATTCTGGGTCTCCAAGAATTA
GTGTTAGTGCATACACAGTGTCTGATAATCCCCAGAGTGTCTGGTGCCCTTGGATCCTGT
GAAGAAGGCTTGGAGAAAAGAAGATTCATGGCAAGAACTTGTGATGTGATGACAGGGCCT
TTTCTCTGGCTCTTCATTCTTAGTCTGACCTAGGTGTGAGAATTAGGTCAGGGGCCATGA
CTATATTGTGGTGACTCAAACCAGGCCTTTGTTTACTAACTGGGAGATTTTACATTGTA
AGAATCAAGTAGGATCTTTGCCCATGTATTTTGGTCTTAAGAACACAAATGATATGGCTC
CAATGACTGGAGGAACACCAGGGTCCTTGGTCTCACGCTGATTTAGATAAAACGACTGTC
AGGCCTCTGAGCCCAAGCTAAGCCATCCTCCCCTGTGACCTGCACGTATACATCCAGATG
GCCTGAAGTAACCAAAGAATCACAAAAGCAGTGAAAATGGCCTGTTCCTGCCTTAACTGA
TGACATTCCACCATTGTGATTTGTTCCTGCCCCATCTTAACTGAGCGATTAACCTTGTGA
AATTCCTTCTCCTGGCTCAAAACCTCCCCACTGAGCACCTTGTGACCCCGCCCCTGCC
CCTAAGAGAAAACCCCCTTTGATTATAATTTTCCACTACCCACCCAAATCCTATAAAATG
GCCCCACCCCTATCTCCCTTCGCTGACTCCTTTTTCGGACTCAGCCCGCCTGCACCCAGG
TGAAATAAACAGCCTTGTTGCTCACACAAAGCCTGTTTGGTGGACTCTCTTCACACGGAC
```

*FIG. 14N*

AAGCTTTAGTAGAGATCTCAAAATGGTTGGATGGTAGCAAATTACTAAGAACTCTCAAA
GTTTCTAAAGCCTTAGTTTCAGCTTGCTAGAAAACCTATGTTGAGTATTATGGCTAGTTC
CATAGTTGAGTTGGGAAATGTCTTTGAGGAGACACTTTTTCACTTTGTATTCATCTGTAC
ATTTTCTGTTACTTGCATTCTGTCATGCTCAGGCTATTAGAGCAGGTACATTTTTATAAC
TGGAATGTTTATGTGTAGTGAAGCTCTGAGAGGACTTTGCATTAGATCTCAGCAGCATAA
TCAGAAGGTTGTCCTTTGTCTCAGCAATTTTTAAGCTAATAGTAGCAGAAATTGCAGTGG
AAATAGACTGCTTTGCCACAACATTCAGAAAATCATTTATCTTTTTATTGCAGTTCTTGT
CACCAAACAATACATTTAGTACTTCTCAAATTGCAGAACTCTCATAGGGCTGGGAAAAT
GCCTGTAGACACATACATACTATGAATGTGCTAATGTTTTTGTATTTCATAGCCCATC
AAAGCTCCTGAGTCAGTTTCCACTATAATCACTGCAGAATCAATCTTCTACAAGGTAAGC
TTTTGTAGAGTTACTGAAGGAAGAGTTGGGCCTAGTGGGTAATGTGCCACTAAAATGTTG
GATTAGTCTAAAGGTCTCTGCTACTCTTTATTTGTATAAGGTGTGATTATACTTTTTGTT
CCCTTCTTAGCTGTTTTCCCCCATAAGTGGCTGTTATTAAAACATCTCATCTAGAGCTGA
AGTGGGAGGAGAAAGTGCCTACTGACACATGATGTGAGGATCTTAAGTATTTTTTTTAG
TGTAGATTGTAGGAATTATTCTAAAATGCTGATTGTATAGTGTGGAGCCATGGAAGACT
GAGCCGTTAGTGCGATGGCATTGAAGAATGAGAAGGACAGAGACAGGATTTGGACTAGTA
GAGGTTGTCGACTGTGGTGTCAAATGGGTAGAGTAGGCCCAGAGATTCTAAAATGCCTTT
AAGTGGAGTTGAGCTGAGTAAGGGCAGTAGTGAGGATTAACACCTACTAGAAATTCATAG
TGAGAGGAATTCCAAGATGTTTTGATAAAAGAATGAGGAGGTCAGGTTTCCCAGGGCCAA
AGTCCATGAACATCTGATACCTCAGTGAGAGAAGTGACAGATTGTTGTGTTTAAACCAGA
AGTCTTAGGAAAGGAATTAGAACATAGACCCCCAAGGCTCGGCAGGCCTGGCACGGCACA
GGCAGCAACCATTGAAGGCTATTTGGTGTTCGGGATCTGAACTGTCATTTAGGGGACAG
TGGTGTGAGTTAGTACTTTATACTTGACCCAGGTGGACTGAGAAACTCAAGTGATGATGC
CCTTAAGTATACTTTTTTTTAAGCCCACAATCTATATAGTCGAAGTCTGTTCCTCCCAAC
AGGGGTACACTGGCATTCCTCAGCAGGGCTGGAAAAACCAACAACAAAAAAAGTCTGTA
CACAGGCAAACATCTCTCTTATTTTTCCAACATTTAATACATTGTTAATAAAATATCTAA
AGTTTAGCAAACAGTTGCTGTGTATCAGTGGCTGAGCATTTGCATGCTTTATTTCATTC
AGTTCACTCTATGAGGTGGATACTACTATCCCCATTTTCTAGATGAGAACATTGAGGCAC
AGCGAGGTTAATTAACTTGTCCAAGATCACATAGCCAACAAGTCATGGAGTGAGGCAGTC
TCATGCCAGAGCTTAAGCCTAGAGCATAGTTCCTGGCTCTACAGCTTTAGCAAGTGACTG
GCTATGTGACGAGGACCAACCTCTCTAATGTCTCATCTGTAAAATAGGAATTGTAAATAG
TTACTACCTCAGTGGGTCAAATGAAATCATATGTGTTAAGCACTTAGCAGAGTAAGCACT
CAATGAATAGTAGGAGTTATCACATCTTCGTATTTGTGCATTACCTTCACAGTTTACAGA
TTAAGGCCAGAAGCAACTTGTTGAGCTACGGGTTAGTGTACTAACAGTTTCCATGTGTG
TCTCCATGGAAGGGTGTGTGGGACCTGTTATTGTGACTGTCTGTACTTTCGTATTGTTGT
CTGCCACCCATGTTTATTAAATGATAAGGACAATAATGCAACAAAGTAGTCAAGTAATGT
TGCAAATGCCCAGTATTGTAGTGGCTATCACAGCAGTGCCACTGGCAGGCAGCACCATGG
TGGCAAGTTCAAGAGGTCACTGCCAGCCACTGAGCTAGAGCCCAGATCAGGCATGCAAGA
GGAGCCTGAGTGGGAGCCACTGGGGATCACGGCCAAGAGTGTGACCACCCAAGACCCAGA
ATGGCTGAGTGGCCTCCCTGGAGCATGGCAGTGGCAGAACAACTCCATGAACTCAGATCT
GGTGATGCCTAAACTAGTGCTGTTCTCGTGTGGACCCCTTTTCTCTACCAGAAACCTTGA
ATCCTCTCAGCAAATGAGGAGACTACTCAGATCAGTGACTTAGTCCTGTTTGGTGTTATA
TATGTGTACACAACACAGCACATATTAATAAATACCTACTATGTGCCAGGCACTGCCTAC
CACTGGAATCTTTCACTAAGACATTGTTTTTACTTTGCATTTCTGCCTTTACACTATGAA
AGTAGATGTTTTGGATTCATATTCATTCAGCATACATTTGAATATGCTGTGTTATGCATA
GTAAGCCTATGATAAGCAAGTATTCTCATTTAGAATTTGGGAATATTGATTATACATGTG
GACAAACAAACCATAAATGCAAACTATTTATATGATAAATAACTTTGGACTGATGGCTGG
GAGGAAGGACCAGCTATTGATGGGTAGGAACTAGCAAGTAGCGGACTGTGGCCTGCATAG
ACCAGACCCATCCGTAGTGATCCAGATGAAACAGCCACCCTCAGACACTTGGATAAAGGG
TCCACCAGGAAAAAACTCCTGGCCTATCAGGTGCTATGTTACAGTTCAGTTACTGGAAGT
ATTTCCTCAAAGTGTTTTATGGTTGAGGTACACATTCCTACAGCTTTACCTGCTGCCA

*FIG. 15A*

```
AGTCCCTGTTTCAAGGGAAGCAGCAATGAATTACACTGTTCCCGTAGTCAAGGACAGTAT
ATCTTACCAAGAACTATACCCACTTAAGGAGGTGCTGGATGTCATAAAGATTTGGATCAA
CCATTATGGGTGTTCAGAGGAGAGATTATTTCCAGCTCAAGACCCAGGGAAGAGGACATA
GGATGGATACCAGAGTCATAGGGAGGATTTAACACAGGACATGTACACATTAGTTAGTTG
GGTATAAAGTGGAACAGAAATGAATGAGACACAAAGCCTTGAATGCCAGAAATACTAGTA
GTCCTGTTGTGGAAGGATATAAAACTCAACTGGGAGTGGAAGAGAAAGGCAGCAGTGAGT
CTAGGAGATGTACAGTAGGTTGAGGTAAACATATCCTGAAGACTATAATCCAAAGATTAT
TTTTGGTTTGAATTTGTTTTGGTTTGAATTCATGGTATCTATTTTCTTTGAGTGGATGGT
TGGGGAGGGTGGCATGTAGAATGCATTCTTACCAAATCAGCATGATTTTCAAGACAGTAC
AGAGAAAAGACTGCTGAGCTGATGTAGGAGCTTTGGCTGCAGTCTCTATGGCTTTCAGCA
AGCCGTTTAACCTTACTACTGCTTCATGACTGTGGCTAACAAAGTAGGGATAGTACGGAG
CACAGAGGATTTTTAGGGCGGTGAAACTATTAATACTCTCTTTGTATGATACTATAATGG
TGGGTACATGTCATTATACATTTGCCCAACCCCACAGAATACACAGCACCAAGAGTGAAC
CCTAATGTGAACTCTGGTCTTTGATGATGCTATGTCAGTGTACGTTCATCCGTGTAACAA
GTGTACCACTCTAGTGGTGGGAGGGGTTATTGATAATAGGGGAGGATGTGCATGTGTGGG
GGCAGGAAGTATATGGGAAATCTCTCTACTTCTGCTCAATTTTGCTGTAAACCTAAAACC
TCTGTAAAAAATAAAGTCTATTTTTAAAAAGTGGGGATGGTATTACGGCAATATAAAAT
CAAAATACTTTATGAACAAATCTTTTCTCCAGATGTAAACTGTCATATATGCACCCTCGT
ATGTGTATGTATAATTTTCATTCAAACGTGAAACAACTTTAGAATTGGCACCAAACATAT
AAACACTGATACATTAGACTATCTCGAACACCTTTTACTGACCACTTTGAAAACTTGCTT
ACCTATTAAGGTTCATTCATAGCTGTGATGTTCTATTTTTATTTTCAATGTGGGATTATC
TTCTGTTTCCCCCAGGGAGTATATTACCAAATTGGTGATGTTGTTTCTGTGATTGATGAA
CAAGATGGAAAGCCCTACTATGCTCAAATCAGAGGTTTTATCCAGGACCAGTATTGCGAG
AAGAGTGCAGCACTGACGTGGCTCATTCCTACCCTCTCTAGCCCCAGAGACCAATTTGAT
CCCGCCTCCTATATCATAGGTAAGTTTGACAAATGGCACAGGTTTTTTTTTAACTTAGTT
AACTCTCCAATATTATGTAAAAGAGTGTGTTAGTCAGCTTGGGCTGTCAGGACAAAATAT
CACAGACTGAGTGGCTTAAACAACAGAAAGTCACTTTCTCACAGTTGTGGAGGCTGAAGT
CCAACATCAAGGTGCTGGCAACACGGATTTCTGGGGAGGCTTTTCTTCCTGGCATATAGA
TGGTCACCTTCTTGCTGTGTCCTCACATGGCCTTTCATGGAGTGAGAGCTCTTTGGTGTA
TCTTCTTATAAGGACACCATTTCTGTCAGATGAGGGCCCCACCCTTATGGTTTCATTTAA
CCTTAATTGCCTCCCTAAAGGTCTCATCTCCAAGTACCATCACATTGGGGATTAGGGCTT
CAACATATAAATTTGGAGGGTGGCGGGGGGGATGCAATTCAGTCCATAACAAAAAAAGC
ATGAGTATTATTAAGTACAAAAAAATTAGAGAGCTTTATAGAAAATATGAGGCATTTTAT
GTAGCTGGAGTGTGAGTGCTATCAGTTATTTGAGTTAGAGCAATGTGCATCTACTAAGA
AGTGGTATGGATAAGATTTTTTTGGAGTGACCCAGGGTTAAACTGTACTACAAGAATGTA
TTGCTCAGGAACTAGGTTATTTAGGTTACTTATTTATACAAACCTATTCAAAAATAATTT
AGGAAAGAACTATCCCAGTTATCCCATACTTGCAAATTCTCAATATGTGTGCCTCTGCAT
GCTACACATGTCATCTTAGGCCTTTATAGTATAAAGGCTGATAGTTGAAATGGCAGCTGC
TGTGCTTTTGTTAATTTCAAAGCTGCCAAAACAGTTGTGAGATAGACTCACAAGAATTTA
CTGATTAATACAATTTTTAAAGTTTTCAGATTTTTACAGTTACTTCAGACTTTTTATCTT
TCTGCAGTGAGCATGCATCATTACTTTTGCATCCTGAGAACAAGCATAAGTGTGTTTTTG
GAGAGAACTCCAGGGACAAATAATATACCACTGTTATTCTCACCTATATGTCAAGTTTGA
TACATTACCAAACAATTCTAGCCTTCTGCTTATAAGTATATAGAATTTTTATTTACCTTA
TCTATGGATCAGGATCTCAGCAGAGGCAGTGATGTATCAGAATCACCTTCGGGATTCCTC
TACTGCCTCCTCTTTCTAATCCCCAGATTCTGATATGCATCCTTGTCCTACAGCGAGGCA
GCATGGCATGAGGTCAGAACACCAGTTCTGGAGCCAGACTGTCTAGGTTCACAGCCTGCC
ATTTACCGGCCATGTGACTTTGGCAAGTTCTTAGTCTCTCTTGCCTCACTTTCCTCATA
TGTAAAATGGGAATAATAATAGTGCCTACCTCAGAAGGTTGATGTGAGGAATGAAGGTAT
TGATACATGTAAACTTAGAGCAGTGTGGGTACAAAATAAACATGATGCAAGTGTTCAATC
ACTGTTTTTGGGAGAATGCCATATTCTTTAAGCCGTTAAAGAAGAAAAAATGATTAAGAA
TAATTTCAAAGTAATGCATGTTTCAAGGGCTAATGCCAGGTTGCTCCCAGAGTGGTCTCT
CCCAGTGTCTAGAAATTTTAACATCTTATGAAAATGATATATATGGTCAAAAATGTATTT
```

FIG. 15B

```
AACCTTTCCCTTGGCTGCCTTCCAGGGCCAGAGGAAGATCTTCCAAGGAAGATGGAATAC
TTGGAATTTGTTTGTCATGCACCTTCTGAGTATTTCAAGTCACGGTCATCACCATTTCCC
ACAGTTCCCACCAGACCAGAGAAGGGCTACATATGGACTCATGTTGGGCCTACTCCTGCA
ATAACAATTAAGGAATCAGTTGCCAACCATTTGTAGTTCACAAATTAAAACTGGGTTTCC
AGGCCTGGTGTGGTGGCTCACGCCTGTAGCCCCAGCTATTGCACCACTGCTCTCCAAGCT
GGGCAATGGAGTCAGATTCTCTTTCTTAAAAAACCACAAAAAACTGGATTTCCAGTTCT
CTAATATTCTTAGTACCACAAGATATGTCATAGGTATCTTTAAATGAAATTCTTAGCTGG
AAAAGTGACTAAAAGTTTTTCTCCTGCTACCTAGTAATAAACAAATCATTGTTTATTAC
TGGTCACTTAGAAAATTAAAGGGATAGGGCCAGGCACAGTGGCTTATGCCTGTAATTGC
AGCACTTTTAGAGGCCGAGGCAGGCGGATCACCTGAGGTCGGGAAGTGGATCGCCTGAGG
TCAGGAGTTCGAGACCAGCCTGGCCAACATGGCGAAACCCCGTCGCTACTAAAAATACAA
AAATTAGCCAGGTGTGGTGGCATGTGCCTGTAATCCCAGCTATTGGGAGGCTGAGGCAG
GAGAATCGCCTAAACCCAGGAGGTGGAGGTTGTAGTGAGCCAAGATTGCACCGCTGTGCT
CCAGCCTGGGCAACAGAGTGAGACTCTTGTCTCGGAAAAAAAAAAAAAAAAAAAGGCTG
GGCACAGTGGCTCACGCCTTTAATCCCAGCACTTTGGGAGGCTGAGGCAGATGGATCGCC
TGAGGTTGGGAGTTCGAGACCAGCCTGGCCAGCATGGTGAAACCCTGTCTCTACTAAAAA
TACAAAAATTAGCCAGGTGTGGTGGCGCACACCTGTAGTCCCAGCTACTCGGGAGGCTGA
GGCAGGAGAATTGGTTGAACCCAGGAGGCGGAGGTTGCAGTGAGCAGAGATCGTGCCACT
GCACTCCAGCCTGGGTGGACAGAGCAAGACTCCGTCTCAAAGAAACAAACAAAAATTAA
AAGGGATAGAATATAATGAAATATATTTTGAACTTAAATTATATTCTATATGTGTATCTT
CCTAGGCAAAAGCTGTAATTTCCAGAGAGACCATTAGGAACAGGTAGTATCTATTTTTCT
CCATTATTTATTTCTAGAAACTCATAAAATGGATTGTATTTTTCTATAAGAACAAATAT
TAATTAAGGTATAGATGACTGACCAAGGGCTTAATCAAATAAAATGACTAACAGCATCTA
TCATAAAGCCACACAAGCCTTATGTTCTCATCTCAAAAATGCTGTGACAGCTTTTTGGCT
GCTTTAACCATAAGAAAATGATTGGTGGATGATTTTATTAGCCCAGGCTTTTAAAAACT
TTCATCTAGGCCACGTGCGGTGGCTCATGCCTGTAATCCCGGCACTTTGGGAGGCCTGAG
TGGATGGATCACTTGAGGTCAGGAGTTCAGGACCAGCCTGGCCAACATGATGAAACCCTG
TCTCTACTAAATATACAAAAATTAGTTGGGTGTTATGGTGCATGCCTGTAATCCCAGCTA
CTCGGGAGGCTGAGGCAGGAGAATTGCTTGAACTCGGGAGGTGGAGATTGCAGTAAGCCG
AGATCGTGCCACTGCACTCCAGCCTGGGTGATAGAGCAAGACTGTCTCAAAAAAGAAAAA
AAAGAAAAAATTTTAATTTAATCCTTCTGTAGAAACAGGCATTCAGAACCATTCCATTGA
TCTTAATAAAGCTGCTCTTTACTGTTTCTAGTCAAAAATGAGACTTCGATCAAACCATAA
GATTTTATACTGCAGATAGTCAGCTTCACCAAAGCCGCAGAGGAAACATGTCGAGATCAG
GCTTCCTGCTTGATAGTCTCTTGACTACCATTAAAACGAATATTGGGAGGTCATGAAAGT
CATTGGTAGGCCATTAGCATTGATATCTTTAAAACATCTACCCTAAACCATCTGCTATGG
ACCCATAATAAGAGGCCTGTTGTATATGAAATTGTCTAGAATTCAGGTGCAGGTCTTTGC
CGGTTAAGTAAGGGAGCAACACGTAAAATGGGAGAGGAGTGGGGTGTACTCACTTGCCTC
CTCTTTTGTCCTGATTTAACCAGCATTTTCAACCCTGGGAAAATTTGCAGAATCTAAGT
TGATTGTAATGATTTTGAGCTGCAGCAGCTTTAACTCTTACCCTTTTCCACATAGTTAT
GGTGTTTGAGTTGGAAAGAAACAACTATAGGTAGCTACACGTACATAATTATCTCTTTAT
TCACAAAGGGTATAGTAAAATTGATTGTAAATAACTTTCTAAGTGCCAATATTCAAAACT
TTTGGATTAAAATGTATTTTTCACCGTGCATTTACTTTGGATGTATTTATTTCATTTAAA
CAATTTAAATGGGGCTCTTTAACCAAAATGGTATTTAAAACCAAAACAGTATCGTACTT
AGAATTTGGAGTAGAGGCCGGGCACAGTGGCTCACGCCTGTAATCCCAGCACTTTGGAAG
GCTGAGGCAGGCGGATCACCTGAGGTCAGGAGTTCGAGACCAGCCTGGTCAACATGAAAC
CCCGTCTCTACTAAAAATACAAAAATTAGCTGGGCGTGGTGGCGTGCGCCTATAATCCCA
GCTAGTCTACTCGGGAGGCTGAGGCAGGAGAATCGCTGGAACTCAGGAGGCAGAGACTGC
AGTGAGCCGAGATCGCGCCACTGCACTCCAGTCTGGGTGACGGCATGACTCCATCTCCAA
AAAAAAAAAAAAGATTTTGGAGTAGATTCATCATTAATAAGTAACAGATTTTAGGAAA
ATCAAAAATGGCTAATAAAATGAACACAATGTAAAACATTTATTAAAATGTAGACTTTT
AAAAATCTATAAATTGATCATCTGTTTATAAATTGGCAGATGGTTGTGTACCATCTTTTA
AAATAAAGATTGAATTTCACCCAGTGTGATGGTTCCCATTGCTTATATTTCTCCTGCTGA
```

FIG. 15C

```
GGCCGGACCTGATATGGCCCTGGTCTGTGTTCCCAGCCTTGTTTCCTCATTACCACTAAA
ATCTTTCCCCTGTATGCCCGCCCAATTTTTCTGGCTCTGAGTCCTTGTTCATACTGTTCT
CTCCAATTCTACCTTCCAAAGGCCTTTCTTAACACCTTCGGATTCTTTCTTTGAGAACTT
TCCAGATTCCCATGCCTTTTTGGAATCAATCTCTATCCTATTGTCATCACATTTAAGTTT
CTACTTCCATCATCCTCACTCCTATCCCTTTGGTCCTGGGATGACAGGGATGCTGTGTTT
TATTTACTCATCTTTGTAACTTCCACATAACCTAACCCCGGTTCTTGCTTATGGGAGATG
CTGATTGTAGGGTCTGAGTTAGATACTGTTAACTAAAATGCTTGTTGATATTTTAGTTAT
TAATTCATATTAACTTTGGCTGAAACTTTTAAATTCTATTGTGAATAGTCAAGTAAAATT
TAGATTGTTACATTCTGGGTTAGTATTAGATTGTTTTAAGATTGTTTTAAACAAGATGT
TTTTAAGATGAGTTTTAAATAGTTCTCTTAACACAAATAAAGCTTAATATGAGTATTTGA
AGGAAATTATCCCAAACCATTCCAGTTCCTGGCTGTGAAAGGCTTTTCCAGGCCTAATAA
GTTTTCCACTTCAGCCGTAAGTAGGTGAAATCAAATGAACAATAGAGGGAAATGTATTTA
TTTGCTTTATACACATGCATGTGTGTTGTGTCTACATATAAACATTGCACACGCTTAGAA
TGAAGTTTCTGTCATGCCCAGAAAAGGGAGAGGCATTTTGTGGATTTTGTCTGGCTGCC
CTGGGGATGTTTGAAGAACTGTGCTGTTTACTTCATACCAGGTGTGTGAGCCATACCTTT
GGTAGGAGGGTATACCTCCTACACCCAAGAAATATAAGCCAGGAGAAGGTCTGTGCCAAG
AGAAGGAACCCAAATGACCCACAAGAGGTGGGCCATTAATTATTGGGTCAGATGCATAAA
TGCACAGTAATTTATTTAAGCACCTCTTAATGGTGACCCACAAGGAAGATTGCTCGTAGT
AGCGGAAAGGTTCACAATAAATAAGAGAAAAAAGCAGAATGTAGAACTGTATGATAGCAA
TTCTGCAAACAAGAAGCATCTTTTATAAAAGATGGAAGGAGCCCAGGCACAGTAGCTCAT
GCCTGTAATCCCAGCACTTTAAGAGGCTGAGGTGGAGGATCACTTGAGCTGCAGTGACCC
ATGATTGTGCCACCACTCCAGCCTGGGTGATAGAAGTGAGACCTTCTCTCAAAAAAAAAA
AAAAAAAAAAAAGACGGAAATTCCTCCAGAATTTTAACATGTCAACAGAGGTTTTCTGC
AGCTACTTTTTTCAGCTTTATACTTCGCAGTATTTTCCAAATTTTCTCTAACAAGCAGTA
TTTTCCAAATTTTTTACAATAAGCACACACACACACACGTTTGTTTGCATAAGTGCCC
AACTGGTGGTGAACAACCGCTGGCTTTTAGTCTATACATATCTAGAATATTTTATAAATA
GTAGTTCTTAAACCCTTGAAAGGGAGTGAATGACCAGCTGAGAAAATAAAGTCAGTGATT
TCATTATTTTCCTATATTCACATCATGATTCTAGGAAAGAACTTGGGAGTGACTTCCTTC
AGCTTCAGCCACTCCTGGGCCAGGCGCATGCTTAGCTCTGTGGTAAAGGTCACCAGCTTC
TTCTGCAGGGTGCCTGTATCATCTGAATTGGAGGTTTGGCGAGGGTAAGAGACTGATGTA
GGTTCAAGTTTTTCTTTCCTGTCCTCCACTTGAAATCTGTCTTCCCTTCCAGACTGCCTG
CGCTGCTGACTTAAGGCCCCAACACCAAACACAGAAGCAACAGCCTTACACAGAGTGTTC
AGCAAGCTCCAACAATTGTGTAAGGTAAAGTTTCCTTTATAGATTCCTTTTCTATATCGC
TCCTAGTGGTTCTGTTTCTCTGATCGAATTCTGGCTGATAACAGTTGCTGAGACTCTGAA
AGAGAAGGCAAGGAACTACTGTTTCTCATTATAAACTGTTTAGAATTATTTGGCCATCTT
TTTGCTATGAATATGTAGTGCTTTGATACATTTTTAAATCAAAAGTAATGAAAGAGAT
CACATAGGGAAAGATAGATTGGATTATTTTTAAAGTTTATATACTAAATTGAAAAGCAAA
GAATAAAATGGGAGAAACAGCTCCCTCATGTGGCTGTTGGCAGGAAGCTTCCATTCCTCT
CTGTGGGCCTCCACAGGTTTGCTCACAGCAAATGGTCCGTGACAGAAAGACGCAAGGGCA
GTTGCACCCAAGATGGAAGCCACCATCTTTTCTATAACCTAATCTGAAAGAAGGGACATA
CCAGCACTTCTGCCATATGCTGTTGGGTCACACAGACCAACTCTGGTACAGTGTGAACAC
AGGACCACACAAGGGCGTGAATTCCAAGGGCAGAGACCACTAGGGACCACCTCAGAGGCA
CAGAGGGACACCCTATCCAGCTGGTGGCCAATGTAAATTAACATAGCTTTTTAGAATAGC
AATATGTATCTATAATCTTAAAAGTATTAAAAGTACTTCTTGATCCAGTAATTTCATTTC
TAAGAATCCATGCTAAGAGGATTTAAAATGTGGACCAAAAATGGGTATAAAAGAAGTT
GTTAACAGTATTTAAAGTTGTGAAAAACCAGAAACAATCTAAAGGTCCAACAATAGGAAA
ATGAATTTTGATATTTTTCTAATAGAATTTTATGCTGTCATCAGAAATACCATTTACAAA
TAATTTTTAATAACGCAAAAAAAGTTTATAAAATGTTTAGTGTAAAACCTGGACACAAC
TACATAATGATTCTGATTTTGTAAAAAAAAAAAACAAAACACACACATATACACATGCA
TACATATGCATATAAAGAAAACTGGAACAAACAAAATAACAAGCATAGTTGGAATTACAG
TCATTTTAATATTCTTTATGCTTTTAAAAATTTTGAAGTTTGTATTACTAGCATCCACTA
CTTACGTAGTCAGGAAAAAAATACAACTTTAAAATAGATATTTAGGTCCAAAGATGGTAA
```

*FIG. 15D*

```
TCTAAATGGTGTTACAGGCTGAATGTGTGCCTGATCCCCATGCCCCAAGTTCATATGTTA
AAGCCCTGGCCCCCAAGGCAATGGTATTAGGGGAGTAGGGCCTTTGGGAGGTAATCAGAT
TTCTACGAGGTCATGAGGGTGGAGCCCGCATAGTGGAATTAGTGTCCTTTTAGGAAGAGG
AGAACAGACCAAAGCCTTCCTTTCTCCTCACTATGTAAGAAGACAGCCAGAAGGTGGC
CACAGCCAGGAAGAGAGCTCTCACCAGAACCCAAATCTGCTAGCACCTTGCTCTTGGGTT
CTCAGCATCCAGAACTGTGAGAAATGAATGTGTGTTGTTTAAACCACTCAGGCTACGGTA
TTTTGTTGCAGCAGCCCAAGCTGACAGAGATAGAAACAACACAAGGACCCATCAGCAGAC
GAATGGATGATCAAAACGTGGTGAGGTCGTGCAGTGGGATATTATTCAGCCGTAGAAGGA
ATGAAATTCTGATACATGCTATAATGATGAACCTTGAAAACATGTTAATGGAAATAAGCC
AAACTTAAAAGGACAAATATTGTATAATTCCACTTATATGAGTTAGTTACCTAGAATAGG
CAAATTATGTCATAGATACAGAACATTAGAGGTTACCAGGGTTGTGGGAAGAGGGGTATT
GTGGGTACAAATTTTCGGTTTGGAGTGATTTTGAAAAAATTCTGGAAATGGGTAGTGACA
GTAGTCAACATGATGAATGTACTTAATGACACTAAATTGTACACTTAAAAATGGTTAATA
CTGGGCTGGCGCAGTGGCTCATGGCTGTAAATCCCAGAACTTTGGGAGGCCAAGACAGGC
GGATCATGAGGTCAGGAGATTGAGACCATTCTGGCTAACATGGTGAAACCCTGTCTCTAC
TAAAAAATAAAAACAAATAAAAAAAAAATTAGCCGGGCATGGTGGCAGGCACCTGTAGTC
CCAGCTACTCGGGAGGCTGAGGCAGGAGAATGGTGTGACCTGGGAGTCGGAGCTTGCAGT
GAGCTGAGATCGCGCCACTGCACTCCAGCCTGGGCAACAGAGCCAGATTCCGTCTCAAAA
AAAAAAAAAAAAAGGTTGATACCTGGGTGCGGTGGCTCATGCCTGTAATTTCAGCACTTT
GGGAGGCCAAGGCAGGCAGATCAGTTGAGGTCAAGAGTTAAGGACCAGCCTGGCCAACGT
GGCGAAACCCCATCTCTATTAAAAATACAAAAATTAGTCGAGTGTGGTGGTGGGTGCCTG
TAGTCCCAGCTGCTGGGAGGATGAGGCCTAGGAATTGCTTGAACCCAGGAGGCAGAGGTT
GCAGTGAGTTGAGATTGCGCCACTGCACTCCAGCCTGGGGACAGAGCGAGACTTAGTCT
CAAAAAAAAGGTTAAAATTGTAAGTTTTGTTATGCATATTTTACCATAATCTTTAAAAAA
TAGATATATAGGAGATAAAGTCAACAGAATTTAATAACCAGTTGTAAATAGAGACTGAGT
GAGGAGGATGAATTAAGGAAGACATTGAGTACAACTTTTTGGTAGGTGAAAAACTCTTAA
AAAAATACGTGGGCAAAGATCCTACTTGATTCTTATAATTTAAAAATCTCCCAGTTAGTA
AACAAGGCTAGGTGGAGATTTGCATGTGATGTGAGGTGTGTGTTCTGTTTTGTAATGTGA
GGACTGTGAGCCATCTCCTGGACTTGAATATCCATTAGATAATTGAAAATACGGATTTGA
GAACTCAGGAGACGTGCAATGCAGTAACAAAACTCTGCACCTAGTTGATTTCTGTCTCCT
AATTTAATGCTTTTATGGGACAAACTGTTAGGCAGGTGGGCAAGATGGACAGCCATATTT
TTGTGGGTTTCTGGCCTGTGGGCCAGCCTCAGTGCTCACTCTGAGGTCATGTCCAAACTT
AGAACACATTCAGGCCTACCACAGTCAAGGCTCCCTTTCTCAACTCTAGTCCTCTGCACA
AATATCCGAAGCCTAGAAATAATAATCATCTGTCCTTGTGTCTTGCATTATGAAAGCCTA
GGAAAGGGCCTTGGGAATTAAGAAGAATGGAAAAACTGGTCTAACTGCTGCATGCTTCAG
CTTGCAGGGGAATCACTGAAATGGGGACAGGCCATAAAAGGACAACCAGAAGAGTGGCTT
CAGCAAAGGCATCGTTTTTCAGAGCAAGCTAGAGAATCCTGCCAGCGTCCTCAGGCAGGG
CCCCTGGGCACAGAGGTTAGGCAAGGGAGTGTCCCAGCATGTTGATGCCCTGAGCATCAG
AATAATGCCATAGAGGAGCTTCCAAAGAGTTCATTTCAGGTTTTGTAAGCCGAACATTTC
TAGGCAAATAAAATTTGATTTGTGAATAAAGCTTGTTTCTTCAACTCCAGTGCAGATTC
TCATAGATTGATAGTGGCTTGTGATCCAGATAAAGAAAACAATTTTTCAAAGATTCATAT
TCTTTGTAGATGTACGGATTTAGAGACCATCTAATCTAACTCCCTCATTCTACAGATAGG
AAAAATGAGGCCTAAAGAAGTTAAGAAAATACCATGGAAATGTCACTGCTGAACTGCCAT
ACGTAGGATCCGAAAGAAATTGGGTAAATGCTACTGTGAGAAATACAGTACTAGGTCCAA
AGAATCTAATACAAATTAAAAATCTAAATGTTATTTCTAAAGCATCCCTGCACATGGCTG
AACTTACATAGTTTCATTTTCTTTCTTTTCTGTTGAAGAAGAGGCAATTGGCTGGGTGCA
GTGGCTCATGCCTGTAATCCCTGGCACTTTGAGAGGCCGAGGCGGGTGGATCACCTGAGGT
CAGGAGTTTGAGACCAGCCTGGCCAACATGGTGAAACCCCATCTCTACTAAAAATACAAA
AATTAGCTGGCTGTGGTGGCCGCTGCCTGTAATCCCAGCTACTCCAGAGGCTGAGGCAGG
AGAATTACTTGAATCTGGGAGGTGGAGGTTGCAGTGAGCCAAGATCACGCCATTGCACTC
TAGCCTGGATGACAAGAGGGAAACTCCATCTCAAAAAAAAAAAGAAAAAAGCAATCACT
AACCTGTGTTGTTTATTAAACATGACAGACTGGCATGAAGTAATTACCAAACTGTAAACA
```

```
AAAAAGCTACAATCTGCCAGGCATGGTGGCTCATGCCTGTAATCCCCCACCTTGGGAGGC
CAGGTTGGGGGATCACCTGAGGCCTGGAGTTCAAGACTAGCCTGGTCAACATGGTGAAAC
CTCGTCTCTACTAAAAATACAAAAATTAGCCCGGCGTGGTGGCACATCCTGTAATCCCA
GTTACTCAGGAGGCTGAGGCAGGAGAATCACTTGAACCTGGGCAGTGGGGAGGTTGCAGT
GAGCCAAGATCGCACCGTTGTACTCCAGTCTGGGCCGACAGAGTGAGACTCGGTCTCAAA
AAAAAGAAAAAGAAAAGCTACAACCTTAATCTCAACTTCTCATAACATCATCTCTACTT
CTGATTAGAAGAGTGGAAGTGGGGAGGTTTATTACAAAAAGACTGTTATACCTTACACAC
TTCTCCCCATGAATAGTGAAGGTGTGAGTGAAAAGACAGCAATTTTATTTTTTTTTGA
AACAGGTTCTTGCACTGTCACCCGGGCTGGAGTGCACTGTTGTGATCACTGCTCACTGCA
GCCTCCACCTCCCAGGCTCAAGTGATCCTCCTACCTCAGCCTCCTGAGTAGCTGGGACCA
CAGTTGTGCACTACCATGCCCAGCTATTTTTTTTAAGAGATGGGGTCTCACTATATTGC
TTAGGCTAGTTCTCAAACTCCTGGCCTCAAGCAGTCCTCCGACCTTGGCCTCCCAAAGGG
TTGTGATTACAGGCATAAGCCACCACACCCAGCCAGCAGTTTTAGAATAAAGGGTGAAGG
TGCTGTTGGGGAAATATAATTTAAAAAACAAAATCTTCTCTCAACCCAGAAATCCTCTCC
ATGAAGGCAGTAGAGAAGATAAGCTTTATTATTGAATAAAAATTAAATGAGAATGTGAT
GCACATCACAGGCACTTTGCTAAGAGATCACAAAGACAGAAGGAAATTTCACCATTTTGT
ACAGCCAAGCAGGTACAGCCCATTACATGTATGTTTTCGAGATAAATAGTCCTCAACTAA
GAGAACTTGACAGCACCACTGGTCACACAGTTCATTCTAACTTTACCTGATAATTGATGT
GACCACTTGTGTTATCTAAGATATCAACTTTTCGGGGGTGGGGAGTGTGGAAACAGGAG
TTACTTTTATAGCTTGGTGCAAGGTACTCATTAAGATTAGGCTGTTACCCTCCCACAGAA
ACTGGAAGATAGGTATGCTATCTGGTAATGTTTACATTTCCCAGATCCTTGAGAAAGACA
TTCCTAGGTCATAAAGCTGACAAAGGCTGATTCAGTTTTTAAATATATATATCTGTATA
TGTATTTCA
```

*FIG. 15F*

```
actgagagacaggactagctggatttcctaggctgactaagaatccctaagcctagctgg
||||||||||||||||||||||||||||| |||| ||||||||||| |||||||||||||
actgagagacaggactagctggatttcccaggccgactaagaattcctaagcctagctgg g-aaggtgaccacatccacctttaaacacggggcttgcaacttagctcacacctgaccaa
| ||||||||||||| || ||||||||||| | ||||| |||| |||||||||| ||||||
ggaaggtgaccacaccctcctttaaacacagagcttgtaactcagctcacacccgaccaa tcag--------agagctcactaaaatgctaattaggc-aaagacaggaggtaaagaaa
||||        ||||||||||||| | |||||||| ||| |||||||||||||||||
tcaggtagtaaagagagctcactaaaataccaattaggctaaaaacaggaggtaaagaaa tagccaa-tcatctattgcctgagagcacagcaggagggacaatgatcgggatataaacc
|| ||| ||||||||| |||||||||||||||| |||||||||||||||||||||||||
taatcaaatcatctatcgcctgagagcacaggggggagggacaatgatcgggatataaacc caagtcttcgagccggcaacggcaaccccctttgggtcccctcctttgtatgggagctc
|| | || |||||| |  || ||||| |||||||||||||| | ||||||||||||||
caggcatttgagccagatcaggtaaccctctttgggtcccctcacactgtatgggagctc tgttttcatgctatttcactctattaaatcttgcaactgcac--tcttctggtccatgtt
||||        |||||||||||||||||||||||||||||  ||||||||||||||||
tgtt--------ttcactctattaaatcttgcaactgcacactcttctggtccatgtt tcttacggcttgagctgagctttcgctcgccatccaccactgctgtttgccgccaccgca
| || ||||| |||||||||||| ||||||| |||||||||||||| ||||||| |||
tgttccggctcaagctgagcttttgctcgccgtccaccactgctgaatgccgccattgca gacccgccgctgactccatccctctggatcatgcaggtgtccgctgtgctcctgatcc
|||| ||| ||||| ||||| ||||| |||| |||||||| ||||||||
gacctgcccttgacttccaccccctccggatccggcagagtgtccgctgcactcctgatcc agcgaggcacccattgccgctcccaatcgggctaaaggcttgccattgttcctgcatggc
|||||||||||||||||  ||||| ||| |||||||||||||||||||||||||||| ||
agcgaggcacccattgccactccgatcaggctaaaggcttgccattgttcctgcacagc taagtgcctgggttcatcctaattgagctgaacactagtcactgggttccatggttctct
||||||||||||||||||||||   |||||||| ||| |||||||||| ||||||||
taagtgcctgggttcatcctaatcaggctgaacactggtcgctgggttccacggttctct tctgtgacccacagcttctaatagagctataacactcaccgcatggcccaaggttccatt
|| |||| |||||||||||||||||||||||||||||| ||||||||||||||||||||
tccatgactcacagcttctaatagagctataacactcaccacatggcccaaggttccatt cctt-gaatccataaggccaagaaccccaggtcagagaacacgaggcttgccaccatctt
| || ||||||||| ||||||||||||||||||||||| | |||| ||| |||||||||
cgttggaatccatgaggccaagaaccccaggtcagagaataaaaggcccgcc-ccatctt gggag
|||||
gggag
```

*FIG. 16*

```
TCCTGTGAAC CTCTAGAGGA TTTGCGCCTG CTCTTCAAAC AACAACCAGG AGGAAAGTAA    7660
CTAAAATCAT AAATCCCCAT GGCCCTCCCT TATCATATTT TTCTCTTTAC TGTTCTTTTA    7920
CCCTCTTTCA CTCTCACTGC ACCCCCTCCA TGCCGCTGTA TGACCAGTAG CTCCCCTTAC    7980
CAAGAGTTTC TATGGAGAAT GCAGCGTCCC GGAAATATTG ATGCCCATC  GTATAGGAGT    8040
CTTTCTAAGG GAACCCCCAC CTTCACTGCC CACACCCATA TGCCCCGCAA CTGCTATCAC    8100
TCTGCCACTC TTTGCATGCA TGCAAATACT CATTATTGGA CAGGAAAAT  GATTAATCCT    8160
AGTTGTCCTG GAGGACTTGG AGTCACTGTC TGTTGGACTT ACTTCACCCA AACTGGTATG    8220
TCTGATGGGG GTGGAGTTCA AGATCAGGCA AGAGAAAAAC ATGTAAAAGA AGTAATCTCC    8280
CAACTCACCC GGGTACATGG CACCTCTAGC CCCTACAAAG GACTAGATCT CTCAAAACTA    8340
CATGAAACCC TCCGTACCCA TACTCGCCTG GTAAGCCTAT TTAATACCAC CCTCACTGGG    8400
CTCCATGAGG TCTCGGCCCA AACCCTACT  AACTGTTGGA TATGCCTCCC CCTGAACTTC    8460
AGGCCATATG TTTCAATCCC TGTACCTGAA CAATGGAACA ACTTCAGCAC AGAAATAAAC    8520
ACCACTTCCG TTTTAGTAGG ACCTCTTGTT TCCAATCTGG AAATAACCCA TACCTCAAAC    8580
CTCACCTGTG TAAAATTTAG CAATACTACA TACACAACCA ACTCCCAATG CATCAGGTGG    8640
GTAACTCCTC CCACACAAAT AGTCTGCCTA CCCTCAGGAA TATTTTTTGT CTGTGGTACC    8700
TCAGCCTATC GTTGTTTGAA TGGCTCTTCA GAATCTATGT GCTTCCTCTC ATTCTTAGTG    8760
CCCCCTATGA CCATCTACAC TGAACAAGAT TTATACAGTT ATGTCATATC TAAGCCCCGC    8820
AACAAAAGAG TACCCATTCT TCCTTTTGTT ATAGGAGCAG GAGTGCTAGG TGCACTAGGT    8880
ACTGGCATTG GCGGTATCAC AACCTCTACT CAGTTCTACT ACAAACTATC TCAAGAACTA    8940
AATGGGGACA TGGAACGGGT CGCCGACTCC CTGGTCACCT TGCAAGATCA ACTTAACTCC    9000
CTAGCAGCAG TAGTCCTTCA AAATCGAAGA GCTTTAGACT TGCTAACCGC TGAAAGAGGG    9060
GGAACCTGTT TATTTTTAGG GGAAGAATGC TGTTATTATG TTAATCAATC CGGAATCGTC    9120
ACTGAGAAAG TTAAAGAAAT TCGAGATCGA ATACAACGTA GAGCAGAGGA GCTTCGAAAC    9180
ACTGGACCCT GGGGCCTCCT CAGCCAATGG ATGCCCTGGA TTCTCCCCTT CTTAGGACCT    9240
CTAGCAGCTA TAATATTGCT ACTCCTCTTT GGACCCTGTA TCTTTAACCT CCTTGTTAAC    9300
TTTGTCTCTT CCAGAATCGA AGCTGTAAAA CTACAAATGG AGCCCAAGAT GCAGTCCAAG    9360
ACTAAGATCT ACCGCAGACC CCTGGACCGG CCTGCTAGCC CACGATCTGA TGTTAATGAC    9420
ATCAAAGGCA CCCCTCCTGA GGAAATCTCA GCTGCACAAC CTCTACTACG CCCCAATTCA    9480
GCAGGAAGCA GTTAGAGCGG TCTCGGCCAA CCTCCCCAAC AGCACTTAGG TTTTCCTGTT    9540
```

*FIG. 17*

```
AAGCTCCTTCAGGAGAACAAAGAACAGGCCATTACCCTGGAGAAGACTGGCAACTGATTTTACCCACAAGCCCAA
LysLeuLeuGlnGluAsnLysGluGlnAlaIleThrLeuGluLysThrGlyAsn...PheTyrProGlnAlaGln
  SerSerPheArgArgThrLysAsnArgProLeuProTrpArgArgLeuAlaThrAspPheThrHisLysProLys
    AlaProSerGlyGluGlnArgThrGlyHisTyrProGlyGluAspTrpGlnLeuIleLeuProThrSerProAsn

ACCTCAGGGATTTCAGTATCTACTAGTCTGGGTAGATACTTTCACGGGTTGGGCAGAGGCCTTCCCCTGTAGGAC
ThrSerGlyIleSerValSerThrSerLeuGlyArgTyrPheHisGlyLeuGlyArgGlyLeuProLeu...Asp
  ProGlnGlyPheGlnTyrLeuLeuValTrpValAspThrPheThrGlyTrpAlaGluAlaPheProCysArgThr
    LeuArgAspPheSerIleTyr...SerGly...IleLeuSerArgValGlyGlnArgProSerProValGlyGln

AGAAAAGGCCCAAGAGGTAATAAAGGCACTAGTTCATGAAATAATTCCCAGATTCGGACTTCCCCGAGGCTTACA
ArgLysGlyProArgGlyAsnLysGlyThrSerSer...AsnAsnSerGlnIleArgThrSerProArgLeuThr
  GluLysAlaGlnGluValIleLysAlaLeuValHisGluIleIleProArgPheGlyLeuProArgGlyLeuGln
    LysArgProLysArg......ArgHis...PheMETLys...PheProAspSerAspPheProGluAlaTyrArg

GAGTGACAATAGCCCTGCTTTCCAGGCCACAGTAACCCAGGGAGTATCCCAGGCGTTAGGTATACGATATCACTT
Glu...Gln...ProCysPheProGlyHisSerAsnProGlySerIleProGlyValArgTyrThrIleSerLeu
  SerAspAsnSerProAlaPheGlnAlaThrValThrGlnGlyValSerGlnAlaLeuGlyIleArgTyrHisLeu
    ValThrIleAlaLeuLeuSerArgProGln...ProArgGluTyrProArgArg...ValTyrAspIleThrTyr

ACACTGCGCCTGAAGGCCACAGTCCTCAGGGAAGGTCGAGAAAATGAATGAAACACTCAAAGGACATCTAAAAAA
ThrLeuArgLeuLysAlaThrValLeuArgGluGlyArgGluAsnGlu...AsnThrGlnArgThrSerLysLys
  HisCysAla...ArgProGlnSerSerGlyLysValGluLysMETAsnGluThrLeuLysGlyHisLeuLysLys
    ThrAlaProGluGlyHisSerProGlnGlyArgSerArgLys...METLysHisSerLysAspIle...LysSer

GCAAACCCAGGAAACCCACCTCACATGGCCTGCTCTGTTGCCTATAGCCTTAAAAAGAATCTGCAACTTTCCCCA
              385       395       405       415       425       435       445
AlaAsnProGlyAsnProProHisMETAlaCysSerValAlaTyrSerLeuLysLysAsnLeuGlnLeuSerPro
  GlnThrGlnGluThrHisLeuThrTrpProAlaLeuLeuProIleAlaLeuLysArgIleCysAsnPheProGln
    LysProArgLysProThrSerHisGlyLeuLeuCysCysLeu...Pro...LysGluSerAlaThrPheProLys

AAAAGCAGGACTTAGCCCATACGAAATGCTGTATGGAAGGCCCTTCATAACCAATGACCTTGTGCTTGACCCAAG
LysSerArgThr...ProIleArgAsnAlaValTrpLysAlaLeuHisAsnGln...ProCysAla...ProLys
  LysAlaGlyLeuSerProTyrGluMETLeuTyrGlyArgProPheIleThrAsnAspLeuValLeuAspProArg
    LysGlnAspLeuAlaHisThrLysCysCysMETGluGlyProSer...ProMETThrLeuCysLeuThrGlnAsp

ACAGCCAACTTAGTTGCAGACATCACCTCCTTAGCCAAATATCAACAAGTTCTTAAAACATTACAAGGAACCTAT
ThrAlaAsnLeuValAlaAspIleThrSerLeuAlaLysTyrGlnGlnValLeuLysThrLeuGlnGlyThrTyr
  GlnProThr...LeuGlnThrSerProPro...ProAsnIleAsnLysPheLeuLysHisTyrLysGluProIle
    SerGlnLeuSerCysArgHisHisLeuLeuSerGlnIleSerThrSerSer...AsnIleThrArgAsnLeuSer

CCCTGAGAAGAGGGAAAAGAACTATTCCACCCTTGTGACATGGTATTAGTCAAGTCCCTTCCCTCTAATTCCCCA
Pro...GluGluGlyLysGluLeuPheHisProCysAspMETValLeuValLysSerLeuProSerAsnSerPro
  ProGluLysArgGluLysAsnTyrSerThrLeuValThrTrpTyr...SerSerProPheProLeuIleProHis
    LeuArgArgGlyLysArgThrIleProProLeu...HisGlyIleSerGlnValProSerLeu...PheProIle

TCCCTAGATACATCCTGGGAAGGACCCTACCCAGTCATTTTATCTACCCCAACTGCGGTTAAAGTGGCTGGAGTG
SerLeuAspThrSerTrpGluGlyProTyrProValIleLeuSerThrProThrAlaValLysValAlaGlyVal
  Pro...IleHisProGlyLysAspProThrGlnSerPheTyrLeuProGlnLeuArgLeuLysTrpLeuGluTrp
    ProArgTyrIleLeuGlyArgThrLeuProSerHisPheIleTyrProAsnCysGly...SerGlyTrpSerGly
```

*FIG. 18A*

```
GAGTCTTGGATACATCACACTTGAGTCAAATCCTGGATACTGCCAAAGGAACCTGAAAATCCAGGAGACAACGCT
GluSerTrpIleHisHisThr...ValLysSerTrpIleLeuProLysGluProGluAsnProGlyAspAsnAla
  SerLeuGlyTyrIleThrLeuGluSerAsnProGlyTyrCysGlnArgAsnLeuLysIleGlnGluThrThrLeu
   ValLeuAspThrSerHisLeuSerGlnIleLeuAspThrAlaLysGlyThr...LysSerArgArgGlnArg...

AGCTATTCCTGTGAACCTCTAGAGGATTTGCGCCTGCTCTTCAAACAACAACCAGGAGGAAAGTAACTAAAATCA
SerTyrSerCysGluProLeuGluAspLeuArgLeuLeuPheLysGlnGlnProGlyGlyLys...LeuLysSer
  AlaIleProValAsnLeu...ArgIleCysAlaCysSerSerAsnAsnAsnGlnGluSerAsn...AsnHis
   LeuPheLeu...ThrSerArgGlyPheAlaProAlaLeuGlnThrThrThrArgArgLysValThrLysIleIle

TAAATCCCCATGGCCCTCCCTTATCATATTTTTCTCTTTACTGTTCTTTTACCCTCTTTCACTCTCACTGCACCC
...IleProMETAlaLeuProTyrHisIlePheLeuPheThrValLeuLeuProSerPheThrLeuThrAlaPro
  LysSerProTrpProSerLeuIleIlePhePheSerLeuLeuPhePheTyrProLeuSerLeuSerLeuHisPro
   AsnProHisGlyProProLeuSerTyrPheSerLeuTyrCysSerPheThrLeuPheHisSerHisCysThrPro

CCTCCATGCCGCTGTATGACCAGTAGCTCCCCTTACCAAGAGTTTCTATGGAGAATGCAGCGTCCCGGAAATATT
ProProCysArgCysMETThrSerSerSerProTyrGlnGluPheLeuTrpArgMETGlnArgProGlyAsnIle
  LeuHisAlaAlaVal...ProValAlaProLeuThrLysSerPheTyrGlyGluCysSerValProGluIleLeu
   SerMETProLeuTyrAspGln...LeuProLeuProArgValSerMETGluAsnAlaAlaSerArgLysTyr...

GATGCCCCATCGTATAGGAGTCTTTCTAAGGGAACCCCCACCTTCACTGCCCACACCCATATGCCCCGCAACTGC
AspAlaProSerTyrArgSerLeuSerLysGlyThrProThrPheThrAlaHisThrHisMETProArgAsnCys
  METProHisArgIleGlyValPheLeuArgGluProProProSerLeuProThrProIleCysProAlaThrAla
   CysProIleVal...GluSerPhe...GlyAsnProHisLeuHisCysProHisProTyrAlaProGlnLeuLeu

TATCACTCTGCCACTCTTTGCATGCATGCAAATACTCATTATTGGACAGGAAAAATGATTAATCCTAGTTGTCCT
TyrHisSerAlaThrLeuCysMETHisAlaAsnThrHisTyrTrpThrGlyLysMETIleAsnProSerCysPro
  IleThrLeuProLeuPheAlaCysMETGlnIleLeuIleIleGlyGlnGluLys...LeuIleLeuValValLeu
   SerLeuCysHisSerLeuHisAlaCysLysTyrSerLeuLeuAspArgLysAsnAsp...Ser...LeuSerTrp

GGAGGACTTGGAGTCACTGTCTGTTGGACTTACTTCACCCAAACTGGTATGTCTGATGGGGGTGGAGTTCAAGAT
GlyGlyLeuGlyValThrValCysTrpThrTyrPheThrGlnThrGlyMETSerAspGlyGlyGlyValGlnAsp
  GluAspLeuGluSerLeuSerValGlyLeuThrSerProLysLeuValCysLeuMETGlyValGluPheLysIle
   ArgThrTrpSerHisCysLeuLeuAspLeuLeuHisProAsnTrpTyrVal...TrpGlyTrpSerSerArgSer

CAGGCAAGAGAAAAACATGTAAAAGAAGTAATCTCCCAACTCACCCGGGTACATGGCACCTCTAGCCCCTACAAA
GlnAlaArgGluLysHisValLysGluValIleSerGlnLeuThrArgValHisGlyThrSerSerProTyrLys
  ArgGlnGluLysAsnMET...LysLys...SerProAsnSerProGlyTyrMETAlaProLeuAlaProThrLys
   GlyLysArgLysThrCysLysArgSerAsnLeuProThrHisProGlyThrTrpHisLeu...ProLeuGlnArg

GGACTAGATCTCTCAAAACTACATGAAACCCTCCGTACCCATACTCGCCTGGTAAGCCTATTTAATACCACCCTC
GlyLeuAspLeuSerLysLeuHisGluThrLeuArgThrHisThrArgLeuValSerLeuPheAsnThrThrLeu
  Asp...IleSerGlnAsnTyrMETLysProSerValProIleLeuAlaTrp...AlaTyrLeuIleProProSer
   ThrArgSerLeuLysThrThr...AsnProProTyrProTyrSerProGlyLysProIle...TyrHisProHis

ACTGGGCTCCATGAGGTCTCGGCCCAAAACCCTACTAACTGTTGGATATGCCTCCCCCTGAACTTCAGGCCATAT
ThrGlyLeuHisGluValSerAlaGlnAsnProThrAsnCysTrpIleCysLeuProLeuAsnPheArgProTyr
  LeuGlySerMETArgSerArgProLysThrLeuLeuThrValGlyTyrAlaSerPro...ThrSerGlyHisMET
   TrpAlaPro...GlyLeuGlyProLysProTyr...LeuLeuAspMETProProProGluLeuGlnAlaIleCys

GTTTCAATCCCTGTACCTGAACAATGGAACAACTTCAGCACAGAAATAAACACCACTTCCGTTTTAGTAGGACCT
ValSerIleProValProGluGlnTrpAsnAsnPheSerThrGluIleAsnThrThrSerValLeuValGlyPro
  PheGlnSerLeuTyrLeuAsnAsnGlyThrThrSerAlaGlnLys...ThrProLeuProPhe......AspLeu
   PheAsnProCysThr...ThrMETGluGlnLeuGlnHisArgAsnLysHisHisPheArgPheSerArgThrSer
```

*FIG. 18B*

```
CTTGTTTCCAATCTGGAAATAACCCATACCTCAAACCTCACCTGTGTAAAATTTAGCAATACTACATACACAACC
LeuValSerAsnLeuGluIleThrHisThrSerAsnLeuThrCysValLysPheSerAsnThrThrTyrThrThr
  LeuPheProIleTrpLys...ProIleProGlnThrSerProVal...AsnLeuAlaIleLeuHisThrGlnPro
   CysPheGlnSerGlyAsnAsnProTyrLeuLysProHisLeuCysLysIle...GlnTyrTyrIleHisAsnGln

AACTCCCAATGCATCAGGTGGGTAACTCCTCCCACACAAATAGTCTGCCTACCCTCAGGAATATTTTTTGTCTGT
AsnSerGlnCysIleArgTrpValThrProProThrGlnIleValCysLeuProSerGlyIlePhePheValCys
  ThrProAsnAlaSerGlyGly...LeuLeuProHisLys...SerAlaTyrProGlnGluTyrPheLeuSerVal
   LeuProMETHisGlnValGlyAsnSerSerHisThrAsnSerLeuProThrLeuArgAsnIlePheCysLeuTrp

GGTACCTCAGCCTATCGTTGTTTGAATGGCTCTTCAGAATCTATGTGCTTCCTCTCATTCTTAGTGCCCCCTATG
GlyThrSerAlaTyrArgCysLeuAsnGlySerSerGluSerMETCysPheLeuSerPheLeuValProProMET
  ValProGlnProIleValVal...METAlaLeuGlnAsnLeuCysAlaSerSerHisSer...CysProLeu...
   TyrLeuSerLeuSerLeuPheGluTrpLeuPheArgIleTyrValLeuProLeuIleLeuSerAlaProTyrAsp

ACCATCTACACTGAACAAGATTTATACAGTTATGTCATATCTAAGCCCCGCAACAAAAGAGTACCCATTCTTCCT
ThrIleTyrThrGluGlnAspLeuTyrSerTyrValIleSerLysProArgAsnLysArgValProIleLeuPro
  ProSerThrLeuAsnLysIleTyrThrValMETSerTyrLeuSerProAlaThrLysGluTyrProPhePheLeu
   HisLeuHis...ThrArgPheIleGlnLeuCysHisIle...AlaProGlnGlnLysSerThrHisSerSerPhe

TTTGTTATAGGAGCAGGAGTGCTAGGTGCACTAGGTACTGGCATTGGCGGTATCACAACCTCTACTCAGTTCTAC
PheValIleGlyAlaGlyValLeuGlyAlaLeuGlyThrGlyIleGlyGlyIleThrThrSerThrGlnPheTyr
  LeuLeu...GluGlnGluCys...ValHis...ValLeuAlaLeuAlaValSerGlnProLeuLeuSerSerThr
   CysTyrArgSerArgSerAlaArgCysThrArgTyrTrpHisTrpArgTyrHisAsnLeuTyrSerValLeuLeu

TACAAACTATCTCAAGAACTAAATGGGGACATGGAACGGGTCGCCGACTCCCTGGTCACCTTGCAAGATCAACTT
TyrLysLeuSerGlnGluLeuAsnGlyAspMETGluArgValAlaAspSerLeuValThrLeuGlnAspGlnLeu
  ThrAsnTyrLeuLysAsn...METGlyThrTrpAsnGlySerProThrProTrpSerProCysLysIleAsnLeu
   GlnThrIleSerArgThrLysTrpGlyHisGlyThrGlyArgArgLeuProGlyHisLeuAlaArgSerThr...

AACTCCCTAGCAGCAGTAGTCCTTCAAAATCGAAGAGCTTTAGACTTGCTAACCGCTGAAAGAGGGGGAACCTGT
AsnSerLeuAlaAlaValValLeuGlnAsnArgArgAlaLeuAspLeuLeuThrAlaGluArgGlyGlyThrCys
  ThrPro...GlnGln...SerPheLysIleGluGluLeu...ThrCys...ProLeuLysGluGlyGluProVal
   LeuProSerSerSerProSerLysSerLysSerPheArgLeuAlaAsnArg...LysArgGlyAsnLeuPhe

TTATTTTTAGGGGAAGAATGCTGTTATTATGTTAATCAATCCGGAATCGTCACTGAGAAAGTTAAAGAAATTCGA
LeuPheLeuGlyGluGluCysCysTyrTyrValAsnGlnSerGlyIleValThrGluLysValLysGluIleArg
  TyrPhe...GlyLysAsnAlaValIleMETLeuIleAsnProGluSerSerLeuArgLysLeuLysLysPheGlu
   IlePheArgGlyArgMETLeuLeuLeuCys...SerIleArgAsnArgHis...GluSer...ArgAsnSerArg

GATCGAATACAACGTAGAGCAGAGGAGCTTCGAAACACTGGACCCTGGGGCCTCCTCAGCCAATGGATGCCCTGG
AspArgIleGlnArgArgAlaGluGluLeuArgAsnThrGlyProTrpGlyLeuLeuSerGlnTrpMETProTrp
  IleGluTyrAsnValGluGlnArgSerPheGluThrLeuAspProGlyAlaSerSerAlaAsnGlyCysProGly
   SerAsnThrThr...SerArgGlyAlaSerLysHisTrpThrLeuGlyProProGlnProMETAspAlaLeuAsp

ATTCTCCCCTTCTTAGGACCTCTAGCAGCTATAATATTGCTACTCCTCTTTGGACCCTGTATCTTTAACCTCCTT
IleLeuProPheLeuGlyProLeuAlaAlaIleIleLeuLeuLeuLeuPheGlyProCysIlePheAsnLeuLeu
  PheSerProSer...AspLeu...GlnLeu...TyrCysTyrSerSerLeuAspProValSerLeuThrSerLeu
   SerProLeuLeuArgThrSerSerSerTyrAsnIleAlaThrProLeuTrpThrLeuTyrLeu...ProProCys
```

*FIG. 18C*

```
GTTAACTTTGTCTCTTCCAGAATCGAAGCTGTAAAACTACAAATGGAGCCCAAGATGCAGTCCAAGACTAAGATC
ValAsnPheValSerSerArgIleGluAlaValLysLeuGlnMETGluProLysMETGlnSerLysThrLysIle
 LeuThrLeuSerLeuProGluSerLysLeu...AsnTyrLysTrpSerProArgCysSerProArgLeuArgSer
  ...LeuCysLeuPheGlnAsnArgSerCysLysThrThrAsnGlyAlaGlnAspAlaValGlnAsp...AspLeu

TACCGCAGACCCCTGGACCGGCCTGCTAGCCCACGATCTGATGTTAATGACATCAAAGGCACCCCTCCTGAGGAA
TyrArgArgProLeuAspArgProAlaSerProArgSerAspValAsnAspIleLysGlyThrProProGluGlu
 ThrAlaAspProTrpThrGlyLeuLeuAlaHisAspLeuMETLeuMETThrSerLysAlaProLeuLeuArgLys
  ProGlnThrProGlyProAlaCys...ProThrIle...Cys......HisGlnArgHisProSer...GlyAsn

ATCTCAGCTGCACAACCTCTACTACGCCCAATTCAGCAGGAAGCAGTTAGAGCGGTCGTCGGCCAACCTCCCCA
IleSerAlaAlaGlnProLeuLeuArgProAsnSerAlaGlySerSer...SerGlyArgArgProThrSerPro
 SerGlnLeuHisAsnLeuTyrTyrAlaProIleGlnGlnGluAlaValArgAlaValValGlyGlnProProGln
  LeuSerCysThrThrSerThrThrProGlnPheSerArgLysGlnLeuGluArgSerSerAlaAsnLeuProAsn

ACAGCACTTAGGTTTTCCTGTTGAGATGGGGG
ThrAlaLeuArgPheSerCys...AspGlyGly
 GlnHisLeuGlyPheProValGluMETGly
  SerThr...ValPheLeuLeuArgTrpGly
```

*FIG. 18D*

LysLeuLeuGlnGluAsnLysGluGlnAlaIleThrLeuGluLysThrGlyAsn...PheTyrProGlnAlaGln

ThrSerGlyIleSerValSerThrSerLeuGlyArgTyrPheHisGlyLeuGlyArgGlyLeuProLeu...Asp

ArgLysGlyProArgGlyAsnLysGlyThrSerSer...AsnAsnSerGlnIleArgThrSerProArgLeuThr

Glu...Gln...ProCysPheProGlyHisSerAsnProGlySerIleProGlyValArgTyrThrIleSerLeu

ThrLeuArgLeuLysAlaThrValLeuArgGluGlyArgGluAsnGlu...AsnThrGlnArgThrSerLysLys

AlaAsnProGlyAsnProProHisMETAlaCysSerValAlaTyrSerLeuLysLysAsnLeuGlnLeuSerPro

LysSerArgThr...ProIleArgAsnAlaValTrpLysAlaLeuHisAsnGln...ProCysAla...ProLys

ThrAlaAsnLeuValAlaAspIleThrSerLeuAlaLysTyrGlnGlnValLeuLysThrLeuGlnGlyThrTyr

Pro...GluGluGlyLysGluLeuPheHisProCysAspMETValLeuValLysSerLeuProSerAsnSerPro

SerLeuAspThrSerTrpGluGlyProTyrProValIleLeuSerThrProThrAlaValLysValAlaGlyVal

GluSerTrpIleHisHisThr...ValLysSerTrpIleLeuProLysGluProGluAsnProGlyAspAsnAla

SerTyrSerCysGluProLeuGluAspLeuArgLeuLeuPheLysGlnGlnProGlyGlyLys...LeuLysSer

...IleProMETAlaLeuProTyrHisIlePheLeuPheThrValLeuLeuProSerPheThrLeuThrAlaPro

ProProCysArgCysMETThrSerSerSerProTyrGlnGluPheLeuTrpArgMETGlnArgProGlyAsnIle

AspAlaProSerTyrArgSerLeuSerLysGlyThrProThrPheThrAlaHisThrHisMETProArgAsnCys

TyrHisSerAlaThrLeuCysMETHisAlaAsnThrHisTyrTrpThrGlyLysMETIleAsnProSerCysPro

GlyGlyLeuGlyValThrValCysTrpThrTyrPheThrGlnThrGlyMETSerAspGlyGlyGlyValGlnAsp

GlnAlaArgGluLysHisValLysGluValIleSerGlnLeuThrArgValHisGlyThrSerSerProTyrLys

GlyLeuAspLeuSerLysLeuHisGluThrLeuArgThrHisThrArgLeuValSerLeuPheAsnThrThrLeu

ThrGlyLeuHisGluValSerAlaGlnAsnProThrAsnCysTrpIleCysLeuProLeuAsnPheArgProTyr

ValSerIleProValProGluGlnTrpAsnAsnPheSerThrGluIleAsnThrThrSerValLeuValGlyPro

LeuValSerAsnLeuGluIleThrHisThrSerAsnLeuThrCysValLysPheSerAsnThrThrTyrThrThr

AsnSerGlnCysIleArgTrpValThrProProThrGlnIleValCysLeuProSerGlyIlePhePheValCys

GlyThrSerAlaTyrArgCysLeuAsnGlySerSerGluSerMETCysPheLeuSerPheLeuValProProMET

ThrIleTyrThrGluGlnAspLeuTyrSerTyrValIleSerLysProArgAsnLysArgValProIleLeuPro

PheValIleGlyAlaGlyValLeuGlyAlaLeuGlyThrGlyIleGlyGlyIleThrThrSerThrGlnPheTyr

TyrLysLeuSerGlnGluLeuAsnGlyAspMETGluArgValAlaAspSerLeuValThrLeuGlnAspGlnLeu

*FIG. 19A*

AsnSerLeuAlaAlaValValLeuGlnAsnArgArgAlaLeuAspLeuLeuThrAlaGluArgGlyGlyThrCys
LeuPheLeuGlyGluGluCysCysTyrTyrValAsnGlnSerGlyIleValThrGluLysValLysGluIleArg
AspArgIleGlnArgArgAlaGluGluLeuArgAsnThrGlyProTrpGlyLeuLeuSerGlnTrpMETProTrp
IleLeuProPheLeuGlyProLeuAlaAlaIleIleLeuLeuLeuLeuPheGlyProCysIlePheAsnLeuLeu
ValAsnPheValSerSerArgIleGluAlaValLysLeuGlnMETGluProLysMETGlnSerLysThrLysIle
TyrArgArgProLeuAspArgProAlaSerProArgSerAspValAsnAspIleLysGlyThrProProGluGlu
IleSerAlaAlaGlnProLeuLeuArgProAsnSerAlaGlySerSer...SerGlyArgArgProThrSerPro
ThrAlaLeuArgPheSerCys...AspGlyGly

*FIG. 19B*

SerSerPheArgArgThrLysAsnArgProLeuProTrpArgArgLeuAlaThrAspPheThrHisLysProLys
ProGlnGlyPheGlnTyrLeuLeuValTrpValAspThrPheThrGlyTrpAlaGluAlaPheProCysArgThr
GluLysAlaGlnGluValIleLysAlaLeuValHisGluIleIleProArgPheGlyLeuProArgGlyLeuGln
SerAspAsnSerProAlaPheGlnAlaThrValThrGlnGlyValSerGlnAlaLeuGlyIleArgTyrHisLeu
HisCysAla...ArgProGlnSerSerGlyLysValGluLysMETAsnGluThrLeuLysGlyHisLeuLysLys
GlnThrGlnGluThrHisLeuThrTrpProAlaLeuLeuProIleAlaLeuLysArgIleCysAsnPheProGln
LysAlaGlyLeuSerProTyrGluMETLeuTyrGlyArgProPheIleThrAsnAspLeuValLeuAspProArg
GlnProThr...LeuGlnThrSerProPro...ProAsnIleAsnLysPheLeuLysHisTyrLysGluProIle
ProGluLysArgGluLysAsnTyrSerThrLeuValThrTrpTyr...SerSerProPheProLeuIleProHis
Pro...IleHisProGlyLysAspProThrGlnSerPheTyrLeuProGlnLeuArgLeuLysTrpLeuGluTrp
SerLeuGlyTyrIleThrLeuGluSerAsnProGlyTyrCysGlnArgAsnLeuLysIleGlnGluThrThrLeu
AlaIleProValAsnLeu...ArgIleCysAlaCysSerSerAsnAsnAsnGlnGluGluSerAsn...AsnHis
LysSerProTrpProSerLeuIleIlePhePheSerLeuLeuPhePheTyrProLeuSerLeuSerLeuHisPro
LeuHisAlaAlaVal...ProValAlaProLeuThrLysSerPheTyrGlyGluCysSerValProGluIleLeu
METProHisArgIleGlyValPheLeuArgGluProProProSerLeuProThrProIleCysProAlaThrAla
IleThrLeuProLeuPheAlaCysMETGlnIleLeuIleIleGlyGlnGluLys...LeuIleLeuValValLeu
GluAspLeuGluSerLeuSerValGlyLeuThrSerProLysLeuValCysLeuMETGlyValGluPheLysIle
ArgGlnGluLysAsnMET...LysLys...SerProAsnSerProGlyTyrMETAlaProLeuAlaProThrLys
Asp...IleSerGlnAsnTyrMETLysProSerValProIleLeuAlaTrp...AlaTyrLeuIleProProSer
LeuGlySerMETArgSerArgProLysThrLeuLeuThrValGlyTyrAlaSerPro...ThrSerGlyHisMET
PheGlnSerLeuTyrLeuAsnAsnGlyThrThrSerAlaGlnLys...ThrProLeuProPhe......AspLeu
LeuPheProIleTrpLys...ProIleProGlnThrSerProVal...AsnLeuAlaIleLeuHisThrGlnPro
ThrProAsnAlaSerGlyGly...LeuLeuProHisLys...SerAlaTyrProGlnGluTyrPheLeuSerVal
ValProGlnProIleValVal...METAlaLeuGlnAsnLeuCysAlaSerSerHisSer...CysProLeu...
ProSerThrLeuAsnLysIleTyrThrValMETSerTyrLeuSerProAlaThrLysGluTyrProPhePheLeu
LeuLeu...GluGlnGluCys...ValHis...ValLeuAlaLeuAlaValSerGlnProLeuLeuSerSerThr
ThrAsnTyrLeuLysAsn...METGlyThrTrpAsnGlySerProThrProTrpSerProCysLysIleAsnLeu
ThrPro...GlnGln...SerPheLysIleGluGluLeu...ThrCys...ProLeuLysGluGlyGluProVal

*FIG. 20A*

TyrPhe...GlyLysAsnAlaValIleMETLeuIleAsnProGluSerSerLeuArgLysLeuLysLysPheGlu

IleGluTyrAsnValGluGlnArgSerPheGluThrLeuAspProGlyAlaSerSerAlaAsnGlyCysProGly

PheSerProSer...AspLeu...GlnLeu...TyrCysTyrSerSerLeuAspProValSerLeuThrSerLeu

LeuThrLeuSerLeuProGluSerLysLeu...AsnTyrLysTrpSerProArgCysSerProArgLeuArgSer

ThrAlaAspProTrpThrGlyLeuLeuAlaHisAspLeuMETLeuMETThrSerLysAlaProLeuLeuArgLys

SerGlnLeuHisAsnLeuTyrTyrAlaProIleGlnGlnGluAlaValArgAlaValValGlnProProGln

GlnHisLeuGlyPheProValGluMETGly

FIG. 20B

AlaProSerGlyGluGlnArgThrGlyHisTyrProGlyGluAspTrpGlnLeuIleLeuProThrSerProAsn
LeuArgAspPheSerIleTyr...SerGly...IleLeuSerArgValGlyGlnArgProSerProValGlyGln
LysArgProLysArg......ArgHis...PheMETLys...PheProAspSerAspPheProGluAlaTyrArg
ValThrIleAlaLeuLeuSerArgProGln...ProArgGluTyrProArgArg...ValTyrAspIleThrTyr
ThrAlaProGluGlyHisSerProGlnGlyArgSerArgLys...METLysHisSerLysAspIle...LysSer
LysProArgLysProThrSerHisGlyLeuLeuCysCysLeu...Pro...LysGluSerAlaThrPheProLys
LysGlnAspLeuAlaHisThrLysCysCysMETGluGlyProSer...ProMETThrLeuCysLeuThrGlnAsp
SerGlnLeuSerCysArgHisHisLeuLeuSerGlnIleSerThrSerSer...AsnIleThrArgAsnLeuSer
LeuArgArgGlyLysArgThrIleProProLeu...HisGlyIleSerGlnValProSerLeu...PheProIle
ProArgTyrIleLeuGlyArgThrLeuProSerHisPheIleTyrProAsnCysGly...SerGlyTrpSerGly
ValLeuAspThrSerHisLeuSerGlnIleLeuAspThrAlaLysGlyThr...LysSerArgArgGlnArg...
LeuPheLeu...ThrSerArgGlyPheAlaProAlaLeuGlnThrThrThrArgArgLysValThrLysIleIle
AsnProHisGlyProProLeuSerTyrPheSerLeuTyrCysSerPheThrLeuPheHisSerHisCysThrPro
SerMETProLeuTyrAspGln...LeuProLeuProArgValSerMETGluAsnAlaAlaSerArgLysTyr...
CysProIleVal...GluSerPhe...GlyAsnProHisLeuHisCysProHisProTyrAlaProGlnLeuLeu
SerLeuCysHisSerLeuHisAlaCysLysTyrSerLeuLeuAspArgLysAsnAsp...Ser...LeuSerTrp
ArgThrTrpSerHisCysLeuLeuAspLeuLeuHisProAsnTrpTyrVal...TrpGlyTrpSerSerArgSer
GlyLysArgLysThrCysLysArgSerAsnLeuProThrHisProGlyThrTrpHisLeu...ProLeuGlnArg
ThrArgSerLeuLysThrThr...AsnProProTyrProTyrSerProGlyLysProIle...TyrHisProHis
TrpAlaPro...GlyLeuGlyProLysProTyr...LeuLeuAspMETProProGluLeuGlnAlaIleCys
PheAsnProCysThr...ThrMETGluGlnLeuGlnHisArgAsnLysHisHisPheArgPheSerArgThrSer
CysPheGlnSerGlyAsnAsnProTyrLeuLysProHisLeuCysLysIle...GlnTyrTyrIleHisAsnGln
LeuProMETHisGlnValGlyAsnSerSerHisThrAsnSerLeuProThrLeuArgAsnIlePheCysLeuTrp
TyrLeuSerLeuSerLeuPheGluTrpLeuPheArgIleTyrValLeuProLeuIleLeuSerAlaProTyrAsp
HisLeuHis...ThrArgPheIleGlnLeuCysHisIle...AlaProGlnGlnLysSerThrHisSerSerPhe
CysTyrArgSerArgSerAlaArgCysThrArgTyrTrpHisTrpArgTyrHisAsnLeuTyrSerValLeuLeu
GlnThrIleSerArgThrLysTrpGlyHisGlyThrGlyArgArgLeuProGlyHisLeuAlaArgSerThr...
LeuProSerSerSerSerProSerLysSerLysSerPheArgLeuAlaAsnArg...LysArgGlyAsnLeuPhe

FIG. 21A

IlePheArgGlyArgMETLeuLeuLeuCys...SerIleArgAsnArgHis...GluSer...ArgAsnSerArg

SerAsnThrThr...SerArgGlyAlaSerLysHisTrpThrLeuGlyProProGlnProMETAspAlaLeuAsp

SerProLeuLeuArgThrSerSerSerTyrAsnIleAlaThrProLeuTrpThrLeuTyrLeu...ProProCys

...LeuCysLeuPheGlnAsnArgSerCysLysThrThrAsnGlyAlaGlnAspAlaValGlnAsp...AspLeu

ProGlnThrProGlyProAlaCys...ProThrIle...Cys......HisGlnArgHisProSer...GlyAsn

LeuSerCysThrThrSerThrThrProGlnPheSerArgLysGlnLeuGluArgSerSerAlaAsnLeuProAsn

SerThr...ValPheLeuLeuArgTrpGly

*FIG. 21B*

```
TTGGTCTTAAGAACACAAATGATATGGCTCCAATGACTGGAGGAACACCAGGGTCCTTGG
TCTCACGCTGATTTAGATAAAACGACTGTCAGGCCTCTGAGCCCAAGCTAAGCCATCCTC
CCCTGTGACCTGCACGTATACATCCAGATGGCCTGAAGTAACCAAGAATCACAAAGCA
GTGAAAATGGCCTGTTCCTGCCTTAACTGATGACATTCCACCATTGTGATTTGTTCCTGC
CCCATCTTAACTGAGCGATTAACCTTGTGAAATTCCTTCTCCTGGCTCAAAACCTCCCCC
ACTGAGCACCTTGTGACCCCGCCCCTGCCCTAAGAGAAACCCCCTTTGATTATAATT
TTCCACTACCCACCCAAATCCTATAAAATGGCCCCACCCCTATCTCCCTTCGCTGACTCC
TTTTTCGGACTCAGCCCGCCTGCACCCAGGTGAAATAAACAGCCTTGTTGCTCACACAAA
GCCTGTTTGGTGGACTCTCTTCACACGGACGCTCATGACATTTGGTGCCAAAACCTGGGA
TAGGAGGACTCCTTCAGGAGACCAGTCCCCTGTCCTTGCCCTCACTCTGTGAGGACATCC
ACCTACAACCTTGGGTCCTCAGACCAACCAGCCCAAGGAACAGCTCACCAATTTCAAATC
AGGTAAGCAGTCTTTTCACTCTCTTCTCCAGCCTCTCTTGCTACCCTTCAAACTCCCTCT
CTCACTACCCTTCAATCTCCCTGTCCTTCCAATTCCAGTTCTTTTTCATCTCTAGTAGAG
ACAAAGGAGACACATTTTATCCATGGACCCAAAACTCCAGCACCAGTCACGGACTTGGGA
AGACAGTCTTCCCTTGGTGTTTAATCACTGCGGGACGCCTGCCTGATTATTCACCCACA
CTCCATTGGTGTCTGATCACGGTGGGACACCTGCCTTGGTCACTCACCCACATTCCCTT
GGTGGTACGTCAACTGCAAAGCAGGGACGCCTGCTTTGGCTGCTCACCCACCCCTTC
TCTGTGTCTCTACCTTTCTCTTTAAACTTACCTCCTTCACTATGGGCAAACTTCTGCCCT
CCATTCCCCCTTCTTCTCCCTTAGCCTGTGTTCTTAAAAACCTAAAACCTCTTCAACTCA
CACCTGACCTAAAACCTAAATGCCTTATTTTCTTCTGCAACACTGCGTGGCTGCAGTACA
AACTTGATAATAGCTTTAAATGGCCAGAATATGGCACTTTCAATTTCTCCATCCTACAAG
ATCTAGATAATTTTTGTGGAAAAATGGAAAAATGGTCTGAGATGCCTGACGTCCAGGCAT
TCTTTTACACATTGGTCCCTCCCTAGTCTCTGCTCCCAATGCGACTCATCCCAAATCTTT
CTTCTTTCTCTCCTGTCTGTTCCTTCAGTCTCCACCCCAAGCTCTGAGTCCTTTGAATCC
TCCTTTGCTACAGACCCATCTGAACTCTCCCCTCCTCCCCAGGCTGCTCCTCACCAGGCC
GAGCCAGGTCCCAATTCTTCCTCAGCCTCTGCTCCCCACCCTATAATCCTTTTATCACC
TCCTCTCCTCACACTCAGTCCGGCTTACAGTTTCGTTCTGTGACTAGCCCTCCCCCATCT
GCCCAACAATTTCCTCTTAAAGAGGTGGCTGGAGCTAAAGGCATAGTCAAGGTTAATGCT
CCTTTTTCTTTATCTGACCTCTCCCAAATCAGTTAGCGTTTACGCTCTTTTTCATCAAAT
ATAAAAACCCAGCCAGTTCATGGCCCATCTGGCAACAACCCTTACAGGCTTTACAGCCCT
AGACCCTGAAGGGTCAGAAGGCCGTCTTATTCTCAATATGCATTTTATTACCCAATCCGC
TCCCAACATTAAATAAAGCTCCAAAAATTAAATTCTGGCCCTCAAACCCCACAACAGGAC
TTAATTAACCTCACTTCAAGGTGTACAAGAATAGAGTAGAGGCAGCCAAGTAGCAACGTA
TTTGAGTTGCAATTCCTTGCCTCAACTCTGAGAGAAACCCCAGCCACATCTCCAGCAAAC
AAGAACTTCAAAACACCTGAACTGCAGCAGCCAGGCGTTCCTCCAGGACCACCTCCCCCA
GGATCTTGCTTCAAGTGCCGGAAATCTGACCATTGGGCCAAGGAATGCCTGCAGCCCAGG
ATTCCTCCTAAGCCACGTCCCATTTGTGCAGGACCCCACTGGAAATCGGACTGTCCAACT
CACCCGGCAGCCAATCCCAGAGCCCCTGGAACTCTGGCCCAAGGCTCTCTGACTGACTCC
TTCCCAGATCTTCTCGGCTTAGCAGCTGAAGACTGACACTGCCCGATCACTTCAGAAGTC
CCCTGGACCATCACGGATACTGAGCTTCAGGTAACTCTCACAGTGGAGGCTAAGTCCATC
CCCTGTTTAATCGATACAGGGGCTACCCACTCCACATCACCTTCTTTTCAAGGGCCTGTT
TCCCTTTCCCCATAACTGTTGTGGGTATTGACGGCCAAGCTTCAAAACCCCTTAAAACT
CCCCCACTCTGGTGCCAACTTGGACAACATTCTTTTATGCACTCTTTTTCAGTTATCCTC
ACCTGCCCAGTTCCCTTATTAGGCCGAGACATTTTAACCAAATTATCTGCTTCCCCGACT
ATTCCTGGGCTACAGCCACATCTCCTTGCCGCCCTTCTTCCCAACCCAAAGCCTCCTTCA
TATCTTCCTCTCATATCCCCCCACCTTAACCCACAAGTATGGGACACCTCTACTCCCTCC
CTGGCAACCGATCACACGCCCATTACTATCCCATTAAAACCTAATCACCCTTACCCTGCT
CAATGCCAGTATCCCATACCACAACAGGCTTTAAAGGGATTGAAGCCTGTTATCACTTGC
```

*FIG. 22A*

```
CTGCTACAGCACGGGCTTCTAAACCTATAAACTCTCCATACAATTCCCCCATTTTACCT
GTCTAAAAACCAGATAAGTCTTACAGGTTAGTTCAGAATCTGCACCTTATCAACCAAATT
GTTTTGCCTATCCACCCTGTAGCACCCAACTCGTACACTCTTTTGTCCTCAATGCCTTCC
CCCACAACTCACTATTCCGTTCTTGATCTTAAAGATGCTTTTTTCACTATTCCCCTGCAC
CCCTCATCCCAGCCTCTCTTTGCTTTTACCTGGACTGACCCTGACACCCATCAGTCCCAG
CAGCTTACCTGGGCTGTACTGCCGCAAGGCTTCAGGGACAGCCCTCATTACTTCAGCCAA
GCTCTTTCTCATGATTTACTTTCTTTCCACCTCTCTGCTTCTCACCTTATTCAATATATT
GATGACCTTCTACTTTGTAGCCCCTCCTTTAAATCTTCTCAACAAGACACCCTCCTGCTC
CTTCAACATTTGTTCTCCAAAGGATATCGGGTATCCCCCTCCAAAGCTCAAATTTCTTCT
CCATCTGTTACATACCTCGGCATAATTCTTCATGAAAACACATGTGCTCTCCCTGCCAAT
TGCGTCTCCAACTGATCTCTCAATCCCAACCTCTTCTACAAAACAACAACTCCTTTCCC
TCCTAGGCATGGTTGGATACTTTTGCCTTTGGATACCTGGTTTTGCCATCCTAACAAAAT
CATTATATAAACTCACAAAAGGAAACCTAGCTGACCCCATAGATTCTAAATCCTTTCCCC
ACTCCTCTTTCCATTCCTTGAAGACAGCTTTAGAGACTGCTCCCACACTAGCTCTCCCTG
TCTCATCCCAACCCTTTTCATTACACACAGCCGAAGTGCAGGGCTGTGCAGTCGGAATTC
TTACACAAGGACCGGGACCATGCCCTGTAGCCTTTTGTCCAAACAACTTGACCTTACTG
TTTTAGGCTCGCCATCATGTCTCCATGCGGTAGCTTCCGCTGCCCTAATACTTTTAGAGG
CCCTCAAAATCACAAACTATGCTCAACTCACTCTCTACAGCTCTCACAACTTCCAAAAATC
TATTTTCTTTCTCACACCTGACGCATATACTTTCTGCTCCCCGGCTCCTTCAGCTGTATT
CACTCTTTGTTGAGTCTCCCACAATTACCATTCTTCCTGGCCCAGACTTCAATCTGGCCT
CCCACATTATTCTGGATACCACACCTGACCCTGATGATTGTATGTCTCTGATCTACCTGA
CATTCACCCCATTTCCCCATATTTCCTTCTTTTCTGTTCCTCATGTTGATCACATTTGGT
TTACTGACGGCAGTTCCACCAGGCCTGATCGCCACTCACCAGCAAAGGCAGGCTATGCTA
TAGAATCTTCCACATCCATCATTGAGGCTACTGCTCTGCCCCCCTCCACTACCTCTCAGC
AAGCCGAACTGATTGCCTTAACTCGGGCCTTCACTCTTGCAAAGGGACTACACGTCAATA
TTTATACTGACTCTAAATATGCCTTCCATATCTTGCACCACCATGCTGTTATATGGGCTG
AAAGAGGTTTCCTCACTACGCAAGGGTCCTCCATCATTAATGCCTCTTTAATAAAAACTC
TTCTCAAGGCTGCTTTACTTCCAAAGGAAGCTGGAGTCACACACTGCAAGGGCCACCAAA
AGGCGTCAGATCCCATTACTCTAGGAAATGCTTATGCTGATAAGGTAGCTAAAGAAGCAC
CTAGCGTTCCAACTTCTGTCCCTCATGGCCAGTTTTTCTCCTTCCCATCAGTCATTCCCA
CCTACTCCCCCATTGAAACTTCCGCCTATCAATCTCTTCTCACACAAGGCAAATGGTTCT
TAGACCAAGGAAAATATCTCCTTCCAGCCTCACAGGCCCATTCTATTCTGTCATCATTTC
ATAACCTCTTCCATGTAGGTTACAAGCCACTAGTCCACCTCTTAGAACCTCTCATTTCCT
TCCATCGTGGAAACATATCCTCAAGGAAATCACTTCTCAGTGTTCCATCTGCTATTCTAC
TACCCCTCAGGGATTGTTCAGGCCCCTCCCCTCCCTACACATCAAGCTCGGGGATTTGC
CCCTGCCCAGGACTGGCAAATTGACTTTACTCACATGCCCTGAGTCAGGAAACTAAAATA
CCTCTTGGTCTGGGTAGACACTGTCACTGGATGGGTAGAGGCCTTTCCCACAGGGTCTGA
GAAGGCCACTGCAGTCATTTCTTCCCTTCTGTCAGACATAATTCCTTGGGTTGGCCTTCC
CACCTCTATACAGTCCAATAACGGAGCAGCCTTTATTAGTCAAATCACCTGAGCAGTTTT
TCAGGCTCTTGGTATTCAGTGGAACCTTCGTACCCCTTACTGTCCTCAATCTTCAGGAAA
GGTAGAATGGACTAATGGTCTTTTAAAAACACACCCCACCAAACTCAGCCTCCAACTTAA
AAAGGAGGATAGAGCCCAAAAACTCGCAACCAAGCTAGTAATTATGCTGAACCCCCTTGG
GCACTCTCTAATTGGATGTCTTAGGTCCTCCCAAATCTTAGTCCTTTAATATCTGTTTTT
CTCCTTCTCTTATTCGGACCTTGTGTCTTCCGTTTAGTTTTTCAATTCATACAAAACCGC
ATCCAGGCCATCACCAATCGTTCTATACAATAAATGCTCCTTCTAACAACCCCACAATAT
CGCCCCTTACCACAAAATCTTCCTTCAGCTTAATCTCTCCCACTCTAGGTTCCCATGCCG
CCCATAATCCCTCTCGAAGCAGCCCTGAGAAACATAGCCCATTATCTCTCCATACCACCC
CCAAAATTTTTGCTGCCCCAACACTTCAACACTATTTTACATTATTTTTCTTATTAATAT
```

FIG. 22B

```
AAGAAGACAGCAATGTCAGGCCTCTGAGCCCAAGCCATCATATCCCCTGTGACCTGCACA
TATACATCCAGATGGCCTGAAGTAACTGAAGAATCACAAAAGAAGTGAAAATGGCCTGTT
CCTGCCTTAACCGATGACATTCCACCACTGTGATTTGTTCCTGCCCCACCTTAACTGAGC
AATTAACCTTGGGAAATTCCTTCTCCTGGCTCAAAACCTCCCCCACTGAGCACCTTGTGA
CCCCTGCCCCTCCACTACCCACCCAAATCCTATAAAATGGCCCCACCCCATCTCCCTTAG
CTGACTCCTTTTTTGGACTCAGCCCGCCTGCACCCAGGTGAAATAAACAGCCTTGTTGCT
CACACAAAGCCTGTTTGGTGGACTCTCTTCACAGGGACGGGGGTGACAACAACACGGACA
CACATGGAGTGGTTTTAAGGAGCAGAGAGTTTAATACGCAAAAAGAAGGAAGAGGCTCC
CCTGTACAGACACAGAGGGAGGGGGCTCCAAGCCGAGAGAAGGAAACCCCATGTGCAGTG
GAAAAGTGGTTGATTATACTGGGAGGCTGGAGGAGGCGGTGTCTGATTTGCACAGGGCCC
AGGGGATTGGGTTGACCAGGTGTATCATTCATGTACCCCGCAAAAAACCTGGCCCTCCCA
CCTCAGCCCTTTAATATGCAAATGTGGGTTGCCATGATGTTCTGAAAACACATGAATTAT
CTGGAGGGGGCCATGACACTTGGTACATGTGCTGACAAGAAGAGGGTGGGAATCGCCATG
GTGGCCATGTTGGGTGGACCTAGTTTTAATAGCCTGCATTTGCATATCAAAGTTTGCTG
GCCTGGCTCTTTAAGCTGTCTTTTCTGTTAGAAAAGGAATGGTTTGGAATGGGTGAGGGT
TGCTTCTTATTACAAGAAAATTTCCAAAAACCTTTACTCTTTCTAGCTGCCAAAAAACTA
TTTCTTAATAACTTATGTATTACCATAATTAGGCAGCACCAAAGATCCCTGCAGGTCAGA
CCACTGCAATTAACATGCTGGCTTTACTGCTGATTATGGTAGCTGCATCCACCTAGCCTC
TCATATTGCAACTGCCTGACCTCTGCCACCCCACGAGCCACTTATCCCCACTTATAATCA
GCCCATTTCGATTGTAACATCTGCCACTTATTCCCGACGTTGTGGTATATCCTATAGATG
AATTCATTCAACATCCATTCCAACACCACCTCTCTTGCCTTCCTATACTCTCTGGAGAGT
GAATTACTGAGTCACATGATCTTCACTGCAGTCATTTGTGGCTATGTGACATAGTTCTGG
ACAGTGAACATAGACAGAAGT*CCCTGGGGCGGGCTTCCTTTCTGGGATGAGGGCAAAACG*
```

*FIG. 22C*

```
GATCTCTTGATCCCAGGAGGTCAAGGCTGCAATGAGCTAAGATCAAGCCACTGCATTCCA
GCCTGAGTGATAGTGGGAGACCTTGTCTTTAAAACACACACACACACACACACACACACG
AGGGCCTTTGACCACTCTTGAGTAGAAGACTCGAGAAGAACAAAGTAGAAGGCCAGAGAA
GAACAAAGTTACTTGAAAGATCTCTTATTAAAGAGAATGTACAAGCTATGAAAAAAAAAA
AACACACACACACACACAAACCTCATCTGGAATGAAAAAAACATAATGCATTTGGTTTCT
GGTTCCTTAGGCTGTTATGGAACAACCAAAGAACATTATTTTGGTTTCTGAGGTCAGAAC
TATTTTATTCCCCTCAAGCACACTATGCTTATGGTTTGAGGGAGAATGAGAAATAGGAAA
CTAGGAACAGGCTGAAATGGTCTAATCTTGACCATCTAATTCTGCAGTGTCTTATTCTCA
TTCTAAAAGAGAATGGTTATATTCGCTGTTCTAGCATAAAAAGTAATGATAAAAATAAAA
GATCCCGTATTACCAGACAATAATCCCCTAGACTGTTTTAATGCTTGGTTGAGTATTTGC
TTATGATCTCAGACTTTAAAAGATGGTCTCCCCCTATGGTGAAGCTTGTTAATTATGTAG
GCATCATTAATGTCTGTTTACTTATCAAAATTTTATCATTGTTAGTTGTATTACTACTTG
ACAGTCCAATTTATTTAATTGAAAAGATTGGTTAACATTTTATAGTCAAAGTAATTGTTT
CCTGTGTTTTTTCCTGTTTAGGTTATTGGAGTGATGAGTAAAGAATACATACCAAAGGGC
ACACGTTTTGGACCCCTAATAGGTGAAATCTACACCAATGACACAGTTCCTAAGAACGCC
AACAGGAAATATTTTTGGAGGGTAAGTAAGGGAAATTTCTTCAGACCCATTAAATGTTAG
GAAAAAATGGAGCTAAAAGAGCTGGGTGGCTCACCTTTCTCATCCTGTGCTGAGAAATGC
TGGGGCTCACCCATAAGTATCCAGCATCCCCATGGACACAGGGAATTCTGAACAAATGTG
ATGAAACCGATGAAATGTCTGGCCTGTAGGTGGTTAGTGATGGAGATACGGGCTATATGT
GAATCTTGATTTTTGCAATTCATTAGAGCTTTGTAATGAAAGGAAACAGTTTGTTGCTTG
CTTTAAGGATAGGTTCATTTGCATTTCTCCGCAAGGAAGTAGTAATGAGTTACCAAGCCT
TAGATTTCACCCCTTTTTGATTTCTTGCTGACTTAACTTTAATTGAATGGAAGAGTTATC
ACAAATGAATTATCTTTTTGGTTTTTTTTTTTGAGATGGAGTCTCACTCTGTCACCAG
GCTGGAGTGCAATGGCATGATCTCGGCTCACTGCAACCTCCGCCTCCCAGGTTCAAGCAA
TTGTCCTGCCTCAGCCTCCCGAGTAGCTGGGACTAAGGTGCGCGCCACCATGCCCAGTTA
ATTTTTGTATTTTTAGTAGAGACGGGGTTCCACTATGTTGGCCATGATGGTCTCGATCTC
TGGACCTCGTGATCCGCCCACCTTGGCCTCCCAAAGTGCTGGAATTACAGGCAAGAGCCA
CCGCGCCCAGCCAGGAATGACAAATGAATTACCTTATAAGTAAATGCCATTAAGGAAGGA
TAGCTGGAAGATGGGTTGAGGGAATGGAGGACCACAGAACTAGTCCTATTTAAATACAT
GTGCATGGTAAAATGATTCCATTTGACAATAGGTTAATTATCTCATAGCATAAGGAAAAT
GCTTAACAGTCATATGCAAGATGATAAGCTTTCCTATAGCATCCAACCAAAAGATCTAGC
CAGTACAATTTCCTTTGCTATATTAGGGTTAGAAAGGCCCCCAGAGGTGAACCAATTAGA
TGGAATCCTTGAATAAAACACTGGATTAGCAGTGAACAGAAAAAAGTCAGATTGCTTTCC
TTCTTCCCATAGATGTCTCAGGGATATTTAGTTTCCTCAGAAGATAAAGAATTTAGTAAG
CGTTTTTTTGTGCATACTTACATGAAATGTACATTATTTGAATTCTTTAAAAAGAAACAG
CTGCATGATAACAAAAATTGTGTTATGCTTGCTTTAGCTGGTATTTTTGCCTAGAACGAT
TATATCGTTCGGACAAGAAGCTATTCCTAAGAAACAATATTTTTAATCCAGGAAGTTTTT
CATTTTTAGAAATTTATCTTACTATTTCCCAAGCAAAAGAGGGTAGTTACAGATTCACTA
AGAATCATGTGCTCACAATTTTTATTTAATAATTATTCCTCCTTAAAATATATTAATCAC
CTGACTTACAATGGTGGAACCATGAGTGCATTTTGCCTTTATTGTCAATAACGTCTTCT
CAGAAGTGAGCCACAAAGGTGCATAGTTCTTGGAGTTAAAGGTCTGAATTAAGACAATCC
AGCATAAGTCTCATTAATGTGTGATTATTTTGAGAAAAGGCAAGAAGTACCTAAGAATCT
CCCCGCTCACTGTCCAGTTCCCTGTTTCATTTAAAGATTCACTGTAAGTAACTGAAAGGCT
TTCCTTGGGAGGATTTATTTGAATCAGTCTTTCACATGCAAAGGATATTGTAGAACATCT
CGTTTTGCTGGCAGGAATATGAACATCTGTTGTGAGGAAAGAAAAGTTTCATGCAAAT
TACACTGCCAAAGAAGGGATGTTCAAGTTGAGAAACCAGTGACATTTCTTGTAACTGTAC
TATGAATCAGCGCATTTTAATCTTCTAGATAATATATGGAAGTGCAGGAAGGTGGTAGGA
AACGGTGTTCATTTTACATATGCGTTATTTTATTCTGTGTGAGTGACTTCATGGCACCGA
CATTGCTGTTTTTAAATGAGGATACAGTAAATTGCAGTCCGAGGAAGGCTAACTGGAATC
AACATACCCGTAGCTTTAGAAAGCAGTTTCCGCACCAGCGAAGAGTACAAGAGCGATGGA
ACCCCATGTTCCTGGAAGTTTGCACATCAGAGTAAACAAACTTGAAAACCCCTCTTGATA
```

*FIG. 23A*

```
GCAGAATTCACCCAGCCTTGTTCCATTTTCTCTTAACAAAACACACCGCAAAGCTCTCA
CAAGCTGCTTTGATGAAGCCACATGTATTTCCCCCTTCACAATTTACAGGAAGTTACTCT
TAAAAGAAAGTGATTCTGGTGTTTACCGCCTGTGTTAAAGGGACAGAGTTCCTTTTTATT
TCTGATAACGTTTGAGCGAAATACAGAAACTATCTGTAGACTAGCATAGTCGGTACGTGA
GTAAGGAAAAGCAATAACCTGCTGTCCGGTGAGCACAAAATTCCTGCTACGAACAGTGCC
TTACTGCTGCTTGGAGACTGCAAGTCGCAGATCACACTAGGTATTGACTGATTGTATAAG
GAAATTTCTTAAAGTCTAAAGTAAAGGTGGTACCTCCTAAAAAGAGGGGAAGAGAGAAAA
CTTTGTGTGGAAGGATAAGGAGTGTGTTTATAGTTTCAGTAAGAGTGTACGTTTTAATTT
TTCTTCTTCCTCTGCCTCTTTGCCAAGTAGCCTGAGTGCATCTGTTATCCAGAAGTAGTA
TTACTCTAGGACAAACTTCAAATTCTTCATTCTGCGTTGCCTTTAAGGAACAACATACTT
TCTTCCTGTTCTTTTTCCAAAAACACACGCCTATGGCTCTGTGTGGTGTTTTAGCCAG
CCTCCTCCCAGATAAGGGGTTCCCTTCCCTCCTTTGCATTGAAAGGAAAGTGCAAGTCTG
GACATGTTTATCAAGAGGAAAAGTGACTTCTCAGTAATAGACTGTCAAATTCGGGCTGCT
GCCCGAGTGTTCGCTTTGTTATGGCAGGTGAAGTTCACCTTTGCCCCACCCAGTGTTTCC
ACAAAAAGGCAAGGTTCCAAGTATTCATATGAACAAGTGTTACTTTAGGACTTGGAGGGT
TGGGGGTGGAGGATGTTTGCATAGTTGAAGCCTTGGGCGGGGGTGTAGGAAACGGCGAGT
ACAGAGGCCATAGAAAAAGCTAAGACTCAGTTTGACGTCGTCAGCCGGCTTGGTCTTCTA
CCCAGTGACTCAAAGCACTAAAAGTCAGCATAATCGGAACTGAAGTCAGTAGCATCGCCC
ATTTGCCATTCACTGCAGTAGCAAAAGTAGTACTCTGTGGTGGGTTAATCGGTTTGAGGC
AGCTCCTTAAATGAACATTTGTGTTTCATTTTTCTGTTATTTTCCCGAACATGAAAAGAC
GATAAAACTGAAATGGAAAAGGTAACTGACAAAAGTGTGCCTTACCTGTTTCCGCCCTGA
TTTCTGCTGATTCAAGACTATTCTGGCTAAACTGATTGGATTCTTTTTCTAACTAGGCAG
TAGGGGATCAGAAATCACACACGGTACCGGCTGTGTTTATTCTGAGAGGTGCTGGGGAGC
TTTGGGTCTGACTTCCTTTTACATGCCTGTCTTCTCTTTTGGACAGATCTATTCCAGAGG
GGAGCTTCACCACTTCATTGACGGCTTTAATGAAGAGAAAGCAACTGGATGCGCTATGT
GAATCCAGCACACTCTCCCCGGGAGCAAACCTGGCTGCGTGTCAGAACGGGATGAACAT
CTACTTCTACACCATTAAGCCCATCCCTGCCAACCAGGAACTTCTTGTGTGGTATTGTCG
GGACTTTGCAGAAAGGCTTCACTACCCTTATCCCGGAGAGCTGACAATGATGAATCTCAG
TAAGTGGATTACAGAACAAAAAATAAAAAATGCCAGTAATGTCGGTTCTGCCCCTTTGA
ACTAATAACATGTTGTTTAATTATACGGCTTTGTCATGTGTTGGATGAAGTAGGTGGCTT
AAGCTAGGGACTAGGAAGAGGAAAAACATTTTTTGAGTCCCTATTAACTATTAGGAAACT
TGATCATTTAAAAGTATATATATATATGAGGAGCTACCTTGAGTTTTGAATTCAGGATGT
TACAGGAAGAAATATATGTCCAATTCTAATTTATCCAAAAGCAGTTGGGAGAATTACAGG
GATTGGTCCAGACATGCTGCGTATGCAAGGTATAGCCCTCATCTGTGGTACTTTGGCAGG
GCTTAGACTGCATCAAAATATTTATAGATGTACATTTGAGTGTACAGTTAGGATCTGATG
TGGAACATTGTAAGATCATTGCTAGAAAACTTTGTCATAATTTTTCAATATTATTCTAA
GTGAATAACCGTAAAGATTTTACATCTTAGCTTCCTTCCTTACAGTAAAAAAACTATCTG
ATCTCTTGATCAGTATTATAGTAGCCACCTATCACTTTATCTTAACAAATTCTCAATTCC
TTAGGTTTATGTGCTTTTACTTCTTTTATTTGATTAAAATTGCTGTCATGACCTCTCTCT
GCAGAGGGCTGCATCATTTTGGTCATTCTCAAGTGATCTCTTTGAGCAATTTAAGAATTG
CCATAAGATTCTAACCTCTGCTGTAACTATGGTTGTGTGTTCTTGGTTAGACCACTAAAT
CTTATTGCAGTTTTAAAAATTATTCCTTTTGGTTTAGAAGTTAAGACTAAATGCTGAAG
TTTTTGTAACTTTTGGTTTTGATATCATTTCAAACTTAAGAAAACATTTGAAGAAAAGGA
CAAAGAATTTCCACTTACCCTTTACCCAGGTTTACCAGTTATTGATAAGTATATCCATTT
GCTTTACCAGAAGGCTAACTTGTTTTAGTTCTCATTTTCACCTTTGAGACATTTGGAATA
AATATCAATGTTAACATAAATTGGAATTTTGACTTTGATTTTAGGACCAATGAACAAGCC
AAGTACTTACCCTAGTCATATATAATCCAACTGTATGGTTATTTGGTATTCATTCCACAC
TTCATTTTACTTGATCTCCCTTAAGATTGCAAGATTGTGTTTGCAGTTTTTCTGAAAATC
TGGGGCTATAAAAGCATCAGGACCTCCCCCGTAGGGGAGGTCGTGTGTTTGGGGTCCTTA
CACAACAGGTTACCCTTGAGCTTCAGGAAAAGAACTGGCTCTCAGTTCCCCAGTTCCAGC
TTAATGGGTCTAATTAGGTCCTGACCAAAAAGGTGGCAGTTCTTTTCCCTCATGTCTCTT
CAGCGCTCCCCGAGACTCTGGAGACTCTGTCATATCCCTAGGGCTGAGCCTCCCAGGAAC
CATTCGGCTGTTGTGGCATCTGTGTATGCCATGCCCAGTGCTGAGGACCTAGTAACAAAC
```

*FIG. 23B*

```
GACAAATGCACAGGCACAGTGGCATTTTTGTGGAACTCGTATTCCAGCTGTGCGTCTCAG
AAGAAGCGCACAGCTCCCTCCTGGCTTTCTTAACATAGTGAGCCACTTCCACTTAAGGGT
CTCCTTACATTCCTTGAGTTTAATCATTCATGGATTCAGAGGAAAGTCTTTTGATTTTTG
CTTTTCTTTAAACAGTTCATTTGAGGTGACCTACCCCAGTGACTTTGCACCAACCACCAA
GAAACTTTTTTGCATGCTTCCCGCACCCTGTGCCAATCAAGGGAAGGGTTTAAAGGCCTG
GCGTTTTTATTCCTCAAAGAAAGGTTTTGCACAGTATTTTAAGGTTCAAGTGCTTCTACT
TTGTGTTCAGAAGCAACTGTCATATATACTGTGAAATGACACCTTTTATTTATCCCTTTT
TATTTATGCAGTATGTCCCCTTTTATTTTGGCAGAATTTTTTCTAAATGGTGGTTTAACA
TTTTCAAGCACATTTCATTGTCCAATATTCATAGTAAAGAATGAGAGTTAACAATAACCA
GTCACATTAAAACAAGATTCCTGCTGCCAGTTGTGAAACCGGTTGTCTTAGGCGTGGCAG
CTGATGATTGAGACTGTGATCAGGAAAATTTCCACTATTTCATCAGGCCTAATAGGTAGA
TTGTGTCTCCAAATGAACTGTGTTGGGTTTCCATGCTTAAAGCACAATAGAGGTGGTGCA
AGAATCTCCATGAGGGCTTAAATGGCAGTGATGGTTCAGGCGGTAGAGTTTGGAGAAGAA
GGGATTTGAAACAAACCAAAGGAAAGAAAAGTAAGTAGCCAGAAATCACAAAATGGCATT
TTTCTAAAAACAAAGGAAAAGGAATAAAAGAACTAATAAGTTTGAAACCCCTACCCCTCC
CAAATTTGGCAGGGGGGAGGTATTTTTTTTCTATCTATCTAACTAACCCATCTAGAAAA
CAGTTGACCAAATTATAGACTTCTAAATGTTAATCTGCTTTCTCAGTTTCAGTTGAAAAG
AGACTTTGTTTTGCCTACTGCAGAACTTCTAGGTTCTTTCTTATAGTCTTGGGGTTCTTA
TTATAGATCGAAAATGTGAGTCGGCATAATTAAGCCATTCGGAGTCTTCAGAAGCAGTTC
ACTCTTGAAATGACTCCGTCCGCCTACAGCCATTTAAGATTTCAGAACAAAAACAGATCT
TGATTTTCTTTTTCATGTTAACTCAAGCTGTTGCTGAGTGGGAGAGTCAGAAATGACACC
AGCTCCACTGATTACTCAGCTGCTGAAGGATGATTTTTTAAAATGCACCTTTACTGTATA
TGGACTTCCTAATTTCCACCTGTAGAGCATCTTAGGGAGGCTAACATGTCACTCTGGATG
TTCTTTTAGAATAAGATGCAAATCTATTTTCTGAAGGCATTAGAGATAGCAAACATTTA
TTGTGAGTTTACTATATACTAGGCACTGTGCTAAGTGTTTGCATAGAAAGTTTAAAATT
CTGGCTTTTTTGTTGGCCCAATCATAAGTTTCATATCAGTTCAACATTCAAATTATATTA
AGGTACTTAAGAAGAATCCCTGGCTAAATGTGAGGGGCAGTGCCACAGATGGACTGAAAC
TTTATGCTTATTGCACATTTATGCTATTATTATTTGTTGAATTATAGAACCAAGGGAGTG
TGGAAGCCACTGGAAAAAATATGAGACTTAGATACATAATTTGAGTAAAAATGGCTCAAA
GTCATGAGGGTAAAGTTTTTTGTATTTCCATTTTATTCGAGCGGCATCGTTTTTAAAAAT
CATTATGAATTTGACCCTATATAGATGTTTCCAAATAATTCTTTTTCACCTTCATAAAAT
TCCTTCCTGTGGCTGTGAGATGCCTTGCCTATCAGTTTTCAAGCTTAGTTGTCTTTCTCA
TCCTTTACCATTTTAGCTTTAAAAAACAAAAGTGACAATTAGAACTTCCTGCCTGCTGGG
CCTCACTGAAAGACCGATATTGGCCTGATAAGGAGATATTTATTTGTTTTAGTGGCTTC
AGAAATCCCTCTCCCTCAGCAAGCTTTCCATCACGGCCCCCCGTCAGCATCTTCCCTGA
TAGCGTTCTTCTCTGTGTTTATTCTGGGGCTTCAGGCTCGCCCAGGAGGAACTGATAACC
GCTGGCAGGAGATAACATTCTCTAAGGGGCTCTCAAATTGGAATCGAATCCCTCAAGCCA
GTCAGCCTAGAGAATACATTTAAAGGGTTCAGTTCTGGAGTTTCACAGAGTTCATTTCTA
GACCTATCAGATAGCAAGTGTGGAGTTCTTTCTCAACTAAATTCAAGCAGAGACATTTTT
TAGACGATGAAGGATATTTGCACAAAGGCTTCAGCATGATCCCCCAAACCTGCTGCCTCT
GAAGGCATCTCCACACATTGACAGCCAATGCCTTCAGTGCGTTCCTAGGGCAGGTGTCCT
GGCTTGAGTGACTGTCCTCCAATAATCAGAGCTCAAACTAAACATCGTATGTTTTACTTT
TGGTTTCCAGGCAAGGCTGAGCAGGGAATTTTCAGTTTTCCCTGCCCAGATGGGTGTTTT
TTCCTGAAGGCATCATTTATTGTGTAGCGAGGAGACAGGGCTGGCTGTGGCAGGGATAGT
CTAGAACTGTCCTCATTGCTGCTGTTCCTAAATAGTATCTTTACCAAGTAATAACGTGCC
GTCTTTGGGAATAAGTGCTTTCCTCTTAGCCTGTTCTGTTTTCTTGGGTGCGCTAAGTAA
TTGAACTGGCTCAGGAAGTACCTATTGTGGTTTGGCAGAGGTGACTGTCACGCCTTGTGA
CTCCAGGGGCCAGCACTGCTGGGATCCTGGCTAGACCAGACAGAGCCTTGGTGAAGTGCT
TAGGCTGTCTGCACATCGCGAGGAAGGTGGTATTCACTTCGCTAAGCTCCTTGGCATAGG
CAGTTGAACAGGGCTTTATCAAATTCGTATTCAACAAGAGTAGAAGCGAAAATTGATGA
CTGTGTATTACTTGAAATGAGTCTTAATCTTTCACATTTAGTTCTCAGGGTATGCTGATT
TCCTTTAGGTAAACCATGAACATCAGAAAGACTTTTATTAACCTATGACAGGGTCCCCAC
```

*FIG. 23C*

```
CCCAGTATTTTTCCACTCCATTAAAATGGAAGTTTTTTTTTTTTTTCTTTTTTGAGAC
AGAGTTTGCTCTTGTTGCCCAGTCTGGAGTGCAATGGCACAATCTCGGCTCACCACAAC
CTCCACCTCCCAGATTCAAGCGATTCTTCTGCCTCAGCCTCCCAAGTAGCTGGGATTACA
GGTGTGCGCCACCACGCCCAGCTAATTTTGTATTTTTAGTAGAGATGGGGTTTCTCCATG
TTGGTCAGGCTGGTCTCGAACTTCCGACCTCAGGTGATCCGCCCACCTCGGCCTCCCAAA
GTGCTGGGATTACAGGCAAGAGCCACTGCATCCAGCTTAGGCTATCTTACTCCAGCCTAA
ACAGCAATTTTCTATCATAAGGTCTGTACTAATGAAAACAGAATCACCCAAGGCTGCTGT
TTGTTCTGTCTGTGCTGCCATTGTCCGCATTTTGCTGAGGAGGAAACGGAACTGCACTTT
TGAGTGAGTGGCCCAGAGCCTTCTAGAATGAGAGTGCGTTGGAAGCCAGATATGTGGCGA
TTGTGTCGCCAGCTGTTACTCAGGTTTTCTCAAGAAGGAGGAGCAACTTTGGCAGTTTTG
CTTCAGTTCTCTCTAGCCCTCTGTGTAATCGCCCCTTTTTCTTTATTTCAGCACAAACAC
AGAGCAGTCTAAAGCAACCGAGCACTGAGAAAAATGAACTCTGCCCAAAGAATGTCCCAA
AGAGAGAGTACAGCGTGAAAGAAATCCTAAAATTGGACTCCAACCCCTCCAAAGGAAAGG
ACCTCTACCGTTCTAACATTTCACCCCTCACATCAGAAAAGGACCTCGATGACTTTAGAA
GACGTGGGAGCCCCGAAATGCCCTTCTACCCTCGGGTCGTTTACCCCATCCGGGCCCCTC
TGCCAGAAGACTTTTTGAAAGCTTCCCTGGCCTACGGGATCGAGAGACCCACGTACATCA
CTCGCTCCCCCATTCCATCCTCCACCACTCCAAGCCCTCTGCAAGAAGCAGCCCCGACC
AAAGCCTCAAGAGCTCCAGCCCTCACAGCAGCCCTGGGAATACGGTGTCCCCTGTGGGCC
CCGGCTCTCAAGAGCACCGGGACTCCTACGCTTACTTGAACGCGTCCTACGGCACGGAAG
GTTTGGGCTCCTACCCTGGCTACGCACCCTGCCCCACCTCCCGCCAGCTTTCATCCCCT
CGTACAACGCTCACTACCCCAAGTTCCTCTTGCCCCCTACGGCATGAATTGTAATGGCC
TGAGCGCTGTGAGCAGCATGAATGGCATCAACAACTTTGGCCTCTTCCCGAGGCTGTGCC
CTGTCTACAGCAATCTCCTCGGTGGGGCAGCCTGCCCCACCCCATGCTCAACCCCACTT
CTCTCCCGAGCTCGCTGCCCTCAGATGGAGCCCGGAGGTTGCTCCAGCCGGAGCATCCA
GGGAGGTGCTTGTCCCGGCGCCCACAGTGCCTTCTCCTTTACCGGGGCCGCCGCCAGCA
TGAAGGACAAGGCCTGTAGCCCCACAAGCGGGTCTCCCACGGCGGGAACAGCCGCCACGG
CAGAACATGTGGTGCAGCCCAAAGCTACCTCAGCAGCGATGGCAGCCCCAGCAGCGACG
AAGCCATGAATCTCATTAAAAACAAAAGAAACATGACCGGCTACAAGACCCTTCCCTACC
CGCTGAAGAAGCAGAACGGCAAGATCAAGTACGAATGCAACGTTTGCGCCAAGACTTTCG
GCCAGCTCTCCAATCTGAAGGTAGGCCTTGAGAGAGAGCAGTCCAAGGGGCTGTGAGTGC
ATGCTTGTGTTTGTATTTAGCTTGCTTTCCATGGGGTATCGATTGCATTTGCAGTAGTAT
GAGCCCCCGGTTGGGGATAGTGGGTATGGATTCCGCCTGGCTTTTGCCACTTCTAGCTCT
TTGACTTTGGACAAGTGACTTCCCTTCTCCTGATTTTCTTCTGAATAATAAAAAAATTAG
GGGTTTGGACTAGAAGATTAGGTGAAACTCCCTGCTAGCCTGTGATTTTTGTGCTTTTAA
GAAAAACACCATTCTGAAAACATGAAGATTTCTTCTTTTTAAGACTGTCTTGATGCTTTT
CTTAAGATATTTGCATCAACACTTGAGTCTTGGAGCAGAAATGTTAGGTCTCAGAGCCAG
CTTGAGAGCAGAGCTAACACATGTGGCTTCTTCCCAGGTCCACCTGAGAGTGCACAGTGG
AGAACGGCCTTTCAAATGTCAGACTTGCAACAAGGGCTTTACTCAGCTCGCCCACCTGCA
GAAACACTACCTGGTACACACGGGAGAAAAGCCACATGAATGCCAGGTGCGCAGTATTTT
CTGGGTAGACCTTCTGACCTTTGTAGAAAATGTCTGTGAGTCACCCTCCCATGTCCTATA
TAGCCCGTAGTTAAAGCCAACACCAGATTCTGCGTTGTCCCATCCTGGACTGATGGCACT
ATGGTCCTTCCCAGTACTTTGTATCTGCTGATGACTTGAGATGGCACAGCCAGCTTCAG
TGGGTGGGAAAATGGTAGGGAAATAAACAGCCCCTCGTGTGCTGTGTGCCCACATCCCC
CCGTTTGCTTAATACCACACTGGAGGTGCCACAAGGAGGCTTCTCACCTCCTAGGTTGCT
GGGCGTTGGCCGGTAAGCCTGCCCCTCCCGTTGGCAACTCTTAATCTTCTGGCCTTCCTG
TCTCCCTTCCTGCTGTCTCTCTCCCCTACACTGTAGGTCTGCCACAAGAGATTTAGCAC
CACCAGCAATCTCAAGACCCACCTGCGACTCCATTCTGGAGAGAAACCATACCAATGCAA
GGTGTGCCCTGCCAAGTTCACCCAGTTTGTGCACCTGAAACTGCACAAGCGTCTGCACAC
CCGGGAGCGGCCCCACAAGTGCTCCCAGTGCCACAAGAACTACATCCATCTCTGTAGCCT
CAAGGTTCACCTGAAAGGGAACTGCGCTGCGGCCCCGGCGCCTGGGCTGCCCTTGGAAGA
TCTGACCCGAATCAATGAAGAAATCGAGAAGTTTGACATCAGTGACAATGCTGACCGGCT
CGAGGACGTGGAGGATGACATCAGTGTGATCTCTGTAGTGGAGAAGGAAATTCTGGCCGT
```

FIG. 23D

```
GGTCAGAAAGAGAAGAAGAAACTGGCCTGAAAGTGTCTTTGCAAGAAACATGGGGAA
TGGACTCCTCTCCTCAGGGTGCAGCCTTTATGAGTCATCAGATCTACCCCTCATGAAGTT
GCCTCCCAGCAACCCACTACCTCTGGTACCTGTAAGGTCAAACAAGAAACAGTTGAACC
AATGGATCCTTAAGATTTTCAGAAAACACTTATTTTGTTTCTTAAGTTATGACTTGGTGA
GTCAGGGTGCCTGTAGGAAGTGGCTTGTACATAATCCCAGCTCTGCAAAGCTCTCTCGAC
AGCAAATGGTTTCCCCTCACCTCTGGAATTAAAGAAGGAACTCCAAAGTTACTGAAATCT
CAGGGCATGAACAAGGCAAAGGCCATATATATATATATATATATCTGTATACATATTA
TATATACTTATTTACACCTGTGTCTATATATTTGCCCCTGTGTATTTGAATATTTGTGT
GGACATGTTTGCATAGCCTTCCCATTACTAAGACTATTACCTAGTCATAATTATTTTTC
AATGATAATCCTTCATAATTTATTATACAATTTATCATTCAGAAAGCAATAATTAAAAAA
GTTTACAATGACTGGAAAGATTCCTTGTAATTTGAGTATAAATGTATTTTTGTCTTGTGG
CCATTCTTTGTAGATAATTTCTGCACATCTGTATAAGTACCTAAGATTAGTTAAACAAA
TATATGACTTCAGTCAACCTCTCTCTCTAATAATGGTTTGAAAATGAGGTTTGGGTAATT
GCCAATGTTGGACAGTTGATGTGTTCATTCCTGGATCCTATCATTTGAACAGCATTGTA
CATAACTTGGGGGTATGTGTGCAGGATTACCCAAGAATAACTTAAGTAGAAGAAACAAGA
AAGGGAATCTTGTATATTTTGTTGATAGTTCATGTTTTCCCCCAGCCACAATTTACC
GGAAGGGTGACAGGAAGGCTTTACCAACCTGTCTCTCCCTCCAAAAGAGCAGAATCCTCC
CACCGCCCTGCCCTCCCCACCGAGTCCTGTGGCCATTCAGAGCGGCCACATGACTTTTGC
ATCCATTGTATTATCAGAAAATGTGAAGAAGAAAAAATGCCATGTTTTAAAACCACTGC
GAAAATTTCCCCAAAGCATAGGTGGCTTTGTGTGTGCGATTTGGGGCTTGAGTCTGG
GTGGTGTTTGTTGTTGGTTTTGTTGCTTTTTTTTTTTTTTTTTTTTAATGTCAAAAT
TGCACAAACATGGTGCTCTACCAGGAAGGATTCGAGGTAGATAGGCTCAGGCCACACTTT
AAAAACAAACACACAAACAACAAAAAACGGGTATTCTAGTCATCTTGGGGTAAAAGCGGG
TAATGAACATTCCTATCCCCAACACATCAATTGTATTTTTCTGTAAAACTCAGATTTTC
CTCAGTATTTGTGTTTTACATTTATGGTTAATTTAATGGAAGATGAAAGGGCATTGCA
AAGTTGTTCAACAACAGTTACCTCATTGAGTGTGTCCAGTAGTGCAGGAAATGATGTCTT
ATCTAATGATTTGCTTCTCTAGAGGAGAAACCGAGTAAATGTGCTCCAGCAAGATAGACT
TTGTGTTATTCTATCTTTTATTCTGCTAAGCCCAAAGATTACATGTTGGTGTTCAAAGTG
TAGCAAAAATGATGTATATTTATAAATCTATTTATACCACTATATCATATGTATATATA
TTTATAACCACTTAAATTGTGAGCCAAGCCATGTAAAAGATCTACTTTTTCTAAGGGCAA
AAAAAAAAAAAAAAAAAAAAAGAACACTCCTTTCTGAGACTTTGCTTAATACTTGGTGACC
TCACAATCACGTCGGTATGATTGGGCACCCTTGCCTACTGTAAGAGACCCTAAAACCTTG
GTGCAGTGGTGGGGACCACAAAACAACCAGGGAGGAAGAGATACATCATTTTTTAGTATT
AAGGACCATCTAAGACAGCTCTATTTTTTTTTGCCACTTTATGATTATGTGGTCACACC
CAAGTCACAGAAATAAAAAACTGACTTTACCGCTGCAATTTTTCTGTTTTCCTCCTTACT
AAATACTGATACATTACTCCAATCTATTTATAATTATATTTGACATTTTGTTCACATCA
ACTAATGTTCACCTGTAGAAGAGAACAAATTTCGAATAATCCAGGGAAACCCAAGAGCCT
TACTGGTCTTCTGTAACTTCCAAGACTGACAGCTTTTTATGTATCAGTGTTTGATAAACA
CAGTCCTTAACTGAAGGTAAACCAAAGCATCACGTTGACATTAGACCAAATACTTTTGAT
TCCCAACTACTCGTTTGTTCTTTTTCTCCTTTTGTGCTTTCCCATAGTGAGAATTTTTAT
AAAGACTTCTTGCTTCTCTCACCATCCATCCTTCTCTTTTCTGCCTCTTACATGTGAATG
TTGAGCCCACAATCAACAGTGGTTTTATTTTTTCCTCTACTCAAAGTTAAAACTGACCAA
```

*FIG. 23E*

```
GTCTGGACTTGTGGTGCGCTGCCAGGGATCCGCAGCGTTGCCGGTTGTATTCGCTGGATACCAGAGGGCG
GAAGTGCAGCAGGGTTCAGCTCCGACCTCCGCGCCGGTGCTTTTTGCGGCTGCGCGGGCTTCCTGGAGTC
CTGCTACCGCGTCCCCGCAGGACAGTGTGTCAGGCGGGCAGCTTGCCCCGCCGCCCCACCGGAGCGCGGA
ATCTGGGCGTCCCCACCAGTGCGGGGAGCCGGAAGGAGGAGCCATAGCTTGGAGTAGGTTTGGCTTTGGT
TGAAATAAGAATTTAGCCTGTATGTACTGCTTTAACTCCTGGAAGAATGACAGATGACAAAGATGTGCTT
CGAGATGTGTGGTTTGGACGAATTCCAACTTGTTTCACGCTATATCAGGATGAGATAACTGAAAGGGAAG
CAGAACCATACTATTTGCTTTTGCCAAGAGTAAGTTATTTGACGTTGGTAACTGACAAAGTGAAAAAGCA
CTTTCAGAAGGTTATGAGACAAGAAGACATTAGTGAGATATGGTTTGAATATGAAGGCACACCACTGAAA
TGGCATTATCCAATTGGTTTGCTATTTGATCTTCTTGCATCAAGTTCAGCTCTTCCTTGGAACATCACAG
TACATTTTAAGAGTTTTCCAGAAAAAGACCTTCTGCACTGTCCATCTAAGGATGCAATTGAAGCTCATTT
TATGTCATGTATGAAAGAAGCTGATGCTTTAAAACATAAAGTCAAGTAATCAATGAAATGCAGAAAAAA
GATCACAAGCAACTCTGGATGGGATTGCAAAATGACAGATTTGACCAGTTTGGGCCATCAATCGGAAAC
TCATGGAATATCCTGCAGAAGAAATGGATTTCGTTATATCCCCTTTAGAATATATCAGACAACGACTGA
AAGACCTTTCATTCAGAAGCTGTTTCGTCCTGTGGCTGCAGATGGACAGTTGCACACACTAGGAGATCTC
CTCAAAGAAGTTTGTCCTTCTGCTATTGATCCTGAAGATGGGGAAAAAAAGAATCAAGTGATGATTCATG
GAATTGAGCCAATGTTGGAAACACCTCTGCAGTGGCTGAGTGAACATCTGAGCTACCCGGATAATTTTCT
TCATATTAGTATCATCCCACAGCCAACAGATTGAAGGATCAACTATTTGCCTGAACAGAATCATCCTTAA
ATGGGATTTATCAGAGCATGTCACCCTTTTGCTTCAATCAGGTTTGGTGGAGGCAACCTGACCAGAAACA
CTTCGCTGCTGCAAGCCAGACAGGAAAAAGATTCCATGTCAGATAAGGCAACTGGGCTGGTCTTACTTTG
CATCACCTCTGCTTTCCTCCACTGCCATCATTAAACCTCAGCTGTGACATGAAAGACTTACCGGACCACT
GAAGGTCTTCTGTAAAATATAATGAAGCTGAAACCTTTGGCCTAAGAAGAAAATGGAAGTATGTGCCACT
CGATTTGTATTTCTGATTAACAAATAAACAGGGGTATTTCCTAAGGTGACCATGGTTGAACTTTAGCTCA
TGAAAGTGGAAACATTGGTTTAATTTTCAAGAGAATTAAGAAAGTAAAAGAGAAATTCTGTTATCAATAA
CTTGCAAGTAATTTTTGTAAAAGATTGAATTACAGTAAACCCATCTTTCCTTAACGAAAATTTCCTATG
TTTACAGTCTGTCTATTGGTATGCAATCTTGTAACTTTGATAATGAACAGTGAGAGATTTTAAATAAAG
CCTCTAAATATGTTTTGTCATTTAATAACATACAGTTTTGTCACTTTTCAAGTACTTTCTGACTCACATA
CAGTAGATCACTTTTTACTCTGTGTTACCATTTTGACTGGTCGTCATTGGCATGGGGTGGATATAGGGCA
TAGGATTACTTGTCTCAGAAGCTGTCATAGAATTTCTTGCTGCCAATTAAAAAACCTGTGTTCTTTACAC
ACTACACGTATAAATATTGTAACTGTTCATCTTTGTTGTTTATCACTGTAAGCCTGTCAAATCATAGTA
TCCTAAGCATCTGTAAATGCTAATTTTGCATTTTGGAAAAACCCATTCCTTCCAAGCTAGTGTTTTTCA
TTGGCTCCAGGTCTAATTTTTCACTGTGGTCCCTGGCAGCCAGTCTTTTGAAGTTTAAAGATTACCTGTC
TCTTGACTGCAGTACCTTTTCTTTAATTTTTACCAAAAATATCCAGAGGTTACTGGAGTTCTTATTCAAT
ATAAGGAAAGTTTGCTGCACTTTATTACCAAGCCTCTGGGATTTTACCAGTCAAACATATTTGTGCATTA
CATTTCATTTCTTGTGAGCTAGCTGGCTGTCCATATTGAATGTTGACCCATTTGAGTACGCTAAAAGGCT
TACAGTATCAGACACGATCATGGTTTTAGATCCCATAATAAAAATGRATGTTTTCTTATAAAAAATTAT
ACAAATGCTGAAGTGAGATTCTACTATTGTTCATTGCTTCCTTTTCTTTTTCCTTTTGCGATTTTCACTG
ATTAATAGCACATTTCTTCACAAAATTAGATAAAGTTGGTCAAAGACCAGATATTCTGGAATGGAAATTG
TAAAGCTTAATCAAAAGAATAGCCAGTACAGCATACAATCTCAGAAACTTAGAAGCAAGTAGAAAATAA
TTGGTTGATGTAAACGAAAGTGCCATTTTAGTAAAGGCAGGAAAAAAATAGCAATATTTGAGTTATGTAA
GGATAAAAAATCCACTGACTTGTATTTTGCACAAGAGGCTGGTCTGAATATGATTGTTCACATTAAGAG
TGTTTATTCGTCGGTTCATTTGGGGATTTTCCCCCTTGATGTTTTGACAGATTGAAGTGAGCTTTAGTG
AGCAAAAGGATCAGAATGCAGGGAACACTAAGCTGTGATGAAGAAAGTGTGGTAAAAAGCCAGAGTAGTT
TTATACAGACAAAACCAGTGTCAGGCCTTTGCAGTAGGCTTGAGTGAACTTCTGATCTAGATTTGAAAGT
AAATTTTATGAAGACATTGCCCATTTTTACTTCCTCATTCATTATTGTACCAGCATCATAGCTTTATTAC
TCTAATCCCAGGTAAGTCAAGCCTACAATGCCCTAGAGGAAGAGTAAAACCAGAAATTCATGCTGGCTTA
AATAATCTATTTTTGTTTCTTTTCATTTGAATATTTAAATTTTATGGTTTATTAAAAAATTAAATAAAAA
AGAAAAAAAAAAAAAAAAAAAA
```

FIG. 24

```
GAATTCCGGGAAGCCAGACGGTTAACACAGACAAAGTGCTGCCGTGACACTCGGCCCTCCAGTGTTGCGG
AGAGGCAAGAGCAGCGACCGCGCACCTGTCCGCCGGAGCTGGGACGCGCGCCCGGGCGGCCGGACGAAG
CGAGGAGGGACCGCCGAGGCTGCCCCCAAGTGTAACTCCAGCACTGTGAGGTTTCAGGGATTGGCAGAGG
GGACCAAGGGACATGAAAATGGACATGGAGGATGCGGATATGACTCTGTGGACAGAGGCTGAGTTTGAA
GAGAAGTGTACATACATTGTGAACGACCACCCCTGGGATTCTGGTGCTGATGGCGGTACTTCGGTTCAGG
CGGAGGCATCCTTACCAAGGAATCTGCTTTTCAAGTATGCCACCAACAGTGAAGAGGTTATTGGAGTGAT
GAGTAAAGAATACATACCAAAGGGCACACGTTTTGGACCCCTAATAGGTGAAATCTACACCAATGACACA
GTTCCTAAGAACGCCAACAGGAAATATTTTGGAGGATCTATTCCAGAGGGGAGCTTCACCACTTCATTG
ACGGCTTTAATGAAGAGAAAAGCAACTGGATGCGCTATGTGAATCCAGCACACTCTCCCGGGAGCAAAA
CCTGGCTGCGTGTCAGAACGGGATGAACATCTACTTCTACACCATTAAGCCCATCCCTGCCAACCAGGAA
CTTCTTGTGTGGTATTGTCGGGACTTTGCAGAAAGGCTTCACTACCCTTATCCGGAGAGCTGACAATGA
TGAATCTCACACAAACACAGAGCAGTCTAAAGCAACCGAGCACTGAGAAAAATGAACTCTGCCCAAAGAA
TGTCCCAAAGAGAGAGTACAGCGTGAAAGAAATCCTAAAATTGGACTCCAACCCCTCCAAAGGAAAGGAC
CTCTACCGTTCTAACATTTCACCCCTCACATCAGAAAAGGACCTCGATGACTTTAGAAGACGTGGGAGCC
CCGAAATGCCCTTCTACCCTCGGGTCGTTTACCCCATCCGGGCCCCTCTGCCAGAAGACTTTTTGAAAGC
TTCCCTGGCCTACGGGATCGAGAGACCCACGTACATCACTCGCTCCCCATTCCATCCTCCACCACTCCA
AGCCCCTCTGCAAGAAGCAGCCCCGACCAAAGCCTCAAGAGCTCCAGCCCTCACAGCAGCCCTGGGAATA
CGGTGTCCCCTGTGGGCCCCGGCTCTCAAGAGCACCGGGACTCCTACGCTTACTTGAACGCGTCCTACGG
CACGGAAGGTTTGGGCTCCTACCCTGGCTACGCACCCTGCCCCACCTCCCGCCAGCTTTCATCCCCTCG
TACAACGCTCACTACCCAAGTTCCTCTTGCCCCCTACGGCATGAATTGTAATGGCCTGAGCGCTGTGA
GCAGCATGAATGGCATCAACAACTTTGGCCTCTTCCCGAGGCTGTGCCCTGTCTACAGCAATCTCCTCGG
TGGGGGCAGCCTGCCCCACCCCATGCTCAACCCCACTTCTCTCCCGAGCTCGCTGCCCTCAGATGGAGCC
CGGAGGTTGCTCCAGCCGGAGCATCCCAGGGAGGTGCTTGTCCCGGCGCCCCACAGTGCCTTCTCCTTTA
CCGGGGCCGCCGCCAGCATGAAGGACAAGGCCTGTAGCCCCACAAGCGGGTCTCCCACGGCGGGAACAGC
CGCCACGGCAGAACATGTGGTGCAGCCCAAAGCTACCTCAGCAGCGATGGCAGCCCCAGCAGCGACGAA
GCCATGAATCTCATTAAAAACAAAAGAAACATGACCGGCTACAAGACCCTTCCCTACCCGCTGAAGAAGC
AGAACGGCAAGATCAAGTACGAATGCAACGTTTGCGCCAAGACTTTCGGCCAGCTCTCCAATCTGAAGGT
CCACCTGAGAGTGCACAGTGGAGAACGGCCTTTCAAATGTCAGACTTGCAACAAGGGCTTTACTCAGCTC
GCCCACCTGCAGAAACACTACCTGGTACACACGGGAGAAAAGCCACATGAATGCCAGGTCTGCCACAAGA
GATTTAGCAGCACCAGCAATCTCAAGACCCACCTGCGACTCCATTCTGGAGAGAAACCATACCAATGCAA
GGTGTGCCCTGCCAAGTTCACCCAGTTTGTGCACCTGAAACTGCACAAGCGTCTGCACACCCGGGAGCGG
CCCCACAAGTGCTCCCAGTGCCACAAGAACTACATCCATCTCTGTAGCCTCAAGGTTCACCTGAAAGGGA
ACTGCGCTGCGGCCCGGCGCCTGGGCTGCCCTTGGAAGATCTGACCCGAATCAATGAAGAAATCGAGAA
GTTTGACATCAGTGACAATGCTGACCGGCTCGAGGACGTGGAGGATGACATCAGTGTGATCTCTGTAGTG
GAGAAGGAAATTCTGGCCGTGGTCAGAAAAGAGAAAGAAGAAACTGGCCTGAAAGTGTCTTTGCAAAGAA
ACATGGGGAATGGACTCCTCTCCTCAGGGTGCAGCCTTTATGAGTCATCAGATCTACCCCTCATGAAGTT
GCCTCCCAGCAACCCACTACCTCTGGTACCTGTAAAGGTCAAACAAGAAACAGTTGAACCAATGGATCCT
TAAGATTTTCAGAAAACACTTATTT
```

FIG. 25

```
CGCCGCCTGTGCAGCCGCTGCCGCCGCCGCGCCGCCGCCGCCGCCGCCGCCGCCGCCGCCGCTGCC
GCCCGGCTGCCGCGCCGCGCCGCTGCCTCTGCCCGGCCGCCCCGCCGCCGCTGCCGCCGCCGGCCCG
CAGCCAGCCAGGCGGGCGGCCCAGCCCGCCTGAGCCCGCAGCGGCTGCCGCCGCAGCGTCGGGTCGCTGG
GTGCGCGGGCTACCGCGGACCGAGCGGACCCGAGTGGGCGACCAGGCGCTTGCCCGCCCAGTGCCACTGC
CGCCGCTTCCTCGCCGGAGCACAGGACCAGACACCTCCAGCGCCCGCTGCTGCTGCCGATGCGGCCCGGA
CACTTTTAGCTGGGCGGGAGGGCTGGAGAGCCGGGGGCCGCCGAGAACCGCCAGCGAGCTGTGCCGAGAG
CCGCGCCGACCCGCTGCGATCAGGGACAGGCGCCCGCCCGCCGCCGCCGCCTGGCCGCTATGGATCTATT
CGACTTTTTCAGAGACTGGGACTTGGAGCAGCAGTGTCACTATGAACAAGACCGTAGTGCACTTAAAAAA
AGGGAATGGGAGCGGAGGAATCAAGAAGTCCAGCAAGAAGACGATCTCTTTTCTTCAGGCTTTGATCTTT
TTGGGGAGCCATACAAGGTAGCTGAATATACAAACAAAGGTGATGCACTTGCCAACCGAGTCCAGAACAC
GCTTGGAAACTATGATGAAATGAAGAATTTGCTAACTAACCATTCTAATCAGAATCACCTAGTGGGAATT
CCAAAGAATTCTGTGCCCCAGAATCCCAACAACAAAAATGAACCAAGCTTTTTCCAGAACAAAAGAACA
GAATAATTCCACCTCACCAGGATAATACCCATCCTTCAGCACCAATGCCTCCACCTTCTGTTGTGATACT
GAATTCAACTCTAATACACAGCAACAGAAAATCAAAACCTGAGTGGTCACGTGATAGTCATAACCCTAGC
ACTGTACTGGCAAGCCAGGCCAGTGGTCAGCCAAACAAGATGCAGACTTTGACACAGGACCAGTCTCAAG
CCAAACTGGAAGACTTCTTTGTCTACCCAGCTGAACAGCCCCAGATTGGAGAAGTTGAAGAGTCAAACCC
ATCTGCAAAGGAAGACAGTAACCCTAATTCTAGTGGAGAAGATGCTTTCAAAGAAATCTTTCAATCCAAT
TCACCGGAAGAATCTGAATTCGCCGTGCAAGCGCCTGGGTCTCCCCTAGTGGCTTCCTCTTTATTAGCTC
CTAGCAGTGGCCTTTCAGTTCAAAACTTCCCACCAGGGCTTTACTGCAAAACAAGCATGGGGCAGCAAAA
GCCAACTGCATACGTCAGACCCATGGATGGCCAGGACCAGGCACCGGACATCTCACCAACACTGAAACCT
TCAATTGAATTTGAGAACAGCTTTGGGAATCTGTCATTTGGAACACTCTTGGATGGAAAACCCAGTGCAG
CCAGTTCAAAGACTAAACTGCCAAAGTTCACCATCCTCCAAACAAGTGAAGTAAGCCTTCCCAGTGATCC
AAGCTGTGTTGAAGAAATCTTGCGGGAGATGACCCATTCCTGGCCTACTCCTCTCACTTCCATGCATACT
GCTGGACACTCTGAGCAGAGCACCTTTTCCATCCCAGGACAGGAATCGCAGCATCTGACCCCAGGATTCA
CCTTACAAAAGTGGAATGACCCAACCACCAGAGCTTCTACAAAGTCAGTGTCTTTCAAATCGATGCTTGA
GGATGACCTGAAGCTGAGCAGTGATGAAGATGACCTTGAGCCTGTGAAGACCTTGACCACTCAGTGCACT
GCCACTGAGCTCTACCAGGCTGTTGAAAAGGCAAAACCTAGGAATAATCCTGTGAACCCACCCTTGGCCA
CTCCCCAGCCCCCACCTGCAGTGCAAGCCAGCGGGGGTTCTGGCAGCTCCAGCGAATCGGAGAGCAGCTC
TGAGTCGGATTCAGACACTGAAAGTAGCACCACTGACAGCGAATCTAATGAGGCACCTCGTGTGGCAACT
CCAGAGCCTGAGCCACCCTCAACCAACAAGTGGCAACTGGATAAATGGCTTAACAAAGTGACATCCCAGA
ACAAGTCTTTTATTTGTGGCCCAAATGAAACACCCATGGAGACTATTTCTCTGCCTCCTCCAATCATCCA
ACCAATGGAAGTCCAGATGAAAGTGAAGACGAATGCCAGTCAGGTCCCAGCTGAACCCAAAGAAAGGCCT
CTCCTCAGTCTCATTAGGGAGAAAGCCCGTCCACGGCCCACTCAGAAAATTCCAGAAACAAAGGCTTTGA
AGCATAAGTTGTCAACAACTAGTGAGACAGTGTCTCAAAGGACAATTGGGAAAAAACAGCCCAAAAAAGT
TGAGAAGAACACCAGCACTGACGAGTTTACCTGGCCCAAACCAAATATTACCAGCAGCACTCCCAAAGAA
AAAGAAAGTGTGGAGCTTCATGACCCACCAAGAGGCCGCAACAAAGCCACTGCCCACAAACCAGCCCCTA
GGAAAGAACCAAGACCTAACATCCCTTTGGCTCCCGAGAAGAAGAAGTACAGAGGGCCTGGCAAGATTGT
GCCAAAGTCTCGGGAATTCATTGAAACAGATTCATCTACATCTGACTCCAACACAGATCAGGAAGAGACC
CTGCAAATCAAAGTCCTGCCTCCGTGCATTATTTCTGGAGGTAATACTGCCAAATCCAAGGAAATCTGTG
GTGCCAGCCTGACCCTCAGCACCTTAATGAGTAGCAGTGGCAGCAACAACAACTTATCCATCAGTAATGA
AGAGCCAACATTTTCACCTATTCCTGTCATGCAAACTGAAATCCTGTCCCTCTGCGAGATCATGAGAAC
CTGAAAAACCTCTGGGTGAAGATTGACTTGACTTACTCTAGAGTACCTGGCCACAGCTCACTCCATG
CAGCACCTGCCAAGCCAGACCACAAGGAGACTGCCACAAAACCCAAGCGTCAGACAGCTGTCACAGCTGT
GGAGAAACCAGCCCCTAAGGGCAAACGTAAGCACAAGCCAATAGAAGTTGCAGAGAAGATCCCTGAGAAG
AAGCAGCGCCTGGAGGAGGCCACAACTATCTGCTTGCTCCCTCCTTGCATCTCACCAGCCCCACCCCACA
AGCCTCCCAACACTAGAGAAAATAATTCATCCAGGAGAGCAAATAGAAGAAAGGAAGAAAAACTATTTCC
TCCTCCACTTTCCCCACTGCCAGAGGACCCTCCACGCCGCAGAAATGTCAGTGGCAATAATGGTCCCTTT
GGTCAAGACAAAAACATCGCCATGACTGGACAAATCACATCTACCAAACCTAAGAGAACTGAAGGCAAAT
TCTGTGCTACTTTCAAAGGGATATCGGTAAATGAGGGAGACACTCCAAAAAAGGCATCCTCTGCCACCAT
CACTGTCACCAATACTGCTATTGCCACTGCTACTGTCACTGCTACTGCCATTGTCACCACCACTGTCACA
```

FIG. 26A

```
GCTACTGCCACCGCCACGGCCACCACCACAACTACTACCACTACCATTTCCACCATCACCTCTACCATCA
CTACTGGCCTCATGGATAGCAGTCACCTGGAGATGACGTCCTGGGCGGCTCTGCCCCTTCTATCCAGCAG
CAGCACTAATGTCCGGAGACCCAAGCTCACTTTTGATGACTCGGTTCACAATGCTGATTATTACATGCAA
GAAGCTAAGAAGCTGAAGCACAAAGCTGATGCACTGTTCGAGAAATTTGGCAAAGCTGTGAATTATGCTG
ATGCCGCCCTCTCCTTCACTGAATGTGGCAATGCCATGGAACGCGACCCTCTGGAAGCAAAGTCCCCATA
CACCATGTACTCTGAGACTGTGGAGCTCCTCAGGTATGCAATGAGGCTGAAGAACTTTGCAAGTCCCTTG
GCTTCGGATGGGGACAAAAAGCTAGCAGTACTATGCTACCGATGTTTATCACTCCTCTATTTGAGAATGT
TTAAGCTGAAGAAGGACCATGCTATGAAGTACTCCAGATCACTGATGGAATATTTTAAGCAAAATGCTTC
AAAAGTCGCACAGATACCCTCTCCATGGGTAAGCAATGGAAAGAACACTCCATCCCCAGTGTCTCTCAAC
AACGTCTCCCCCATCAACGCAATGGGGAACTGTAACAATGGCCCAGTCACCATTCCCAGCGCATTCACC
ACATGGCTGCCAGCCACGTCAACATCACTAGCAATGTGTTACGGGCTATGAACACTGGGATATGGCCGA
CAAACTGACAAGAGAAAACAAAGAATTCTTTGGTGATCTGGACACGCTGATGGGCCTCTGACCCAGCAC
AGCAGCATGACCAATCTTGTCCGCTACGTTCGCCAAGGACTGTGTTGGCTGCGCATCGATGCCCACTTGT
TGTAGTGGGTGTTCTCAGATCTCTAGCATCACGACCCATCACTCTACCTCTACCAGCGCACTGATGGTCA
CTGGTGGAACTCCACTCACTGGGGAACGTTCTCTTTGGTTATGTTTGTTTTATGCTTCTTTTGTTATCT
GTAAAAAACAGAAGTCATTGTAAGTTGACACTACAACTTAAGGGCAGTGTACGTTTTATTACTTAGTCAT
TTTTTTTCTTTTAGCATTTGATATGCATTTCTCAGATTCCACCATCTTTTTGTGCTTTATGGAATGACAG
TCCCTACAATATTGTTTTAAGCCCACACTACCCAAAACAAAGAATGGGAAGCACTTGTGATAAAGACAGG
CTCCTGAGAAATGCAACAAGTGGTCTTACATATACATGAGAACTTAGACACAAGGGACCATCCCCCAAAC
TCTACTCTTATACCCAGAAAAGAACATATTTCAGAATCTGTCAAACTTTTGTGTATCCCACAGATTCAAT
CTTCAGGTGAGAATTTTCATTGTCAAAACCCACTGGTTAGATGTTGTAGCAACATCATAAAATCAAGAGT
ATCAAGAAAATAAATGAGCATAGCAATGCTACTCTTAAAAAGATGCTATGCCACACAACCAGAGGACTTT
CTTGTTAGCATCCCTTTCCTGATTCCCTATTTGTTAATTTTAATGATAAGAAGAAAGGGTGACATTTAT
TTTGACAAGTTTTAGGCATCAGCTGGCATCAGTGTTTTTCAACTCCATTATTTGAAGTGTAAATCCTCAC
CTGGGGTTCTCTGTGTGCAAAGCTGTCCTTTTGAAGAACAGTTTGGTTGATGCATGCCTTAGTAGCCAAA
ATGCTACACTCTAGACTTACAAGTGGGAGTTAAGAGAGGTCTGGAAAGTGTCCAACAAGGAATTCACACC
TCTGCCTCCTTTGCAACAACAACATTTACACAGTTGGTAAGTGGGTCCATAACTGGCAGGATTTTTAAAT
TGTATTTTGCTCAAATCTATGGGAACAAAAGTCAAGGTATCACTACCTAGAAGTAATGATATACAGTTTT
CTTCCTAGTGGCTTGAAAATCTGGACTTCCTCAATTATTATTCACATTTTCTCTCTTATAGGTTTTCTGT
TTTCTACTTTCTTTTTTCTCTTATCTGTGTTTCCCTTTCCTTTGTTTGGCTCATTAACTTTGACTGAAT
TACAATTACTCCTTTTATTAAAGTCCATATTATTGTGAATCATTTCCATGAAAATTTCTAAGAAAACTCC
AAACTCTCTAAATAGTAGCTAACTTTTATTTTTTAAAATGAGTCGTGGGGTAGTGCTTCACCTTGAGAT
GCTTTGAAAGAGCCCTAAACATTGGGAACCATTCACCTAATTTGGAGACATTTCTCACTGGTTGTGACTA
CCCCCTTATGATCCTTCACATTCATTTTATGTCCCTAAACATCACAATGTAAATATCATTTTTGATGTTC
CAGCTCACCAGAAGATTCTTACACTTGGGGTAAACACTATCCATGCATTACTTACTGGTAATTACCTGCT
GGTATATAATTCCATGTAGCCTTTAATATGCTGGGTTATCAAATTCTGTTCACTGAGTTATGACCAGATA
AATAATAGATATGCACATGAAAGATGCAAACTTGTGTGATTATTAAAGCCAGCCATGCAGGTCCATGATA
GAAACAGCAGGTGATGACTCTGCACTCTCATTGTCAAGGTTAGCTATATCCCCAGTTGCAAAACAGCCAG
ACTTGAGCTGTGCTCTGGTCATCTTTGAGTTTAAGGCCTTTTGTTGTATAAGGCTGTGGAAGTTGTACTC
CAATGGCTGAAGCCATGTTGTTAATATGGCTGATGGGAGCATCCCTGCAGCTGAACCCAGCACTTTTTAT
GCTCCCACTGTGGTTGAGCTTTATGTTTACAGTCTCAGCAACAACACTTATGCATCCAAACACTCACAAA
TGAAACCTGAAAGAATCTTTTCTGAGCCTCTTAAAAGAGGAAAATGATGATAACATTAAAGACTCTGAAC
ACCCAAGGTTGGTGTCACATATAAAAATTAAGCTGATGACTTTGCAGTGACTCAAGTTGTCTCTTTATCA
TGGTTTACCAGGTAGAGTGCCTGGCTATTACTATATAATGAAGCCCACTGGCTTGACTTGTAAGTTCAAC
CTAAACCACAATCCTAGACCATCATGGATTTAGGAGTAGATTCTTCTTGAAATCCCACATCCAGAAACTA
GACATTAGAATGTTGAGGCAGTTTCCCAGAGAAACAAGCATATTGCCTCATGGATGAAAGACTTGTAGTT
CTAGTTTCAGTGACTTGTTATATCTACTTACATACAACAGGGAGGCAAGAGGATTCTCTGTCATCTCTGG
TGACTGAGTGTAAAATATGTGCCAAGTCTGCAGCACAGTGACCAAATCTGACAATCGAGCTCTGGATCAC
CACTTGATTATGTAGTAGACTCATTTATAAAGCAGCTTAGGAACTAATTAAACATGGAGGATGAATTACC
TTCCTATCCCTTGAGATAAGACATCTTTCAGTTTCATGATTAAGGATTGTTGCTGTTTTATAGTTACTCT
GTTCATCACAGTGTAAATGGTGATGCGTGTCGTAGGTGTGCAGCTATTTGAGGGACTAAGGGATGGAGAT
ATTCTGTCAAATGAATCTCTTCAGTATACCAGTTTGTGGGAGGGATATGAGACATGTGGATGGCAGTGAG
```

*FIG. 26B*

```
AGATCGTGCCTCTAGATCTTGATGGAGGCTTGGTGAGACACACTTAAATAAGCACGTGGAGGTTAGAATA
GAGGGCAGAGTAAAAGGAAGCTCCATCTGAGCAAGTACACCAAATGATCTCAGCCCTGCAACTTGACCCA
GGTAGGGCCACCACTACGCCTTCACTTGTCACCCAAGCTCCAACCACAGAGAGTTTGACAAGTTTGTGTT
ATGATGTTGGCTTGGCTTTGTATTTTTAATTAACTTTGGATTTTTAGTGGTTTTGTCATATAACTGTCTG
AGTTTGGTAGGTAGGATTACTTTGAAAAGGGTTTACTAGTGTGGTCCTCCGGGTAGAATTTAGCTGTAAC
ATGTTGTTAGCCAGCCTGTAGACTGTTAATTACTTAATAATCTCATTGGGAAAATACTAGTAGTTTTATA
TTTGGATGACATAATTGGAAAAAGCAGATTAGCTGCTACTACTTTTAAAAGACTTAAGGTCGGGATGCCT
TTTTTTCCATGTAAGGAAATGAAAAGACCCAAAATCTTCAGGCAAAAAGCAAGTTGCAAAATTAGAAACC
ATTGGCTAAAAATGTGTTTGTTGAGTTTCCAAATGGATGAATTTTCATTTGGACATTACATCACTAAAT
TCATTAGATTTTGTCTGCATTGGAAAGATACTCTTCTAGCATATCTTTCCCAAAGATATCTAATTTGGAT
TCTGTTTCATGCAAATTTGCATCCCGGAGGTTGAAGTTGGAGTTTGAGGTTGGAAAATATCTTTGAAGGC
AGAATCAGTTGAGTTGTGAGGGTGAAGCCTCACATACTTCTCAACAGACATGATAAAATTCACCTGCATG
AGTTGGCAGGTGGGAGAACCAAACTGGATCACTGGGTAAGACTACTCAGTAAAGCAATGAACTGCTTGCT
TAGAGAAGCATCACTATCCCCATTGAGAAAAATGTGTGGCAAGATGATACAGCTACACAGTATCAAATGA
ATGGGTCAATTCAGCACCCCCAAATTTAATTCTGTGGGGAAAAATTATTGAGCCAGTTGTCAGTGTTCTG
TTACATGACTGGCAGACTAAATTCTTCATCGTTGTTGTTATTGTTGTTGTTTCTCATTTTCACTCGC
ACGGCCTTATTCTCATAATTAAAATCTAATTCATTTTCTCTTTAGTGTTAGTAGACTCCAACAACAGAAG
TGGCATCTGTGTATTCATAATCAGCATTTACCCTGGCAGGAGACTAATCAGATAGGCCGGTCTCAGACAT
TAATCCTACCATCTGATATTTTGGTGAAGGAAAAAGTATTAATTCTCTTTCCATCCTCCTCCTCAGAAA
TATAGAAGCCCTCTTTACCAAAATCATCACATTTTACTCTGTAATCTACCAGCTAAAAGAAAATTGCATT
GAAGCCCCACAAAGCCAGATTGCAGTTCTTGCCCCTTTTTGCGTCTGACATGAGATGTTAAAGAATTATT
CATTGTGCTCACATTGGGTTAGGGGACACTGAACTGCTTTTTAGATCCATGATCAGTCATCATTCTTCTA
AGAGATTGGAGCTTTGCTGTTTCATTAACTGTGCAGTGTAGACTAATGGTGTTTAATAAAAATCATTCAA
AATTTCAAACTCTTTTGCCAGTGACCTCAATTTTGTTGGCTCTGTGATTTGTATCAGACTTTGAGGAGGG
AAGGGGGAAGTGAAGGAAGCCTACGTCCAGGCCCCTGACAGGATGCTGCAGTAGCAAGCTCAAGCTCGCC
TGCCTGCCAGCAGTTGCTGGTGAGCAGCAGCATGCAGACCAGCTGTGGGAAGCCTCCTGAAGAATGCCCC
AGCTGATGCTTTCAGCTGGGAATAGTTTGTTCCTATTGGGGAACTCATTGTTCTCCAGTCTCTGCAGCAG
GAAGCCAGCTGTCATATTCGGAGGGAATTTCAGATGCTTTACCTTTTGGTTTTGTCCTGCATCACTCAT
GTGGCTACGAAAGTGTCTCTGAGAATAGAGCCCAATGTGGTGACAATGGGTAGTCAAATGCACCCCAGAT
GCTCAAGCCCTGTTGTGGTTCTGCAGTGTTTATGAAATTGGGAGGAAGGAGACCCTGGACAGTAAGCAAA
ATTGGAGACACTCCAACGAGGCTAAGTTAATGCCGTGTTGCCCAGAACAAGATCTAGCTTCTCATTTGGT
CAGCCTAGCATGCAACCAGTGGTGTGCTGGTAAAATGTTTAACAACCAGCTCGCTGAGAATAGAAAGCAC
CTGGTTTGCACCATTTGCCAATTTCCATGGCATAAATACTACCACTTTAGATGATTTTAAGCTACCAACT
GTGATGTCACTGAACACATGGTTGGAAAGAGATGCACGCAGTTGGCTCTTGCAAGCCTGGGCAAAAATGC
TTCAACACGCCACTGGATGCAGCCAGTCAGAGGGTTCATATTTAATATATGTGTTCATGTGGACACACAC
AGACACACACACACAAACTCACCCTTACACACACACTTCGATGACTAAAACAATTACATAGTTTTAAGAT
ATGAATCAATGTGTGAATGTAGAAAGCTTATGATAAGGCCCTAGAGGTATGGGTTGCCCTGGAAGCCTAG
GTTTTAAGCAGGAGAATAGCTGAGAAGAATGAAGCCCTCCTGAGCTGAAAGGAGAGATGGATCAATGGAG
ATGGTTCCATCATCTCCTTCCATATCTCACAGGTAAAATGGGCACTCAGAAAACCCTCACGATTGATTTT
TTAAAAAGATAAGTGAGTGTTTTTATTTTATTATTATTGTCATCATTATTTTGATTTACAAATGCTATT
TGTAACTTTTACATGTAACTAGGATAAAGTATTTACGGGAACTCTATGGAGAATAGCACAATCCAGAATT
TACTGTGTTTTTCTTTTATGTGACGTGGAAACTCAGTAATTCTCCCACCTTCACATTGTTGTTCATAAGA
ATTTTACTTTAGTTATTAGGGAATCTAAGTTTTTTGTTAACATTTGTTTTTAGTTAAAAGTATCTACTTA
CTGTTTTAGCTCTGAACTCAAACCAGAATATCTCTGTATCAATTGCATGACTATTCAGAAACAATAATCC
AAACCAAAATAATTCTTTTTCCACCCAGTACGAAGAAAACTAAGCTCAGTAACAAGAAGGCATAAACTAA
AGTATATAATGAGGCTTTCATTAAATACACACACACACACTCACACACACACACATACACTTTTTAAA
TTTTTAAATTAGGCCTCCACACATAAATCATTTTGAAAGTAGAATAGAAAATCTCAAAGAATTCATTCTC
CTGGTCCTGTGCATCTTCTGCAGTTAATAAGAGGTTTGTATCTGGAAAGATGGAAGAACTTGTTCTAAAA
TCTTATTTTTCAAAAAAAAATTTCCATTTTCTCTCTGGGCCTGTATCCATGGTTGAATGTTAGCCCTGGA
GGAGATCCATGTCTTACTCGCTCTTTCTGGCCCTTCTGTCTTTTGCCTCTGCAATTCTTTTTGTAGCTGG
CACGATAGCAGGGACTGGGGGTCTATCCTTTCATGGTATTGCTACAATATTTGTCCTTACTGGAAAATGG
TAACATCCGGGTCTGATTTAATTGGCATTACACTTACACAGGGACTCTGAGCACCCCCGTCACCACACCA
```

*FIG. 26C*

```
GACAGTGGACCAGTTTTCACAGCTACAAAGAGCTAGAAATGTGTTTAACATCATCCAGTGCATCCCCTAA
TTCAAAACCATCCTCACTAATCAATCATATTCACCCATAAATATTACAAATGAGATTGATTCCATCTCAA
GACAATTTGTCAAATACTTAATTTTCTTCCTGGATGATTCTACTTACTGGATATTTAGAAAGAGAAATG
TCTGAGATAAAATCCCTCACATTTACTCAATATAACAAATTACTGTTTCTACTCCTATTCTGAGTAGTGC
TTCTGAAGATTGTTTGCTGTAGTGTTGTCTTTGATAAAATGAATGTCAGTAGTGAGCCTTTTAGAGATAC
CATGCTCAGACATCCTCTTTGGGATCAGAAGATACCTAAAATTCTCCCTTTTGCCCACTTGGTTAGATG
AGTGATATATTCTTTGGATCCTGCAAAGAAGAGATTGGTTTCTTTTCTTTTCTGGTGGTGGTAGTGGTTG
TATCTGTGGCTGTGATGGTTGTTGTTACTTGTCTCTCTCTCTCTGGCTCTGGCTTTGCTTTCCTGCT
AGTGTTCTTTCTCTTTCCAAACAAATAGTTAAATTAAACGTGAGCTTCTGAATTGTACTTGTTCATACTT
TCAAAACATAACAGATTAATAAAAATAGATGTGTCCTGATTTAAAACATGCCCCCTGGAAAGGCATGCTG
TATTATGAAATCGTGATAATATAACTGCATTATTACATGGCAGTATAAATATTAGTCTGTTGAATTCATT
TGTCCAATTGTATAACTTTGTGGAGCAGTGTTTTGACCTTTGATACATAATTCTGGAGCAAGTGGAGTGG
TTGCAGGCAGATGAGACAGTGTTATATCAGGATTTTTCAATCAACTTTAGTTGGAGGCCTGGCAATTACA
AACATCTTCAGATGTTTCTGTAACCATTATAAATATGAAAAAAACCTCTTCAAAAAATTTCCCATAGTAC
TTCAGTCAAGACTTTTTAGGTTTATCTTTTTTTTTTCATTTCTCCTTTTCCTTTTCCATTATTTTTCGAT
GGGGGGGTTGTTATCATTGACTGAAGAAATATTTTGATTGCAATGGTCTCTCTCTCTCTCCCCTCTCTC
TCTCTCTCCTCTATTCTTTCCTCCTTCCCTCTGTCCATCACCCCTCATTAAAATATTGAAATCTGGAGTC
TTTGATAAATCTGCATTAGACCAGGCTATATGCTAGGAATGAAATCTGGGCAAATATCGATGGGTTTTCA
AAGAATGCTCCATGTTCATTGGGCCCTTTCACACCCCACAGTGATAAATGAAAAGGATAGAGGTAGTTTT
TTCAAAAGAGCACTTTAATAATATCCTCTGAGACCTAATGCAGTTTAACAAATGACTCCACCTATTTTTC
CAGTAGGTAAATTGACTGAGACTTGCAAAATACCCCTGAGAGTTGTCAGGGGTGTCTTCTGCCTGGTCTA
TAGCGTGTGTGTTTGCTTTGTATCTAACAGGCACATTCACGTCTCGTGTACTCATATGAAGTATTTCCTA
ACATTCCCATTAGCCTGTATATAAGAATCAGAAAGATAATCCCAACATGTTGTAAATGAAGATGTGACTC
TATAACCTTTCTCTTCTTCCTGGAAAAAAAAGGACATTTTCATGCATATTTTAAACAGAAATTTTGTATA
TTTAAGTGTCATAGAAAATATTTATTGAGTAACTGGGACACAAATGGGAATTTAATTGTCATCATATGCT
TTGTGTGTGGGGATGCTTACCAACACCATGTCGCTGGACCATTGTGGCAAGCCATAACTGCACAAAGAGT
ACACATCGTCAGTGTGTGTGTGTGTGTGCGCGCACGCACGTGCGTGTGTGTCCCTGCATGTG
CAACATGTCTAGCTTGCTGTCCTTCATGGGATTTTAGCTTTCCCTTCTTGAAAAACATTATTTTACAGTT
CCAGGAGGCCCTGGTTACATTACTATATGAAGGCAGTGATTTGAAATGAAAATTCCTTTCCTCTTGGAAG
CTTTGGTCATAATATCATGGTTCAATTAAACGGATTCCACCGGACTTTGTGATGAAAAGGCTCTGTTAA
AATCCAATTGAGTTTCCAAGAGGAAATTGTAGTAGGTCAAGATGCATGAGAGGGAAGATGGAGGCCACCT
CAGCTGGAGAACATGAGCTGAGTTGAGCCCTCAGTGTTGAAGTTGACTTGCTCCAAGCTGCAGTCTAAAA
CCCTGGGGCCCGTGCCTGGCCTATGCTCCCTCCCAAGTAAGTAGAGGAGCAGAACCATCAGGAACAGCCT
GCCTGGCTCCTATGAAGAAAACTTCCTGACGTCCTGTCCCCAAAGGAAGACCCTTTCCCCAAGGGCACCC
CAGGTGGCCATTAAATTGTGATGATCATTCAGAAAGTGCCCCCTTGGCTTTATGAGAATCCAATTAGTCT
TCTGAACCACCTTTTCTTGGGTGCAGATTTCCAACATTCATGCTCATTGCAGATCCACCAACTGTCACTG
TTCTTAACAAGCATGCTCGTCTTGTCAGAATTTCAGTAAGTTCCAATTTCCTGTACAGACCAGGGTAAAC
TGTTCTAAAATCAATCAATTAATGAAATGTTATCTGGTTTTTAAAAGCTGGTTTCATGTGCTTTATGTGT
ATAAAACTATATCTGCCTGTGTGGCTTTGCATTTCAAATGTGTGGCGCACAAGCGTTTTGTTGGTGCTTT
GTTCTCAGTACAGTAACTCTGTGTACAAACATTTAATGTGGTTTTGTTGTTTCCAACAAGATGTCTCT
GTAAAAATGATATTGGCTGAGCTGGTGCGTTGGTTTCTCTCATAGAGGCATTAACTATACTGCCAATGCA
TTGAATTATTTAAAAATGCAAAATAAAATTTTTATGAAAATCTCA
```

*FIG. 26D*

NUCLEIC SEQUENCE AND DEDUCED PROTEIN SEQUENCE FAMILY WITH HUMAN ENDOGENOUS RETROVIRAL MOTIFS, AND THEIR USES

CROSS-REFERENCE TO A RELATED APPLICATION

The present application is a divisional of U.S. Ser. No. 09/719,554 (now U.S. Pat. No. 6,919,438, filed on Jan. 18, 2001, which is a National Stage (371) of International Application PCT/FR99/01513, filed on Jun. 23, 1999, which claims priority to French Patent Application No. FR 98 07920, filed on Jun. 23, 1998.

The present invention relates to a novel nucleic sequence and deduced protein sequence family with complete or partial human endogenous retroviral motifs, and sequences flanking or adjacent to said sequences, and controlled by the latter; modification of the expression or impairment of the structure (polyadenylation, alternative splicing and the like) of said flanking sequences.

The invention also relates to the detection and/or use of said nucleic sequences and of said corresponding protein sequences in the context of diagnostic, prophylactic and therapeutic applications, in particular for neuropathological conditions with an autoimmune component such as multiple sclerosis.

The invention also relates to the production of antisense double-stranded and single-stranded nucleic probes, of ribozymes, capable of modulating viral replication (T. R. Cech, Science, 1987, 236, 1532-1539; R. H. Symons, *Trends Biochem. Sci.*, 1989, 14, 445-450) of the corresponding recombinant molecules, and associated antibodies.

Retroviruses are viruses which replicate solely by using the opposite route to the conventional processing of genetic information. This process, called reverse transcription, is mediated by an RNA dependent DNA polymerase or reverse transcriptase, encoded by the pol gene. Retroviruses also encode at least two additional genes. The gag gene encodes the proteins of the skeleton, matrix, nucleocapsid and capsid. The *env* gene encodes the envelope glycoproteins. Retroviral transcription is regulated by promoter regions or "enhancers" situated in highly repeated regions or LTR (Long Terminal Repeat) and which are present at both ends of the retroviral genome.

During the infection of a cell, polymerase makes a DNA copy of the RNA genome; this copy may then integrate into the human genome. Retroviruses do not kill the cells which they infect, but on the contrary often enhance their rate of growth. Retroviruses can infect germ cells or embryos at an early stage; they can, under these conditions, integrate the germ line and be transmitted by vertical Mendelian transmission, which constitutes the closest relationship between a host and its parasite. These endogenous viruses can degenerate during generations of the host organism and lose their initial properties. However, some of them may conserve all or part of their properties or of the properties of their constituent motifs, or acquire novel functional properties having an advantage for the host organism, which would explain the preservation of their sequence.

The existence of endogenous motifs having long open reading frames and/or subjected to a strong selection pressure can therefore be an indication of a preserved or acquired biological function, which may correspond to a benefit for the host organism. These retroviral sequences can also undergo, over the generations, discrete modifications which will be able to trigger some of their potentials and generate or promote pathological processes. It has recently appeared necessary to carry out a review and to identify these sequences so as to be able to evaluate their functional impact.

Human endogenous retroviral sequences or HERVs represent a substantial part of the human genome. These retroviral regions exist in several forms:
complete endogenous retroviral structures combining gag, pol and env motifs, flanked by repeat nucleic sequences which exhibit a significant analogy with the LTR-gag-pol-env-LTR structure of infectious retroviruses,
truncated retroviral sequences; for example the retrotransposons lack their env domain and the retroposons do not possess the env and LTR regions.

Up until now, the study of these regions of the genome has been neglected in humans for essentially two reasons:
the existence of insertions/deletions which can shift the reading frame and of mutations which modify the sequence. These modifications cause impairment of the structure and consequently of the biological function of these motifs,
the absence of confirmed associations with human pathological conditions.

The recent knowledge of fragments which are significantly representative of the human genome and an orientation of research studies toward a study of structure/function of endogenous retroviral motifs have made it possible to specify the importance of these regions. The involvement of truncated or complete endogenous sequences in pathological conditions in animals is documented; for example their association with tumor processes has been clearly demonstrated (S. K. Chattopadhyay et al., 1982, Nature, 295, 25-31). Research aimed at specifying the association or the influence of HERVs in human pathological conditions is now therefore justified.

A classification of the HERV elements has been proposed (Tönjes R. R. et al., *AIDS & Hum. Retroviral.*, 1996, 13, p261-p267; A. M. Krieg et al., FASEB J., 1992, 6, 2537-2544). It is based on a homology of these sequences with retroviruses isolated in animals, with the aid of heterologous retroviral probes. Indeed, in general, the HERVs exhibit relatively little homology with known human infectious retroviruses.

The class I families exhibit a sequence homology with the type C mammalian retroviruses; there may be mentioned in particular the ERI superfamily, close to the MuLV virus (murine leukemia virus) and to the BaEV virus (baboon endogenous virus).

The class II families exhibit a sequence homology with the type B mammalian retroviruses such as MMTV (mouse mammary tumor virus) or the type D retroviruses such as SRV (squirrel monkey retrovirus).

Other families have also been described; among these, there may be mentioned HERVs which exceptionally exhibit partial homology with HTLV-1 (RTVL-H) or primate viruses; HRES-1, for example, exhibits sequence homology with HTLVs.

Programmes for very large sequencing of the human genome now make it possible to have available a significant number of novel retroviral sequences. The use of data processing software packages makes it possible to identify and analyse these genes. In this context, a systematic search relating to the entire information available to date has been initiated in order to identify novel human endogenous retroviral sequences as a function of certain analytical criteria:
presence of long open reading frames conserved during evolution of the host organism and which may suggest a biological function, analogy with sequences already characterized outside or inside the retrovirus domain, location in regions of susceptibility for certain pathological conditions or close to essential genes, for example in the cancer domain, regulation of the immune system or in certain neuropathological conditions.

The work carried out by the inventors on sequence databases allowed them to identify a set of endogenous retroviral sequences or motifs whose normal or pathological expression can promote or disrupt a protective effect in relation to pathological processes, or play a role in the onset or worsening of pathological conditions.

The subject of the present invention is a purified nucleic acid fragment, characterized in that it comprises all or part of a sequence encoding a human endogenous retroviral sequence, which has at least env-type retroviral motifs, corresponding to the sequence SEQ ID NO: 1 or to a sequence exhibiting a level of homology with said sequence SEQ ID NO: 1 greater than or equal to 80% on more than 190 nucleotides or greater than or equal to 70% on more than 600 nucleotides for the env-type domains.

The expression homologous sequence is understood to mean both a sequence which exhibits complete or partial identity with the above-mentioned sequence SEQ ID NO: 1 and a sequence which exhibits partial similarity with said sequence SEQ ID NO: 1.

According to an advantageous embodiment of said fragment, it has retroviral motifs corresponding to an env domain and corresponding to the sequence SEQ ID NO: 1 and retroviral motifs corresponding to a gag domain and corresponding to the sequence SEQ ID NO: 2 or to a sequence exhibiting a level of homology greater than or equal to 80% on more than 190 nucleotides or greater than or equal to 0.70% on more than 600 nucleotides for the env-type domains and a level of homology greater than or equal to 90% on more than 700 nucleotides or greater than or equal to 70% on more than 1 200 nucleotides for the gag-type domains, said motifs having no insertion or deletion of more than 200 nucleotides.

Said fragments constitute a novel family of human endogenous retroviral sequences (HERV-7q family) which exhibits sequence homology with the MSRV retro-viruses, as described in International Application WO 97/06260; said fragments according to the present invention have:

two repeat nucleotide motifs of 711 bp (FIG. 3), having characteristic signals identified in LTRs (Long Terminal Repeats): transcription promoters of the TATAA or CCAAT box type. These repeat domains delimit three deduced motifs of the gag, pol and env type (FIG. 2), an env-type motif (positions 6965 nt-9550 nt on the sequence SEQ ID NO: 3 or in FIG. 1) which contains a long open reading frame of 1 620 nucleotides (positions 7874-9493 of the sequence ID NO: 3 and FIG. 1) encoding a protein having an unpublished sequence of 540 amino acids called enverin (FIG. 4 and SEQ ID NO: 26) and underlined fragment in FIG. 18. There is present inside the transmembrane domain of this env domain a peptide motif of the CKS-25/CKS-17 type (FIG. 5), recognized as having immunosuppressive functions on the host lymphocytic cells (M. Mitani et al., 1987, *Proc. Natl. Acad. Sci.* USA, 84, 237-240). A zinc finger type domain $HX_{3-4}HX_{22-33}CX_2C$ (Kulkolski et al., 1992, *Mol. Cell. Biol.*, 12, 2331-2338), which is present in integrase-type domains is identified in another reading frame. This particular env domain signatures the characteristic of novel endogenous retroviral motifs, the motif (positions 3065 nt-4390 nt on the sequence SEQ ID NO: 3) of the gag type encoding protein motifs according to FIG. 6 (SEQ ID NO: 58) (positions 3118-4198 of SEQ ID NO: 3) was identified by virtue of analogies with known gag domains. The region of major homology $QX_3EX_7R$ is for example present (Benit et al., 1997, *J. Virol.*, 71, 5652-5657). The nucleic acid binding motif $CX_2CX_{3-4}HX_4C$, situated at the C-terminal position, is identified in another reading frame (Covey et al., 1986, *Nucleic Acids Res.*, 14, 623-633). Upstream of the gag domain, a motif of 182 nucleotides is detected which is repeated twice (FIG. 1), the pol domain exhibits the conventional consensus of a retrovirus pol region at the level of the protease, reverse transcriptase and RNAse H domains. A motif close to the consensus LLDTGA is found in pol (Weber et al., 1988, Science, 243, 928-931). The motifs D and AF, LPQ and SP, and YVDD (Xiong and Eickbush, 1990, EMBO J., 9, 3353-3362) are respectively found in the 3rd, 4th and 5th homology boxes. The motifs YTDGSS and TDS are present in the RNAse H region, the gag and pol regions could be considered as being joined with a passage from the gag region to the pol region by a reading frame shift.

The present invention includes the sequences belonging to the HERV-7q family as defined above (presence of the SEQ ID NO: 1 sequence or of a homologous sequence or presence of both the sequences SEQ ID. NO: 1 and SEQ ID NO: 2) and in particular the sequences SEQ ID NO: 3-22, 28 and 61; it also includes the complementary nucleic sequences and the reverse sequences complementary to the preceding sequences as well as fragments derived from the coding regions of the preceding sequences corresponding to a shifting frame greater than or equal to 14 nucleotides or their complementary sequences (SEQ ID NO: 37-57, 59-60 and 121-122).

These various fragments may be advantageously used as primers or as probes (reagents A); they hybridize specifically under high stringency conditions to a sequence of the HERV-7q family.

Among these fragments, the following fragments may be preferably mentioned:

a fragment of 182 nucleotides, repeated twice, situated upstream of the gag domain at positions 2502-2611/ 2613-2865 of SEQ ID NO: 3:

Primers and Probes Specific for the gag Region a sense primer G1F located in the region upstream of the gag domain of HERV-7q:

5'GGACCATAGAGGACACTCCAGGACTA3';   (SEQ ID NO: 37)

an antisense primer G1R located in the terminal 3' region of the gag domain:

5'CCTCAGTCCTGCTGCTGGATCATCT3'    (SEQ ID NO: 38)

the fragment of 1505 nt amplified by the pair G1F-G1R is used in order to generate the probes capable of hybridizing the various PCR amplification products:

a nested sense primer G2F:
5'CCTCCAAGCAGTGGGAGGAAGAGAATT3'   (SEQ ID NO: 39)

a nested antisense primer G2R:
5'CCTTCCCTGTGTTATTGTGGACATCATT3'  (SEQ ID NO: 40)

a nested sense primer G4F:

```
                                    -continued
5'GGAAGAAGTCTATGAATTATTCAATGATGT3'    (SEQ ID NO: 41)

a nested sense primer G3F:
5'GGGACACAGAATCAGAACATGGAGATT3'       (SEQ ID NO: 42)

a nested antisense primer G4R:
5'GCCTTCAGAAGAGTCAGGTGACAGAGA3'       (SEQ ID NO: 43)

a nested antisense primer G5R:
5'GAGCCTCCAAAGTCCACTTGCCTGA3'         (SEQ ID NO: 44)
```

Primers and Probes Specific for the env Region

```
a sens primer E1F:
5'GATTTCAGTATCTACTAGTCTGGGTAGAT3'     (SEQ ID NO: 45)

an antisense primer E1R:
5'CTAGGAAATCCAGCTAGTCCTGTCTCA3'       (SEQ ID NO: 46)
``` the fragment of 2529 nt, amplified by the pair of primers E1F-E1R, is used to generate the probes capable of hybridizing the various PCR amplification products:

```
a sense primer E2F:
5'CCAAGACAGCCAACTTAGTTGCAGACAT3'      (SEQ ID NO: 47)

an antisense primer E2R:
5'GGACGCTGCATTCTCCATAGAAACTCTT3'      (SEQ ID NO: 48)

a sense primer E3F:
5'GCAATACTACATACACAACCAACTCCCAA3'     (SEQ ID NO: 49)

an antisense primer E3R:
5'GGGGGAGGCATATCCAACAGTTAGTA3'        (SEQ ID NO: 50)

a sense primer E4F:
5'CCATCTACACTGAACAAGATTTATACACTT3'    (SEQ ID NO: 51)

an antisense primer E4R:
5'AATGCCAGTACCTAGTGCACCTAGCACT3'      (SEQ ID NO: 52)

a sense primer E5F:
5'CGAATACAACGTAGAGCAGAGGAGCTTCGAA3'   (SEQ ID NO: 53)

a sense primer E6F:
5'AGCCCAAGATGCAGTCCAAGACTAAGAT3'      (SEQ ID NO: 54)

a primer E5R:
5'GCGTAGTAGAGGTTGTGCAGCTGAGAT3'       (SEQ ID NO: 55)

a primer ExF:
CCCTTACCAAGAGTTTCTATGGAGAAT           (SEQ ID NO: 56)

a primer ExR:
ACCGCTCTAACTGCTTCCTGCTGAATT           (SEQ ID NO: 57)
```

All the oligonucleotides are designed to be able to generate a sense primer and an antisense primer by a shift in the sequence of the reference primer of 1 to 7 nucleotides toward the 5' side or toward the 3' side; the modification of the sequence may cause a modification of the size of the primer of 1 to 7 nucleotides depending on the cases. The primers chosen may be optimized depending on the cases by shortening or extension affecting 1 to 9 nucleotides.

Preferably, the hybridization, cloning, subcloning, production, preparation and analysis of the nucleic acids, peptides and antibodies, the sequencing of the nucleic acids and peptides, the in situ hybridization and the immunohistochemistry are carried out under the conditions described in the following books:

Current Protocols in Molecular Biology, Eds. F. M. Ausubel, R. Brent & R. E. Kingston et al. Green Publishing associates and Wiley Interscience.

Molecular Cloning: a laboratory manual. Eds. J. Sambrook, E. F. Fritsch & T. Maniatis, Cold Spring Harbor Laboratory Press, Cold Spring Harbor.

The Practical Approach series. Eds. D. Rickwood & B. D. Ames, IRL Press and Oxford University Press. In particular antibodies I & II; DNA cloning I, II, III; Nucleic acid and protein sequence analysis; Nucleic acid hybridization; Nucleic acid sequencing; Oligonucleotide synthesis; Protein purification applications; Protein purification methods; Protein sequencing; Transcription and translation; Gels electrophoresis of nucleic acids; Gels electrophoresis of proteins; Genome analysis; HPLC of macromolecules; Human genetic diseases; Microcomputing in biology; Molecular neurobiology; Mutagenicity testing; Essential molecular biology I & II.

Proteome research: New frontiers in functional genomics, Eds. M. R. Wilkins et al., Springer.

The human endogenous retroviral sequence (SEQ ID NO: 3) situated on the long arm of chromosome 7 corresponds to the HERV-7q sequence; it has 10.5 kb (FIGS. 1 and 2) and satisfies the criteria defined above.

The search for domains exhibiting total or partial similarity with the gag and env regions of HERV-7q resulted in the identification of novel endogenous retroviral sequences. These sequences may have the structure of a complete endogenous retrovirus such as the endogenous retroviral sequence situated close to the gene for the alpha and delta subunits of the T cell receptor, and consequently called HERV-TcR; by way of example, FIG. 7 shows the comparison of the nucleic alignments of the respective gag domains of HERV-7q and HERV-TcR (sequence HG12, SEQ ID NO: 19). Partial retroviral structures also exist. These retroviral domains, similar to HERV-7q, are identified in independent nucleic sequences as shown by their chromosomal location. Nucleic motifs (called here HEx or HGx, and analogous to env or gag type domains, respectively) resembling the env or gag domains of HERV-7q were found, with the aid of the above-mentioned databases:

HE2: chromosome 17 (SEQ ID NO: 4),
HE3 and HG3: chromosome 6 (SEQ ID NO: 5 and 6),
HE4: chromosome X (SEQ ID NO: 7),
HE5: chromosome X q22 (SEQ ID NO: 8).,
HE6 and HG6: chromosome 1 q23.3-q24.3 (SEQ ID NO: 9 and 10),
HE7: chromosome 7 p15 (SEQ ID NO: 11),
HE8 and HG8: chromosome 19 (SEQ ID NO: 12 and 13),
HE9: chromosome X (SEQ ID NO: 14),
HE10: chromosome X q13.1-21.1 (SEQ ID NO: 15),
HE11 and HG11: chromosome 7 q21-22 (SEQ ID NO: 16 and 17),
HE12 and HG12, in HERV-TcR: chromosome 14 q11.2 (SEQ ID NO: 18 and 19),
HE13 (SEQ ID NO: 61): chromosome 6 q24.1-24.3

The present invention also includes the coding and non-coding fragments for all or part of enverin comprising at least 14 nucleotides and in particular the fragments encoding the C-terminal part of enverin, either from amino acid 291, or from amino acid 321, starting from the first methionine.

These fragments comprise in particular a critical zone where two inserts of 12 nucleotides were characterized:

a first insert was identified (sequence A) in individuals of 2 groups (patients and controls). This insert, situated between amino acids 487 and 488, makes it possible to insert the tetrapeptide VLQM. A comparative analysis shows that this insert is identified in a homologous region situated in the sequence HE13, belonging to the HERV-7q family. The amplification of the HE13 type sequence could indicate that there is an impairment of the enverin sequence of HERV-7q, which would promote the amplification of the sequence contained in HE13. This observation also makes it possible to use this insert as a specific element for amplification of sequences of the HE13 type.

A second insert (sequence B) was identified in a patient with MS. The insert of 12 nucleotides is situated at the level of amino acid 495 and encodes the tetrapeptide MQSM. It is remarkable to observe that this insert is also identified in a homologous region situated in HE13.

```
Sequence A:
TAAACTACAAATGGTTCTTCAAATGGAGCCCA (SEQ ID NO: 59)

Sequence B:
GATGCAGTCCAAGATGCAGTCCATGACTAAGA (SEQ ID NO: 60)
```

These observations demonstrate modifications of the enverin sequence of the HERV-7q type which constitute the basis for a detection strategy by allele-specific amplification (AS-PCR), making it possible to detect these differences in a population and which could correspond either to a mutation/deletion associated with a degree of susceptibility, or to a polymorphism, or to a mutation/deletion associated with a pathological condition such as multiple sclerosis.

The alignments of the env (FIG. 8) and gag (FIG. 9) domains explain the levels of homology observed between the sequences described above and the homologous sequences in HERV-7q. The analogies can extend to the flanking retroviral motifs.

Analysis of the sequence tags available in databases shows that transcripts belonging to some members of this family, in particular HERV-7q, are essentially expressed in tissues of foetal or placental origin.

Polypeptide sequences generated by these transcripts can therefore be potentially produced and biological functions or activities can be envisaged, by analogy with biologically active polypeptides of viral or retroviral origin; for example, the peptide motifs of the CKS-17 type (Haraguchi et al., PNAS, 1995, 92, 5568-5571) (FIG. 5) or CKS-25 type (Huang S. S. and Huang J. S., J. Biol. Chem. 1998, 273, 4815-4818) which have immuno-modulatory functions on the lymphocytic host cells. The differences in sequence which are observed and possible normal or pathological modifications are in particular responsible for modulation of the function.

HERV-7q represents the paradigm of the novel family of human endogenous retroviral sequences or of endogenous retroviral motifs.

HERV-7q and some of the endogenous retroviral sequences belonging to its family have a pol-type domain analogous to pol-type retroviral sequences such as for example the pol region identified in the MSRV retrovirus associated with multiple sclerosis and described by H. Perron et al. (1997, Proc. Natl. Acad. Sci. USA, 94, 7583-7588; International Application PCT WO 97/06260).

However, the sequences according to the present invention are distinguishable from the infectious exogenous retroviral sequences analogous to MSRV previously described in that the gag and env sequences according to the invention are significantly different according to the criteria defined above and as a function of certain specific characteristics, for example the long open reading frame of the env domain of HERV-7q; they would be able to allow the signaturing of a pathological condition when they have insertions, deletions, reading frame shifts or mutations.

Indeed, the differences observed between the human sequences of the HERV-7q type, which are isolated from individuals reputed to be normal, and the sequences derived from some samples of pathological origin are not randomly distributed. Comparisons carried out between the gag region obtained from infectious retroviral particles (EMBL accession No.: A60168, A60200, A60201, A60171 and the like) and the corresponding gag sequence of HERV-7q (FIG. 9), make it possible to observe that the mutations preferably affect non-sense codons. For example, two non-sense codons in HERV-7q are replaced by an arginine codon in A60200, which makes it possible to obtain a deduced sequence of 109 amino acids for HERV-7q and of 166 amino acids for A60200. The base changes consequently make it possible to extend the reading frame and to potentially encode larger sized polypeptide structures (FIG. 10).

Likewise, an env-type sequence obtained from infectious retroviral particles exhibits a significant analogy with the env domain of HERV-7q (FIG. 11). These marked analogies between exogenous and endogenous retroviral sequences could be responsible for the triggering or worsening of certain pathological processes, in particular certain autoimmune diseases such as multiple sclerosis. In this regard, it is possible to note that certain endogenous retroviral sequences described in the invention are situated close to or in regions reputed to exhibit susceptibility for multiple sclerosis: for example HERV-7q and the 7q21-22 region of chromosome 7, likewise for HE12 and HG12 in HERV-TcR and the region of the gene encoding the alpha and delta chains of the T cell receptor, HE2 and chromosome 17, or HE3, HE13 and HG3 and chromosome 6, for example, the sequences HE11 and HG11, around the region 7q 21-22 or HE4, HE5, HE6, HE9, HE10 or HG10 on the X chromosome. These sequences would therefore be capable of providing the means for locating or identifying the genes for predisposition.

No significant homology is observed with endogenous retroviral sequences already described; on the other hand, a limited homology may be noted, which makes it possible to identify a general structure of the env domain; however, said homology is less than the criteria defined according to the invention between the env domains of the sequence HERV-7q (SEQ ID NO: 1) and the sequence HERV-9 (FIG. 12). FIG. 11 shows extensive homologies between the sequence HERV-7q with an exogenous retroviral sequence (accession No. EMBL: A60170).

The human endogenous retroviral sequences belonging to the HERV-7q family can protect against attacks linked to the environment or can be beneficial for the individual. This beneficial effect could be one of the possible reasons for the selection pressure exerted on some of these sequences and the potentially functional character of the deduced protein structures identified: for example the long open reading frame capable of encoding a novel protein and corresponding to the env domain of HERV-7q.

The human endogenous retroviral sequences belonging to the HERV-7q family could be associated, for example, with pathological conditions related to processes linked to cancer, to neuropathological conditions with an autoimmune component or to any other pathological process in association or otherwise with endogenous or exogenous viruses or retroviruses. Their action could be related to the outbreak, the worsening, the modification of the time of appearance or the protection against the disease.

In the context of application to autoimmune pathological conditions (such as for example lupus, Sjögren's syndrome, rheumatoid arthritis, multiple sclerosis and the like), significant analogies may be detected between the endogenous retroviral motifs identified and motifs found in retroviral structures characterized in patients with autoimmune pathological conditions such as multiple sclerosis; for example, fragments of gag domain (recently available in databases) obtained from infectious retroviral particles or the complete sequence of the pol domain corresponding to the MSRV virus associated with multiple sclerosis. These retroviral motifs possess significant analogies with homologous endogenous sequences of the HERV-7q type, which makes it possible to envisage direct or indirect association with pathological processes, including multiple sclerosis, in association or otherwise with MSRV.

The importance of these sequences goes beyond the context of autoimmune diseases. Apart from the general importance of retroviral motifs in the triggering or worsening of a tumor process, which is well established in particular in murine models (H. Fan in *The retroviridiae*, 1994, ed. J. A. Levy, Plenum, New York, p. 313-353), these sequences could be present close to or inside important genes and could alter the expression thereof: for example HERV-TCR and the genes for the alpha and delta subunits of the receptor for the T cells involved in disruptions of the immune system.

The present invention includes, in addition, the use of sequences combined with the sequences of the HERV-7q family for the detection and/or prognosis of various autoimmune diseases (neuropathological conditions in particular); these sequences encode all or part of a factor whose function, the regulation/de-regulation or alteration (polyadenylation, alternative splicing), is associated with the normal or pathological expression or with the regulation/de-regulation of the motifs belonging to the HERV-7q family and correspond to transcripts or cDNAs of the nucleotide sequences encoding genes situated in regions flanking or delimiting retroviral sequences of the HERV-7q family.

The expression flanking region is understood to mean any region situated close to (contained in or including) an endogenous retroviral sequence belonging to the HERV-7q family, as defined above, up to and including the genes immediately contiguous and/or situated at a distance which cannot exceed 120 kb.

The inventors have now found that the presence of the retroviral sequences as defined above disrupts the expression or impairs the structure of the flanking sequences defined below.

The transcripts of said flanking sequences (and fragments thereof, in particular those underlined or in italics in FIGS. 14-16, 22-26, as defined below:

at 1021 bp upstream of HERV-7q, there is identified an endogenous retroviral sequence called RH7 (SEQ ID NO: 62 and FIG. 22); this sequence is situated in 5' of the HERV-7q sequence; in FIG. 22, the portion in italics corresponds to the beginning of the HERV-7q sequence; the RH7 sequence is underlined; two putative polyadenylation sites are in bold. This sequence SEQ ID NO: 62 exhibits significant homology, on more than 6 kb, with RGH-type endogenous retroviral sequences (FIG. 13). Sequences belonging to this family are expressed in particular in patients with rheumatoid osteoarthritis (Nakagawa et al., (1997), Arthritis, Rheum., 40, 627-638). The present invention also includes fragments of the sequence SEQ ID NO: 62, comprising between 14 and 50 nucleotides (used as primers), preferably between 14 and 25 nucleotides, or at least 25 nucleotides (used as probe), which fragments have the following characteristics: the 4 nucleotides of the 3' end are different from the corresponding motifs of the sequence RGH2 (bottom sequence in FIG. 13, GenBank accession No.: D110 18), at less than 9 kb upstream of HERV-7q, there is identified the sequence RAM75 (SEQ ID NO: 63 and FIG. 14) containing the 24 coding exons (which cover close to 41 kb) of the gene for peroxisomal ATPase PEX1. PEX1, in combination with PEX6, is responsible for the import of peroxisomal proteins and for stabilizing the PEX5 receptor. A disruption/alteration affecting PEX1 is responsible for various neuropathological conditions such as Zellweger syndrome, neonatal adrenoleukodystrophy and the infantile form of Refsum's disease (Reuber et al., (1997), Nature Genet., 17, 445-448). It can be recalled that the main function of the peroxisomes is associated with the metabolism of fatty acids, in particular by β-oxidation processes. Impairment of the gene identified in the sequence RAM75, or of its expression, by modification of the function of the regulatory 5' and 3' regions or by modification of the splicings or of the polyadenylation processes, in particular under the influence of neighboring retroviral motifs, would be able to disrupt the expression and the structure of ATPase and consequently to disrupt one of the peroxisomal functions, in particular the metabolism of lipids, in particular myelin lipids, with consequences for certain pathological conditions, including neuropathological conditions such as multiple sclerosis; the underlined portions (FIG. 14) correspond to the 24 coding exons.

The present invention also includes the fragments of the sequence SEQ ID NO: 63, included in the abovementioned 24 coding exons and comprising at least 14 nucleotides.

Analysis of the expression profile (transcripts and proteins) of the sequence RAM75 (SEQ ID NO: 63) is a good indicator for the differential diagnosis of neuropathological conditions with an autoimmune component.

In FIG. 14, the coding exons are underlined. The initiation and non-sense codons as well as the putative polyadenylation sites are in bold and underlined;

at 0.7 kb downstream of the sequence HERV-7q and on nearly 17 kb (SEQ ID NO: 64 and FIG. 15), there is identified the nucleotide sequence RAV73, where there are detected sequence tags and potential exons capable of producing one or more polypeptide sequences; the invention also includes fragments of this sequence SEQ ID NO: 64 included in the sequence tags and the potential exons as they appear (portions underlined) in FIG. 15, which fragments comprise at least 14 nucleotides, at 120 kb upstream of the sequence HG3, and on 15 kb, there is the nucleotide sequence RBP3 (SEQ ID NO: 65 and FIG. 23), which covers the 3' end of the gene encoding a transcription factor of the Blimp-1 family (SEQ ID NO: 119 and FIG. 25), a protein of 789 amino acids which is a repressor of the expression of the interferon-beta gene (Keller and Maniatis, Genes Dev., (1991), 5, 868-879), which is already associated with certain malignant pathological conditions (Mock et al., Genomics, (1996), 37, 24-28), and which could play a role in the differentiation and the pathogenesis of B cells. The possible association of the endogenous retroviral sequence containing the motifs HG3 and HE3 and of Blimp-1 has many benefits, in the case of pathological conditions, and in particular multiple sclerosis. Blimp-1 acts in particular on the B cells whose contribution in inflammatory processes associated with multiple sclerosis is known. Blimp-1 is capable of blocking the viral induction of the INFβ promoter whose capacity to reduce the frequency of attacks and the progression of lesions in patients with MS is known. Disruption in the expression or the structure of Blimp-1, in relation to a retroviral element of the HERV-7q type, is consequently associated with neuropathological conditions or with diseases having an autoimmune character, such as multiple sclerosis; this nucleotide sequence RBP3 (SEQ ID NO: 65) contains nucleotide motifs identified in the nucleic sequence encoding the Blimp-1 gene; the invention also includes the detection of the mRNA sequences for the Blimp-1 protein (SEQ ID NO: 119), the endogenous retroviral sequence of the HERV-7q type, containing HE3 and HG3, is situated in the HI3 region corresponding to an intron extending over more than 46 kb (SEQ ID NO: 66), of a gene which could encode the analogue of APS (FIG. 24), a protein of 275 amino acids specific to apoptosis, overexpressed in various cells in culture after triggering an apoptotic process (Hammond et al., FEBS Lett., (1998), 425, 391-395). The intron is situated at the level of amino acid 231 of APS. The end of HE3 is at more than 12 kb from the 5' end of the intron, whereas HG3 is situated at more than 28 kb from the 3' end of the intron. Apoptotic processes are associated with multiple sclerosis. In particular, there has been described an apoptotic process affecting astrocytes and oligodendrocytes in the presence of a purified fraction of cerebrospinal fluid of patients suffering from multiple sclerosis (Ménard et al., J. Neurol. Sci., (1998), 154, 209-221).

Finally, it should be stressed that the nucleic region containing HE3, HG3, HI3 and RBP3 is located at the level of the short arm of chromosome 6, in 6p21, which is a proposed region of susceptibility to multiple sclerosis (The Multiple Sclerosis Genetic Group, Nature Genet., (1996), 13, 469-472).

The interaction between the HERV-7q type sequences and the flanking sequences and the importance of establishing a profile of expression including one or more of the abovementioned sequences in order to establish a differential diagnosis of a neuropathological condition is even more evident because it is observed that the sequences HG12 and HE12 are situated in an intron region of the gene encoding the alpha and delta subunits of the T cell receptors. The T cell receptors are involved in the immune regulation process and their influence has been proposed in the case of autoimmune diseases, including multiple sclerosis.

The subject of the invention is also transcripts generated from the abovementioned sequences as well as those optionally exhibiting modifications in the reference sequences described in the invention when they are expressed in certain patients.

Indeed, the systems for regulating the the expression of the retroviral proteins of HERV-7q, which are present in the LTR type motifs, could influence the expression of genes situated in the close or distant chromosomal vicinity and could induce disruptions of an immunological and/or neurological character. For example, the endogenous retroviral sequence HERV-TcR exists in the immediate vicinity of the genes for the alpha and delta subunits of the T cell receptor previously described. The LTR-type motifs could also encode superantigens (Acha-Orbea and Palmer, 1991, Immunol. Today, 12, 356-361). In general, retroviral proteins of the HERV-7q or related type, or their truncated or partial forms could be involved in cytotoxicity or superantigenicity phenomena, such as for example those derived from the long open reading frame identified in the env domain (FIG. 4).

Sequences of the HERV-7q 5' and 3' LTR type, which are highly conserved, are involved in such regulatory effects. By way of example, LTX is described, which is a sequence comparable to that of an HERV-7q LTR (SEQ ID NO: 67 and FIG. 16), and which is present in the center of an intron of more than 49 kb, but at 2 kb from the donor 5' site of the FMR2 gene associated with fragile X and encoding a protein of 1311 amino acids (FIG. 26). The LTRs modulate the alternative splicing (Kapitonov and Jurka, (1999), J. Mol. Evol., 48, 248-251), the expression of the gene, the binding to nuclear proteins (Akopov et al., (1998), FEBS Lett., 421, 229-233), or allow the production of an alternative polyadenylation signal (Goodchild et al., (1992), Gene, 121, 287-294).

In general, there may be noted the existence of several endogenous retroviral sequences of the HERV-7q type (HE4, HE5, HE9, HE10), situated at the level of chromosome X which represents the chromosome associated with the largest number of pathological conditions.

In this regard, it is possible to note that retroviral motifs derived from defective regions are capable of having biological functions; for example, the envelope protein p15E, derived from defective retroviral motifs, possesses an anti-inflammatory and immunosuppressive activity (Snyderman and Ciancolo, 1984, Immunol. Today, 5, 240-244).

These structures are probably capable of causing breaks or of amplifying deregulations in the immune defense processes. Some of the motifs of the gag, env and LTR-type domains may be associated with a particular function or may contribute to the normal or pathological function of the flanking domains as defined above (SEQ ID NO: 62-67). Recombinations with an element of exogenous, retroviral origin or otherwise can give rise to the production of nucleic or protein motifs which could either protect or trigger or promote or worsen a pathological condition. Likewise, a retroviral structure containing endogenous retroviral elements according to the invention would be capable of causing a pathological process after passing through an exogenous transient cycle followed by reintegration into a sensitive or critical region of the human genome.

It is thus possible to obtain expression profiles (transcripts and optionally proteins) which correspond to the abovementioned neuropathological conditions.

Likewise, the combination of motifs belonging to the HERV-7q family, or of elements induced by motifs belonging to the HERV-7q family, with motifs of exogenous origin or induced exogenously would be capable of triggering or worsening a pathological process or on the contrary of promoting protection or partial remission or a complete and permanent cure.

The detection made possible of the HERV-7q type domains suggests possible applications at the prophylactic, prognostic and diagnostic level; for example, immunological approaches or gene amplification, which make it possible to compare normal individuals serving as reference with patients, would be capable of promoting screening, of improving early detection of the outbreak of the disease and/or of monitoring the progression of a pathological condition in patients which may exhibit a susceptibility or in whom there has been an outbreak of the disease or in individuals considered to be normal, based on current clinical criteria.

The specific nucleic and immunological probes, as defined, in the present invention are capable of promoting the identification and detection of motifs which are abnormally expressed in the context of pathological conditions associated with cancer, or of neuropathological conditions, in particular autoimmune pathological conditions, at the forefront of which is multiple sclerosis.

The subject of the present invention is also hybrid nucleic sequences, characterized in that they comprise sequences or motifs belonging to the HERV-7q family, or of elements induced by motifs belonging to the HERV-7q family, with motifs of exogenous origin or induced exogenously (exogenous retroviral sequences); such hybrid sequences are probably capable of triggering or worsening a pathological process or on the contrary of promoting protection or partial remission or a complete and permanent cure.

The subject of the present invention is also a diagnostic reagent for the differential detection of complete or partial human endogenous nucleic sequences, having retroviral motifs, selected from the sequences SEQ ID NO: 1 and/or SEQ ID NO: 2, characterized in that it is selected from the group consisting of the sequences SEQ ID NO: 1-22, 28, 37-57, 59-61 and 121-122, the complementary nucleic sequences and the reverse sequences complementary to the preceding sequences, of nucleotide fragments capable of defining or of identifying the sequences SEQ ID NO: 1 and/or SEQ ID NO: 2 and any flanking sequence or any sequence overlapping them as well as of fragments derived from the coding regions of the sequences SEQ ID NO: 1-22 and 61, corresponding to a shifting frame greater than or equal to 14 nucleotides or their complementary sequences, optionally labeled with an appropriate marker as well as of sequences as defined in FIGS. 18-21.

The sequences of the nucleic, ribonucleic and oligonucleotide probes used will be chosen from the env and gag regions or their flanking regions; for example the oligonucleotide primers for HERV-7q will be chosen from the regions situated between nucleotides 3065 and 4390, nucleotides 6965 and 9550 or nucleotides 2502-2865 of SEQ ID NO: 3, as well as from any adjacent sequence (upstream or downstream) capable of allowing specific amplification (FIG. 1).

Among the appropriate markers, there may be mentioned radioactive isotopes, enzymes, fluorochromes, chemical markers (biotin), haptens (digoxygenin) and antibodies or appropriate base analogues.

Preferably:
said reagent is selected from the sequences SEQ ID NO: 37-57 and is capable of being used as a primer,
said reagent is selected from the following sequences:
  a fragment of 1505 nt amplified by the pair of primers SEQ ID NO: 37 and SEQ ID NO: 38 (primers G1F and G1R),
  a fragment of 2529 nt amplified by the pair of primers SEQ ID NO: 45 and SEQ ID NO: 46 (primers E1F and E1R),
  a fragment of 182 nucleotides, repeated twice, situated upstream of the gag domain at positions 2502-2611/2613-2865,
  fragments encoding or not encoding all or part of enverin, comprising at least 14 nucleotides and in particular the fragments encoding the C-terminal portion of enverin, either from amino acid 291, or from amino acid 321, starting from the first methionine,
and is capable of being used as a probe.

The subject of the present invention is also a method for the rapid and differential detection of the endogenous retroviral nucleic sequences of the env or env and gag type, their normal or pathological variants, by hybridization and/or gene amplification, carried out using a biological sample, which method is characterized in that it comprises:
(a) a step in which a biological sample to be analysed is brought into contact with at least one probe as defined above, and
(b) a step in which the product(s) resulting from the nucleotide sequence-probe interaction is detected by any appropriate means.

In accordance with said method, it may comprise:
prior to step (a):
a step of preparing the relevant biological tissue or fluid,
a step of extracting the nucleic acid to be detected, and
at least one gene amplification cycle, and
subsequent to step (b):
a step of comparing the nucleic sequences obtained in said biological sample with the human endogenous retroviral sequences according to the invention by any appropriate means and in particular by sequencing, Southern blotting, restriction cleavage, SSCP or any other method which makes it possible to identify an insertion or a deletion or a single mutation between the various sequences compared.

In accordance with the invention, the human endogenous retroviral sequences according to the invention are thus compared with the nucleic sequences present in the biological sample to be analysed and allow the detection of homologous sequences from patients suffering from pathological conditions likely to involve a modification of their genome.

Advantageously, said gene comparisons are carried out using genomic DNA obtained from control individuals and from patients.

A conventional gene amplification by PCR will be carried out with the aid of 5'-sense and 3'-antisense primers delimiting or comprising the zone to be studied (env zone or gag zone).

Also advantageously, the sequences of the nucleic, ribonucleic and oligonucleotide probes used are chosen from the env and gag regions or their flanking regions; for example the oligonucleotides which are primers for HERV-7q will be chosen from the regions situated between nucleotides 3065 and 4390 and nucleotides 6965 and 9550, and from any adjacent sequence (upstream or downstream) capable of allowing specific amplification (FIG. 1), as specified above. They are preferably selected from the group consisting of
  a fragment of 1505 nt amplified by the pair of primers SEQ ID NO: 37 and SEQ ID NO: 38 (primers G1F and G1R),
  a fragment of 2529 nt amplified by the pair of primers SEQ ID NO: 45 and SEQ ID NO: 46 (primers E1F and E1R).

The gene amplification step is in particular carried out with the aid of one of the following gene amplification techniques: amplification using Qβ-replicase, PCR, LCR, ERA, CPR or SDA.

The subject of the present invention is also chimeric sequences, characterized in that they consist of a fragment of 17 to 40 nucleotides of a flanking sequence as defined above combined with an endogenous retroviral motif of the HERV-7q type comprising between 17 and 40 nucleotides, as defined above.

The subject of the present invention is also a method of detecting transcripts as defined above, characterized in that it comprises:
collecting messenger RNAs obtained from control biological samples (biological tissues, cells or fluids) and from a similar sample collected from patients, and
the qualitative and/or quantitative analysis of said mRNAs by in situ hybridization, by dot-blot, Northern blotting, RNAse mapping or RT-PCR, with the aid of a diagnostic reagent as defined above.

The subject of the present invention is also a method for the detection and/or evaluation of an overexpression/underexpression or of a modification of at least one of the endogenous retroviral sequences or fragments of sequences of the HERV-7q type and/or of their associated flanking sequences, characterized in that it comprises:

depositing on an appropriate support, such as for example a nylon filter, a glass slide or their equivalent, cDNA or its equivalent obtained from clones, PCR products obtained from genomic DNA, RT-PCR products obtained from transcripts or from specific oligonucleotide sequences, said DNA sequences being endogenous retroviral sequences or fragments of sequences of the HERV-7q type and/or their flanking sequences, as defined above, consisting of transcripts and cDNAs of the genomic sequences, which encode all or part of a factor, whose function, regulation/de-regulation or alteration is associated with the normal or pathological expression or with the regulation/deregulation of motifs belonging to said HERV-7q family, these sequences corresponding to nucleotide sequences encoding genes situated in flanking regions situated upstream and/or downstream of a retroviral sequence of said HERV-7q family and in which one of the ends cannot be at a distance exceeding 120 kb, and/or a chimeric sequence as defined above, the hybridization of said support with at least one appropriately labeled probe obtained, for example, by retrotransposition of an RNA mixture obtained from biological cells, tissues or fluids obtained from controls reputed to be normal, from members of various ethnic populations, from patients suffering from pathological conditions often associated with expression of retroviruses, such as tumor processes, or such as autoimmune diseases, and the detection of the hybrids formed.

According to an advantageous embodiment of said method, said transcript or cDNA is selected from the group consisting of the sequences SEQ ID NO: 62-67 and 119 and their fragments corresponding to a shifting frame greater than or equal to 14 nucleotides or their complementary sequences.

According to another advantageous embodiment of said method, said support comprises, in addition, any endogenous or exogenous retroviral sequence.

The method of DNA chips (Bowtell, (1999), Nature Genet., 21, 25-32), is used to evaluate the modification of the expression of all or part of some of the sequences of retroviral origin of the HERV-7q type and flanking sequences. Briefly, DNA obtained from clones, PCR products obtained from genomic DNA, RT-PCR products obtained from transcripts or specific oligonucleotide sequences are deposited on a support, such as for example a nylon filter, a glass slide or their equivalent. The deposited nucleic sequences cover the various retroviral domains described above, as well as the contiguous sequences and the flanking genes. In order to detect possible alternative splicing processes, specific DNAs are synthesized per step of 500-600 nucleotides with an overlap of 250-300 nucleotides on either side. The alternative splicings already identified will be the subject of a specific synthesis. The hybridization is carried out with the aid of a probe obtained, for example, by retrotransposition of an RNA mixture obtained from biological cells, tissues or fluids obtained from controls reputed to be normal, members of the various ethnic populations, patients suffering from pathological conditions often associated with expression of retroviruses, such as tumor processes, or such as autoimmune diseases, including multiple sclerosis. In this case, a µg fraction and up to a few µg of mRNA or up to a few µg or a few tens of µg of RNA, depending on the method used and the size of the DNA chip involved, are sufficient for the synthesis of the nucleic probe. The nucleic probe is suitably labeled so as to allow subsequent detection, such as for example by fluorescence or by an equivalent method.

The use of bi- or even multicolored probes makes it possible to specify the concerted expression of several genes in parallel, while taking advantage, furthermore, of a precise normalization. The results are acquired automatically, such as for example by a laser scanning system or its equivalent.

Two types of DNA chips are designed, on the one hand chips having an exhaustive set of sequences, and on the other hand specific DNA chips enabling targeting to a more specific application.

For example, a critical sequence in that it would contain a difference relating to a deletion or even a mutation is detected with the aid of specific oligonucleotides (Wang et al., (1998), Science, 280, 1077-1082). The polymorphism associated with a base or with a mutation is detected with the aid of four oligonucleotides possessing one of the four sequence possibilities at the level of a base (A, C, G or T); for each point difference, the 4 oligonucleotides are deposited and the hybridization intensities are compared. Furthermore, an alternative splicing is detected using DNAs corresponding to a single effective or putative exon; the gene is therefore analyzed exon by exon. The DNA chips also relate, by extension, to any endogenous or exogenous retroviral sequence, such as for example ERV-9, ERV-K, ERV-L, ERV-H, ERV-4, ERV-6, ERV-8, ERV-10, ERV-15, ERV-16, ERV-17, ERV-18, ERV-21, ERV-24, ERV-33, ERV-34, ERV-36, ERV-40, ERV-42, ERV-MLN, ERV-FRD, ERV-FTD and the like), as well as all the putative exon sequences (identified by the existence of sequence tags and corresponding transcripts) or effective exon sequences, and which are situated on either side up to a distance of 120 kb of the endogenous retroviral sequences of the HERV-7q type.

The comparative study is carried out between a control sample and the sample to be tested, in a prophylactic, diagnostic or therapeutic perspective, such as for example the early detection of a modification of the expression of one of the sequences, in a cell, a tissue or an organism, the identification of a sequence associated with a susceptibility or with any pathological condition, the monitoring of the progression of the pathological condition or the monitoring of a treatment and the evaluation of its efficacy.

Apart from the applications already mentioned, the advantage of the method makes it possible, more generally, to make an assessment of the changes observed in an individual, which constitutes to a certain extent an identity card, which facilitates an epidemiological approach which makes it possible to establish novel correlations between a particular observed profile and a pathological condition, in the absence of an a priori regarding this pathological condition.

The subject of the present invention is also a kit for the detection and/or evaluation of an autoimmune disease and in particular of neuropathological conditions with an autoimmune etiology, characterized in that it comprises, in addition to the buffers necessary for carrying out the methods as defined above:

diagnostic reagents A as defined above, and reagents B consisting of the transcripts and cDNAs of the genomic sequences, which encode all or part of a factor, whose function, regulation/de-regulation or alteration is associated with the normal or pathological expression or with the regulation/de-regulation of motifs belonging to said HERV-7q family, these sequences corresponding to nucleotide sequences encoding genes situated in flanking regions situated upstream and/or downstream of a retroviral sequence of said HERV-7q family, of which one of the ends cannot be at a distance exceeding 120 kb, which reagents are preferably attached to an appropriate support.

According to an advantageous embodiment of said kit, said reagents B are selected from the group consisting of the sequences SEQ. ID NO: 62-67 and 119 and their fragments corresponding to a shifting frame greater than or equal to 14 nucleotides or their complementary sequences, as well as the sequences represented in FIGS. 13-17, 22-26.

The subject of the present invention is also products of translation, characterized in that they are encoded by a nucleotide sequence as defined above.

The subject of the present invention is also a peptide, characterized in that it is capable of being expressed with the aid of a nucleotide sequence selected from the group consisting of the sequences SEQ ID NO: 1-22, 28 and 61, as defined above, according to the combinations offered by the use of the various possible reading frames (see also FIGS. 18-21).

Said peptide also includes the derived peptides or polypeptides comprising between 5 and 540 amino acids (SEQ ID NO: 23-36 and SEQ ID NO: 58 and their fragments of at least 5 amino acids) and in particular a fragment of 538 amino acids, starting at the first methionine of the sequence SEQ ID NO: 26 (enverin).

According to an advantageous embodiment of said peptides they are in particular selected from the sequences SEQ ID NO: 23-36, 58, in particular the sequence SEQ ID NO: 26 and its C-terminal fragments, either from the amino acid 291, or from the amino acid 321, starting from the first methionine.

According to another advantageous embodiment of said peptides, they are obtained from nucleic sequences as defined above, in which at least one non-sense codon may be replaced with a codon encoding one of the following amino acids: Phe (F), Leu (L), Ser (S), Tyr (Y), Cys (C), Trp (W), Gln (O), Arg (R), Lys (K), Glu (E) or Gly (G).

The invention thus includes the deduced peptides or the deduced proteins corresponding to all or part of the nucleic sequences described in the invention, and optionally exhibiting modifications with the reference sequences described in the invention, when they are expressed in some patients. In particular, the invention includes the complete or partial sequences obtained according to the 3 sense reading frames and the 3 reverse and complementary reading frames (see FIGS. 18-21).

Advantageously, the analysis of the structure of the env domain of HERV-7q, called enverin, made it possible to demonstrate successively:

an N-terminal signal peptide (region 1-21) and two transmembrane domains (region 320-340; 455-477), responsible for interactions with membrane lipid or protein motifs, an immunomodulatory motif of the CKS-17 (Haraguchi et al., (1995), 92, 5568-5571)/CKS-25 type. It is possible to note, in this regard, the presence of an RalD motif inside the peptide of the CKS-17/CKS-25 type of HERV-7q and a motif RvaD at position 363 which correspond to the consensus W/RxxD, proposed for the active site of the TGF-βs (Huang et al., J. Biol. Chem., 1997, 272, 27155-27159), potent factors associated with growth, with differentiation and with morphogenesis and which are associated with many human pathological conditions, such as tumor processes (Tang et al., (1998), Nat. Med., 4, 802-807) or neurodegenerative diseases (Flanders et al., (1998), Prog. Neurobiol., 54, 71-85). The peptides according to the invention containing these motifs can advantageously serve as antagonists by inhibiting the attachment of the TGF-βs to their natural receptors, N-glycosylation motifs. The glycosylation of the envelope proteins of retroviruses appears to be directly associated with their functional properties, for example by influencing the number of determinants available in the T cells or by promoting recognition of antigens by the T cells. Glycosylation could play a role in the outbreak or the spread of a pathological condition with an autoimmune component. The glycosylations are necessary for maintaining the conformation of certain epitopes, in particular during the production of a recombinant envelope protein so as to develop a diagnostic reagent and to promote the efficacy of a possible vaccine. Positions 171, 210, 216, 236, 244, 283 and 411. Expected number at random: 3.2 prenylation sites. Prenylation is an essential mechanism for attachment to the cell membrane and for the targeting of certain proteins. This targeting process could be essential for the production of specific therapeutic agents capable of interfering with the production and regulation of the traffic of cellular complexes calling into play proteins involved in the cell interactions, growth and movement. Positions 188 and 290. Expected number at random: 1.8 targeting sites in the endoplasmic reticulum. These sites could make it possible to bring about the targeting toward the endoplasmic reticulum in order to carry out the modifications necessary for promoting membrane crossing. Positions 353 and 431. Expected number at random: 0.2

Moreover, the inventors have shown that a number of peptides derived from the env protein of HERV-7q (enverin) have a high affinity/half-life for the class I HLA alleles. CADD analysis has made it possible to select candidate peptides, for which the best scores are indicated in Table I:

TABLE I

| Location | Sequence | HLA molecule | Score | Sequence No. |
|---|---|---|---|---|
| 399 | FLGEECCYYV | A-0201 | 7214 | SEQ ID NO: 68 |
| 462 | LLFGPCIFNL | A-0201 | 1792 | SEQ ID NO: 69 |
| 189 | CLPLNFRPYV | A-0201 | 1453 | SEQ ID NO: 70 |
| 439 | GLLSQWMPWI | A-0201 | 488 | SEQ ID NO: 71 |
| 263 | CLPSGIFFV | A-0201 | 5103 | SEQ ID NO: 72 |
| 444 | WMPWILPFL | A-0201 | 897 | SEQ ID NO: 73 |
| 252 | IRWVTPPTQI | B-2705 | 3000 | SEQ ID NO: 74 |
| 432 | LRNTGPWGLL | B-2705 | 2000 | SEQ ID NO: 75 |
| 158 | LRTHTRLVSL | B-2705 | 2000 | SEQ ID NO: 76 |
| 316 | KRVPILPFVI | B-2705 | 1800 | SEQ ID NO: 77 |
| 25 | CRCMTSSSPY | B-2705 | 1000 | SEQ ID NO: 78 |
| 137 | TRVHGTSSPY | B-2705 | 1000 | SEQ ID NO: 79 |
| 124 | AREKHVKEVI | B-2705 | 600 | SEQ ID NO: 80 |
| 478 | SRIEAVKLQM | B-2705 | 600 | SEQ ID NO: 81 |
| 442 | SQWMPWILPF | B-2705 | 500 | SEQ ID NO: 82 |
| 405 | CYYVNQSGI | Kd | 2400 | SEQ ID NO: 83 |
| 346 | FYYKLSQEL | Kd | 2400 | SEQ ID NO: 84 |
| 244 | TYTTNSQCI | Kd | 2400 | SEQ ID NO: 85 |

TABLE I-continued

| Location | Sequence | HLA molecule | Score | Sequence No. |
|---|---|---|---|---|
| 291 | SFLVPPMTI | Kd | 1600 | SEQ ID NO: 86 |
| 406 | YYVNQSGIV | Kd | 1200 | SEQ ID NO: 87 |
| 167 | LFNTTLTGL | Kd | 1152 | SEQ ID NO: 88 |
| 463 | LFGPCIFNL | Kd | 960 | SEQ ID NO: 89 |
| 253 | RWVTPPTQI | Kd | 480 | SEQ ID NO: 90 |
| 449 | LPFLGPLAAI | B-5102 | 2200 | SEQ ID NO: 91 |
| 3 | LPYHIFLFTV | B-5102 | 1210 | SEQ ID NO: 92 |
| 331 | GALGTGIGGI | B-5102 | 798 | SEQ ID NO: 93 |
| 321 | LPFVIGAGVL | B-5102 | 550 | SEQ ID NO: 94 |
| 499 | RRPLDRPAS | B-2705 | 600 | SEQ ID NO: 95 |
| 194 | FRPYVSIPV | B-2705 | 600 | SEQ ID NO: 96 |
| 383 | RRALDLLTA | B-2705 | 600 | SEQ ID NO: 97 |
| 39 | WRMQRPGNI | B-2705 | 600 | SEQ ID NO: 98 |
| 423 | DRIQRRAEEL | B14 | 1800 | SEQ ID NO: 99 |
| 158 | LRTHTRLVSL | B14 | 600 | SEQ ID NO: 100 |
| 359 | ERVADSLVTL | B14 | 540 | SEQ ID NO: 101 |
| 463 | LFGPCIFNLL | Kd | 1658 | SEQ ID NO: 102 |
| 345 | QFYYKLSQEL | Kd | 1152 | SEQ ID NO: 103 |
| 443 | QWMPWILPFL | Kd | 691 | SEQ ID NO: 104 |
| 405 | CYYVNQSGIV | Kd | 500 | SEQ ID NO: 105 |
| 474 | NFVSSRIEAV | Kd | 480 | SEQ ID NO: 106 |
| 221 | GPLVSNLEI | B-5102 | 1320 | SEQ ID NO: 107 |
| 190 | LPLNFRPYV | B-5102 | 726 | SEQ ID NO: 108 |
| 449 | LPFLGPLAAI | B-5101 | 1144 | SEQ ID NO: 109 |
| 488 | EPKMQSKTKI | B-5101 | 968 | SEQ ID NO: 110 |
| 3 | LPYHIFLFTV | B-5101 | 629 | SEQ ID NO: 111 |
| 125 | REKHVKEVI | Kk | 1000 | SEQ ID NO: 112 |
| 312 | KPRNKRVPIL | B7 | 800 | SEQ ID NO: 113 |
| 378 | VVLQNRRAL | Db | 792 | SEQ ID NO: 114 |
| 377 | AVVLQNRRAL | Db | 660 | SEQ ID NO: 115 |
| 321 | LPFVIGAGV | B-5101 | 629 | SEQ ID NO: 116 |
| 304 | DLYSYVISK | A3 | 540 | SEQ ID NO: 117 |
| 301 | TEQDLYSYVI | Kk | 500 | SEQ ID NO: 118 |

This Table I indicates an estimation of the dissociation half-life of a peptide of enverin with an allele of the class I HLA system (the tables of Parker coefficients: J. Immunol, (1994), 152, 163-175). The location indicates the position of the first amino acid of the peptides tested in the enverin sequence. The one-letter code is used for the amino acid sequence. The scores around 500 or greater than 500 were selected. By way of comparison, an analysis was carried out on a concatenation of peptides (polypeptide of 4968 amino acids) reputed to bind the molecules of the class I major histocompatibility complex (Rammensee, Immunogenetics, (1995), 41, 178-228); the ten best scores recorded for non-apeptides and the HLA type A_0201 are respectively 4984, 4047, 2406, 1267, 800, 705, 607, 591, 591 and 577.

It can be seen from this Table I that some molecules of the type I major histocompatibility complex are capable of binding peptides derived from enverin, thus assimilated with peptides of viral or tumor origin, at the level of the endoplasmic reticulum. The complexes formed at the level of the endoplasmic reticulum are then transported to the cell surface, which causes the destruction of the target cell by the cytotoxic T lymphocytes. The peptides identified generally comprise 8 to 10 amino acids. Studies have shown that some alleles of the class I HLA system are thus associated with certain pathologies, in particular with an autoimmune character, such as HLA-B27 with rheumatoid spondylitis or HLA-B51 with Behçet's disease.

A peptide capable of binding a particular class I molecule is consequently capable of functioning as a T cell epitope.

Consequently, the present invention also includes the fragments 399-471 and 244-271 of enverin which advantageously group together several epitopes having high affinity for various haplotypes of the class I HLA system. The use of all or some of these polypeptides is consequently capable of promoting an increase in the T cell repertoire, by allowing better efficacy of the immune response in the context of the various immunotherapeutic, prophylactic or vaccine strategies. These polypeptides may be advantageously delivered for example by the use of viral vectors, viral or synthetic particles, lipopeptides, conventional adjuvants, naked nucleic acids or nucleic acids adsorbed on particles, or liposomes.

For the purposes of the present invention, the peptides may be chemically or biochemically modified; some of the amino acids may be replaced with an analogous amino acid, according to conventional criteria for homologies (A or G; S or T; I, L or V; F, Y or W; N or Q; D or E).

The subject of the present invention is also immunogenic or vaccine compositions for protecting against autoimmune diseases, in particular in at-risk subjects, characterized in that it comprises at least one peptide comprising at least one motif of the CKS type and/or at least one peptide consisting of a motif having affinity with one of the haplotypes of the class I or class II HLA system and a pharmaceutically acceptable vehicle.

According to an advantageous embodiment of said composition, said motif is selected from the group consisting of peptides, as defined in Table I above.

According to another advantageous embodiment of said composition, said peptide has the following sequence:

sequence CKH:
L<u>QNRRALDLLTAERGGTc1</u>FLGEECCYYV.     (SEQ ID NO: 120)

It is remarkable to note at the level of position 380 of the enverin protein, the contiguousness of the motifs of the CKS-17 type (underlined) and of the peptide having the highest score (in bold; see peptide at position 399 in Table I, SEQ ID NO: 68) in the sequence CKH.

The clonal activation of the subgroups of lymphocytes, for example of cytotoxic lymphocytes, by the peptides in Table I and by extension their homologues, is blocked by conventional immunotherapy means such as for example serotherapy and vaccination.

The combination of two sequences or of the sequences analogous to the CKH peptide (SEQ ID NO: 120), is capable of causing a synergistic process in the immune response, which could bring into play additional signaling and activation pathways capable of modulating the lymphocyte activation.

The vaccination relates to the production of antibodies directed against the peptides of Table I, according to the rules of the prior art and according to the methods of release controlled by artificial or cellular implants using a composition as defined above and by using gene therapy means, such as for example expression of nucleic sequences encoding the peptides of Table I. Consequently, the subject of the invention is also immunogenic or vaccine compositions, characterized in that they comprise a vector including at least one nucleic sequence encoding a peptide as defined in Table I, optionally combined with a sequence encoding a motif of the CKS-17 type.

The serotherapy relates to the use of neutralizing antibodies produced from the peptides of Table I and their homologues.

The protein products generated by the endogenous retroviral sequences or produced in parallel may be advantageously characterized by micro-methods of analysis and quantification of peptides and proteins: HPLC/FPLC or equivalent, capillary electrophoresis or equivalent, microsequencing techniques (Edman method or equivalent, mass spectrometry and the like).

The subject of the invention is also antibodies directed against one or more of the peptides described above and their use either for carrying out a method, in particular a differential method, of in vitro detection of the presence of such a sequence in an individual, or for the preparation of a composition capable of being used in serotherapy in neuropathological conditions with an autoimmune component.

Said antibodies are advantageously polyclonal or monoclonal antibodies obtained by an immunological reaction from a human, mammalian or avian organism or other species toward the proteins, as defined above.

The subject of the present invention is a method for the differential immunological screening of normal or pathological human endogenous retroviral sequences of the HERV-7q family, characterized in that it comprises bringing a biological sample into contact with an antibody according to the invention, the reading of the result being visualized by an appropriate means, in particular EIA, ELISA, RIA, fluorescence.

By way of illustration, such an in vitro diagnostic method according to the invention comprises bringing a biological sample collected from a patient into contact with antibodies according to the invention and detecting with the aid of any appropriate method, in particular with the aid of labeled anti-immunoglobulins, the immunological complexes formed between the proteins produced normally or pathologically and the antibodies.

Monoclonal or polyclonal antibodies, produced from antigens corresponding to synthetic peptides, or recombinant polypeptide or proteins make it possible to monitor the expression of the peptides or proteins produced normally or pathologically. The analysis is preferably carried out by ELISA or equivalent, Western blotting or equivalent, or by immunohistochemistry.

The peptides or proteins, derived from the endogenous retroviral sequences or whose expression is associated with the expression of these endogenous retroviral sequences, are tested for and identified.

The subject of the present invention is also a method for the identification and detection of endogenous retroviral motifs which are abnormally expressed in the context of pathological conditions associated with cancer, or of neuropathological conditions, in particular autoimmune neuropathological conditions, at the forefront of which is multiple sclerosis, characterized in that it comprises the comparative analysis of the sequences extracted from a biological sample and the sequences according to the invention.

The subject of the present invention is also the application of the nucleic sequences or of the protein sequences according to the invention to the diagnosis of, to the prognosis of, to the evaluation of genetic susceptibility to, any induced, congenital or acquired human diseases, in particular those with cancerous, autoimmune and/or neurological components, such as multiple sclerosis, the associated syndromes and the neurodegenerative diseases in which all or part of the nucleic sequences according to the invention and related endogenous or exogenous forms are involved.

The subject of the present invention is also hybrid nucleic sequences, characterized in that they comprise nucleic sequences or motifs according to the invention, combined with sequences or motifs of endogenous origin or of exogenous origin or induced exogenously.

The subject of the present invention is, in addition, a recombinant cloning or expression vector, characterized in that it comprises a nucleic sequence in accordance with the invention.

Therapeutic strategies may be envisaged by using some of the nucleic sequences contained in HERV-7q and the sequences of the same family or deduced polypeptide structures or by the use of peptides or proteins, or of specific antibodies.

In accordance with the invention, all or part of the endogenous retroviral nucleic sequences of the HERV-7q type may be used for use as a vector or as vector elements for therapeutic use, in particular the LTR sequences and the gag region (SEQ ID NO: 2, 21 and 22).

The advantage of such sequences lies in the safety of the vector thus formed, in the possibility of a targeted specific insertion in a well-defined region by a strategy similar to homologous recombination, in cellular targeting, which is optionally transient in the case of a placental expression in women. Another aspect relates to the possibility of combining with the genes of interest the biologically active retroviral motifs (immunomodulatory peptides, as represented in the sequences SEQ ID NO: 68-118, below, fusogenic peptide and the like).

The subject of the present invention is also transgenic animals, characterized in that they comprise all or part of a sequence of the HERV-7q type (SEQ ID NO: 1-22 and 61).

Table II below establishes the correspondences between the sequence numbers as they appear in the sequence listing and the name of the various sequences.

TABLE II

| SEQ ID NO: | DESIGNATION |
|---|---|
| 1 | Nucleic acid: 7 env |
| 2 | Nucleic acid: gag |
| 3 | Nucleic acid: HERV-7q |
| 4 | Nucleic acid: HE2 |
| 5 | Nucleic acid: HE3 |
| 6 | Nucleic acid: HG3 |
| 7 | Nucleic acid: HE4 |
| 8 | Nucleic acid: HE5 |

TABLE II-continued

| SEQ ID NO: | DESIGNATION |
|---|---|
| 9 | Nucleic acid: HE6 |
| 10 | Nucleic acid: HG6 |
| 11 | Nucleic acid: HE7 |
| 12 | Nucleic acid: HE8 |
| 13 | Nucleic acid: HG8 |
| 14 | Nucleic acid: HE9 |
| 15 | Nucleic acid: HE10 |
| 16 | Nucleic acid: HE11 |
| 17 | Nucleic acid: HG11 |
| 18 | Nucleic acid: HE12 |
| 19 | Nucleic acid: HG12 |
| 20 | Nucleic acid: R1 |
| 21 | Nucleic acid: RIF |
| 22 | Nucleic acid + deduced env protein: HERV-7q |
| 23 | Fragment of deduced env protein according to SEQ ID NO: 22 |
| 24 | Fragment of deduced env protein according to SEQ ID NO: 22 |
| 25 | Fragment of deduced env protein according to SEQ ID NO: 22 |
| 26 | Protein: enverin |
| 27 | Fragment of deduced env protein according to SEQ ID NO: 22 |
| 28 | Nucleic acid + protein deduced from gag: HERV-7q |
| 29 | Fragment of deduced gag protein according to SEQ ID NO: 28 |
| 30 | Fragment of deduced gag protein according to SEQ ID NO: 28 |
| 31 | Fragment of deduced gag protein according to SEQ ID NO: 28 |
| 32 | Fragment of deduced gag protein according to SEQ ID NO: 28 |
| 33 | Fragment of deduced gag protein according to SEQ ID NO: 28 |
| 34 | Fragment of deduced gag protein according to SEQ ID NO: 28 |
| 35 | env protein: reading frame 1 |
| 36 | gag protein |
| 37 | Nucleic acid: G1F (primer) |
| 38 | Nucleic acid: G1R (primer) |
| 39 | Nucleic acid: G2F (primer) |
| 40 | Nucleic acid: G2R (primer) |
| 41 | Nucleic acid: G4F (primer) |
| 42 | Nucleic acid: G3F (primer) |
| 43 | Nucleic acid: G4R (primer) |
| 44 | Nucleic acid: G5R (primer) |
| 45 | Nucleic acid: E1F (primer) |
| 46 | Nucleic acid: E1R (primer) |
| 47 | Nucleic acid: E2F (primer) |
| 48 | Nucleic acid: E2R (primer) |
| 49 | Nucleic acid: E3F (primer) |
| 50 | Nucleic acid: E3R (primer) |
| 51 | Nucleic acid: E4F (primer) |
| 52 | Nucleic acid: E4R (primer) |
| 53 | Nucleic acid: E5F (primer) |
| 54 | Nucleic acid: E6F (primer) |
| 55 | Nucleic acid: E5R (primer) |
| 56 | Nucleic acid: ExF (primer) |
| 57 | Nucleic acid: ExR (primer) |
| 58 | Protein gag |
| 59 | Nucleic acid: Sequence A (insertion sequence) |
| 60 | Nucleic acid: Sequence B (insertion sequence) |
| 61 | Nucleic acid: HE13 |
| 62 | Nucleic acid: RH7 |
| 63 | Nucleic acid: RAM75 |
| 64 | Nucleic acid: RAV73 |
| 65 | Nucleic acid: RBP3 |
| 66 | Nucleic acid: HI3 |
| 67 | Nucleic acid: LTX |
| 68 | Peptide Table I |
| 69 | Peptide Table I |
| 70 | Peptide Table I |
| 71 | Peptide Table I |
| 72 | Peptide Table I |
| 73 | Peptide Table I |
| 74 | Peptide Table I |
| 75 | Peptide Table I |
| 76 | Peptide Table I |
| 77 | Peptide Table I |
| 78 | Peptide Table I |
| 79 | Peptide Table I |
| 80 | Peptide Table I |
| 81 | Peptide Table I |
| 82 | Peptide Table I |
| 83 | Peptide Table I |
| 84 | Peptide Table I |
| 85 | Peptide Table I |
| 86 | Peptide Table I |
| 87 | Peptide Table I |
| 88 | Peptide Table I |
| 89 | Peptide Table I |
| 90 | Peptide Table I |
| 91 | Peptide Table I |
| 92 | Peptide Table I |
| 93 | Peptide Table I |
| 94 | Peptide Table I |
| 95 | Peptide Table I |
| 96 | Peptide Table I |
| 97 | Peptide Table I |
| 98 | Peptide Table I |
| 99 | Peptide Table I |
| 100 | Peptide Table I |
| 101 | Peptide Table I |
| 102 | Peptide Table I |
| 103 | Peptide Table I |
| 104 | Peptide Table I |
| 105 | Peptide Table I |
| 106 | Peptide Table I |
| 107 | Peptide Table I |
| 108 | Peptide Table I |
| 109 | Peptide Table I |
| 110 | Peptide Table I |
| 111 | Peptide Table I |
| 112 | Peptide Table I |
| 113 | Peptide Table I |
| 114 | Peptide Table I |
| 115 | Peptide Table I |
| 116 | Peptide Table I |
| 117 | Peptide Table I |
| 118 | Peptide Table I |
| 119 | Nucleic acid: BLIMP-1 |
| 120 | Peptide: CKH |
| 121 | Nucleic acid: F645 (primer) |
| 122 | Nucleic acid: PS5D (primer) |

BRIEF DESCRIPTION OF THE DRAWINGS

In addition to the preceding arrangements, the invention also comprises other arrangements which will emerge from the description which follows, which refers to exemplary embodiments of the method which is the subject of the present invention as well as to the appended drawings, in which:

FIG. 1A-1B. Human nucleic sequence HERV-7q (SEQ ID NO:3), whose analysis and treatment make it possible to characterize a novel endogenous retroviral structure. The repeat nucleic regions of type R1 and R2 and the gag, pol and env domains are underlined. The gag and env type domains are in italics. The region homologous to a noncoding 3' portion of Rab7 is double underlined.

FIG. 3. Comparison of the repeat nucleic sequences situated at the boundaries of HERV-7q. The 5' (SE ID NO: 20; top) and 3' (SE ID NO: 21; bottom) repeat nucleic regions are compared and the identical bases are indicated by two dots.

FIG. 4. Deduced sequence (SEQ ID NO: 26) having an open reading frame in the env-type domain of HERV-7q according to the longest open reading frame rule.

FIG. 5. Sequences around the CKS-17 domain identified in various deduced env domains of the HERV-7q family and comparison with reference CKS 17 motifs.

Figure 2:
FIG. 2. Map of the human endogenous retro-viral region HERV-7q. The upper part of the figure corresponds to an anonymous region of the human genome situated on the long arm of chromosome 7. The repeat domains (1), gag (2), pol (3) and env (4) of HERV-7q can be identified. The C-terminal env region (4.3) is prolonged upstream in the form of a long open reading frame (4.2). The domain 4.1 corresponds to the N-terminal region of the env domain.

1) HE2 (SEQ ID NO: 123)-2) HERV-7q (SEQ TD NO: 124)-3) GenBanik accession No.: M85205 (SEQ ID NO: 125)-4) HE7 (SEQ ID NO: 126)-5) HE9 (SEQ ID NO: 127)-6) CKS-17 (SEQ IID NO: 128); the peptide motif endowed with immunomodulatory properties is underlined-7) gp20 of retrovirus type D (SRV-Pc; SEQ ID NO: 129).

FIG. 6. Possible deduced sequence (SEQ TD NO: 58) of the gag-type domain identified in HERV-7q established according to the longest open reading frame rule. X and / correspond to a non-sense codon and to a reading frame shift, respectively. The underlined sequence corresponds to the beginning of the pol domain.

FIG. 7. Comparison of the nucleic regions covering the gag region of HERV-7q (SE ID NO: 2; top) and HERV-TcR (SE ID NO: 19; bottom) and their flanking regions. The identical bases are specified by two dots.

FIG. 8A-8C. Example of nucleic alignments of the env-type domain of HERV-7q with similar env-type domains present in human endogenous retroviral sequences of the same family. The non-sense codons are underlined: 1) HERV-7q (SEQ ID NO: 1)-2) HE2 (SEQ ID NO: 4) 03) HE3 (SEQ ID NO: 5)-04) HE4 (SEQ ID NO: 7).

FIG. 9A-9B. Nucleic alignments between the gag domain of HERV-7q and the corresponding domains belonging to the same family. Comparison with fragments of gag domains isolated from infectious retroviral agents. Sequences of infectious retroviral origin: EMBL database accession No.: 1) A60168 (SEQ ID NO: 130)-2) A60201 (SEQ ID NO: 131)-3) A60200 (SEQ ID NO: 132)-4) A60171 (SEQ ID NO: 133). Human endogenous retroviral sequences: 5) HERV-7q (SEQ ID NO: 2)-6) HG11 (SEQ ID NO: 17)-7) HG3 (SEQ ID NO: 6). The figures indicated in the endogenous sequences correspond to the number of nucleotides inserted in order to optimize the alignment with the gag-type sequences identified in retroviruses of infectious origin.

FIG. 10. Alignment of a deduced gag protein motif (SEQ ID NO: 134; top) belonging to an infectious retrovirus (EMBL accession No.: A60200) with the deduced gag protein motif (SE ID NO: 58; bottom) identified in HERV-7q. The non-sense codons are in bold and underlined. The identical amino acids are specified by 2 dashes. One dash indicates a deletion or a homologous amino acid.

FIG. 11. Alignment of an env motif (SEQ ID NO: 135; top) belonging to an infectious retrovirus (EMBL accession No.: A60170) with the env motif (SEQ ID NO: 1; bottom) identified in HERV-7q. The homologous nucleotides are specified by two dots and the deletions by a dash.

FIG. 12. Comparison between the env domain of HERV-7q (SEQ ID NO: 1; top) and the env domain of HERV-9 (SEQ ID NO: 136; bottom). The 66% homology is limited to the 3' region of the env domain of HERV-7q and HERV-9, respectively between nucleotides 8976 nt and 9500 nt of HERV-7q and nucleotides 2898 nt and 3465 nt of HERV-9 (GenBank accession No.: X57147). Numerous insertions/deletions are also observed.

FIG. 13A-13D. Homology between a portion of the sequence of the transcript encoding RH7 (top, SEQ ID NO: 62) and an RGH2 motif(bottom, SEQ ID NO: 137)-GenBank accession No.: D11018).

FIG. 14A-14N. Identification of the sequence of the transcript encoding RAM75 (SEQ ID NO: 63), corresponding to the gene for an ATPase of PEX1 type. The coding exons are underlined. The initiation and non-sense codons as well as the putative poly- adenylation sites are in bold and underlined. The region in italics corresponds to the beginning of the endogenous retroviral sequence RH7.

FIG. 15A-15F. Sequence of the transcript encoding RAV73 (SEQ ID NO: 64), situated at 0.7 kb downstream of HERV-7q; the nucleic sequences capable of encoding one or more polypeptides are underlined.

FIG. 16. Comparison between the 3' LTR sequence (SEQ ID NO: 21; top) of HERV-7q and the intron sequence LTX (SEQ ID NO: 67), situated in the FMR2 gene, associated with fragile X (bottom).

FIG. 17. Detection of modifications on the nucleotide sequence (SEQ ID NO: 22), in patients suffering from MS. The modified bases, in at least one patient, are underlined. The primers used are in italics (sequences SEQ ID NO: 121 and 122). The initiation ATG and the non-sense codon are in bold.

FIG. 18A-18D. The env coding portion of the HERV-7q sequence (SEQ ID NO: 1), with 3 reading frames.

FIG. 19A-19B (SEQ ID NO: 23 to 27 and 35), FIG. 20-20B (SEQ ID NO: 138). FIG. 21A-21B (SEQ ID NO: 139). Separate presentation of the env protein according to the 3 reading frames.

FIG. 22A-22C. Nucleic sequence (SEQ ID NO: 140) containing the retroviral sequence RH7 situated in 5' of the HERV-7q sequence. The sequence in italics corresponds to the beginning of the HERV-7q sequence. The RH7 sequence is underlined. Two putative polyadenylation sites are in bold.

FIG. 23A-23E. Sequence (SEQ ID NO: 141) of the transcript encoding RBP3 containing nucleotide motifs identified in the nucleic sequence encoding the Blimp-1 gene.

FIG. 24. Sequence (SEQ ID NO: 142) of the transcript encoding APS.

FIG. 25. Sequence (SEQ ID NO: 119) of the transcript encoding Blimp-1; the coding portion is underlined; the initiation and termination codons are in bold.

FIG. 26A-26D. Sequence (SEQ ID NO: 143) of the transcript encoding FMR2. The coding portion is underlined. The initiation and non-sense codons are in bold.

It should be clearly understood, however, that these examples are given solely by way of illustration of the subject of the invention and do not in any manner constitute a limitation thereto.

EXAMPLE 1

Detection, by gene amplification, of a nucleic sequence belonging to a domain of the gag or env type according to the invention, in a genomic dna sample of human or mammalian origin The gene amplification is carried out using genomic DNA isolated from blood. An anticoagulant treatment is carried out with 1 ml of a citrate solution (per liter: 4.8 g of citric acid, 13.2 g of sodium citrate, 14.7 g of glucose) per 6 ml of fresh blood. After centrifugation of 20 ml of blood for 15 min at 130 000 g, the supernatant is removed and the fraction enriched with white blood cells is transferred into a new tube and then recentrifuged under the same conditions as above. The fraction enriched with white blood cells is resuspended in an extraction buffer (10 nM Tris-HCl, 0.1 M EDTA, 20 µg/ml of pancreatic RNAse treated so as to eliminate the DNAses, 0.5% SDS, pH 8.0), and then incubated for 1 hour at 37° C. Proteinase K is added at a final concentration of 100 µg/ml. The suspension of lyzed cells is incubated at 50° C. for 3 hours, with occasional stirring, and then treated with an equal volume of phenyl equilibrated with 0.5 M Tris-HCl, pH 8.0. The emulsion formed is placed on a wheel for one hour and then centrifuged at 5 000 g for 15 min at room temperature. The aqueous solution is treated and deproteinized by a triple phenyl extraction in order to obtain a level of purification corresponding to an absorbance A260/A280 final ratio greater than 1.75. The aqueous fraction is precipitated with 0.2 vol. of 10 M sodium acetate and 2 vol. of ethanol. The DNA is then either collected with the tip of a bent Pasteur pipette, or centrifuged at 5 000 g for 5 min at room temperature. The DNA or the DNA pellet is washed twice with 70% ethanol and then taken up in 1 ml of TE, pH 8.0 so as to be eluted, with gentle stirring, for 12 to 24 hours.

Oligonucleotides specific for the endogenous sequences described according to the invention are chosen in order to amplify the gag or env region of the endogenous retroviral regions described according to the invention. The genomic DNA studied is obtained from patients having pathological conditions such as multiple sclerosis and from individuals reputed to be healthy.

The thermostable DNA polymerases used were chosen for their high accuracy during the amplification process, such as Vent DNA polymerase (Biolabs) and the like, and are used according to the conditions recommended by the supplier.

The amplification strategy uses, depending on the case, a simple PCR, or a nested or seminested PCR.

Oligonucleotides used to amplify the gag region:
primer G1F, sense, located in the region upstream of the gag domain of HERV-7q (SEQ ID NO: 37),
primer G1R, antisense, located in the 3' terminal region of the gag domain (SEQ ID NO: 38).

The fragment of 1505 nt amplified by the pair G1F-G1R; 1505 nt is used to generate the probes capable of hybridizing the various PCR amplification products.

primer G2F, sense nested (SEQ ID NO: 39),
primer G2R, antisense nested (SEQ ID NO: 40),
primer G4F, sense nested (SEQ ID NO: 41),
primer G3F, sense nested (SEQ ID NO: 42),
primer G4R, antisense nested (SEQ ID NO: 43),
primer G5R, antisense nested (SEQ ID NO: 44).

Oligonucleotides used to amplify the env region of HERV-7q:
primer E1F, sense (SEQ ID NO: 45),
primer E1R, antisense (SEQ ID NO: 46).

The fragment of 2529 nt amplified by the pair of primers E1F-E1R is used to generate the probes capable of hybridizing the various PCR amplification products.

primer E2F, sense (SEQ ID NO: 47),
primer E2R, antisense (SEQ ID NO: 48),
primer E3F, sense (SEQ ID NO: 49),
primer E3R, antisense (SEQ ID NO: 50),
primer E4F, sense (SEQ ID NO: 51),
primer E4R, antisense (SEQ ID NO: 52),
primer E5F, sense (SEQ ID NO: 53),
primer E6F, sense (SEQ ID NO: 54),
primer E5R (SEQ ID NO: 55),
primer ExF (SEQ ID NO: 56),
primer ExR (SEQ ID NO: 57).

The PCR is carried out using 50 to 200 ng of genomic DNA. The PCR conditions are those recommended by the supplier. The amplification cycle conditions are carried out in 50 µl: denaturation of 94° C. for 1 min, hybridization of 70° C. for 1 min, and extension at 72° C. for 1 to 2 min, depending on the amplified fragments. After 35 cycles, a terminal reaction is carried out at 72° C. for 10 min. Automated sequencing of the amplified samples is carried out with the aid of an Applied Biosystems type ABI 377 sequencer or another comparable model, according to the protocols provided by the manufacturer.

In the case of a nested or seminested PCR, the same experimental conditions are used, the only difference being that the genomic DNA sequence is replaced with 5 to 10 µl of the amplification product derived from the first PCR.

Two independent amplifications are carried out using the same sample. A control reaction is carried out by replacing the DNA sample with water in order to detect possible contaminants.

EXAMPLE 2

Detection, by gene amplification, of a nucleic sequence according to the invention in a biological sample of genomic dna collected from patients having an existing candidate pathological condition or suspected of having this pathological condition The amplification protocol is the same as in Example 1, apart from the origin of the sample which is obtained from patients having a candidate pathological condition. A genomic DNA sample reputed to be normal is systematically integrated into the set of amplified pathological samples and then analyzed.

The PCR products are separated on a 1.5% agarose gel and then transferred in the presence of 0.4 N sodium hydroxide on a charged nylon membrane. Hybridization is carried out with a specific probe corresponding to the PCR fragments amplified either with the pair G1F-G1R or the pair E1F-E1R. The probe is labeled by incorporating dUTP-digoxygenin according to the supplier's protocol (Boehringer Mannheim). The hybridization is carried out in a hybridization buffer (5×SSC, 50% formamide, 0.1% lauroylsarcosine, 0.02% SDS, 2% blocking reagent Boehringer) overnight at 42° C. The Southern is washed for twice 5 min at room temperature in a 2×SSC solution containing 0.1% SDS. Next, a high stringency wash is carried out twice for 15 min at 55° C. in a 0.1×SSC solution containing 0.1% SDS. The hybridization is visualized according to the supplier's protocol (Boehringer Mannheim), in the presence of a chemiluminescent substrate for alkaline phosphatase, of the CSPD or CDP-STAR type. The filter is visualized after a 15 min exposure at 60° C.

SSCP (single strand conformation polymorphism) analysis makes it possible to detect discrete modifications of the sequence of the fragments amplified by PCR. The PCR is carried out in the presence of dCTP labeled with $^{32}P$. The sample to be analyzed is denatured at 95° C. for 10 min in the presence of loading buffer, and then immediately loaded onto a 10% polyacrylamide gel containing 7.5% glycerol. The migration is carried out at 4° C. at 8-10 W. The gel is dried and then autoradiographed.

The PCR fragments likely to exhibit an alteration of their nucleotide sequence are sequenced according to Example 1.

Hybridization with the aid of a specific oligonucleotide (17 mers to 20 mers) corresponding to the modified nucleotide region makes it possible to identify the samples having an identical modification (ASO method). Briefly, the southern is hybridized with an oligonucleotide which is distally labeled either with $^{32}P$, or in the presence of digoxygenin (according to the Boehringer Mannheim protocol) and then washed under stringent conditions at 65° C. in a 6×SSC solution containing 0.05% sodium pyrophosphate.

For example, an automated nucleotide sequencing was carried out on six PCR fragments obtained from 5 patients suffering from MS and a control reputed to be normal, and which were amplified using the primers F645: CTTCAAA- CAACAACCAGGAGG (SEQ ID NO: 121) (situated 26 nucleotides upstream of the initiation methionine of enverin) and PS5D: TTGGGGAGGTTGGCCGACGA (SEQ ID NO: 122) (situated 6 nucleotides downstream of the non-sense codon of enverin). Modifications of the sequence of enverin were observed on the DNA from some patients (FIG. 17).

EXAMPLE 3

Detection of a protein according to the invention in a biological sample

Preparation of a Purified Protein Fraction of Cerebrospinal Fluid from Patients Suffering from MS After a treatment at 56° C. for 30 min and removal of the immunoglobulins on a G HiTrap protein column (Pharmacia), the equivalent of 10 ml of CSF is deposited on a DEAE Sepharose CL-6B column (Pharmacia). The elution is carried out in 20 mM Tris-HCl, pH 8.8, and a gradient from 0 to 0.4 M NaCl, and then the fraction is dialyzed twice against a phosphate-NaCl buffer (PBS). After concentration on Ultrafree-MC (Millipore), the fraction is deposited on a Superose 12 column (FPLC Pharmacia) and eluted in the presence of PBS. After separation by polyacrylamide-SDS gel electrophoresis and electrotransfer onto an Immobilon-P membrane (Millipore), the protein bands are subjected to controlled trypsin hydrolysis.

Analysis of the Protein Fraction by Mass Spectrometry

The peptides digested in the presence of trypsin are analyzed by the MALDI-TOF method, which allows the analysis of peptides present in a mixture (COTTRELL J. S., Pept. Res., 1997, 7, 115-124). The peptides characterized according to their mass are compared with the proteins and with the associated proteins according to the invention.

EXAMPLE 4

Detection of Specific Antibodies to the env Domain of HERV-7q

The identification of a long open reading frame in the env sequence of HERV-7q made it possible to determine a deduced protein sequence SEQ ID NO: 22 and 35 and FIGS. 18-20 of a region of the said gene.

The protein sequences deduced from the sequences ID NO: 22, 35 and FIGS. 18-20 are positioned as follows with respect to FIG. 1 or the sequence ID NO: 3:
  SEQ ID NO: 22 (reading frame 1) and FIG. 19: beginning of the coding sequence: position 7874, end of the coding sequence 1st nonsense codon (position 9493)
  SEQ ID NO: 35: beginning of the coding sequence: position 7874, end of the coding sequence 1st nonsense codon (position 9493) (reading frame 1)
  FIG. 19: beginning of the coding sequence: position 6970, end of the coding sequence 1st nonsense codon (position 9493) (reading frame 1)
  FIG. 20: beginning of the coding sequence: position 6971, the end of the reading frame is shifted depending on the case by 1, 2 or 3 codons
  FIG. 21: beginning of the coding sequence: position 6972, the end of the reading frame is shifted depending on the case by 1, 2 or 3 codons Various peptides corresponding to all or part of SEQ ID NO: 22 (see SEQ ID NO: 23-27 and 35) were synthesized by genetic engineering in order to test their antigenic specificity toward sera or tissues from patients suffering from MS, for example. Briefly, all or part of the env region of HERV-7q is subcloned into the vectors pQE30, 31 and 32. The vectors pQE30, 31 and 32 contain, in 5' of the multiple cloning site, the consensus sequences for transcription (the strong T5 bacteriophage promoter, 2 operators of the lactose operon) and translation (one synthetic ribosome binding site). Likewise, pQE30, 31 and 32 possess, in 3', the phage 1 transcription terminator as well as a Stop codon for translation. The expression of the protein is carried out after transformation in *E. coli* M15. The plasmid pQE30, 31 and 32 possess, upstream of the multiple cloning site, the coding sequence for a succession of 6 histidines having affinity for nickel ions. This stretch allows the purification of the expressed chimeric protein by adsorption on a resin consisting of a chelating ligand, nitrotriacetic acid (NTA), charged with 4 nickel ions (NI-NTA resin, Qiagen).

The transformation is carried out by electroporation or treatment with calcium chloride. For example, an *E. coli* M15 colony is incubated in 100 ml of LB medium containing 250 µg of kanamycin, with stirring at 37° C. until an $OD^{600}$ of 0.5 is obtained. After centrifugation for 5 minutes at 2000 g at 4° C., the bacterial pellet is taken up in 30 ml of TFB1 solution (100 mM rubidium chloride, 50 mM manganese chloride, 30 mM potassium acetate, 10 mM $CaCl_2$, 15% glycerol, pH 5.8), at 4° C. for 90 minutes. After a centrifugation of 5 minutes at 2000 g at 4° C., the bacterial pellet is taken up in 4 ml of TFB2 solution (10 mM rubidium chloride, 10 mM MOPS, 75 mM $CaCl_2$, 15% glycerol, pH 8). The cells may be kept at −70° C. in aliquots of 500 ml. 20 µl of the ligation and 125 µl of competent cells are mixed and placed on ice for 20 minutes. After a heat shock of 42° C. for 90 seconds, the cells are stirred for 90 minutes at 37° C. in 500 ml of Psi-broth medium (LB medium supplemented with 4 mM $MgSO_4$, 10 mM potassium chloride). The transformed cells are plated on LB-agar dishes supplemented with 25 µg/ml of kanamycin and 100 µg/ml of ampicillin, and the dishes are incubated overnight at 37° C.

The potentially recombinant clones are subcultured in an orderly manner on a nylon filter deposited on an LB-agar dish supplemented with 25 µg/ml of kanamycin and 100 µg/ml of ampicillin. After one night at 37° C., the recombinant clones are located by hybridization of the plasmid DNA with the nucleotide probe amplified by PCR with the pair of primers according to SEQ ID NO: 45 and SEQ ID NO: 46.

An independent colony containing the insert is inoculated at 20 ml of LB medium supplemented with 25 µg/ml of kanamycin and 100 µg/ml of ampicillin. After one night at 37° C., with stirring, 500 ml of the same medium are incubated at 1/50 with this preculture until an $OD^{600}$ of 0.8 is obtained, and then 1 to 2 mM final of IPTG is added. After 5 hours, the cells are centrifuged for 20 minutes at 4 000 g.

A portion of the cellular pellet is taken up in 5 ml of sonification buffer (50 mM of sodium phosphate, pH 7.8, 300 mM NaCl) and then placed on ice. After rapid sonification, the cells are centrifuged for 20 minutes at 10 000 g. A portion of the cellular pellet is taken up in 10 ml of a 30 mM Tris/HCl-20% sucrose solution pH 8. The cells are incubated for 5 to 10 minutes, with stirring, after addition of 1 mM EDTA. After a centrifugation of 10 minutes at 8 000 g at 4° C., the pellet is taken up in 10 ml of 5 mM ice cold $MgSO_4$. After 10 minutes on the ice, with stirring, the cells are centrifuged for 10 minutes at 8 000 g at 4° C.

The pellet is taken up in 5 ml/g in buffer A (6 M GuHCl (guanidine hydrochloride), 0.1 M sodium phosphate, 0.01 M Tris/HCl, pH 8), 1 hour at room temperature. The lysate is centrifuged for 15 minutes at 10 000 g at 4° C., and the supernatant is supplemented with 8 ml of Ni-NTA resin, pre-equilibrated in buffer A. After 45 minutes at room temperature, the resin is poured into a column, washed with 10 times the column volume with buffer A and then with 5 times the column volume with buffer B (8 M urea, 0.1 M sodium phosphate, 0.01 M Tris/HCl, pH 8). The column is washed with buffer C (8 M urea, 0.1 M sodium phosphate, 0.01 M Tris/HCl, pH 6.3) until A280 is less than 0.01. The recombinant protein is eluted with 10 to 20 ml of buffer D (8 M urea, 0.1 M sodium phosphate, 0.01 M Tris/HCl, pH 5.9) and then with 10 to 20 ml of buffer E (8 M urea, 0.1 M sodium phosphate, 0.01 M Tris/HCl, pH 4.5), and then with 20 ml of buffer F (6 M HCl, 0.2 M acetic acid). After SDS-PAGE analysis, the purified fraction(s) containing the chimeric protein allowed the production of antibodies in rabbits. The antibodies obtained are tested by Western blotting after visualization with a secondary antibody coupled to alkaline phosphatase.

Antibodies are obtained in the same manner, using peptides synthesized chemically according to the Merrifield technique (G. Barany and B. Merrifield, 1980, in *The peptides*, 2, 1-284, E. Gross and J. Meienhofer, Academic Press, New York).

The specific antibodies obtained are used for detection of the serum or tissue expression of all or part of the endogenous retroviral sequences according to the invention, in normal and pathological cases.

The proteins of serum or tissue origin are separated on acrylamide-SDS gel and then transferred onto a nitrocellulose filter with the aid of a Novablot 2117-2250 apparatus (LKB). The transfer is carried out on a Hybond C-extra sheet (Amersham) using a 100 mM CAPS buffer pH 11, methanol, water (V/V/V: 1/1/8) containing 1 mM $CaCl_2$. After a transfer of 1 hour at 0.8 $mA/cm^2$, the sheet is saturated for 1 hour at room temperature in PBS-0.5% gelatin. The sheet is brought into contact with the specific antibody at the concentration of 1/1 000 in PBS-0.25% gelatin. After 2 hours, the filter is washed 3 times 15 minutes in PBS-0.1% Tween-20, and then the filter is incubated for 30 minutes in the presence of a secondary antibody coupled to alkaline phosphatase (Promega), diluted 1/7 500 in PBS-0.25% gelatin. After three washes in PBS-0.1% Tween-20, the filter is equilibrated in a buffer (100 mM Tris-HCl, pH 9.5, 100 mM NaCl, 5 mM $MgCl_2$). The visualization is carried out in the presence of 45 μl of NBT at 75 mg/ml and 35 μl of BCIP at 50 mg/ml, per 10 ml of alkaline phosphatase buffer.

The chimeric proteins obtained by genetic engineering are also used for tests of biological activity, such as for example the test for biological activity of the CKS-17-type peptide identified in the env domain of HERV-7q (FIG. 5).

EXAMPLE 5

Production of Ribonucleic Probes Encoding the env Sequences of HERV-7q

The PCR fragments obtained are subcloned into the plasmid PGEM 4Z (Promega) which possesses on either side of its multiple cloning site, promoter sequences for the SP6 and T7 RNA polymerases.

The method of competence used is electroporation. The plasmid and the PCR fragment are hybridized in a ratio of 50 ng of vector (SmaI cleavage) to 100 ng of PCR fragment (made blunt ended by treatment with the Klenow fragment of DNA polymerase). The incubation takes place overnight at 22° C. in ligation buffer (66 mM Tris-HCl, pH 7.5, 5 mM $MgCl_2$, 1 mM dithioerythritol, 1 mM ATP) in the presence of 1 u of T4 DNA ligase and is then stopped by denaturation for 10 minutes at 65° C. In parallel, the *E. coli* JM 105 strain is inoculated overnight at 37° C. in LB medium. This preculture is diluted 1/500 and placed at 37° C. until an $OD^{600}$ equal to 1 is obtained. For the remainder of the procedure, the cells will always be stored at cold temperature. After centrifugation for 5 minutes at 3 500 g at 4° C., the cellular pellet is resuspended in ¼ vol. of ultra-pure ice-cold water. This step is repeated 5 to 6 times. The pellet is then resuspended in ¼000 vol. of water; 10% of sterile glycerol is added, allowing preservation of the electrocompetent cells, in aliquots of 10 μl at 20° C. 1 μl of the ligation is added to 50 μl of electrocompetent cells; the mixture is subjected to an electrical discharge of 12.5 kV/cm, applied for 5.8 ms. The cells are rapidly resuspended in the SOC medium, incubated for 1 hour at 37° C. and then plated in the presence of 2% X-Gal in dimethylformamide, and 10 mM IPTG, on an LB-agar dish supplemented with ampicillin (100 μg/ml). After one night at 37° C., the potentially recombinant white clones are subcultured in an orderly manner on an LB/ampicillin dish and in parallel on a nylon filter deposited on an LB/ampicillin dish. These two dishes are incubated overnight at 37° C. The recombinant clones are then located by hybridization with a nucleic probe amplified by PCR with the pair or primers according to SEQ ID NO: 45 and SEQ ID NO: 46 and labeled with digoxygenin.

The recombinant clones are cultured in 50 ml of LB/ampicillin medium (100 μg/ml), with stirring, overnight at 37° C. After centrifugation at 3 500 g for 15 minutes at 4° C., the bacterial pellet is taken up in 4 ml of P1 buffer (50 mM Tris-HCl, 10 mM EDTA, 400 μg/ml RNase A, pH 8) and 4 ml of P2 buffer (200 mM NaOH, 1% SDS). The medium is incubated at room temperature for 5 minutes. After addition of 4 ml of P3 buffer (2.55 M potassium acetate, pH 4.8), the mixture is centrifuged at 12 000 g for 30 minutes at 4° C. This supernatant is applied to a Qiagen type 100 column, pre-equilibrated with 2 ml of QBT buffer (750 mM NaCl, 50 mM MOPS, 15% ethanol, pH 7), the column is washed with twice 4 ml of QC buffer (1 M NaCl, 50 mM MOPS, 15% ethanol, pH 7) and the DNA is eluted with 2 ml of QF buffer (1.2 M NaCl, 50 mM MPOS, 15% ethanol, pH 8). The DNA is precipitated with 0.8 vol. of isopropanol and centrifuged at 12 000 g at 4° C. for 30 minutes. The pellet is washed with 70% ice-cold ethanol and then the plasmid DNA is taken up in twice 150 μl of TE buffer.

The ribonucleic probes are used as specific probes, in particular for the detection of the transcripts expressed by the endogenous retroviral sequences according to the invention.

EXAMPLE 6

Construction of a Transgenic Mouse Containing all or Part of the Gene for Enverin A transgenic mouse containing all or part of the HERV-7q sequence (SEQ ID NO: 3) is constructed so as to identify the sequences responsible for the tissue specificity, and to evaluate the role of all or part of the endogenous retroviral motifs of the HERV-7q type, in particular all or part of the peptide motifs of enverin. The microinjection technique used refers to the conventional technique (Hogan et al., (1994), Manipulating the mouse embryo, Cold Spring Harbor, Cold Spring Harbor Laboratory Press) or to its equivalents. Forms identical to the normal human molecule of motifs of the HERV-7q type, including enverin, or forms which are mutated, deleted, having insertions, or truncated are tested in order to determine the motifs which are critical both from the normal and pathological point of view, and more particularly during fetal development and during tumor processes.

BIBLIOGRAPHIC REFERENCES

Benit L. et al., 1997. Cloning of a new murine endogenous retrovirus MuERV-L, with strong similarity of the human HERV-L element and with a gag coding sequence closely related to the Fv1 restriction gene. J. Virol. 71, 5652-5657.

Coffin J. M. 1985. Endogenous retrovirus, In: "RNA tumor viruses" (Weiss R. A., Varmus H. E., Teich N. M., and Coffin J. M. eds), Cold Spring Harbor Laboratory Press, Cold Spring Harbor, N.Y.

Conrad B., Weissmahr R. N., Boni J., Arcari R., Schupbach J., and Mach B. 1997. A human endogenous retroviral superantigen as candidate autoimmunogene in type 1 diabetes. Cell 90, 303-313.

Covey S. N. 1986. Amino acid sequence homology in gag region of reverse transcribing elements and the coat protein gene of cauliflower mosaic virus, Nucleic Acids Res. 14, 623-633.

Hertig C., Coupar B. E., Gould A. R., and Boyle D. B. 1997. Field and vaccine strains of fowlpox virus carry integrated sequences from the avian retrovirus, reticuloendotheliosis virus. Virology 235, 367-376.

Hohenadl C., Leib-Mösch C., Hehlemann R., and Erfle Y. 1996. Biological significance of human endogenous retroviral sequences. J. Acqui. 1 mm. Def. Synd. Hum. Retrovir. 13, S268-S273.

Kulkoski J. K., Jones S., Katz R. A., Mack J. P. G., and Skalka A. M. 1992. Residues critical for retroviral integrative recombination in a region that is highly conserved among retroviral/retrotransposon integrases and bacterial insertion sequence transposases. Mol. Cell. Biol. 12, 2331-2338.

La Mantia G. et al., N. A. R., 1991, 19, 7, 1513-1520

Patience C., Wilkinson D. A., and Weiss R. A. 1997. Our retroviral heritage. Trends Genet. 13, 116-120.

Pearson W. R. 1994. Using the FASTA program to search protein and DNA sequence databases. Methods Mol. Biol. 24, 307-331.

Perron H., Garson J. A., Bedin F., Beseme F., Paranhos-Baccala G., Komurian-Pradel F., Mallet F., Tuke P. W., Voisset C., Blond J. L., Lalande B., Seigneurin J. M., Mandrand B. and the Collaborative Research Group on Multiple Scelerosis. 1997. Molecular identification of a novel retrovirus repeatedly isolated from patients with multiple sclerosis. Proc. Natl. Acad. Sci. USA 94, 7583-7588.

Tönjes R. R. et al., J. AIDS and Hum. Retrovirol. 1996, 13. S261-S267.

Vitelli R., Chiarillo M., Lattero D., Bruni C. B., and Bucci C., 1996. Molecular cloning and expression analysis of the human Rab7 GTP-ase complementary deoxyribonucleic acid. Biochem. Biophys. Res. Commun. 229, 887-890.

Weber L. T., Miller M., Jaskolski M., Leis J., Skalka M., and Wlodawer A., 1989. Molecular modeling of the HIV-1 protease and its substrate binding site. Science 243, 928-931.

Wilkinson D., Mager D. L., and Leong J. A. C. 1994. Endogenous human retroviruses. In: "The Retroviridae" (Levy J. A. ed). Plenum Press New York., Vol. 3, 465-535.

Xiong Y., and Eickbush, T. 1990. Origin and evolution of retroelements based upon their reverse transcriptase sequences. EMBO J. 9, 3353-3362.

As is evident from the above, the invention is not at all limited to its embodiments, implementations and applications which have just been described more explicitly; it embraces on the contrary all the variants which may occur to a specialist in this field, without departing from the framework or scope of the present invention.

The invention claimed is:

1. An isolated polypeptide derived from a human endogenous retroviral sequence containing an env-type motif, wherein said polypeptide consists of the sequence from the first methionine to the amino acid at position 540 of the sequence SEQ ID NO: 26.

2. An isolated peptide derived from the polypeptide according to claim 1, which consists of the sequence from positions 293 to 540 of the sequence SEQ ID NO: 26.

3. An isolated peptide derived from the polypeptide according to claim 1, which consists of the sequence from positions 323 to 540 of the sequence SEQ ID NO: 26.

* * * * *

SEQUENCE LISTING

```
<160> NUMBER OF SEQ ID NOS: 122

<210> SEQ ID NO 1
<211> LENGTH: 2599
<212> TYPE: DNA
<213> ORGANISM: Homo sapiens

<400> SEQUENCE: 1
atcccctgcc ttaatcgcca agctccttca ggagaacaaa gaacaggcca ttaccctgga        60
gaagactggc aactgatttt acccacaagc ccaaacctca gggatttcag tatctactag       120
tctgggtaga tactttcacg ggttgggcag aggccttccc ctgtaggaca gaaaaggccc       180
aagaggtaat aaaggcacta gttcatgaaa taattcccag attcggactt ccccgaggct       240
tacagagtga caatagccct gctttccagg ccacagtaac ccagggagta tcccaggcgt       300
taggtatacg atatcactta cactgcgcct gaaggccaca gtcctcaggg aaggtcgaga       360
aaatgaatga aacactcaaa ggacatctaa aaaagcaaac ccaggaaacc cacctcacat       420
ggcctgctct gttgcctata gccttaaaaa gaatctgcaa ctttccccaa aaagcaggac       480
ttagcccata cgaaatgctg tatggaaggc ccttcataac caatgacctt gtgcttgacc       540
caagacagcc aacttagttg cagacatcac ctccttagcc aaatatcaac aagttcttaa       600
aacattacaa ggaacctatc cctgagaaga gggaaaagaa ctattccacc cttgtgacat       660
```

| | |
|---|---|
| ggtattagtc aagtcccttc cctctaattc cccatcccta gatacatcct gggaaggacc | 720 |
| ctacccagtc attttatcta ccccaactgc ggttaaagtg gctggagtgg agtcttggat | 780 |
| acatcacact tgagtcaaat cctggatact gccaaaggaa cctgaaaatc caggagacaa | 840 |
| cgctagctat tcctgtgaac ctctagagga tttgcgcctg ctcttcaaac aacaaccagg | 900 |
| aggaaagtaa ctaaaatcat aaatccccat ggccctccct tatcatattt ttctctttac | 960 |
| tgttcttta ccctctttca ctctcactgc accccctcca tgccgctgta tgaccagtag | 1020 |
| ctccccttac caagagtttc tatggagaat gcagcgtccc ggaaatattg atgcccatc | 1080 |
| gtataggagt ctttctaagg gaaccccccac cttcactgcc cacacccata tgccccgcaa | 1140 |
| ctgctatcac tctgccactc tttgcatgca tgcaaatact cattattgga caggaaaaat | 1200 |
| gattaatcct agttgtcctg gaggacttgg agtcactgtc tgttggactt acttcaccca | 1260 |
| aactggtatg tctgatgggg gtggagttca agatcaggca agagaaaaac atgtaaaaga | 1320 |
| agtaatctcc caactcaccc gggtacatgg cacctctagc ccctacaaag gactagatct | 1380 |
| ctcaaaacta catgaaaccc tccgtaccca tactcgcctg gtaagcctat ttaataccac | 1440 |
| cctcactggg ctccatgagg tctcggccca aaacccctact aactgttgga tatgcctccc | 1500 |
| cctgaacttc aggccatatg tttcaatccc tgtacctgaa caatggaaca acttcagcac | 1560 |
| agaaataaac accacttccg ttttagtagg acctcttgtt tccaatctgg aaataaccca | 1620 |
| tacctcaaac ctcacctgtg taaaatttag caatactaca tacacaacca actcccaatg | 1680 |
| catcaggtgg gtaactcctc ccacacaaat agtctgccta ccctcaggaa tattttttgt | 1740 |
| ctgtggtacc tcagcctatc gttgtttgaa tggctcttca gaatctatgt gcttcctctc | 1800 |
| attcttagtg cccccatga ccatctacac tgaacaagat ttatacagtt atgtcatatc | 1860 |
| taagccccgc aacaaagag tacccattct tccttttgtt ataggagcag gagtgctagg | 1920 |
| tgcactaggt actggcattg gcggtatcac aacctctact cagttctact acaaactatc | 1980 |
| tcaagaacta aatggggaca tggaacgggt cgccgactcc ctggtcacct tgcaagatca | 2040 |
| acttaactcc ctagcagcag tagtccttca aaatcgaaga gctttagact tgctaaccgc | 2100 |
| tgaaagaggg ggaacctgtt tatttttagg ggaagaatgc tgttattatg ttaatcaatc | 2160 |
| cggaatcgtc actgagaaag ttaaagaaat tcgagatcga atacaacgta gagcagagga | 2220 |
| gcttcgaaac actggaccct ggggcctcct cagccaatgg atgccctgga ttctccccctt | 2280 |
| cttaggacct ctagcagcta taatattgct actcctcttt ggaccctgta tctttaacct | 2340 |
| ccttgttaac tttgtctctt ccagaatcga agctgtaaaa ctacaaatgg agcccaagat | 2400 |
| gcagtccaag actaagatct accgcagacc cctggaccgg cctgctagcc cacgatctga | 2460 |
| tgttaatgac atcaaaggca cccctcctga ggaaatctca gctgcacaac tctactacg | 2520 |
| ccccaattca gcaggaagca gttagagcgg tctcggccaa cctcccccaac agcacttagg | 2580 |
| ttttcctgtt gagatgggg | 2599 |

<210> SEQ ID NO 2
<211> LENGTH: 1326
<212> TYPE: DNA
<213> ORGANISM: Homo sapiens

<400> SEQUENCE: 2

| | |
|---|---|
| gccgcctggc actcctgagg gaagtataaa ttataacacc atcttacagc tagacctctt | 60 |
| ttgtagaaaa ggcaaatgga gtgaagtgcc ataagtacaa actttctttt cattaagaga | 120 |

-continued

| | |
|---|---|
| caactcacaa ttatgtaaaa agtgtgattt atgccctaca ggaagccttc agagtctacc | 180 |
| tccctatccc agcatccccg actccttccc caactaataa ggaccccct tcaacccaaa | 240 |
| tggtccaaaa ggagatagac aaaagggtaa acagtgaacc aaagagtgcc aatattcccc | 300 |
| aattatgacc cctccaagca gtgggaggaa gagaattcgg cccagccaga gtgcatgtgc | 360 |
| cttttctct cccagactta aagcaaataa aaacagactt aggtaaattc tcagataacc | 420 |
| ctgatggcta tattgatgtt ttacaagggt taggacaatt ctttgatctg acatggagag | 480 |
| atataatgtc actgctaaat cagacactaa ccccaaatga gagaagtgcc accataactg | 540 |
| cagcctgaga gtttggcgat ctctggtatc tcagtcaggt caatgatagg atgacaacag | 600 |
| aggaaagaga atgattcccc acaggccagc aggcagttcc cagtctagac cctcattggg | 660 |
| acacagaatc agaacatgga gattggtgct gcagacattt gctaacttgt gtgctagaag | 720 |
| gactaaggaa aactaggaag aagtctatga attactcaat gatgtccacc ataacacagg | 780 |
| gaagggaaga aaatcctact gccttctgg agagactaag ggaggcattg aggaagcgtg | 840 |
| cctctctgtc acctgactct tctgaaggcc aactaatctt aaagcgtaag tttatcactc | 900 |
| agtcagctgc agacattaga aaaaaacttc aaaagtctgc cgtaggcccg gagcaaaact | 960 |
| tagaaaccct attgaacttg gcaacctcgg ttttttataa tagagatcag gaggagcagg | 1020 |
| cggaacagga caaacgggat taaaaaaaag gccaccgctt tagtcatgac cctcaggcaa | 1080 |
| gtggactttg gaggctctgg aaaagggaaa agctgggcaa attgaatgcc taatagggct | 1140 |
| tgcttccagt gcggtctaca aggacacttt aaaaaagatt gtccaagtag aagtaagccg | 1200 |
| ccccctcgtc catgcccctt atttcaaggg aatcactgga aggcccactg ccccagggga | 1260 |
| caaaggtcct ctgagtcaga agccactaac cagatgatcc agcagcagga ctgagggtgc | 1320 |
| ctgggg | 1326 |

<210> SEQ ID NO 3
<211> LENGTH: 10499
<212> TYPE: DNA
<213> ORGANISM: Homo sapiens

<400> SEQUENCE: 3

| | |
|---|---|
| ccctggggcg ggcttccttt ctgggatgag ggcaaaacgc ctggagatac agcaattatc | 60 |
| ttgcaactga gagacaggac tagctggatt tcctaggccg actaagaatc cctaagccta | 120 |
| gctgggaagg tgaccacgtc caccttttaaa cacgggctt gcaacttagc tcacacctga | 180 |
| ccaatcagag agctcactaa aatgctaatt aggcaaagac aggaggtaaa gaaatagcca | 240 |
| atcatctatt gcctgagagc acagcaggag ggacaacaat cgggatataa acccaggcat | 300 |
| tcgagctggc aacagcagcc ccccttggg tccctcccct ttgtatggga gctgttttca | 360 |
| tgctatttca ctctattaaa tcttgcaact gcactcttct ggtccatgtt tcttacggct | 420 |
| cgagctgagc ttttgctcac cgtccaccac tgctgtttgc caccaccgca gacctgccgc | 480 |
| tgactcccat ccctctggat cctgcagggt gtccgctgtg ctcctgatcc agcgaggcgc | 540 |
| ccattgccgc tcccaattgg gctaaaggct tgccattgtt cctgcacggc taagtgcctg | 600 |
| ggtttgttct aattgagctg aacactagtc actgggttcc atggttctct tctgtgaccc | 660 |
| acggcttcta atagaactat aacacttacc acatggccca agattccatt ccttggaatc | 720 |
| cgtgaggcca agaactccag gtcagagaat acgaggcttg ccaccatctt ggaagcggcc | 780 |
| tgctaccatc ttggaagtgg ttcaccacca tctgggagc tctgtgagca aggaccccc | 840 |
| ggtaacattt tggcaaccac gaacggacat ccaaagtggt gagtaatatt ggaccacttt | 900 |

```
cacttgctat tctgtcctat ccttccttag aattggagga aaataccggg cacttgtcgg      960
ccagttaaaa acgattagtg tggccaccgg acttaagact caggtgtgag gctatctggg     1020
gaagggcttt ctaacaaccc ccaacccttc tgggttgggg acttggtttg cctcaagcca     1080
gcttccactt tcagttttct tggggaagcc gagggccgac tagaggcaga aagctgtcgt     1140
cctgaactcc cggcagtagc cggttgagat catggtgtag ccagaagtct caacagtcgc     1200
ccatgcatgc acccctatct ttccttctga cccatacctc ctgggtccca accacaactt     1260
tcttcaaagt gtagcccaaa aattctcctt acctctgaat atacttcctc tgatccctgc     1320
ctcctaggta ctattggttc agacttccat ttcctctagc aagttgtatc tccaaaggga     1380
tctaaggaag ctctgcgctg cgtccttagg cacctaggct ataacccagg gagtcttatc     1440
cctggtgtcc ctcccaattt aggcatacag ctcttgacat gggcagttat gtaggaccca     1500
ctccccacca cccttgccag ggccccaagt ttgtaaatgg ctgagggaaa agagagacag     1560
aggagagaga gagaaatgga ggagaaagag agagagacag agaggagaga gagacagtga     1620
gagagacaga agagagagag agacaaagag gagagagaga gagtcaaaga gagaaagaaa     1680
gagaaagaaa tagtaaaaaa cagtgtgccc tattccttta aaagccaggg taaatttaaa     1740
acctgtactt gataattgaa ggtcttctct gtgaccctat agcactccaa tccactttgt     1800
ggtcagtgta aataagagca taggccgaaa gcactgaggc cattgacaac ccgtagcttc     1860
cctatcaaaa atccttaacc cagtaacccg cagatggacc aaatgcattc agtcggtagc     1920
gcaactgctt tgctaaaagt agaaaagtaa cttttagagg aaacctcatt gtgagcacac     1980
ctcacctgtt cagaattatt ctaataaaaa aagcaaaaag gtagcttact aactcaaaaa     2040
tcttaaagta tggggctatt ctgttagaaa aaggtaatgt aactccaacc actgataatt     2100
cccttaaccc agcagatttc ctaacgggat ttaaatctta attaccatac aaaggtccga     2160
ccagacctag gcggaactcc cttcaggaca ggacgataga tggttcctcc caggtgattg     2220
aggaaaaaaa ccacaatggg tattcagtaa ttgatacggg gactcttgtg gaagcagagt     2280
tagaaaaatt gcctaataac tggtctcctc aaacgtgtga gctgtttgca ctcagccaag     2340
ccttaaagta cttacagaat caaaagacta tctcaatcct gattcaaaag gttagctaca     2400
ccctctctgt aatgcatttg cataagaact tgtttatggg aatgcatctt gatggggcag     2460
ctgggttgtt ataaaatagg aacccagccc agctctagga ctcacccctg agcgcaaagg     2520
caatgttggg catgctggta aaggaccact agaatccagc agcccagacc cctttctttg     2580
tggtcaagaa aggcgggaaa aggggtgcag gactgctaca tcggtaagca taactaatcc     2640
gataaacaga ggtccatggg tggttacgca ccctggaaag gaactcaccc ctgagcacaa     2700
aggcaatgtt gggcacgctg gtaaaggacc actagaatcc agcagcctgg accccttct     2760
ttgtggtcaa gagaggcagg aaaacaggtg caggactgca acatcagtga gcataactaa     2820
ttcgataagc agaggtccat gggtggtgat gcaccctgga aagaataagc attaggacca     2880
tagaggacac tccaggacta aagctcatcg gaaaatgact agggttgctg gcatccctat     2940
gttctttttt cagatgggaa acgttccccg caagacaaaa acgcccctaa gacgtattct     3000
ggagaattgg gaccaatttg accctcagac actaagaaag aaacgactta tattcttctg     3060
cagtgccgcc tggcactcct gagggaagta taaattataa caccatctta cagctagacc     3120
tcttttgtag aaaaggcaaa tggagtgaag tgccataagt acaaactttc ttttcattaa     3180
gagacaactc acaattatgt aaaaagtgtg atttatgccc tacaggaagc cttcagagtc     3240
```

-continued

```
tacctcccta tcccagcatc cccgactcct tccccaacta ataaggaccc cccttcaacc   3300
caaatggtcc aaaaggagat agacaaaagg gtaaacagtg aaccaaagag tgccaatatt   3360
ccccaattat gaccccctcca agcagtggga ggaagagaat tcggcccagc cagagtgcat   3420 gtgcctttt ctctcccaga cttaaagcaa ataaaaacag acttaggtaa attctcagat   3480
aaccctgatg gctatattga tgttttacaa gggttaggac aattcttga tctgacatgg   3540 agagatataa tgtcactgct aaatcagaca ctaaccccaa atgagagaag tgccaccata   3600
actgcagcct gagagtttgg cgatctctgg tatctcagtc aggtcaatga taggatgaca   3660
acagaggaaa gagaatgatt ccccacaggc cagcaggcag ttcccagtct agaccctcat   3720
tgggacacag aatcagaaca tggagattgg tgctgcagac atttgctaac ttgtgtgcta   3780
gaaggactaa ggaaaactag gaagaagtct atgaattact caatgatgtc caccataaca   3840
cagggaaggg aagaaaatcc tactgccttt ctggagagac taagggaggc attgaggaag   3900
cgtgcctctc tgtcacctga ctcttctgaa ggccaactaa tcttaaagcg taagtttatc   3960
actcagtcag ctgcagacat tagaaaaaaa cttcaaaagt ctgccgtagg cccggagcaa   4020
aacttagaaa ccctattgaa cttggcaacc tcggttttt ataatagaga tcaggaggag   4080
caggcggaac aggacaaacg ggattaaaaa aaaggccacc gctttagtca tgaccctcag   4140
gcaagtggac tttggaggct ctggaaaagg gaaaagctgg gcaaattgaa tgcctaatag   4200
ggcttgcttc cagtgcggtc tacaaggaca ctttaaaaaa gattgtccaa gtagaagtaa   4260
gccgccccct cgtccatgcc ccttatttca agggaatcac tggaaggccc actgccccag   4320
gggacaaagg tcctctgagt cagaagccac taaccagatg atccagcagc aggactgagg   4380
gtgcctgggg caagcgccat cccatgccat cacccctcaca gagccctggg tatgcttgac   4440
cattgagggc caggaggttg tctcctggac actggtgcgg tcttcttagt cttactcttc   4500
tgtcccggac aactgtcctc cagatctgtc actatctgag ggggtcctaa gacgggcagt   4560
cactagatac ttctcccagc cactaagtta tgactgggga gctttattct tttcacatgc   4620
ttttctaatt atgcttgaaa gccccactac cttgttaggg agagacattc tagcaaaagc   4680
aggggccatt atacacctga acataggaga aggaacaccc gtttgttgtc ccctgcttga   4740
ggaaggaatt aatcctgaag tctgggcaac agaaggacaa tatggacgag caaagaatgc   4800
ccgtcctgtt caagttaaac taaaggattc cacctccttt ccctaccaaa ggcagtaccc   4860
cctcagaccc aaggcccaac aaggactcca aaagattgtt aaggacctaa agcccaagg   4920 cctagtaaaa ccatgcagta accctgcag tactccaatt ttaggagtac agaaacccaa   4980
cagacagtgg aggttagtgc aagatctcag gattatcaat gaggctgttg ttcctctata   5040
gccagctgta cctagcccctt atactctgct ttcccaaata ccagaggaag cagagtggtt   5100
tacagtcctg gaccttcagg atgccttctt ctgcatccct gtacatcctg actctcaatt   5160
cttgtttgcc tttgaagata cttcaaaccc aacatctcaa ctcacctgga ctattttacc   5220
ccaagggttc agggatagtc cccatctatt tggccaggca ttagcccaag acttgagcca   5280
atcctcatac ctgacacttt gtccttcggt aggtggatga tttactttg gccgcccatt   5340 cagaaacctt gtgccatcaa gccacccaag cgctcttcaa tttcctcgct acctgtggct   5400
acatggtttc caaccaaag gctcaactct gctcacagca ggttacttag ggctaaaatt   5460
atccaaaggc accagggccc tcagtgagga acacatccag cctatactgg cttatcctca   5520
tcccaaaacc ctaaagcaac taaggggatt ccttggcgta ataggtttct gccgaaaatg   5580
gattcccagg tatggcgaaa tagccaggtc attaaataca ctaattaagg aaactcagaa   5640
```

```
agccaatacc catttagtaa gatggacaac tgaagtagaa gtggctttcc aggccctaac    5700
ccaagcccca gtgttaagtt tgccaacagg gcaagacttt tcttcatatg tcacagaaaa    5760
aacaggaata gctctaggag tccttacaca gatccgaggg atgagcttgc aacctgtggc    5820
atacctgact aaggaaattg atgtagtggc aaagggttga cctcattgtt tacgggtagt    5880
ggtggcagta gcagtcttag tatctgaagc agttaaaata atacagggaa gagatcttac    5940
tgtgtggaca tctcatgatg tgaatggcat actcactgct aaaggagact tgtggctgtc    6000
agacaactgt ttacttaaat gtcaggctct attacttgaa gggccagtgc tgcgactgtg    6060
cacttgtgca actcttaacc cagccacatt tcttccagac aatgaagaaa agataaaaca    6120
taactgtcaa caagtaattt ctcaaaccta tgccactcga ggggacctttt tagaggttcc    6180 tttgactgat cccgacctca acttgtatac tgatggaagt tcctttgtag aaaaaggact    6240
tcgaaaagtg gggtatgcag tggtcagtga atggaata cttgaaagta atccctcac    6300 tccaggaact agtgctcagc tagcagaact aatagccctc acttgggcac tagaattagg    6360
agaagaaaaa agggcaaata tatatacaga ctctaaatat gcttacctag tcctccatgc    6420
ccatgcagca atatggaaag aaagggaatt cctaacttct gagagaacac ctatcaaaca    6480
tcaggaagcc attaggaaat tattattggc tgtacagaaa cctaaagagg tggcagtctt    6540
acactgccgg ggtcatcaga aaggaaagga aagggaaata gaagagaact gccaagcaga    6600
tattgaagcc aaaagagctg caaggcagga ccctccatta gaaatgctta taaaacaacc    6660
cctagtatag ggtaatcccc tccgggaaac caagccccag tactcagcag gagaaacaga    6720
atggggaacc tcacgaggac agttttctcc cctcgggacg gctagccact gaagaaggga    6780
aaatactttt gcctgcaact atccaatgga aattacttaa aacccttcat caaacctttc    6840
acttaggcat cgatagcacc catcagatgg ccaaatcatt atttactgga ccaggccttt    6900
tcaaaactat caagcagata gtcagggcct gtgaagtgtg ccagagaaat aatcccctgc    6960
cttatcgcca agctccttca ggagaacaaa gaacaggcca ttaccctgga gaagactggc    7020
aactgatttt acccacaagc ccaaacctca gggatttcag tatctactag tctgggtaga    7080
tactttcacg ggttgggcag aggccttccc ctgtaggaca gaaaaggccc aagaggtaat    7140
aaaggcacta gttcatgaaa taattcccag attcggactt ccccgaggct acagagtga    7200 caatagccct gctttccagg ccacagtaac ccagggagta tcccaggcgt taggtatacg    7260
atatcactta cactgcgcct gaaggccaca gtcctcaggg aaggtcgaga aaatgaatga    7320
aacactcaaa ggacatctaa aaaagcaaac ccaggaaacc cacctcacat ggcctgctct    7380
gttgcctata gccttaaaaa gaatctgcaa cttttcccaa aaagcaggac ttagcccata    7440
cgaaatgctg tatggaaggc ccttcataac caatgacctt gtgcttgacc caagacagcc    7500
aacttagttg cagacatcac ctccttagcc aaatatcaac aagttcttaa acattacaa    7560 ggaacctatc cctgagaaga gggaaaagaa ctattccacc cttgtgacat ggtattagtc    7620
aagtcccttc cctctaattc cccatcccta gatacatcct gggaaggacc ctacccagtc    7680 atttttatcta ccccaactgc ggttaaagtg gctggagtgg agtcttggat acatcacact    7740
tgagtcaaat cctggatact gccaaaggaa cctgaaaatc caggagacaa cgctagctat    7800
tcctgtgaac ctctagagga tttgcgcctg ctcttcaaac aacaaccagg aggaaagtaa    7860
ctaaaatcat aaatccccat ggccctccct tatcatattt ttctctttac tgttctttta    7920
ccctctttca ctctcactgc acccccctcca tgccgctgta tgaccagtag ctccccttac    7980
```

-continued

```
caagagtttc tatggagaat gcagcgtccc ggaaatattg atgccccatc gtataggagt    8040 cttctctaagg gaaccccac cttcactgcc cacacccata tgccccgcaa ctgctatcac    8100
tctgccactc tttgcatgca tgcaaatact cattattgga caggaaaaat gattaatcct    8160
agttgtcctg gaggacttgg agtcactgtc tgttggactt acttcaccca aactggtatg    8220
tctgatgggg gtggagttca agatcaggca agagaaaaac atgtaaaaga agtaatctcc    8280
caactcaccc gggtacatgg cacctctagc ccctacaaag gactagatct ctcaaaacta    8340
catgaaaccc tccgtaccca tactcgcctg gtaagcctat ttaataccac cctcactggg    8400
ctccatgagg tctcggccca aaaccctact aactgttgga tatgcctccc cctgaacttc    8460
aggccatatg tttcaatccc tgtacctgaa caatggaaca acttcagcac agaaataaac    8520
accacttccg ttttagtagg acctcttgtt tccaatctgg aaataaccca tacctcaaac    8580
ctcacctgtg taaaatttag caatactaca tacacaacca actcccaatg catcaggtgg    8640
gtaactcctc ccacacaaat agtctgccta ccctcaggaa tatttttttgt ctgtggtacc    8700 tcagcctatc gttgtttgaa tggctcttca gaatctatgt gcttcctctc attcttagtg    8760 cccctatga ccatctacac tgaacaagat ttatacagtt atgtcatatc taagcccgc     8820 aacaaaagag tacccattct tccttttgtt ataggagcag gagtgctagg tgcactaggt    8880
actggcattg gcggtatcac aacctctact cagttctact acaaactatc tcaagaacta    8940
aatggggaca tggaacgggt cgccgactcc ctggtcacct gcaagatca acttaactcc    9000 ctagcagcag tagtccttca aaatcgaaga gctttagact tgctaaccgc tgaaagaggg    9060
ggaacctgtt tattttttagg ggaagaatgc tgttattatg ttaatcaatc cggaatcgtc    9120
actgagaaag ttaaagaaat tcgagatcga atacaacgta gagcagagga gcttcgaaac    9180
actggaccct ggggcctcct cagccaatgg atgccctgga ttctcccctt cttaggacct    9240
ctagcagcta taatattgct actcctcttt ggacctgta tctttaacct ccttgttaac    9300
tttgtctctt ccagaatcga agctgtaaaa ctacaaatgg agcccaagat gcagtccaag    9360
actaagatct accgcagacc cctggaccgg cctgctagcc cacgatctga tgttaatgac    9420
atcaaaggca cccctcctga ggaaatctca gctgcacaac ctctactacg ccccaattca    9480
gcaggaagca gttagagcgg tctcggccaa cctcccaac agcacttagg ttttcctgtt    9540
gagatggggg actgagagac aggactagct ggatttccta ggctgactaa gaatccctaa    9600
gcctagctgg gaaggtgacc acatccacct ttaaacacgg ggcttgcaac ttagctcaca    9660
cctgaccaat cagagagctc actaaaatgc taattaggca aagacaggag gtaaagaaat    9720
agccaatcat ctattgcctg agagcacagc aggagggaca atgatcggga tataaaccca    9780
agtcttcgag ccggcaacgg caaccccctt tgggtcccct ccctttgtat gggagctctg    9840
ttttcatgct atttcactct attaaatctt gcaactgcac tcttctggtc catgtttctt    9900
acggcttgag ctgagctttc gctcgccatc caccactgct gtttgccgcc accgcagacc    9960
cgccgctgac tcccatccct ctggatcatg cagggtgtcc gctgtgctcc tgatccagcg   10020
aggcacccat tgccgctccc aatcgggcta aaggcttgcc attgttcctg catggctaag   10080
tgcctgggtt catcctaatt gagctgaaca ctagtcactg ggttccatgg ttctcttctg   10140
tgacccacag cttctaatag agctataaca ctcaccgcat ggcccaaggt tccattcctt   10200
gaatccataa ggccaagaac cccaggtcag agaacacgag gcttgccacc atcttgggag   10260
ctctgtgagc aaggacccc aagtaacaca accatgaggg tgcaaatgca tgggccacta   10320
atggtagagc aagaaaacag aagggccctg gttcctcgaa ggcatcagtg agctgaaatg   10380
```

```
cctgccctgg atgtcctatt cctaggtgtt tttctgcctg aagcagatta aacccttgt    10440 tcacttctcc aagtagggct tctattacag cccaaatcaa tccccacccc agatgacat    10499

<210> SEQ ID NO 4
<211> LENGTH: 2784
<212> TYPE: DNA
<213> ORGANISM: Homo sapiens

<400> SEQUENCE: 4
ctccttcagg agaacaaaga acaggccact acccaagaga agactggcaa ctagatttta      60
cccatatgcc caaatctcag ggatttcagt atctactagt ttgggtagat actttcactg     120
gttgggcaga ggccttcccc tgtaggacag aaaaggccca agaggtaata aacgttcatg     180
aaataattcc cagattcgga cttccccaag gcttacagag tgacaatggc cctgctttca     240
aggctacagt aacccaagga gtatcccagg tgttaggtat acaatatcac tcacactgcg     300
cctggaggcc acagtcctca ggaaaggtgg agaaaatgaa caaaacactc aaatgacatc     360
taaaaaagct aatccaggaa acccaccctcg catggcctgc tctgttgcct atagccttac     420
taagaatccg aaactctccc caaaaagcag gacttagtcc atacaaaatg ctgtatggac     480
ggcccttcct aaccaatgaa cttgggcttg accgagagac agccaactta gttgcagaca     540
tcatctcctt agccaaatat caacaggttc ttaaaacatt acagggagcc tgtccccaag     600
aagagggaaa ggaactattc caccctggtg acatggtatt agtcaagtcc cttccctcta     660
attccccatc cctagataca tcctgggaag gaaactaccc agccatttta tctaccctaa     720
cggcagttaa agtggctgga gcggagtctt ggatacatca cactcaagtc aaaccctgga     780
tactgccaaa ggaactcaaa aatccatgag acaatgctag ctattcctgt gaacctctag     840
aggatctgcg cctgctcttc aaatgacaac caggggggaaa gtaactaaaa tcgtaaatcc     900
cctggccctc cctatcata ttttttctctt tactgttctc ttaccccctt tcactctcac     960
tgcaccccgt ccatgccact gcacccgtc catgccccgt ccatgccagt agctcccctt    1020
agcaagagtt tctatggaga atgcagcgtc ccggaaatat tgatgcccca ttgtataggga    1080 gtttatctaa gggaaccccc accttcactg cccacaccca tatgccccac aactgctata    1140
actctgccac tcttttgcatg catgcaaata ctcattattg gacaggaaaa acgattaatc    1200
ccagttgtcc tggaggactt ggaggactca cttcactcat accagtatgt ctgatggggg    1260
tggagttcaa gatcaggcaa cagaaaaaca cataaaggaa gtaatctccc aactgacctg    1320
ggtacatagc acccctggcc cctacaaagg actagatctc tcaaaactac atgaaaccct    1380
ccatacccat actggcctgg taagcctatt taataccacc ctgactgggc tccatgaggt    1440
ctcggcccaa aaccctacta actgttggat gtgcctcccc ctgcacttta ggccatacat    1500
ttcaatccct atacctgaac aatggaacaa cttcagcaca gaaataaaca ccacttctgt    1560
tttagtaggt cctctttcca atctggaaat aacccatacc tcaaacctca cctgtgtaaa    1620
atttagcaat actatagaca cagccaactc ccaatgcatc aggtgggtaa ctcctcccac    1680
acgaatagtc tgcctaccct caggaatatt ttttgtctgt ggtacctcag cctatcattg    1740
tttgaatggc tcttcagaat ctgtgtgctt cctctcattc ttagtggccc ctatgcccat    1800
ctacactgaa caagatttat acaatcatgt catacctaag ccccgcaaca aaagagtacc    1860
cattcttcct tttgttattg gagcaggagt gctaggcgga gtagctactg gcattggcgg    1920
tatcacaacc tctactcagt tctactacaa actgtctcaa gaactaaatg gtgacatgga    1980
```

```
atgggtcgct gatacctgg tcaccttgca agatcaactt aactccctag cagcagtagt      2040
ccttcaaaat cgaagagctt tagacttgct aaccgcggaa agcggggaa ccttttatt       2100 tttagaggaa aaatgctgtt gttatgttaa tcaatccgga atcatcaccg agaaagttaa      2160
agaaattcaa ggtcgaatat aacgtagagc aaaggagctg caaaacactg gaccctgggg     2220
cctcctcagc caatgatgc cctggattct ccccttctta ggacctctag cagctataat      2280
attgttactc ctctttggac cctgtatctt taacctcctt gttaagtttg tcttttccag     2340
aatcgaagca gtaaaactac aaatcgttct tcaaatggag ccccagatgc agtccatgag     2400
taaaatctac cacggacccc tggaccggcc tgctagcca tgctctgatg ttaatgacat      2460
caaaggcacc cctcccgagg aaatctcaac tgcacaacct ctactacgcc ccaattcagc    2520
aggaagcagt tagagtggtt gttggccaac ctccccaaca gcagttgggt tttcctgttg     2580
agagggggga ctgagagaca ggaataacta gatttcctag accaactaag aatccctaag    2640
actagctggg aaggtgaccg cttccacctt taaacaccgg gcttgcaact tagctcacgc    2700
ccaaccaatc agatactaaa gagagctcac taaaatgcta attaggcaaa aacaggagat    2760
aaagaaatag ccaatcatct gttg                                            2784
```

<210> SEQ ID NO 5  
<211> LENGTH: 1799  
<212> TYPE: DNA  
<213> ORGANISM: Homo sapiens

<400> SEQUENCE: 5

```
gggattctta gtcggcctag gaaatccagc taatcctgtc tctcagtccc ccactcaac       60 aggaaaaccc aagtgctgtt ggggagggttg gctgacgacc agtctaactg cttcctgcgg    120
aattggggca tagtaggggt tgtgcagttg agatttcctc gggagggtg cgttcgatat      180 cattacaatt ggagcatggg ctagtaggcc ggtccagggg tccacggtag atcttagtca     240
tggacttcat ctggggttcc atttgaagaa cgatttgtag ctttacaact ttgattctgg     300
aagagacaaa cttaacaagg aggttaaaga tacagggtcc aaagaggagt atcaatatta     360
gagctgctag agatcctaag aagggagaa tccagggcat ccattggctg aggaggcccc     420
agggtctggt gttttgaag ctcctctgtt ctacgttgta ttcaatctcg aatttcttca      480
actttctctg tgacaattca ggattgatta acataataac aacattcttc cgctaaaata    540
acataataac aacattcttc ccctaaaaat aaacagcttc cccctctttc agaggttagc    600
aagtctaaag ctcttcaatt ttgaaggact actgatgcta ggaagttaag ttgatcttgc    660
aaggtgacca gggagtcggc aacccattcc atgtcaccat tgagttcttg agatagtttg    720
tagtagaact gagtagaggt tgtggtaccg ccaatgccaa aacctagtcc acctagcact    780
cctgctccga taacaaaagg aagaatgagt actcttttgt tgtggggctt aggtacaaca    840
taattgtata aatcttgttc agtgtaaatg gtcatggggg cactaagaat gagaggaagc    900
acatagattc tgaagagcca ttcaaacaac gataggctaa ggtaccacag acaaaaaata    960
ttcctgaggg taggcagact attcgtgtgg gaggagttac ccacctgatg cattgggagt   1020
tggttgtgtc tacagtattg ctaaatttta cacaggtgag gtttgaggta tgggttattt   1080
ccagattgga aacaagaggt cctactaaaa cggaagtggt gtttatttct gtgctgtagt   1140
tgttccattg ttcaggtaca gggattgaaa tgcatggcct gaaatacagg gggaggcaca   1200
accaacagtt agtagggttt tggaccgaga cctcatggag cccagtgagg gtggtattaa   1260
ataggcttac caggcaagta tgggtatgga gggtttcatg tagttttaag agatctagtc   1320
```

```
ctttgtaggg gctaggggtg ctatgtaccc gggtcagttg ggaggttact tcctttacat    1380 gttttctct tgcctgatct tgaactccac ccccctcaga cataccagta tgggtgaagt    1440
aagtccgaca gacagtggct ccaagtcttc caggacaact aggattaatc attttccctg    1500
tccaataatg agtatttgca tgcatgcaaa gagtggcaga gttatagcag ttgtggggca    1560
tatgggtgtg ggcagtgaag gtggagtttc ctttaggtaa actcctattt gatgggcat    1620 caatatttct gggaagccgc attcttcata gaaactcttg gtaagggag ctgctggttg    1680 tacagcagca tggaggggt gcagtgagag tgaaagggg taagagaaca gtaaagagaa    1740
aaatatgata agggagggcc atggggattt acgattttag ttactttcct cacggttgt    1799

<210> SEQ ID NO 6
<211> LENGTH: 1489
<212> TYPE: DNA
<213> ORGANISM: Homo sapiens

<400> SEQUENCE: 6
tggtgcttgc cccgggcact ctcagtcctg ctgctggatc atctggttag tggcttctga      60
ctcagaggac ctacgtcccc tggggcagtg ggccttacag tgattccctt gacacgaggt     120
gcatggacga gggggcggct tatttctatt tggacaatct ttttaaagt gtccttgtag      180 accgcactgg aagcaaaccc tattaggcat ttgatttgcc tagcttttcc cttttccagt     240
gcctccaaag tccgcttgcc tgagggccca gactaaagcg gtggccttt ttttatccca     300 tttgtcccat tctgcctgct catcctgatc tctattataa aaaactgagg ttgccaagtt     360
caatagggtt tctaagtttt gttccgggcc taaggcagac ttttgaagtt ttttcctaat     420
gtctgtagct gactgagtga taaacttatc ctttaagatt agttggcctt cagtagagtc     480
agttgacaga gagaggtatg cttcctcaat gcctccgtta gtcactccag aaaggcggta     540
ggattttctt cctttccctg tgttatagtg acatcattg aataactcac aggcttcttt     600
ctagttttcc ttagtccttc tagcacgcaa gttagcaaat gtctgcggca ccaatctcca     660
tgttctgatt ctgtgtccca gtgagggtct acactgggaa ctgcctgctg gcctgtgggg     720
aatcgttctc tttcctctgt tgtcgaccta tcattgacct gactgagata ccagagatcg     780
ccaaactctc aggctgcagt tacggcgaca cttctgtcat ttggggttag tgtctgattt     840
agcagtaaca ttatatctct ccatatcaga tcaaaggatt gtcctaaacc ttgtaaaaca     900
tcaatatagc cattagggtt atctgagaat ttacctaggt ctatttaat ttaaagtctg     960 ggagagaaaa aggcacatgc actctggctg ggccgaattc tcttcctccc actgcgtctg    1020
agagagaaaa aggtacgtgc actctggctg ggccgaattc tcctcccacc gcttggaggg    1080
ggcataatcg gggaatattg gcattctttg gttagttgtt taccccttg tctatctcct    1140 tttgaccgt ttggggttgaa gggggtcct tattatttgg ggaaggagtc tgggggatgc    1200
tggggtaggg aggtagactc tgagggcttc ctgtagggca taaatcacac ttttacata    1260 attgcgagtt gtctcttaat gaaaagaaag tttgtacgta tgacacttca caccatttgc    1320
cttcttttct acaaaagagg tctagctgta agatggtgtt ataatttatg cttccctcag    1380
gatgccaggt ttctccccct taaagagtat atcgttgcca ggcggtactg cagaagaata    1440
tgtctttttt ttcttagcat ctgagagtca aattggtccc aattctcca                1489

<210> SEQ ID NO 7
<211> LENGTH: 1216
<212> TYPE: DNA
```

<213> ORGANISM: Homo sapiens

<400> SEQUENCE: 7

```
taaagataca gggattgaaa tgtatggcct gaagtgcagg gtcatatagg tgtgggtggt      60
gaaaatgggg tttcctttag aaaaactcct atacgatggg tcatcaatat ttccaggaag     120
ccgcattctc catagaagct cttggtaatg ggagctactg gtagtacagt ggcatggagg     180
gggtgcagtg agagtgaaag agggtaaaag aacagtaaag agaaaatat gataaggggag    240
gggttcagtg agagtgaaag ggggtaagag aacagtaaag aaaaaatat gacaaggagg     300
gccatgagga tctacgattc tagttacttt cctcacggtt gtcgcttgaa gagcaggtgc    360
agatcctcta gaggttcaca ggaatagcta gcgttgtctc ctggattttc gggttccttt    420
ggcagtatac agagtttgac tcgagtgtga tgtattcaag actccactcc agccacttta    480
accgcagttg gggtagataa atgactggg tagggtcctt cccaggatgt atctaaggat     540
ggggacttag aaggaaggga cttgactaat accatgtcac cagggtgcaa taattacttt    600
ccctcttctc gggaacaggt tccctgtaat gttttaagaa cttgttgata tttggccaag    660
gaggtgatgt ctgcaactaa gctggccatc tctcggtcaa gcacaaggtc cttggttagg    720
aagggccatc catacagcat tttgtatggg ctaagtcctg cttttttgggg agagttttgg   780
attcttagta aggctgtagg caacagagca ggccatgcaa ggtgggtttc ttgggttagc    840
tttttaaat gtcgtttgag tgcttcattc attttcttga cttttcctga ggattgtggc     900
ctccacgcgc agtgtaagtg atattgtatg cctaatgcct gggatactcc ctgggttact    960
gtagccttga aaacggggcc attgtcactc tgtaagcctc ggggaagtcc gaatctggga   1020
attatttcat gaattagtgc ctttattaca tcttggtcct tttctgtcct acaaaggaag   1080
gcctctgccc aaccagtgaa aatatctacc cagactagta gatactgaaa tccctgagat   1140
ttgggcatgt gggtaaaatc tagttgccag tcttctcctg agtaatggcc tgttcttttgt 1200
tctcctgaag gagctt                                                   1216
```

<210> SEQ ID NO 8
<211> LENGTH: 976
<212> TYPE: DNA
<213> ORGANISM: Homo sapiens

<400> SEQUENCE: 8

```
agtgataatg gaatacttga aagtaatccc ctcactccag gaactagtgc tgagctggcc     60
aaactaatag ccctcactcg ggcactagaa ttaggagaag agaaagggt aaatatatat     120
acagactata agtatgctta cctagtcctt catgcccatg cagcaatatg gagagaaagg    180
gaattcctaa cttccaaagg aacacctatc aaacatcagg aagccattag gatattatta    240
ttggtggtac agaaacctaa agaggtggca gtcctacact gctggggtca tcagaaaaaa    300
aaggaaaggg aaatagaagg gaactaccaa gcagatattg aagccaaaag agccgcaagg    360
caggaccctc cattagaaat gcttatagaa ggaccctag tgtgggtaa cccctccag       420
gaaagcaatc cccagtactc agcaggagaa ataaaatgga gaacctcacg aggacatact    480
ttcctcccct caggatggct agccaccaaa gaaggaaaaa tgcttttgcc tgcagctaac    540
caatggaaat tacttaaaac ccttcaccaa acctttcact taggattgat agcacccatc    600
agatggccaa attattattt actggatcag gccttttcaa aactatcaag caggtagtca    660
gggcctgtaa agtgtgccaa agaaataatc tcctgcactg caagccatac atttcaatcc    720
ctgtatcttt aacctccttg ttaagtttgt ctcttccaga atcaaagctg taaaactaca    780
```

```
aatggttctt caaatggagt ctcagatgca gtccatgact aagatatacc gcagccccct    840 ggaggggggcc tgctagccca tgctccaatg ttaatgacat cgaaggcacc cctcccgggg    900
aaatctcaac tgcacaaccc ctactatgtc ccaattcagc aggaagcagt taaagcggtc    960
atcggccaac ctcccc                                                    976
```

<210> SEQ ID NO 9
<211> LENGTH: 942
<212> TYPE: DNA
<213> ORGANISM: Homo sapiens

<400> SEQUENCE: 9

```
agaggagaac agcagcataa gcggctggca gaggtaggga aagaccagca agaagaaaag     60
agagaaagag aaagagaaag tcagagaaag agacagagag aggaagagac aaagagacag    120
aaagtcaaag aggtagtagt cagaaacaga gacaaaaaaa aggagtcaga agagggaca    180 gacacagaaa gtcaaaaaaa aagttaagaa gaaaggaaaa gacaaagaag aagtcgaaga    240
ggagaaagag agagatagaa gtagtaaaga aaaaaacagc atatcccatt ccttaaagc     300 cagggtaaat ttctatctac ccagccaagg catattctac ttatgtggat cttcaaccca    360
tatctgcctc tcagacagtt tgcaagaaat aatgaaatct atccttactt tacaatccca    420
aatagactct ttggcagcag tgactctcca aaactgcaga ggcctagacc tcctcactgc    480
tgaaaaagga ggacactaca ccttcttagg ggaagaatgt tgttttaca ctaaccagtc     540 ggggatagta tgagatgctg cccggagttt acaggaaaag gcttctgaaa tcagacaacg    600
cctttcaaat tcttatacca acttctggag ttaggcaaca tggcttctcc cctttctagg    660
tcctgtggca gccatcttgc tgttactcgc ctttgggccc tgtattttta accttcttgt    720
caaatttgtt cctctagaa tcgaggccat caagctacag atggtcttac aaatggaacc     780
ccaaaagagt tcaactaaca acttctaccg aggaccctg gatcaaccca ctggcacttc     840
ccctggccta gagagttccc ctctgaagga caccgcaact gcagggccct tctttgcccc    900
atccagcagg agtagctaga gtggtcatcg gccaaattgc ca                       942
```

<210> SEQ ID NO 10
<211> LENGTH: 1375
<212> TYPE: DNA
<213> ORGANISM: Homo sapiens

<400> SEQUENCE: 10

```
ccccaatatt ctctttctga tggggaaaaa tggccacctg agggaagcac aaattacaat     60
actatcctgc agcttgatct tttctgtaag agggaaggca aatggagtga ataccttat    120 gtccaagctt tcttttcatt gagggagaat acacaactat gcaaagcttg caatttacat    180
cccacaggag gacccctcag cttaccccca tatcctagcc tccctatagc ttccccttcct    240 attgatgata ctcctcctct aatctcccct gcccagaagg aaataagcaa agaaatctcc    300
aaaggtccac aaaaccccc gggctatcgg ttatgtcccc ttcaagctgt agggggaggg    360
gaatttggcc caacccgggt gcatgtcccc ttctccctct ctgatttaaa gcagatcagg    420
cagacctggg gaagttttca gatgatcctg ataggtacat agatgtccta cagggtctag    480
ggcaaacctt tgacctcact tggagagacg tcatgctact gttagatcaa accctggcct    540
ttaatgaaaa gaatgcggct ttagctgcag cctgagagtt tggagatacc tggtatccta    600
gtcaagtaaa tgaaagaatg acagccgaag aaagggacaa cttccctact ggtcagcaag    660
```

```
ccatccccag tatggatccc cactgggact ttgactcaga tcatggggac tggagtcgta    720
aacatctgtt gatctgtgtt ctggaaggac taaggagaat tgggaaaaag cccatgaatt    780
attcaatgat atccaccata acccagggaa aggaagaaaa tccttctgcc ttcctcgagc    840
ggctacaaga ggccttaaga aaatatactc ccctgtcacc cgaatcactc gagggtcaat    900
tgattctaaa agataagttt attacccaat cagccacaga tatcaggaga aagctccaaa    960
agcaagccct gagccctgaa caaaatctag agacattatt aaacctggca accttggtgt   1020
tctataatag ggaccaagag gaacaggccc aaaaggaaaa gcgagatcag agaaaggccg   1080
cagccttagt catggccctc agacaaacaa accttggtgg ttcagagagg tcagaaaatg   1140
gagcaggcca atcacctggt acggcttgtt atcagtgcgg tttactagga cactttaaaa   1200
aagattgtcc aataagaaac aagctgcccc ctcatccgtg tccactatgc cgaggcaatc   1260
actggaaggt gcactgcccc agaggatgaa ggttccctgg gttagaagcc cccaaccaga   1320
tgatccaaca acaggactga gggtgcccgg ggcaagcacc agctcatgtc atcac         1375
```

<210> SEQ ID NO 11
<211> LENGTH: 944
<212> TYPE: DNA
<213> ORGANISM: Homo sapiens

<400> SEQUENCE: 11

```
acctaggagg aactgtcttc aggacaggac tatagatgct tcctcccagg cgattaaggg     60
aaaaagacac aatgggtatt cagtaagtga taaggaaact cttgtagaag cagagttagg    120
aaaattgcct aataattggt ctgctcaaat gtgcgagctg tttgcactca gccaaacctt    180
aaaagtatta cagaatcagg aagaagccat ctataccaat tctaagttaa tatggactga    240
acgagaactt attaatagca aagaataatt gaaatcccaa acttacaagg ttttcaacaa    300
aagcacagtt tgctaaaagt taactgtgta acatgtatta tcctactacc acaaactctc    360
aaatgatttc tcagacagtt tgcaagaaac aatgaaacct atccttactc tacaatccca    420
aatagactct ttggcagcag tgactctcca aaaccaccaa ggcctagacc tcctcactgc    480
tgagaaagga ggactctgca ccttcttagg ggaagattgt tgttttttaca ctaaccagtc    540 agggatagtg tgagatgcca cccagcgttt acaggaaaag gcttctgaaa tcagacacaa    600
tgcttttcaa accttatagc aacctctgga gttcggcgac tggctttttcc cctttctagg    660 tcctgtgaca gccatcttgc tattactcgc cttcgggccc tgtattttta acctcctcgt    720
caaatttgtt tcctctagga tcgaggccat caagctacag atggtcttac aaatggaacc    780
ccaaatgagc tcgactaaca acttctactg aggaccoctg accgaccoca ctggccttt    840 aactggctta aagagtttcc ctctggagga cactacaact gcagggcccc ttctttgccc    900
catccacagg aagttagcta gagcagtcat cacccaattc ccaa                     944
```

<210> SEQ ID NO 12
<211> LENGTH: 963
<212> TYPE: DNA
<213> ORGANISM: Homo sapiens

<400> SEQUENCE: 12

```
tacaggaacc ccataatacg tccttggcaa attctattca gctccaactg ctaggagtgg     60
cccatttgtc ctgaaccctc aaatcatggg aatgagaaat gaatttagac tgaccacagc    120
ccttatgagt tttcagctac aggggtgtat agaaccctga taaggagttt ctttgtgtg    180 tggaagatcc ttctatattt gcctccccac caactggaca ggaacttgta ctttagccta    240
```

| | |
|---|---|
| catagtacct cctgtgactt atccttttca gaagaggcag tagctgtgcc cattcatgct | 300 |
| aagcttcagc cgagagcaat ctcactactt cctctattgg ctggtttagg atttactacc | 360 |
| acctaggaag tggactcaca gcctagatga atctctctc caacttactc aaatccagga | 420 |
| ccaaatagac tcattagcag ctgtggttct ccgaaccagt gagcactaga tctccaatct | 480 |
| cctcactgcc gaaaggggag gaacatgcct ttttctgaac aaggaatgtt gtttttatgt | 540 |
| caataaatca ggcatagtga gagatggaat taaatgactt caggatagag ctagcagact | 600 |
| acatggtggg acaaccgaaa ctacctcagg gttctcacag cctgttctcc actggcttct | 660 |
| tccatttta ggtcccttcc ttatgattat tctaggagta acctttggcc catgtctttt | 720 |
| cagttcctc atcctttcgt ttcttcctga atagaatcaa tgaaactaga atgttactg | 780 |
| cagatggaac ctcagatgac ttcaaccagc acctattatc aaggacccct aaaccagcct | 840 |
| gccggcccat acccggacgt tgacacccaa accacctctc acgaggaaac ctcagctaca | 900 |
| gaacccctc tatgccccta ttcagcagga agcaattaga gtggtcatcc tcccacaccc | 960 |
| caa | 963 |

<210> SEQ ID NO 13
<211> LENGTH: 1362
<212> TYPE: DNA
<213> ORGANISM: Homo sapiens

<400> SEQUENCE: 13

| | |
|---|---|
| ccacaatatc ctcttccagg aggagaacga tggccacctg agggaagtat acactataat | 60 |
| accatcctgc aactagatct gttttgtaaa caagaaggca gtggattta ggtaccatat | 120 |
| gttcagacct ttttctcatt aagggatgat aacccacgat tgtgtaagac atgtaacctg | 180 |
| caccccacag ggagtcctca aattctaccc ccatacccag tcctcccac ggctcctcct | 240 |
| actaatgcca aaccctctct ggcttctaca gcccaaaagg gaacaaataa agagccttc | 300 |
| agagagccaa gagaccccac tggcccctgg ctatgtcctc ttcaggctgt aggaggggaa | 360 |
| tttggcccaa cccgagtaca tgttcccttt tctctctctg atctaaagca aattaaggca | 420 |
| gacttggatg aaagttctca gatgacccca atagatacgt agatggcctg ctgggtctgg | 480 |
| gacaatctt tgacctttcc tggagagaga tcatgttatt gcttgatcag acctaacctc | 540 |
| taatgagaag aatgctgctt taacaggagc ccgagagttt ggggatacct ggtacctcag | 600 |
| ttaagtaagt gatagaatga catcagaaga gagcagtttc ctactggcca gcaagcagtc | 660 |
| cccagtatgg atccccactg ggaccctgac tcggatcatg gggactggag tcacaaacat | 720 |
| ttactgacct gtatcctaga agggttaagg agaactagga aaagcccat gaactattca | 780 |
| atgatgtcta ctataaccca agggaaggaa gaaaacccta ttgccttcct caaaaggctg | 840 |
| agggaggctt tgagaaaata tactcccctg tcaccagatt ccctcgaagg ccagttaatt | 900 |
| ttaaaggaca aatttattac tcagtcagct gcagacatta ggaaaaagct ccaaaagtta | 960 |
| gccttgggcc gagcaaaatt tggaggcatc attaaacctg caacctcag tgttctatca | 1020 |
| tagggaccaa gaggaacagg ccgaaaagga aagcaggat aagagaaagg ctgcagattt | 1080 |
| agtcatgccc tcagacaaac cttggcggtt caaagaggaa aaaaatgga gcaggccaat | 1140 |
| cacccagcag ggcttattat cagtgcagtt tacaaggaca ctttaaacaa gattgtccaa | 1200 |
| agagaaataa gccgcctct cacccatgtc cactatgcca aggtgatcac tggaaggcac | 1260 |
| actgtcccag aggacaaagg ttctctgggc cagaagtccc caaccagatg atccagcaac | 1320 | aggatggagg gtgcccgggg caagcaccag ctcgtgttgt ca             1362

<210> SEQ ID NO 14
<211> LENGTH: 945
<212> TYPE: DNA
<213> ORGANISM: Homo sapiens

<400> SEQUENCE: 14
ttgcagatca atctcagact gctgtgctag caatgagtga ggcttcgtgg gcatgggacc    60
ctctgagcca ggcatgggat ataatgtcct tgtgtgccat ttgctaagac tgttggaata   120
gcacagtatt agggtgggag tggcccgatt ttccaggtgc tgtctgtcac cgcttccctt   180
ggctaggaaa gagaattccc tgacccctttg ttcttcccag gtaaggcagt gcctcaccct   240
gcttcagctc acactcaggt gactgcaccc actgtcctgc ccccactgtc ggacaagccc   300
cagtgagatg aacctggtac ctcagttgga aatgcagaaa tcacctgtct tctgcgtcac   360
tcacactggg agctgtagac tggagctgtt cctatttggc catcttggaa ccatctccca   420
aatagactct ttggcagcag tgactctcca aaaccaccaa ggcctagacc tcctcattgc   480
tgagaaagga ggactctgca ccttcttagg ggaggagtgt tgttttttata ctgaccagtc   540
agggatggta cgagatgcca cccgatgttt acaggaaaag gcttctgaaa tcacacaaca   600
cctttcaaac tcttatacca acctctggag ttgggcaaca tggcttctcc cctttctcgg   660
tcccattgca gccatcttgc tattactcgc cttcaggctg tgtattttta acctccttgt   720
caaatttgtt cctctagaa ttgaggccgt caagctacag atggtcttac aaatgggacc   780
ccaaatgagc tcaactaaca acttctgcca aggacccctg gaccaacctg ctggcccttt   840
cactggcctt aagagttccc ctctggaggg cactacaact gcagggcccc ttctttgccc   900
ctatccagca ggaagtagct agagcagtca tcacccaatt cccaa                  945

<210> SEQ ID NO 15
<211> LENGTH: 939
<212> TYPE: DNA
<213> ORGANISM: Homo sapiens

<400> SEQUENCE: 15
agagctacct tggcaagtac tctaggagta tgggaaaatg aaaacaacaa actcacacac    60
cattttaaca tacacaatca ggtctgccca cccagcaagg tatattcttt gtatgtggaa   120
catcgaccta tatctgcctc cccactaact agacagccac ctgaatctta gtctttctaa   180
gtcccaacag taacattgcc ccaggaaatc agaccatatc agtatccctc aaagctcaag   240
tctgtcagtg cagagccata caactaatac ccctacttat agggtaagga atggctactg   300
ctacaggaac cagaatagct agtttgttta cttcattatc ctactaccac acactctcaa   360
atgatttctc agacagtttg caagaaataa cgaaatctat ccttactcta caatcccaaa   420
tagactcctt ggcagcagtg accctccaaa acggctgagg cctagacctc ctcactgcca   480
agaaaggagg actctgcatt ttcttagggg aagagtgttt ttacactaac cagtcaggga   540
cagtatgaga tgccactcgg agtttacagg aaaaggcttc tgaagtcaga caatgccttt   600
caaactctat accaaactct ggagttgggc aacatggctt ctcccctttc taggtcccgt   660
gacagccatc ttgctattat ttgcctttga gccctgtatt tttaatctcc ttttcaaatt   720
tgtttcctct ggatcgaggc catcgagcta cagatggtct tcacaaatgg aaccccaaat   780
gagctcaact aacaacttct actgaggacc cctggactaa cctgctgacc ctttcactgg   840
cctgaagaat tccctctgg aggacactac aactgcaggg ctccttcttt gccctatcc   900

```
agcaggaagt agctagagct gtcattgcct aattcctaa                        939
```

<210> SEQ ID NO 16
<211> LENGTH: 979
<212> TYPE: DNA
<213> ORGANISM: Homo sapiens

<400> SEQUENCE: 16

```
agtgataatg gaatacttga aagtaatccc ctcactcccc aggaactagt gctcagctgg   60
cagaactaat agccctcact cgggtactag aatcaggaga aggaaaaagg gtaaatatat  120
atacagactc taagtgtgct tacctagtcc tccatgccca tgcagcaata tggagagaaa  180
gggaattcct aacttccgag ggaacaccta tcaaacatca ggaagccatt aggaaattat  240
tattggctgt acagaaacct aaagaggtgg cagttttaca ctgccggggt catcagaaag  300
gaaaggaaag ggaaatacaa gggagccacc aagttgatat tgaagtcaaa agagccacaa  360
ggctggaccc tccattagaa atgcttatag gaggacccct agtatggggt aatcccctcc  420
gggaagccaa gccccagtac tcagcaggag aaatagaata gggaacttca tgaggacata  480
cttccctccc ctccagatgg ctagccacca ataaggaaa aatactttg cctgcagcta   540
accaatagaa attacttaaa acccttcatc aaaccttcca cttaggcatt gatagcaccc  600
atgagatggc caaattatta tttactggac caggcctttt caaaactatc aagcagatag  660
tcagggcctg taaagtctgc caaagaaata atcccctgca ctgcaggcca tacatttcaa  720
tccctgtatc tttaacctcc ttcttaaatt tgtctcttcc agaatcaaag ctgtaaaatt  780
acaaatagtt cttcaaatgg agccacagat gcagtccatg actaagatcc accacagacc  840
cctggaccag cctgctagcc catgctccaa tgttaatgac atcgaaggca ccccctcctg  900
aggaaatctc aactgcacaa cccctactac gccccaattc agcagaaagc agttagagtg  960
gtcatcagcc aacctcccc                                              979
```

<210> SEQ ID NO 17
<211> LENGTH: 1774
<212> TYPE: DNA
<213> ORGANISM: Homo sapiens

<400> SEQUENCE: 17

```
catgctggta aaggaccgct agaatccagc agccaggacc actttctttg tggtcaagaa   60
aggtgggaaa acaggtgcag gactgctaca ctggtaagca taactaatcc gataagcaga  120
ggtccatggg tggttacgca ccctggaaag gaataagcat taggactata gaggacactc  180
taggactaat gctcatcgga aaatgactag gggtactggc atccctatgt tctttttca   240
gatgggaaat gttcccccca aggcagaaat gcccctaaga tgtattctgg agaaatggga  300
ccaatctgac catcagacac taagaaagaa atgacttata ttcttctgca gtaccacctg  360
gccacaatat cttcttcaag gggcagaaac ctggcctcct gagggaagta taaattataa  420
caccatctta cagctagacc tcttttgtag aaaagaaggc aaatggagtg aagtgccata  480
tgtacaaact ttcttttcat taagagataa ctcccaatta tgtaaaaagt gtgatttatg  540
ccctacagga agccctcaga gtctacctcc cgacccagc aagacccaa ctccttctcc    600
aactaataag gaccccccctt caacccaaat ggtccaaaag gagatagaca aagggtaaa   660
caatgaacca aagagtgcca atattacacg attatactcg ctccaagcag tgggaggaga  720
atttggccca gccagcgtgc atgtaccttt ttctctctca gatttaaagc aaattaaaat  780
```

-continued

```
agacctaggt aaattctcag ataaccctga tggctatatt gatgttttac aagggttagg      840
acaatccttt gatctgacat ggagagatat aatgttactg ctaaatcaga cactaacccc      900
aaatgaaaaa agtgctgcca taacagcagc ctgagagttt ggcgaactct ggtatctcag      960
tcaggtcaat gataggatga caacagatga aagagaatga ttccccacag gccagcaggc     1020
agttcccagt gtagaccctc attaggacac agaatcagaa cttggagatt ggtgccacag     1080
acatttgcta acttgcgtgc tagaaggact aaggaaaact aggaagaagc ccatgaatta     1140
ttcaatgatg tcccctataa cacagggaaa ggaagaaaat cctactgcct ttctggagag     1200
actaagggaa ggattgagga agcataccto cctgtcacct gactctatta aaggccaact     1260
aatcttaaag gataagttta tcactcagtc agctgcagag attaagaaaa aacttcaaaa     1320
gtatgcctta ggcccagagc aaaacttaga accctactg aacttggcaa cctcagtttt      1380
ttataataga gatcaggaag agcagggaa tgggacaaat gggataaaaa aaaaaaaaaa      1440
aggtgactgc tttagtcgtg gccctcaggc aaatggactt tggaggctcc agaaaaggga     1500
aaagctgagc aaattgaatg cctaacaggg cttgcttcta gtgtggtcta caaggacact     1560
ttaaaaaaga ttgtccaagt agaaacaagc tgccccctttg tccatgcccc ttatgtcaag    1620
ggaatcactg gaaggcccac tgccccagga gatgaaggtc ctctgagtca gaagccacta    1680
accagatatt ccagcagcag gactgaggat gcccagggca agcgccagcc catgccatca    1740
ccctcacaga gccttgggta tgcttgacca ttga                                 1774
```

<210> SEQ ID NO 18
<211> LENGTH: 938
<212> TYPE: DNA
<213> ORGANISM: Homo sapiens

<400> SEQUENCE: 18

```
tgtaggaaga actcccttca ggacaggaca atagatggtt cctcccaggt gattaaggaa       60
aaaagacaca gtattcagta agtgataagg aaactcttgt agaagcagag ttagaaaaat      120
tgcctaataa ttggtctgct caaatgtgtg agttgtttgc actcagccaa atcttaaagt      180
acttacagaa tcaggaagca gccatctata ccaattctaa gttaatatgg actaaacgag      240
gttttattag tagcaaagaa aaattaaaat cccaaactta caaggttttc aactaaagtt      300
tgccaaaagt taacagtgta acatgtatta tcctactatc acacactctc aaaggatttc      360
tcagacagtt tgcaagaaat aacgtaatct atccttactc tacagtccca aatagactct      420
ttggtagcag tgactctcca aaactgccga ggtctagacc tcctcaatgc tgagaaagga      480
gaactctgca ccttcttagg ggaagagtgc tgttttttaca ctaaccagtc agggatagta     540
tgagatactg cctgacgttt acaggaaaag gcttctgaaa tcgacaacg cctttcaagc      600 tcttatacca acctctggag ttgggcaaca tggcttctcc ccttgctagg tcctgtggca     660
gccatcttgc tattacttgc cttcgggccc tgtatttttta acctccttgt caaatttgtt    720
tcctctagga tcaaggccat caagctacag atggtcttac aaatggaacc ccaaatgagc     780
tcaactaaca acttctactg aggacacctg gactgaccca ctggcccttt cactggccta     840
aagagttccc ttctggagga cactacaact gcagggcccc gtcttcaccc ctatccagca     900
ggaagtagct agatcagtca ttgcccaatt cccaacag                              938
```

<210> SEQ ID NO 19
<211> LENGTH: 1308
<212> TYPE: DNA
<213> ORGANISM: Homo sapiens

<400> SEQUENCE: 19

```
gatgcttgcc ccaggcaccc tcagtcctgt tgttggatca tctggtcggg ggcttctggc      60
ccaaagaacc tttgtcctct gaggcagtgc accttccagt gattgcctca gcattgtgga     120
catgggcaag ggggcagctt gtttctcact ggacaatctt ttttaaggtg tccttccaaa     180
ccacactggt aacaagccct accaggtgat tggcctgctc tatttctgt cctctctgaa      240
ccaccaaggt ttgtctgtct gagggtcatg actaaggctg tggcctttct ctgatcttgc     300
tttttccttt tggcctgttc ctcttggtac ctattataga acactgaggt tgccaggttt     360
aacaatggct ccagattttg ttcagggcac agggctcatt ttggagcttt ctcctgatat     420
ctgcagctga ttgggtaata aacttatctt ttaggatcaa ttgactctca agagagttgg     480
gtgacagggg agtatatttc cttgaggcct cccatagccg ctctaggaag cagaaggat      540
tttcttcctt tccctgagtt ataaaagaca tcattgaaca actcatggac ttttccccaa     600
ttctccgtag tccttctaga acacaggtca gcagatgttt acgactccag tccccatgat     660
ctgagtctag acaccagtgg ggatccatac tggggatggc ctgctgactg gtagggaatt     720
tgtcccttc ttggctgtc attctatcat ttacttgact aagataccaa gtatctccaa       780
attctcaggc tgcagctaaa gctgcattct tttcattaaa ggccagggtt tgatctaata    840
gcatgacatc tctccaagtg aggtcaaagg tttgccctag atccatagga catcagagaa     900
ggagaagggg acatacacct gagttagcca aattcccctc cctctacagc ttgaagggga     960
cataagcaat agcctgggga ttttgtggt cctttgagga tttctttgct tgtttccttc     1020
tgggtgggg agattagagg aggcttatca gtaataggaa ggggagctat agggaggcta    1080
ggatatgggg gtaagctgag aggtcatctt gtgggatgta aattgcaagc tttgcatagt     1140
tgtggatttt ccttacaatg aaaataaagc ttggacataa ggtatttcac tccatttgcc     1200
ttccctctta cagaaaaggt caagctgcag gatagtactg taatttatac ttccttcagg     1260
tggccatttc ttcccatcag agagagaata ctggggctgg gccatagt                 1308
```

<210> SEQ ID NO 20
<211> LENGTH: 711
<212> TYPE: DNA
<213> ORGANISM: Homo sapiens

<400> SEQUENCE: 20

```
actgagagac aggactagct ggatttccta ggccgactaa gaatccctaa gcctagctgg      60
gaaggtgacc acgtccacct ttaaacacgg ggcttgcaac ttagctcaca cctgaccaat     120
cagagagctc actaaaatgc taattaggca aagacaggag gtaaagaaat agccaatcat     180
ctattgcctg agagcacagc aggagggaca acaatcggga tataaaccca ggcattcgag     240
ctggcaacag cagccccct ttgggtccct tcccttgta tgggagctgt tttcatgcta      300
tttcactcta ttaaatcttg caactgcact cttctggtcc atgtttctta cggctcgagc     360
tgagcttttg ctcaccgtcc accactgctg tttgccacca ccgcagacct gccgctgact     420
cccatccctc tggatcctgc agggtgtccg ctgtgctcct gatccagcga ggcgcccatt     480
gccgctccca attgggctaa aggcttgcca ttgttcctgc acggctaagt gcctgggttt     540
gttctaattg agctgaacac tagtcactgg gttccatggt tctcttctgt gacccacggc     600
ttctaataga actataacac ttaccacatg gcccaagatt ccattccttg gaatccgtga     660
ggccaagaac tccaggtcag agaatacgag gcttgccacc atcttggaag c              711
```

<210> SEQ ID NO 21
<211> LENGTH: 711
<212> TYPE: DNA
<213> ORGANISM: Homo sapiens

<400> SEQUENCE: 21

```
actgagagac aggactagct ggatttccta ggctgactaa gaatccctaa gcctagctgg      60
gaaggtgacc acatccacct ttaaacacgg ggcttgcaac ttagctcaca cctgaccaat     120
cagagagctc actaaaatgc taattaggca aagacaggag gtaaagaaat agccaatcat     180
ctattgcctg agagcacagc aggagggaca atgatcggga tataaaccca agtcttcgag     240
ccggcaacgg caaccccctt tgggtcccct ccctttgtat gggagctctg ttttcatgct     300
atttcactct attaaatctt gcaactgcac tcttctggtc catgtttctt acggcttgag     360
ctgagctttc gctcgccatc caccactgct gtttgccgcc accgcagacc cgccgctgac     420
tcccatccct ctggatcatg cagggtgtcc gctgtgctcc tgatccagcg aggcacccat     480
tgccgctccc aatcgggcta aaggcttgcc attgttcctg catggctaag tgcctgggtt     540
catcctaatt gagctgaaca ctagtcactg ggttccatgg ttctcttctg tgacccacag     600
cttctaatag agctataaca ctcaccgcat ggcccaaggt tccattcctt gaatccataa     660
ggccaagaac cccaggtcag agaacacgag gcttgccacc atcttgggag c              711
```

<210> SEQ ID NO 22
<211> LENGTH: 2055
<212> TYPE: DNA
<213> ORGANISM: Homo sapiens
<220> FEATURE:
<221> NAME/KEY: CDS
<222> LOCATION: (1)..(2055)
<223> OTHER INFORMATION:

<400> SEQUENCE: 22

```
ccc aag aca gcc aac tta gtt gca gac atc acc tcc tta gcc aaa tat       48
Pro Lys Thr Ala Asn Leu Val Ala Asp Ile Thr Ser Leu Ala Lys Tyr
1               5                   10                  15 caa caa gtt ctt aaa aca tta caa gga acc tat ccc tga gaa gag gga       96
Gln Gln Val Leu Lys Thr Leu Gln Gly Thr Tyr Pro     Glu Glu Gly
            20                  25                  30 aaa gaa cta ttc cac cct tgt gac atg gta tta gtc aag tcc ctt ccc      144
Lys Glu Leu Phe His Pro Cys Asp Met Val Leu Val Lys Ser Leu Pro
        35                  40                  45 tct aat tcc cca tcc cta gat aca tcc tgg gaa gga ccc tac cca gtc      192
Ser Asn Ser Pro Ser Leu Asp Thr Ser Trp Glu Gly Pro Tyr Pro Val
    50                  55                  60 att tta tct acc cca act gcg gtt aaa gtg gct gga gtg gag tct tgg      240
Ile Leu Ser Thr Pro Thr Ala Val Lys Val Ala Gly Val Glu Ser Trp
65                  70                  75 ata cat cac act tga gtc aaa tcc tgg ata ctg cca aag gaa cct gaa      288
Ile His His Thr     Val Lys Ser Trp Ile Leu Pro Lys Glu Pro Glu
80                      85                  90 aat cca gga gac aac gct agc tat tcc tgt gaa cct cta gag gat ttg      336
Asn Pro Gly Asp Asn Ala Ser Tyr Ser Cys Glu Pro Leu Glu Asp Leu
95                  100                 105                 110 cgc ctg ctc ttc aaa caa caa cca gga gga aag taa cta aaa tca taa      384
Arg Leu Leu Phe Lys Gln Gln Pro Gly Gly Lys     Leu Lys Ser
                115                 120 atc ccc atg gcc ctc cct tat cat att ttt ctc ttt act gtt ctt tta      432
Ile Pro Met Ala Leu Pro Tyr His Ile Phe Leu Phe Thr Val Leu Leu
125                 130                 135                 140
```

```
ccc tct ttc act ctc act gca ccc cct cca tgc cgc tgt atg acc agt      480
Pro Ser Phe Thr Leu Thr Ala Pro Pro Pro Cys Arg Cys Met Thr Ser
                145                 150                 155 agc tcc cct tac caa gag ttt cta tgg aga atg cag cgt ccc gga aat      528
Ser Ser Pro Tyr Gln Glu Phe Leu Trp Arg Met Gln Arg Pro Gly Asn
            160                 165                 170 att gat gcc cca tcg tat agg agt ctt tct aag gga acc ccc acc ttc      576
Ile Asp Ala Pro Ser Tyr Arg Ser Leu Ser Lys Gly Thr Pro Thr Phe
        175                 180                 185 act gcc cac acc cat atg ccc cgc aac tgc tat cac tct gcc act ctt      624
Thr Ala His Thr His Met Pro Arg Asn Cys Tyr His Ser Ala Thr Leu
    190                 195                 200 tgc atg cat gca aat act cat tat tgg aca gga aaa atg att aat cct      672
Cys Met His Ala Asn Thr His Tyr Trp Thr Gly Lys Met Ile Asn Pro
205                 210                 215                 220 agt tgt cct gga gga ctt gga gtc act gtc tgt tgg act tac ttc acc      720
Ser Cys Pro Gly Gly Leu Gly Val Thr Val Cys Trp Thr Tyr Phe Thr
                225                 230                 235 caa act ggt atg tct gat ggg ggt gga gtt caa gat cag gca aga gaa      768
Gln Thr Gly Met Ser Asp Gly Gly Gly Val Gln Asp Gln Ala Arg Glu
            240                 245                 250 aaa cat gta aaa gaa gta atc tcc caa ctc acc cgg gta cat ggc acc      816
Lys His Val Lys Glu Val Ile Ser Gln Leu Thr Arg Val His Gly Thr
        255                 260                 265 tct agc ccc tac aaa gga cta gat ctc tca aaa cta cat gaa acc ctc      864
Ser Ser Pro Tyr Lys Gly Leu Asp Leu Ser Lys Leu His Glu Thr Leu
    270                 275                 280 cgt acc cat act cgc ctg gta agc cta ttt aat acc ctc act ggg          912
Arg Thr His Thr Arg Leu Val Ser Leu Phe Asn Thr Thr Leu Thr Gly
285                 290                 295                 300 ctc cat gag gtc tcg gcc caa aac cct act aac tgt tgg ata tgc ctc      960
Leu His Glu Val Ser Ala Gln Asn Pro Thr Asn Cys Trp Ile Cys Leu
                305                 310                 315 ccc ctg aac ttc agg cca tat gtt tca atc cct gta cct gaa caa tgg     1008
Pro Leu Asn Phe Arg Pro Tyr Val Ser Ile Pro Val Pro Glu Gln Trp
            320                 325                 330 aac aac ttc agc aca gaa ata aac acc act tcc gtt tta gta gga cct     1056
Asn Asn Phe Ser Thr Glu Ile Asn Thr Thr Ser Val Leu Val Gly Pro
        335                 340                 345 ctt gtt tcc aat ctg gaa ata acc cat acc tca aac ctc acc tgt gta     1104
Leu Val Ser Asn Leu Glu Ile Thr His Thr Ser Asn Leu Thr Cys Val
    350                 355                 360 aaa ttt agc aat act aca tac aca acc aac tcc caa tgc atc agg tgg     1152
Lys Phe Ser Asn Thr Thr Tyr Thr Thr Asn Ser Gln Cys Ile Arg Trp
365                 370                 375                 380 gta act cct ccc aca caa ata gtc tgc cta ccc tca gga ata ttt ttt     1200
Val Thr Pro Pro Thr Gln Ile Val Cys Leu Pro Ser Gly Ile Phe Phe
                385                 390                 395 gtc tgt ggt acc tca gcc tat cgt tgt ttg aat ggc tct tca gaa tct     1248
Val Cys Gly Thr Ser Ala Tyr Arg Cys Leu Asn Gly Ser Ser Glu Ser
            400                 405                 410 atg tgc ttc ctc tca ttc tta gtg ccc cct atg acc atc tac act gaa     1296
Met Cys Phe Leu Ser Phe Leu Val Pro Pro Met Thr Ile Tyr Thr Glu
        415                 420                 425 caa gat tta tac agt tat gtc ata tct aag ccc cgc aac aaa aga gta     1344
Gln Asp Leu Tyr Ser Tyr Val Ile Ser Lys Pro Arg Asn Lys Arg Val
    430                 435                 440 ccc att ctt cct ttt gtt ata gga gca gga gtg cta ggt gca cta ggt     1392
Pro Ile Leu Pro Phe Val Ile Gly Ala Gly Val Leu Gly Ala Leu Gly
```

-continued

```
                    445                 450                 455                 460
act ggc att ggc ggt atc aca acc tct act cag ttc tac tac aaa cta      1440
Thr Gly Ile Gly Gly Ile Thr Thr Ser Thr Gln Phe Tyr Tyr Lys Leu
                465                 470                 475 tct caa gaa cta aat ggg gac atg gaa cgg gtc gcc gac tcc ctg gtc      1488
Ser Gln Glu Leu Asn Gly Asp Met Glu Arg Val Ala Asp Ser Leu Val
            480                 485                 490 acc ttg caa gat caa ctt aac tcc cta gca gca gta gtc ctt caa aat      1536
Thr Leu Gln Asp Gln Leu Asn Ser Leu Ala Ala Val Val Leu Gln Asn
        495                 500                 505 cga aga gct tta gac ttg cta acc gct gaa aga ggg gga acc tgt tta      1584
Arg Arg Ala Leu Asp Leu Leu Thr Ala Glu Arg Gly Gly Thr Cys Leu
    510                 515                 520 ttt tta ggg gaa gaa tgc tgt tat tat gtt aat caa tcc gga atc gtc      1632
Phe Leu Gly Glu Glu Cys Cys Tyr Tyr Val Asn Gln Ser Gly Ile Val
525                 530                 535                 540 act gag aaa gtt aaa gaa att cga gat cga ata caa cgt aga gca gag      1680
Thr Glu Lys Val Lys Glu Ile Arg Asp Arg Ile Gln Arg Arg Ala Glu
                545                 550                 555 gag ctt cga aac act gga ccc tgg ggc ctc ctc agc caa tgg atg ccc      1728
Glu Leu Arg Asn Thr Gly Pro Trp Gly Leu Leu Ser Gln Trp Met Pro
            560                 565                 570 tgg att ctc ccc ttc tta gga cct cta gca gct ata ata ttg cta ctc      1776
Trp Ile Leu Pro Phe Leu Gly Pro Leu Ala Ala Ile Ile Leu Leu Leu
        575                 580                 585 ctc ttt gga ccc tgt atc ttt aac ctc ctt gtt aac ttt gtc tct tcc      1824
Leu Phe Gly Pro Cys Ile Phe Asn Leu Leu Val Asn Phe Val Ser Ser
    590                 595                 600 aga atc gaa gct gta aaa cta caa atg gag ccc aag atg cag tcc aag      1872
Arg Ile Glu Ala Val Lys Leu Gln Met Glu Pro Lys Met Gln Ser Lys
605                 610                 615                 620 act aag atc tac cgc aga ccc ctg gac cgg cct gct agc cca cga tct      1920
Thr Lys Ile Tyr Arg Arg Pro Leu Asp Arg Pro Ala Ser Pro Arg Ser
                625                 630                 635 gat gtt aat gac atc aaa ggc acc cct cct gag gaa atc tca gct gca      1968
Asp Val Asn Asp Ile Lys Gly Thr Pro Pro Glu Glu Ile Ser Ala Ala
            640                 645                 650 caa cct cta cta cgc ccc aat tca gca gga agc agt tag agc ggt cgt      2016
Gln Pro Leu Leu Arg Pro Asn Ser Ala Gly Ser Ser     Ser Gly Arg
        655                 660                 665 cgg cca acc tcc cca aca gca ctt agg ttt tcc tgt tga                  2055
Arg Pro Thr Ser Pro Thr Ala Leu Arg Phe Ser Cys
    670                 675
```

<210> SEQ ID NO 23
<211> LENGTH: 28
<212> TYPE: PRT
<213> ORGANISM: Homo sapiens

<400> SEQUENCE: 23

Pro Lys Thr Ala Asn Leu Val Ala Asp Ile Thr Ser Leu Ala Lys Tyr
1               5                   10                  15

Gln Gln Val Leu Lys Thr Leu Gln Gly Thr Tyr Pro
            20                  25

<210> SEQ ID NO 24
<211> LENGTH: 55
<212> TYPE: PRT
<213> ORGANISM: Homo sapiens

<400> SEQUENCE: 24

```
Glu Glu Gly Lys Glu Leu Phe His Pro Cys Asp Met Val Leu Val Lys
1               5                   10                  15

Ser Leu Pro Ser Asn Ser Pro Ser Leu Asp Thr Ser Trp Glu Gly Pro
                20                  25                  30

Tyr Pro Val Ile Leu Ser Thr Pro Thr Ala Val Lys Val Ala Gly Val
                35                  40                  45

Glu Ser Trp Ile His His Thr
    50              55

<210> SEQ ID NO 25
<211> LENGTH: 38
<212> TYPE: PRT
<213> ORGANISM: Homo sapiens

<400> SEQUENCE: 25

Val Lys Ser Trp Ile Leu Pro Lys Glu Pro Glu Asn Pro Gly Asp Asn
1               5                   10                  15

Ala Ser Tyr Ser Cys Glu Pro Leu Glu Asp Leu Arg Leu Leu Phe Lys
                20                  25                  30

Gln Gln Pro Gly Gly Lys
            35

<210> SEQ ID NO 26
<211> LENGTH: 540
<212> TYPE: PRT
<213> ORGANISM: Homo sapiens

<400> SEQUENCE: 26

Ile Pro Met Ala Leu Pro Tyr His Ile Phe Leu Phe Thr Val Leu Leu
1               5                   10                  15

Pro Ser Phe Thr Leu Thr Ala Pro Pro Cys Arg Cys Met Thr Ser
                20                  25                  30

Ser Ser Pro Tyr Gln Glu Phe Leu Trp Arg Met Gln Arg Pro Gly Asn
                35                  40                  45

Ile Asp Ala Pro Ser Tyr Arg Ser Leu Ser Lys Gly Thr Pro Thr Phe
    50                  55                  60

Thr Ala His Thr His Met Pro Arg Asn Cys Tyr His Ser Ala Thr Leu
65                  70                  75                  80

Cys Met His Ala Asn Thr His Tyr Trp Thr Gly Lys Met Ile Asn Pro
                85                  90                  95

Ser Cys Pro Gly Gly Leu Gly Val Thr Val Cys Trp Thr Tyr Phe Thr
                100                 105                 110

Gln Thr Gly Met Ser Asp Gly Gly Val Gln Asp Gln Ala Arg Glu
            115                 120                 125

Lys His Val Lys Glu Val Ile Ser Gln Leu Thr Arg Val His Gly Thr
    130                 135                 140

Ser Ser Pro Tyr Lys Gly Leu Asp Leu Ser Lys Leu His Glu Thr Leu
145                 150                 155                 160

Arg Thr His Thr Arg Leu Val Ser Leu Phe Asn Thr Thr Leu Thr Gly
                165                 170                 175

Leu His Glu Val Ser Ala Gln Asn Pro Thr Asn Cys Trp Ile Cys Leu
            180                 185                 190

Pro Leu Asn Phe Arg Pro Tyr Val Ser Ile Pro Val Pro Glu Gln Trp
                195                 200                 205

Asn Asn Phe Ser Thr Glu Ile Asn Thr Thr Ser Val Leu Val Gly Pro
            210                 215                 220
```

```
Leu Val Ser Asn Leu Glu Ile Thr His Thr Ser Asn Leu Thr Cys Val
225                 230                 235                 240

Lys Phe Ser Asn Thr Thr Tyr Thr Thr Asn Ser Gln Cys Ile Arg Trp
            245                 250                 255

Val Thr Pro Pro Thr Gln Ile Val Cys Leu Pro Ser Gly Ile Phe Phe
                260                 265                 270

Val Cys Gly Thr Ser Ala Tyr Arg Cys Leu Asn Gly Ser Ser Glu Ser
            275                 280                 285

Met Cys Phe Leu Ser Phe Leu Val Pro Pro Met Thr Ile Tyr Thr Glu
    290                 295                 300

Gln Asp Leu Tyr Ser Tyr Val Ile Ser Lys Pro Arg Asn Lys Arg Val
305                 310                 315                 320

Pro Ile Leu Pro Phe Val Ile Gly Ala Gly Val Leu Gly Ala Leu Gly
                325                 330                 335

Thr Gly Ile Gly Gly Ile Thr Thr Ser Thr Gln Phe Tyr Tyr Lys Leu
            340                 345                 350

Ser Gln Glu Leu Asn Gly Asp Met Glu Arg Val Ala Asp Ser Leu Val
    355                 360                 365

Thr Leu Gln Asp Gln Leu Asn Ser Leu Ala Ala Val Val Leu Gln Asn
370                 375                 380

Arg Arg Ala Leu Asp Leu Leu Thr Ala Glu Arg Gly Gly Thr Cys Leu
385                 390                 395                 400

Phe Leu Gly Glu Glu Cys Cys Tyr Tyr Val Asn Gln Ser Gly Ile Val
                405                 410                 415

Thr Glu Lys Val Lys Glu Ile Arg Asp Arg Ile Gln Arg Arg Ala Glu
            420                 425                 430

Glu Leu Arg Asn Thr Gly Pro Trp Gly Leu Leu Ser Gln Trp Met Pro
    435                 440                 445

Trp Ile Leu Pro Phe Leu Gly Pro Leu Ala Ala Ile Ile Leu Leu Leu
450                 455                 460

Leu Phe Gly Pro Cys Ile Phe Asn Leu Leu Val Asn Phe Val Ser Ser
465                 470                 475                 480

Arg Ile Glu Ala Val Lys Leu Gln Met Glu Pro Lys Met Gln Ser Lys
                485                 490                 495

Thr Lys Ile Tyr Arg Arg Pro Leu Asp Arg Pro Ala Ser Pro Arg Ser
            500                 505                 510

Asp Val Asn Asp Ile Lys Gly Thr Pro Pro Glu Glu Ile Ser Ala Ala
    515                 520                 525

Gln Pro Leu Leu Arg Pro Asn Ser Ala Gly Ser Ser
530                 535                 540

<210> SEQ ID NO 27
<211> LENGTH: 15
<212> TYPE: PRT
<213> ORGANISM: Homo sapiens

<400> SEQUENCE: 27

Ser Gly Arg Arg Pro Thr Ser Pro Thr Ala Leu Arg Phe Ser Cys
1               5                   10                  15

<210> SEQ ID NO 28
<211> LENGTH: 1080
<212> TYPE: DNA
<213> ORGANISM: Homo sapiens
<220> FEATURE:
<221> NAME/KEY: CDS
```

-continued

<222> LOCATION: (1)..(1080)
<223> OTHER INFORMATION:

<400> SEQUENCE: 28

| | | | | | | | | | | | | | | | | |
|---|---|---|---|---|---|---|---|---|---|---|---|---|---|---|---|---|
| acc | tct | ttt | gta | gaa | aag | gca | aat | gga | gtg | aag | tgc | cat | aag | tac | aaa | 48 |
| Thr | Ser | Phe | Val | Glu | Lys | Ala | Asn | Gly | Val | Lys | Cys | His | Lys | Tyr | Lys | |
| 1 | | | | 5 | | | | | 10 | | | | | 15 | | |
| ctt | tct | ttt | cat | taa | gag | aca | act | cac | aat | tat | gta | aaa | agt | gtg | att | 96 |
| Leu | Ser | Phe | His | | Glu | Thr | Thr | His | Asn | Tyr | Val | Lys | Ser | Val | Ile | |
| | | | 20 | | | | | 25 | | | | | 30 | | | |
| tat | gcc | cta | cag | gaa | gcc | ttc | aga | gtc | tac | ctc | cct | atc | cca | gca | tcc | 144 |
| Tyr | Ala | Leu | Gln | Glu | Ala | Phe | Arg | Val | Tyr | Leu | Pro | Ile | Pro | Ala | Ser | |
| | | | 35 | | | | | 40 | | | | | 45 | | | |
| ccg | act | cct | tcc | cca | act | aat | aag | gac | ccc | cct | tca | acc | caa | atg | gtc | 192 |
| Pro | Thr | Pro | Ser | Pro | Thr | Asn | Lys | Asp | Pro | Pro | Ser | Thr | Gln | Met | Val | |
| | | 50 | | | | | 55 | | | | | 60 | | | | |
| caa | aag | gag | ata | gac | aaa | agg | gta | aac | agt | gaa | cca | aag | agt | gcc | aat | 240 |
| Gln | Lys | Glu | Ile | Asp | Lys | Arg | Val | Asn | Ser | Glu | Pro | Lys | Ser | Ala | Asn | |
| 65 | | | | | 70 | | | | | 75 | | | | | | |
| att | ccc | caa | tta | tga | ccc | ctc | caa | gca | gtg | gga | gga | aga | gaa | ttc | ggc | 288 |
| Ile | Pro | Gln | Leu | | Pro | Leu | Gln | Ala | Val | Gly | Gly | Arg | Glu | Phe | Gly | |
| 80 | | | | | 85 | | | | | 90 | | | | | | |
| cca | gcc | aga | gtg | cat | gtg | cct | ttt | tct | ctc | cca | gac | tta | aag | caa | ata | 336 |
| Pro | Ala | Arg | Val | His | Val | Pro | Phe | Ser | Leu | Pro | Asp | Leu | Lys | Gln | Ile | |
| 95 | | | | 100 | | | | | 105 | | | | | 110 | | |
| aaa | aca | gac | tta | ggt | aaa | ttc | tca | gat | aac | cct | gat | ggc | tat | att | gat | 384 |
| Lys | Thr | Asp | Leu | Gly | Lys | Phe | Ser | Asp | Asn | Pro | Asp | Gly | Tyr | Ile | Asp | |
| | | | | 115 | | | | | 120 | | | | | 125 | | |
| gtt | tta | caa | ggg | tta | gga | caa | ttc | ttt | gat | ctg | aca | tgg | aga | gat | ata | 432 |
| Val | Leu | Gln | Gly | Leu | Gly | Gln | Phe | Phe | Asp | Leu | Thr | Trp | Arg | Asp | Ile | |
| | | | 130 | | | | | 135 | | | | | 140 | | | |
| atg | tca | ctg | cta | aat | cag | aca | cta | acc | cca | aat | gag | aga | agt | gcc | acc | 480 |
| Met | Ser | Leu | Leu | Asn | Gln | Thr | Leu | Thr | Pro | Asn | Glu | Arg | Ser | Ala | Thr | |
| | | 145 | | | | | 150 | | | | | 155 | | | | |
| ata | act | gca | gcc | tga | gag | ttt | ggc | gat | ctc | tgg | tat | ctc | agt | cag | gtc | 528 |
| Ile | Thr | Ala | Ala | | Glu | Phe | Gly | Asp | Leu | Trp | Tyr | Leu | Ser | Gln | Val | |
| 160 | | | | | 165 | | | | | 170 | | | | | | |
| aat | gat | agg | atg | aca | aca | gag | gaa | aga | gaa | tga | ttc | ccc | aca | ggc | cag | 576 |
| Asn | Asp | Arg | Met | Thr | Thr | Glu | Glu | Arg | Glu | | Phe | Pro | Thr | Gly | Gln | |
| | 175 | | | | | 180 | | | | | | 185 | | | | |
| cag | gca | gtt | ccc | agt | cta | gac | cct | cat | tgg | gac | aca | gaa | tca | gaa | cat | 624 |
| Gln | Ala | Val | Pro | Ser | Leu | Asp | Pro | His | Trp | Asp | Thr | Glu | Ser | Glu | His | |
| | 190 | | | | | 195 | | | | | 200 | | | | | |
| gga | gat | tgg | tgc | tgc | aga | cat | ttg | cta | act | tgt | gtg | cta | gaa | gga | cta | 672 |
| Gly | Asp | Trp | Cys | Cys | Arg | His | Leu | Leu | Thr | Cys | Val | Leu | Glu | Gly | Leu | |
| 205 | | | | | 210 | | | | | 215 | | | | | 220 | |
| agg | aaa | act | agg | aag | aag | tct | atg | aat | tac | tca | atg | atg | tcc | acc | ata | 720 |
| Arg | Lys | Thr | Arg | Lys | Lys | Ser | Met | Asn | Tyr | Ser | Met | Met | Ser | Thr | Ile | |
| | | | | 225 | | | | | 230 | | | | | 235 | | |
| aca | cag | gga | agg | gaa | gaa | aat | cct | act | gcc | ttt | ctg | gag | aga | cta | agg | 768 |
| Thr | Gln | Gly | Arg | Glu | Glu | Asn | Pro | Thr | Ala | Phe | Leu | Glu | Arg | Leu | Arg | |
| | | | 240 | | | | | 245 | | | | | 250 | | | |
| gag | gca | ttg | agg | aag | cgt | gcc | tct | ctg | tca | cct | gac | tct | tct | gaa | ggc | 816 |
| Glu | Ala | Leu | Arg | Lys | Arg | Ala | Ser | Leu | Ser | Pro | Asp | Ser | Ser | Glu | Gly | |
| | | 255 | | | | | 260 | | | | | 265 | | | | |
| caa | cta | atc | tta | aag | cgt | aag | ttt | atc | act | cag | tca | gct | gca | gac | att | 864 |
| Gln | Leu | Ile | Leu | Lys | Arg | Lys | Phe | Ile | Thr | Gln | Ser | Ala | Ala | Asp | Ile | |
| | 270 | | | | | 275 | | | | | 280 | | | | | |
| aga | aaa | aaa | ctt | caa | aag | tct | gcc | gta | ggc | ccg | gag | caa | aac | tta | gaa | 912 |
| Arg | Lys | Lys | Leu | Gln | Lys | Ser | Ala | Val | Gly | Pro | Glu | Gln | Asn | Leu | Glu | |

```
                  285                 290                 295                 300
acc cta ttg aac ttg gca acc tcg gtt ttt tat aat aga gat cag gag        960
Thr Leu Leu Asn Leu Ala Thr Ser Val Phe Tyr Asn Arg Asp Gln Glu
                    305                 310                 315 gag cag gcg gaa cag gac aaa cgg gat taa aaa aaa ggc cac cgc ttt       1008
Glu Gln Ala Glu Gln Asp Lys Arg Asp     Lys Lys Gly His Arg Phe
            320                 325                         330 agt cat gac cct cag gca agt gga ctt tgg agg ctc tgg aaa agg gaa       1056
Ser His Asp Pro Gln Ala Ser Gly Leu Trp Arg Leu Trp Lys Arg Glu
                335                 340                 345 aag ctg ggc aaa ttg aat gcc taa                                       1080
Lys Leu Gly Lys Leu Asn Ala
        350
```

<210> SEQ ID NO 29
<211> LENGTH: 20
<212> TYPE: PRT
<213> ORGANISM: Homo sapiens

<400> SEQUENCE: 29

```
Thr Ser Phe Val Glu Lys Ala Asn Gly Val Lys Cys His Lys Tyr Lys
1               5                   10                  15

Leu Ser Phe His
            20
```

<210> SEQ ID NO 30
<211> LENGTH: 63
<212> TYPE: PRT
<213> ORGANISM: Homo sapiens

<400> SEQUENCE: 30

```
Glu Thr Thr His Asn Tyr Val Lys Ser Val Ile Tyr Ala Leu Gln Glu
1               5                   10                  15

Ala Phe Arg Val Tyr Leu Pro Ile Pro Ala Ser Pro Thr Pro Ser Pro
            20                  25                  30

Thr Asn Lys Asp Pro Pro Ser Thr Gln Met Val Gln Lys Glu Ile Asp
        35                  40                  45

Lys Arg Val Asn Ser Glu Pro Lys Ser Ala Asn Ile Pro Gln Leu
    50                  55                  60
```

<210> SEQ ID NO 31
<211> LENGTH: 79
<212> TYPE: PRT
<213> ORGANISM: Homo sapiens

<400> SEQUENCE: 31

```
Pro Leu Gln Ala Val Gly Gly Arg Glu Phe Gly Pro Ala Arg Val His
1               5                   10                  15

Val Pro Phe Ser Leu Pro Asp Leu Lys Gln Ile Lys Thr Asp Leu Gly
            20                  25                  30

Lys Phe Ser Asp Asn Pro Asp Gly Tyr Ile Asp Val Leu Gln Gly Leu
        35                  40                  45

Gly Gln Phe Phe Asp Leu Thr Trp Arg Asp Ile Met Ser Leu Leu Asn
    50                  55                  60

Gln Thr Leu Thr Pro Asn Glu Arg Ser Ala Thr Ile Thr Ala Ala
65                  70                  75
```

<210> SEQ ID NO 32
<211> LENGTH: 21
<212> TYPE: PRT

```
<213> ORGANISM: Homo sapiens

<400> SEQUENCE: 32

Glu Phe Gly Asp Leu Trp Tyr Leu Ser Gln Val Asn Asp Arg Met Thr
1               5                   10                  15

Thr Glu Glu Arg Glu
            20

<210> SEQ ID NO 33
<211> LENGTH: 142
<212> TYPE: PRT
<213> ORGANISM: Homo sapiens

<400> SEQUENCE: 33

Phe Pro Thr Gly Gln Gln Ala Val Pro Ser Leu Asp Pro His Trp Asp
1               5                   10                  15

Thr Glu Ser Glu His Gly Asp Trp Cys Cys Arg His Leu Leu Thr Cys
            20                  25                  30

Val Leu Glu Gly Leu Arg Lys Thr Arg Lys Lys Ser Met Asn Tyr Ser
        35                  40                  45

Met Met Ser Thr Ile Thr Gln Gly Arg Glu Glu Asn Pro Thr Ala Phe
    50                  55                  60

Leu Glu Arg Leu Arg Glu Ala Leu Arg Lys Ala Ser Leu Ser Pro
65                  70                  75                  80

Asp Ser Ser Glu Gly Gln Leu Ile Leu Lys Arg Lys Phe Ile Thr Gln
                85                  90                  95

Ser Ala Ala Asp Ile Arg Lys Lys Leu Gln Lys Ser Ala Val Gly Pro
            100                 105                 110

Glu Gln Asn Leu Glu Thr Leu Leu Asn Leu Ala Thr Ser Val Phe Tyr
        115                 120                 125

Asn Arg Asp Gln Glu Glu Gln Ala Glu Gln Asp Lys Arg Asp
    130                 135                 140

<210> SEQ ID NO 34
<211> LENGTH: 29
<212> TYPE: PRT
<213> ORGANISM: Homo sapiens

<400> SEQUENCE: 34

Lys Lys Gly His Arg Phe Ser His Asp Pro Gln Ala Ser Gly Leu Trp
1               5                   10                  15

Arg Leu Trp Lys Arg Glu Lys Leu Gly Lys Leu Asn Ala
            20                  25

<210> SEQ ID NO 35
<211> LENGTH: 685
<212> TYPE: PRT
<213> ORGANISM: Homo sapiens
<220> FEATURE:
<221> NAME/KEY: misc_feature
<222> LOCATION: (29)..(29)
<223> OTHER INFORMATION: Xaa is any amino acid
<220> FEATURE:
<221> NAME/KEY: misc_feature
<222> LOCATION: (85)..(85)
<223> OTHER INFORMATION: Xaa is any amino acid
<220> FEATURE:
<221> NAME/KEY: misc_feature
<222> LOCATION: (124)..(124)
<223> OTHER INFORMATION: Xaa is any amino acid
<220> FEATURE:
<221> NAME/KEY: misc_feature
<222> LOCATION: (128)..(128)
```

```
<223> OTHER INFORMATION: Xaa is any amino acid
<220> FEATURE:
<221> NAME/KEY: misc_feature
<222> LOCATION: (669)..(669)
<223> OTHER INFORMATION: Xaa is any amino acid
<220> FEATURE:
<221> NAME/KEY: misc_feature
<222> LOCATION: (685)..(685)
<223> OTHER INFORMATION: Xaa is any amino acid

<400> SEQUENCE: 35

Pro Lys Thr Ala Asn Leu Val Ala Asp Ile Thr Ser Leu Ala Lys Tyr
1               5                   10                  15

Gln Gln Val Leu Lys Thr Leu Gln Gly Thr Tyr Pro Xaa Glu Glu Gly
            20                  25                  30

Lys Glu Leu Phe His Pro Cys Asp Met Val Leu Val Lys Ser Leu Pro
        35                  40                  45

Ser Asn Ser Pro Ser Leu Asp Thr Ser Trp Glu Gly Pro Tyr Pro Val
    50                  55                  60

Ile Leu Ser Thr Pro Thr Ala Val Lys Val Ala Gly Val Glu Ser Trp
65                  70                  75                  80

Ile His His Thr Xaa Val Lys Ser Trp Ile Leu Pro Lys Glu Pro Glu
                85                  90                  95

Asn Pro Gly Asp Asn Ala Ser Tyr Ser Cys Glu Pro Leu Glu Asp Leu
            100                 105                 110

Arg Leu Leu Phe Lys Gln Gln Pro Gly Gly Lys Xaa Leu Lys Ser Xaa
        115                 120                 125

Ile Pro Met Ala Leu Pro Tyr His Ile Phe Leu Phe Thr Val Leu Leu
130                 135                 140

Pro Ser Phe Thr Leu Thr Ala Pro Pro Cys Arg Cys Met Thr Ser
145                 150                 155                 160

Ser Ser Pro Tyr Gln Glu Phe Leu Trp Arg Met Gln Arg Pro Gly Asn
                165                 170                 175

Ile Asp Ala Pro Ser Tyr Arg Ser Leu Ser Lys Gly Thr Pro Thr Phe
            180                 185                 190

Thr Ala His Thr His Met Pro Arg Asn Cys Tyr His Ser Ala Thr Leu
        195                 200                 205

Cys Met His Ala Asn Thr His Tyr Trp Thr Gly Lys Met Ile Asn Pro
210                 215                 220

Ser Cys Pro Gly Gly Leu Gly Val Thr Val Cys Trp Thr Tyr Phe Thr
225                 230                 235                 240

Gln Thr Gly Met Ser Asp Gly Gly Val Gln Asp Gln Ala Arg Glu
                245                 250                 255

Lys His Val Lys Glu Val Ile Ser Gln Leu Thr Arg Val His Gly Thr
            260                 265                 270

Ser Ser Pro Tyr Lys Gly Leu Asp Leu Ser Lys Leu His Glu Thr Leu
        275                 280                 285

Arg Thr His Thr Arg Leu Val Ser Leu Phe Asn Thr Thr Leu Thr Gly
290                 295                 300

Leu His Glu Val Ser Ala Gln Asn Pro Thr Asn Cys Trp Ile Cys Leu
305                 310                 315                 320

Pro Leu Asn Phe Arg Pro Tyr Val Ser Ile Pro Val Pro Glu Gln Trp
                325                 330                 335

Asn Asn Phe Ser Thr Glu Ile Asn Thr Thr Ser Val Leu Val Gly Pro
            340                 345                 350

Leu Val Ser Asn Leu Glu Ile Thr His Thr Ser Asn Leu Thr Cys Val
```

```
                355                 360                 365

Lys Phe Ser Asn Thr Thr Tyr Thr Thr Asn Ser Gln Cys Ile Arg Trp
    370                 375                 380

Val Thr Pro Pro Thr Gln Ile Val Cys Leu Pro Ser Gly Ile Phe Phe
385                 390                 395                 400

Val Cys Gly Thr Ser Ala Tyr Arg Cys Leu Asn Gly Ser Ser Glu Ser
                405                 410                 415

Met Cys Phe Leu Ser Phe Leu Val Pro Pro Met Thr Ile Tyr Thr Glu
                420                 425                 430

Gln Asp Leu Tyr Ser Tyr Val Ile Ser Lys Pro Arg Asn Lys Arg Val
                435                 440                 445

Pro Ile Leu Pro Phe Val Ile Gly Ala Gly Val Leu Gly Ala Leu Gly
                450                 455                 460

Thr Gly Ile Gly Gly Ile Thr Thr Ser Thr Gln Phe Tyr Tyr Lys Leu
465                 470                 475                 480

Ser Gln Glu Leu Asn Gly Asp Met Glu Arg Val Ala Asp Ser Leu Val
                485                 490                 495

Thr Leu Gln Asp Gln Leu Asn Ser Leu Ala Ala Val Val Leu Gln Asn
                500                 505                 510

Arg Arg Ala Leu Asp Leu Leu Thr Ala Glu Arg Gly Gly Thr Cys Leu
                515                 520                 525

Phe Leu Gly Glu Glu Cys Cys Tyr Tyr Val Asn Gln Ser Gly Ile Val
                530                 535                 540

Thr Glu Lys Val Lys Glu Ile Arg Asp Arg Ile Gln Arg Arg Ala Glu
545                 550                 555                 560

Glu Leu Arg Asn Thr Gly Pro Trp Gly Leu Leu Ser Gln Trp Met Pro
                565                 570                 575

Trp Ile Leu Pro Phe Leu Gly Pro Leu Ala Ala Ile Ile Leu Leu Leu
                580                 585                 590

Leu Phe Gly Pro Cys Ile Phe Asn Leu Leu Val Asn Phe Val Ser Ser
                595                 600                 605

Arg Ile Glu Ala Val Lys Leu Gln Met Glu Pro Lys Met Gln Ser Lys
610                 615                 620

Thr Lys Ile Tyr Arg Arg Pro Leu Asp Arg Pro Ala Ser Pro Arg Ser
625                 630                 635                 640

Asp Val Asn Asp Ile Lys Gly Thr Pro Pro Glu Glu Ile Ser Ala Ala
                645                 650                 655

Gln Pro Leu Leu Arg Pro Asn Ser Ala Gly Ser Ser Xaa Ser Gly Arg
                660                 665                 670

Arg Pro Thr Ser Pro Thr Ala Leu Arg Phe Ser Cys Xaa
                675                 680                 685

<210> SEQ ID NO 36
<211> LENGTH: 360
<212> TYPE: PRT
<213> ORGANISM: Homo sapiens
<220> FEATURE:
<221> NAME/KEY: misc_feature
<222> LOCATION: (21)..(21)
<223> OTHER INFORMATION: Xaa is any amino acid
<220> FEATURE:
<221> NAME/KEY: misc_feature
<222> LOCATION: (85)..(85)
<223> OTHER INFORMATION: Xaa is any amino acid
<220> FEATURE:
<221> NAME/KEY: misc_feature
<222> LOCATION: (165)..(165)
<223> OTHER INFORMATION: Xaa is any amino acid
```

```
<220> FEATURE:
<221> NAME/KEY: misc_feature
<222> LOCATION: (187)..(187)
<223> OTHER INFORMATION: Xaa is any amino acid
<220> FEATURE:
<221> NAME/KEY: misc_feature
<222> LOCATION: (330)..(330)
<223> OTHER INFORMATION: Xaa is any amino acid
<220> FEATURE:
<221> NAME/KEY: misc_feature
<222> LOCATION: (360)..(360)
<223> OTHER INFORMATION: Xaa is any amino acid

<400> SEQUENCE: 36
```

| | | | | | | | | | | | | | | |
|---|---|---|---|---|---|---|---|---|---|---|---|---|---|---|
| Thr | Ser | Phe | Val | Glu | Lys | Ala | Asn | Gly | Val | Lys | Cys | His | Lys | Tyr | Lys |
| 1 | | | | 5 | | | | | 10 | | | | | 15 | |

Leu Ser Phe His Xaa Glu Thr Thr His Asn Tyr Val Lys Ser Val Ile
              20                25                  30

Tyr Ala Leu Gln Glu Ala Phe Arg Val Tyr Leu Pro Ile Pro Ala Ser
        35                40                45

Pro Thr Pro Ser Pro Thr Asn Lys Asp Pro Pro Ser Thr Gln Met Val
    50              55                60

Gln Lys Glu Ile Asp Lys Arg Val Asn Ser Pro Lys Ser Ala Asn
65                70                75              80

Ile Pro Gln Leu Xaa Pro Leu Gln Ala Val Gly Gly Arg Glu Phe Gly
            85                90              95

Pro Ala Arg Val His Val Pro Phe Ser Leu Pro Asp Leu Lys Gln Ile
        100              105              110

Lys Thr Asp Leu Gly Lys Phe Ser Asp Asn Pro Asp Gly Tyr Ile Asp
        115              120              125

Val Leu Gln Gly Leu Gly Gln Phe Phe Asp Leu Thr Trp Arg Asp Ile
    130              135              140

Met Ser Leu Leu Asn Gln Thr Leu Thr Pro Asn Glu Arg Ser Ala Thr
145                150              155              160

Ile Thr Ala Ala Xaa Glu Phe Gly Asp Leu Trp Tyr Leu Ser Gln Val
        165              170              175

Asn Asp Arg Met Thr Thr Glu Glu Arg Glu Xaa Phe Pro Thr Gly Gln
        180              185              190

Gln Ala Val Pro Ser Leu Asp Pro His Trp Asp Thr Glu Ser Glu His
        195              200              205

Gly Asp Trp Cys Cys Arg His Leu Leu Thr Cys Val Leu Glu Gly Leu
    210              215              220

Arg Lys Thr Arg Lys Lys Ser Met Asn Tyr Ser Met Met Ser Thr Ile
225                230              235              240

Thr Gln Gly Arg Glu Glu Asn Pro Thr Ala Phe Leu Glu Arg Leu Arg
        245              250              255

Glu Ala Leu Arg Lys Arg Ala Ser Leu Ser Pro Asp Ser Ser Glu Gly
        260              265              270

Gln Leu Ile Leu Lys Arg Lys Phe Ile Thr Gln Ser Ala Ala Asp Ile
        275              280              285

Arg Lys Lys Leu Gln Lys Ser Ala Val Gly Pro Glu Gln Asn Leu Glu
    290              295              300

Thr Leu Leu Asn Leu Ala Thr Ser Val Phe Tyr Asn Arg Asp Gln Glu
305                310              315              320

Glu Gln Ala Glu Gln Asp Lys Arg Asp Xaa Lys Lys Gly His Arg Phe
                325              330              335

Ser His Asp Pro Gln Ala Ser Gly Leu Trp Arg Leu Trp Lys Arg Glu

```
                340               345               350
Lys Leu Gly Lys Leu Asn Ala Xaa
         355               360
```

<210> SEQ ID NO 37
<211> LENGTH: 26
<212> TYPE: DNA
<213> ORGANISM: Homo sapiens

<400> SEQUENCE: 37
ggaccataga ggacactcca ggacta                                        26

<210> SEQ ID NO 38
<211> LENGTH: 25
<212> TYPE: DNA
<213> ORGANISM: Homo sapiens

<400> SEQUENCE: 38
cctcagtcct gctgctggat catct                                         25

<210> SEQ ID NO 39
<211> LENGTH: 27
<212> TYPE: DNA
<213> ORGANISM: Homo sapiens

<400> SEQUENCE: 39
cctccaagca gtgggaggaa gagaatt                                       27

<210> SEQ ID NO 40
<211> LENGTH: 28
<212> TYPE: DNA
<213> ORGANISM: Homo sapiens

<400> SEQUENCE: 40
ccttccctgt gttattgtgg acatcatt                                      28

<210> SEQ ID NO 41
<211> LENGTH: 30
<212> TYPE: DNA
<213> ORGANISM: Homo sapiens

<400> SEQUENCE: 41
ggaagaagtc tatgaattat tcaatgatgt                                    30

<210> SEQ ID NO 42
<211> LENGTH: 27
<212> TYPE: DNA
<213> ORGANISM: Homo sapiens

<400> SEQUENCE: 42
gggacacaga atcagaacat ggagatt                                       27

<210> SEQ ID NO 43
<211> LENGTH: 27
<212> TYPE: DNA
<213> ORGANISM: Homo sapiens

<400> SEQUENCE: 43
gccttcagaa gagtcaggtg acagaga                                       27

<210> SEQ ID NO 44
<211> LENGTH: 25
<212> TYPE: DNA

<213> ORGANISM: Homo sapiens

<400> SEQUENCE: 44
gagcctccaa agtccacttg cctga                                    25

<210> SEQ ID NO 45
<211> LENGTH: 29
<212> TYPE: DNA
<213> ORGANISM: Homo sapiens

<400> SEQUENCE: 45
gatttcagta tctactagtc tgggtagat                                29

<210> SEQ ID NO 46
<211> LENGTH: 27
<212> TYPE: DNA
<213> ORGANISM: Homo sapiens

<400> SEQUENCE: 46
ctaggaaatc cagctagtcc tgtctca                                  27

<210> SEQ ID NO 47
<211> LENGTH: 28
<212> TYPE: DNA
<213> ORGANISM: Homo sapiens

<400> SEQUENCE: 47
ccaagacagc caacttagtt gcagacat                                 28

<210> SEQ ID NO 48
<211> LENGTH: 28
<212> TYPE: DNA
<213> ORGANISM: Homo sapiens

<400> SEQUENCE: 48
ggacgctgca ttctccatag aaactctt                                 28

<210> SEQ ID NO 49
<211> LENGTH: 29
<212> TYPE: DNA
<213> ORGANISM: Homo sapiens

<400> SEQUENCE: 49
gcaatactac atacacaacc aactcccaa                                29

<210> SEQ ID NO 50
<211> LENGTH: 26
<212> TYPE: DNA
<213> ORGANISM: Homo sapiens

<400> SEQUENCE: 50
gggggaggca tatccaacag ttagta                                   26

<210> SEQ ID NO 51
<211> LENGTH: 30
<212> TYPE: DNA
<213> ORGANISM: Homo sapiens

<400> SEQUENCE: 51
ccatctacac tgaacaagat ttatacactt                               30

<210> SEQ ID NO 52
<211> LENGTH: 28

```
<212> TYPE: DNA
<213> ORGANISM: Homo sapiens

<400> SEQUENCE: 52
aatgccagta cctagtgcac ctagcact                                             28

<210> SEQ ID NO 53
<211> LENGTH: 31
<212> TYPE: DNA
<213> ORGANISM: Homo sapiens

<400> SEQUENCE: 53
cgaatacaac gtagagcaga ggagcttcga a                                         31

<210> SEQ ID NO 54
<211> LENGTH: 28
<212> TYPE: DNA
<213> ORGANISM: Homo sapiens

<400> SEQUENCE: 54
agcccaagat gcagtccaag actaagat                                             28

<210> SEQ ID NO 55
<211> LENGTH: 27
<212> TYPE: DNA
<213> ORGANISM: Homo sapiens

<400> SEQUENCE: 55
gcgtagtaga ggttgtgcag ctgagat                                              27

<210> SEQ ID NO 56
<211> LENGTH: 27
<212> TYPE: DNA
<213> ORGANISM: Homo sapiens

<400> SEQUENCE: 56
cccttaccaa gagtttctat ggagaat                                              27

<210> SEQ ID NO 57
<211> LENGTH: 27
<212> TYPE: DNA
<213> ORGANISM: Homo sapiens

<400> SEQUENCE: 57
accgctctaa ctgcttcctg ctgaatt                                              27

<210> SEQ ID NO 58
<211> LENGTH: 420
<212> TYPE: PRT
<213> ORGANISM: Homo sapiens
<220> FEATURE:
<221> NAME/KEY: misc_feature
<222> LOCATION: (21)..(21)
<223> OTHER INFORMATION: Xaa is any amino acid
<220> FEATURE:
<221> NAME/KEY: misc_feature
<222> LOCATION: (86)..(86)
<223> OTHER INFORMATION: Xaa is any amino acid
<220> FEATURE:
<221> NAME/KEY: misc_feature
<222> LOCATION: (166)..(166)
<223> OTHER INFORMATION: Xaa is any amino acid
<220> FEATURE:
<221> NAME/KEY: misc_feature
<222> LOCATION: (188)..(188)
<223> OTHER INFORMATION: Xaa is any amino acid
<220> FEATURE:
```

```
<221> NAME/KEY: misc_feature
<222> LOCATION: (331)..(331)
<223> OTHER INFORMATION: Xaa is any amino acid
<220> FEATURE:
<221> NAME/KEY: misc_feature
<222> LOCATION: (361)..(361)
<223> OTHER INFORMATION: Xaa is any amino acid
<220> FEATURE:
<221> NAME/KEY: misc_feature
<222> LOCATION: (362)..(362)
<223> OTHER INFORMATION: Xaa is any amino acid
<220> FEATURE:
<221> NAME/KEY: misc_feature
<222> LOCATION: (374)..(374)
<223> OTHER INFORMATION: Xaa is any amino acid
<220> FEATURE:
<221> NAME/KEY: misc_feature
<222> LOCATION: (380)..(380)
<223> OTHER INFORMATION: Xaa is any amino acid
<220> FEATURE:
<221> NAME/KEY: misc_feature
<222> LOCATION: (382)..(382)
<223> OTHER INFORMATION: Xaa is any amino acid
<220> FEATURE:
<221> NAME/KEY: misc_feature
<222> LOCATION: (408)..(408)
<223> OTHER INFORMATION: Xaa is any amino acid
<220> FEATURE:
<221> NAME/KEY: misc_feature
<222> LOCATION: (413)..(413)
<223> OTHER INFORMATION: Xaa is any amino acid

<400> SEQUENCE: 58

Thr Ser Phe Val Glu Lys Ala Asn Gly Val Lys Cys His Lys Tyr Lys
1               5                   10                  15

Leu Ser Phe His Xaa Glu Thr Thr His Asn Tyr Val Lys Ser Val Ile
            20                  25                  30

Tyr Ala Leu Gln Glu Ala Phe Arg Val Tyr Leu Pro Ile Leu Pro Ala
        35                  40                  45

Ser Pro Thr Pro Ser Pro Thr Asn Lys Asp Pro Pro Ser Thr Gln Met
    50                  55                  60

Val Gln Lys Glu Ile Asp Lys Arg Val Asn Ser Glu Pro Lys Ser Ala
65                  70                  75                  80

Asn Ile Pro Gln Leu Xaa Pro Leu Gln Ala Val Gly Gly Arg Glu Phe
                85                  90                  95

Gly Pro Ala Arg Val His Val Pro Phe Ser Leu Pro Asp Leu Lys Gln
            100                 105                 110

Ile Lys Thr Asp Leu Gly Lys Phe Ser Asp Asn Pro Asp Gly Tyr Ile
        115                 120                 125

Asp Val Leu Gln Gly Leu Gly Gln Phe Phe Asp Leu Thr Trp Arg Asp
    130                 135                 140

Ile Met Ser Leu Leu Asn Gln Thr Leu Thr Pro Asn Glu Arg Ser Ala
145                 150                 155                 160

Thr Ile Thr Ala Ala Xaa Glu Phe Gly Asp Leu Trp Tyr Leu Ser Gln
                165                 170                 175

Val Asn Asp Arg Met Thr Thr Glu Glu Arg Glu Xaa Phe Pro Thr Gly
            180                 185                 190

Gln Gln Ala Val Pro Ser Leu Asp Pro His Trp Asp Thr Glu Ser Glu
        195                 200                 205

His Gly Asp Trp Cys Cys Arg His Leu Leu Thr Cys Val Leu Glu Gly
    210                 215                 220

Leu Arg Lys Thr Arg Lys Lys Ser Met Asn Tyr Ser Met Met Ser Thr
225                 230                 235                 240
```

```
Ile Thr Gln Gly Arg Glu Glu Asn Pro Thr Ala Phe Leu Glu Arg Leu
            245                 250                 255

Arg Glu Ala Leu Arg Lys Arg Ala Ser Leu Ser Pro Asp Ser Ser Glu
        260                 265                 270

Gly Gln Leu Ile Leu Lys Arg Lys Phe Ile Thr Gln Ser Ala Ala Asp
    275                 280                 285

Ile Arg Lys Lys Leu Gln Lys Ser Ala Val Gly Pro Glu Gln Asn Leu
290                 295                 300

Glu Thr Leu Leu Asn Leu Ala Thr Ser Val Phe Tyr Asn Arg Asp Gln
305                 310                 315                 320

Glu Glu Gln Ala Glu Gln Asp Lys Arg Asp Xaa Lys Lys Gly His Arg
            325                 330                 335

Phe Ser His Asp Pro Gln Ala Ser Gly Leu Trp Arg Leu Trp Lys Arg
        340                 345                 350

Glu Lys Leu Gly Lys Leu Asn Ala Xaa Xaa Gly Leu Leu Pro Val Arg
    355                 360                 365

Ser Thr Arg Thr Leu Xaa Lys Arg Leu Ser Lys Xaa Lys Xaa Ala Ala
370                 375                 380

Pro Ser Ser Met Pro Leu Ile Ser Arg Glu Ser Leu Glu Gly Pro Leu
385                 390                 395                 400

Pro Gln Gly Thr Lys Val Leu Xaa Val Arg Ser His Xaa Pro Asp Ser
            405                 410                 415

Ser Ser Arg Thr
            420

<210> SEQ ID NO 59
<211> LENGTH: 32
<212> TYPE: DNA
<213> ORGANISM: Homo sapiens

<400> SEQUENCE: 59
taaactacaa atggttcttc aaatggagcc ca                              32

<210> SEQ ID NO 60
<211> LENGTH: 32
<212> TYPE: DNA
<213> ORGANISM: Homo sapiens

<400> SEQUENCE: 60
gatgcagtcc aagatgcagt ccatgactaa ga                              32

<210> SEQ ID NO 61
<211> LENGTH: 1740
<212> TYPE: DNA
<213> ORGANISM: Homo sapiens

<400> SEQUENCE: 61
aggttggctg acaaccgctc ttaactgctt catgctgaat tggggcatag tagggtcgt     60 gcagttgaga tttccttggg aggggtgcct tcaatgtcat caacattgga gcatgggcta   120
gcaggccagt ccaggggtcc gcggtagatc ttagtcatgg actgcatctg ggctccatt   180 tgaagaacca tttgtagttt tacagcttcg attctggaag agacaaacgt aacaaggagg   240
ttaaagatac aaggattgaa atgtacggcc tgaagtgcag gggcatatga gtgtgggcgg   300
tgcaagtggg gtttcctttg aaaaactccg atacaatag gcatcaata tttctaggaa    360 gccacattct cctagaaagc tctcggtaag ggagctact ggtagtacag cagcatacag    420
ggggtgcagt gagagtgaaa gggggtaaga gaacagtaaa aagaaaaata tgacaaggga   480
```

```
gggccaagag gatctacgat tctagttact ttcctcacgg ttgtcgcctg aagagcaggc    540
gcagatcctc tagaggttca caggaatagc tagcattgtc tgctggattt tcgggttcct    600
ttggcagtat ccagggtttg gctcgagtgt gacttatcca agactccact ccagccactt    660
aactgcggtt agggtagata aaatgactgg gtagggtcct tcccaggatg tgtgtaggga    720 tgggaatta aaggggaagg gacttgacta ataccatgtc accagggtgg aataattcct    780
ttccctcctc tcagggacag gttccctgta atgttttaag aactcgttga tatttggcta    840
aggaggtgat gtctgcaact aagttggccg tctctcagtc aagcacaagg tcattggtta    900
ggaagggctg tccatacagc atctcatatg gactaagtcc tgcttttgg ggacagtttc    960 ggattcttag taaggctata gcaacagag caggccatgc aagtgggtt tcttgggtta    1020 gctttttag atgtcgtttg agtgtttcat tcatttctc aacttttcct gaggatcgtg    1080
gcctccaggc acagtgtaag tgatattgta tacctaacgc ctgggatact ccctgcgtta    1140
ctgcagcctt gaaattgggg ccattgtcac tctgtaaacc tcagggaagt ccgaatctgg    1200
gaattatttc atgaattagt acttttatta cctcttgggc cttttctgtc ctacaaggga    1260
aggcctccac ccaaccagtg aaagtaccca gattagtaga tactgaaatc tctgagattt    1320
gggcatgtgg gtaaaatcta gttgctagtc ttctcctggg taatggcctg ttctttgttc    1380
tcctgaagga gcttggcaat aaggcagggg attatttctt tggcacactt cacaggccct    1440
gactatctgc ttgacagttt tgaaaaggcc tggtccagta aataatgatt tggccatctg    1500
atgggtgctg tcaatgccta agtgaaaggt ctggtgaagg gttttaagta atttccattg    1560
gttagctgca ggcaaaagta ttttttcttt ggtggctggc catcctgagg agaggaaact    1620
atgtcctcgt gagtttcccc attccatttc ttctgctgag tactgagct tggtttccca    1680 gaggggatta ccccatacta ggggtccttc tgtaagcatt tctaatggag agtcctgcct    1740
```

<210> SEQ ID NO 62
<211> LENGTH: 7140
<212> TYPE: DNA
<213> ORGANISM: Homo sapiens

<400> SEQUENCE: 62

```
ttggtcttaa gaacacaaat gatatggctc caatgactgg aggaacacca gggtccttgg     60
tctcacgctg atttagataa aacgactgtc aggcctctga gcccaagcta agccatcctc    120
ccctgtgacc tgcacgtata catccagatg gcctgaagta accaaagaat cacaaaagca    180
gtgaaaatgg cctgttcctg ccttaactga tgacattcca ccattgtgat tgttcctgc     240 cccatcttaa ctgagcgatt aaccttgtga aattccttct cctggctcaa acctccccc     300 actgagcacc ttgtgacccc cgcccctgcc cctaagagaa aacccccttt gattataatt    360
ttccactacc cacccaaatc ctataaaatg gccccacccc tatctccctt cgctgactcc    420
tttttcggac tcagcccgcc tgcacccagg tgaaataaac agccttgttg ctcacacaaa    480
gcctgtttgg tggactctct tcacgcgac gctcatgaca tttggtgcca aaacctggga    540
taggaggact ccttcaggag accagtcccc tgtccttgcc ctcactctgt gaggacatcc    600
acctacaacc ttgggtcctc agaccaacca gcccaaggaa cagctcacca atttcaaatc    660
aggtaagcag tcttttcact ctcttctcca gcctctcttg ctacccttca aactccctct    720
ctcactaccc ttcaatctcc ctgtccttcc aattccagtt cttttcatc tctagtagag     780 acaaaggaga cacattttat ccatggaccc aaaactccag caccagtcac ggacttggga    840
```

-continued

```
agacagtctt cccttggtgt ttaatcactg cggggacgcc tgcctgatta ttcacccaca    900
ctccattggt gtctgatcac ggtggggaca cctgccttgg tcactcaccc acattccctt    960
ggtggtacgt caactgcaaa agcagggggac gcctgctttg gctgctcacc cacccccttc   1020
tctgtgtctc tacctttctc tttaaactta cctccttcac tatgggcaaa cttctgccct   1080
ccattccccc ttcttctccc ttagcctgtg ttcttaaaaa cctaaaacct cttcaactca   1140
cacctgacct aaaacctaaa tgccttattt tcttctgcaa cactgcgtgg ctgcagtaca   1200
aacttgataa tagctttaaa tggccagaat atggcacttt caatttctcc atcctacaag   1260
atctagataa ttttgtgga aaaatggaaa atggtctga gatgcctgac gtccaggcat    1320
tcttttacac attggtccct ccctagtctc tgctcccaat gcgactcatc ccaaatcttt   1380
cttctttctc tcctgtctgt tccttcagtc tccaccccaa gctctgagtc ctttgaatcc   1440
tcctttgcta cagacccatc tgaactctcc cctcctcccc aggctgctcc tcaccaggcc   1500
gagccaggtc ccaattcttc ctcagcctct gctcccccac cctataatcc ttttatcacc   1560
tcctctcctc acactcagtc cggcttacag tttcgttctg tgactagccc tcccccatct   1620
gcccaacaat ttcctcttaa agaggtggct ggagctaaag gcatagtcaa ggttaatgct   1680
ccttttctct tatctgacct ctcccaaatc agttagcgtt tacgctcttt ttcatcaaat   1740
ataaaaccc agccagttca tggcccatct ggcaacaacc cttacaggct ttacagccct   1800
agaccctgaa gggtcagaag gccgtcttat tctcaatatg cattttatta cccaatccgc   1860
tcccaacatt aaataaagct ccaaaaatta aattctggcc ctcaaacccc acaacaggac   1920
ttaattaacc tcacttcaag gtgtacaaga atagagtaga ggcagccaag tagcaacgta   1980
tttgagttgc aattccttgc ctcaactctg agagaaaccc cagccacatc tccagcaaac   2040
aagaacttca aaacacctga actgcagcag ccaggcgttc ctccaggacc acctccccca   2100
ggatcttgct tcaagtgccg gaaatctgac cattgggcca aggaatgcct gcagcccagg   2160
attcctccta agccacgtcc catttgtgca ggaccccact ggaaatcgga ctgtccaact   2220
cacccggcag ccaatcccag agcccctgga actctggccc aaggctctct gactgactcc   2280
ttcccagatc ttctcggctt agcagctgaa gactgacact gcccgatcac ttcagaagtc   2340
ccctggacca tcacggatac tgagcttcag gtaactctca cagtggaggc taagtccatc   2400
ccctgtttaa tcgatacagg ggctacccac tccacatcac cttctttca agggcctgtt   2460
tcccttccc ccataactgt tgtgggtatt gacggccaag cttcaaaacc ccttaaaact   2520
ccccactct ggtgccaact tggacaacat tcttttatgc actcttttc agttatcctc    2580
acctgcccag ttcccttatt aggccgagac attttaacca aattatctgc ttccccgact   2640
attcctgggc tacagccaca tctccttgcc gcccttcttc ccaacccaaa gcctccttca   2700
tatcttcctc tcatatcccc ccaccttaac ccacaagtat gggacacctc tactccctcc   2760
ctggcaaccg atcacacgcc cattactatc ccattaaaac ctaatcaccc ttaccctgct   2820
caatgccagt atcccatacc acaacaggct ttaaagggat tgaagcctgt tatcacttgc   2880
ctgctacagc acgggcttct aaaacctata aactctccat acaattcccc cattttacct   2940
gtctaaaaac cagataagtc ttacaggtta gttcagaatc tgcaccttat caaccaaatt   3000
gttttgccta tccaccctgt agcacccaac tcgtacactc ttttgtcctc aatgccttcc   3060
cccacaactc actattccgt tcttgatctt aaagatgctt ttttcactat tcccctgcac   3120
ccctcatccc agcctctctt tgcttttacc tggactgacc ctgacaccca tcagtcccag   3180
cagcttacct gggctgtact gccgcaaggc ttcagggaca gccctcatta cttcagccaa   3240
```

```
gctctttctc atgatttact ttctttccac ctctctgctt ctcaccttat tcaatatatt    3300
gatgaccttc tactttgtag cccctccttt aaatcttctc aacaagacac cctcctgctc    3360
cttcaacatt tgttctccaa aggatatcgg gtatccccct ccaaagctca aatttcttct    3420
ccatctgtta catacctcgg cataattctt catgaaaaca catgtgctct ccctgccaat    3480
tgcgtctcca actgatctct caaatcccaa cctcttctac aaaacaacaa ctcctttccc    3540
tcctaggcat ggttggatac ttttgccttt ggatacctgg ttttgccatc ctaacaaaat    3600
cattatataa actcacaaaa ggaaacctag ctgaccccat agattctaaa tccttttccc    3660
actcctcttt ccattccttg aagacagctt tagagactgc tcccacacta gctctccctg    3720
tctcatccca acccttttca ttacacacag ccgaagtgca gggctgtgca gtcggaattc    3780
ttacacaagg accgggacca tgccctgtag ccttttttgtc caaacaactt gaccttactg    3840
ttttaggctc gccatcatgt ctccatgcgg tagcttccgc tgccctaata cttttagagg    3900
ccctcaaaat cacaaactat gctcaactca ctctctacag ctctcacaac ttccaaaatc    3960
tattttcttt ctcacacctg acgcatatac tttctgctcc ccggctcctt cagctgtatt    4020
cactctttgt tgagtctccc acaattacca ttcttcctgg cccagacttc aatctggcct    4080
cccacattat tctggatacc acacctgacc ctgatgattg tatgtctctg atctacctga    4140
cattcacccc atttccccat atttccttct tttctgttcc tcatgttgat cacatttggt    4200
ttactgacgg cagttccacc aggcctgatc gccactcacc agcaaaggca ggctatgcta    4260
tagaatcttc cacatccatc attgaggcta ctgctctgcc cccctccact acctctcagc    4320
aagccgaact gattgcctta actcgggcct tcactcttgc aaagggacta cacgtcaata    4380
tttatactga ctctaaatat gccttccata tcttgcacca ccatgctgtt atatgggctg    4440
aaagaggttt cctcactacg caagggtcct ccatcattaa tgcctcttta ataaaaactc    4500
ttctcaaggc tgctttactt ccaaaggaag ctggagtcac acactgcaag ggccaccaaa    4560
aggcgtcaga tcccattact ctaggaaatg cttatgctga taggtagct aaagaagcac    4620 ctagcgttcc aacttctgtc cctcatggcc agttttctc cttccatca gtcattccca    4680 cctactcccc cattgaaact tccgcctatc aatctcttct cacacaaggc aaatggttct    4740
tagaccaagg aaaatatctc cttccagcct cacaggccca ttctattctg tcatcatttc    4800
ataacctctt ccatgtaggt tacaagccac tagtccacct cttagaacct ctcatttcct    4860
tccatcgtgg aaacatatcc tcaaggaaat cacttctcag tgttccatct gctattctac    4920 taccccctcag ggattgttca ggccccctcc cctccctaca catcaagctc ggggatttgc    4980
ccctgcccag gactggcaaa ttgactttac tcacatgccc tgagtcagga aactaaaata    5040
cctcttggtc tgggtagaca ctgtcactgg atgggtagag gcctttccca cagggtctga    5100
gaaggccact gcagtcattt cttcccttct gtcagacata attccttggg ttggccttcc    5160
cacctctata cagtccaata acggagcagc ctttattagt caaatcacct gagcagtttt    5220
tcaggctctt ggtattcagt ggaaccttcg tacccttac tgtcctcaat cttcaggaaa    5280
ggtagaatgg actaatggtc ttttaaaaac acccccacc aaactcagcc tccaacttaa    5340
aaaggaggat agagcccaaa aactcgcaac caagctagta attatgctga accccttgg    5400 gcactctcta attggatgtc ttaggtcctc ccaaatctta gtcctttaat atctgttttt    5460
ctccttctct tattcggacc ttgtgtcttc cgtttagttt ttcaattcat acaaaaccgc    5520
atccaggcca tcaccaatcg ttctatacaa taaatgctcc ttctaacaac cccacaatat    5580
```

-continued

```
cgccccttac cacaaaatct tccttcagct taatctctcc cactctaggt tcccatgccg    5640
cccataatcc ctctcgaagc agccctgaga aacatagccc attatctctc cataccaccc    5700
ccaaaatttt tgctgcccca acacttcaac actattttac attatttttc ttattaatat    5760
aagaagacag caatgtcagg cctctgagcc caagccatca tatcccctgt gacctgcaca    5820
tatacatcca gatggcctga agtaactgaa gaatcacaaa agaagtgaaa atggcctgtt    5880
cctgccttaa ccgatgacat tccaccactg tgatttgttc ctgccccacc ttaactgagc    5940
aattaacctt gggaaattcc ttctcctggc tcaaaacctc ccccactgag caccttgtga    6000
cccctgcccc tccactaccc acccaaatcc tataaaatgg ccccacccca tctcccttag    6060
ctgactcctt ttttggactc agcccgcctg cacccaggtg aaataaacag ccttgttgct    6120
cacacaaagc ctgtttggtg gactctcttc acagggacgg gggtgacaac aacacgaca    6180 cacatggagt ggttttaagg agcagagagt ttaatacgca aaaagaagg aagaggctcc    6240 cctgtacaga cacagaggga gggggctcca agccgagaga aggaaacccc atgtgcagtg    6300
gaaaagtggt tgattatact gggaggctgg aggaggcggt gtctgatttg cacagggccc    6360
aggggattgg gttgaccagg tgtatcattc atgtaccccg caaaaaacct ggccctccca    6420
cctcagccct ttaatatgca aatgtgggtt gccatgatgt tctgaaaaca catgaattat    6480
ctggaggggg ccatgacact tggtacatgt gctgacaaga agagggtggg aatcgccatg    6540
gtggccatgt tgggtggacc tagttttttaa tagcctgcat ttgcatatca aagtttgctg    6600
gcctggctct ttaagctgtc tttttctgtta gaaaaggaat ggtttggaat gggtgagggt    6660
tgcttcttat tacaagaaaa tttccaaaaa cctttactct ttctagctgc caaaaaacta    6720
tttcttaata acttatgtat taccataatt aggcagcacc aaagatccct gcaggtcaga    6780
ccactgcaat taacatgctg gctttactgc tgattatggt agctgcatcc acctagcctc    6840
tcatattgca actgcctgac ctctgccacc ccacgagcca cttatcccca cttataatca    6900
gcccatttcg attgtaacat ctgccactta ttcccgacgt tgtggtatat cctatagatg    6960
aattcattca acatccattc caacaccacc tctcttgcct tcctatactc tctggagagt    7020
gaattactga gtcacatgat cttcactgca gtcatttgtg gctatgtgac atagttctgg    7080
acagtgaaca tagacagaag tccctggggc gggcttcctt tctgggatga gggcaaaacg    7140
```

<210> SEQ ID NO 63
<211> LENGTH: 44100
<212> TYPE: DNA
<213> ORGANISM: Homo sapiens

<400> SEQUENCE: 63

```
tgcctttatt tccgtaggct ggtcatatgg cgctagcact cacataaagc taccgaggag      60
agcgaatgaa accaaaatca ctttaccttc acagcacgag gccgtcgtcc ctctcgatat     120
ttggcccgtg tgtcgcatac cgccctctgg acgtggtgat caaataaact ccctagctcc     180
ccgccgctcg acgccatctt gcctactttg atcctcgcag ggaggacaac atccgcccta     240
ctgagctccc ttttatccaa taagagagcg ggatgagtta aggagtgcca ggattggctg     300
gagaatcgac agcgtcggcc atcgtttcct gcgtgcgaag atttgatgaa cgaggtgccg     360
cccccgagcg gctcggcgga gaggcgcggt gggtgacaga agctttcttg tcccacccac     420
tacaggctta cggcaggatg cgcagcgggg agaggggcg gggccgcagg ggcggggcc     480 gatcgatctc ctccggctcc gacgtcctcg gcctgccggg tcccgggtcc tttgcggcgc     540
tagggtgggc gaacccagag cgacgctccg ggacgatgtg gggcagcgat cgcctggcgg     600
```

-continued

```
gtgctgggggg aggcggggcg gcagtgactg tggccttcac caacgctcgc gactgcttcc      660
tccacctgcc gcggcgtctc gtggcccagc tgcatctgct gcaggtaacc tgccggcccc      720
gagccacctg atcttcagcc tggggtcgga cgaggccgaa gcctctcagg gacgcggcgg      780
gacaccggct gccacccggg cgccgccgaa gcgcgcagag atcagggtcc ctcgacggca      840
gggcccttct gggtagtctc tggatcccac aagtccagtg cagccctggg ctcgtcttat      900
cccaggtctt ttcacttggt gaaactgaac ctagaaacgt cctaatattc taccactgtt      960
tttataaata ttccttattc caggctgaaa agctcctga gaagtggttt gttttatta       1020 ttttaaaagg tgttttcctt gccagccatt ccagttaac ctgcgctgct gccgtccggg       1080
ccgcgagagc gggacgcaga gttgttggcg gagccctgt cggttcccgg ggactaagca       1140
ccgcgtccca tgagcgggaa aggttaatac aatgatggtt ctgccctgcg tcgctgacgc      1200
ggaacacagc tgtagtgtgt taggaacaca taacgtagtt aagatcactt gaagctctgc      1260
gatcagtcgc ccttctggac gttgtggtta ggatgtttca cagttctaac cactggtgga      1320
gatacagcgt ccatttttc ataattaaaa atagaggcac atggtctcac gagtttgagt       1380
gtacttatgg gggcaaaagg acggcgtatt tgaaatcctc ataaatcctg gatgcatggt      1440
acccaccagt ggctaatcta tgcaatgaat agagtttgca ataatttcaa gcatcccttc     1500
tttccacttg agttacttcc ccatacctag gggaagatat ttttggtcca ctgaaaacat      1560
gagttcagca gaatcctcct atcatcgtcg ttattatttt ttaccactaa gtagacaatc     1620
ttttggtttt tgatgggctt tatggctaga dacaaatcag tcactgtcac caagttccag      1680
gtagaagttg gttcagtgct ctgtcagctt cgatgggatt tttcaacatg tttcaaatc      1740 tgcacttaat agtaggaatg ctttcttaca gtaactctaa tttgatccta agatgtagtt     1800
gttaccttac attcatcact gtttaagaat ttagtggtct tgatctttgt tttaaatttt     1860
gagccttcgg gaagtactta taagaattaa ttcatgcata tcttttttgaa atgtaaatgt    1920 ctttagccct ggaacaaatt gctgtttctg ttcagcccat attagcagaa taggtcaact    1980
ttactttcta attatcaatg taataagttt attacttat agattccata aatctataca     2040
tttattcctc gatgaattat ataaatttat agaatttatg ttttatagaa aatttggaaa    2100
gcatggaaaa ttattaacaa gaaaataagt tacccataat cccagaactt agaggtgact    2160
aatgttgaca gtttggatca aatcttccag ttttgtttct aatctttatt tttaacataa    2220
atgaggtcct gtatacacac gtacagtttt gtgtcctggt gtttttatttt aatgttatta  2280 tgagtgtttt attttgttaa aaggtcatca ttttaagttg ttaattagta ttctagcaca    2340
aatttgccat aatttatta attgtttact atgattgacc attagattg tacttaatt      2400 ttaggcatta gaagtgataa actatatttt aatcagacgt tgaaaataac acatctttgt    2460
ttagaaaaca tcattttatt tctggttgtc taggatagat tcccagaatt cttgggttag    2520
aggccataga taattatgaa agcagaaaga ttcacaagtt gggagttaat acttgaatta    2580
ctttatttgg ggtgaagcat tgagtgcata atacagatca tgcagtaatg ggaagaaggg    2640
ttggaacaat ggttttctgg cctatgtcag acttaccttg aagcttttaa gaatacagat    2700
gttctgatca accctcagac ctattaaatc agacctaaaa tcttagggaa taggcttttag   2760 gcatctctaa ttttaaaaaa tttattcagg ctacttggat gcacaaaaga gttgagacct    2820
actgtcctag aatcatagaa ttttaatgac gatagagacc ttaagcatct aggtcgtttc    2880 tgtacttta catgtaagga aactggcatt cctaggccag taccattgcc atgcagctaa     2940
```

```
tttgccctct tgtctatagc tcactctgca tcacccaacc taccgttctc actgtttctt    3000
ctataaccaa tctccttccc acttctgttc tcttactcat gccattcttc cctcagtcat    3060
ttttcttcct tccatacaaa ttccatgtct ttaaaaagga ataatcctac ctcctccaca    3120
tagctttcca attctctgtt gcccacattt gtctcccttt caatacttct ctgttgtgtt    3180
atgtgacaca tcacatttga tatactctgt actgtgtttc aagtattgta ttctcttgtt    3240
tactcaagtc attatttcag gactgactac ccagtagatg ctttaagtca ggatttctca    3300
accttggcac tgttgacatt ttgagctgga tatttttttg tttttggggc tctcctgtac    3360
attttaagat gtttaacagc acccttggcc tctatccagt agacgcctgt actgcctccc    3420
cctatctgtg acaaccaaaa aggtcttcag acattgtcag atgtctactg aaggacaaaa    3480
tcacctctgg ttgagaacca ccgcttcaac taagttatct tctctgtact cagaacttga    3540
tgtgattgca gcaggggag aggattcata tacacagtga atgcaaacga acctaaatca    3600
ccattcggat atggccacac aattttcatt tcccttgtgt tagcaagaga tacccctaggc   3660 tttggacctg attattccta aggcattctg atgtatggtt ttacctgcag atttcctggt    3720
aatactgata cctcagtttg ggtcaaagaa ggtcaattaa ttgattgatt tgatttgact    3780
cctggaaaag acgctccttt ctagctgtct cttctcttc tttacctgaa tagccagggc     3840
tctgtggttc aagtgaagta ttttgacata aaaattaact tagaacattg gtctgcagag    3900
tttgctcaat ataactgagc acatattgtg ctttatgga gctggttact acttttttgac    3960 caaataaata attagaagta ttttttcctcc tcaataaggt tcattttttcc ttttttcagt   4020 gagctggtag agtttccttt tttgatattt cagggcatct ttcatatttc catctcttaa    4080
gtttcttcat atgaagtaga atttatctgg attatgtatt gctgactctg atgaaaaccc    4140
atagaaagca tctggggctt gatcaccttc attcttgtaa tagctcacac ggttacagct    4200
gatatggtaa cttaagactt ttgattccaa atctaggcaa atacactca gttgaaagaa     4260 tttgtcagcc agaacagttg gactgttctg tgaaaattgt gagaaaaatt acacaactaa    4320
gtgatacatg atgatggctt tcttaaatat aaaattgtaa taacatggtt aatttccagt    4380
acgttatatt gtcccagaag tggctccaac attgtttgaa atttgtctca tttaaagaaa    4440
cataagctgg ctatggtggc tcacgcctgt aatcccagca ctttgggagg ctgaggcagg    4500
cagatcacct gaggtcagga gttcgagacc agcctggcca acatggtaaa accccatctc    4560
tactaaaaat acaaaaatta gccgggcatt tggtgggggc ctgtaatccc agctacttgg    4620
gaggctgagg caggagaatt gcttgaatct gggaggtgga ggttgcagtg agccgagatt    4680
gtgccactgc cctccagcct gggtgacaga gtgagtctcc gtctcaagaa aaaaaaaaa     4740 aaaagcaaga aacataaaga ctgggcatgt ggctcatgc ctgtaatccc agcactttga     4800
gagactgagg tgggaagatc acttgagccc aggaggttaa ggctgcagtg agccgtgatt    4860
ttgccactgt actcgagcct gggcaacaca gtgagatcct gtctcaggaa aaaaaaatt     4920 gcatgtaaat gaatgaattt gatatttaat attttaaatt atgaaaactg ttctgtagag    4980
atgtagatct tgccatgttg cccaggctgg ctttgaactt ctgggctcaa acaatcctcc    5040
tgtctcagtc tcccaaagta taaagattac acatgtgagc cactgcacct ggcctaatat    5100
ttttaactta atgaatttat tttgatataa ataaattaat aacactgaag cttcctgata    5160
taataagtct ttttgtgtgt gtgacgggtt ctcactctgt tgcccagact ggagtgtaat    5220
ggcactatca tggctcactg tagcctcaac ctccctgact caagtgatcc tcccacctcg    5280
gcttcctgag tagatgggac cacaggcgta tgccaccaca cctggctgat tttttaaaatt   5340
```

```
tattattgat acatattaat aaaattattt ttatttaaaa aatgatatat gtggctgggc    5400
atggtggctc atgcctgtaa tcccgacagt ttgggaggcc gaggtgggag gatcacttga    5460
gaccaggagc ttaagaccag cctaagcaac atagtgagat cccatctcta tagaaaaaaa    5520
aaatggctag gtgtggtggt gtatgcctat attcccagct actcaggaga ctgaggtgag    5580
aggattgcta gagcccagga gtttcaagtt acagtgacct atgattgtgc cagtgcactc    5640
cagcctgggc aacagagcaa atcctgtct caaaaaaaa aaagttcga aatgcttat       5700 gatgcaatat aagtagtgga aaaggatatt aaattgtgcc tatatgaaca caactatatg    5760
aaaaacttgc acatagagaa aaggattaac aagaaataga ccaaattgtt cacatggttg    5820
tcttgtttgt ggagagaata tcagtagttc atttgtttcc ttccaagttt atatgttttc    5880
cgaggtctct ataatgagtt tgtaattgtt taatcataga aaacccttt ttggtccttg     5940 gccacaaact tacatgtttt aatgtaattg cttttttaat gagaataaat gttatatttt    6000
gcttttttaa aacctatatt cccatagtta tatgagccct tacaattatt aagaggctgc    6060
ataatataac gtttctggaa gggtacagaa gaaacagcag taattacctc tgagaacaga    6120
gacatggctt cacattttac ccttttgtac gttttgtgct tttgccacat gcatttatta    6180
ttcttccaat aaataagtaa ataaatatgg attgtatact ccatctggtt ggtgtttcat    6240
aattctaaaa ttatattgct acatttttaa agatgatatg tgtttctact tattaacgta    6300
tatgttaaaa tagtaaattt atatcttatt taataatttc cctattgata gacatttaag    6360
acagtctcaa gtgttcacta tcatagaaaa tactgcacag atagcttttg ctatagtttc    6420
ttttttcttt gaatcgttaa ttgggaataa atgctcaaat agttatatgt ggctcaactg    6480
ctatttaagt ttattgactg actgctgcca ttttgaattc tgaaggggtt gattaaattt    6540
ataatgctgc cataagaata taagggtatt ggcttcatta gcatccacca gcattgggtg    6600
ttggaaatga ttatagattt ttaaatgcta caacaaatgt agataacaga gaactatcta    6660
tagaactctt tttggacatg tgaattgtaa taatagttta ttttcatgtg aatccagaaa    6720
aatgtatacg aaaaccttt ttcctctcat ttcttatatg aatagaatca agctatagaa     6780
gtggtctgga gtcaccagcc tgcattcttg agctgggtgg aaggcaggca ttttagtgat    6840
gggggacagg taagcacatg tgatggcaat aactttcttc taatatcaca taatatagca    6900
atagaaataa aattaaaagt ttagattttt tgttaaagga ggtgagatgt cacctaattt    6960
gtatgctatt atgtaactag tctaggatat tgaagctgac tatactctgt ttttaggtca    7020
ttatcttgta gtttaccata ctccctactt gcttcttatt ctactattta actcatttc     7080 cacatcccct aattttggtt tcatgaaatt attttccctt ctgaattact aggttctact    7140
tactattatt aaactttatt tctgacatat tttataacct tccatggtct cacttgatta    7200
aaaataaaaa attcagctgg gtgcggtggc tcacacctat aatcccagca ctttgggagg    7260
ccaaggtggg cggataattt gaggtcagga gttggagacc agcctgccca acgtggtgaa    7320 acccccctc tctactaaaa attcaaaaat tagctgggca tggtggcagg tgcctgtaat     7380
cccagctact caggaggctg aggcaggaga attgcttgaa cctgggaggt ggaggttgca    7440
gtgagctgag attgcactgc tgcacttcag ctgggtgaca agagcgaaac aatgtcttga    7500
aaaaaaataa aaaataaaaa attctacaac acagggttat tattttttcca tttttgtttt   7560 cccttatgag tttaatatgt ttagattata aacctgaaag cttgaatacc tatgtctatc    7620 ttttgtttc ttatgtttat caagttattc ctttaaacat tttctaaact gtaagaataa     7680
```

-continued

```
tgtgaggctg ggctcaatgg cttatgcctg taatcccagt gctttgggag gccaaggtgg   7740
gaggaccact tgaggccacg agttcaagat tagcctggct aggcaacata gcaagaccct   7800
atctctataa aaaaattaaa aaaattagct gggcatggta gcaaatgctt gtagtcccag   7860
ctactcagca gactgaggta ggaggaatgc ttgagaccag gaatttgagt gacctatgat   7920
tatgcactcc agcccgggca atagcaagac cctatctctt aaaagaagaa gatgtagtaa   7980
taatacatat tcattataac tattttacca ttgaaagtaa aaaatgagtt tttaccttt    8040 cccagtccca tcctcagaat ggggatctca gtagaccttt aggattggaa gaatgagatc   8100
attcatattt tctgcaatta ttccccaca aaatatttca gatacctttc catgtattac    8160
aaacaatgtg catttaacat gtctctctct ttctctctct ctctgtgtgc gtcttcatga   8220
tcctctgttg cagccctgcc agtaagacac tatctcctga agaatcactg ataggaacag   8280
aaagtggact ggctaggcca ggagtcctta gcttcttagg gggcaggagc tgctttgtgc   8340
tttctcagaa tcagatatat atgtggactg aaacatttaa aaacagaata gccaagggtg   8400
ctatacgttt aaaacttata tagatggggc tacattgctc tctattacta atttcccatg   8460 acaatcacg agagtgccat gtcttttta cttgttttga gcacagacta atcttgttta    8520
tgcatgtttt ttgatgagaa taggctactc atgagaaatc tgtaaaccta acactagtcc   8580
cttgcatact ctaaattgtt gctagaatct taaaattta gcaccagacg gaccttagaa    8640
atcattaact ttggtgcttt gttctacaat acaaggagat ggaatatttt acccaggatt   8700
gcttagcagg ttacagttct gccctctgag tacccagcac ttccctgtgg gcaacatcaa   8760
cttcctgatt ttcaagtctt aattagtact ctgaagaatc ctacttgttt ttaactccca   8820
tttgctttga agtgacttta cctgattttt ttagatccct tattgcagca atgccactaa   8880
gaaactgagt ctctagcttc ttggtgggca ggagctgctt tgtgcttgct cagaatcatc   8940
cttttcagta agggagatat tgaagagaaa tctactgagg agtctggggg tgaggcactc   9000
agggaaatcc tgctccagtc cacaaaagca gagaggaagg gttggttacc tagagtattt   9060
aacatgcaga ggctttggat tttactcctt taatccttgg aaatgcctat ggaaggggaa   9120
aggaagtaag atggtgactc cagcttatag acatactagt gttacatata tttaaactat   9180
aataggaggg tattattagt tttacttaac tttcaactgt gaaggattat acttctcaat   9240
atttgtctcc agtgtctatt tcagtgtatt tttcacttt cttgaagcag catgtctgtt    9300
gcaaaacttc tagaaataat gagaatattt atatattaga tcaagccata acttgatgat   9360
atagtcattt cttcttatat ttttactta cattttaca ttttaatgat tactttcatt     9420
tttgaaaaac atgtcatgct gagatgtatt tttcttcatt ctgtaattag ttatgaaaca   9480
gtttttccta aaatgctgag tatatcaagt cttggctaag aataagtaat aaatatttgc   9540
cacatgaaag actacacata tagccaggtg cagtggcttg cacctgtttt cccagctacc   9600
caggaggctg aggcaggagg attgcttgag cccagggttt ccaggctgca gtgaactatg   9660
attgtaccac tctactccag aatgggtgac agagccaggc cccatctctc aaaacagaaa   9720
agaaagatta catagactac atatacaccc ccatccaaaa catacacaca catctactta   9780
acctaaaatg gtaagaagat aacttcttat tttctaatat atgacacaga aaagttttt    9840 taaagtagtt ttaattttt aattttttct aggtatttct caagccatgt tcccatgtgg    9900
tatcttgtca acaagttgag gtggaacccc tctcagcaga tgattgggag atactggtaa   9960
agaaaaccaa ataagaacta tctcatttaa ggttaaatta cttcacaata tcaatgtctt  10020
tagctttctc taagctttat tatatattct gagttggttt tgaattataa gaatgaattg  10080
```

```
gggccaggca cagtagctca tgcctatagt cccagcactt tgggaggcca aggcaggtgg    10140
attgcttgag tccaggagtt caagaccagg ctgggcaaca tggtgaaacc ccgtatctac    10200
taaaaataca aaaattagcc aggcatggta gtgcatgcca ttagtcccag tcacttggga    10260
ggctgaggca ggagaatcgc ttgagcccgt aaagtcaagg ctgcagtgag tcaggatctt    10320
gccattgtac tccagtctgg aaaacagagt gagaccttgt ctcaaataaa aaagaatga    10380 attgatagag atctaatgta caacctgaca actataggta ataaaattgt attggggatt    10440
catgttaaat gagtagattt taactactct taccacaaaa acacaaaagt gggtaactgt    10500
gagatgatgt atatgttaat ttacttcact atagtaacca ttatactatc tatatgtagc    10560
tcataacacc atgtcgtgta tattaaatat gcacattaaa atttgttttt taaaaaaaga    10620
attgagattt tttttaacta gatatggagt ggacaaaatg taaagtgaat tgatcttttc    10680
gtctgttggt tctaggagct gcatgctgtt tcccttgaac aacatcttct agatcaaatt    10740
cgaatagttt ttccaaaagc catttttcct gtttgggttg atcaacaaac gtacatattt    10800
atccaaattg gtaggtgcta ttgtaatatt tgctgtcata ttctacacta tagcattgag    10860
tccaaagtag aaatgaatgt gcactaatga gctttatttt ctacacagtt gcactaatac    10920
cagctgcctc ttatggaagg ctggaaactg acaccaaact ccttattcag ccaaagacac    10980
gccgagccaa agagaataca ttttcaaaag ctgatgctga atataaaaaa cttcatagtt    11040
atggaagaga ccagaaagga atgatgaaag aacttcaaac caagcaactt cagtcaaata    11100
ctgtgggaat cactgaatct aatgaaaacg agtcagagat tccagttgac tcatcatcag    11160
tagcaagttt atggactatg ataggaagca ttttttcctt tcaatctgag aagaaacaag    11220
agacatcttg gggtttaact gaaatcaatg cattcaaaaa tatgcagtca aaggttgttc    11280
ctctagacaa tattttcaga gtatgcaaat ctcaacctcc tagtatatat aacgcgtcag    11340
caacctctgt ttttcataaa cactgtgcca ttcatgtatt tccatgggac caggaatatt    11400
ttgatgtaga gcccagcttt actgtgacat atggaaagct agttaagcta ctttctccaa    11460
agcaacagca aagtaaaaca aaacaaaatg tgttatcacc tgaaaaagag aagcagatgt    11520
cagagccact agatcaaaaa aaaattaggt cagatcataa tgaagaagat gagaaggcct    11580
gtgtgctaca agtagtctgg aatggacttg aagaattgaa caatgccatc aaatatacca    11640
aaaatgtaga agttctccat cttgggaaag tctgggttag tataaatttt ataacttggg    11700
agaaatttta tgtggcttaa acatccccaa attatgaatt agaatagtat ttcatatata    11760
aattgaaaat caattaaaaa gaaacacagt gcctaaaggc acttggggga cacatttacg    11820
ctttgcagta aagtccttgt ttggataaag attgtatgtt ttctggccaa gtaagcttga    11880
ataggtacaa gcttagatag gttcaggcca gagaggtcaa aattacttgc ctgagattgc    11940
atagctagtg ttacaactag gattcaaacc caggcagatt gacttggggg ttcatcagga    12000
tggagtgccc tacaaagcct cccatctta atgcttgcag atttgttccc cagttaccga    12060
aagcaacttg ttaatattag ggaaaagggc cagtgtaggg agagatccat ggcatgaggt    12120
aaccttcctg ctgcatgtgg tggcacctgg attggaatgc atccaggagc tgcttaccct    12180
gccggtgtct gctctttaat ttgtgtataa cggagaggaa gtagacaggg caactagtgc    12240
tccagcccct catcctggcc acaaatatta atgctacctt tatatgacat aagtcactag    12300
tccatttatt ggaaccctaaa tttgaaccac tgtaaagtaa gacttcatag tgataaagag    12360
aggaacttgt taggaaagag aataaaatag aaagagaagg ttgtctcctt ttgtagattt    12420
```

```
ttttttttttc tccaacagtt ttacctgtga cctttataca aataactgac aaagcattaa    12480
tctctttggc ctacatcatt ttcttttcta tttttttttt ccacaagatg gagtttcact    12540
cttcttgccc aagctggagt gcagtggcat gatctggctc actgcaacct ccgcctccca    12600
cgttcaagtg gttctcctgc ctcagcctcc tgagtagctg ggactacagg catgcaccac    12660
cacgcctggc taattttttg tattttttagt agaaactggg tttcaccatg ttagccagcc    12720
tggtctggaa ctcctgacct caggtgatct gcctgcctcg gcctcccaaa gtgctgggat    12780
tacaggcatg agccactgct cctggccggc ctacatcatt ttctaaagct ccagaccatt    12840
cttttctttt cttttctttt cttttctttt ctttttcttt ctttttcttt cttttttctc    12900
ttctcttctc ttctcttctc ttctcttctc ttctcttctc ttttctttt tttttttgag    12960 ttagaagctt gctttgttgc ccaggctgga gtgcagtggc accacctcca ctcactacaa    13020
cctccacctc ccaggttcaa atgattctcc tgcctcagcc ttcagagtag ctgggactac    13080
aagtgtgcgc caccactcct ggctaatttt tgtatttta gtagggacga ggtttcacca    13140
tgttggccag gctagtcttg aactcctggt ctcaagtgat ccgcctgcct cagtctccca    13200
aggtgctggg attacaggcg tgagccactg tgcctggcct cagatcatta ttttctgtta    13260
gctttaaact gtccgttcag gagatcccac tgcatcctca aattcaaaat atctaacact    13320
gagcttatga tttagctggt tctgtcatta gatgggaata tccttttatt tccttgaaat    13380
tatatggtga gaacagggag aagtgctgat ggtaaagtcc tgtgattaag atagcaataa    13440
ggactccgcc cttcccactc cactgaaggt tgaagagcca tggacaatga gaagtcacag    13500
taggtgaaat caggtactaa aatggacttg gcttgagaga tcaaaattga tcacttggtg    13560
atacaactaa caaattcatg ttaacttgaa cctttattac cctgtgaagc atggtgatta    13620
aaaaaaaaca acaaacaaac aggaaacttg attgttaaat tctctttaag tcagaatatg    13680
taccttagag ttttttattta tgcttttgtc taccattaat atgtctgcac ctgctcttta    13740
gaagttaata gagagtaaag tcgtctttat gtctttcagt gcttacttat atttgggaag    13800
ttgagaaaaa ttttaacat cattattgat atatatat atatatat atatatat    13860 atatatatat atatatatat atagataatt tttttttttt tcttgagacg gagtctcact    13920
ctgtcgccca ggccggagtg tggtggcgat ctccactcaa tgcaagctct gcctcccagg    13980
ttcaagcgat tctcttgcct cagcctcccg agtagctagg atacaggctc ccaccaccac    14040
gcctggctaa ttttttgtagt tttagtagag acgagggttc accatattgg ccacgctggt    14100
ctcaaactcc tgaccttgtg atccgcccac ctcggcctcc caaagtgctg ggattacagg    14160
cgtgagccac tgcgcccggc tgaggtaaaa tttaaagtgt acaattcagt cattttagt    14220 atatttatac tagttgtaca gccatcacca caatctaagt ttagaacatt ttcattaggg    14280
ggtgggagaa attttactct gcttttagga ttaagtttct gtctggatct aatcatttaa    14340
tcagacaatc aggcagattg tctgtgatta gttttggcca ttccagcttc ttcattggtt    14400
gttaactttc acaaataaag gctgctcaaa gattagaaat aacatttaat ttgaatgtaa    14460
atgtgccata gtttaaaaga tgggtttggt gaatacagtc aaatacatac atttaaagct    14520
ctaattctga agattatgta aagaaaagga agaaatgta gggagaggat tgaaatgttc    14580
atggtataac aatatctgaa catccatctg gtcacaccgt tggtatttga atgttttgtc    14640
ctcctcaaat tcatatgtcg aaatcccaac tcccaaggtg atcgtattag gaggtgtggt    14700
ctttgggaag tgattaggtc atgaaggtga agccttcatg aatgggattc gtgctcttat    14760
aaaagagaac tgtgagaaat aagtttctgt cgtttgttag ccacccagtt taggatattt    14820
```

```
tgatatagca gcctgcatgg actgagacaa ctatgagtta ttatgatagc ttctgttatt    14880
tcacctaaat tcatagaagc taatatatca atatttatgc tatgaaatat ttcttaacca    14940
agctttgaat atatttatat ttttgtttat tttttaaattt cagattccag atgacctgag   15000
gaagagacta aatatagaaa tgcatgccgt agtcaggata actccagtgg aagttacccc    15060
taaaattcca agatctctaa agttacaacc tagagagaat ttagtgagtt caaatatata    15120
tgttacatca aaattctttt acacgttttg taagatttct agttgcttta gctaagtaat    15180
aagaatgttg tattccttttt tgatacaaat cttttttttat tgtgttaaac tatatataac   15240
ataaaatatg ccatgttcgc catttttaag tgtataattc aaaggcatta attacattca    15300
taatattgta caaccatcac cactatctat atccagaact tttccatcac cccaaagaga    15360
aacttggtac ccattaaaca ataattcccc gtccactcct ttccccagtc cctggtaatc    15420
tctaatgtat attgtgtctc tatgaattta cttattctag atatttcata tataagtaga    15480
agtatgcatt tgtcttatgt atctgactta tttcatttaa cataatgttt tcaaggctca    15540
tctgtgttgt atgtatcaga atgttattcc ttttcatggc tgaatactat tccattgact    15600
gcatatacca catttgttta tccattcatc tgttgatgga cacttgggtt gtttccacat    15660
ttttggctgc tgtgaataat gctacagtga acattggtgt acaagtatct gtttgagttc    15720
ctcttttcag ctcctttggg atatacctag gaattatgtt taactttttg agaagctgag    15780
aaatctttaa taaatgataa cacaaatact tatatttgcc aatgcaaata tgaatatttt    15840
tggcttttaa gagattgatc attttgccac gtggttgtaa ttaaaaaaaa ttgtcccatg    15900
ttgtttcagt attaatattg tagcctaaaa gagtgctaga ctgtttttact ttttactcag   15960 ttaattcttt ggatactggt agagtcagga aatgagatat tgaacttaaa gatctttgca    16020
ggtggggtcc agtggctcac acctgtaatc ctagcacttt gggaagctga ggtgggagga    16080
ttgcttgagg ccaagagttt gagaatagcc tgggcaacat agcaagaccc catctctaca    16140
aaaaaattaa aaaaaaaatt aagccaggcg tggtagctca cgcctgttat cccaacactt    16200
cgggaggctg agatgggtgg atcacttgag gtcaggagtt ggagaccagc ctggccaaca    16260
tggtgaaacc ccatctctac taaaaatacc aaaattatcg gggcgtggtg ctaatcctgt    16320
aatctcagct actcaggagg ctgaggcagg agaaccactt gaactgagga ggtggaagtt    16380
gcagtgagcc tagatctcac cactgcactc cagcctgggt aacagagcga gactctattt    16440
caaaaaaagt aaaaataaaa attagacaca tgtggtggca catgcctgta gtcctagcta    16500
ctcaggaggc tgactgaagt gggaggatct cttgagccca ggagttccac actgcagtga    16560
gctatgattg tgccactgca ctccagccta ggcaatatct caaaaaaaat ttttttaaat    16620
agattattag ccagacgtg gtggctcatg ccagtaatcc cagcactttg aaggccaag     16680 gcaggcggat cacctgaggc caggagtttg agaccagcct ggccaacatg gtgaaacccc    16740
atgtctacca aaaatacaaa aattagctgc aatgtctata atcccagcta cttgggagcc    16800
tgaggcaagc gaatcgcttg aacccgggag gcagaggttg cagtgagtgg agactgcgcc    16860
actgcactcc agcctgggcg atacagcgag attctgtctc aaagaaaaag gaatttgttt    16920
tcctgtcttt atcgtagagg gaggaaaggg agaatgggt tggaatggtt attgagtgag     16980
ccacattatg gtagatgtat cactgggcat agagaaaagg agcatttaaa acttttccgc    17040
ctaacagatg tttcttcagg ctacactgca ctcattgtgc taactgtaat gtcaaatccc    17100
agacctgtgc ctatagaaca tgaacatcct tcattggatt tgtttggtca ggcttacact    17160
```

-continued

```
ttattaggaa gatcagatgt taaaataagg gtgttaaagt taagttcaga tatgaggata    17220
attcattact attcctttt ctggcagcct aaagacataa gtgaagaaga cataaaaact    17280
gtattttatt catggctaca gcagtctact accaccatgc ttcctttggt aatatcagag    17340
gaagaattta ttaagctgga aactaaagat ggtgagtaca tttgttattt tgactttttt    17400
ttctatttaa atagttgtac attttaatt gttcttgcaa cctgtcatac ctgtgaacag     17460
tatgtgaata gtgaaatata attatgataa ttaaacagta gttttatgt attgaaaaat     17520
atctttggcc gggtgcagtg gctcatgcct gtaatcccag cactttggga ggccgaggca    17580
ggcggatcac ttgaggccag gagttcgaga gcagcctgcc aacatggcgc aaccctatct    17640
atacaaaaaa atacaaaaat tagcctgaca tagtggtgta tgcctgtagt cccagctact    17700
tgggaggctg aggcagaagg atcacttgag cccaggaggg ctgtgttcct gccactgcac    17760
tccagcctgg gcagcagagt gagaccctgt tgggggaaa aaaaaaaaag tctttaactt     17820
aaataaattt gacatttaaa atcttaaatt atttcatctc tgtttcagta ctaactctgc    17880
atttattact ttctttttaa taggactgaa ggaattttct ctgagtatag ttcattcttg    17940
ggaaaagaa aaagataaaa atatttttct gttgagtccc aatttgctgc agaagactac     18000
aatacaagta atagcatgtt attgaatatt taataaaata ctatttgtta catatgattg    18060
ataataaagt atgaagttcc ttgtaacacc ttgcattgtg aagtgtatta aaaacctgct    18120
aagagtaagg aataacttga tttaaaatat tttattctgt aatctcttta aattatctgt    18180
acaaattatt gacttaacct aaatttaaaa atgaatgcct tagcacaatt aagttccaag    18240
aatagagttg atcatgttaa ctggtaaatg gatcatgatt taaaattctt ctaggattga    18300
aacaaatgaa aacgtagttt taagggtttg atttttttaaa ttcctatttt tacatgcaat   18360
tttactgcac aacccatctt attttgacag ttcttaaatt cgcaactctt cagaaatatt    18420
atcagatcac ttttctttgc ttccataagt ttttttatta ttatattatt attttttttt    18480
tttaaaagac ggtgtctcac tttgtcgccc aggctggagt gcagtggcat gatcatggct    18540
cactgcagcc tcgacctccc aggctcaggt gattctccca cctcagcctc ccaagtagct    18600
gggaccacag gcgaatgcca tgatgcctgg ctaattttg tatgttttgt agagataggg     18660
tttcaccatg ttgcccagaa ttgtcttgaa ctcctgggtt caagcagttg ttctgccttg    18720
cccacccaaa gttgtgggat tacaagtgtg agccactgcg cccagctatt ctagaagtat    18780
tttaagagtc atctttttt tttttttgag atggagtctc actctgtcac ccaggctgga    18840
gtgcagtggc acactctcgg ctcactgcaa cctccacctc ctgggttcaa gtgattctcc    18900
tgcctcagct tccctagtag ctaggattac aggcgcatgc caccatgccc tgctattttt    18960
tgtagtttta gtagagacga gatttcacca tgttggccag gctgctcttg aactcctgac    19020
ctcaagtgat ctgccctcct cagcctccca agtgctggg attctaagtg taaaccacca     19080
cacccagcca agagtggtct ttttacaata ttatttttg attaggacat tcattcttgt     19140
cataaaattg aagatactct agtcatttag aatttcattg ttttggaact agacattgtt    19200
tctttatttt tgaaatgtta ttgaaggaat accatttgga gaagatacaa atgtaagaat    19260
tgtgaaaagg ataattgtga cacaaatcaa aattatagat aaaaatatac ctgtaaaatg    19320
tattaaggca ataacattct ttctgcttgt tgaccataaa tatttatatt ccctggatgg    19380
gtacattgtt attgtcaagg gtgtttaaat aatgatcttg catgcataat ttattctctc    19440
tggtataaca gaatcagcaa tttagttttc tgggacccga gaaaaacatg caaaagacat    19500
actttgaaat gtaaaactga tttttccttg caactgtagg tccttctaga tcctatggta    19560
```

```
aaagaagaaa acagtgagga aattgacttt attcttcctt ttttaaagct gagctctttg    19620
gggtaagaag ttatggccaa actagcatgt tagacatgtt tttaacacta tatctggcag    19680
agttttcaat gtaaatatta aagtagatgt taatgtcaat aagtgatctt aataatgcat    19740
cagtagatat tttttcaagg attgtctcta tcttcacgcc tagcttataa tttgccttgt    19800
cgtctttttt tttttctctt tattttatg tttttatcca tccctggtgg taggggataa    19860
ccttgtcttc ttcgataaca agaagtctga agcttattag aaattttact ttgagaattg    19920
atcgatgaga agaaagcaac tagatatcac gtggatcata tatgcttgaa taaaacaata    19980
attcttagaa caaataaata cattttaaaa gttaaagcca aaaacattag ttgaatgttt    20040
aaaaatattt caaattaagt tattccttca ctgtcttgta ttactgtaat aatttggatt    20100
atttgtgttt ttctcaactt ttaaaacaaa tatttaaaaa attcctcttt tgattaagta    20160
gggctagata aaatataaaa aatattttt aaactcctct taatttccat atttcttata    20220
taatatgaga atctcttata aacactacct cttagaagtc tccacagaag ctttggtaga    20280
tgtagtagta gggatttgat ttcttagaat ggtataatct gtaaatgttt tagtaaaagg    20340
attaaacgat aaagtcaaaa tgtttatagc acagtgttta ttaatataaa ataaaatctc    20400
tttttttttt tttgagatgg actctcactt tgtcactcag gctggagtgc agtgttgcaa    20460
tctcagctca ttgcaacctc cgcctcctgg gttcaagcaa tccttccgca tcagcctcct    20520
aagtagctgg gattacaagc atgcaccacc acacctgcct aatttttgt atttttagta    20580 gagatggggt ttcaccatgt tggccaggct ggtctcaagt gatccgcctg cctcagcctc    20640
ccaaagtgct gggattacag gcgtgaacca ctgtgcccag cataaagtaa aatctcttca    20700
gactctcatg tgatcatgta aagtggcagg cagtcacagt caagaagtag tttaaagttc    20760
atgtttgtaa aatataatct acagattgat actggatttc ataggtaatg tttaagagaa    20820 aataagttttt tagttatcct cagtacttca aaagcaccca tttatgatta tgttgattac    20880
taaactaaat catttggggg ctagaggtgt ttttttatgt gttaagattc cttaaggagt    20940
tctattaggg caaaactttt agtaactgca tattttaaaa gtaataaaac taattttaaa    21000
agcttggagg ctgggcgcgg tggctcacac ctgtaattcc agcactttgg gaggccaagg    21060
cgggtggatc acttgaggtc aggagtttga gacgagcctg agcaacatgg tgaaaccttg    21120
tctctactaa aaatacagaa attagccagg tgtggtggtg ggcacctgta atcccagcta    21180
ctcgggaggc taaggcagga gaattgctcg aacttgggag gcagaggttg cagtgagccg    21240
agatcatgcc actgcactcc agcctgggtg acagagcaag actccgtctc aaaaaaaaaa    21300
aaaaaaaaaa gcttgaagtc agattcgaca ttaatcagta tactttctct caagtagggg    21360
acaatttcta agattttagt cttttaaaat ttattaacta gtctgagcat ggtggcttgt    21420
gtctataatc ccagcacttt gtggggccga ggcagatgga tcacttgagc ccaggagttg    21480
gagactagcc tgggcaacat ggcaaaaccc cgtctctaca acaaatgcac acacaaaaaa    21540
cccaatcagc tgggtgtggt gttacactcc tgaagtccca gctactcggg aggctgaggc    21600
aggaggatca cctttgccag ggcgtttgag gctgcaggga gctgggttca caccactgcg    21660
ctccagcctg gatgacacag caagccccctt tctcaaaaaa aaaagataaa aaattaaat    21720 taaattaatt aactacactg ggaaggcaaa attcagcatt tttttatagc taaatttat    21780 cctgcttcag tcttttatca tgtaactatg tatattttt acagaggagt gaattcctta    21840
ggcgtatcct ccttggagca catcactcac agcctcctgg gacgcccttt gtctcggcag    21900
```

```
ctgatgtctc ttgttgcagg acttaggaat ggagctcttt tactcacagg aggaaaggta    21960
agtggttaag gtgtgttcat ttttctgtaa catttaataa cttttcattt atctttcttt    22020
gggttttgac catctattat ataggGtggg ttttgaccat ctattatata ggGtttatac    22080
gacatatgga aagcattcat ttattcacta atatttctgt gtgtctgctt ttaggtgttg    22140
ggggagtgat gacgaataag actgatgttc tccatgccct ttttctgtgt cagttgatac    22200
aattatatgg ttttctttt ttaggctatt aggtgttgat agggttgagt aacttacaaa    22260
tgttgaacca gccttgcata cctgtgataa ataccacgta gttgtggtgt atcattcttt    22320
ctacattgct gagttttatc tgctaatgtt ctgttgagct tttgtccatt taagtttgaa    22380
agtgattagt ttgcagtttt ctgttttttgt gttgtctttg tctggttttg ctatccgtgt    22440
aaatctggcc tcataaaatg agatgggaag tattctctcc tcttcttttg ttttttttgga    22500 agaggttgta taaaattgag gctgaatctt ggtggttgcc acaatgacag gaactatttc    22560
tgtgactgaa tatattggga attcctataa agcaattatt ttctagggaa gtggaaaatc    22620
aactttagcc aaagcaatct gtaaagaagc atttgacaaa ctggatgccc atgtggagag    22680
agttgactgt aaagctttac gaggtatgag tatggtaaca ctctatataa atcccttttt    22740
cattagaaag acaggaatgt tatacataat gctgtcaatc taataaatac acatatcatc    22800
tagtctttaa ctttctgtt tatcatttag tcattaaaat ttcttggct ttctaatgtt    22860 tttgataaaa tttctaaaac tctccatatt taatggaggc ctattttttt ttctagccag    22920
aactttttgt agactacatt tctggaagtg ctcactgaca ccactctgaa aaattagtac    22980
ttagaatata ctctaattgg tataaatgat ctctgaattg ctatggaaaa ctgggagaat    23040
ggttgcttca ggggagagaa agtaggaggc tgtggacagc aatgaggaga attacagttc    23100
accatataac acttttgtac ttttaaagtc cttaacattt acattattat ctattcaatt    23160
aaaaaatatt gggaagattt tactttgaac agttaatttt tcccccatgg gtaccgctgt    23220
catatagttc caactaatca tgaacttgtg tatttcctgt tctttgtaaa tttaaacttt    23280
gtaactcacc aggaagtttg aagccaaatt tgtgtttcaa atatagcaac tccaggatct    23340
ctaggcagat gcatttgcat ttgatttta atgaatcttg atcccttact ctcacttatg    23400
ttttcccaca tcctactttt tttattttgt tgtaagccat ctaaaattct caatgggatg    23460
aaactgggta taaatgaata catgcataca ggaattatag tagcatattc cttttctttt    23520 ttctttttt tttttttga cacagagtct tgctctgtag cccaggctgg agtgcagtgg    23580
tgcgatctcg gctcactata gcctccacct cccaggttca agcaattctc gtgcctcaac    23640
ctcccgagta attgggacta caggtgcatg ccaccacacc tggctaattt ttgtattttt    23700
tagtagagat ggggtttcac catgttggcc aggctgatct caaactcctg acctcaaagt    23760
gatctgcctg ccttggtttc ccaaagtgct gggattacta gcataagcca ctgcacctgg    23820
cctccttttc tgagttttat aaaatttgat acttactgc acgctttgag actgtattaa    23880
ttgaaccatg ttgatgaaca agttttgtg atgggtatat taataaaata tagatcaaat    23940
ttttatagtt aaatcaatat cgagcttttc tagtgctttc aaaaggacaa cctgaatttt    24000
cccagcactg aaatgatact gaaaccattt catatcttct gtattaagga aaaggcttg    24060 aaaacataca aaaaacccta gaggtggctt tctcagaggc agtgtggatg cagccatctg    24120
ttgtcctgct ggatgacctt gacctcattg ctggactgcc tgctgtcccg gaacatgagc    24180
acagtcctga tgcggtgcag agccagcggc ttgctcatgg taaatgcatc caccactggc    24240
ttaaggtctt gttctttttgt cagtcagcat ttttagtctt aacaataaat ctactctctt    24300
```

```
cagagaataa tatatgtgtt atgttaagtg ttgtgtttga ggccctgat ggcattctac    24360 agttgtccta tagactgtaa tagcaaaatt ggtagagtaa aaacagtgtg aaaattctgc    24420
aacttcatgg ttagtccttt agggttttc attctcccctt acttattgtt taatttacag    24480
atttactctt ttgttcattt gacaaatatt tgtcaaatgc ttgtgcacag tctgtattct    24540
caaattctag gagaaaaaga agggtgaaca gtattagcgc agaacgatac taataatgat    24600
ggctactgtg tatgagtagc cagcccttttc ttggctttct tggattgctt tgtattctac    24660
atgaagatat tccctgggct ttacaggtca ataaatggaa attcagagag attaatttga    24720
ccagggtgac caacaaggag atgacagcat acactatgcg agaagtatac acagagtagt    24780
gtaggagcat ataacctaaa ctgggggtga ggtgggataa ggagttatca gggaaggctt    24840
tttggaggag ttgacaactg agccgagttt tgatggaaga gtagaaatta gcatgaacca    24900
atttcatgct aataaagaag caaggaagc gtggtctaca ggcaaaagca cagaggtaca    24960
ggaagtaatg atatgttggg gaatacctg ttgactggag cttagagtgc aaggagagga    25020
gtgctaggga ggtgaggttg gagggtttgg cagcattgac ttgcttcaag gttcttaaga    25080
gctgaaatag atataaaatg caactaagag tggcttggat tattattacc tagtgtgtta    25140
atctcaaatt ttgaaatcta tagcatctat aggactggtg ttactaatct tacactcgat    25200
ctgttactgt tcttatacta gatctattag tccagtgttt aagggagtgg tgcagatttc    25260
taggtcagga caggactcag atgtacatta ttaatgccta tttcagttct gaccttctca    25320
tatgaaacct tataagacct ggggtaggaa gagattgttc tggaagtcat aggaaatgaa    25380
actgtatttt gtttaacaaa caatacagta tggaaattta tcacccttcc agaatattta    25440
tttcagagac aaatttttat cattcgttca tttatttcat aagatccacg agtagggaac    25500
ctcactagac attgctctga gtatatggtc tgagtttgca gtacctcttg tgtctccatt    25560
agatttatta ggtcctcaat agataaatca gggaataact agatggattc attttttaaa    25620
gacatgaaag agcgatacca tacatactgc accttaaagg tcaaccttag agtatcatta    25680
tttttaatga atgtataatt tttaaatttc atgtttactt ttcctaagct tttgcactat    25740
attgcttaat tccagctttg aatgatatga taaaagagtt tatctccatg ggaagtttgg    25800
ttgcactgat tgccacaagt cagtctcagc aatctctaca tcctttactt gtttctgctc    25860
aaggagttca catatttcag tgcgtccaac acattcagcc tcctaatcag gtaatacact    25920
acttgtaagg attattgaat tatgtcccctt ttatagaaat tatttttcaa ttttattagt    25980
aattcgtggc tttaaattta tgcttctctt aatgatttta aggatatgta agtcaacatt    26040
tggtgcatat tgtgctagag gcataaatta taatttatag ccacctgaaa tgttagtatg    26100
cgctttccaa gaaaatgact ttttgaaaa tggtatttct ttgaatgaga aagaacagag    26160
agaaatagat agatggcttt taaacacttc attaattaaa cttttttttt ccaccatcac    26220
ataatggcac ttagtcccct tgggaactc atgagggttt tagtggtagt gagctgaaag    26280
aaatatgttc caggactggc aaacatattc taaattcttt aaaattttca cctagcatct    26340
accctaaata ttcagaccct gtgctagtta actgctattg aagaacaaag gtattatatc    26400
tattattaag gataatagaa tggtatttga gatattggtc attgaatatg aatatgtttt    26460
gagaaataag tttataggaa ccaaaaaaa aattcttaaa ggaaccatat attactaaaa    26520
atgcttctta ttggagaaag aaatgacaat catttattaa tgtgattttt tcacaacttt    26580
attaagatat aatttaagta caacaaactc acataaagtg tacaatttga tcagttttaa    26640
```

```
catatgtaga tgccatgaaa ccatcaccac aattaaggaa acaaacattt tcatcactcc   26700
agaagtctcc tagcccttttt actacccatt cctccctgc  tccatcccca gacaactacc   26760
aatttgcttt ctgtcactat agatttgtca acctgatttt ctccaaatat acattcaaaa   26820
atatacagtt gaatacaatt ggaaattcga attttgtgtt tttttcttta ggaacaaaga   26880
tgtgaaattc tgtgtaatgt aataaaaaat aaattggact gtgatataaa caagttcacc   26940
gatcttgacc tgcagcatgt agctaaagaa actggcgggt tgtggctag  agattttaca   27000 gtacttgtgg atcgagccat acattctcga ctctctcgtc agagtatatc caccagagaa   27060
agtatgtttt actattaaaa cctgaacttg gaatcttctt tctattgtgg agaaatgtaa   27120
ttgtagtaag acaagaatta aatatattcc attgtagtat ttgaataagc agttatttga   27180
gtagaaaatt agtgtttcca gctaagatga tggcatattt tgaaaattca tatagtgaat   27240
ataactagta aaagaagttt tgtttatttt taaacagaat tagtttaac  aacattggac   27300 ttccaaaagg ctctccgcgg atttcttcct gcgtctttgc gaagtgtcaa cctgcataaa   27360
cctagagacc tgggttggga caagattggt gggttacatg aagttaggca gatactcatg   27420
gatactatcc agttacctgc caaggtatgt ttaaaaaaag aaaaagtgaa tacttactcc   27480
cagaagaacc actgtattat tggctttggc tttatgtgtc agcttgccca atctccgtgt   27540
gagtcaacaa gtgtttactg agttaccaaa taaatgtctt aacactattt taggtacttt   27600
aacaaatttt aattttatta attaattttt tattagaatt gagacctcac tctgtcatct   27660
aggctggagt acactcacag ctcactgcaa cctcaaactc ctgggctcaa gcaatcctcc   27720
tgcctcagcc tccccagtag ctagaactac aggcatgaac caccatgccc ggccaactct   27780
ttaattttct tagagacgga gtcttgctat gttgcccagg cagacagatt ttaatgtgta   27840
tgatgcagtc tttgatgata agaaacttat aatggaaagc tgaggtgata gttacagtaa   27900
atacattttg atgtataatt ctgtttgctt taatcattca aattgtagta aagcaagatg   27960
aactgtctgc tgggatttga gcagaaatgg ataggaataa actaggaggt agaagagtta   28020
tcaaggttca caggactgat gggtgaagct agatttccag acccgggatg tcagtccttg   28080
aaaagcagac ttggcaggca tagacgaggc agatagcagg ataaaggaga caaatgtaga   28140
ttgttcttca gaagatcaga tggtagagtc taggaggtag tgtgttttaa tcagagatct   28200
gagaggcaaa gatcattgca tgagatcagg gacccatgca aaggagtgag aaaaaaaact   28260
gggttaagga gcctgctgca tggcaactcc tgggaacagt ggccactggg gcctgggaca   28320
tgttgattgc agcccaggac tgttaaaacc agtgtgagag aacatgggta tggaagtact   28380
agctagcagg atcatgaccc cgatgctggg atggggcatc aagcattagt acatggagat   28440
tcagtacatc cagatgcagt acatggagac tatatgcgta actgctgact ttgggcttct   28500
ttcagattgg agcagaggta gaggtgagtg ggaatattct caatagaggg aactaaatag   28560
gcatacctaa taaggagac  caggatattg cagacagtag cctcatgttt ggctcacctg   28620
ttcaaaaagt tctcttgttc ttgagcagtg gtgccttaaa aggtaacttg agaagcagtc   28680
gattatttgt tcagcctgga gactcttggg atattttact atctttgatt gaatagattt   28740
aaatgtacac agctctcata acttgcccca tgaagcatat ccatgaaagg cactatactt   28800
gttaaaagat tggtttgtac ttttttaaatg tagtactttt aataaaacag gaaaaataga   28860
agttctgatg cagttatatg catttatat  agaatgtgtt cttaattgga aaaaatttgt   28920
cgtagttcct ttgagttcat ttacagtttt tagtaggaat tgtattttct actgttgtac   28980
ttgctgttac taaagaaaga tggtcgtgat taccatctga attttttttc tatacattga   29040
```

```
tctttagctg ctacttagtc atttctgttt agacttgagc tcttttcat atttttttt      29100
tttgtttctc agtatccaga attatttgca aacttgccca tacgacaaag aacaggaata    29160
ctgttgtatg gtccgcctgg aacaggaaaa accttactag ctggggtaat tgcacgagag    29220
agtagaatga attttataag tgtcaaggta tgttgtctac ttatcttctt tttttattta    29280
ggtaaaatta acataaatgc agttagccat ttcaaagtgt aaattcactg gcatttagtg    29340
cattcacaat gctatgcaac caccacctct ctctaatttc aaaactttt cattccactc     29400
ctcctcttgc ttatcccctg gcaaccattc atctgctttt tgtctctatg gatttgcctt    29460
ttctgtatat ttcatataaa acaaatcatg caatatgtga ccttttttgt ctggcttctt    29520
tcacttatgt aatgttttca tggttcatcc aggtagtagc atgtatcagt acttcattcc    29580
tttgcatgac tgaataatgt taccatactt tgtttatcca cttatcagtg gtgaacattt    29640
gaattgtttc tacctttga ctattatgaa taatgttgct gtaaatattc atgcacaaat     29700
ttctccacgg atatgttttc atttctcttg ggtataaact gaggagtaga attcttgggt    29760
cttagggtaa ttctctaact tttcaaagaa ccaccaaact gtctttcaca ccaactgcac    29820
cattcccact agcagtgtgg ggggttcctg attctccaca tctttaccaa caccattatg    29880
tttctcaatt gtgggctagt ctcacatttg gaaagctagt gggagcagcg atccatctat    29940
taaaagttgt atgaaattga gtaatgagcc acctctctct tgtagggctt attatgttct    30000
tgcttaaggc aatcttcatg cattgtgaac agaattatac ataaatgctc agataaaagg    30060
gcaaaccatt cttaaaggga gtagacaact agaggcagga gaccatactg aggcaggaag    30120
ctggggtttt tatggttctg ttactttga ctatatctca ccattgcttt tgtcaaagtg     30180
agactaggtc taagttttt tcaggtataa ggtgagtgtg gtaattaagg ggcatgctag     30240
cagatcattt tgggtaatgc ttcacagtcc accactggtg tgtcattgtg gtcgcagatc    30300
cagtatctta gctgtgtaat ttcagacatc agcaatatta gtttaacaaa gggcaattag    30360
attccaagac aaaggaatcg tgtattattc tagccttatt caaacttgat ttataaatca    30420
gtttagtaat ttatttattt gtttctgtat ttatttttat ttctttgaga tggagtctca    30480
ctctattggc caggctggag tgtagtgatg caatcttggc ttactgcaac ctctgcctcc    30540
tgggttcaag ctattctcct gcctcagcct cccgagtagc tgggattaca ggctaatttt    30600
tgtattttta gtagagatgg ggtttcacca tgttggccag gctggtcttg aactcctgac    30660
ctcgagtgat ctgcccgcct tggcctccca aagttctggg attacagacg tgagctaccg    30720
tgcccagctc agtttagtaa tgtataactg ggttttaccc agttgtaaat tactcttttg    30780
tcgtgttttt ttgagaactg gcaatgacgg agaaactaaa agtgccaggc tgttgccttg    30840
ttcctgttat tttgccttag tttttttttt tttttttttt ttctctgaga ctgagtcttg    30900
ttgtgttacc aggctagagt ggagtggcat gatctcggct cactgcaacc tctgcctcct    30960
gggttcaagt gattcctgcc tcagcctccc gagtagctgg gattacaggc gcctgccacc    31020
gcacccggtg aatttttgta tttttagtag agacgggatt ttaccatgtt ggccaggctg    31080
gcctcgacct cctgacctca tgatccacca gcttcggcct cccaaagtgc tgggattaca    31140
ggcgagaacc accgtgcccg gtcttgcctt agttatttct tgttccctcc tctagtccta    31200
tagttctctg actgtattga ggaaatgtaa ttaaatatta ttatgttaat agatatttat    31260
gtggttgaat attagaaatt ccttatttg gtcacatatc ctgatcagta gttggtcttc     31320
tggagatagt gattttcac tagagatgac tttaggacct attcaggttt ttttttaagat    31380
```

```
cccaatttaa ggaaagacta ttctcattat tgattttgct atatgcaggg aaatttattt    31440
cgaaaggttt ttcagttggc ttttagggaa gattatatat tctctttttt ttttttggc    31500 cttttcccac atgttctaaa aatgatatat tctttaactc ctatgaaaat acattgtttc    31560
agtaattgaa gatgctgatt aaagtcatat ctctacacat ttttttaaaat ttgagataga   31620 tgggactttg tcccttctta caccattcac ttattcactt ggaaaaacta ttatccaata    31680
cttatgtggc agacactgtt tctggcacaa gggattcagc agtgaacaaa actgccttt     31740 tggagtttac attctactag tggaaagcga caacaagcag atagacacat tcagtatata    31800
attcactgtc agatggtggt ggtaagtcct atgtaggaag aaaagcaggg taaggaggct    31860
tggagtaact ggagtgagtc atagatggac ttgtcaggaa agggtttctg aagaggtggt    31920
atttgggcag agatctaaat aaaatgaagc aacaagccat gagaatatcc ggggaaaat     31980 gttctgggca gaagcatcaa gcatagaact tgtggtatga tatttattct agcacacatt    32040
aattttaaaa atgtataaaa gacatccatt taatcatatt aaagatttcc atgattcatt    32100
tagacttagt cagaaaccaa atttatattt tcttttaaa aattttatc tcaactctta      32160 ttttacccaa taggggccag agttactcag caaatacatt ggagcaagtg aacaagctgt    32220
tcgggatatt tttattaggt tggtagccta tgaatgtttt taaagtaact gactctgtta    32280
ttatttatca atcagtgctt tttttggtct tgttttttga agaactgata tttgaaacct    32340
gtggtttatg tgaattatta ataagctaga ggacgtggat tctctatttc atcaaataat    32400
acaaaacatt ttagatatta aattttggaa attatttggt tttgttttac aatagaaata    32460
ctcctcaaag tggaatcgaa gtggttattc aaagaaatct cagagtagat tcttatatga    32520
agcaaataat tgcccctaat ttatctctaa attttgtaag ttctaaattc ttttttcccc    32580
cagtttctaa tttatctctt ataagtcaag agtccatctg gccaatttaa tttcagtgag    32640
tgtaactatt ttgcatatat taaaaaactg tatatgaata cagaagatgg tatttaagga    32700
tgaaaataat tattcaaatg tgatagcatt atggggagtt ttaaaataaa agttactgtt    32760
ttattcttcc aaaaatttta ttataaagta tacagttaag agaatataca taaaatacat    32820
atgcagctta aggaagaata ataaaatgaa tacttcatgt attcaccacc gagtttacca    32880
ggaaaaagca taaacaaaat aaacctcttc cacgtaattc ctgggttaaa gagaagttat    32940
agtggaaaat atttgggagc aaacgataat gaaaatacta tccattaaaa ttgttagatg    33000
ttgcaaaact gatttcaagg aaaatttata gtgttaaatg tttagaaaag aaaaaaggtt    33060
agaagttaac cacttatgta tctatctcat gaaattagga aaattataga tataaactaa    33120
aaaatatgtt aaaagggaaa taataaagat aagaatgaag tttaatgaaa cacaaaacag    33180
agaagctcac aaagccaaga tttattttt gaacaccgag tacaattgac aaatctctaa     33240
caagtttgat taagaaaaaa gaaagcatga ataaacaatt ttagggataa aaagggaaac    33300
atcgctaaag atatcccaga aatgtaaaag ataataaggg aatattatga aaatattcat    33360
gccaatacat ttgaaaactt aggtgacata gacaaaaaca aaattgacca aaattgagca    33420
aaaaagaaac aaaatctgag tagtcctgta acttagtaaa aattgagtta gaaaagttaa    33480
agaagtcttt acacaaatca aacatcagac tcagttttct aggagagttt tgccaaacat    33540
tcaagtagca gataattctg gtctattttt ggccccagaa gatatatttt acttgccatg    33600
catttaatga gatagctgtt gattttttc aatcaccgtg acaggtgttt tatattaggt     33660
gttattcgcc agacatctag tccacctgtt gccagatatg gaattaatat tcacttattt    33720
tgaattaaaa tttgttaata aattaataaa acaaagtcaa agttcaaatt attaaaaaag    33780
```

```
taaaagaaat aaaatatatt ttatagagag cccttacaaa acagtaccaa cataatgagc    33840
tttccaaatt ttgaatgggc aaaataaatg aataggcatt tcacaaaaga aggaagggtg    33900
gccaataagt atatattaat ataaaaatgg ttacttgtaa taggaatcaa aagtgtttga    33960
cttattgact aagagtcagt ttttgttttg atccctgtta gtctatccag aaggcatggg    34020
tcttaataaa caccttgacc tcaacagttt actgaataca agggtaattt catatgcctt    34080
gccttcttta agggtttgtt gtaaagatta aaataaatac ataaatatat ataaatacat    34140
ttatatgtat ttatatgtaa ttacatacaa cttgccttct ttaagggttt gttgtaaaaa    34200
ttaaaagaag tatataaata tatataaata cataaaataa atacattcat atatgtatat    34260
gaaatcactt tgccaactat gaagcctgat tcaaatatga aatgttgttt gttttttccca   34320 gagcacaggc tgcaaagccc tgcattcttt tctttgatga atttgaatcc attgctcctc    34380
ggcggggtca tgataataca ggagttacag accgagtagt taaccagttg ctgactcagt    34440
tggatggagt agaaggctta cagggtaata attataaata cagaaataga atgttataac    34500
aaaatgtcat catgtcatca gattttggta aaaaaatgtt cttttttcct ctaggtgttt    34560
atgtattggc tgctactagt cgccctgact tgattgaccc tgccctgctt aggcctggtc    34620
gactagataa atgtgtatac tgtcctcctc ctgatcaggt gacaatttca tatttagagt    34680
ccaaaaccca acaaatgcta cactcttttcc ttgtgagctt tacttctgcc aggtaatggc    34740
aattgtcctt agaagaccag ctttcttagg gaaaagcttt agccactgtt tgctcaaagc    34800
ataaaaagat tctgaattag atgcaaagcc ttttttttggc ccagtgcaag tctgaaaact    34860
ttgtaatcct tctgtgttgg ctgattgggg aaaaaaaaat gcaagaaacc taatgtatta    34920 tatttttcaca ttatcttctg ttcaaagatt acatacttcc attatcctgt caaaaaaaaa    34980
actctgatac agaatcaagc atgtgaatcg taagcatgta agcaggtttc atagagataa    35040 ttttttcaact cttccttgtc ctgtgttgtt ccaactctta ttctccaatt tagaagcaaa    35100
caaataaatg aatgaaagaa cagatagaca aatgaatagt caaaggtata aagtatctgt    35160
atatatgtta catgtagcta ttatttaaat tatttagatt ttccttttga aataccttct    35220
tggcacactt gcctaaatct agaaaataag cactgtgtga ataagaaatt atttacactg    35280
aatattttgt aggttttttgg gttttttgttt ttcagacaag gtctcacttt gtcacccagg    35340
ctggagtaca ctggtacgat cacaactcac tgcagcctct atggcccagg ctcaagcaat    35400
ctccccacct cagcctcccg agtagctggg accacaggca cacgctacca tgcccagata    35460
attttattat taattttttgt atagagatgg ggtctccctg tgttgcccag gctttcttga    35520
actccagggc tcaagtgatc ctcccacctc aacctcccaa agtgttggga ttacaggcgt    35580
gagccaccat gcccagcctt aagagtgttt gattttcatt cattttccta tatatattat    35640
ttctgttggg gaaaaaattc caaggaagat aaatagtagg ctgttggtac atttctcaac    35700
ttacttataa agcttttttag atatataagg ttaatttatg aagaaaatca taagatacac    35760
aatttaagat aatattttta atttttatttt ttatttgtta aataaatttt tctccttttca    35820 ggtgtcacgt cttgaaattt taaatgtcct cagtgactct ctacctctgg cagatgatgt    35880
tgaccttcag catgtagcat cagtaactga ctccttttact ggagctgatc tgaaagcttt    35940
actttacaat gcccaattgg aggccttaca tggaatgctg ctctcgagtg gactccaggc    36000
aagttatatg aggaagttgt tatgacattt tatgagtgat aaaagaagta caatgtcaaa    36060
atttccacct taaaaaatgc tatttttttaa acaactttgg taaaactgta tagaaacata    36120
```

```
aatttacctt tagttgaatg ttccatagtt ggaatatggg ttttgcagag aatttataat    36180
tatgaagttt gatgtctgtt tctttaacat taccttaata ttggcaaaaa catgttggtg    36240
tttgcaagga tattatttaa attgggatac catgaattaa atactacaaa caaaaataat    36300
tagagttttt tgtttgtttg tactttaact tttaaaaaat aatcagttaa agttgttgtt    36360
ttgaagctca cattgttcca atctggccaa taggagcccc ttttgtatgg ctcctgtatc    36420
tttatgacat gtcctcatca ttcttgaatc acttcctcac ttccagatac agtaagttat    36480
tcttggccag gtgcagtggt tcacgcctgt aatcccagca ctttggcagg ccaaggcagg    36540
aggatcattt gggcctagtt tgagaccaaa tcatggttgc acaaactgta cccactatgg    36600
acaacagagt gggatcttgt ctctgtgaaa aatttaaaaa ttagctgggc atggtggcac    36660
atacctgtag tcctagcttc ttgggagagg ctgtggcagg aggatcgctt gagtaaatcc    36720
aggatgcagt gagccatgct tgtgccactg cactccagca tggatgacag aatgagaccc    36780
tgcccccaaa aaagaaaaat attcttggtt tatcttgtac tttctgtatc ccagccctag    36840
catcagcctt ttctctaaag acagtattat gattttaata tttacagtag atatttgaac    36900
tgttacatta tagactttac catatatttt ctaggaagga ttattctatt actcttcttt    36960
accacatttg tttggaatgt ctacagaacc tacagtttct aaatcagaaa ctccctaggt    37020
ttttgctatt ttggcaagcc attgaagttc ttccctctcc ctttactacc agaaaggtgt    37080
gtatttgtag agctctctat aatgagaaag cactctataa catggttgat tcatcatttt    37140
ggagtagaaa agtatgaatg gaaagtcaga gacataaaaa taaagcccag aggtctgagt    37200
cttagcttca ttacagactt tcttggggga tggttggtaa attatctaca cattctatct    37260
tgtctttata atttaatag ttaaatttt accatgtgcc tcaaaaccgt tagagaatta    37320
atgagctctt tgaaaaatgc ttctaagttt cttgtattgc tctaatagaa tgctatctat    37380
gttattattt atttctgaga ctaaaattgt ttacatcttt aaactggttg tccttttgtg    37440
tattttagga tggaagttcc agctctgata gtgacctaag tctgtcttca atggtctttc    37500
ttaaccatag cagtggctct gacgattcag ctggagatgg agaatgtggc ttagatcagt    37560
cccttgtttc tttagagatg tccgagatcc ttccagatga atcaaaattc aatatgtacc    37620
ggctctactt tggaagctct tatgaatcag aacttggaaa tggaacctct tctgatttgg    37680
tatcttgtgc agtcatcatt atacagttct gaaatataaa gctatatgtt ggtgtaaagt    37740
tgcagtgatt tctctcctaa ccagccccac atattcttcc tggttggttg gttcttcagt    37800
aaaatagtct tgtttcttgc ttacactaat tggtaatttg cattccttgt taagattttc    37860
aagacagggc tgggagcaag gaaccaaagt agcgcgtggt tgtgattacc tttggtttct    37920
ttgaggtttc tcttacctag tggctttaaa acatctttag gagcagttcc atttttatagt    37980
aaacttaaat tctgttatca tgaacagttg aggataatga ataatttgat acaataatgt    38040
aagaaattcc tgaaaacaaa gtgttatctg tgatactttt gctgcatagt aagcacaatg    38100
aagtgtactg ataatgtttc aacaggaaag tgttttgatt aaatgtgggc agtatcactg    38160
ttctactagc attcaacatc tcttctaaaa attaatagtg gttcactgta attttattgg    38220
tacatgtaac atctgtacat gtgtttggtt atctatatgt ttcctggttt tttgtacatt    38280
tgctttatta atttaggctt tttttttttt ttttttttga cagtctcca ctctatcatc    38340
cagactagag tgcagtggca caattatggc tcactgcagc cttgacctcc tgggcttagg    38400
tgattcttcc acctcagcct cctgagtagc tgggactaca ggcacatgcc accatgccca    38460
gctaattttt gtatgttttg tagagacgag gtttcaccat attgcccagg ctggtctcaa    38520
```

```
actcctgggc tcaagctatc tgcgtgcctt gacctcccaa agtgctagga ttacaggtgt   38580
gagccactat gcctagccta actcagactt taaaaatata aaagcaattc attttttattc  38640 ccaagaacag taaggtggtg gtttaatttt agtctttaat tctgttttta atttattcta   38700
tttagaaatg tcccagaaac ttagtataac tttactttct gaaaatgaag aaacctgtcc   38760
ttgggcatta gtgtgttgga tttaagcaac aaagttaaaa aaacctaccc tgtgttatgg   38820
caattttcac ttgatggtgg ttctataaca caggtatcag tgaacctta taaaagatga    38880 acaacttttc agcttgctta atttcagtta attaacatgt atacttatct atgttaatgt   38940
tttattgctt aaaatgttta attttatat ttggtaaaca gatagttttt tctctccccc    39000
tcttccttcc atctttcatt actacaattt accatgcaga gctcacaatg tctctctgca   39060
ccaagctcca tgactcagga tttgcctgga gttcctggga agaccagtt gttttcacag    39120 cctccagtgt taaggacagc ttcacaagag ggttgccaag aacttacaca agaacaaaga   39180
gatcaactga gggcagatat cagtattatc aaaggcagat accggagcca agtggagta    39240 tggcttttc cccctcatta taattgttaa aacttcttaa aaattgtttc acccttttga    39300
tatatatttc tttgacttat aaacgagcta tatttataaa caagggacca gaacacatta   39360
actcagtcat ggttatgtgc ttccttgctt tcaatgtttc attatcttat aaggaagaga   39420
acgtatggtc tcttgaaaaa actgacaata agaagtaaca actggactac cacattttt    39480 tttacatcct taatttaact cttcgtcaat ttcttttttt acttaaggag gacgaatcca   39540
tgaaccaacc aggaccaatc aaaaccagac tggctattag tcagtcacat ttaatgactg    39600
cacttggtca cacaagacca tccattagtg aagatgactg gaagaatttt gctgagctgt   39660
aagtaacaga ttctgttttg gaagtacagc tactattaca agtgacatag tattcacttt   39720 aaaccttaa agttcgtgtt taaaataaaa atatttgaa tatttaaaag ctaattcaaa     39780
aaatatgtgt cgtagctatg cattaaaaaa ccccaaaatg tcagaagtac agaagtcaaa   39840
attgagtttt cattaaccag ttcatttgat tatatttgaa ttattcataa tggactcatt   39900
taattttagt aactttgggc tgggtgctgt ggctcatgcc tgtaatccca gctctttggg   39960
aggccaaggc aggtggatca cctgaggtca ggagttcgag gcaagcctaa ccaacacggg   40020
gaaaccccat ctctactaaa aatacaaaaa ttagccaggt gtggtggcat gtgcctgtag   40080
tcccagctac ttgggaggct gagacaggag aattgcttga acccaggagg tggaggttgc   40140
agtgagccga gattgcacca ctgcactcca tccagcctgg gccacagagc gagactgtgt   40200
ctcaaaaaaa aaaaaaaaa atttagtaac ttcgaagaaa taagaaggaa aattaaaagt    40260
tgaaagtgat tctaatgtat agtttataaa attttgttat aaaaatacct gttttgcctt   40320
caaaataatt tatattaata ttttattgac ctcaagaaca tttaaataca ttcagattta   40380
ttcatttgtg gaccacattt gttatacatt ggatttaaag gatccttgca attgagttta   40440
tggccaccta tgcatctgag acccatggac tgggaaccat tctaggtcaa tgattcagtg   40500
tgattcaatt taagagatgt ttattcctgg tctttagaag ctgctacctt ttgttatcta   40560
attttgcagt actttgaagt atgtatgtat gtgtacatac gttagtgcta tgtatttatt   40620
aaagaagaat cagaaaacag aggtaaggaa aaataaggaa acaaatttct gttaagccca   40680
ccacctccca aagcatattt gtttatatgc ttatatatgt tttcctatta tggtaagaac   40740
agtctgtaca tattgctata tagcagtccc cctttatcca catacatcct gaaaattgtt   40800
ttacatttta aatgttaact actttattgt ttttaaatgt cattttatag tgtagctatg   40860
```

```
ccacaatatc caattttttag acatttaaat tgctcccagg caatgtggta atgaacattc   40920
ttgcagctga atatatgcac atatctaatt gtttcactag gatagaggtg gaattgtata   40980
acagggagct cacattttt aaggcttttg aaatgtattg ccaaattgcc tgccagatat   41040
actgcaccat cactaacatt gtgtgttgca gtattttct aaacttggcc cttttgattt   41100
tagaaaaatg atatcaataa tttacatttc tttgattaaa gtgtagaagt tataattttt   41160
catattattc attgtcattt gtattttatc ttttctaact tgtctcttca tccccttttgc   41220 tccgttttct attggagtgc aactttattt gtaagaattc ttttaatt ctgtgactgg   41280 aatttttttt tctagtttgt tatttcccgt tcatttctta aaatataatt gtgtttgcca   41340
acaatccatt atcttttgtt ttgtaatggt agtattata catattaaat tatctctttc   41400 tttttcaga tatgaaagct ttcaaaatcc aagaggaga aaaaatcaaa gtggaacaat   41460
gtttcgacct ggacagaaag taacttagc ataaaatata cttcttttg atttggttct   41520 gttaagtttt ttgatggctt ttccatatgt tgtaacagga aaaaaatggt gtctatgaat   41580
ttcttcttaa tttaacaaat ttggttaatt tataaaatca cagattggta aatgctataa   41640
ttatgtaatg atcaggattg agattaatac tgtagtataa attgggacat tataacagat   41700 tccatattt atttcctaaa atctaaattc agtctttaat gaaataatat tagccaaatg   41760
gtggaactaa tttatttctt ttgaggaaaa gataataaag aatgtaatta aatttaaatt   41820
tcttggaatt cccagttgta tattcatcac ctttgtagca tttgacaaat tttatgctta   41880
gcagcttctt cactgttttg aaataaaata tcctattacc tactgataca attatctgtt   41940
ctttgtatat caaaaaatgt gaaatttaca cataattcaa atacatttaa ttatccgctc   42000
aaccagaaat gaaatcacat ccctctacta tactacatcc agctccaagc ccaagatatt   42060
taaatgacat ccattcctct cctagttcca gttatgattt tatcttgata ttctctcata   42120
tatgaactaa attataaagt tagccaccat caatacaatc tgcgtatcta atatcttaac   42180
tatatagtaa tgggtaagg gaacagcaaa aaggagaaca ttaattaaaa tatacaagta   42240
agcctgggca acatagtgag acccatctc ttaaaaaaaa aattagccat gcatgatggt   42300
atgcctctag tcccagctac ttgggaggct gaggtaggag gatcacttgc tcccaggagg   42360
ttcaaggttc taaccagca aagctcagaa tcccagggga tagaaacaaa gacttagtgg   42420
atcactagta ttaaactgag acacgtcacc ctgcattgca ctttgtttct cagttctttg   42480
atgaaatcac tgagctgaca tacctgcct cttttcacca taaagtgagt ttcatgatca   42540
gaagcaatgt ctatgggata gcctaacaaa caatgtaaaa accatttagt aagttcatga   42600
agggtggtgg tggtaaaaat ttggagaaca tacaaaacaa atacaattcc aaggtgtgtc   42660
ccctccagga aggacaaatt gctgcctgct ctgtgataga agaggatcag atgtaatcaa   42720
cctgccgtca gacttgggct gttctctcct gggtgtggac ttgcctggtt ggtcactgct   42780
gctgacaagt aggctgtcaa tatagctggg ttgtcatgtc agctgtggtg aggggaagt   42840 ccacattgtg gaggccacat ccctgcactc ttggccaatt tgaccatgaa tcttaagcac   42900
tggggtggct ggaaaagaca gccgattgac atccatacag aggtcatctt gaccacttga   42960
ttagtataag cactgaaggc ttttaactga gcattcacat aggacacaaa tattctgatt   43020
ctttgggccc attccaagaa ctctgggcat acttttcctc cagacctcat acccagttgt   43080 gttcttttcca aatttctggt catctggtta tgttattagc cactatctgt gaatcagcat   43140
agatttttat atcagacatc tctacctcct gacagaatgg aggagatatg ttacttaaca   43200
attctgttcc cttggaagat ttcctgtctc cactgtttgt aagggctact ccctcaatgt   43260
```

```
agcagtaatg ctttcactct gatgggaagt cacagtggaa ttctgggtct ccaagaatta    43320
gtgttagtgc atacacagtg tctgataatc cccagagtgt ctggtgccct ggatcctgt     43380 gaagaaggct tggagaaaag aagattcatg gcaagaactt gtgatgtgat gacagggcct    43440
tttctctggc tcttcattct tagtctgacc taggtgtgag aattaggtca ggggccatga    43500
ctatattgtg gtgactcaaa ccaggccttt gtttactaac tgggagattt ttacattgta    43560
agaatcaagt aggatctttg cccatgtatt ttggtcttaa gaacacaaat gatatggctc    43620
caatgactgg aggaacacca gggtccttgg tctcacgctg atttagataa acgactgtc     43680 aggcctctga gcccaagcta agccatcctc ccctgtgacc tgcacgtata catccagatg    43740
gcctgaagta accaaagaat cacaaaagca gtgaaaatgg cctgttcctg ccttaactga    43800
tgacattcca ccattgtgat tgttcctgc cccatcttaa ctgagcgatt aaccttgtga     43860
aattccttct cctggctcaa aacctcccc actgagcacc ttgtgacccc cgcccctgcc     43920
cctaagagaa aaccccctttt gattataatt ttccactacc cacccaaatc ctataaaatg    43980
gccccacccc tatctccctt cgctgactcc ttttcggac tcagcccgcc tgcacccagg      44040
tgaaataaac agccttgttg ctcacacaaa gcctgtttgg tggactctct tcacacggac    44100

<210> SEQ ID NO 64
<211> LENGTH: 16869
<212> TYPE: DNA
<213> ORGANISM: Homo sapiens

<400> SEQUENCE: 64
aagctttagt agagatctca aaaatggttg gatggtagca aattactaag aactctcaaa       60
gtttctaaag cctagttttc agcttgctag aaaacctatg ttgagtatta tggctagttc      120
catagttgag ttgggaaatg tctttgagga gacactttt cactttgtat tcatctgtac      180
attttctgtt acttgcattc tgtcatgctc aggctattag agcaggtaca ttttataac      240 tggaatgttt atgtgtagtg aagctctgag aggactttgc attagatctc agcagcataa      300
tcagaaggtt gtcctttgtc tcagcaattt ttaagctaat agtagcagaa attgcagtgg      360
aaatagactg ctttgccaca acattcagaa aatcatttat cttttttattg cagttcttgt     420 caccaaacaa tacattttag tacttctcaa attgcagaac tctcataggg ctgggaaaat      480
gcctgtagac acatacatac tatgaatgtg ctaatgtttt ttgtatttc atagcccatc       540 aaagctcctg agtcagtttc cactataatc actgcagaat caatcttcta caaggtaagc      600
ttttgtagag ttactgaagg aagagttggg cctagtgggt aatgtgccac taaaatgttg     660
gattagtcta aaggtctctg ctactctta tttgtataag gtgtgattat acttttttgtt      720 cccttcttag ctgtttttccc ccataagtgg ctgttattaa acatctcat ctagagctga      780 agtgggagga gaaagtgcct actgacacat gatgtgagga tcttaagtat ttttttttag      840
tgtagattgt aggaattatt cttaaaatgc tgattgtata gtgtggagcc atggaagact      900
gagccgttag tgcgatggca ttgaagaatg agaaggacag agacaggatt tggactagta      960
gaggttgtcg actgtggtgt caaatgggta gagtaggccc agagattcta aaatgccttt     1020
aagtggagtt gagctgagta agggcagtag tgaggattaa cacctactag aaattcatag     1080
tgagaggaat tccaagatgt tttgataaaa gaatgaggag gtcaggtttc ccagggccaa     1140
agtccatgaa catctgatac ctcagtgaga gaagtgacag attgttgtgt ttaaaccaga    1200
agtcttagga aaggaattag aacatagacc cccaaggctc ggcaggcctg gcacggcaca    1260
```

-continued

```
ggcagcaacc attgaaggct atttggtgtt tcgggatctg aactgtcatt taggggacag    1320
tggtgtgagt tagtacttta tacttgaccc aggtggactg agaaactcaa gtgatgatgc    1380
ccttaagtat actttttttt aagcccacaa tctatatagt cgaagtctgt tcctcccaac    1440
aggggtacac tggcattcct cagcagggct gggaaaaacc aacaacaaaa aaagtctgta    1500
cacaggcaaa catctctctt attttttccaa catttaatac attgttaata aaatatctaa    1560
agtttagcaa acagttgctg tgtatcagtg gctgagcatt ttgcatgctt tatttcattc    1620
agttcactct atgaggtgga tactactatc cccattttct agatgagaac attgaggcac    1680
agcgaggtta attaacttgt ccaagatcac atagccaaca agtcatggag tgaggcagtc    1740
tcatgccaga gcttaagcct agagcatagt tcctggctct acagctttag caagtgactg    1800
gctatgtgac gaggaccaac ctctctaatg tctcatctgt aaaataggaa ttgtaaatag    1860
ttactacctc agtgggtcaa atgaaatcat atgtgttaag cacttagcag agtaagcact    1920
caatgaatag taggagttat cacatcttcg tatttgtgca ttaccttcac agtttacaga    1980
ttaaggccag aagcaacttg ttgagctacg ggtttagtgt actaacagtt tccatgtgtg    2040
tctccatgga agggtgtgtg ggacctgtta ttgtgactgt ctgtactttc gtattgttgt    2100
ctgccaccca tgtttattaa atgataagga caataatgca acaaagtagt caagtaatgt    2160
tgcaaatgcc cagtattgta gtggctatca cagcagtgcc actggcaggc agcaccatgg    2220
tggcaagttc aagaggtcac tgccagccac tgagctagag cccagatcag gcatgcaaga    2280
ggagcctgag tgggagccac tggggatcac ggccaagagt gtgaccaccc aagacccaga    2340
atggctgagt ggcctccctg gagcatggca gtggcagaac aactccatga actcagatct    2400
ggtgatgcct aaactagtgc tgttctcgtg tggaccccctt ttctctacca gaaaccttga    2460
atcctctcag caaatgagga gactactcag atcagtgact tagtcctgtt tggtgttata    2520
tatgtgtaca caacacagca catattaata aatacctact atgtgccagg cactgcctac    2580
cactggaatc tttcactaag acattgtttt tactttgcat ttctgccttt acactatgaa    2640
agtagatgtt ttggattcat attcattcag catacatttg aatatgctgt gttatgcata    2700
gtaagcctat gataagcaag tattctcatt tagaatttgg gaatattgat tatacatgtg    2760
gacaaacaaa ccataaatgc aaactattta tatgataaat aactttggac tgatggctgg    2820
gaggaaggac cagctattga tgggtaggaa ctagcaagta gcggactgtg gcctgcatag    2880
accagaccca tccgtagtga tccagatgaa acagccaccc tcagacactt ggataaaggg    2940
tccaccagga aaaactcct ggcctatcag gtgctatgtt acagttcagt tactggaagt    3000
atttcctcaa aagtgttttt atggttgagg tacacattcc tacagcttta cctgctgcca    3060
agtccctgtt tcaagggaag cagcaatgaa ttacactgtt cccgtagtca aggacagtat    3120
atcttaccaa gaactatacc cacttaagga ggtgctggat gtcataaaga tttggatcaa    3180
ccattatggg tgttcagagg agagattatt tccagctcaa gacccaggga agaggacata    3240
ggatggatac cagagtcata gggaggattt aacacaggac atgtacacat tagttagttg    3300
ggtataaagt ggaacagaaa tgaatgagac acaaagcctt gaatgccaga aatactagta    3360
gtcctgttgt ggaaggatat aaaactcaac tgggagtgga agagaaaggc agcagtgagt    3420
ctaggagatg tacagtaggt tgaggtaaac atatcctgaa gactataatc caaagattat    3480
ttttggtttg aatttgtttt ggtttgaatt catggtatct attttctttg agtggatggt    3540
tggggagggt ggcatgtaga atgcattctt accaaatcag catgattttc aagacagtac    3600
agagaaaaga ctgctgagct gatgtaggag ctttggctgc agtctctatg gctttcagca    3660
```

```
agccgtttaa ccttactact gcttcatgac tgtggctaac aaagtaggga tagtacggag    3720
cacagaggat ttttagggcg gtgaaactat taatactctc tttgtatgat actataatgg    3780
tgggtacatg tcattataca tttgcccaac cccacagaat acacagcacc aagagtgaac    3840
cctaatgtga actctggtct tgatgatgc tatgtcagtg tacgttcatc cgtgtaacaa    3900
gtgtaccact ctagtggtgg gagggttat tgataatagg ggaggatgtg catgtgtggg    3960
ggcaggaagt atatgggaaa tctctctact tctgctcaat tttgctgtaa acctaaaacc    4020
tctgtaaaaa ataaagtcta ttttttaaaa agtggggatg gtattacggc aatataaaat    4080
caaaatactt tatgaacaaa tcttttctcc agatgtaaac tgtcatatat gcaccctcgt    4140
atgtgtatgt ataattttca ttcaaacgtg aaacaacttt agaattggca ccaaacatat    4200
aaacactgat acattagact atctcgaaca ccttttactg accactttga aaacttgctt    4260
acctattaag gttcattcat agctgtgatg ttctattttt attttcaatg tgggattatc    4320
ttctgtttcc cccagggagt atattaccaa attggtgatg ttgtttctgt gattgatgaa    4380
caagatggaa agccctacta tgctcaaatc agaggtttta tccaggacca gtattgcgag    4440
aagagtgcag cactgacgtg gctcattcct accctctcta gccccagaga ccaatttgat    4500
cccgcctcct atatcatagg taagtttgac aaatggcaca ggtttttttt taacttagtt    4560
aactctccaa tattatgtaa aagagtgtgt tagtcagctt gggctgtcag gacaaaatat    4620
cacagactga gtggcttaaa caacagaaag tcactttctc acagttgtgg aggctgaagt    4680
ccaacatcaa ggtgctggca acacggattt ctggggaggc ttttcttcct ggcatataga    4740
tggtcacctt cttgctgtgt cctcacatgg cctttcatgg agtgagagct ctttggtgta    4800
tcttcttata aggacaccat ttctgtcaga tgagggcccc acccttatgg tttcatttaa    4860
ccttaattgc ctccctaaag gtctcatctc caagtaccat cacattgggg attagggctt    4920
caacatataa atttggaggg tggcgggggg ggatgcaatt cagtccataa caaaaaaagc    4980
atgagtatta ttaagtacaa aaaattaga gagctttata gaaaatatga ggcatttat     5040
gtagctggag tgtgagtgct atcagttatt ttgagttaga gcaatgtgca tctactaaga    5100
agtggtatgg ataagatttt tttggagtga cccagggtta aactgtacta caagaatgta    5160
ttgctcagga actaggttat ttaggttact tatttataca aacctattca aaataatttt    5220
aggaaagaac tatcccagtt atcccatact tgcaaattct caatatgtgt gcctctgcat    5280
gctacacatg tcatcttagg cctttatagt ataaaggctg atagttgaaa tggcagctgc    5340
tgtgcttttg ttaatttcaa agctgccaaa acagttgtga gatagactca caagaattta    5400
ctgattaata caattttaa agttttcaga ttttacagt tacttcagac ttttatctt     5460
tctgcagtga gcatgcatca ttacttttgc atcctgagaa caagcataag tgtgtttttg    5520
gagagaactc cagggacaaa taatatacca ctgttattct cacctatatg tcaagtttga    5580
tacattacca aacaattcta gccttctgct tataagtata tagaattttt atttacctta    5640
tctatggatc aggatctcag cagaggcagt gatgtatcag aatcaccttc gggattcctc    5700
tactgcctcc tctttctaat ccccagattc tgatatgcat ccttgtccta cagcgaggca    5760
gcatggcatg aggtcagaac accagttctg gagccagact gtctaggttc acagcctgcc    5820
atttaccggc catgtgactt tggcaagttt cttagtctct cttgcctcac tttcctcata    5880
tgtaaaatgg gaataataat agtgcctacc tcagaaggtt gatgtgagga atgaaggtat    5940
tgatacatgt aaacttagag cagtgtgggt acaaaataaa catgatgcaa gtgttcaatc    6000
```

```
actgttttg  ggagaatgcc  atattcttta  agccgttaaa  gaagaaaaaa  tgattaagaa    6060
taatttcaaa  gtaatgcatg  tttcaagggc  taatgccagg  ttgctcccag  agtggtctct    6120
cccagtgtct  agaaatttta  acatcttatg  aaaatgatat  atatggtcaa  aaatgtattt    6180
aacctttccc  ttggctgcct  tccagggcca  gaggaagatc  ttccaaggaa  gatggaatac    6240
ttggaatttg  tttgtcatgc  accttctgag  tatttcaagt  cacggtcatc  accatttccc    6300
acagttccca  ccagaccaga  gaagggctac  atatggactc  atgttgggcc  tactcctgca    6360
ataacaatta  aggaatcagt  tgccaaccat  ttgtagttca  caaattaaaa  ctgggtttcc    6420
aggcctggtg  tggtggctca  cgcctgtagc  cccagctatt  gcaccactgc  tctccaagct    6480
gggcaatgga  gtcagattct  ctttcttaaa  aaccacaaa   aaaactggat  ttccagttct    6540
ctaatattct  tagtaccaca  agatatgtca  taggtatctt  taaatgaaat  tcttagctgg    6600
aaaagtgact  aaaagttttt  tctcctgcta  cctagtaata  aacaaatcat  tgtttattac    6660
tggtcactta  gaaaattaaa  agggataggg  ccaggcacag  tggcttatgc  ctgtaattgc    6720 agcacttta   gaggccgagg  caggcggatc  acctgaggtc  gggaagtgga  tcgcctgagg    6780
tcaggagttc  gagaccagcc  tggccaacat  ggcgaaaccc  cgtcgctact  aaaaatacaa    6840
aaattagcca  ggtgtggtgg  catgtgcctg  taatcccagc  tatttgggag  gctgaggcag    6900
gagaatcgcc  taaacccagg  aggtggaggt  tgtagtgagc  caagattgca  ccgctgtgct    6960
ccagcctggg  caacagagtg  agactcttgt  ctcggaaaaa  aaaaaaaaa   aaaaaggctg    7020 ggcacagtgg  ctcacgcctt  taatcccagc  actttgggag  gctgaggcag  atggatcgcc    7080
tgaggttggg  agttcgagac  cagcctggcc  agcatggtga  aaccctgtct  ctactaaaaa    7140
tacaaaaatt  agccaggtgt  ggtggcgcac  acctgtagtc  ccagctactc  gggaggctga    7200
ggcaggagaa  ttggttgaac  ccaggaggcg  gaggttgcag  tgagcagaga  tcgtgccact    7260
gcactccagc  ctgggtggac  agagcaagac  tccgtctcaa  agaaacaaac  aaaaaattaa    7320
aagggataga  atataatgaa  atatattttg  aacttaaatt  atattctata  tgtgtatctt    7380
cctaggcaaa  agctgtaatt  tccagagaga  ccattaggaa  caggtagtat  ctatttttct    7440
ccattattta  tttctagaaa  ctcataaaat  ggattgtatt  tttctataag  aacaaaatat    7500
taattaaggt  atagatgact  gaccaagggc  ttaatcaaat  aaaatgacta  acagcatcta    7560
tcataaagcc  acacaagcct  tatgttctca  tctcaaaaat  gctgtgacag  cttttttggct   7620 gctttaacca  taagaaaaat  gattggtgga  tgatttattt  agcccaggct  tttaaaaact    7680
ttcatctagg  ccacgtgcgg  tggctcatgc  ctgtaatccc  ggcactttgg  gaggcctgag    7740
tggatggatc  acttgaggtc  aggagttcag  gaccagcctg  gccaacatga  tgaaaccctg    7800
tctctactaa  atatacaaaa  attagttggg  tgttatggtg  catgcctgta  atcccagcta    7860
ctcgggaggc  tgaggcagga  gaattgcttg  aactcgggag  gtggagattg  cagtaagccg    7920
agatcgtgcc  actgcactcc  agcctgggtg  atagagcaag  actgtctcaa  aaagaaaaa    7980 aaagaaaaaa  ttttaattta  atccttctgt  agaaacaggc  attcagaacc  attccattga    8040
tcttaataaa  gctgctcttt  actgtttcta  gtcaaaaatg  agacttcgat  caaaccataa    8100
gattttatac  tgcagatagt  cagcttcacc  aaagccgcag  aggaaacatg  tcgagatcag    8160
gcttcctgct  tgatagtctc  ttgactacca  ttaaaacgaa  tattgggagg  tcatgaaagt    8220
cattggtagg  ccattagcat  tgatatcttt  aaaacatcta  ccctaaacca  tctgctatgg    8280
acccataata  agaggcctgt  tgtatatgaa  attgtctaga  attcaggtgc  aggtctttgc    8340
cggttaagta  agggagcaac  acgtaaaatg  ggagaggagt  ggggtgtact  cacttgcctc    8400
```

```
ctcttttgtc ctgatttaac cagcattttt caaccctggg aaaatttgca gaatctaagt    8460
tgattgtaat gattttgagc tgcagcagct ttaactctta ccctttttcc acatagttat    8520
ggtgtttgag ttggaaagaa acaactatag gtagctacac gtacataatt atctctttat    8580
tcacaaaggg tatagtaaaa ttgattgtaa ataactttct aagtgccaat attcaaaact    8640
tttggattaa aatgtatttt tcaccgtgca tttactttgg atgtatttat ttcatttaaa    8700
caatttaaat ggggctcttt aaccaaaaat ggtatttaaa accaaaacag tatcgtactt    8760
agaatttgga gtagaggccg ggcacagtgg ctcacgcctg taatcccagc actttggaag    8820
gctgaggcag gcggatcacc tgaggtcagg agttcgagac cagcctggtc aacatgaaac    8880
cccgtctcta ctaaaaatac aaaaattagc tgggcgtggt ggcgtgcgcc tataatccca    8940
gctagtctac tcgggaggct gaggcaggag aatcgctgga actcaggagg cagagactgc    9000
agtgagccga gatcgcgcca ctgcactcca gtctgggtga cggcatgact ccatctccaa    9060
aaaaaaaaaa aaaagatttt ggagtagatt catcattaat aagtaacaga ttttaggaaa    9120
atcaaaaaat ggctaataaa atgaacacaa tgtaaaacat ttattaaaat gtagactttt    9180
aaaaatctat aaattgatca tctgtttata aattggcaga tggttgtgta ccatctttta    9240
aaataaagat tgaatttcac ccagtgtgat ggttcccatt gcttatattt ctcctgctga    9300
ggccggacct gatatggccc tggtctgtgt tcccagcctt gtttcctcat taccactaaa    9360
atctttcccc tgtatgcccg cccaattttt ctggctctga gtccttgttc atactgttct    9420
ctccaattct accttccaaa ggcctttctt aacaccttcg gattctttct ttgagaactt    9480
tccagattcc catgcctttt tggaatcaat ctctatccta ttgtcatcac atttaagttt    9540
ctacttccat catcctcact cctatccctt tggtcctggg atgacaggga tgctgtgttt    9600
tatttactca tctttgtaac ttccacataa cctaaccccg gttcttgctt atgggagatg    9660
ctgattgtag ggtctgagtt agatactgtt aactaaaatg cttgttgata ttttagttat    9720
taattcatat taactttggc tgaaactttt aaattctatt gtgaatagtc aagtaaaatt    9780
tagattgtta cattctgggt tagtattaga ttgtttttaa gattgtttta aacaagatgt    9840
ttttaagatg agttttaaat agttctctta acacaaataa agcttaatat gagtatttga    9900
aggaaattat cccaaaccat tccagttcct ggctgtgaaa ggcttttcca ggcctaataa    9960
gttttccact tcagccgtaa gtaggtgaaa tcaaatgaac aatagaggga aatgtattta    10020
tttgctttat acacatgcat gtgtgttgtg tctacatata aacattgcac acgcttagaa    10080
tgaagtttct gtcatgccca gaaaagggag aggcattttt gtggattttg tctggctgcc    10140
ctggggatgt ttgaagaact gtgctgttta cttcatacca ggtgtgtgag ccatacccttt   10200
ggtaggaggg tatacctcct acacccaaga aatataagcc aggagaaggt ctgtgccaag    10260
agaaggaacc caaatgaccc acaagaggtg ggccattaat tattgggtca gatgcataaa    10320
tgcacagtaa tttatttaag cacctcttaa tggtgaccca caaggaagat tgctcgtagt    10380
agcggaaagg ttcacaataa ataagagaaa aaagcagaat gtagaactgt atgatagcaa    10440
ttctgcaaac aagaagcatc ttttataaaa gatggaagga gcccaggcac agtagctcat    10500
gcctgtaatc ccagcacttt aagaggctga ggtggaggat cacttgagct gcagtgaccc    10560
atgattgtgc caccactcca gcctgggtga tagaagtgag accttctctc aaaaaaaaaa    10620
aaaaaaaaaa aaagacgaaa attcctccag aattttaaca tgtcaacaga ggttttctgc    10680
agctacttttt ttcagcttta tacttcgcag tattttccaa attttctcta acaagcagta   10740
```

```
ttttccaaat tttttacaat aagcacacac acacacacac gtttgtttgc ataagtgccc    10800
aactggtggt gaacaaccgc tggcttttag tctatacata tctagaatat tttataaata    10860
gtagttctta aacccttgaa agggagtgaa tgaccagctg agaaaataaa gtcagtgatt    10920
tcattatttt cctatattca catcatgatt ctaggaaaga acttgggagt gacttccttc    10980
agcttcagcc actcctgggc caggcgcatg cttagctctg tggtaaaggt caccagcttc    11040
ttctgcaggg tgcctgtatc atctgaattg gaggtttggc gagggtaaga gactgatgta    11100
ggttcaagtt tttctttcct gtcctccact tgaaatctgt cttcccttcc agactgcctg    11160
cgctgctgac ttaaggcccc aacaccaaac acagaagcaa cagccttaca cagagtgttc    11220
agcaagctcc aacaattgtg taaggtaaag tttcctttat agattccttt tctatatcgc    11280
tcctagtggt tctgtttctc tgatcgaatt ctggctgata acagttgctg agactctgaa    11340
agagaaggca aggaactact gtttctcatt ataaactgtt tagaattatt tggccatctt    11400
tttgctatga atatgtagtg ctttgataca ttttttaaat caaaaagtaa tgaaagagat    11460 cacatagggga aagatagatt ggattatttt taaagtttat atactaaatt gaaaagcaaa    11520
gaataaaatg ggagaaacag ctccctcatg tggctgttgg caggaagctt ccattcctct    11580
ctgtgggcct ccacaggttt gctcacagca aatggtccgt gacagaaaga cgcaagggca    11640
gttgcaccca agatggaagc caccatcttt tctataaacct aatctgaaag aagggacata    11700
ccagcacttc tgccatatgc tgttgggtca cacagaccaa ctctggtaca gtgtgaacac    11760
aggaccacac aagggcgtga attccaaggg cagagaccac tagggaccac ctcagaggca    11820
cagagggaca ccctatccag ctggtggcca atgtaaatta acatagcttt ttagaatagc    11880
aatatgtatc tataatctta aaagtattaa aagtacttct tgatccagta atttcatttc    11940
taagaatcca tgctaagagg atttaaaatg tggaccaaaa aatgggtata aaagaagtt    12000 gttaacagta tttaaagttg tgaaaaacca gaaacaatct aaaggtccaa cataggaaa    12060 atgaattttg atattttct aatagaattt tatgctgtca tcagaaatac catttacaaa    12120 taattttaa taacgcaaaa aaaagtttat aaaatgttta gtgtaaaacc tggacacaac    12180
tacataatga ttctgatttt gtaaaaaaaa aaaacaaaaa cacacacata tacacatgca    12240
tacatatgca tataaagaaa actgaacaa acaaaataac aagcatagtt ggaattacag    12300 tcatttttaat attctttatg ctttttaaaaa ttttgaagtt tgtattacta gcatccacta    12360
cttacgtagt caggaaaaaa atacaacttt aaaatagata tttaggtcca aagatggtaa    12420
tctaaatggt gttacaggct gaatgtgtgc ctgatcccca tgccccaagt tcatatgtta    12480
aagccctggc ccccaaggca atggtattag gggagtaggg cctttgggag gtaatcagat    12540
ttctacgagg tcatgagggt ggagcccgca tagtggaatt agtgtccttt taggaagagg    12600
agaacagacc aaagccttcc tttctctcct cactatgtaa gaagacagcc agaaggtggc    12660
cacagccagg aagagagctc tcaccagaac ccaaatctgc tagcaccttg ctcttgggtt    12720
ctcagcatcc agaactgtga gaatgaatg tgtgttgttt aaaccactca ggctacggta    12780
ttttgttgca gcagcccaag ctgacagaga tagaaacaac acaaggaccc atcagcgac    12840 gaatggatga tcaaaacgtg gtgaggtcgt gcagtgggat attattcagc cgtagaagga    12900
atgaaattct gatacatgct ataatgatga accttgaaaa catgttaatg gaaataagcc    12960
aaacttaaaa ggacaaatat tgtataattc cacttatatg agttagttac ctagaatagg    13020
caaattatgt catagataca gaacattaga ggttaccagg gttgtgggaa gagggggtatt    13080 gtgggtacaa attttcggtt tggagtgatt ttgaaaaat tctggaaatg ggtagtgaca    13140
```

```
gtagtcaaca tgatgaatgt acttaatgac actaaattgt acacttaaaa atggttaata    13200
ctgggctggc gcagtggctc atggctgtaa atcccagaac tttgggaggc caagacaggc    13260
ggatcatgag gtcaggagat tgagaccatt ctggctaaca tggtgaaacc ctgtctctac    13320
taaaaaataa aaacaaataa aaaaaaaatt agccgggcat ggtggcaggc acctgtagtc    13380
ccagctactc gggaggctga ggcaggagaa tggtgtgacc tgggagtcgg agcttgcagt    13440
gagctgagat cgcgccactg cactccagcc tgggcaacag agccagattc cgtctcaaaa    13500
aaaaaaaaaa aaaggttgat acctgggtgc ggtggctcat gcctgtaatt tcagcacttt    13560
gggaggccaa ggcaggcaga tcagttgagg tcaagagtta aggaccagcc tggccaacgt    13620
ggcgaaaccc catctctatt aaaaatacaa aaattagtcg agtgtggtgg tgggtgcctg    13680
tagtcccagc tgctgggagg atgaggccta ggaattgctt gaacccagga ggcagaggtt    13740
gcagtgagtt gagattgcgc cactgcactc cagcctgggg gacagagcga gacttagtct    13800
caaaaaaaag gttaaaattg taagtttgt tatgcatatt ttaccataat ctttaaaaaa    13860
tagatatata ggagataaag tcaacagaat ttaataacca gttgtaaata gagactgagt    13920
gaggaggatg aattaaggaa gacattgagt acaactttt ggtaggtgaa aaactcttaa    13980
aaaaatacgt gggcaaagat cctacttgat tcttataatt taaaaatctc ccagttagta    14040
aacaaggcta ggtggagatt tgcatgtgat gtgaggtgtg tgttctgttt tgtaatgtga    14100
ggactgtgag ccatctcctg gacttgaata tccattagat aattgaaaat acggatttga    14160
gaactcagga gacgtgcaat gcagtaacaa aactctgcac ctagttgatt tctgtctcct    14220
aatttaatgc ttttatggga caaactgtta ggcaggtggg caagatggac agccatattt    14280
ttgtgggttt ctggcctgtg ggccagcctc agtgctcact ctgaggtcat gtccaaactt    14340
agaacacatt caggcctacc acagtcaagg ctccctttct caactctagt cctctgcaca    14400
aatatccgaa gcctagaaat aataatcatc tgtccttgtg tcttgcatta tgaaagccta    14460
ggaaagggcc ttgggaatta agaagaatgg aaaaactggt ctaactgctg catgcttcag    14520
cttgcagggg aatcactgaa atggggacag gccataaaag gacaaccaga agagtggctt    14580
cagcaaaggc atcgtttttc agagcaagct agagaatcct gccagcgtcc tcaggcaggg    14640
cccctgggca cagaggttag gcaagggagt gtcccagcat gttgatgccc tgagcatcag    14700
aataatgcca tagaggagct tccaaagagt tcatttcagg ttttgtaagc cgaacatttc    14760
taggcaaata aaatttgatt ttgtgaataa agcttgtttc ttcaactcca gtgcagattc    14820
tcatagattg atagtggctt gtgatccaga taaagaaaac aattttttcaa agattcatat    14880 tctttgtaga tgtacggatt tagagaccat ctaatctaac tccctcattc tacagatagg    14940
aaaaatgagg cctaaagaag ttaagaaaat accatggaaa tgtcactgct gaactgccat    15000
acgtaggatc cgaaagaaat tgggtaaatg ctactgtgag aaatacagta ctaggtccaa    15060
agaatctaat acaaattaaa aatctaaatg ttatttctaa agcatccctg cacatggctg    15120
aacttacata gtttcatttt ctttctttc tgttgaagaa gaggcaattg gctgggtgca    15180
gtggctcatg cctgtaatcc tggcactttg agaggccgag gcgggtggat cacctgaggt    15240
caggagtttg agaccagcct ggccaacatg gtgaaacccc atctctacta aaaatacaaa    15300
aattagctgg ctgtggtggc cgctgcctgt aatcccagct actccagagg ctgaggcagg    15360
agaattactt gaatctggga ggtggaggtt gcagtgagcc aagatcacgc cattgcactc    15420
tagcctggat gacaagaggg aaactccatc tcaaaaaaaa aagaaaaaaa agcaatcact    15480
```

```
aacctgtgtt gtttattaaa catgacagac tggcatgaag taattaccaa actgtaaaca    15540
aaaaagctac aatctgccag gcatggtggc tcatgcctgt aatccccac cttgggaggc    15600 caggttgggg gatcacctga ggcctggagt tcaagactag cctggtcaac atggtgaaac    15660
ctcgtctcta ctaaaaatac aaaaattagc ccggcgtggt ggcacatccc tgtaatccca    15720
gttactcagg aggctgaggc aggagaatca cttgaacctg gcagtgggg aggttgcagt     15780 gagccaagat cgcaccgttg tactccagtc tgggccgaca gagtgagact cggtctcaaa    15840
aaaaagaaaa aagaaaagct acaaccttaa tctcaacttc tcataacatc atctctactt    15900
ctgattagaa gagtggaagt ggggaggttt attacaaaaa gactgttata ccttacacac    15960
ttctccccat gaatagtgaa ggtgtgagtg aaaagacag caatttttatt tttttttttga   16020 aacaggttct tgcactgtca cccgggctgg agtgcactgt tgtgatcact gctcactgca    16080
gcctccacct cccaggctca agtgatcctc ctacctcagc ctcctgagta gctgggacca    16140
cagttgtgca ctaccatgcc cagctatttt ttttaagag atggggtctc actatattgc    16200
ttaggctagt tctcaaactc ctggcctcaa gcagtcctcc gaccttggcc tcccaagggg    16260
ttgtgattac aggcataagc caccacaccc agccagcagt tttagaataa agggtgaagg    16320
tgctgttggg gaaatataat ttaaaaaaca aaatcttctc tcaacccaga aatcctctcc    16380
atgaaggcag tagagaaaga taagctttat tattgaataa aaattaaatg agaatgtgat    16440
gcacatcaca ggcactttgc taagagatca caaagacaga aggaaatttc accattttgt    16500
acagccaagc aggtacagcc cattacatgt atgttttcga gataaatagt cctcaactaa    16560
gagaacttga cagcaccact ggtcacacag ttcattctaa ctttacctga taattgatgt    16620
gaccacttgt gttatctaag atatcaactt ttcgggggtg ggggagtgtg gaaacaggag    16680 ttactttttat agcttggtgc aaggtactca ttaagattag gctgttaccc tcccacagaa    16740
actggaagat aggtatgcta tctggtaatg tttacatttc ccagatcctt gagaaagaca    16800
ttcctaggtc ataaagctga caaaaggctg attcagtttt taaatatata tatctgtata    16860
tgtatttca                                                           16869

<210> SEQ ID NO 65
<211> LENGTH: 15000
<212> TYPE: DNA
<213> ORGANISM: Homo sapiens

<400> SEQUENCE: 65
gatctcttga tcccaggagg tcaaggctgc aatgagctaa gatcaagcca ctgcattcca       60
gcctgagtga tagtgggaga ccttgtcttt aaaacacaca cacacacaca cacacacacg     120
agggcctttg accactcttg agtagaagac tcgagaagaa caaagtagaa ggccagagaa     180
gaacaaagtt acttgaaaga tctcttatta aagagaatgt acaagctatg aaaaaaaaaa     240
aacacacaca cacacacaaa cctcatctgg aatgaaaaaa acataatgca tttggtttct     300
ggttccttag gctgttatgg aacaaccaaa gaacattatt ttggtttctg aggtcagaac     360
tattttattc ccctcaagca cactatgctt atggtttgag ggagaatgag aaataggaaa     420
ctaggaacag gctgaaatgg tctaatcttg accatctaat tctgcagtgt cttattctca     480
ttctaaaaga gaatggttat attgctgttc ctagcataaa aagtaatgat aaaaataaaa     540
gatcccgtat taccagacaa taatccccta gactgttta atgcttggtt gagtattgc     600 ttatgatctc agactttaaa agatggtctc ccctatggt gaagcttgtt aattatgtag     660
gcatcattaa tgtctgttta cttatcaaaa tttttatcatt gttagttgta ttactacttg     720
```

```
acagtccaat ttatttaatt gaaaagattg gttaacattt tatagtcaaa gtaattgttt    780
cctgtgtttt ttcctgttta ggttattgga gtgatgagta agaatacat accaaagggc     840
acacgttttg gacccctaat aggtgaaatc tacaccaatg acacagttcc taagaacgcc    900
aacaggaaat attttggag ggtaagtaag ggaaatttct tcagacccat taaatgttag     960
gaaaaaatgg agctaaaaga gctgggtggc tcaccttct catcctgtgc tgagaaatgc   1020
tggggctcac ccataagtat ccagcatccc catggacaca gggaattctg aacaaatgtg   1080
atgaaaccga tgaaatgtct ggcctgtagg tggttagtga tggagatacg ggctatatgt   1140
gaatcttgat ttttgcaatt cattagagct ttgtaatgaa aggaaacagt ttgttgcttg   1200
ctttaaggat aggttcattt gcatttctcc gcaaggaagt agtaatgagt taccaagcct   1260
tagatttcac cccttttga tttcttgctg acttaacttt aattgaatgg aagagttatc    1320
acaaatgaat tatcttttg gtttttttt ttttgagatg gagtctcact ctgtcaccag     1380
gctggagtgc aatggcatga tctcggctca ctgcaacctc cgcctcccag gttcaagcaa   1440
ttgtcctgcc tcagcctccc gagtagctgg gactaaggtg cgcgccacca tgcccagtta   1500
attttgtat tttagtaga gacggggttc cactatgttg gccatgatgg tctcgatctc     1560
tggacctcgt gatccgccca ccttggcctc ccaaagtgct ggaattacag gcaagagcca   1620
ccgcgcccag ccaggaatga caaatgaatt accttataag taaatgccat taaggaagga   1680
tagctggaag atgggttgag gggaatggag gaccacagaa ctagtcctat ttaaatacat   1740
gtgcatggta aaatgattcc atttgacaat aggttaatta tctcatagca taaggaaaat   1800
gcttaacagt catatgcaag atgataagct ttcctatagc atccaaccaa aagatctagc   1860
cagtacaatt tccttttgcta tattagggtt agaaaggccc ccagaggtga accaattaga   1920
tggaatcctt gaataaaaca ctggattagc agtgaacaga aaaagtcag attgctttcc    1980
ttcttcccat agatgtctca gggatattta gtttcctcag aagataaaga attagtaag    2040
cgttttttg tgcatactta catgaaatgt acattatttg aattcttta aaagaaacag     2100
ctgcatgata acaaaaattg tgttatgctt gctttagctg gtattttgc ctagaacgat     2160
tatatcgttc ggacaagaag ctattcctaa gaaacaatat ttttaatcca ggaagttttt   2220
catttttaga aatttatctt actatttccc aagcaaaaga gggtagttac agattcacta   2280
agaatcatgt gctcacaatt ttatttaat aattattcct ccttaaaata tattaatcac    2340
ctgacttaca atggtggaac catgagtgca tttttgcctt tattgtcaat aacgtcttct   2400
cagaagtgag ccacaaaggt gcatagttct tggagttaaa ggtctgaatt aagacaatcc   2460
agcataagtc tcattaatgt gtgattattt tgagaaaagg caagaagtac ctaagaatct   2520
cccccctcact gtccagttcc ctgtttcatt taaagattca ctgtaagtaa ctgaaaggct   2580
ttccttggga ggatttattt gaatcagtct ttcacatgca aaggatattg tagaacatct   2640
cgttttgct ggcaggaata tgaacatctg ttgtgaggaa agaaaagtt tcatgcaaat     2700
tacactgcca aagaagggat gttcaagttg agaaaccagt gacatttctt gtaactgtac   2760
tatgaatcag cgcattttaa tcttctagat aatatatgga agtgcaggaa ggtggtagga   2820
aacggtgttc attttacata tgcgttattt tattctgtgt gagtgacttc atggcaccga   2880
cattgctgtt tttaaatgag gatacagtaa attgcagtcc gaggaaggct aactggaatc   2940
aacatacccg tagctttaga aagcagtttc cgcaccagcg aagagtacaa gagcgatgga   3000
accccatgtt cctggaagtt tgcacatcag agtaaacaaa cttgaaaacc cctcttgata   3060
```

-continued

```
gcagaattca cccagccttg ttccatttc tcttaacaaa acacaccgca aaagctctca      3120
caagctgctt tgatgaagcc acatgtattt ccccccttcac aatttacagg aagttactct    3180
taaaagaaag tgattctggt gtttaccgcc tgtgttaaag ggacagagtt ccttttatt     3240 tctgataacg tttgagcgaa atacagaaac tatctgtaga ctagcatagt cggtacgtga     3300
gtaaggaaaa gcaataacct gctgtccggt gagcacaaaa ttcctgctac gaacagtgcc    3360
ttactgctgc ttggagactg caagtcgcag atcacactag gtattgactg attgtataag    3420
gaaatttctt aaagtctaaa gtaaggtgg tacctcctaa aaagagggga agagagaaaa      3480
ctttgtgtgg aaggataagg agtgtgttta tagtttcagt aagagtgtac gttttaattt    3540
ttcttcttcc tctgcctctt tgccaagtag cctgagtgca tctgttatcc agaagtagta    3600
ttactctagg acaaacttca aattcttcat tctgcgttgc ctttaaggaa caacatactt    3660
tcttcctgtt cttttttccaa aaacacacgc ctatggctct gtgtgtggtg ttttagccag   3720
cctcctccca gataagggt tcccttccct cctttgcatt gaaaggaaag tgcaagtctg    3780
gacatgttta tcaagaggaa aagtgacttc tcagtaatag actgtcaaat tcgggctgct   3840
gcccgagtgt tcgctttgtt atggcaggtg aagttcacct ttgccccacc cagtgtttcc   3900
acaaaaaggc aaggttccaa gtattcatat gaacaagtgt tactttagga cttggagggt   3960
tgggggtgga ggatgtttgc atagttgaag ccttgggcgg gggtgtagga aacggcgagt   4020
acagaggcca tagaaaaagc taagactcag tttgacgtcg tcagccggct tggtcttcta    4080
cccagtgact caaagcacta aaagtcagca taatcggaac tgaagtcagt agcatcgccc   4140
atttgccatt cactgcagta gcaaaagtag tactctgtgg tgggttaatc ggtttgaggc    4200
agctccttaa atgaacattt gtgtttcatt tttctgttat tttcccgaac atgaaaagac    4260
gataaaactg aaatggaaaa ggtaactgac aaaagtgtgc cttacctgtt tccgccctga   4320
tttctgctga ttcaagacta ttctggctaa actgattgga ttctttttct aactaggcag   4380
taggggatca gaaatcacac acggtaccgg ctgtgtttat tctgagaggt gctggggagc   4440
tttgggtctg acttcctttt acatgcctgt cttctctttt ggacagatct attccagagg    4500
ggagcttcac cacttcattg acggctttaa tgaagagaaa agcaactgga tgcgctatgt    4560
gaatccagca cactctcccc gggagcaaaa cctggctgcg tgtcagaacg ggatgaacat    4620
ctacttctac accattaagc ccatccctgc caaccaggaa cttcttgtgt ggtattgtcg    4680
ggactttgca gaaaggcttc actaccctta tcccggagag ctgacaatga tgaatctcag    4740
taagtggatt acagaacaaa aaaataaaaa atgccagtaa tgtcggttct gcccctttga    4800
actaataaca tgttgtttaa ttatacggct ttgtcatgtg ttggatgaag taggtggctt    4860
aagctaggga ctaggaagag gaaaaacatt ttttgagtcc ctattaacta ttaggaaact    4920
tgatcattta aaagtatata tatatatgag gagctaccttt gagttttgaa ttcaggatgt    4980
tacaggaaga aatatatgtc caattctaat ttatccaaaa gcagtgggaa gaattacagg    5040
gattggtcca gacatgctgc gtatgcaagg tatagccctc atctgtggta ctttggcagg    5100
gcttagactg catcaaaata tttatagatg tacatttgag tgtacagtta ggatctgatg    5160
tggaacattg taagatcatt gctagaaaaa ctttgtcata attttccaat attattctaa    5220
gtgaataacc gtaaagattt tacatcttag cttccttcct tacagtaaaa aaactatctg    5280
atctcttgat cagtattata gtagccacct atcactttat cttaacaaat tctcaattcc    5340
ttaggtttat gtgcttttac ttcttttatt tgattaaaat tgctgtcatg acctctctct    5400
gcagagggct gcatcatttt ggtcattctc aagtgatctc tttgagcaat ttaagaattg    5460
```

```
ccataagatt ctaacctctg ctgtaactat ggttgtgtgt tcttggttag accactaaat    5520
cttattagca gttttaaaaa ttattccttt tggtttagaa gttaagacta aatgctgaag    5580
tttttgtaac ttttggtttt gatatcattt caaacttaag aaaacatttg aagaaaagga    5640
caaagaattt ccacttaccc tttacccagg tttaccagtt attgataagt atatccattt    5700
gctttaccag aaggctaact tgttttagtt ctcattttca cctttgagac atttggaata    5760
aatatcaatg ttaacataaa ttggaatttt gactttgatt ttaggaccaa tgaacaagcc    5820
aagtacttac cctagtcata tataatccaa ctgtatggtt atttggtatt cattccacac    5880
ttcattttac ttgatctccc ttaagattgc aagattgtgt ttgcagtttt tctgaaaatc    5940
tggggctata aaagcatcag gacctccccc gtagggagg tcgtgtgttt ggggtcctta     6000
cacaacaggt taccctgag cttcaggaaa agaactggct ctcagttccc cagttccagc     6060
ttaatgggtc taattaggtc ctgaccaaaa aggtggcagt tcttttccct catgtctctt    6120
cagcgctccc cgagactctg gagactctgt catatcccta gggctgagcc tcccaggaac    6180
cattcggctg ttgtggcatc tgtgtatgcc atgcccagtg ctgaggacct agtaacaaac    6240
gacaaatgca caggcacagt ggcattttg tggaactcgt attccagctg tgcgtctcag     6300
aagaagcgca cagctccctc ctggcttct taacatagtg agccacttcc acttaagggt     6360
ctccttacat tccttgagtt taatcattca tggattcaga ggaaagtctt ttgatttttg    6420
cttttcttta aacagttcat ttgaggtgac ctaccccagt gactttgcac caaccaccaa    6480
gaaactttt tgcatgcttc ccgcaccctg tgccaatcaa gggaagggtt taaaggcctg     6540
gcgtttttat tcctcaaaga aaggttttgc acagtatttt aaggttcaag tgcttctact    6600
ttgtgttcag aagcaactgt catatatact gtgaaatgac accttttatt tatccctttt    6660
tatttatgca gtatgtcccc ttttattttg gcagaatttt ttctaaatgg tggtttaaca    6720
ttttcaagca catttcattg tccaatattc atagtaaaga atgagagtta acaataacca    6780
gtcacattaa aacaagattc ctgctgccag ttgtgaaacc ggttgtctta ggcgtggcag    6840
ctgatgattg agactgtgat caggaaaatt tccactattt catcaggcct aataggtaga    6900
ttgtgtctcc aaatgaactg tgttgggttt ccatgcttaa agcacaatag aggtggtgca    6960
agaatctcca tgagggctta aatggcagtg atggttcagg cggtagagtt tggagaagaa    7020
gggatttgaa acaaaccaaa ggaaagaaaa gtaagtagcc agaaatcaca aaatggcatt    7080
tttctaaaaa caaggaaaaa ggaataaaag aactaataag tttgaaaccc ctaccctcc     7140
caaatttggc aggggggag gtatttttt tctatctatc taactaaccc atctagaaaa      7200
cagttgacca aattatagac ttctaaatgt taatctgctt tctcagtttc agttgaaaag    7260
agactttgtt ttgcctactg cagaacttct aggttctttc ttatagtctt ggggttctta   7320
ttatagatcg aaaatgtgag tcggcataat taagccattc ggagtcttca gaagcagttc    7380
actcttgaaa tgactccgtc cgcctacagc catttaagat ttcagaacaa aaacagatct    7440
tgattttctt tttcatgtta actcaagctg ttgctgagtg ggagagtcag aaatgacacc    7500
agctccactg attactcagc tgctgaagga tgatttttta aaatgcacct ttactgtata    7560
tggacttcct aatttccacc tgtagagcat cttagggagg ctaacatgtc actctggatg    7620
ttcttttaga ataagatgca aatctatttt tctgaaggca ttagagatag caaacattta    7680
ttgtgagttt actatatact aggcactgtg ctaagtgttt tgcatagaaa gtttaaaatt    7740
ctggcttttt tgttggccca atcataagtt tcatatcagt tcaacattca aattatatta    7800
```

-continued

```
aggtacttaa gaagaatccc tggctaaatg tgaggggcag tgccacagat ggactgaaac    7860
tttatgctta ttgcacattt atgctattat tatttgttga attatagaac caagggagtg    7920
tggaagccac tggaaaaaat atgagactta gatacataat ttgagtaaaa atggctcaaa    7980
gtcatgaggg taaagttttt tgtatttcca ttttattcga gcggcatcgt ttttaaaaat    8040
cattatgaat ttgaccctat atagatgttt ccaaataatt cttttcacc ttcataaaat     8100
tccttcctgt ggctgtgaga tgccttgcct atcagttttc aagcttagtt gtctttctca    8160
tcctttacca ttttagcttt aaaaaacaaa agtgacaatt agaacttcct gcctgctggg    8220
cctcactgaa agaccgatat tggcctgata aggagatatt tattttgttt tagtggcttc    8280
agaaatccct ctccctcagc aagctttcca tcacggcccc cccgtcagca tcttccctga    8340
tagcgttctt ctctgtgttt attctggggc ttcaggctcg cccaggagga actgataacc    8400
gctggcagga gataacattc tctaaggggc tctcaaattg gaatcgaatc cctcaagcca    8460
gtcagcctag agaatacatt taagggttc agttctggag tttcacagag ttcatttcta     8520
gacctatcag atagcaagtg tggagttctt tctcaactaa attcaagcag agacattttt    8580
tagacgatga aggatatttg cacaaaggct tcagcatgat cccccaaacc tgctgcctct    8640
gaaggcatct ccacacattg acagccaatg ccttcagtgc gttcctaggg caggtgtcct    8700
ggcttgagtg actgtcctcc aataatcaga gctcaaacta acatcgtat gttttacttt      8760
tggtttccag gcaaggctga gcagggaatt ttcagttttc cctgcccaga tgggtgtttt    8820
ttcctgaagg catcatttat tgtgtagcga ggagacaggg ctggctgtgg cagggatagt    8880
ctagaactgt cctcattgct gctgttccta aatagtatct ttaccaagta ataacgtgcc    8940
gtctttggga ataagtgctt tcctcttagc ctgttctgtt ttcttgggtg cgctaagtaa    9000
ttgaactggc tcaggaagta cctattgtgg tttggcagag gtgactgtca cgccttgtga    9060
ctccaggggc cagcactgct gggatcctgg ctagaccaga cagagccttg gtgaagtgct    9120
taggctgtct gcacatcgcg aggaaggtgg tattcacttc gctaagctcc ttggcatagg    9180
cagtttgaac agggctttat caaattcgta ttcaacaaga gtagaagcga aaattgatga    9240
ctgtgtatta cttgaaatga gtcttaatct ttcacattta gttctcaggg tatgctgatt    9300
tcctttaggt aaaccatgaa catcagaaag acttttatta acctatgaca gggtccccac    9360
cccagtattt ttccactcca ttaaaatgga agttttttt ttttttttct tttttgagac      9420
agagttttgc tcttgttgcc cagtctggag tgcaatggca caatctcggc tcaccacaac    9480
ctccacctcc cagattcaag cgattcttct gcctcagcct cccaagtagc tgggattaca    9540
ggtgtgcgcc accacgccca gctaatttttg tattttttagt agagatgggg tttctccatg   9600
ttggtcaggc tggtctcgaa cttccgacct caggtgatcc gcccacctcg gcctcccaaa    9660
gtgctgggat tacaggcaag agccactgca tccagcttag gctatcttac tccagcctaa    9720
acagcaattt tctatcataa ggtctgtact aatgaaaaca gaatcaccca aggctgctgt    9780
ttgttctgtc tgtgctgcca ttgtccgcat tttgctgagg aggaaacgga actgcacttt    9840
tgagtgagtg gcccagagcc ttctagaatg agagtgcgtt ggaagccaga tatgtggcga    9900
ttgtgtcgcc agctgttact caggtttttct caagaaggag gagcaacttt ggcagttttg    9960
cttcagttct ctctagccct ctgtgtaatc gccccttttt ctttatttca gcacaaacac   10020
agagcagtct aaagcaaccg agcactgaga aaatgaact ctgcccaaag aatgtcccaa    10080
agagagagta cagcgtgaaa gaaatcctaa aattggactc caaccctcc aaaggaaagg     10140
acctctaccg ttctaacatt tcacccctca catcagaaaa ggacctcgat gactttagaa   10200
```

```
gacgtgggag ccccgaaatg cccttctacc ctcgggtcgt ttaccccatc cgggccsctc   10260
tgccagaaga cttttgaaa gcttccctgg cctacgggat cgagagaccc acgtacatca   10320
ctcgctcccc cattccatcc tccaccactc aagcccctc tgcaagaagc agccccgacc    10380
aaagcctcaa gagctccagc cctcacagca gccctgggaa tacggtgtcc cctgtgggcc   10440
ccggctctca agagcaccgg gactcctacg cttacttgaa cgcgtcctac ggcacggaag   10500
gtttgggctc ctaccctggc tacgcacccc tgccccacct cccgccagct ttcatcccct   10560
cgtacaacgc tcactacccc aagttcctct gccccccta cggcatgaat tgtaatggcc    10620
tgagcgctgt gagcagcatg aatggcatca acaactttgg cctcttcccg aggctgtgcc   10680
ctgtctacag caatcctc ggtggggca gcctgcccca cccatgctc aaccccactt       10740 ctctcccgag ctcgctgccc tcagatggag cccggaggtt gctccagccg gagcatccca   10800
gggaggtgct tgtcccggcg ccccacagtg ccttctcctt taccggggcc gccgccagca   10860
tgaaggacaa ggcctgtagc cccacaagcg ggtctcccac ggcgggaaca gccgccacgg   10920
cagaacatgt ggtgcagccc aaagctacct cagcagcgat ggcagccccc agcagcgacg   10980
aagccatgaa tctcattaaa aacaaaagaa acatgaccgg ctacaagacc cttccctacc   11040
cgctgaagaa gcagaacggc aagatcaagt acgaatgcaa cgtttgcgcc aagactttcg   11100
gccagctctc caatctgaag gtaggccttg agagagagca gtccaagggg ctgtgagtgc   11160
atgcttgtgt ttgtatttag cttgctttcc atggggtatc gattgcattt gcagtagtat   11220 gagccccgg ttggggatag tgggtatgga ttccgcctgg cttttgccac ttctagctct    11280
ttgactttgg acaagtgact tcccttctcc tgattttctt ctgaataata aaaaaattag   11340
gggtttggac tagaagatta ggtgaaactc cctgctagcc tgtgattttt gtgcttttaa   11400
gaaaaacacc attctgaaaa catgaagatt tcttcttttt aagactgtct tgatgctttt   11460
cttaagatat ttgcatcaac acttgagtct tggagcagaa atgttaggtc tcagagccag   11520
cttgagagca gagctaacac atgtggcttc ttcccaggtc cacctgagag tgcacagtgg   11580
agaacggcct ttcaaatgtc agacttgcaa caagggcttt actcagctcg cccacctgca   11640
gaaacactac ctggtacaca cgggagaaaa gccacatgaa tgccaggtgc gcagtatttt   11700
ctgggtagac cttctgacct ttgtagaaaa tgtctgtgag tcaccctccc atgtcctata   11760
tagcccgtag ttaaagccaa caccagattc tgcgttgtcc catcctggac tgatggcact   11820
atggtccttc ccagtacttt gtatctgctg atgacttgag atggcacagc cagcttccag   11880
tgggtgggaa aatggtaggg gaaataaaca gcccctcgtg tgctgtgtgc ccacatcccc   11940
ccgtttgctt aataccacac tggaggtgcc acaaggaggc ttctcacctc ctaggttgct   12000
gggcgttggc cggtaagcct gcccctcccg ttggcaactc ttaatcttct ggccttcctg   12060
tctcccttcc ctgctgtctc tctccctac actgtaggtc tgccacaaga gatttagcag   12120
caccagcaat ctcaagaccc acctgcgact ccattctgga gagaaaccat accaatgcaa   12180
ggtgtgccct gccaagttca cccagtttgt gcacctgaaa ctgcacagc gtctgcacac    12240 ccgggagcgg ccccacaagt gctcccagtg ccacaagaac tacatccatc tctgtagcct   12300
caaggttcac ctgaaaggga actgcgctgc ggccccggcg cctgggctgc ccttggaaga   12360
tctgacccga atcaatgaag aaatcgagaa gtttgacatc agtgacaatg ctgaccggct   12420
cgaggacgtg gaggatgaca tcagtgtgat ctctgtagtg gagaaggaaa ttctggccgt   12480
ggtcagaaaa gagaaagaag aaactggcct gaaagtgtct ttgcaaagaa acatggggaa   12540
```

```
tggactcctc tcctcagggt gcagccttta tgagtcatca gatctacccc tcatgaagtt    12600
gcctcccagc aacccactac ctctggtacc tgtaaaggtc aaacaagaaa cagttgaacc    12660
aatggatcct taagattttc agaaaacact tattttgttt cttaagttat gacttggtga    12720
gtcagggtgc ctgtaggaag tggcttgtac ataatcccag ctctgcaaag ctctctcgac    12780
agcaaatggt ttcccctcac ctctggaatt aaagaaggaa ctccaaagtt actgaaatct    12840
cagggcatga acaaggcaaa ggccatatat atatatatat atatatctgt atacatatta    12900
tatatactta tttacacctg tgtctatata tttgcccctg tgtattttga atatttgtgt    12960
ggacatgttt gcatagcctt cccattacta agactattac ctagtcataa ttattttttc    13020
aatgataatc cttcataatt tattatacaa tttatcattc agaaagcaat aattaaaaaa    13080
gtttacaatg actggaaaga ttccttgtaa tttgagtata aatgtatttt tgtcttgtgg    13140
ccattctttg tagataattt ctgcacatct gtataagtac ctaagattta gttaaacaaa    13200
tatatgactt cagtcaacct ctctctctaa taatggtttg aaaatgaggt ttgggtaatt    13260
gccaatgttg gacagttgat gtgttcattc ctgggatcct atcatttgaa cagcattgta    13320
cataacttgg gggtatgtgt gcaggattac ccaagaataa cttaagtaga agaaacaaga    13380
aagggaatct tgtatatttt tgttgatagt tcatgttttt cccccagcca caattttacc    13440
ggaagggtga caggaaggct ttaccaacct gtctctccct ccaaaagagc agaatcctcc    13500
caccgccctg ccctcccccac cgagtcctgt ggccattcag agcggccaca tgacttttgc    13560
atccattgta ttatcagaaa atgtgaagaa gaaaaaaatg ccatgtttta aaaccactgc    13620
gaaaatttcc ccaaagcata ggtggctttg tgtgtgtgcg atttgggggc ttgagtctgg    13680
gtggtgtttt gttgttggtt tttgttgctt tttttttttt ttttttttta atgtcaaaat    13740
tgcacaaaca tggtgctcta ccaggaagga ttcgaggtag ataggctcag gccacacttt    13800
aaaaacaaac acacaaacaa caaaaaacgg gtattctagt catcttgggg taaaagcggg    13860
taatgaacat tcctatcccc aacacatcaa ttgtatttt tctgtaaaac tcagattttc    13920
ctcagtattt gtgtttttac attttatggt taatttaatg gaagatgaaa gggcattgca    13980
aagttgttca acaacagtta cctcattgag tgtgtccagt agtgcaggaa atgatgtctt    14040
atctaatgat ttgcttctct agaggagaaa ccgagtaaat gtgctccagc aagatagact    14100
ttgtgttatt ctatctttta ttctgctaag cccaaagatt acatgttggt gttcaaagtg    14160
tagcaaaaaa tgatgtatat ttataaatct atttatacca ctatatcata tgtatatata    14220
tttataacca cttaaattgt gagccaagcc atgtaaaaga tctactttt ctaagggcaa    14280 aaaaaaaaaa aaaaaaaaaa gaacactcct ttctgagact ttctgcttaata cttggtgacc    14340 tcacaatcac gtcggtatga ttgggcaccc ttgcctactg taagagaccc taaaaccttg    14400
gtgcagtggt ggggaccaca aaacaaccag ggaggaagag atacatcatt ttttagtatt    14460
aaggaccatc taagacagct ctattttttt tttgccactt tatgattatg tggtcacacc    14520
caagtcacag aaataaaaaa ctgactttac cgctgcaatt tttctgttttt cctccttact    14580 aaatactgat acattactcc aatctatttt ataattatat ttgacatttt gttcacatca    14640
actaatgttc acctgtagaa gagaacaaat ttcgaataat ccagggaaac ccaagagcct    14700
tactggtctt ctgtaacttc caagactgac agctttttat gtatcagtgt ttgataaaca    14760
cagtccttaa ctgaaggtaa accaaagcat cacgttgaca ttagaccaaa tacttttgat    14820
tcccaactac tcgtttgttc tttttctcct tttgtgcttt cccatagtga gaattttttat    14880 aaagacttct tgcttctctc accatccatc cttctctttt ctgcctctta catgtgaatg    14940
```

```
ttgagcccac aatcaacagt ggttttattt tttcctctac tcaaagttaa aactgaccaa    15000

<210> SEQ ID NO 66
<211> LENGTH: 46340
<212> TYPE: DNA
<213> ORGANISM: Homo sapiens

<400> SEQUENCE: 66
tattttactt cagtaacaga aaatgaaaga aatgttttaa tgttgctgat tgtattacct       60
tcaggatcaa tagcagaagg acaaacttct tgaggagat ctcctagtgt gtgcaactgt      120
ccatctgcag ccacaggacg aaacagcttc tgaatgaaag gtctttcagt cgttgtctat      180
ttgaaaaagg aaaaaatgat tcaagcaatt aagtctttgt tgctgccaat tacaaattta      240
tatatcataa actttatgtt ggcattaggt gccttttgat acggtgttag cataattaca      300
caacatcaca gatgtggtat cactgtgaaa aatgtttaac atgataaatt caggtaaatc      360
taattctgag gaaacagaca atccaaagt tgggtgggac attctaaaga taattggctg       420
ggacccttca aaaacttaaa gacattaaaa agcaaacaac acaaaaagat atcaacaaaa      480
gcattttttc tcagtatctc ttaaagagac taacaaagca aatacaaaac ataaaccatg      540
gctgaatact aaattgaaga aggacatttt ttagaaatcc aactatgaaa cacagttttg      600
ggataaatgg ggaaatacag aatggacaac tgataatatt attgagttaa tgtcaaattt      660
cttaggtaca ataaggacaa tccttatttt taagaaattc attgttcaag tgtttaggaa      720
agaagtgcca tgatatccaa aacttaatct tctttctctt tttttggaga cagagtctcg      780
ctctgccacc ccggctggag tgcagtggcg cgatctcagc tcactgcaac ctctactttc      840
caggttcaag tgattctcat ggctcagcct cccaagtagc tgggactaca ggagtgcgcc      900
accatgtcca gctaactttt tgtattttta ctagagatgg ggtttcacca tgttgcccag      960
gctggtctca aactcctgag ctcaggcaat ctgccggctt cggcctccca gagtgttagg     1020
gttacaggcg tgagccaacc gctcctggcc ccaaaactta accatctaat ggttgagaga     1080
gagacagaga gagagagaaa gagagagaca gagaatgtgt gtgtgtgtga agacaaagca     1140
aaaataaaaa aatattaact aatggtgatt ctaggtagag ggtgtatgat tttagtagtt     1200
tcattatttc aacttttcga taggtttcac aattttccaaa acagcagatc cagccatttc     1260
atctgacaaa aactgttagc agcactacat cgtaatttat tgctaataat ctcattgttt     1320
tactcttaaa attgtttcat ttactaaatt tccttagtga tgatggaggc tttatcatga     1380
cagagtacag aggctctgaa atgagccagt gtctatgaag agcaccactg tttgcaagat     1440
ctatgatctt gtacccagtt tcctttatct gttaatttgg gacattccat atctcttgag     1500
tttgttgtgg aaataaatga gcaactttgc caaccacaga gtaaataaat aaatgttaaa     1560
gagaataaaa gcattttttac ctcctctctc cctcttaacg gttatttcac tttaagatgg     1620
taaattttaa gctttctgag atgaaaaatc attaaaactt aacaagaaca gagaaatgcc     1680
atacatacat atttttttgtt tgcttgtttc ctgagacaag gttcactct gtcacccagg      1740 ttgaattgca gtggtgcaac ccccaagttg caatcctcca cctaagcctc cagagtagct     1800
gggactacag gtgtgagcca ccatgctcag ctaattttttt tacttttttg tagaaggggg     1860
tctcactatg ttgcccaggc tgcctcatat tttataagaa tatgacttca aacacttagg     1920
cattagcgac aaggttttgt ttttgtcttt taatgacaga ggtatacctc aacatatttg     1980
acacaactgt tagagatttg gtttaaaaag aaatagacat ggatgaagct ggaaactatc     2040
```

```
attctcagca aactaacaca ggaacagaaa accaaacacc tcatgttctc actcacaact    2100
gggagctgaa caacgagaac acatggacac aggcaggga catcacaca ccaaggcctg     2160 tcggggagta gggggctagg ggagggatag cattaggaga aatacctaac gtagatgagg    2220
ggctgatggg tgcagcaaac caccatggca catgcatatc tatgtaacaa acctgcacat    2280
tctgcacatg tattccagaa cttaaagtat aatacaaaat gaaaaaataa ataaaaataa    2340
gtagaaaaaa taaacatgta agcatgtgag ctgcctttcc taattctatg tttatgtatt    2400
cactgaatac atagtatttt aaaatagtaa tccaataata tatttgagtg tttgtgacaa    2460
gtatgaaaat tgtaattttt aaaaaatctt gataatatgc attgaatatg atttaattca    2520
cttcactatt tgaactcttt agggattatt tttaaaaata tgattgatat cctttgatat    2580
gttttggctc tgtgtttcca tccaaatctc atctcaaatt gtaatcccca cccgtctagg    2640
gagggactgt aatccccatg tgtcgaggga gggaggtgat tgggtcatag gggtggtttt    2700
cctcatgttg ttctcgtgat actgagtgaa ttctcatgag atctgatggt tttaaaagtg    2760 gcagttttc ctgcactctc atctctcttt cctgctggct tgtgaaggtg cctgcttccc     2820
tttctgccat gattttaagt ttcctgaggc ccccacaagc catacggaac tgtgagtcaa    2880
ttaaaccttt tgcctttata aattatccag tctcagatat ttcttttaaag cagagtgaaa   2940 acagactaat acattcttca atttaaaaag ccatactttc tcatacaagt tgaaaccaag    3000
aacaatatca tgcataatca agtgattaac tgtgtaaaga taataaggtt gaggagttca    3060
gagaagaaaa gaaatgaata gggaactgta gtgataattt aaaatagcca tccctcactc    3120 agggttttg atcttcaggc catgaagaag cttttaatgc ttttagcaa aggaagtaat      3180 gttggtgaaa gcttttttct gacgactaat ggaaagcagt gctatgtatg gtgacttggt    3240
tatgaaccaa aaccagaatg actggtgaga ggctgactga atacagcaag cttatgtgaa    3300
gacaactgga gctggtgcag tggaaaagga agacagcagg actgtaccca caactcaaag    3360
aaaaaagtca gaaggtacct cccgcagtcc aacctgaaaa caacaaagtc aaaggaatct    3420
tttcaagaat ttggagctct cattcatatc ctaattagtg tatgaaatgt gaggtggctt    3480
tgctataatg aaattacctg gaatatttct aacacaaaga aataataaat gcttgaggtg    3540
gtgaatatcc tcatttgatc attacacatt gcatgcttat agcaaaagat tacatgtacc    3600
ccataaataa ttgcaactat tatgtatcca taataattaa aactaaaaga ttaaaaatta    3660
cctgaaaaaa aatgctaaac aggaaaaggcc aactagtctt ggttacatat taaaaaacag   3720
aaattcttct ctaacctcac tattggagaa atatcctgtt atttttatat atcttttttt    3780 tcacccttc ccaaatctga gcaagtatta taaaggtata accttcaaca atctttatg      3840 atgaggtatt tgcttactgg ggacaaagcc ccagtgctat tacatagtgt agctaaacgc    3900
tgtagaatgg taaaacaag aaaatgctca gcaaagtgtt gtttctcatt taatgaaaat     3960
cttattttaa aacacaaaaa ctcaatatac cccaaccaaa aatctgatga acattttctg    4020
tttaatattt attatacagt acctttaaaa acgtaatatt cttattctta aaaatttagt    4080
gtgctagcaa atagcaatta agtacctaag tcaatcagga cgacaaaaaa atactcaatt    4140
tggggagtta gttacttcta tcatctgaat gcgtccctcc aaaattcatg ctgaaaccta    4200
ttcctcatca tggcagtatt aagaggtgaa gcctttgaga ggtaattagg tcatgagggc    4260
agagtcctca agaatgggat caatgctctt ataaagagg ccccagggag cttgtaaggc     4320 ttttgccct tctgccatgt tggggggtg ggggtgggggg cgcagcaacc agtgctaact     4380
ctgaagcaga gagcagccct caccagaaac cgaatctgtt gaagccttga tctctgactt    4440
```

```
cccagcctcc agaactgtga gaaataattt tctgttgttt ataaattacc cagtctaggc   4500
tgggcgtggt ggatcacctg aggtcaggag ttcaagacca gcctggccaa tatggtgaaa   4560
ccccatctct actaaaaata cagaaaatta gctgggcata gttgtgggcg cctgtaatcc   4620
cagctactca ggaggctgag gcaggagaat cacttgaacc cagaaggcag aggttgcagt   4680
gaatcaagat catgccattg aactccagcc tgggcaacaa gagggaaact gtctcaaaaa   4740
aaaaaaaaaa aagtacacac tctaacatat tttggtatag cagcccaaat ggaatggact   4800
aagacaatta cccttaaaat aaaagctccc atagagagat catgcattca agtacagagg   4860
ttcttaaggg caatgggaat ggaggacata ttcctgcaaa cttttcaaca gctctcatta   4920
gcccgatgtt agagctctgc aaagaagact aaattatact gagaaatatt tttaaatctc   4980
cacaaatagg aatgctgtaa acgttgattt agtatatata aaattagaca agactaacaa   5040
tatccaatgc aatctaaatc ttaggttgac agacaagaaa gccactgcaa acaggaatat   5100
accacaatac ctgatcttgc cacatatttg taaatatgca aagtatttca ataacttcca   5160
agaaacagta ttactctcat gagaaataac atgatgtaag tcacctttga aactgtcctt   5220
gttactttt caaatgtatg ttagtcattt cttaacacca aatgaaatga aaaactgagg   5280
tggtaatggc tggctgctcc catctctcct ctactcatgt gccttcacca atacagcaat   5340
catttttct tatatgggaa atttacagtg ttgatatagc tcagagatat attgaagaaa   5400
agcagaaaaa cgaaacttat aaacatttta ggaaacctta tgtattttct taaatagttc   5460
aagtgtaaaa cttagaattc ttataaataa tgtgtgttac agctatattg taaatggtgg   5520
ctcatgcctg taatcccagc acttcaggag accgaggtgg gaggagagct gagcccatg    5580
agtttgagac tcacccgggc aacacagaga gacctcatct cttaaaaaaa aaagaaagaa   5640
agaaagaaat gaaatgcaaa gaaaagtct ctatttcaaa tgtagccagt agagccaata    5700
ggttaaccaa tattaacatt aacgttgata aaacaagaaa tgatgattta ctataagctg   5760
aaaatcagac aatgtatgga ctttaagagt aacaggcacg atcatcacaa acttaaatca   5820
ggtttgagtc ctatgagtta tatacagtta catgatgcaa caaagatgc cagccagttg    5880
ttaaagagta ttagattcgg ctgggggtgg tggctcatgc ctgtaattcc agcactttgg   5940
gaggccgagg agggaggatc acgaggtcgg gagtccgaga ccagcctggc caatatagtg   6000
aaacctgatc tctactaaaa atacaaaaac tagtcaggca tggtggcacg tgcctgtaat   6060
cccagctact cgggaggctg aggcaggaga attgcttgaa cccaggggc ggaggttgca    6120
gtgagccgaa atcgcgccac tgcactctag cctgggcaac agagcaagac tctgtctcaa   6180
aaagagtat tagattcaag tcctgttct gtcatttatt atggaaccat ggacacaact     6240
acctatcttt cctgaacctc agtttttca actgcaaaac aggaatatat acatatgtgt    6300
atatatacat ctgtgtaaac acatatgtgt atatatacat ctgtgtaaac acatatgtat   6360
atgtataaat ggagataata cctacattat agtttctgag ataataaaat gcacaacaca   6420
attctgacac ataacaattt gtaacttaaa acataccatc accagggcca ctagttttag   6480
aacactgtaa tgcatagtct aatttaatac tatgcaaact gtgttcactc aaggttttat   6540
ttccttttaa tttcattcat ttactcttca gttgtttgta agctaaaaag tccagaatca   6600
tgaaattcag aagtttacgt tttaatgttt ttctatatgg caaggaaaaa aaaaagggca   6660
aagtcatttt aacactactt tcaaaatcag cctagaactt aacactaaag gcatgaccca   6720
taaagggaa tactaataaa tagacttaat taaaattaaa caacaacaac aacagctaag    6780
```

```
cttttgttct gcaaaagatc ctgtgaagag aatgaaaaca taagccgcag gctgggagaa    6840
aatatttgca aaccatattt ccgagaaagg tcttgtgtct ataatatata agaactccca    6900
aaattcaaca gttttaaaa aaagcaaata atccaattag aaaatgggca aaagacatga    6960
acagacattt taccaaagag aatatatagg tggcaaataa gcatatgaaa acatatctca    7020
cacatcatta gccattaaag aaatgcaaat taaaaccaca atgtgatatc attacacacc    7080
taccaaaata tccaaaataa aaattagtgg taacaccaaa tgctggtgcg catgtggaaa    7140
aatagtcctt cacacactga tggtacaaat gcaaaacagt acagtccctc aggaaaggag    7200
tatggcagtt tcttacaaaa ctaaacatgc acttaccata tgaccaagta attatactct    7260
tgaatattcc cagaagtaaa aatgtcttct ccaaaaaact tatacatgaa cgttcatagc    7320
tgttttattc gtgagagtca aaaacagaaa gcaatcccag ggctacccat taaacaggt    7380
gaatgcttat aaactgactg taataggtct gtcccacgga atactactca gcaataaaaa    7440
ggaacaaact actggtatat gcaacaactt ggatagatct caagggagtt atgttatgtg    7500
aaaaaagtca atctcaaaag gttacacact gcatgactcc actgatataa cattagtgaa    7560
atgcacaaaa ttttagaaat ggaaacaaaa ttagtagttg tcagaggtta gggaagaaat    7620
gcagtaaggt aggtggctgt ggctataaaa gggtagccta agagatcctt ctgttgaaac    7680
gggtatattt tgaatatagg gtgaatttac atatgtgata aagattgcat agaactaaat    7740
acacacacac agtatatgta aaactaagga aatctgagta aggtttgtgg attatattaa    7800
tacaatttcc tggttgtgat actgtactgt aattatgcaa gatgttagaa ttgggggaaa    7860
ctagatgaag ggtatgtaga tctttctgta ttatttctta caattgcatg tgaatctgta    7920
attatctcaa aataaaaatt tttttcaaaa tttcaaaaca actagtctag agctttgtta    7980
atcaaagttt tctctgagga cctgtagcat tttggttatc acctggatct tattaaaatg    8040
tagattctca ggctgcatat tggaattcct gaattggaat ccgcatttta acaagatttc    8100
caagtgattc atgtttaaag tttgagaagc actagtctac aacaatgact tttaacctttt    8160
caacctactc taacacactt gaaggccata acaaaattca catcaataac agttgctcgg    8220
ttggacagtg actctcaaca caaatgagtg aggaaaggtg gggactcaag actcaggtag    8280
caggaaaagc cccttaggtg atcctgatga aatgttttct ccatcctggc tgaaaaaccc    8340
agaacagtca attaaggctc aaaacaaaag taatgtttat aatactggag atctttaaaa    8400
ggcagataat atatactata acagagcaaa ggtaattatt acaatgtata atcttataa    8460
gaaccaaaat cagaattaaa atcactaagc acataatgaa aatcctttaa aaagtataaa    8520
aatgaatgta gtctaagtaa atactaataa tggcagttat agtgagaaaa gctctagagt    8580
cttttactct tcatacttcc tagtcacaaa catctatttc caaaactgac ccttcgtatt    8640
tcaaataatt tatggcctgg tacagtaata agagcatgat atttaaagcc agtcagaaga    8700
cacatattct agctctggat ggcacttgat gacgatggat tcagcttatg gttccaatcc    8760
cagctctgtc aattagtacc tatatgaccc tagtcaaata cttaaacctt cttgtgttac    8820
ttgtgtgtca attgtatcat ctataaaatg aggatattaa cagtatatac ctcatagatt    8880
tttttgtgaa ggttatacaa ttaattcata taaagtattt agaacaatgt ctagcacagt    8940
gaattctcaa tgagtgttat aattgttctt tttaaatgtg acttgactct caacagaact    9000
ctactgaatt ctaatatgta ttctgtattg agctgtcaaa aaaaataagg attataataa    9060
catatactat tcttgtagtc aaccctgtta ctatgttatt actagtgtca gttttgttgt    9120
tttggtcata catattgttt tacatacatt aagaattatt agaaatgttg gtttattaaa    9180
```

```
aatgaccatt tatggctaga agggtatata tctggctcac tgactgtgga gtcaatgtcc    9240
ataaagagga ggaagaatgc catcagagta aaaggagatt ctattcactg aaacaaagtg    9300
ataaaaagct atgaaagaga aaacataaaa ataaccaaag gggtgaaact taacagatgc    9360
ccagtagatg cacaatgcac tgggttgtaa aacttaaaat ggccttaatt aaaagccaag    9420
cacggatgga ggtgctgggg gagtctccta cggacacagc aggcagaatg taacaatgac    9480 aagggctca agtttattta aaaagagatt ggacaggccg ggcgtggtgg ctcacgcctg     9540
taatcccagc actttgggag ctgaggcgg gtggatcatg aggtcgggag ttcgaggcca     9600
gcctggccaa catggcgaaa cctcatctct actaaaaata aaaaaaatta gccgggagtg    9660
gtggcgtgca tctgtagtcc cagctactca ggaggctgag gcaggagaat cacttgaacc    9720
tgggaggcaa aggttgcagt gagctgagat catgtcactg cactccagcc tgggcaacag    9780
agtgagactg ctcaggatct cccaaagacc caaatccctg taaactgaat gcataatatc    9840
atttgctcca gtgaggctta gatggacatt ctagtcttct tggttgagct gaagaaacaa    9900
atattatatt gataatttat gtatgttgta tttttcaagg tatagcaaca agttttatt     9960 catcagctac tttgtgtgtg tgctttgttt ttaagtcttt tgaaacagga tggtgattta   10020
ctacatttat aagtaaaatt tatttgattt acaagggttg cttaagtgta tcacaggatt   10080
tcacttgtta tatttgcagg tgcttaaaaa atcagctata ctaaactata actgaatta    10140 gcaaagttca tttattgatt aatcaagaat ataattagat ttgcctaact atataagtag   10200
tactatgtgt tatttaagaa ttaaatctag aaaagggatg gactctggaa atatcaagaa   10260
gtgaaaaaga ctgctctcat ttttgtacaa caattactaa atttctaagt agcattaatt   10320
gaactgaaaa ggcattttag aaaaactaga ttttacaatt tataactcta ataaaacaca   10380
actaactatg agtgtgcttg ttcatgccca aaagctacct tccaaaatta aaaaccctat    10440
tggatggctg ggtgcagagg ctcatgcctg taattccagc actttgggag gccaaggcgg   10500
gcggatcacc tgaggtcagg agttcgagat cagcctggcc aatatggtga cccgtctct    10560 aacaaaaata caaaaattag ccgggcgctg tggcgggtgc ttgtaatccc agctactcgg   10620
gaggctgagg caggagaatc acttgatcct gtgaggcgga ggttgcagtg agctgacacc   10680
gtcccactgc actccagcct gggcgagagc ccagagcgag actccgtata ttaaacaaaa   10740
caaaacaaaa ctcaaaaaac cctattggca attactaggg ccatcaaatc agtatatttt   10800
cacttgacac acaatttga gataatgaac cgaacttact attttgaaa atattacata    10860 ataatatta gtgaagcttc attgctgaaa tggtgacaaa gatgaatagc aataaaactt    10920
ttcttataga tctttagcaa aaacaaaaaa accccaagca tactatggta cattacttta   10980
gagaatcaag tagctgctag ttgagtaata gtggtaatag gcactacaat gatataaaca   11040
aattacaaca aagaatattg ttttttatttc ctgtccatgt tttaaaaaag ctttggtttt   11100
acctatgttt aacaaaagca taggtacaac aacgactact actactaaca tataagtagc   11160
ctggatagaa ttatcttaat agtagtaccc aagtgcagga tctctaagta atgatcagaa   11220
ggcaggaata aattttatca gaaatcttca ttcattacat atttactatg catttaccag   11280
ggtatcacta tgctaatgga tacaaagata aataacatgc aaacaactgt aatacagtgt   11340
tatgtgataa cagaaatatg tacaaagcac tatgaaaaaa attacaaagc ttgagcacaa   11400
attttaactc tggacttact ggcatttaga gcaaaaccaa aacaatccta actggttaat   11460 ttcatttttct aagagttgga agctatatca gtaggtacaa agtaaaatat gctaattgtg  11520
```

```
gtagaaagta aaatattaca acagtagaga atttcaaaag aagataaaaa taatggaggg    11580
aatatagaag gtcttcaagc ttccagcttg aaatacatat ttttttttaa atagagaaag    11640
agataaagtc atttgagtat tcagagggca gactgaatat aatggtactt ctgagaaatc    11700
agtggataag gagagaaaag tggactaaag gccatagcat atagagcttg gaatgtcaaa    11760
tgtagtggaa ataacaaagg tttggttgga atcccaactc ccaacaacgt actgtgtatc    11820
tagagcaaat tacatcaacc tttgggagta ctgtttctga atctgaaaaa tgaggaaaac    11880
ttatctttga acaattgatg tgataattaa atgagatata tgaaatatct aatgtaacaa    11940
gtgcttaaca atgactagtt cttttcattc ctctcttgaa ccattgtgaa acgtagaacc    12000
aagaaaggta acagtattta gttgttacag aacccattaa gagagaataa aaaataactg    12060
gtattctaac ttcagtttcc tttgaagtct tgttaatgag aataaatatt atgtggcaca    12120
aagaaaaaga aaacaggggt ttacacagga tatgctgcca gactttacca acaatgacac    12180
atgatatctg cttcaactgt cccatgcata tttggcttaa gatatattca tgcatatcaa    12240
attttacatc acatggtttt caaaagaaga ttcattaaaa ttagcttaag aatgtacaca    12300
atatacaata cctcattaaa taaaaagaac agaccatttc caaatgaatg cttttagagc    12360
tttacagtaa acagtctttt ggtggtagaa agaggggggaa cagagagggg agtgggtggg    12420
agtctgtagc acttatcaga ctacttttat cctttatgta gagaaatagg agagttgaaa    12480
ataagcactt tctgtactta tgttgagagt ctgaagccca cttttaatag tcttgacaac    12540
actaaaaaat aataattaac atttgaaaag ctgtcattat tatagtcagg gacacttaat    12600
ctccaaagga gaagtttctt aattgatact atgattaaat aaaagcatcc atcagaatta    12660
tatccacaat ctggtttgga gtttatgttt tgtcttattt aaattgttat acttattata    12720
attctgtcta gacagtgcca aatgtacttt gtcatacaaa cacttgaggc aaattttctt    12780
caaataagcg caacactttg tttcctcttc gtatcctttg actgaataac gtgtggtaca    12840
gagaagtaat acttcccttt cttgggatcg agatcaattt gatgcttgtt ataagcccat    12900
ttacagaaca aatggtattg cttttaaatt tttatatgaa cttatcagta gactagccaa    12960
aaaagaagct tcatataaaa gtgctaggat tgatattctt agtaataatt aggtaaaattc    13020 tctaaaattt tctcccaaaa gatctgaaaa atcataccaa gggaagtata gtttaaattt    13080
cattatatat aatagcttta aaatatcttt gctaattcta cccaaagcca cactaaaaag    13140
actaatacaa aaagaatgta attaataaac tattttcctc tgaagaatca aagggcactt    13200
ctgcatatga acatgtttta tccttttggt gtacttacat aaaataatta agaaacactt    13260
ttaattagta taaacaaaga aatcaaaata gcaagaagaa atgtctgagt aaaagcagct    13320
gtgctgacct caaaagtgaa attctgttct cttgatgccc agttaagtgt ctaacccagg    13380
gaaaagtgat tctaaacctg ggctaggagc tagtggagct cttcaaacag tctcacctac    13440 cctcaccccct caaggaatgg tctatgggtt ctgtggtgaa cgctaaagtt tataacatgg    13500
gaatatttat tattttgttt ctaacacaaa taatttttaa aaatttattc tactaaagta    13560
acatcaaagg gaaatttcat aaaaattctt ttgaaatttt tagaagtagc aaataaaggc    13620
aagtgataaa tattttacag atttcaccac ttacgtaatc tgatcaacaa attttaaaaa    13680
catagcactt gaatactatt aaaaatatat taaaaggta acatagtaaa actataaaat    13740
tctttaaaaa aaatataaga ggaaaccttc gtgaccttgg attaggaaat ggtttcttac    13800
atacggcaac ctaaaaatac aagcaaccaa agaaaaaaac agacaaactg gacttcatca    13860
aagttaaaaa cttttgttct tcaaatgaca tcatcaagaa aataaatccc acagaatggg    13920
```

```
acaaaatatt tgcaaaccat atctgataag agaccactat tcagaatatg taaagaattt    13980
gtaaaactta taaataaaaa gttaaagaag tcaattttaa aatgagcaaa ggatctgaag    14040
acaattctcc taagaaatac gaatggctag ttaaatgcat gaaaagatgt ttagcatcac    14100
tggtcattag gaaagagcaa aaaccaaaat gatatactcc ttcataccca ctaagactgc    14160
tgtaattaaa actatagaaa ataagcgttg gcaaggatgt ggacaaattg gaaccctcct    14220
catacactga tggtagaaat gtaaaatggt gcagatgctt tggaaaacag tctgacaata    14280
ccccaaaggt ttaaacgtgg aattaccatg caacccagca attctactcc taagtatcta    14340
cccaagagaa atgaaaatat atgttcacca aaacatttgt acataaatat taactgcagc    14400
ttttattcat aatagccaaa aagtggagac aatccacatg tctatcaatt ggtgaattga    14460
taaacaaaat gtggtatctt catacaacta ttactgggcc ataaaagaa tgatgtattg    14520 atacatgcta caaatgaat gaaccttaaa acaatatgc aagcaaaaga aaccagacac    14580
aaaaggccat atattacatg atgctaatta cataaaatgt ccagaaggga gaaataaatt    14640
agtagttgcc aagggctgga gggagggga atgatataag tgactgccaa tgggcatggg    14700
gtttcttttt agggtgatga aaatgttctg aaatttatc acgggaatgg ttgcacaact    14760
ctgtgtaact tagaattcag tgactcctaa aaccaatgaa tagcatgctt taaaaggtga    14820
cctttgctga gcatagtggc tatagtccta gctacttggg aagctgaggc aagaggatca    14880
cttgagccag gagttccagg ctgtactgca ctatgatcat acctgtaaat agccaccata    14940
cacaccagcc tgggcaacac agaccatgtc tctaaataaa taaacaaata aataaataaa    15000
agggtgacct ctgtagtatt gagattatac ttcaagtaag ctgttattaa aaaaaaaaaa    15060
gttatcatat gggtggcagg ggaaatcatt ctgggatgat ggctaacttc atcagtattt    15120
gatttatacc tatgcatcat accttatgtt tgttttatgc attttgtggg ttttttaaaa    15180
aaattatatt tcataaaaac aaattttaaa aaattaaag tcaagaaccc caaaacaaca    15240
aagatcagag atacatttct accttatcaa ttcagaaaaa ttacaagttt ttttcttaaa    15300
aattgtatag catcatggtg attttaagtt acctgtagga atttaaataa ctttgtctta    15360
actgttcacc aaaactcatt taatattcat gttctgatac tgaaaatgaa gctgaaaagt    15420
tttgaaatta caatatgcta gtttaaaaag gtttactaaa atacataatt tcattataag    15480
gagtaatatg aaataaaagt atcaaatatg ggaccattaa aaatgtcctt actaacaaat    15540
tgctacccac attgtggact cactgcgtcc actgtttgcg agcttttcca gaacgctcgc    15600
caccagttag ggtagccaag aactcctcat cttcactttc ttcctcacta gcttggaacc    15660
tctggattcc cacccacact gctgtgacct gaatggggaa gagaaacgcc atagtaaggg    15720
aactcttcct tttatagatt tctgaattag aatctggcat tacaaaagaa caatgttata    15780
aatccaggtc agagtttata gttctatttc actattactt atatggcttg tcctaggaac    15840
ttaactatta tttacaatgt aagtacctat ttccacaaaa aaattcaaaa ttttggaata    15900
caatatctga agagagaatg gtctattgaa tccaaagtag gctgatacat cccaacagta    15960
tttcagattg agataataat aataccacca attcatcaag tcaaattata tgcttatttt    16020
ccacaatgga agttttaaaa tagtataaac attttaatat atagcaggct taacttatga    16080
ttattaaaca gggttctaag aaaatagtat acatcaaata ttaatgtgct tcttgtataa    16140
tttaggtgac aatttatcca tctgagaaat gcaaaagaga ctttggtaag gggttgagta    16200
aggagcattc tgtgtcaaag aattcactag caaaagaggg tatactgtag ttacaagcta    16260
```

```
taatcactgt acttattta aatccctctt cagaaccagg tcttaaaaga tgataaacat      16320
ggcctcatga ataactatca accaaactat agaaaagagt gcaagagtgt ggtgttctaa      16380
cttaaaatat ggtgttttat tcaaataatt ttatttaagg ctccaaaagc agcagcctca      16440
ttccccagaa atcatagtta aatgaaatct tccttactaa aggaaaaatg aatcacaata      16500
tttaacgtga acattttaaa aacactctaa agcaacaaaa ctattcaatt gtatgtgata      16560
tggcttagaa aggcatgtag gtaaaaagga ctaaaaactc taataatggt tgggccaaaa      16620
gtaaatttgt tagttctact ccattaagca ttcctcaagc agtgtaaaaa tcagagttca      16680
agttacactt tgatgtgtag atcctttgaa agccactcta ccctgtttta tatgaagcat      16740
ccgcagctaa aatgaacacc tagtgaagag tatgaatgct gcaatacata agcagacgtc      16800
agaattgtcc caagctgatt ctaagttact ttaaacatgt atgcagagtc agaatatgac      16860
ttacttctta gaagtaacag ataattaccct ttggcataat gaaaaaaact ttaaatgtaa      16920
gttaatacag gtattttccc tttagcaaag ctttgctttt aaaagaaaac ttcaaaactt      16980
aaattaaaat aggaaatgct ctactatgta gtaaaaatac tttttagatt actgaagcaa      17040
agaaaaggaa ggattctatg agggaggaaa agtgggagaa aatgtaaag aaaaaaagga      17100 agaaggaaag aaaagagaaa aggaggaaag aacacaagga cagaaaggcc tattgaaata      17160
tattatttct ttcaaatttt aaacgagcag aataaattct tttgttttat aactatgaaa      17220
taatctatgt tcctcttatc tatgcttgga aaatttagac aaaatgttaa gagtaagtac      17280
tacattggat ttccgggtct tcagctctga aaacaagctg tttcttaaca tacgtcaatt      17340
ttctatattt catgtcattt ctatttgcaa atgttataaa gttcaatatg atgtaaaaca      17400
tggttaaatg aagttcaaaa ataagtataa catacattag tttggctatt ccaaatttca      17460
tgcacattaa ctcagccaca catctaacac agtcagccct ccctatccag gggttctgca      17520
tctgcagatt caactaacca tgggtcgaaa atgttttgt accaaacatg tacaggcttt      17580
ttttcttgtt atcattccct aactacagta taacaactat tttcacagtg tgtacatgtg      17640
tatgaaatat tataagtaat ctacagataa tttaaagtat acaagagggg atgcataggt      17700
tatatgcaaa tactacacca ttttatatca gactctcaaa catcagtaga atttggtaac      17760
ccagggaggt cctggaacta atcacccaga ggtatcgaca gatggctata tataaatcac      17820
tcagtgaatt caggattcac attatttcac aactagtata atttatgtt gttcacataa      17880 ttgtgtcaca acatatacat gcagacaggt gactttcatg aaaagattac acccaagata      17940
gacatatggt ctactcaaat acggtttcca aatgtgtatc caatcttgtt taattataat      18000
caaactcacc attccattga taagcgacct ctaccaacct gcttatcccc tccaagcaat      18060
ataacagtgg ttctctgaac caatattgac cctcctttaa attgatagcc ttttttaaa      18120 aagctaacca ttgagaagta catactgttg aagacagaac atattctgta aaatgctccc      18180
aagatatcaa agtcagatga tacaactgaa tgtttatgct agattatatt tctaagctga      18240
gaattacatt ttaatatacc ataagcaatc tgcaaaagaa gcaacttgcc taaagatttc      18300
aggagtttca agtatgcata tgtcaatatc tgtatcaata tgtaatatca atataatcaa      18360
tgcacacaac aatacgtaac tgtacttata tcatctcctt agcactaatt attacaaaca      18420
atctgcatgc actgcaaagc aaaagtataa tataaaatcc caaaaaacct tgaaaattta      18480
ataaaaccaa aaaacaggca tcacacacaa gaactgaggc gtatacttca ttaatgagta      18540
tgatatcctg atatgaaatg tcaaacaaaa ttacccaggc tcaggttaga aataaagata      18600
ggacattagt ctttgtattt ttaaattgat ttttctcttct aatattcctt aatgataacc      18660
```

```
ctatatatta cctacttaaa attattagca aatagttatt ttaaaagtat gagtaattag   18720
accaaaagca actctcatat ttacccaaaa gaaggaacca ctaccaagaa tcaaagccta   18780
gtaattctgt tcttaacaga caggtgttgt gtattctggc atgttacatg aaaatcactt   18840
atgagaagaa cagaaaaaaa aattagaagg tagttttcac tatggaaata ggtaagtgat   18900
taagcagatt ttcttacacc atgaaattgt cagcagactc aataatcacc ctaaggggca   18960
tcattctgga tgccgacatt ctctatgatg aaagggact gaaagtaaaa tgcactaatg   19020
acataaagaa accaatatcc aatagtaaag ttgaagaaat aaacattctt tggacaggaa   19080
ctaagctgaa gtttgcaact accaagaatg tattatgcca gcagtaaatt aggaaactaa   19140
agcccatgtc aaccaatgaa aaatgggagg actgaaatca atcattaaag cagcagcaag   19200
gttctaacta ttctaaggta taggctacct ctggcgtata ttatcagagt tgacaattct   19260
tccaagaaat tctaacatca actgtaatct gaggtccttt aaaaaataat ataaaccagg   19320
cagtagactt acattttgta atattttctt ctaagagctg tacattaaga ttttatttgt   19380
gatataaata ctatcaaata attagctata gaacagctct attttcaaca gttataacat   19440
tttaagccat ctcacattta acctaaactt ttatcaaatg tcaaaactga ggccgggtac   19500
ggtggctaac acctgtagtc ccagcacttt gggaggccaa gatgggcgga tcacttgagc   19560
ccaggaattc gagaccaacc tgggcaacat ggtgaaaccc catctctata aaaaatacaa   19620
aaattagctg cgcctggtgg tgtgcgcctg tagtcccagc tactagagag gctgagggag   19680
gagaatcacc agggcctggg agatcaaagc tgcagtgagc tgagatcgtg ccactgcact   19740
ccaccctggg tgacagagtg agaccctgtc tcaaaaaaaa aaaaaaaaag aaagaaagaa   19800
aaaaaaatca aaactgatca cttgaggtcc aacttatgtt tactatatct acttatattc   19860
ccaaagacat cttaaggaga gatgaaatca taaaaaggtg aggatgagaa agaaaatagt   19920
aagtcagtaa ggtcaatttt tacatatatt aggctagcat aataaaaata tgagtgtctt   19980
attattattt ttttttgaga cagagtcttg ctctgttgcc caggctggag tgcagtggtg   20040
caatcatggc ttactgcaat gtctgccttc caggttcaag caatccttgt gcctcagcct   20100
cctgagtagc tgggattaca ggtgtgcgtc accctgccca gctaattttt gtattttcag   20160
tagagacagg gtttcaccac gttaaaccat gagtttggcc aggatggtct caaactccca   20220
aagtgctagg attacatgcg tgagccactg cgtctggcct aaagtgtctt attataacca   20280
agaatttatt tgtggagaga ggtaaagaaa actcattttt agtgaaataa ttaaaactgc   20340
atcattcaca atctatcttt caaaatgagg tattaactat tttggcttct aaaattaccc   20400
catatactac atgcatgagc atgggaattg aagttatttt attcctaagt ttgagacttc   20460
atgttttaat gtgatcacta aaaatttcct aattgatgat taggaaaata actttctgta   20520
aaattccaga attttagctg tttcaatctc ttcatattaa ggggagaaca ttatgttttt   20580
actttctgtg catgcacttt ctttattaga agaaaatgga ctgagggcag taagcaaccg   20640
aaaaggaaga gtaataagaa gcctgatgtg tgtgaaaact ggagaacagt ctcaaatcat   20700
aaaaagttat gacagaagag gcataaaaaa taaagtaat gaacttaata tatgaaaggt   20760
aataatgatt aagagcatag gctataaagc cagactggac tccctggatt caaatcctgg   20820
ctcttctaat tactaggtag gtaaccctga gcaagtttca atgaccaatc ttttttctcaa   20880 ttacctcagg tatataaagg ggacagtaac agcatttaac ccagaggaca ataaggatta   20940
aataaataca tgtaaaataa tttaaaacag tacctggtat tcaataaagc gcaataaatg   21000
```

```
ttagctgcta ttattattca tctaaacttt actttcatta ccagcaatat tttttaatct   21060
taaaaatatt gaataaaaca atgacctagc ttagtaaata aattcataat gagaaaatgt   21120
tgatttcatt taataataac tttagtagtt tgggataaca ctttgcatat tttaatttcc   21180
ccagctataa ataactcaaa taatttgcca tcagatgatc tgttattttg aagttaacaa   21240
ataaagcatt tcctaaaaaa gttctaatac ataactttg ctctcatctt atgttttaaa    21300
aacaaaatgg caaatcatct gcatcaaata gttcctactc ttataacatg acaattgttt   21360
taaaatatat ctgctggaaa aagcaactga agtcctagaa aatagaaatg taatttaa     21420 ctattccaat aaagctggag gaggaagggg aaaaacatat ctgccaaata agcttataat   21480
taatagttgt tttcagttt caaaaatcca cataggaagc aatttaagcc taaattgcct    21540
aagtctcaat ctcagcgtag tagatagctt agggcaatca aaacttgctg tgttgggctg   21600 cccctacag gactcaattt acctatttct tttaaaaggt gtgtaagtag gaaatatgat    21660
tcaagtttta cattaacaat attaatgcta aagcagatga ttatcattca cgcattcact   21720
ataggaggaa acagtctctg agaaccatct atagagatac agagagaaat gaaacaatcc   21780
ttgtccttga ggaattaata gtttactgct tacagagaaa ctacatacat ggtgaaatat   21840
ttaaaaatag ctcatgatat cctctatgat attatgtttg ctatagaaaa agaacaaggc   21900
tgaagatcta agatccaagt tctactgttg gctctgccat caaacaataa gctaaacaat   21960
gtacaagtca gttttgggga agctgtctta ttcccaaaat gaggaggtta aattagttaa   22020
ttcttccagc ctctatggct ctaatattcc acagttacat ttgtcaaaac aaaaggtaga   22080
aggaaatgtt tcaaaaacag acttcgcaga aagaacatct atatgatatg aagggctggg   22140
gcatatgtga agaaatcaag gaagacttct tgaggaaggt gacatctgaa gtaactttag   22200
aagcactctg ggagccaagg ctattcccag gagttaacag agtcagataa taaaagatca   22260
aagatgttta ggggaatagc atgcagtgtt atttggttgc agtctagcta tattttagga   22320
aacatcaaat taatatcagt ataaaactca acagaatgga gggagaaaaa gcaggtagaa   22380
aaatctaaga accactaaaa tagttcatct agaagataaa ggacccatga gctaaatcag   22440
tgcaaatggc aagaagggaa taaatgaaga cagttctggt ccattagaac tgcaactcaa   22500
caaaagtgat caaaagagtt attccaaagt attgacctgg taacttgaag aaaagtaaag   22560
aaagaggaaa ctggacactg aaacagaaga agtagattat gtatttggta gtgaatggaa   22620
gtagattggt gggaccagtt agaacctcac agagaagaac tatgttaaga ccagaaatac   22680
ggccaggtgc ggtggctcat gcctgtaatc ccagcacttt gggaggcctg ggtgggcgga   22740
tcacctgagg tcaggagttc aagaccagcc tgacaaagat ggagaaaccc tgtctcccct   22800
gtctgtacta atacaaaatt agccaggtgt ggtggtgcat gcctgtaatc ccagctactc   22860
aggaggctga ggtaggagaa tcgcttgaac ccgggaggcg gaggttgcag tgagctgaga   22920
tcgcaccatt gcactccagg ctgggcaaaa agagcgaaac tcttgtctca aaaacaaac    22980 aaacaaaaca aacaaaaaca cagaaataca tcaattaaaa aagtgagcta ttcaccagat   23040
atgttccact ggtcataaaa caaaagaata caggaggcat gacaagccat catcattgct   23100
gttaaaataa ctcacagcaa aattataatg atttaagtca ataacatcta ataattccag   23160
ctatagtgtg caatttaatt tattatgtgc caggcacaat agtttattaa aggtattacc   23220
tctaattttc acaataaccc tattttacag attataaaat ggaggcccag agatgtaagg   23280
tgaacgagcc aaatcaccta gttacctgga atataaactc agaactgcct aaatcaaaag   23340
ctctcaatct taaccacatg ctatactgat gcatgtcaaa gattcaattc attcagattt   23400
```

-continued

| | |
|---|---|
| ttcaaggtta tcggaaaacc tatgtagata aaaatttcca aaataatcaa ggatatgtaa | 23460 |
| cttttacaga aagcaatcac tgatcatcta ttgcaatact catgttctta agcaatatac | 23520 |
| tgagttgaaa ttttatatt ttataaataa ttagaaagaa tacatttttt aaaactttaa | 23580 |
| aaaacacctc agtttttatt ctcttcccca aatttcaaca aaatccattt atccaaactt | 23640 |
| gaggttgaat cattaaagtg gtgatatcat cagtaatagc agagtgagga ccctgaatat | 23700 |
| actctcctcc ataaaagcaa caagaacaca aaaattctca aaatgaactt tttctgaaat | 23760 |
| ctttcaaaag ccccactctc agaaaactgt cattatttga tctgccagtt ccctagaaaa | 23820 |
| acctccctca taggacatta tttgacttga ctcagagctc actcagtgca aacaatttta | 23880 |
| tcaccaggag agtttgtgga aaatcagtgg caattgttaa acatcacatc tgccatgaga | 23940 |
| tagcaataac agatgggaca aacaagctaa ccaaaaaatt aaaagaaaaa cctgggaaat | 24000 |
| aagaaatcca aaggggtct gaaaagttct aacatatttc tgataatcca gaaagccata | 24060 |
| cacatgtata gagctgtgta cacgctcaaa aaacatctac gaaggcccta aactctcacc | 24120 |
| tatgggaaac cctgaggctc tgtacaagaa gaaagtaaaa tccagttata aattgcttgc | 24180 |
| cgtatcattg aaggcaatgc cccaacattc acacataggc ccctggcaaa gattggaaga | 24240 |
| tactctagtt ctaggcattc aagaaaatct cttctaatca tcagatgatc actaaactca | 24300 |
| ccaagcagta actttagggg cctgtgtgat aaaaaataaa aacctgaaag aattagttca | 24360 |
| ggaaagaaac taaacaagca acagcaacaa caaaaacaga ccttgggaaa gggggaagc | 24420 |
| atctggtttc cagagttatt ctgttatact atataaaata ttcaggtctc aacaacaaca | 24480 |
| aaattacaaa gacatgcaaa gaaacaagta taagccacaa actggggga aaaagcagca | 24540 |
| gaaactggcc ctgaaaaaga ccagatgctg gacttactgg acaaagactt taagagagtt | 24600 |
| attttaaata tgcgcaaaga actaaaaaaa agtttatcta aagaactaca ggaaagtatc | 24660 |
| agaacaatat ttctgatcct tcagaagaac cacttttgt cactacagat tagttctgtc | 24720 |
| tggtctagaa cttcttaaaa acagaatcat agagtatatt ctctttatat cagctctttt | 24780 |
| tactcaacac aatgttgtgt gagatttatc catgttgttg catgtatcat tcccaaacag | 24840 |
| aaatagaaat tatagagata aataggagtt acaaaaaagt accaaacaaa aattctggag | 24900 |
| ttgaaaagca caaaaactga attaacttga ggggctcaac agctgatttg ggcagccaga | 24960 |
| agaatgaatc agcaaatcta aagataggtc aattgcgaga aagagaggga agaaggaagg | 25020 |
| aaggaaggaa aggaggctca gagacccaag agacaccatc aggcatacca atatacatat | 25080 |
| aatgagaggc ccagaagaag atgcagaaaa agggtcagag tatctgaaaa aataatggcc | 25140 |
| ctaaacttcc cgaacttgac cccaaaaatt aatctacaca tccaagaaga taaacaaact | 25200 |
| aaaagaata aaatcaaagc gatccacacc taggtacatc ataatcaaat gactgaaata | 25260 |
| taaagagaga ctctcaaaac aggcaaggga cttatgtaca aaacatcttc agattaataa | 25320 |
| caaatttctc atcagaaatg atgttgtcaa taggcaatca gatgacataa tcaaagcact | 25380 |
| gaaagaagta gaatgtctgg gacctggaat gctggtggac acctgtaatc tcagtatttt | 25440 |
| gggtggccaa ggtgggagga tcacttgagg caaggagttg aagaccagcc tgggcagcag | 25500 |
| aaagaggctc tgtctctaca agaataaaa agattggctg aatgtggtgg tgtgacctg | 25560 |
| tagtcccagc tactcaggcg gctaaggtgg aaagatcgct tgagcccagg agttggaggc | 25620 |
| tgcagtgagc tatgactgtg ccactgcact cttgcagtgg agaccctgtc tctataaaga | 25680 |
| aaaaatgtca accaaaaact acatgcagaa aaactgcact tcaagaaatg atcagtacct | 25740 |

```
tgaagctctg aaggtgctta agactgtaga tcaataccat agaaaataat ttagtattta    25800
ggaatgtaag aaaattaaga cagccttgtt tgataactac acataatact gtaactgttc    25860
ttgcactgtt ctggttattg tcaagctatg agcacaaact gatgactgaa atacagaata    25920
cagaacagga tataaaatct tatcaggtaa agttaggcaa gcaattacta gttgtaattc    25980
aacttgaagg agaaggaata aggaaccaac tcaaaccagg cagcaatgaa ttgtaaaaaa    26040
gcttaaggta aaacaaacag ggaaataaaa caactcagaa cctaagcata tcgtaagaac    26100
ctaatctaac aaggaggggc ttaaactgat tattttacag cttgggtgca attatcccac    26160
aaaaaacttt caggagtttc accagtccat aaactatttg gttattagaa aatagcttta    26220
ttgggctacc ctctttgggt cccctcccctt tgtatgggag ctctgttttc actctattaa    26280
atcttgcaac tgcactcttc tggtccgtgt ttgttacggc tcgagctgag ctttcactct    26340
ccatccacca ctgctgtttg ccgccatcgc aggcctgcca ctgacttcca tccctctgga    26400
tctagcaggg tgtccgttgt gctcctgatc cagtgagacg cccattgccg atcccgactg    26460
ggctaaagac ttgccattgt tcctacgcgg ctaagtgccc gggttcatcc taattgagct    26520
gaacactagt cactgggttc cacggttctc ttctgtgacc cgtggcttct aatagagcta    26580
taacactcac cgcgtggccc aagattccat ttattggaat ccatgaggcc aagaacccca    26640
ggtcagagaa cacgaggctt gccatcatct tagaagcagc ccgccaccat cttcggagtt    26700
ctgggagcaa ggacccccctg gtaacaattt ggcgaccaca aagggacctg aacccgcaac    26760
catgaaggga tctccaaagc ggtaatattg gaccactttt gcttgctact ctggcctatc    26820
ccttagaatt ggaggaaaat actgggcacc tgtcggccgg ttaaaaacga ttagcatggc    26880
cgccagactt tagactcagg tatgaggcta tctggggaag ggctttctaa caaccctcaa    26940
cccttctggg ttgggaacct tggtctgcct ggagccagct tccactttca attttcctgg    27000
ggaagccaag ggctgactag aggcagaaag ctgtcgtccc gaactcccgg cattagccgg    27060
ttgagatcat gtcgcagcca gaagtctcta ctcaacagtc gcccatgcgt gcgctcctac    27120
cttcccttct gtcccacacc tcctgggtcc caaccacgac tttcttgaaa gtgtagcccc    27180
aaaattctcc ttacctctga atctacttcc tctgatccct gcctcctagg tactaatggt    27240
tgagactttc atttcctcta gcaagttgta tctccaaagg gatctaagga agctctatgc    27300
tgcgcccctta ggcatctagg ctataaaccc agggagtctt gtccctggtg tccctcctga    27360
tttaggtata cagctctaga catgggcagt tatgtgggac ctgttcccca ccacccttgc    27420
cagggcccca agtttgtaaa tggctaagag aggaaacaga gagagacaga gagaaagaga    27480
cagtgagaga cagacagaga cagagagaga gagagacaga gaggagagag agagagacag    27540
ggaggacagg gagagagaca gagaggagag ggagagagac aaagaggaga aagaggcaga    27600
gagacaaaca gggagtcaga gaaagaaaga caaagataga aatagtaaaa aaaaacagtg    27660
tgccctattc ctttaaaagc cagggtaaat gtaaaaccta taattgataa ttgaaggtct    27720
tctccgcgac cctataacac tccaatacta ccttgttgtc agcgtaaaca agggcgtagc    27780
ctgaaaacac taagaccact gacaacccat agccttccta tcaaaaatcc ttaacatcca    27840
gtgacctgcg gatggcccaa atgcattcaa tctgtagcgg caactgcttt gctaacagaa    27900
aaaagtagaa aagtaacttt tagaggaaac ctcattgtga gcacacctca ccggttcaga    27960
attattctaa gtcaaaaaag caaaaaggta gcttattaac tcaaaaatat taaagtatgg    28020
ggctattctg tcagaaaaag gtaatttaac actaaccact gataattccc ttaaccctgc    28080
agatttcctt acaggggatt taaatcttaa ttaccataca aaggtccgac cagacctagg    28140
```

```
aggaactccc ttcaggacag gatgatagat ggttcctccc aaatgactga ggaaaaaacc   28200
acaatgggta ttcagtaatt gatagggaga ctcttgtgga agcagagtta gaaaaattgc   28260
ctaataattg gtctcctcaa atgtcagagc tgtttgcact cagccaagcc ttaacgtact   28320
taccgaatca aaaagactat ctcaatcctg actcaaaagc ttacttatac cctctctgaa   28380
acgaatttgc ctaagaactg ttgtttatgg gaatgcatct tgatgaagca gctgggttgt   28440
tatgaaatac tcaggaactc agcctagctc taggactcac ccctgagcac aaaggcaatg   28500
ttgggcacgc tggtaaagga ccactagaat ccagcagccc ggacccctt  ctttgtgatc   28560 aagaaaggcg ggaaaagggg tgagggctgc tacatcagtg agcataacta atccgataag   28620
cagaggtcca tgggtggtta cacaccccgg aaaggaataa gcattaggac catagaggac   28680
gctctaggac taatgctcat cggaaaatga ctagtggtgc tggcatccct atgttctttt   28740
ttcagatagg aaacgttccc ctcaaggcaa aaacacccct aagatgtatt ctggagaatt   28800
gggaccaatt tgactctcag atgctaagaa aaaaagaca tattcttctg cagtaccgcc   28860
tggcaacgat atactcttta aggggagaaa acctggcatc ctgagggaag cataaattat   28920
aacaccatct tacagctaga cctcttttgt agaaaagaag gcaaatggtg tgaagtgtca   28980
tacgtacaaa cttctttttc attaagagac aactcgcaat tatgtaaaaa gtgtgattta   29040
tgccctacag gaagccctca gagtctacct ccctacccca gcatccccca gactccttcc   29100
ccaaataata aggaccccc  ttcaacccaa acggtccaaa aggagataga caaagggta   29160 aacaactaac caaagaatgc caatattccc cgattatgcc ccctccaagc ggtgggagga   29220
gaattcggcc cagccagagt gcacgtacct ttttctctct cagactttaa attaaaatag   29280
acctaggtaa attctcagat aaccctaatg gctatattga tgttttacaa ggtttaggac   29340
aatcctttga tctgatatgg agagatataa tgttactgct aaatcagaca ctaaccccaa   29400
atgacagaag tgtcgccgta actgcagcct gagagtttgg cgatctctgg tatctcagtc   29460
aggtcaatga taggtcgaca acagaggaaa gagaacgatt ccccacaggc cagcaggcag   29520
ttcccagtgt agaccctcac tgggacacag aatcagaaca tggagattgg tgccgcagac   29580
atttgctaac ttgcgtgcta gaaggactaa ggaaaactag aaagaagcct gtgagttatt   29640
caatgatgtc cactataaca cagggaaagg aagaaaatcc taccgccttt ctggagtgac   29700
taacggaggc attgaggaag catacctctc tctgtcaact gactctactg aaggccaact   29760
aatcttaaag gataagttta tcactcagtc agctacagac attaggaaaa aacttcaaaa   29820
gtctgcctta ggcccggaac aaaacttaga aaccctattg aacttggcaa cctcagtttt   29880
ttataataga gatcaggatg agcaggcaga atgggacaaa tgggataaaa aaaaggccac   29940
cgctttagtc atggccctca ggcaagcgga ctttggaggc actggaaaag ggaaaagcta   30000
ggcaaatcaa atgcctaata gggtttgctt ccagtgcggt ctacaaggac actttaaaaa   30060
agattgtcca aatagaaata agccgccccc tcgtccatgc acctcgtgtc aagggaatca   30120
ctgtaaggcc cactgcccca ggggacgtag gtcctctgag tcagaagcca ctaaccagat   30180
gatccagcag caggactgag agtgcccggg gcaagcacca gcccatgcca tcaccctcac   30240
agagccctgg gtatgcttga ccattgacgg ccaggaggct aactgtctcc tggacactgg   30300
tgtggccttc tcagtcttat tttcctgtcc cagacaacgg tcctccagag ctgtcactat   30360 ccaagggggtc ctaggacagc cagtcactag atacttctcc cagccactaa gttgtgactg   30420
gggaacttca ctcttttcac atgcttttct aattatgcct gaaagcccaa ctcccttgtt   30480
```

```
agggagagac attctagcaa aagcaggggc cattatacac ctgaacatag gagaacaccc   30540
gtttgttgtc ccctgcttga ggaaggaatt aatcttgaag actgggcaac agaaggacaa   30600
tatggacgag caaagaatgc ccgtcctgtt caagttaaac taaaggattc tgcctccttt   30660
ccccaccaaa ggcagtaccc ccttagaccc gaggctcaac aaggactcca aaagattaag   30720
gacctaaaag cccaaggcct agtaaaagca tgcaatagcc cctacaataa tccaacttta   30780
ggagtacaga aacccagtgg acagtggagg ttagtgcaag atctcaggat tatcaatgag   30840
gtcactgtcc ctctatacct agctgtacct aaccccttata ttctgctttc ccaaatacca   30900
gaggaagcag agtggtttac agacctggac cttaaggatg cctttttctg catccctgta   30960
catcctgact ctcaattctt atttgccttt gaagatcctt caaacccaat gtctcaactc   31020
acctggactg tttcacccca agggttcagg atagccccc atctatttgg ccaggcatta   31080
gcccaagact tgagccggtt ctcatacctg ggcactcttg tcctttggta tgtggatgat   31140
ttttactttt agccgccagt tcagaaacct tgtgccatca agtcacccaa gtgctcttaa   31200
attttctcgc tacctgtggc tacaaggttt ccaaaccaaa ggctcagctc tgctcacagc   31260
aggttaaata cttagggcta aaattatcca aaggcaccag ggccctcagt gcctattctg   31320
gcttatcctc atcccaaaac cctaaagcaa ctaagaggat tccttgacat aacaggtttc   31380
tgccaaatat ggattcccag gtacggcgaa atagccagac cattatatac actaattaag   31440
gaaactcaga aagccaatac ccatttagta agatggacac ctgaagcaga agcggctttc   31500
caggccctaa agaaggccct aacccaagcc ccagtgttta gcttgccaac ggggcaagac   31560
ttttctttac atgtcacaga aaaaacaga aatagctcta ggagtcctta cacaggtcga   31620
tgagcttgca acccatggca tacctgagta aggaaattga tgtagtggca aagggttggc   31680
ctcattgttt atgggtagtg gcggcagtag cagtcttagt atctgaagca gttaaaataa   31740
tacaaggaag agatctgtgt agacatctca taacgtgaac ggcatactca ctgctaaagg   31800
agacttgtgg ctgtcagaca accgtgagga aagtaactaa aatcgtaaat ccccatggcc   31860
ctcccttatc atattttctct ctttactgtt ctcttacccc ctttcactct cactgcaccc   31920
cctccatgct gctgtacaac cagcagctcc ccttaccaag agtttctatg aagaatgcgg   31980
cttcccagaa atattgatgc cccatcaaat aggagtttac ctaaaggaaa ctccaccttc   32040
actgcccaca cccatatgcc ccacaactgc tataactctg ccactctttg catgcatgca   32100
aatactcatt attggacagg gaaaatgatt aatcctagtt gtcctggaag acttggagcc   32160
actgtctgtc ggacttactt cacccatact ggtatgtctg aggggggtgg agttcaagat   32220
caggcaagag aaaaacatgt aaaggaagta acctcccaac tgacccgggt acatagcacc   32280
cctagcccct acaaaggact agatctctta aaactacatg aaaccctcca tacccatact   32340
tgcctggtaa gcctatttaa taccaccctc actgggctcc atgaggtctc ggcccaaaac   32400
cctactaact gttggatgtg cctcccctg tatttcaggc catgcatttc aatccctgta   32460
cctgaacaat ggaacaacta cagcacagaa ataaacacca cttccgtttt agtaggacct   32520
cttgttteca atctggaaat aacccatacc tcaaacctca cctgtgtaaa atttagcaat   32580
actgtagaca caaccaactc ccaatgcatc aggtgggtaa ctcctcccac acgaatagtc   32640
tgcctaccct caggaatatt ttttgtctgt ggtaccttag cctatcgttg tttgaatggc   32700
tcttcagaat ctatgtgctt cctctcattc ttagtgcccc catgaccatt tacactgaac   32760
aagatttata caattatgtt gtacctaagc cccacaacaa aagagtactc attcttcctt   32820
ttgttatcgg agcaggagtg ctaggtggac taggttctgg cattggcggt accacaacct   32880
```

```
ctactcagtt ctactacaaa ctatctcaag aactcaatgg tgacatggaa tgggttgccg    32940
actccctggt caccttgcaa gatcaactta acttcctagc atcagtagtc cttcaaaatt    33000
gaagagcttt agacttgcta acctctgaaa gaggggaag ctgtttattt ttaggggaag    33060
aatgttgtta ttatgttatt ttagcggaag aatgttgtta ttatgttaat caatcctgaa    33120
ttgtcacaga gaaagttgaa gaaattcgag attgaataca acgtagaaca gaggagcttc    33180
aaaaacacca gaccctgggg cctcctcagc caatggatgc cctggattct cccttctta    33240 ggatctctag cagctctaat attgatactc ctctttggac cctgtatctt taacctcctt    33300
gttaagtttg tctcttccag aatcaaagtt gtaaagctac aaatcgttct tcaaatggaa    33360
ccccagatga agtccatgac taagatctac cgtggacccc tggaccggcc tactagccca    33420
tgctccaatt gtaatgatat cgaacgcacc cctcccgagg aaatctcaac tgcacaaccc    33480
ctactatgcc ccaattccgc aggaagcagt tagactggtc gtcagccaac ctccccaaca    33540
gcacttgggt tttcctgttg agtgggggga ctgagagaca ggattagctg gatttcctag    33600
gccgactaag aatcccaaag cctagctggg aaggtgacca catccacctt taaacactgg    33660
gcttgcaact tagctcacac ccgaccaatc aggtagtaaa gagagctcac taaaatgcta    33720
attagacaaa aacaggaggt aaaaaaatag ccaatcatct atcgcctgag agcacagcgg    33780
gaaggacaat gatcgggata taaacccagg cattcaagcc ggcaacggct accttctttg    33840
ggtcccctcc ctttgtatgg gagctctctc tgtcttcact ctattaaata ttgcaactgc    33900
aaaaaaaaaa tagcttaatt gaagaataaa ttaatacaat aaaaggaata cattttaagt    33960
atacagttca aactgtaaca gtgttacagt ttcaagagga ccccttcaac aagatattgg    34020
gcatttccat catgccctaa aagttccttc ttgtcccctta ctggttgggt ccatctctac    34080
tacaccctcc tgacctggcc cagaccttgg cctcagaaga atcatttttt tgtcactaca    34140
tattagtttt gtctgttcta gaacttctta aaaacagaat catagagtat gttctctttg    34200
tattggttct ttttactcaa tgtaatgttc tgtgacattt atccatatta ttgcatgtat    34260 tattccttt aatcctgaat agtatgctgt tttaggaata taatgcaatt gtttattcat    34320
ttacctgttg acagatatct gagctattat gatggatatt atgaataatt ctgctatgaa    34380
cacttctgta caatgttttc tcggacatat attttcattt ttcttgagtg gagctgttag    34440
aactgttgga tcagaaagta agcatatgtt gaattttgaa agaaactggt aaactcttgt    34500
ctaaagtgat ttgtaccatt ttacactcct actaataatg tatgagagtt atatttgctc    34560
cacagccttt ttactacttt gttaatcttt ttagtactgt caacctttt aatttatcca    34620 atctagggaa cgtgaagtag tatctcactg ttattttcat tttcctgatg agtaacaata    34680
tcgtgtatct tttcatgtgc ttattagcca ttcctatatc ttttgtgaaa tagttaactt    34740
aaatttgtaa ctaaaggtgc tttcctgagt ttcaggtagt aagcctattt ccctcaagtg    34800
aataaactac agtcttggaa tgaaaaatta aacacagtgg agacattttt tgtataagtt    34860
gttttactct gtgtatgtct ggtttgctta gtctattatt atatgcccca tgaaagcaaa    34920
cacagtgctt atttcactaa tgagtatcac tagcacatag aactgtgctt gcccaaagca    34980
tgaactcaat aaatatgtta atgtgtatgc atgcacatac atctcatgc atgtacatct    35040 atacacacat ataaacatat attaattttt agacccacaa atctaagaaa actaattctt    35100
gagcctctgg tttgaagaat tctcaaatta ttaacatatc tttatgttcc actccacatc    35160
cactgtacct gaaatagccc tactgttcta ctttggtaaa tcaggcaaat ttaattttt    35220
```

```
aaataattaa gattccaact aattttaaaa tataatttga aagttaacaa tgaaatacat    35280
tacataaaaa gaaaattta aataaaagca aaactaaacc caataagagg aaagaaagtt    35340
gggctgtatt tctttaatcc tttaaaattc aaatcacaca atgctccaat gaaatcttca    35400
ttaactgaac caaactatgc ccatgaaaga tctcatatgc aactgctaaa acctcaataa    35460
acatattcat cttcttgcaa aaagatatt tctttataat atgcacatgc agtatatact     35520
attttgaggc agatttgtac tttagtcctt gttccattgc ttaccggctg gctgtccttt    35580
gtctggtcat tgacctccaa cttaaaaaat aatacttgcc ttgtctaccc cacagaagtg    35640
ttatgaaagt caaacaaggt agcataaagg tattttacaa gatataaagt gctataatac    35700
agattttaaa aatcactcta catcccataa tactttgttg tacaattta gagcaatagt     35760 agaaaataac aattattgcc taattgaaaa tccagtcccg aattccataa aatgtatgat    35820
atgaacatta tagtacatca tattacgagc cccaaataat cactgcttat atagttggtt    35880
aggatttcct tagtttgttc atatagttta tatatttatg cagtccctat tttgtgagag    35940
gcattgtgag gagcataaag acataagcac agtacagagc cttagcttct ctacatttac    36000
taaagaagac ttcttcttgg gtatttaatc aatatttaaa gtattctggg aagaaatgaa    36060
attaacttca tagactgacc ttagattact atcattacaa aaagatgcct gagtgatctg    36120
tctttaacat accagtattt atcttataac tgttatattt acttgaatca gaagtgaagt    36180 cctttaagc actaagcatc cattctatac tttcttgtct ttacatatga gatacaaatc     36240 atattttaa aacttttatt tacttttatt ttttagagac ggagtcttgc tctgtagccc      36300
aggctggagt acagtggcat gatcttggct caccacaatc tccacctcca cttcccaggg    36360
ttcaagtgaa caaatcatac ttttaagcac agattctcaa catgtatcct agcatgctac    36420
tgccataact agggtgtgaa ttaagtatta aagacagctt accccaaata ttactgtaac    36480
atatatctct aaatgaaaaa gaacatatta acaactatac ttggatggga ttctgggagc    36540
taacccatcc ctctctcccc tttcctccaa attccatctc ctattaacac accagctctc    36600
ctgagctaag cagctcctgg ggttggggaa gggtgtacat ggagaaagct agaacctcta    36660
cagtgttttc ctctctggga ggaactagca ggcatacgaa cagaaaaagc tgaataaaag    36720
gctgaatcct ttctattcct gaggcagaca gagagaagac cagggaacaa agagacttcg    36780
accaagagcc ctgccaggta ttgataccct tgatactgag aaaatatctg ggatatgaaa    36840
tacaaatgct aaataagtat ctttgaaata ggggtaaaag aataaagggt cttgatgagt    36900
aaaatgggta gtattttta ataacctgat aatgagcttt aggaaaaggg aaggtcaacg     36960
ttatggaatg aaaacacaga ggtaccaaat ttaaaagcat aaaaaaaagt ggagggggg     37020 aacccaataa cttcatcaaa ctagcaaata acttagtatc atttctaatt agaaacgcta    37080
gaaggaaatc acttagatct gataaagact aggctataat tctaactgat gaaacactta    37140
aactgtatca attaatacca gaaacaaac acagaaaagt ctactagaac catcattatt     37200
cagcacagtc ttggtaatgc aatactataa tagcaatgca ataaagcaag aaaaaaaaaa    37260
gtttgtaaaa acacaatagg atgagatttt tgtttttcca atgccataaa taactagaaa    37320
tggaaacaaa ataagaaaa acaaaatcta caaacacct ggaaataaaa agaaaaatgg      37380
tctatttgaa gaaaacctta aaatctatgc agaacataaa acaaaatctg aataaaaga     37440 aatatcatgt tcttgtctgg gaagacttaa tatcataaga agtgaattaa tatcaaaatt    37500
taaatcgaaa tttaatgtat ttccatctct aatcagacag gacactatgg ggaactgaat    37560
aagtgatttt aaaagtcatg gaaaattaat aactgagaat aaccatgaaa agtatgaaaa    37620
```

```
aaggagacaa atgaattgct ccaacagata tcagaacgct aaaattaaat aaaaatacta  37680
ctaggataag aaaatacata tactgatgta atgaataaag aatccagaat tagattccag  37740
taagtcaaac tactttacta taaaccaggg gtggcatatt catccagtgg gaaaaggaca  37800
gtaagaagtg agtaaactat ggcccactgg ccaaattgtg gcctctgcct atttttgcaa  37860 ataaagttt  actgggacaa agccaagcct atcatttgca aattgtctat aaatattttc  37920
atgttacaga atcacacagt ttcaacagag accatcttgt ctacaaagct gaaaatatct  37980
actatctggc ccttgaagaa agtttgccaa accttagttt atataataaa agatcagcta  38040
tctcatagac acctatctca cacaacacat tgtgggaaag gaccttcttt ttttttgag  38100 acggggtctt gctctgttga ccaggctgga ctgtagtggc atgatcatgg ctcactgcag  38160
cctcaacctc ccaggttcaa gtaatgctcc caccacagaa tcccaaacag ctgggagaga  38220
tgtgtgccac tacgcctggc taaggggcct ttttaacaga gaaagaaatc cacatactac  38280
taagaaaaag aagggcatat ttgatatata tttatatttt ttatatagat atcataaaaa  38340
tcaagatgaa ttatacagtt atattttgca atgtgtttga cggtaaaagt ttaatatcta  38400
taaaaattat tttataaaat atctttaata tatttataga tattataata taaaatatct  38460
ataaaattat tttataaaat aaaaagttaa gaagaaaaga taggcaaaac aaaatacagt  38520
gcaatttaca gaaaaccaag tccaaatggt caacaaagat aaaacagatt tataaactca  38580
ctaagtgtga gagaattatt agttaaagta aaaatatctc tctatacccca caatactact  38640 aaaaatcaga gttataatgc cctattgctg gtggagatgt aaggggagaa gcatgctctc  38700
atatactgtt agtgaaaatt taaactaata cattttgaa  aagtaagctg gcaatttttt  38760
ttttaatctc tacctttga  tgcaaaaact cattttggg  tacctattcc ataccttaaa  38820
aaaaatacat atgcttactg tagtactgtt tataatggta aaaactagaa aaaaagaaaa  38880
cttgatagtg aatactgaac aaattacagt gcatctacag attaaacata atgcagccat  38940
taaaaaagaa taaattaggc tgggtgcggt ggctcatgcc cgtaatccca gcactttggg  39000
aggccaaagc aggcggatca cttgaggcca ggagttcgag accagcctgg ccaacatggc  39060
aaaaccctgg ctctacaaaa aatacaaaaa ttagtcgggc atggtggtgg gcacctgtag  39120
tcccagctac tcaggaggct gaggcaggag aatcacttga gcctgggaga cagagattgc  39180
agtgagccaa gatcatgcca cagcattcca gtccaggtga cagaacgaga ctctgtctca  39240
acaaaaagaa caaattaaac cctacaactc atcaacaaaa atacccaaac ccaattcaaa  39300
aatgggcaaa ggacttgaat agacatttct tcaaggatga taaacaagca catgaaaaga  39360
tgcagagcac tattcattag tgattacatc ccacatgcat taggatggct agtatgaaga  39420
acagaaaata ataaatattg gtgaagatct gaaaaacaga aacctttgtg cactgttggt  39480
gggaatgtaa agtggtacag ctactacgga aaacagtatg gccattcctc aagaaaataa  39540
aaataaaatt atcttatgat aggaatatgc atttctgggt aaatacccca ataactgaa   39600 aacagggtgt acacccattt caacatttac atgtcaattc aactgggcca gaatacccag  39660
atatttgttc aaatattctt ctggatgctt ctatatatat gtttttggc tgaggttaac   39720 atttaaattg gtggattctg agtacagcag attaccatcc acaatgtagg tgggcctcat  39780
ctactcagtt gaaggtctta cagaaaaaga ctgacctccc ttgagcaaga aagaattcag  39840
gcaacagact gcctttggac tcaactgcaa ctcttccttg agtcaacagc ccatcccatc  39900
accctggctt ggtgagtcca gggtctgatg aggtaggctg cagactcaag gaagagctgc  39960
```

```
caaaaccagg aaagccaatt cattaaaata aatctctctc tacacaaaca cacacacaca   40020
ctaccaccac caccatgatg gttctgtttc tctggagaat gctaatacac ccctgttcat   40080
ggcagcatta ttcacaatag ccaaaaggtg aagcaactc cagcagatga atggagaagc   40140
aaaatgtggt atgtatatac aatggaatat tattaagcct ttaaaaagtg gaaattatat   40200
ctatctatat ctatacacac atactcacac acacacacac acatttatag aagacagggt   40260
ttcaccatgt tgtcaaggct ggtctcgaac tcctgggctc aagcaaaccg cctgcctcag   40320
cttcccaaag tgctgagatt acatgtgtga gccaccacac ccagccaaaa aaaggacatt   40380
ctgacacata atacaatata gataaacaat gaggacatca tgatatgcga ataagcctg   40440 tcacaaaaag gcaattagtg tatgattcct cttgtatgag gtacctatgg atgtcaaatc   40500
cataaagtag aatggggaaa cagagagttg tttaatgggt atagagtttg ttttgcaaga   40560
agaaaagagt tttggagaat gaatgtacaa cagtgtgaac ataattaaca ctactgaaaa   40620
tggttaagat tataaatttt atgttacatt tattttacca tgattaaaaa ttaaaacaaa   40680
ataatattaa ggaaaaatac tataaataac aacaacaaaa aaaacacctc aagcaactta   40740
cattcacctg ggaaacagaa tacatcctat tctgctagag atatatctgc agttcaaaat   40800
ttattacaaa tgatgttgtg tatcttttg aaatgactga aaaactaaat taaaagcaat   40860
aatattcagt ttactaacca gtaagtcctt ctttcatggt tcctgacttt tctgtaagat   40920
gttattgcaa gatatctact aaaatggaaa acaactgaaa aggcaaaatt ataatttctt   40980
atcaacatcg ctaaaaccct ggaggggaag aatcctaaca aacatggcca taatttgcca   41040
catatttcta ctgtcctcac ttttcaaaat ccagaaatca acatttctgg aaacaaaaca   41100
gagtctaaaa tttggctcct tcttcagttt agaaggtgcc aagttaatcc ctgacatcct   41160
agtttccatt ttcaaaaatg tacttttct ctccccaaac cggtatctag attcttaaat   41220
atttttagca catagaagtt aaatagattt gcttaaccaa aatagccagt aaacctccca   41280
aaagaattaa aatattaatg gcgctttaat gatacaaatg aacaacttta cattcaatcg   41340
tcaatgggaa aggaagcaga attctgagga ttatgaaagt aaacaaaacg aagttcaaat   41400
tctactttat tttacttttt tgtaactaat gaacaacttc ttccaaagac aagtaggaaa   41460
tacaaaaatt agccaggcat ggcacatgcc tgtagtcctg gttacttgga aggctgaagt   41520
gggtggatcg cttgagccgg gaaggcagag gctgtagtga gctgagatca catcactgca   41580
ctcaagcctg ggtgacagag caagaccctc tctgggaaa aaaaaaaaa aaataggctg   41640 ggcgcagtgg ctcacacttg taattccagc actttgggag gctgaggcag gtggttcacc   41700
tgaggtcagg agttctagac cagcctgacc aatatggtga acctgtct ctactaaaaa   41760 tacaaaaatt agccaggcat ggtggtgggc aattgtaatc ctagctactc gggaggctga   41820
ggcaggaaaa tcgcctgaac ccaagaggcg gaggtttcag tgagccgaga ttgcactagt   41880
gcactccagc ctgggcgaca gagcaagact tcatctcaaa ataaataaat aagtaagtaa   41940
ataaaattaa aaatatata aaaataaaac aaagataagt aggaaccatc ctttttttt   42000 tttttttttt ttttttttaa agatagggtc tgtttctgat gcccaggctt gagtgtagtg   42060
gcatgatcat ggctcactgc aaccttgacc tctcaaatac aagtgactct cctacctcag   42120
cctcccaagt agctgggact acaggtgctt accacccat ccggctcatt taaaaaaatt   42180
tttttgtaga ggtggggtct cactatgttg tatccaggct ggtctcattt taactttatt   42240
agaaaacaag cattgtttta tcagcttctt gttttttaa aactaaaaat aacactgcta   42300
ggttgtttct atgaagattc tctaaattta tttataaacct taagaataac atgtagaaca   42360
```

```
aagtagatga ctgaatgatc tttgttgaat aaatatgaat ggatattcaa ataattaaaa   42420
atctcttaag atctcccatt ctttacagga tacagagaaa actcgttaat atggcctgac   42480
ttttaccttt gcagccttat ccaaactctg tggtcaagac aaacaggttg tccttatact   42540
tacaacgtcc cccttttgcct acaaagctct tctcatgact ctttgcctat cttaagttca   42600
cctatctgtc aaatctctgg gaatgcaaca tttcctcaag gtagccttct ctcctcccaa   42660
actagaacaa attcttcctg gggcattagg ttttttattgc actgtatgtc tcttcttcac   42720
agcaatcaca gttccaatgt tatatttgta ttcttagttg atttgtttct ttccacctttt   42780
agactataac cttctaaggg gtcacacata atatcgatca tcagttgtat cccttgtgca   42840
tagcacaggg catggcaggc aaatatgtgt gtaaataaac ttgttgaatg aatcaatgag   42900
acacactttt cttacccaaa gtataatggc aggataacat ttatcaatct attgcttctt   42960
gaaaaacaga tatgatgtgc ttaattttca ttttacatct caaataccaa tgcctaagga   43020
attcacagtc atttttacaaa tcttttttgac aaatgccttc attaatcacc acctgtttac   43080
aagtgctaaa taacattttg gttacattct gtaacatttc ctgcacttaa tgtcatctct   43140
agaatactgg ctaatatgaa gcacctggac ttcaggaaca caaacctgaa actaacacac   43200
caaactaaac tgttatgtaa atgacagaaa tgacacattt tggtctgcaa catctctaga   43260
tggcttttgg accaattcaa cttttaccac taaaaatcgg tcacctgact atagtcattt   43320
tgagctcatg ataaatgaat tacagatgaa aaataaatag tttgatgaca atctttacaa   43380
aagtttatct tcaaagaata ccaccagtca caggtattct aggctcctat caacttattt   43440
ggtcagggca gacttcactt ttcatgataa ttatgttctg aaaattctac aaacttaatg   43500
attacaaaca aaagtcatag tttgctcata aatcaggcct aggtctggat tctagttctt   43560
ccatttttca tttgttcact gaggcaagtg acttaaaatt ccctagcctc agtttcctca   43620
catgtaaaat cagataatga ttcctattcc taagatggtt tgaggcttc aacaagataa   43680
gatgggcctc actcaagcat gctcagtact ctgtctctct ctctccggtt atgcagaaat   43740
tctattagga ttctgcaaag taaaataaat atttcagtaa aaattatgcc ctttattaat   43800
gaatctagat tttcagattt tccttaaatt tacttagtaa cttaagggct caaatattat   43860
agagatttgt atctagtatt ttaaagaaat gaaggtgtt aatcaaaatg ctgcacaaat    43920
aaatgctaca tttaacaaac agaatatcac aaccatacaa actaatcaga tataaagaag   43980
tcagcaacag aaatctgatg ttgcctttag atcacacaat taggcaaaca aaaatagagt   44040
tccatcctcc tttggtcaag gccatggttg aagactgaat accaaatagg gaaataggaa   44100
aagccaggaa atggcaaatt agcaaaaact ggactcctta atttttatat tcattttcat   44160
atctcacttc taaaactttta attaaattca aataaaaacc aaaatggaac tgagataaag   44220
ccaaaaggaa agttatgtag gtcaaatgag aacctatatt gtccttaggc tctttgttgc   44280
tttctgttta aggaaaaact gcccaagtgc cttgacacat taaagatcaa gcaggaggtt   44340
ctgccgagag tccccatctg gcagccaggt tttgtcaagc aaattttgag aattctctac   44400
cctcccactt tctatctaat tatagcactt tataaaaacc attctctctc tgtctctgtc   44460
tctctctctc tctctctctc acacacacac acacacacac acacacacac acacaccc     44520
tttctctctc tctctctctg aaacttatct gtattataat aacacaacac taggtatgga   44580
ttaatctgac aatttttcccc taaaacagaa taaattcaaa aaggaaaaacc tttcctctgt  44640
acacatgcac tatattctga caataataat tcctaaatta agtataatac attttcccta   44700
```

```
caggagttta aagaagttac agtaaagaat ctcttgtata aatatatatg ccagaacttg   44760
acccaaataa gtgctgagag gtataaatct caaaacagtt tccggactct ttgtgaaatg   44820
tcttcagagt ctgcgatata ttttcttcaa ctaaattata caagtaagat attttgctgg   44880
gctgtgggaa tgccttacgg catgttactg tggagctcat ggtaaaatag aaagaatata   44940
aataattaaa ataaaattga caaatgataa atgatttaat aaattagaaa ttcaaatgcc   45000
gggcactttt ctagaacctg gacacaaagc atgaacctaa caataacccc gccttcatga   45060
aaaatatgga ctatttgaaa attatacctg caacactaaa taaatattct tcattcttcc   45120
agtatattga gatgtttact ttcaattaga caatttgctt tcctctctga acacatagtt   45180
atgtgatggc tctataaaag attttaaaat aactatagaa ggaactattg gtaaagactg   45240
tgggatacta aaaatggcta caagaaagt tatgacaaaa cctctgagtt tgaatggaag    45300
tcctactaga ttagagtcta agcctgtgac attatgcttc tggttcttgt tcttaaatgc   45360
ttttctcatt aatagtatgt aacttacttc ctggaatgcc attcattaaa aaatatttta   45420
atatttgcta aatgtcaata tttatgccag cacttttaaa gtacagaaac atggagtttc   45480
tttacctcat gcaaatatgc tgtgagaaag acttaagagc ctattgccta ctttgtggta   45540
caacactgaa gactcaccat ccaaaacaaa cagacttagt aaattcttgt gatttgcagt   45600
agttctgttc tataaggtta ccacaaacac tgaaatcatc gctcctgggg gaatacaagg   45660
ttatgtttcc gtgagccctc ggtcacaaca tgttcattaa ctgatcaata cataaccttg   45720
ttctatgtgt gtttctgttt aaaaagagca cttcagtgct acatttggag tctgttttaa   45780
acagcaaaat cactaataaa aagcacaaaa atgtaaaagc atggcactac atacactgtg   45840
acaagaaggc ttgtttatag tatgacagct gagacaagaa ggtagagcct cgctttgatc   45900
aacctctgct gggaaatgag catcaggtga atcaattttt caccactctg aatgaccgta   45960
aaagtgctcc aagtactgac tttggggtta cacataaatt ttagtaagca tgtgaatctg   46020
ccaatatgaa atctacaaat aatgagtacc aaatgcatat gagtcaaata tttcagtgcg   46080
gtatctgact tgattgccac tgaaagacac agtttggaaa acccctaata aataccgttt   46140
agttactatg cagacaaaga gttctacact agagtgcttc aattaagatg tctgaggctt   46200
tcataaatgg atgttttta aaatgttatt tcctacctga tatattctaa aggggatata    46260
acgaaatcca ttttcttctg caggatattc catgagtttc cgattgatgg cccaaaactg   46320
gtcaaatctg tctgtaatga                                              46340
```

<210> SEQ ID NO 67
<211> LENGTH: 773
<212> TYPE: DNA
<213> ORGANISM: Homo sapiens

<400> SEQUENCE: 67

```
actgagagac aggactagct ggatttccta ggctgactaa gaatccctaa gcctagctgg     60
gaaggtgacc acatccacct ttaaacacgg ggcttgcaac ttagctcaca cctgaccaag    120
gaaggtgacc acaccctcct ttaaacacag agcttgtaac tcagctcaca cccgaccaat    180
caggtagtaa agagagctca ctaaaatacc aattaggcta aaaacaggag gtaaagaaat    240
aatcaaatca tctatcgcct gagagcacag ggggagggac aatgatcggg atataaaccc    300
aggcatttga gccagatcag gtaaccctct ttgggtcccc tcacactgta tgggagctct    360
gttttcactc tattaaatct tgcaactgca cactcttctg gtccatgttt gttccggctc    420
aagctgagct tttgctcgcc gtccaccact gctgaatgcc gccattgcag acctgccctt   480
```

```
gacttccacc cctccggatc cggcagagtg tccgctgcac tcctgatcca gcgaggcacc      540
cattgccact cccgatcagg ctaaaggctt gccattgttc ctgcacagct aagtgcctgg      600
gttcatccta atcaggctga acactggtcg ctgggttcca cggttctctt ccatgactca      660
cagcttctaa tagagctata acactcacca catggcccaa ggttccattc gttggaatcc      720
atgaggccaa gaaccccagg tcagagaata aaaggcccgc ccatcttgg gag              773
```

<210> SEQ ID NO 68
<211> LENGTH: 10
<212> TYPE: PRT
<213> ORGANISM: Homo sapiens

<400> SEQUENCE: 68

Phe Leu Gly Glu Glu Cys Cys Tyr Tyr Val
1               5                   10

<210> SEQ ID NO 69
<211> LENGTH: 10
<212> TYPE: PRT
<213> ORGANISM: Homo sapiens

<400> SEQUENCE: 69

Leu Leu Phe Gly Pro Cys Ile Phe Asn Leu
1               5                   10

<210> SEQ ID NO 70
<211> LENGTH: 10
<212> TYPE: PRT
<213> ORGANISM: Homo sapiens

<400> SEQUENCE: 70

Cys Leu Pro Leu Asn Phe Arg Pro Tyr Val
1               5                   10

<210> SEQ ID NO 71
<211> LENGTH: 10
<212> TYPE: PRT
<213> ORGANISM: Homo sapiens

<400> SEQUENCE: 71

Gly Leu Leu Ser Gln Trp Met Pro Trp Ile
1               5                   10

<210> SEQ ID NO 72
<211> LENGTH: 9
<212> TYPE: PRT
<213> ORGANISM: Homo sapiens

<400> SEQUENCE: 72

Cys Leu Pro Ser Gly Ile Phe Phe Val
1               5

<210> SEQ ID NO 73
<211> LENGTH: 9
<212> TYPE: PRT
<213> ORGANISM: Homo sapiens

<400> SEQUENCE: 73

Trp Met Pro Trp Ile Leu Pro Phe Leu
1               5

<210> SEQ ID NO 74

```
<211> LENGTH: 10
<212> TYPE: PRT
<213> ORGANISM: Homo sapiens

<400> SEQUENCE: 74

Ile Arg Trp Val Thr Pro Pro Thr Gln Ile
1               5                   10

<210> SEQ ID NO 75
<211> LENGTH: 10
<212> TYPE: PRT
<213> ORGANISM: Homo sapiens

<400> SEQUENCE: 75

Leu Arg Asn Thr Gly Pro Trp Gly Leu Leu
1               5                   10

<210> SEQ ID NO 76
<211> LENGTH: 10
<212> TYPE: PRT
<213> ORGANISM: Homo sapiens

<400> SEQUENCE: 76

Leu Arg Thr His Thr Arg Leu Val Ser Leu
1               5                   10

<210> SEQ ID NO 77
<211> LENGTH: 10
<212> TYPE: PRT
<213> ORGANISM: Homo sapiens

<400> SEQUENCE: 77

Lys Arg Val Pro Ile Leu Pro Phe Val Ile
1               5                   10

<210> SEQ ID NO 78
<211> LENGTH: 10
<212> TYPE: PRT
<213> ORGANISM: Homo sapiens

<400> SEQUENCE: 78

Cys Arg Cys Met Thr Ser Ser Ser Pro Tyr
1               5                   10

<210> SEQ ID NO 79
<211> LENGTH: 10
<212> TYPE: PRT
<213> ORGANISM: Homo sapiens

<400> SEQUENCE: 79

Thr Arg Val His Gly Thr Ser Ser Pro Tyr
1               5                   10

<210> SEQ ID NO 80
<211> LENGTH: 10
<212> TYPE: PRT
<213> ORGANISM: Homo sapiens

<400> SEQUENCE: 80

Ala Arg Glu Lys His Val Lys Glu Val Ile
1               5                   10

<210> SEQ ID NO 81
<211> LENGTH: 10
<212> TYPE: PRT
```

<213> ORGANISM: Homo sapiens

<400> SEQUENCE: 81

Ser Arg Ile Glu Ala Val Lys Leu Gln Met
1               5                   10

<210> SEQ ID NO 82
<211> LENGTH: 10
<212> TYPE: PRT
<213> ORGANISM: Homo sapiens

<400> SEQUENCE: 82

Ser Gln Trp Met Pro Trp Ile Leu Pro Phe
1               5                   10

<210> SEQ ID NO 83
<211> LENGTH: 9
<212> TYPE: PRT
<213> ORGANISM: Homo sapiens

<400> SEQUENCE: 83

Cys Tyr Tyr Val Asn Gln Ser Gly Ile
1               5

<210> SEQ ID NO 84
<211> LENGTH: 9
<212> TYPE: PRT
<213> ORGANISM: Homo sapiens

<400> SEQUENCE: 84

Phe Tyr Tyr Lys Leu Ser Gln Glu Leu
1               5

<210> SEQ ID NO 85
<211> LENGTH: 9
<212> TYPE: PRT
<213> ORGANISM: Homo sapiens

<400> SEQUENCE: 85

Thr Tyr Thr Thr Asn Ser Gln Cys Ile
1               5

<210> SEQ ID NO 86
<211> LENGTH: 9
<212> TYPE: PRT
<213> ORGANISM: Homo sapiens

<400> SEQUENCE: 86

Ser Phe Leu Val Pro Pro Met Thr Ile
1               5

<210> SEQ ID NO 87
<211> LENGTH: 9
<212> TYPE: PRT
<213> ORGANISM: Homo sapiens

<400> SEQUENCE: 87

Tyr Tyr Val Asn Gln Ser Gly Ile Val
1               5

<210> SEQ ID NO 88
<211> LENGTH: 9
<212> TYPE: PRT
<213> ORGANISM: Homo sapiens

```
<400> SEQUENCE: 88

Leu Phe Asn Thr Thr Leu Thr Gly Leu
1               5

<210> SEQ ID NO 89
<211> LENGTH: 9
<212> TYPE: PRT
<213> ORGANISM: Homo sapiens

<400> SEQUENCE: 89

Leu Phe Gly Pro Cys Ile Phe Asn Leu
1               5

<210> SEQ ID NO 90
<211> LENGTH: 9
<212> TYPE: PRT
<213> ORGANISM: Homo sapiens

<400> SEQUENCE: 90

Arg Trp Val Thr Pro Pro Thr Gln Ile
1               5

<210> SEQ ID NO 91
<211> LENGTH: 10
<212> TYPE: PRT
<213> ORGANISM: Homo sapiens

<400> SEQUENCE: 91

Leu Pro Phe Leu Gly Pro Leu Ala Ala Ile
1               5                   10

<210> SEQ ID NO 92
<211> LENGTH: 10
<212> TYPE: PRT
<213> ORGANISM: Homo sapiens

<400> SEQUENCE: 92

Leu Pro Tyr His Ile Phe Leu Phe Thr Val
1               5                   10

<210> SEQ ID NO 93
<211> LENGTH: 10
<212> TYPE: PRT
<213> ORGANISM: Homo sapiens

<400> SEQUENCE: 93

Gly Ala Leu Gly Thr Gly Ile Gly Gly Ile
1               5                   10

<210> SEQ ID NO 94
<211> LENGTH: 10
<212> TYPE: PRT
<213> ORGANISM: Homo sapiens

<400> SEQUENCE: 94

Leu Pro Phe Val Ile Gly Ala Gly Val Leu
1               5                   10

<210> SEQ ID NO 95
<211> LENGTH: 9
<212> TYPE: PRT
<213> ORGANISM: Homo sapiens

<400> SEQUENCE: 95
```

-continued

Arg Arg Pro Leu Asp Arg Pro Ala Ser
1               5

<210> SEQ ID NO 96
<211> LENGTH: 9
<212> TYPE: PRT
<213> ORGANISM: Homo sapiens

<400> SEQUENCE: 96

Phe Arg Pro Tyr Val Ser Ile Pro Val
1               5

<210> SEQ ID NO 97
<211> LENGTH: 9
<212> TYPE: PRT
<213> ORGANISM: Homo sapiens

<400> SEQUENCE: 97

Arg Arg Ala Leu Asp Leu Leu Thr Ala
1               5

<210> SEQ ID NO 98
<211> LENGTH: 9
<212> TYPE: PRT
<213> ORGANISM: Homo sapiens

<400> SEQUENCE: 98

Trp Arg Met Gln Arg Pro Gly Asn Ile
1               5

<210> SEQ ID NO 99
<211> LENGTH: 10
<212> TYPE: PRT
<213> ORGANISM: Homo sapiens

<400> SEQUENCE: 99

Asp Arg Ile Gln Arg Arg Ala Glu Glu Leu
1               5                   10

<210> SEQ ID NO 100
<211> LENGTH: 10
<212> TYPE: PRT
<213> ORGANISM: Homo sapiens

<400> SEQUENCE: 100

Leu Arg Thr His Thr Arg Leu Val Ser Leu
1               5                   10

<210> SEQ ID NO 101
<211> LENGTH: 10
<212> TYPE: PRT
<213> ORGANISM: Homo sapiens

<400> SEQUENCE: 101

Glu Arg Val Ala Asp Ser Leu Val Thr Leu
1               5                   10

<210> SEQ ID NO 102
<211> LENGTH: 10
<212> TYPE: PRT
<213> ORGANISM: Homo sapiens

<400> SEQUENCE: 102

Leu Phe Gly Pro Cys Ile Phe Asn Leu Leu
1               5                   10

<210> SEQ ID NO 103
<211> LENGTH: 10
<212> TYPE: PRT
<213> ORGANISM: Homo sapiens

<400> SEQUENCE: 103

Gln Phe Tyr Tyr Lys Leu Ser Gln Glu Leu
1               5                   10

<210> SEQ ID NO 104
<211> LENGTH: 10
<212> TYPE: PRT
<213> ORGANISM: Homo sapiens

<400> SEQUENCE: 104

Gln Trp Met Pro Trp Ile Leu Pro Phe Leu
1               5                   10

<210> SEQ ID NO 105
<211> LENGTH: 10
<212> TYPE: PRT
<213> ORGANISM: Homo sapiens

<400> SEQUENCE: 105

Cys Tyr Tyr Val Asn Gln Ser Gly Ile Val
1               5                   10

<210> SEQ ID NO 106
<211> LENGTH: 10
<212> TYPE: PRT
<213> ORGANISM: Homo sapiens

<400> SEQUENCE: 106

Asn Phe Val Ser Ser Arg Ile Glu Ala Val
1               5                   10

<210> SEQ ID NO 107
<211> LENGTH: 9
<212> TYPE: PRT
<213> ORGANISM: Homo sapiens

<400> SEQUENCE: 107

Gly Pro Leu Val Ser Asn Leu Glu Ile
1               5

<210> SEQ ID NO 108
<211> LENGTH: 9
<212> TYPE: PRT
<213> ORGANISM: Homo sapiens

<400> SEQUENCE: 108

Leu Pro Leu Asn Phe Arg Pro Tyr Val
1               5

<210> SEQ ID NO 109
<211> LENGTH: 10
<212> TYPE: PRT
<213> ORGANISM: Homo sapiens

<400> SEQUENCE: 109

Leu Pro Phe Leu Gly Pro Leu Ala Ala Ile
1               5                   10

```
<210> SEQ ID NO 110
<211> LENGTH: 10
<212> TYPE: PRT
<213> ORGANISM: Homo sapiens

<400> SEQUENCE: 110

Glu Pro Lys Met Gln Ser Lys Thr Lys Ile
1               5                   10

<210> SEQ ID NO 111
<211> LENGTH: 10
<212> TYPE: PRT
<213> ORGANISM: Homo sapiens

<400> SEQUENCE: 111

Leu Pro Tyr His Ile Phe Leu Phe Thr Val
1               5                   10

<210> SEQ ID NO 112
<211> LENGTH: 9
<212> TYPE: PRT
<213> ORGANISM: Homo sapiens

<400> SEQUENCE: 112

Arg Glu Lys His Val Lys Glu Val Ile
1               5

<210> SEQ ID NO 113
<211> LENGTH: 10
<212> TYPE: PRT
<213> ORGANISM: Homo sapiens

<400> SEQUENCE: 113

Lys Pro Arg Asn Lys Arg Val Pro Ile Leu
1               5                   10

<210> SEQ ID NO 114
<211> LENGTH: 9
<212> TYPE: PRT
<213> ORGANISM: Homo sapiens

<400> SEQUENCE: 114

Val Val Leu Gln Asn Arg Arg Ala Leu
1               5

<210> SEQ ID NO 115
<211> LENGTH: 10
<212> TYPE: PRT
<213> ORGANISM: Homo sapiens

<400> SEQUENCE: 115

Ala Val Val Leu Gln Asn Arg Arg Ala Leu
1               5                   10

<210> SEQ ID NO 116
<211> LENGTH: 9
<212> TYPE: PRT
<213> ORGANISM: Homo sapiens

<400> SEQUENCE: 116

Leu Pro Phe Val Ile Gly Ala Gly Val
1               5

<210> SEQ ID NO 117
<211> LENGTH: 9
```

<212> TYPE: PRT
<213> ORGANISM: Homo sapiens

<400> SEQUENCE: 117

Asp Leu Tyr Ser Tyr Val Ile Ser Lys
1               5

<210> SEQ ID NO 118
<211> LENGTH: 10
<212> TYPE: PRT
<213> ORGANISM: Homo sapiens

<400> SEQUENCE: 118

Thr Glu Gln Asp Leu Tyr Ser Tyr Val Ile
1               5                   10

<210> SEQ ID NO 119
<211> LENGTH: 2615
<212> TYPE: DNA
<213> ORGANISM: Homo sapiens

<400> SEQUENCE: 119

| | | | | |
|---|---|---|---|---|
| gaattccggg | aagccagacg | gttaacacag | acaaagtgct | gccgtgacac | tcggccctcc | 60 |
| agtgttgcgg | agaggcaaga | gcagcgaccg | cgcacctgtc | cgcccggagc | tgggacgcgc | 120 |
| gcccgggcgg | ccggacgaag | cgaggaggga | ccgccgaggc | tgcccccaag | tgtaactcca | 180 |
| gcactgtgag | gtttcaggga | ttggcagagg | ggaccaaggg | gacatgaaaa | tggacatgga | 240 |
| ggatgcggat | atgactctgt | ggacagaggc | tgagtttgaa | gagaagtgta | catacattgt | 300 |
| gaacgaccac | ccctgggatt | ctggtgctga | tggcggtact | tcggttcagg | cggaggcatc | 360 |
| cttaccaagg | aatctgcttt | tcaagtatgc | caccaacagt | gaagaggtta | ttggagtgat | 420 |
| gagtaaagaa | tacataccaa | agggcacacg | ttttggaccc | ctaataggtg | aaatctacac | 480 |
| caatgacaca | gttcctaaga | acgccaacag | gaaatatttt | tggaggatct | attccagagg | 540 |
| ggagcttcac | cacttcattg | acggctttaa | tgaagagaaa | agcaactgga | tgcgctatgt | 600 |
| gaatccagca | cactctcccc | gggagcaaaa | cctggctgcg | tgtcagaacg | ggatgaacat | 660 |
| ctacttctac | accattaagc | ccatccctgc | caaccaggaa | cttcttgtgt | ggtattgtcg | 720 |
| ggactttgca | gaaaggcttc | actacccctta | tcccggagag | ctgacaatga | tgaatctcac | 780 |
| acaaacacag | agcagtctaa | agcaaccgag | cactgagaaa | aatgaactct | gcccaaagaa | 840 |
| tgtcccaaag | agagagtaca | gcgtgaaaga | aatcctaaaa | ttggactcca | ccccctccaa | 900 |
| aggaaaggac | ctctaccgtt | ctaacatttc | accccctcaca | tcagaaaagg | acctcgatga | 960 |
| ctttagaaga | cgtgggagcc | ccgaaatgcc | cttctaccct | cgggtcgttt | acccccatccg | 1020 |
| ggcccctctg | ccagaagact | tttgaaagc | ttccctggcc | tacgggatcg | agagacccac | 1080 |
| gtacatcact | cgctccccca | ttccatcctc | caccactcca | agcccctctg | caagaagcag | 1140 |
| ccccgaccaa | agcctcaaga | gctccagccc | tcacagcagc | cctgggaata | cggtgtcccc | 1200 |
| tgtgggcccc | ggctctcaag | agcaccggga | ctcctacgct | tacttgaacg | cgtcctacgg | 1260 |
| cacggaaggt | ttgggctcct | accctggcta | cgcaccctg | ccccacctcc | cgccagcttt | 1320 |
| catccctcg | tacaacgctc | actaccccaa | gttcctcttg | ccccctacg | gcatgaattg | 1380 |
| taatggcctg | agcgctgtga | gcagcatgaa | tggcatcaac | aactttggcc | tcttcccgag | 1440 |
| gctgtgccct | gtctacagca | atctcctcgg | tgggggcagc | ctgccccacc | ccatgctcaa | 1500 |
| ccccacttct | ctcccgagct | cgctgccctc | agatggagcc | cggaggttgc | tccagccgga | 1560 |

-continued

```
gcatcccagg gaggtgcttg tcccggcgcc ccacagtgcc ttctccttta ccggggccgc    1620
cgccagcatg aaggacaagg cctgtagccc cacaagcggg tctcccacgg cgggaacagc    1680
cgccacggca gaacatgtgg tgcagcccaa agctacctca gcagcgatgg cagccccag     1740 cagcgacgaa gccatgaatc tcattaaaaa caaaagaaac atgaccggct acaagaccct    1800
tccctacccg ctgaagaagc agaacggcaa gatcaagtac gaatgcaacg tttgcgccaa    1860
gactttcggc cagctctcca atctgaaggt ccacctgaga gtgcacagtg agaacggcc     1920 tttcaaatgt cagacttgca caagggctt tactcagctc gcccacctgc agaaacacta    1980
cctggtacac acgggagaaa agccacatga atgccaggtc tgccaagga gatttagcag     2040 caccagcaat ctcaagaccc acctgcgact ccattctgga gagaaaccat accaatgcaa    2100
ggtgtgccct gccaagttca cccagtttgt gcacctgaaa ctgcacaagc gtctgcacac    2160
ccgggagcgg ccccacaagt gctcccagtg ccacaagaac tacatccatc tctgtagcct    2220
caaggttcac ctgaaaggga actgcgctgc ggccccggcg cctgggctgc ccttggaaga    2280
tctgacccga atcaatgaag aaatcgagaa gtttgacatc agtgacaatg ctgaccggct    2340
cgaggacgtg gaggatgaca tcagtgtgat ctctgtagtg gagaaggaaa ttctggccgt    2400
ggtcagaaaa gagaagaag aaactggcct gaaagtgtct ttgcaaagaa acatggggaa    2460
tggactcctc tcctcagggt gcagcctta tgagtcatca gatctacccc tcatgaagtt    2520
gcctcccagc aacccactac ctctggtacc tgtaaaggtc aaacaagaaa cagttgaacc    2580
aatggatcct taagattttc agaaaacact tattt                              2615
```

<210> SEQ ID NO 120
<211> LENGTH: 29
<212> TYPE: PRT
<213> ORGANISM: Homo sapiens

<400> SEQUENCE: 120

```
Leu Gln Asn Arg Arg Ala Leu Asp Leu Leu Thr Ala Glu Arg Gly Gly
1               5                   10                  15

Thr Cys Leu Phe Leu Gly Glu Glu Cys Cys Tyr Tyr Val
                20                  25
```

<210> SEQ ID NO 121
<211> LENGTH: 21
<212> TYPE: DNA
<213> ORGANISM: Homo sapiens

<400> SEQUENCE: 121

```
cttcaaacaa caaccaggag g                                              21
```

<210> SEQ ID NO 122
<211> LENGTH: 20
<212> TYPE: DNA
<213> ORGANISM: Homo sapiens

<400> SEQUENCE: 122

```
ttggggaggt tggccgacga                                                20
```